US011352354B2

(12) United States Patent
Deng et al.

(10) Patent No.: US 11,352,354 B2
(45) Date of Patent: Jun. 7, 2022

(54) SUBSTITUTED PENTA-FUSED HEXA-HETEROCYCLIC COMPOUNDS, PREPARATION METHOD THEREFOR, DRUG COMBINATION AND USE THEREOF

(71) Applicant: Xiamen University, Xiamen (CN)

(72) Inventors: Xianming Deng, Xiamen (CN); Wei Huang, Xiamen (CN); Xihuan Sun, Xiamen (CN); Ting Zhang, Xiamen (CN); Zhixiang He, Xiamen (CN); Yan Liu, Xiamen (CN); Xinrui Wu, Xiamen (CN); Baoding Zhang, Xiamen (CN); Xiaoyang Li, Xiamen (CN); Jingfang Zhang, Xiamen (CN); Yun Chen, Xiamen (CN); Li Li, Xiamen (CN); Qingyan Xu, Xiamen (CN); Zhiyu Hu, Xiamen (CN)

(73) Assignee: Xiamen University, Xiamen (CN)

(*) Notice: Subject to any disclaimer, the term of this patent is extended or adjusted under 35 U.S.C. 154(b) by 0 days.

(21) Appl. No.: 16/636,333

(22) PCT Filed: Aug. 3, 2018

(86) PCT No.: PCT/CN2018/098457
§ 371 (c)(1),
(2) Date: Feb. 3, 2020

(87) PCT Pub. No.: WO2019/024908
PCT Pub. Date: Feb. 7, 2019

(65) Prior Publication Data
US 2020/0165246 A1  May 28, 2020

(30) Foreign Application Priority Data

Aug. 4, 2017 (CN) .......................... 201710658894.7

(51) Int. Cl.
| | | |
|---|---|---|
| *C07D 471/04* | (2006.01) | |
| *C07D 487/04* | (2006.01) | |
| *C07D 495/04* | (2006.01) | |
| *C07D 473/34* | (2006.01) | |
| *A61P 35/00* | (2006.01) | |
| *A61P 35/04* | (2006.01) | |
| *A61K 31/437* | (2006.01) | |
| *A61K 31/444* | (2006.01) | |
| *A61K 31/496* | (2006.01) | |
| *A61K 31/4985* | (2006.01) | |
| *A61K 31/519* | (2006.01) | |
| *A61K 31/52* | (2006.01) | |
| *A61K 31/5377* | (2006.01) | |

(52) U.S. Cl.
CPC ............ *C07D 471/04* (2013.01); *A61P 35/00* (2018.01); *C07D 487/04* (2013.01); *C07D 495/04* (2013.01)

(58) Field of Classification Search
CPC .. C07D 471/04; C07D 487/04; C07D 495/04; C07D 473/34; A61P 35/00; A61P 35/04; A61K 31/437; A61K 31/444; A61K 31/496; A61K 31/4985; A61K 31/519; A61K 31/52; A61K 31/5377
See application file for complete search history.

(56) References Cited

U.S. PATENT DOCUMENTS

2020/0165246 A1   5/2020  Deng et al.

FOREIGN PATENT DOCUMENTS

| CN | 1426398 A | 6/2003 | |
|---|---|---|---|
| CN | 101351467 A | 1/2009 | |
| CN | 109384782 A | 2/2019 | |
| EP | 1 277 738 A1 | 1/2003 | |
| WO | WO 2005/014599 A1 | 2/2005 | |
| WO | WO 2007/062805 A1 | 6/2007 | |
| WO | WO-2007087276 A1 * | 8/2007 | ........... C07D 401/14 |
| WO | WO 2010/118367 A2 | 10/2010 | |
| WO | WO 2016/118709 A1 | 7/2016 | |
| WO | WO 2016/210330 A1 | 12/2016 | |
| WO | WO-2019001556 A1 * | 1/2019 | ........... A61K 31/496 |

OTHER PUBLICATIONS

Bouloc, N., "Structure-based design of imidazo [1, 2-a] pyrazine derivatives asselective inhibitors of Aurora-A kinase in cells." Bioorganic & medicinal chemistry letters 20.20 (2010): 5988-5993.*
McKim, A. S., "Dimethyl sulfoxide USP, PhEur in approved pharmaceutical products and medical devices." Pharmaceutical Technology 32.5 (2008): 74-85.*
International Search Report and Written Opinion dated Oct. 31, 2018, in connection with PCT/CN2018/098457.
Huang et al., Discovery and Identification of Small Molecules as Methuosis Inducers with in Vivo Antitumor Activities. J Med Chem. Jun. 28, 2018;61(12):5424-5434. doi: 10.1021/acs.jmedchem. 8b00753. Epub Jun. 19, 2018.
Extended European Search Report for Application No. 18841271.2, dated Mar. 22, 2021.
Chen et al., Synthesis and SAR of novel 4-morpholinopyrrolopyrimidine derivatives as potent phosphatidylinositol 3-kinase inhibitors. J Med Chem. Apr. 22, 2010;53(8):3169-82. doi: 10.1021/ jm901783v.

(Continued)

*Primary Examiner* — John M Mauro
(74) *Attorney, Agent, or Firm* — Wolf, Greenfield & Sacks, P.C.

(57) ABSTRACT

A type of substituted penta-fused hexa-heterocyclic compounds having selective inhibition for PIKfyve kinase, a pharmaceutically acceptable salt and pharmaceutically acceptable solvate thereof, a method for the preparation thereof, a pharmaceutical composition comprising the same, and use of these compounds in the manufacture of a medicament for preventing or treating a disease associated with PIKfyve in vivo, in particular in the manufacture of a medicament for preventing or treating tumor growth and metastasis.

18 Claims, 5 Drawing Sheets

(56) References Cited

OTHER PUBLICATIONS

Martiny-Baron et al., The small molecule specific EphB4 kinase inhibitor NVP-BHG712 inhibits VEGF driven angiogenesis. Angiogenesis. Sep. 2010;13(3):259-67. doi: 10.1007/s10456-010-9183-z. Epub Aug. 29, 2010.

Bouloc et al., Structure-based design of imidazo[1,2-a]pyrazine derivatives as selective inhibitors of Aurora-A kinase in cells. Bioorg Med Chem Lett. Oct. 15, 2010;20(20):5988-93. doi: 10.1016/j.bmcl.2010.08.091. Epub Aug. 21, 2010.

Cho et al., Indolyl-Pyridinyl-Propenone-Induced Methuosis through the Inhibition of Pikfyve. ACS Omega. Jun. 30, 2018;3(6):6097-6103. doi: 10.1021/acsomega.8b00202. Epub Jun. 5, 2018.

Dupuis-Coronas et al., The nucleophosmin-anaplastic lymphoma kinase oncogene interacts, activates, and uses the kinase PIKfyve to increase invasiveness. J Biol Chem. Sep. 16, 2011;286(37):32105-14. doi: 10.1074/jbc.M111.227512. Epub Jul. 7, 2011.

Gayle et al., Identification of apilimod as a first-in-class PIKfyve kinase inhibitor for treatment of B-cell non-Hodgkin lymphoma. Blood. Mar. 30, 2017;129(13):1768-1778. doi: 10.1182/blood-2016-09-736892. Epub Jan. 19, 2017.

Jeffries et al., A selective PIKfyve inhibitor blocks PtdIns(3,5)P(2) production and disrupts endomembrane transport and retroviral budding. EMBO Rep. Feb. 2008;9(2):164-70. doi: 10.1038/sj.embor.7401155. Epub Jan. 11, 2008.

Kim et al., Targeting cancer metabolism by simultaneously disrupting parallel nutrient access pathways. J Clin Invest. Nov. 1, 2016;126(11):4088-4102. doi: 10.1172/JCI87148. Epub Sep. 26, 2016.

Krishna et al., PIKfyve Regulates Vacuole Maturation and Nutrient Recovery following Engulfment. Dev Cell. Sep. 12, 2016;38(5):536-47. doi: 10.1016/j.devcel.2016.08.001.

Oppelt et al., PIKfyve, MTMR3 and their product PtdIns5P regulate cancer cell migration and invasion through activation of Rae1. Biochem J. Aug. 1, 2014;461(3):383-90. doi: 10.1042/BJ20140132.

\* cited by examiner

SUBSTITUTED PENTA-FUSED HEXA-HETEROCYCLIC COMPOUNDS, PREPARATION METHOD THEREFOR, DRUG COMBINATION AND USE THEREOF

RELATED APPLICATIONS

This application is a national stage filing under 35 U.S.C. § 371 of international PCT application, PCT/CN2018/098457, filed Aug. 3, 2018, which claims priority to Chinese Application No. 201710658894.7, filed on Aug. 4, 2017, the entire contents of each of which are incorporated herein by reference.

TECHNICAL FIELD

The invention relates to the field of medicinal chemistry, and in particular a type of compounds having selective inhibition for PIKfyve kinase, a pharmaceutically acceptable salt or pharmaceutically acceptable solvate thereof, a method for the preparation thereof, a pharmaceutical composition comprising the same, and use of these compounds in the manufacture of a medicament for preventing or treating a disease associated with PIKfyve in vivo, in particular in the manufacture of a medicament for preventing or treating tumor growth and metastasis.

BACKGROUND ART

Tumor is a serious threat to human health and life. According to data released by the World Health Organization in 2003, there were 10 million malignant tumor patients worldwide in 2000, and 6.2 million deaths due to malignant tumors, accounting for 12% to 25% of the total death. It is expected that by 2020, there will be 15 million new cases worldwide each year. In recent years, targeted therapeutic drugs imatinib, crizotinib, osimertinib, etc. have been approved successively, benefiting a large number of patients. These drugs selectively inhibit key protein molecules in tumor cell growth and proliferation processes, such as BCR-ABL, ALK, EGFR, etc., and therefore have the advantages of high efficacy, small side effects, etc.

PIKfyve is a phospholipase that can further phosphorylate phosphatidylinositol-3-phosphate to form phosphatidylinositol-3,5-diphosphate. It can perform multiple regulatory functions in vivo, such as regulating release of exosomes, endocytic pathway, etc. When PIKfyve kinase activity is inhibited, cells exhibit significant vacuolation (EMBO Reports 2008, 9, 164-174). In recent years, more and more studies have shown that PIKfyve also plays an important role in promoting tumor growth and metastasis. For example, PIKfyve is involved in the invasion and migration of tumor cells (J Biol. Chem. 2011; 286, 32105-32114; Biochem. J. 2014, 461, 383-390); in mouse embryonic fibroblasts overexpressing K-Ras$^{G12D}$, inhibition of PIKfyve can inhibit serum protein-dependent cell proliferation (Dev. Cell 2016, 38, 536-547); simultaneous inhibition of PIKfyve and cell surface nutrient transporters can kill LS180, SW480, MDA-MB-231 and other tumor cells (J. Clin. Invest. 2016, 126, 4088-4102); in non-Hodgkin's lymphoma cells, the action of small molecule inhibitors on PIKfyve can effectively kill a variety of such cells, and shows good therapeutic effects in animal models (Blood 2017, 129, 1768-1778); inhibition of PIKfyve can induce methuosis of tumor cells (ACS Omega 2018, 3, 6097-6103). It is expected to be applied to the treatment of refractory tumors that have no targeted drug yet (such as triple negative breast cancer) or are drug resistant. Therefore, PIKfyve has become a new target for tumor treatment, and the development of new PIKfyve inhibitors useful for the treatment of PIKfyve-mediated cancer or other related diseases, as well as refractory tumors, has good application value.

SUMMARY OF INVENTION

After extensive and in-depth research, the inventors of the present invention have designed and synthesized a series of substituted penta-fused hexa-heterocyclic compounds having novel structures, high safety and high activity for PIKfyve kinase, and have studied antitumor activity of this novel type of derivatives.

The present invention provides a compound having the general formula:

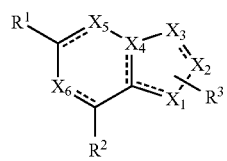

wherein, $X_1$, $X_2$, $X_3$, $X_4$, $X_5$, $X_6$ may comprise a combination of:

I

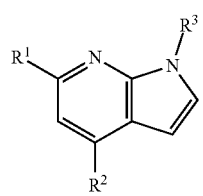

II

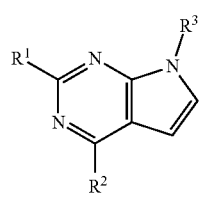

III

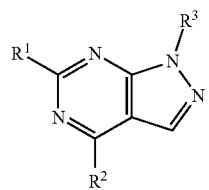

IV

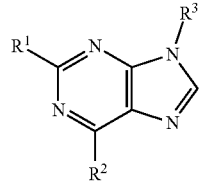

V

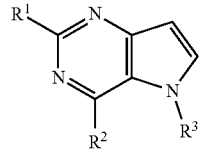

-continued

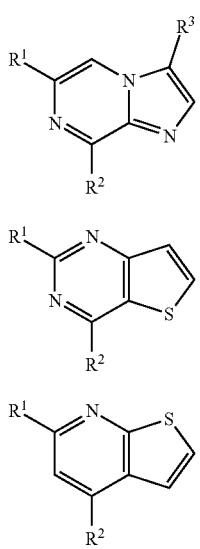

or a stereoisomer thereof, a prodrug thereof, a pharmaceutically acceptable salt thereof or a pharmaceutically acceptable solvate thereof.

The definitions of substituents and symbols are described in detail below.

One object of the present invention is to provide a compound having PIKfyve inhibitory activity, and a stereoisomer thereof, a prodrug thereof, a pharmaceutically acceptable salt thereof or a pharmaceutically acceptable solvate thereof.

Another object of the present invention is to provide a method for the preparation of the above compound.

Another object of the present invention is to provide a pharmaceutical composition comprising the above compound.

Another object of the present invention is to provide use of the above compound and a pharmaceutical composition comprising the above compound in the manufacture of a medicament for preventing or treating PIKfyve-mediated cancer or other related diseases, as well as refractory tumors.

Another object of the present invention is to provide a method of treating cancer, comprising administering to a subject an effective amount of the compound or the composition of the present invention.

SPECIFIC MODES FOR CARRYING OUT THE INVENTION

Figure 1:
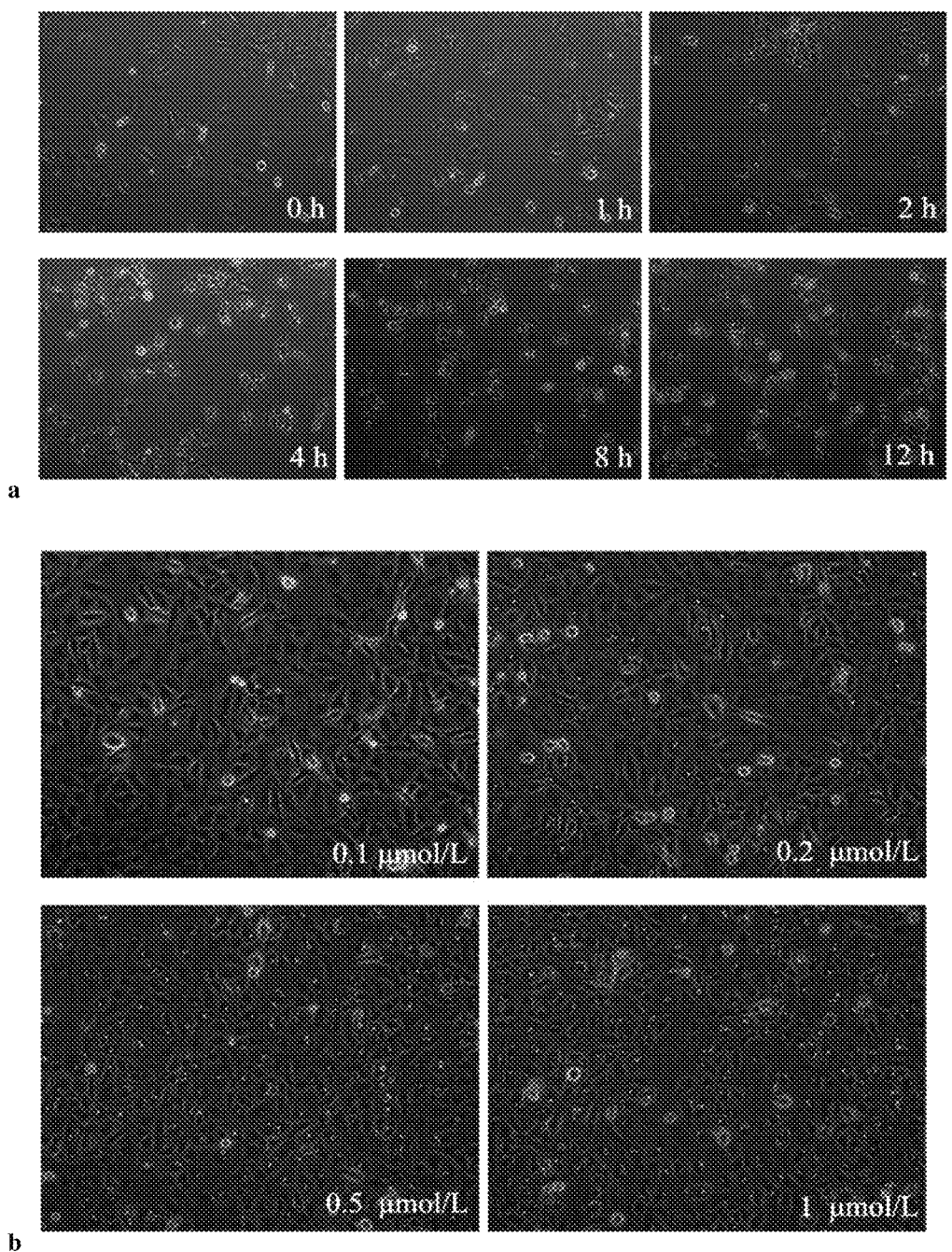
FIG. 1 shows that the compound which inhibits PIKfyve causes vacuolation of cells.
  a. V-c-19 (1 μmol/L) induces vacuolation of MDA-MB-231 cells, with good time dependence.
  b. V-c-19 (1 μmol/L) induces vacuolation of MDA-MB-231 cells, with good concentration dependence.
Figure 2:
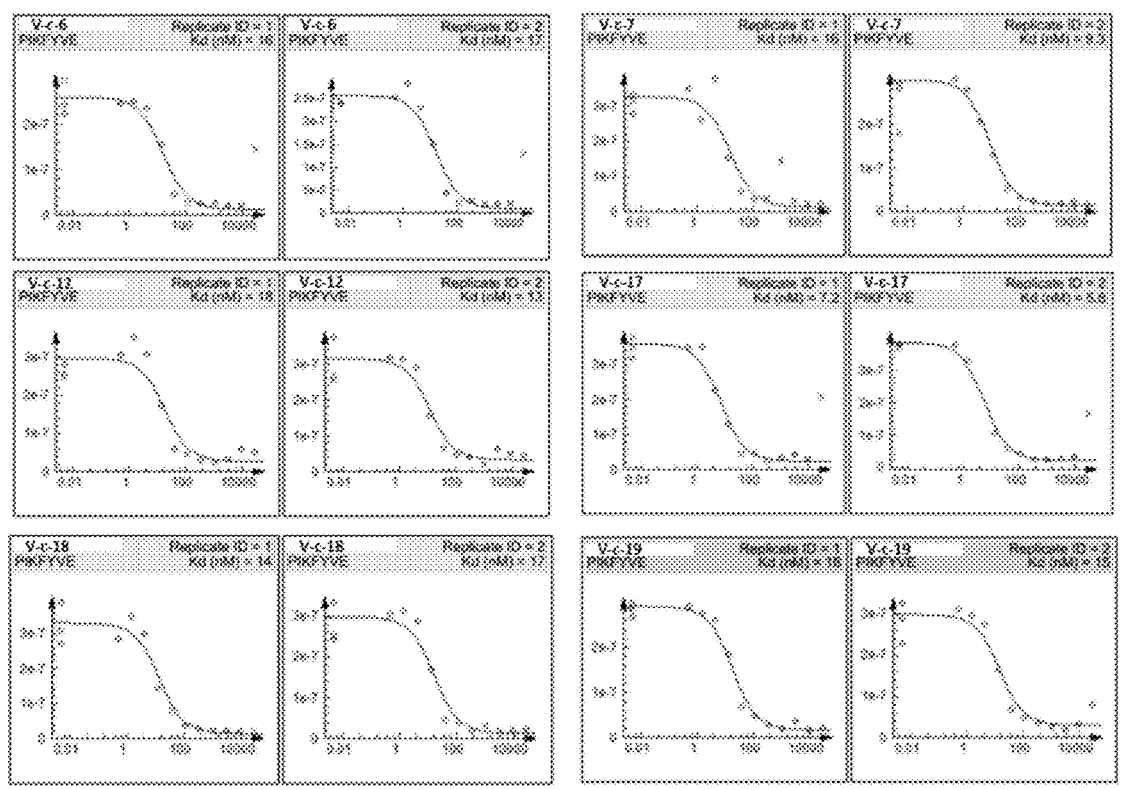
FIG. 2 shows the determination of dissociation equilibrium constant Kd of compound and PIKfyve (replicate 1 and replicate 2 denote 2 replicates tested for each compound).

Various specific embodiments, modes and examples are described herein, including exemplary embodiments and definitions, to understand the claimed invention. While the following detailed description sets forth specific preferred embodiments, those skilled in the art will appreciate that these embodiments are illustrative only, and that the present invention can be practiced in other ways. For the purpose of determining infringement, the scope of the present invention will cover any one or more of the appended claims, including equivalents thereof, and elements or limitations equivalent to those recited.

The present invention is achieved by the following technical solutions.

In one aspect, the present invention provides a compound having the general formula:

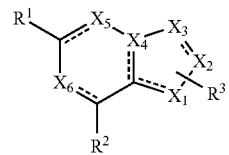

wherein, $X_1$, $X_2$, $X_3$, $X_4$, $X_5$, $X_6$ may comprise a combination of:

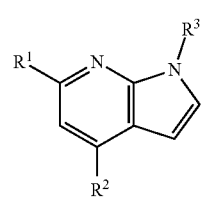

I

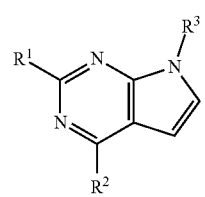

II

-continued

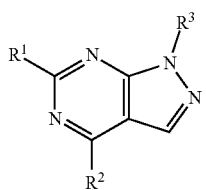
III

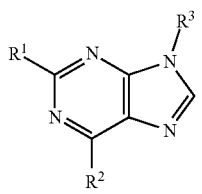
IV

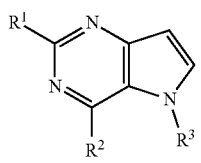
V

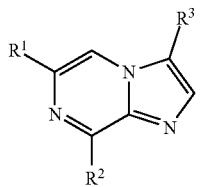
VI

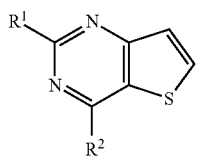
VII

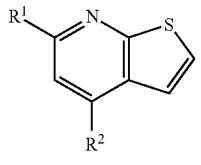
VIII $R^1$, $R^2$ are selected from:

1) substituted or unsubstituted C6-C10 aryl or heteroaryl, the substituent thereof being selected from: halogen atom, C6-C10 aryl, heteroaryl, heterocyclyl, C1-C6 alkyl, C1-C6 alkoxy, C1-C6 oxygen-containing alkyl, C1-C6 fluorine-containing alkyl, C1-C6 fluorine-containing alkoxy, nitro, cyano, amino or hydroxy, wherein the substituent is linked to the C6-C10 aryl or heteroaryl directly or optionally via NHCO, CONH, SO$_2$NH, NHSO$_2$, NHCONH, NHCSNH or CO;

2) substituted or unsubstituted C6-C10 arylamino, heteroarylamino, C1-C6 alkylamino, C3-C7 cycloalkylamino, C1-C6 oxygen-containing alkylamino or C3-C7 oxygen-containing cycloalkylamino, the substituent thereof being selected from: halogen atom, C6-C10 aryl, heteroaryl, heterocyclyl, C1-C6 alkyl, C1-C6 alkoxy, C1-C6 oxygen-containing alkyl, C1-C6 fluorine-containing alkyl, C1-C6 fluorine-containing alkoxy, nitro, cyano, amino or hydroxy, wherein the substituent is optionally linked to the C6-C10 arylamino, heteroarylamino, C1-C6 alkylamino, C3-C7 cycloalkylamino, C1-C6 oxygen-containing alkylamino, or C3-C7 oxygen-containing cycloalkylamino via NHCO, CONH, SO$_2$NH, NHSO$_2$, NHCONH or NHCSNH;

preferably, $R^1$, $R^2$ are selected from:

1) substituted or unsubstituted phenyl, pyridyl, furyl, thienyl, benzofuryl, benzothienyl, benzodioxolyl, imidazolyl, pyrazolyl, thiazolyl, oxazolyl, pyrimidinyl, indolyl or quinolyl, the substituent thereof being selected from halogen atom, C1-C6 alkyl, C1-C6 alkoxy, C1-C6 oxygen-containing alkyl, C1-C6 fluorine-containing alkyl, C1-C6 fluorine-containing alkoxy, nitro, cyano, amino or hydroxy;

2)

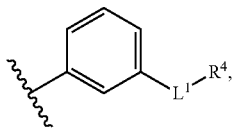

wherein, $L^1$ is selected from NHCO, CONH, SO$_2$NH, NHSO$_2$, NHCONH or NHCSNH, $R^4$ is selected from H, substituted or unsubstituted C6-C10 aryl, heteroaryl, heterocyclyl, C1-C6 alkyl, C1-C6 alkoxy, C1-C6 oxygen-containing alkyl, C1-C6 fluorine-containing alkyl, C1-C6 fluorine-containing alkoxy, nitro, cyano, amino or hydroxy C3-C7 cycloalkyl;

3)

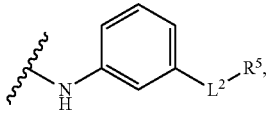

wherein, $L^2$ is selected from NHCO, CONH, SO$_2$NH, NHSO$_2$, NHCONH, NHCSNH or CO, $R^5$ is selected from substituted or unsubstituted C6-C10 aryl, heteroaryl, heterocyclyl, C1-C6 alkyl, C1-C6 alkoxy, C1-C6 oxygen-containing alkyl, C1-C6 fluorine-containing alkyl, C1-C6 fluorine-containing alkoxy, nitro, cyano, amino or hydroxy C3-C7 cycloalkyl;

4)

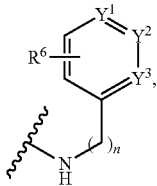

wherein, n=0, 1 or 2;

one of $Y^1$, $Y^2$, $Y^3$ is selected from N;

$R^6$ is selected from H, halogen atom or C1-C6 alkyl;

5) methylamino, ethylamino, propylamino, cyclopropylamino, cyclobutylamino, pyrrolidinyl, piperidyl, morpholinyl, 4-aminopiperidyl, 4-N,N-dimethylaminopiperidyl, 3,5-dimethylmorpholinyl or N-methylpiperazinyl;

$R^3$ is selected from H, halogen, substituted or unsubstituted alkyl or cycloalkyl, the substituent thereof being selected from halogen, amino, hydroxy or alkylsiloxy;

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In the first aspect, according to a specific embodiment of the present invention, the compound, or a stereoisomer thereof, a prodrug thereof, a pharmaceutically acceptable salt thereof or a pharmaceutically acceptable solvate thereof has the following structure:

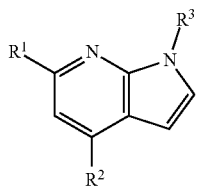

I wherein,
$R^1$ is selected from:
1) optionally substituted heteroaryl, preferably selected from:

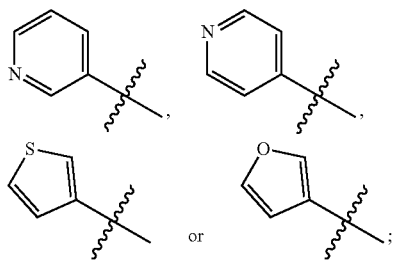

2) optionally substituted C6-C10 aryl, in the case of being substituted, the substituent thereof being C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro or cyano;

preferably

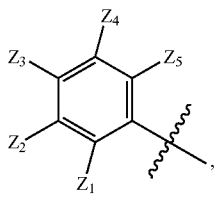

wherein one of $Z_1$, $Z_2$, $Z_3$, $Z_4$, $Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano;

more preferably

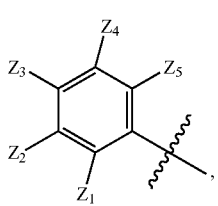

wherein one of $Z_1$, $Z_2$, $Z_3$, $Z_4$, $Z_5$ is selected from the following groups, the rest being H:

H, fluoro, chloro, bromo, amino, hydroxy, C1-C3 alkyl;

most preferably

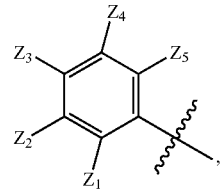

wherein $Z_3$, $Z_2$ or $Z_4$ is selected from the following groups, the rest being H: H, chloro, amino, hydroxy, methyl;

3)

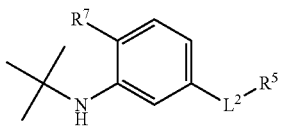

wherein,
$L^2$ is selected from NHCO, CONH, SO$_2$NH, NHSO$_2$, NHCONH or NHCSNH; preferably, $L^2$ is NHCO or CONH; most preferably, $L^2$ is NHCO;

$R^5$ is selected from substituted or unsubstituted C6-C10 aryl, preferably substituted or unsubstituted phenyl;

$R^5$ is preferably

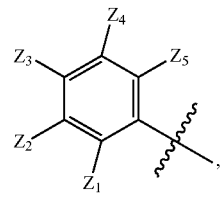

wherein one of $Z_1$, $Z_2$, $Z_3$, $Z_4$, $Z_5$ is selected from the following groups, the rest being H:

H, halogen, amino, hydroxy, C1-C3 fluorine-containing alkyl;

more preferably, $R^5$ is

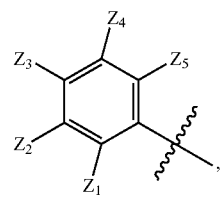

wherein $Z_2$ or $Z_4$ is selected from the following groups, the rest being H: H, chloro, amino, hydroxy, trifluoromethyl;

most preferably, $R^5$ is

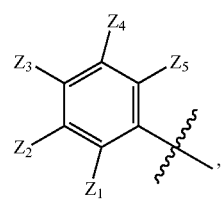

wherein $Z_2$ or $Z_4$ is trifluoromethyl, the rest being H;

R⁷ is selected from H or C1-C6 alkyl; preferably, R⁷ is methyl;

R² is selected from:

1) optionally substituted heteroaryl, preferably selected from:

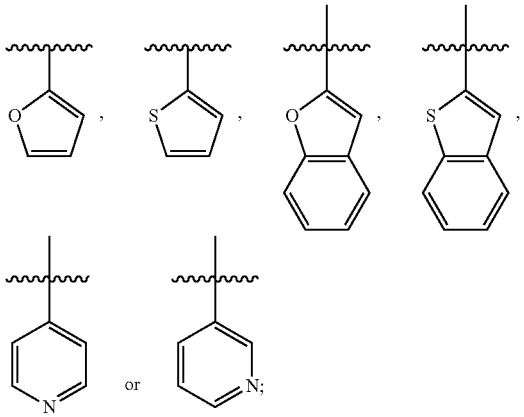

2) optionally substituted C6-C10 aryl, in the case of being substituted, the substituent thereof being C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro or cyano;

preferably

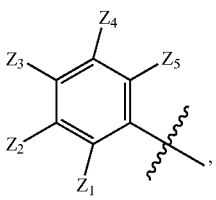

wherein one of $Z_1$, $Z_2$, $Z_3$, $Z_4$, $Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano;

more preferably

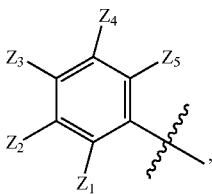

wherein one of $Z_1$, $Z_2$, $Z_3$, $Z_4$, $Z_5$ is selected from the following groups, the rest being H:

H, fluoro, chloro, bromo, amino, hydroxy, C1-C3 alkyl, C1-C3 alkoxy;

most preferably

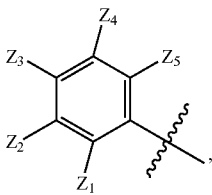

wherein $Z_3$, $Z_2$ or $Z_4$ is selected from the following groups, the rest being H: H, chloro, amino, hydroxy, methyl, methoxy;

3)

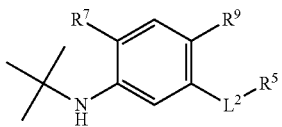

$L^2$ is selected from NHCO, CONH, SO₂NH, NHSO₂, NHCONH, NHCSNH or CO; preferably NHCO, CONH, NHCONH, NHCSNH or CO;

R⁵ is selected from substituted or unsubstituted C6-C10 aryl, heteroaryl, optionally substituted heterocyclyl, C1-C6 alkyl, amino-substituted C1-C6 alkyl, C1-C6 alkoxy, C1-C6 fluorine-containing alkyl, C1-C6 fluorine-containing alkoxy, nitro, cyano, amino or hydroxy C3-C7 cycloalkyl;

preferably, R⁵ is selected from:

when $L^2$ is NHCO, CONH, NHCONH or NHCSNH, R⁵ is

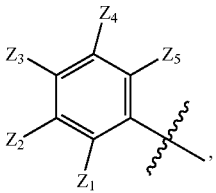

wherein one or two of $Z_1$, $Z_2$, $Z_3$, $Z_4$, $Z_5$ are independently selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano, C1-C6 alkyl substituted by optionally substituted heterocyclyl;

preferably, wherein one or two of $Z_1$, $Z_2$, $Z_3$, $Z_4$, $Z_5$ are independently selected from the following groups, the rest being H: H, chloro, fluoro, methyl, trifluoromethyl, methoxy, trifluoromethoxy,

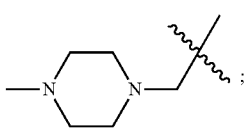 [SMILES: *CN1CCN(C)CC1]

most preferably: $Z_2$ or $Z_4$ is selected from the following groups, the rest being H: H, trifluoromethyl, methoxy, trifluoromethoxy, methyl, chloro, fluoro; or $Z_2$ and $Z_3$ or $Z_2$ and $Z_4$, respectively, are independently selected from trifluoromethyl, chloro or

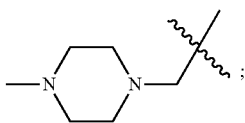 [SMILES: *CN1CCN(C)CC1]

or when $L^2$ is NHCO, Rb further is amino-substituted C1-C6 alkyl, wherein preferably the C1-C6 alkyl is methyl, ethyl or propyl, more preferably the C1-C6 alkyl is methyl; or when $L^2$ is CONH, $R^5$ further is substituted heteroaryl, wherein preferably the substituted heteroaryl is pyrazolyl substituted by multiple C1-C6 alkyl groups; most preferably the substituted heteroaryl is

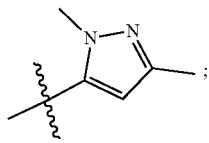 [SMILES: *c1cc(C)nn1C]

or when $L^2$ is CO. $R^5$ further is optionally substituted heterocyclyl, preferably

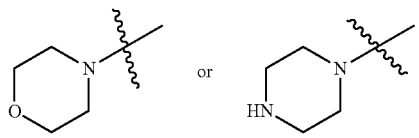 [SMILES: *N1CCOCC1 ; *N1CCNCC1]

optionally substituted by C1-C6 alkyl, wherein preferably the heterocyclyl is

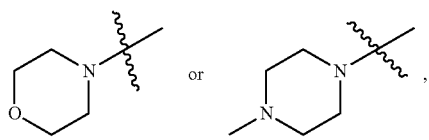

$R^7$ is selected from
1) H, halogen, optionally substituted heterocyclyl;
2) substituted or unsubstituted C1-C6 alkyl, the substituent thereof being optionally substituted heterocyclyl, di-C1-C3 alkyl-substituted amino;
3) di-substituted amino, the substituent thereof being selected from C1-C3 alkyl, di-C1-C3 alkylamino-substituted C1-C3 alkyl;
preferably, $R^7$ is H, methyl, fluoro,

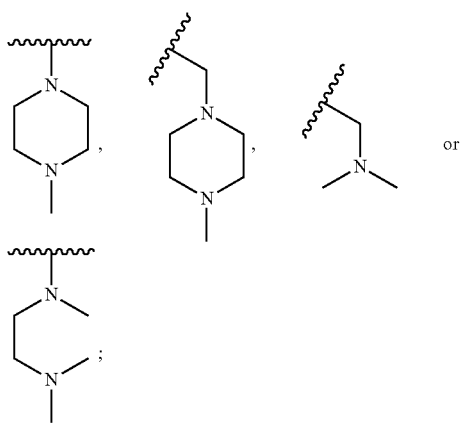

$R^9$ is selected from H or C1-C6 alkoxy; preferably, $R^9$ is H or methoxy;

wherein, when $R^7$ and $R^9$ both are non-hydrogen groups, they don't exist at the same time;

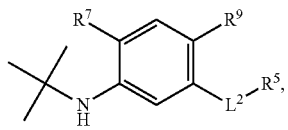

in its entirety, is most preferably selected from:

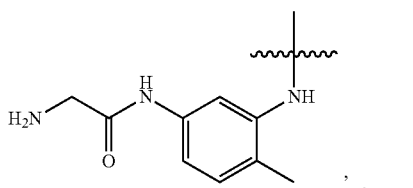

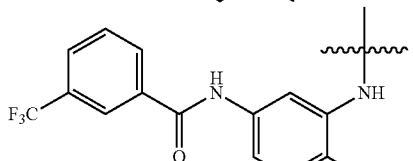

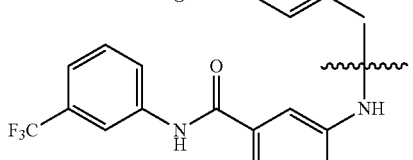

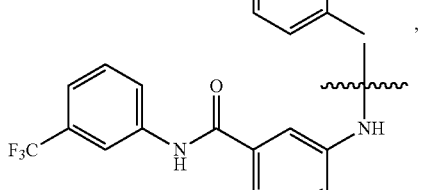

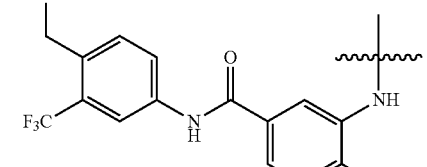

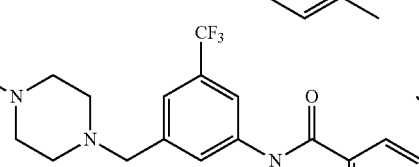

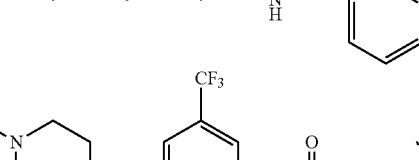

13
-continued
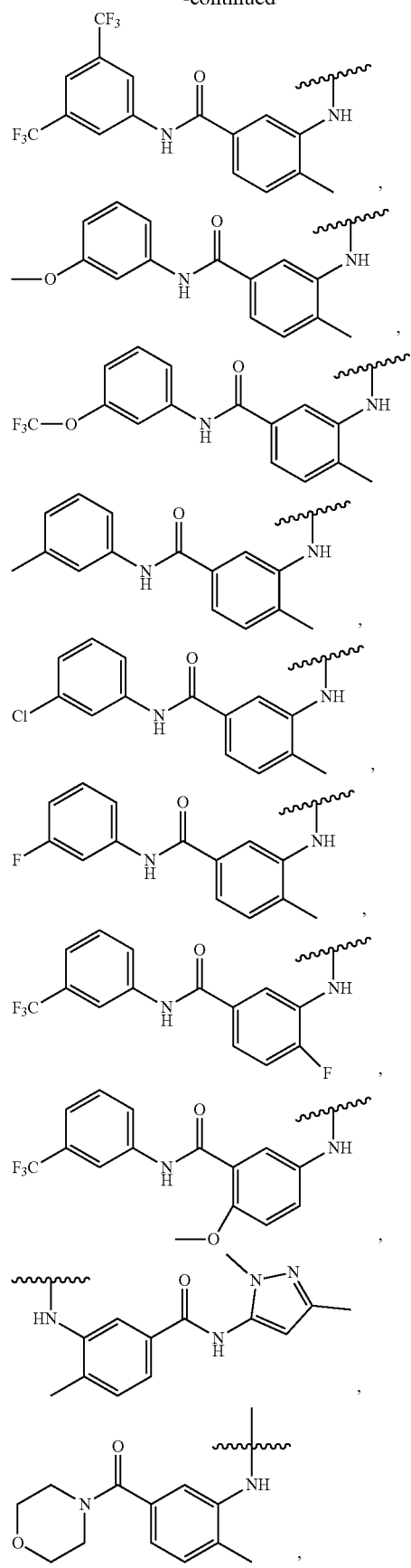
14
-continued
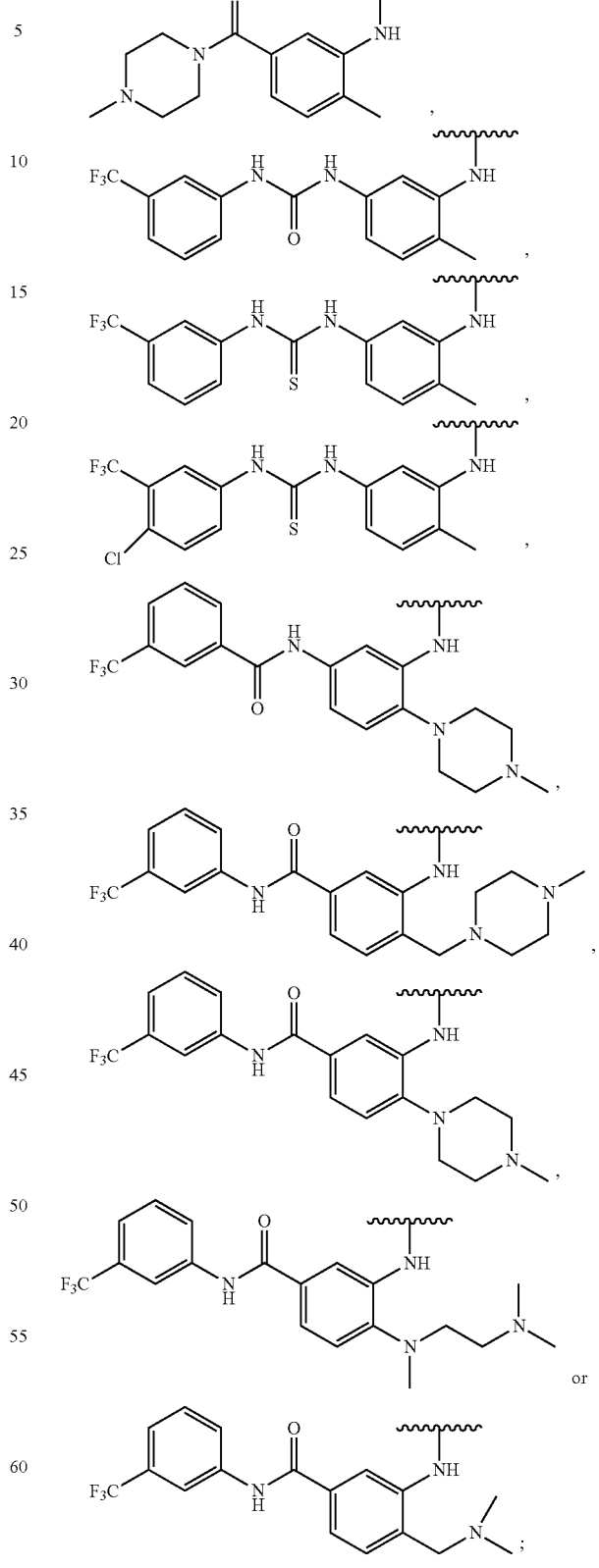
$R^3$ is selected from: —H or C1-C6 alkyl; preferably selected from: —H or —CH$_3$.

In the second aspect, according to a specific embodiment of the present invention, the compound, or a stereoisomer thereof, a prodrug thereof, a pharmaceutically acceptable salt thereof or a pharmaceutically acceptable solvate thereof has the following structure:

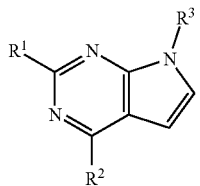

II wherein,
$R^1$ is selected from: optionally substituted heteroaryl, preferably selected from:

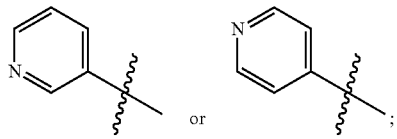 [SMILES: *c1cccnc1 ; *c1ccncc1]

$R^2$ is selected from:

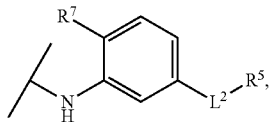

wherein,
$L^2$ is selected from NHCO, CONH, $SO_2NH$, $NHSO_2$, NHCONH or NHCSNH; preferably, $L^2$ is NHCO or CONH;
$R^5$ is selected from substituted or unsubstituted C6-C10 aryl, preferably substituted or unsubstituted phenyl;
$R^5$ is preferably

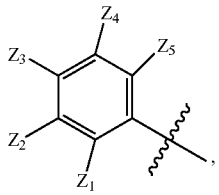

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C6 alkyl substituted by optionally substituted heterocyclyl;
most preferably, $R^5$ is

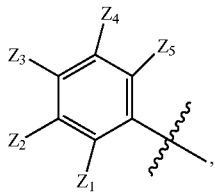

wherein $Z_2$ or $Z_4$ is selected from the following groups, the rest being H: H, trifluoromethyl; or $Z_2$ and $Z_3$ are independently selected from the following groups, the rest being H: trifluoromethyl,

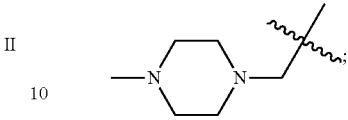

$R^7$ is selected from H or C1-C6 alkyl; preferably, $R^7$ is methyl;

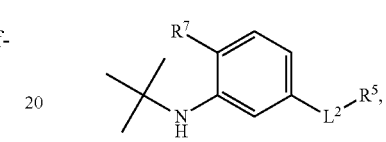

in its entirety, is most preferably selected from:

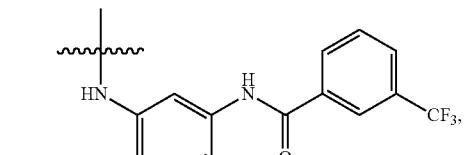

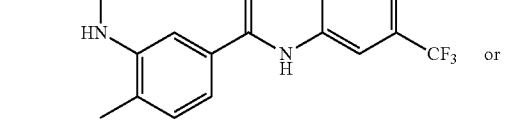

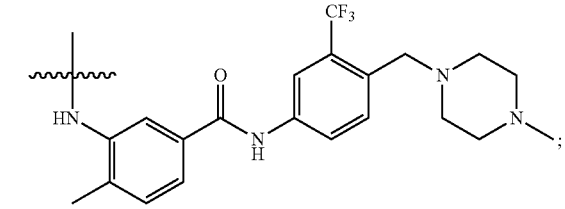

$R^3$ is selected from: —H or C1-C6 alkyl; preferably selected from: —H or —$CH_3$.

In the third aspect, according to a specific embodiment of the present invention, the compound, or a stereoisomer thereof, a prodrug thereof, a pharmaceutically acceptable salt thereof or a pharmaceutically acceptable solvate thereof has the following structure:

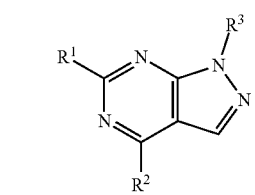

III wherein, $R^1$ is selected from:

1) optionally substituted heteroaryl, preferably selected from:

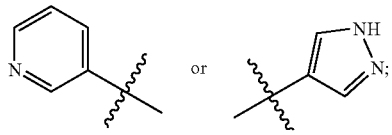 [SMILES: *c1cccnc1 ; *c1cn[nH]c1]

2) optionally substituted C6-C10 aryl, in the case of being substituted, the substituent thereof being C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro or cyano;

preferably

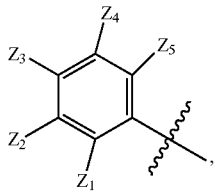

wherein one of $Z_1$, $Z_2$, $Z_3$, $Z_4$, $Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro or cyano;

more preferably

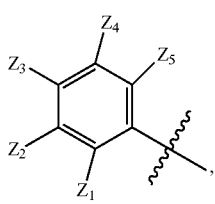

wherein one of $Z_1$, $Z_2$, $Z_3$, $Z_4$, $Z_5$ is selected from the following groups, the rest being H:

H, fluoro, chloro, bromo, amino, hydroxy;

most preferably

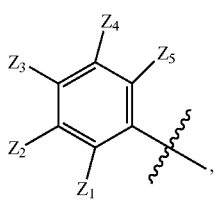

wherein $Z_3$, $Z_2$ or $Z_4$ is selected from the following groups, the rest being H: H, chloro, amino, hydroxy;

3)

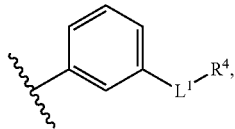

wherein, $L^1$ is selected from NHCO, CONH, $SO_2NH$, $NHSO_2$, NHCONH or NHCSNH; $L^1$ preferably NHCONH or NHCSNH, $R^4$ is selected from H or substituted or unsubstituted C6-C10 aryl, preferably substituted or unsubstituted phenyl;

$R^4$ is preferably

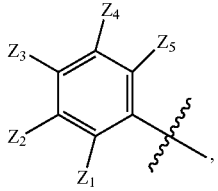

wherein one or two of $Z_1$, $Z_2$, $Z_3$, $Z_4$, $Z_5$ are independently selected from the following groups, the rest being H: halogen, amino, hydroxy, C1-C3 fluorine-containing alkyl;

more preferably, $R^4$ is

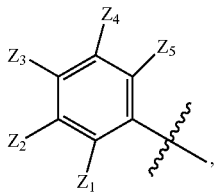

wherein $Z_2$ or $Z_4$ is selected from the following groups, the rest being H: H, chloro, amino, hydroxy, trifluoromethyl; or $Z_2$ and $Z_4$ are independently selected from the following groups, the rest being H: bromo, methoxy, amino, hydroxy;

most preferably, $R^4$ is

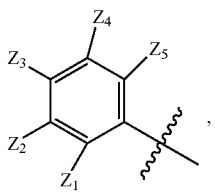

wherein $Z_2$ or $Z_4$ is trifluoromethyl, the rest being H; or $Z_2$ and $Z_4$ are independently selected from the following groups, the rest being H: bromo, methoxy;

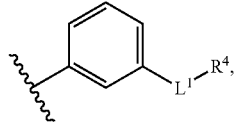

in its entirety, is most preferably selected from:

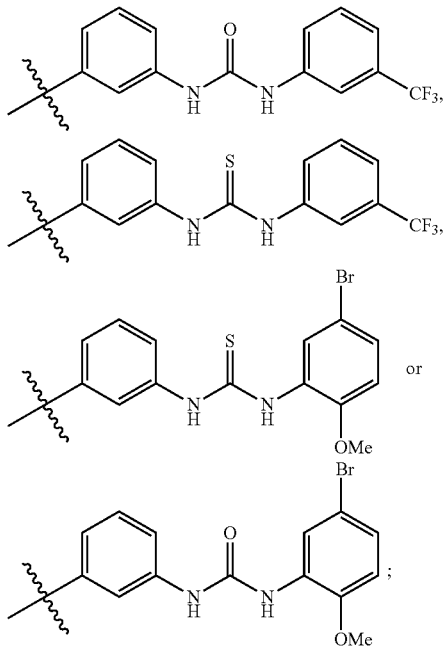

4)

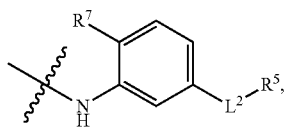

wherein,
L² is selected from NHCO, CONH, SO₂NH, NHSO₂, NHCONH or NHCSNH; preferably, L² is NHCO or CONH; most preferably, L² is CONH;
R⁵ is selected from substituted or unsubstituted C6-C10 aryl, preferably substituted or unsubstituted phenyl;
R⁵ is preferably

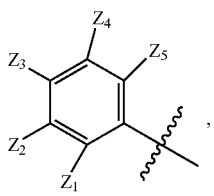

wherein one of $Z_1$, $Z_2$, $Z_3$, $Z_4$, $Z_5$ is selected from the following groups, the rest being H:
H, halogen, amino, hydroxy, C1-C3 fluorine-containing alkyl;
more preferably, R⁵ is

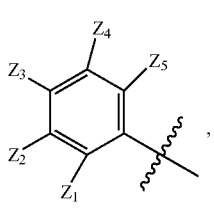

wherein $Z_2$ or $Z_4$ is selected from the following groups, the rest being H: H, chloro, amino, hydroxy, trifluoromethyl;

most preferably, R⁵ is

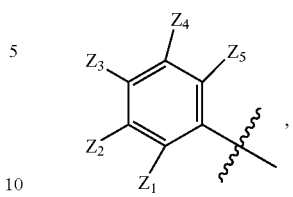

wherein $Z_2$ or $Z_4$ is trifluoromethyl, the rest being H;
R⁷ is selected from H or C1-C6 alkyl; preferably, R⁷ is methyl; R² is selected from:
1)

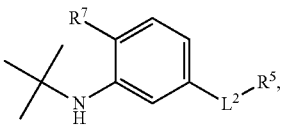

wherein,
L² is selected from NHCO, CONH, SO₂NH, NHSO₂, NHCONH or NHCSNH; preferably, L² is NHCO or CONH;
R⁵ is selected from substituted or unsubstituted C6-C10 aryl, preferably substituted or unsubstituted phenyl;
R⁵ is preferably

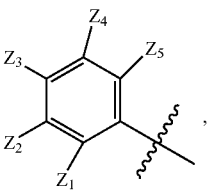

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C6 alkyl substituted by optionally substituted heterocyclyl;
more preferably, R⁵ is

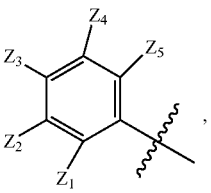

wherein, $Z_2$ or $Z_4$ is selected from the following groups, the rest being H: H, trifluoromethyl, trifluoromethoxy, methyl, methoxy; or $Z_2$ and $Z_3$ or $Z_2$ and $Z_4$, respectively, are independently selected from the following groups, the rest being H: trifluoromethyl,

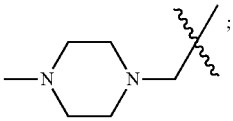 [SMILES: *CN1CCN(C)CC1]

most preferably, R⁵ is

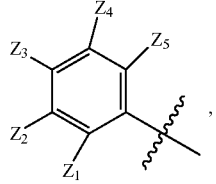, wherein, $Z_2$ or $Z_4$ is trifluoromethyl, the rest being H; or $Z_2$ and $Z_3$ or $Z_2$ and $Z_4$, respectively, are independently selected from the following groups, the rest being H: trifluoromethyl,

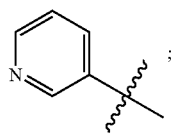 [SMILES: *c1cccnc1];

R⁷ is selected from H or C1-C6 alkyl; preferably, R⁷ is methyl;

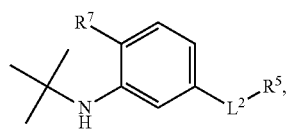

in its entirety, is most preferably selected from:

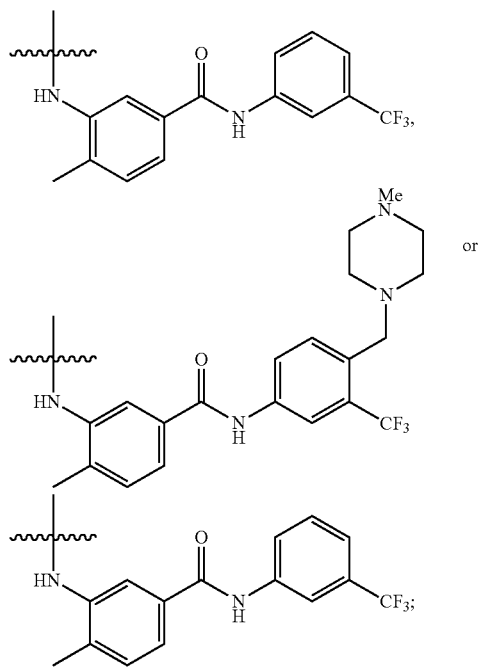

2) amino optionally substituted by heteroaryl-C1-C6 alkyl; preferably amino substituted by pyridyl-methyl; most preferably

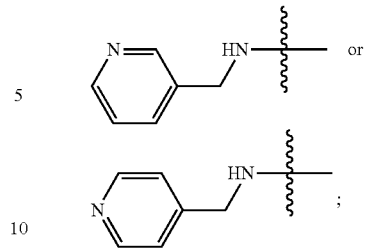

3) optionally substituted heteroaryl, preferably selected from:

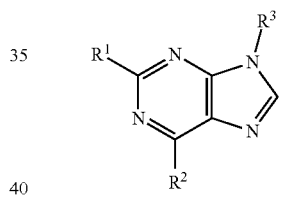

R³ is selected from: —H or C1-C6 alkyl; preferably selected from: —H or —CH₃.

In the fourth aspect, according to a specific embodiment of the present invention, the compound, or a stereoisomer thereof, a prodrug thereof, a pharmaceutically acceptable salt thereof or a pharmaceutically acceptable solvate thereof has the following structure:

IV

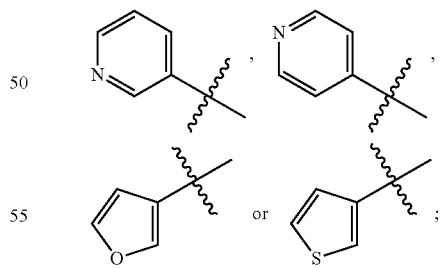

wherein,

R¹ is selected from: optionally substituted heteroaryl, preferably selected from:

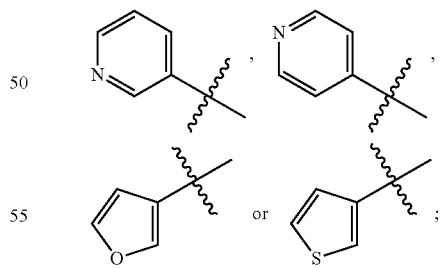

R² is selected from:

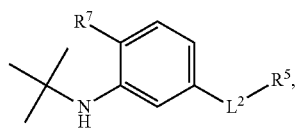

wherein,

L² is selected from NHCO, CONH, SO₂NH, NHSO₂, NHCONH or NHCSNH; preferably, L² is NHCO or CONH;

R⁵ is selected from substituted or unsubstituted C6-C10 aryl, preferably substituted or unsubstituted phenyl;

R⁵ is preferably

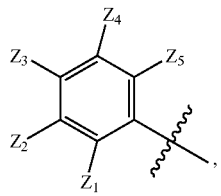

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C3 fluorine-containing alkoxy, C1-C6 alkyl substituted by optionally substituted heterocyclyl;

most preferably, R⁵ is

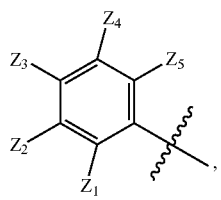

wherein $Z_2$ or $Z_4$ is selected from the following groups, the rest being H: H, trifluoromethyl, trifluoromethoxy; or $Z_2$ and $Z_3$ are independently selected from the following groups, the rest being H: trifluoromethyl,

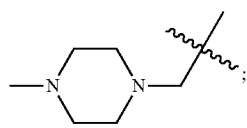 [SMILES: *CN1CCN(C)CC1]

R⁷ is selected from H or C1-C6 alkyl; preferably, R⁷ is methyl;

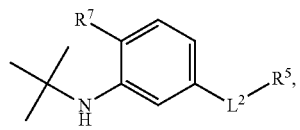

in its entirety, is most preferably selected from:

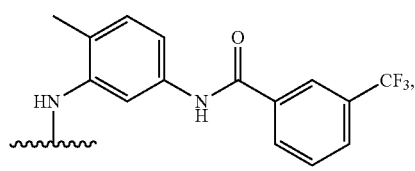 [SMILES: *Nc1cc(NC(=O)c2cccc(C(F)(F)F)c2)ccc1C]

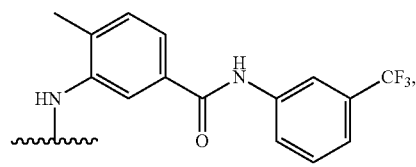

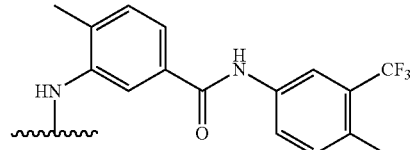

or

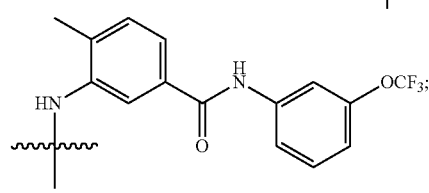

R³ is selected from: —H or C1-C6 alkyl; preferably selected from: —H or —CH₃.

In the fifth aspect, according to a specific embodiment of the present invention, the compound, or a stereoisomer thereof, a prodrug thereof, a pharmaceutically acceptable salt thereof or a pharmaceutically acceptable solvate thereof has the following structure:

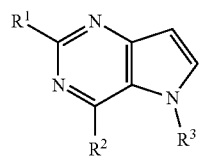

V wherein,

R¹ is selected from:
1) optionally substituted heteroaryl, preferably selected from:

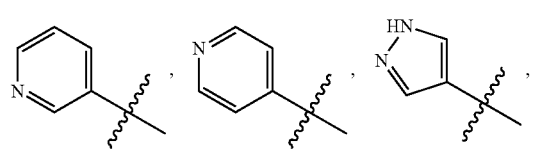

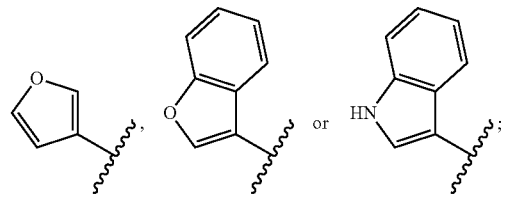

2) optionally substituted C6-C10 aryl, in the case of being substituted, the substituent thereof being C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano, HOOC— or C1-C6 alkoxyformyl;

preferably

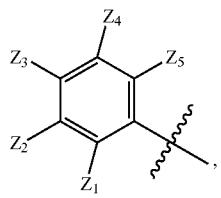

wherein one of $Z_1$, $Z_2$, $Z_3$, $Z_4$, $Z_5$ is selected from the following groups, the rest being H: H, C1-C6 alkyl, C1-C3 alkoxy, C1-C3 fluorine-containing alkyl, C1-C3 fluorine-containing alkoxy, halogen, amino, hydroxy, HOOC—, C1-C6 alkoxyformyl;

more preferably

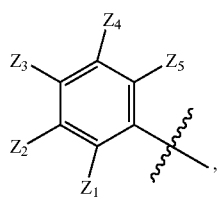

wherein one of $Z_1$, $Z_2$, $Z_3$, $Z_4$, $Z_5$ is selected from the following groups, the rest being H:

H, fluoro, chloro, amino, hydroxy, C1-C3 alkyl, HOOC—, ethoxyformyl (EtOOC—);

most preferably

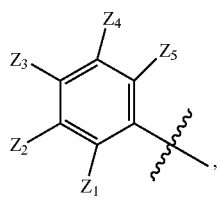

wherein $Z_3$, $Z_2$ or $Z_4$ is selected from the following groups, the rest being H: H, chloro, amino, hydroxy, HOOC—, ethoxyformyl (EtOOC—):

3)

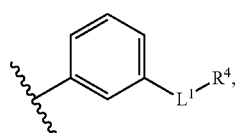

wherein, $L^1$ is selected from NHCO, CONH, $SO_2NH$, $NHSO_2$, NHCONH or NHCSNH; preferably, $L^1$ is NHCO, CONH, NHCONH or NHCSNH;

$R^4$ is selected from H, substituted or unsubstituted C6-C10 aryl, preferably substituted or unsubstituted phenyl, or substituted or unsubstituted heteroaryl, preferably substituted or unsubstituted pyridyl;

$R^4$ is preferably

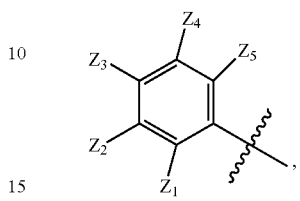

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C3 alkoxy;

most preferably, $R^4$ is

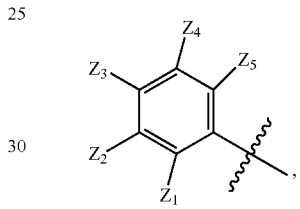

wherein $Z_2$ or $Z_4$ or $Z_3$ is selected from the following groups, the rest being H: H, chloro, amino, trifluoromethyl; or $Z_1$ and $Z_4$ are independently selected from the following groups, the rest being H: bromo, methoxy; or $R^4$ is preferably

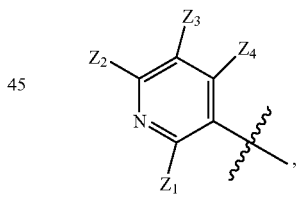

wherein one of $Z_1$, $Z_2$, $Z_3$, $Z_4$ is selected from the following groups, the rest being H: H, halogen, amino, hydroxy; more preferably, $R^4$ is

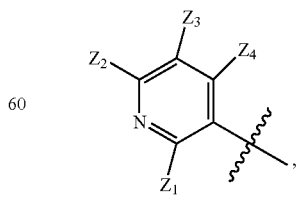

wherein $Z_2$ is selected from the following groups, the rest being H: H, chloro, amino, hydroxy; most preferably, $R^4$ is

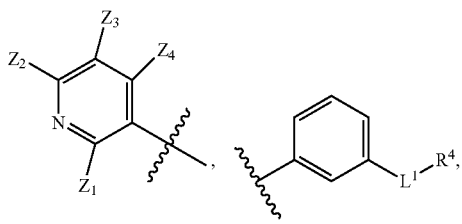

wherein $Z_9$ is amino, the rest being H;
in its entirety, is most preferably selected from:

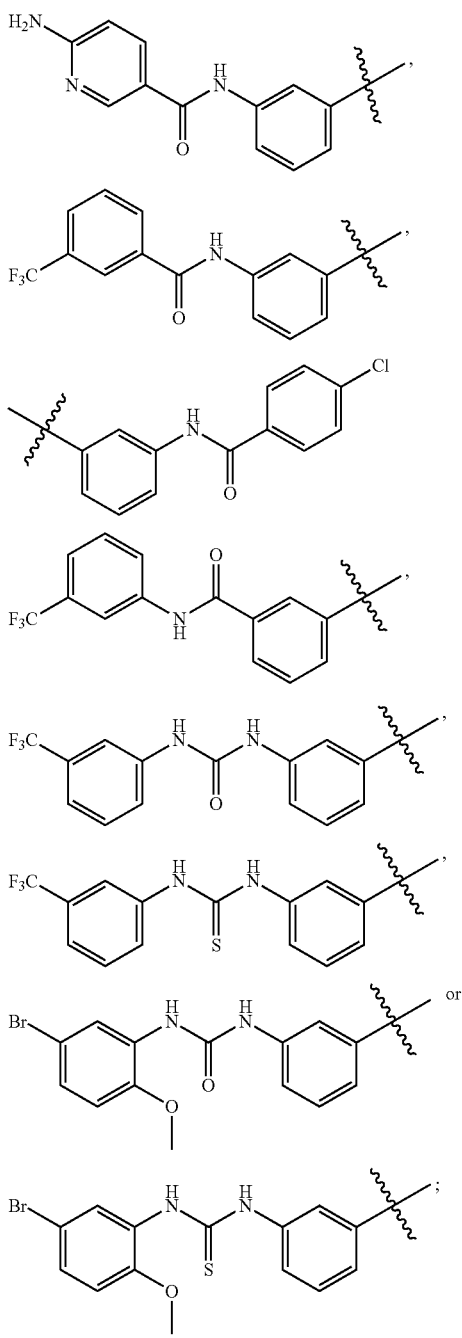

4)

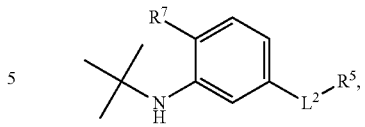

wherein,
$L^2$ is selected from NHCO, CONH, SO$_2$NH, NHSO$_2$, NHCONH or NHCSNH;
preferably, $L^2$ is selected from NHCO, CONH, NHSO$_2$, NHCONH or NHCSNH;
$R^5$ is selected from substituted or unsubstituted C6-C10 aryl, preferably substituted or unsubstituted phenyl;
$R^5$ is preferably

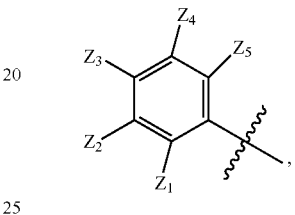

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C3 alkoxy, C1-C6 amido, C1-C6 alkylsulfamido, C1-C3 fluorine-containing alkoxy, nitro, cyano, C1-C6 alkyl substituted by optionally substituted heterocyclyl, optionally substituted heteroaryl;
$R^5$ is more preferably

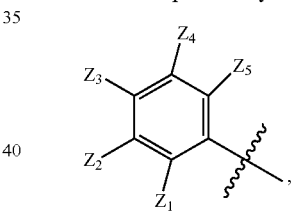

wherein one or two of $Z_1$, $Z_2$, $Z_3$, $Z_4$, $Z_5$ are independently selected from the following groups, the rest being H: H, fluoro, chloro, trifluoromethyl, trifluoromethoxy, nitro, cyano, methoxy, acetamido (—NHAc), amino, methylsulfonylamino (—NHMs),

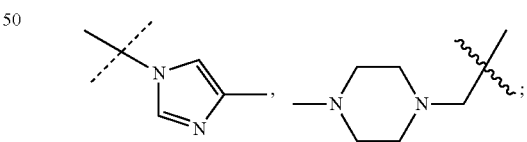

most preferably, $R^5$ is

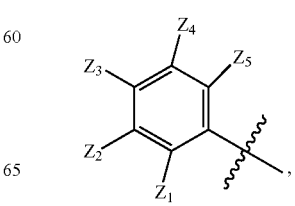

wherein, $Z_2$ or $Z_4$ is H or —$OCF_3$; or $Z_3$ is H, —$NO_2$, —CN or —OMe; or $Z_2$ or one of $Z_4$, $Z_3$ is H, —$CF_3$ or —NHAc; or one of $Z_1$ and $Z_5$, or one of $Z_2$ and $Z_4$, or $Z_3$ is H, —$NH_2$ or —NHMs; or $Z_2$ and $Z_4$ are independently selected from —$CF_3$ or

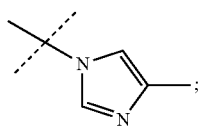

or $Z_2$ and $Z_3$ are independently selected from —$CF_3$ or

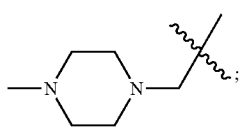 [SMILES: *CN1CCN(C)CC1]

or $Z_1$ and $Z_4$ are independently selected from —$CF_3$, —OMe, —F or —Cl; the rest being H;

$R^7$ is selected from

1) H, optionally substituted heterocyclyl, C1-C6 alkoxy;

2) substituted or unsubstituted C1-C6 alkyl, the substituent thereof being optionally substituted heterocyclyl, di-C1-C3 alkyl-substituted amino;

3) di-substituted amino, the substituent thereof being selected from C1-C3 alkyl, di-C1-C3 alkylamino-substituted C1-C3 alkyl;

preferably, $R^7$ is H, methyl, methoxy,

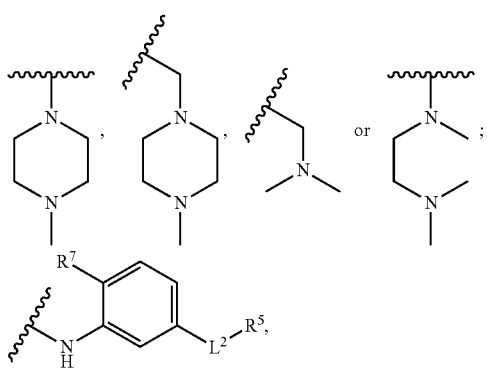

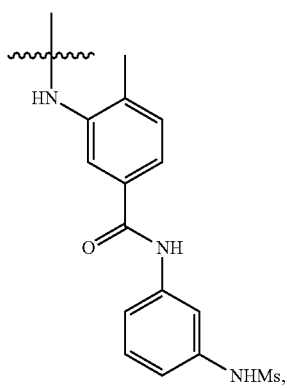

in its entirety, is most preferably selected from:

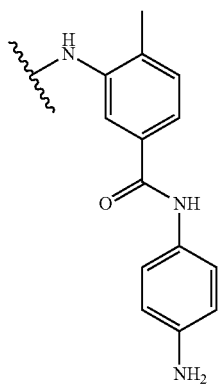

-continued

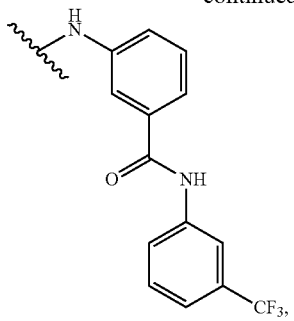

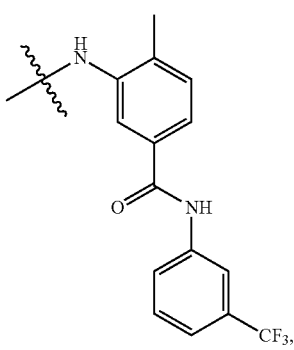

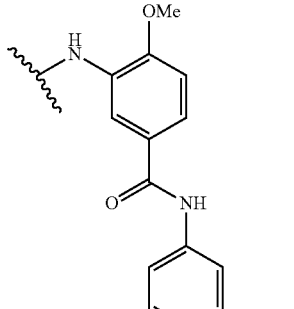

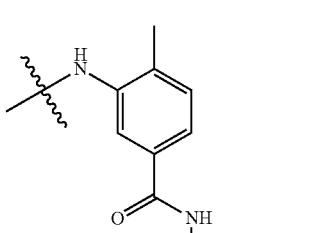

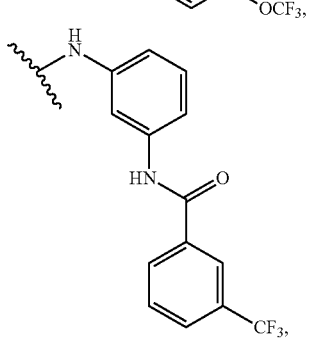

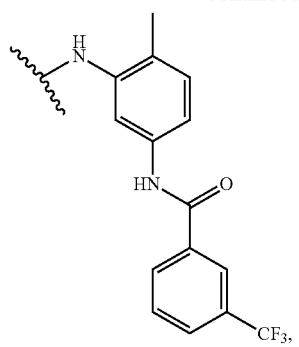
,
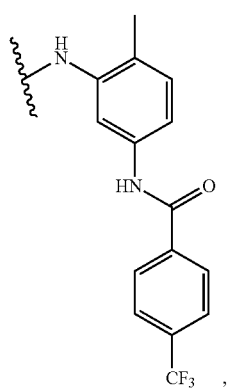
,
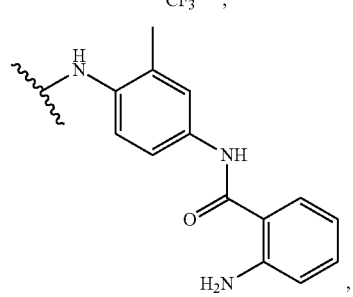
,
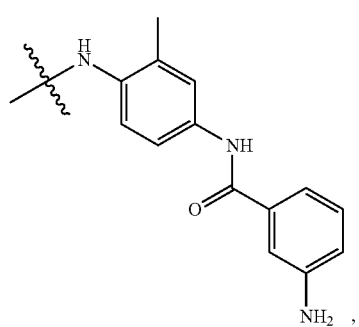
,
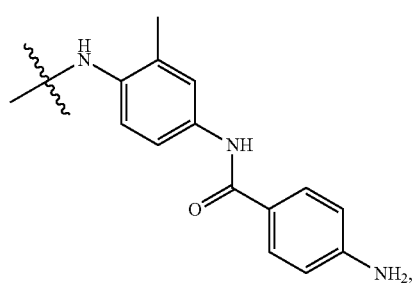
,
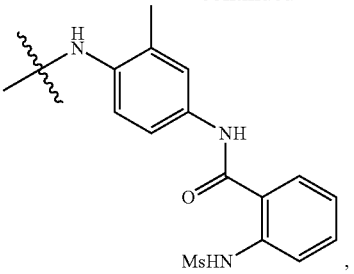
,
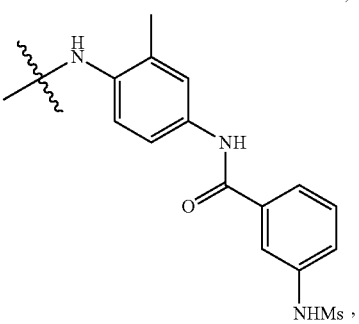
,
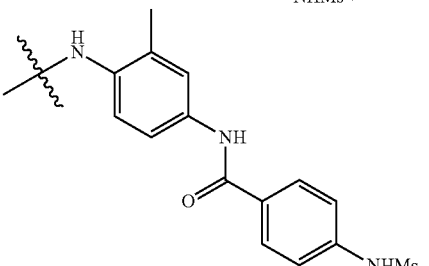
,
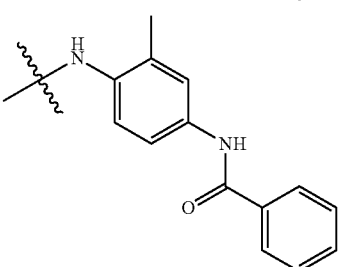
,
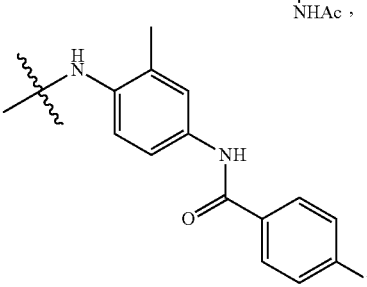
,
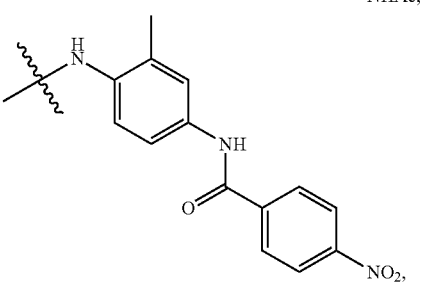
,

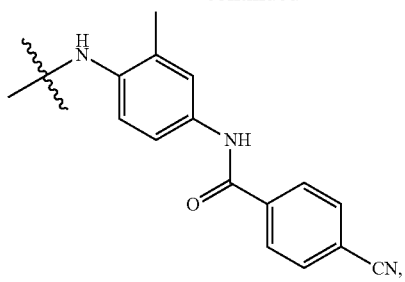
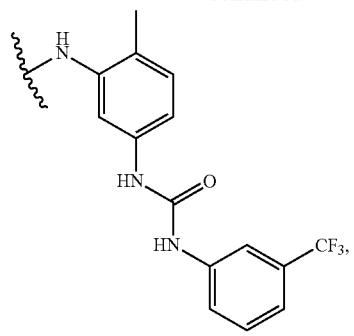
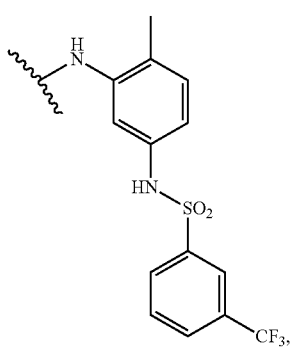
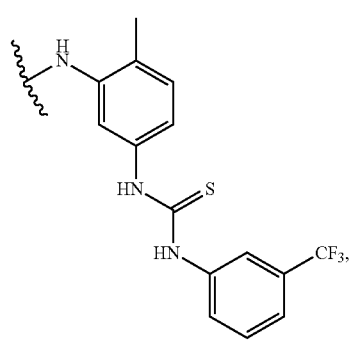
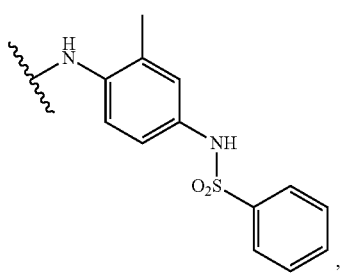
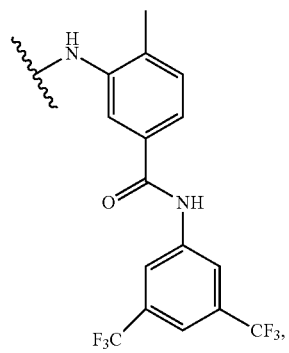
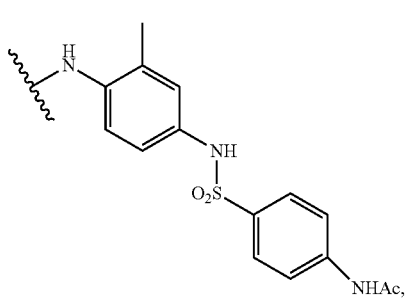
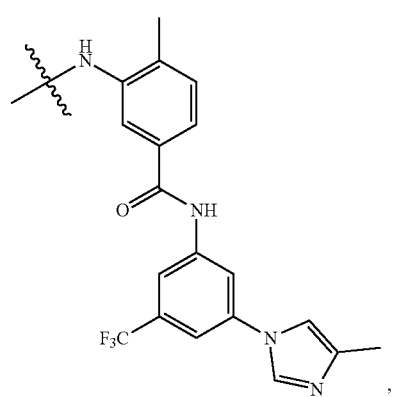
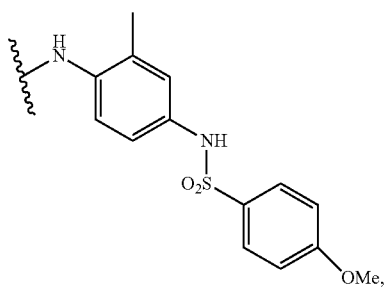

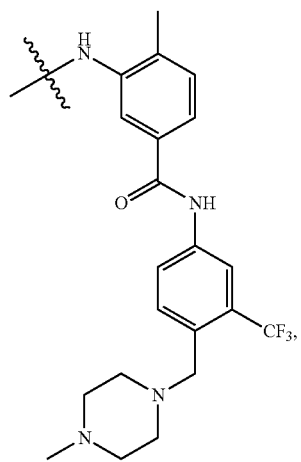
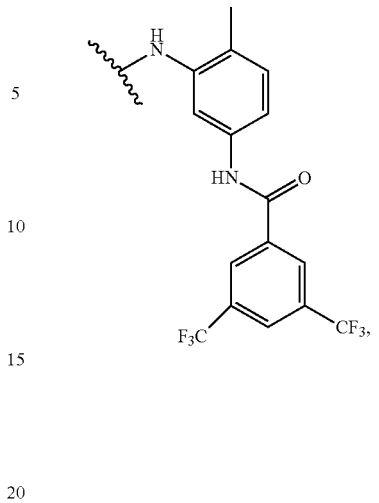
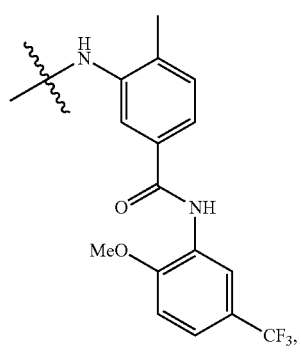
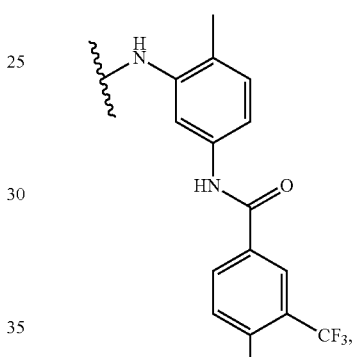
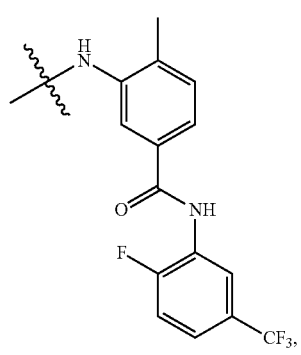
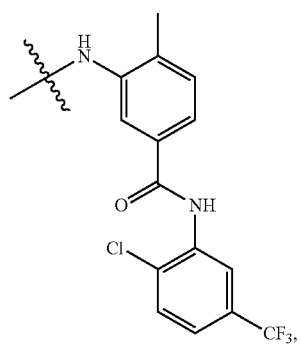
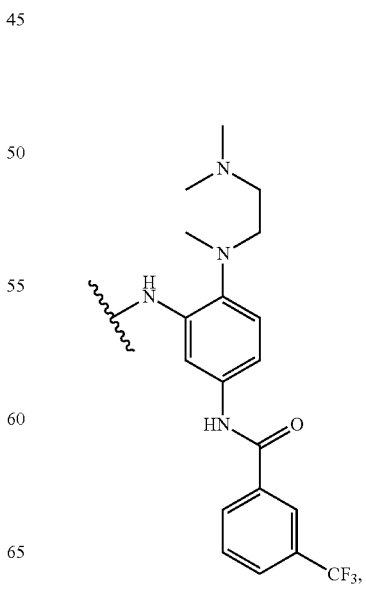

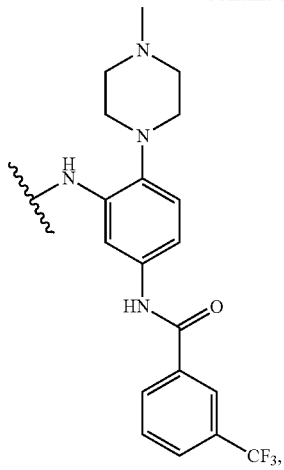

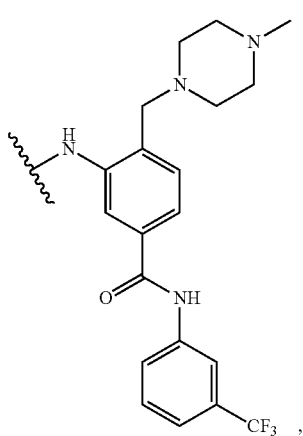

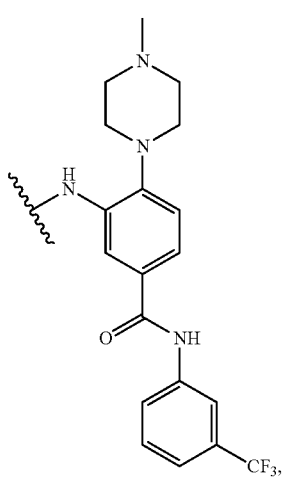 [SMILES: *Nc1cc(C(=O)Nc2cccc(C(F)(F)F)c2)ccc1N(C)CCN(C)C]

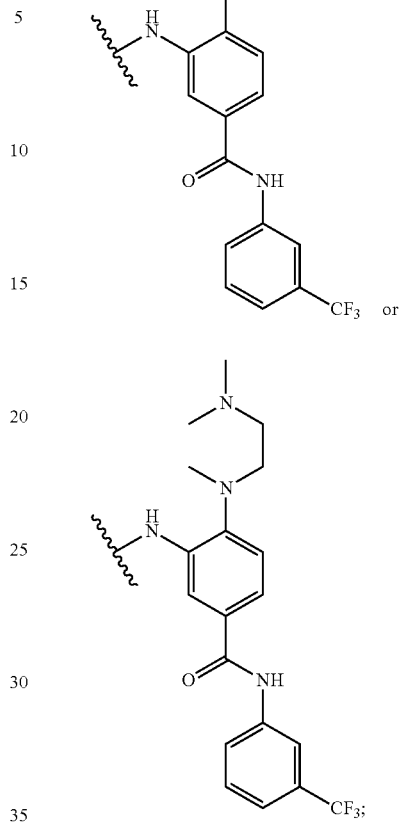

5) amino substituted by optionally substituted phenyl, preferably amino substituted by unsubstituted phenyl or amino substituted by the following substituted phenyl: phenyl mono-substituted by methylsulfonylamino, phenyl di-substituted by heterocyclyl;

most preferably selected from:

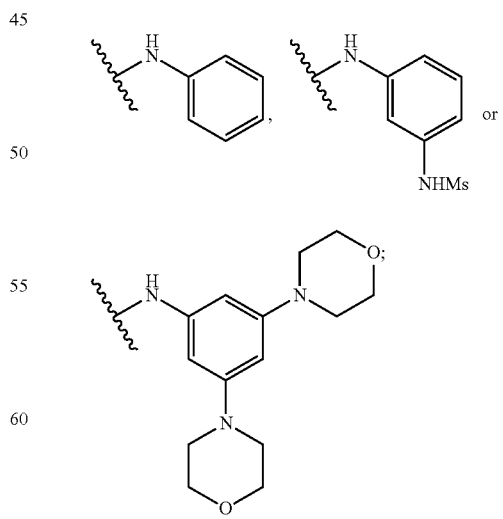

6) heteroaryl-substituted amino, preferably pyridylamino, most preferably:

7) C3-C6 cycloalkylamino, preferably

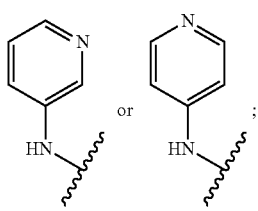 [SMILES: *Nc1cccnc1 ; *Nc1ccncc1]

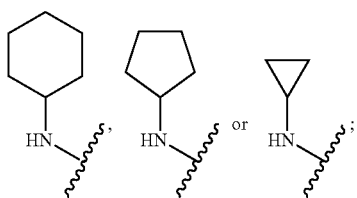

8) optionally substituted heterocyclyl, preferably

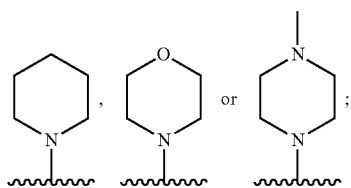

R² is selected from:
1) optionally substituted heteroaryl,
preferably selected from:

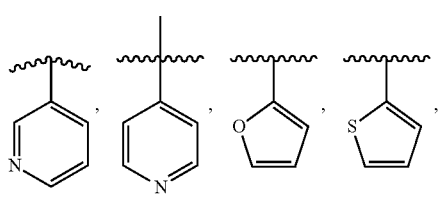

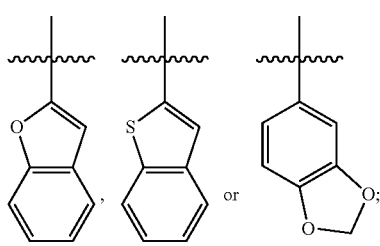

2) optionally substituted C6-C10 aryl, in the case of being substituted, the substituent thereof being C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano or C1-C6 alkylsulfonyl;

preferably

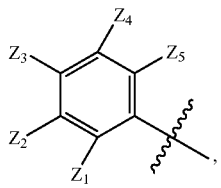

wherein one of $Z_1$, $Z_2$, $Z_3$, $Z_4$, $Z_5$ is selected from the following groups, the rest being H: H, C1-C6 alkyl, C1-C3 alkoxy, C1-C3 fluorine-containing alkyl, C1-C3 fluorine-containing alkoxy, halogen, amino, hydroxy, nitro, cyano, C1-C3 alkylsulfonyl;
more preferably

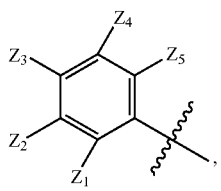

wherein one of $Z_1$, $Z_2$, $Z_3$, $Z_4$, $Z_5$ is selected from the following groups, the rest being H: H, fluoro, chloro, bromo, amino, hydroxy, C1-C3 alkoxy, C1-C3 alkylsulfonyl;
most preferably

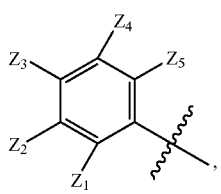

wherein $Z_3$ is selected from the following groups, the rest being H: H, fluoro, chloro, methoxy, methylsulfonyl (-Ms);
3)

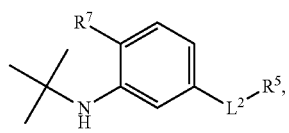

wherein,
L² is selected from NHCO, CONH, SO₂NH, NHSO₂, NHCONH, NHCSNH; preferably, L² is NHCO, CONH, NHSO₂, NHCONH, NHCSNH;
R⁵ is selected from substituted or unsubstituted C6-C10 aryl, preferably substituted or unsubstituted phenyl;
R⁵ is preferably

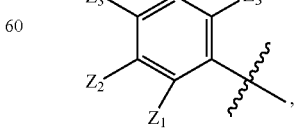

wherein one or two of $Z_1$, $Z_2$, $Z_3$, $Z_4$, $Z_5$ are independently selected from the following groups, the rest being H: H, halogen, amino, di-C1-C3 alkyl-substituted amino, hydroxy, C1-C3 alkyl, C1-C3 alkoxy, C1-C3 fluorine-containing alkyl, C1-C3 fluorine-containing alkoxy, optionally substituted heteroaryl, C1-C6 alkyl substituted by optionally substituted heterocyclyl;

$R^5$ is more preferably

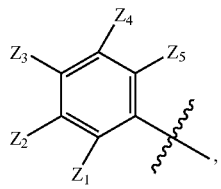

wherein one or two of $Z_1$, $Z_2$, $Z_3$, $Z_4$, $Z_5$ are independently selected from the following groups, the rest being H: H, fluoro, chloro, bromo, amino, di-C1-C3 alkyl-substituted amino, hydroxy, trifluoromethyl, trifluoromethoxy, C1-C6 alkyl-substituted

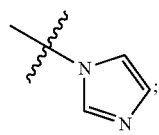 [SMILES: *n1ccnc1]

C1-C6 alkyl, C1-C3 alkyl or C1-C3 alkoxy substituted by heterocyclyl that is optionally substituted by C1-C6 alkyl; most preferably, $R^5$ is

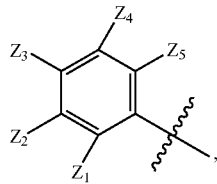

wherein, $Z_2$ or $Z_4$ is selected from the following groups, the rest being H: H, fluoro, chloro, bromo, trifluoromethyl, methyl, methoxy, amino, dimethylamino, trifluoromethoxy, hydroxy; or $Z_2$ and $Z_3$ or $Z_2$ and $Z_4$, respectively, are independently selected from the following groups, the rest being H: trifluoromethyl,

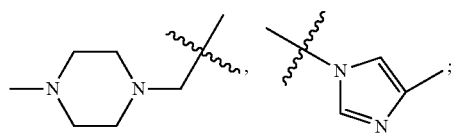

$R^7$ is selected from H or C1-C6 alkyl; preferably, $R^7$ is H or methyl;

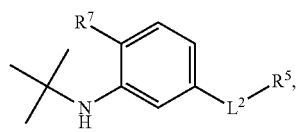

in its entirety, is most preferably selected from:

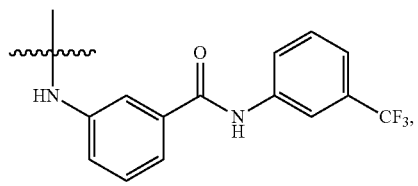

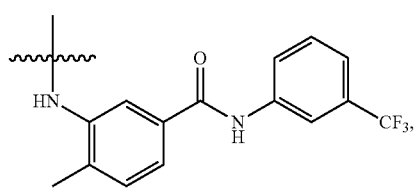

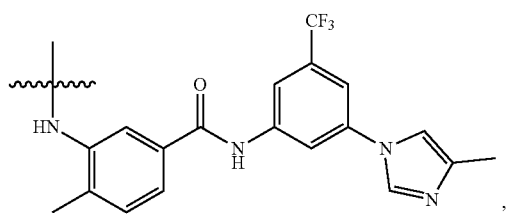

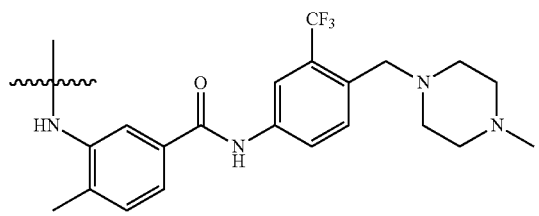

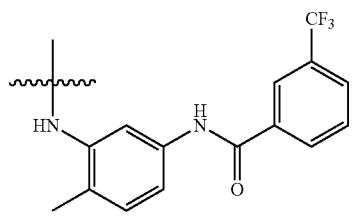

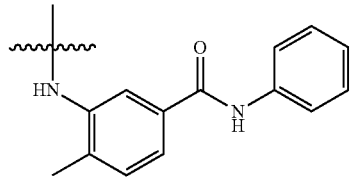

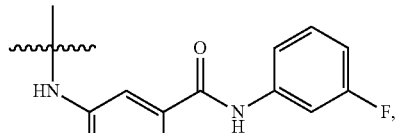

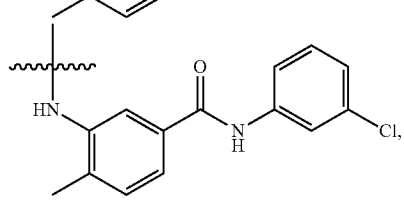

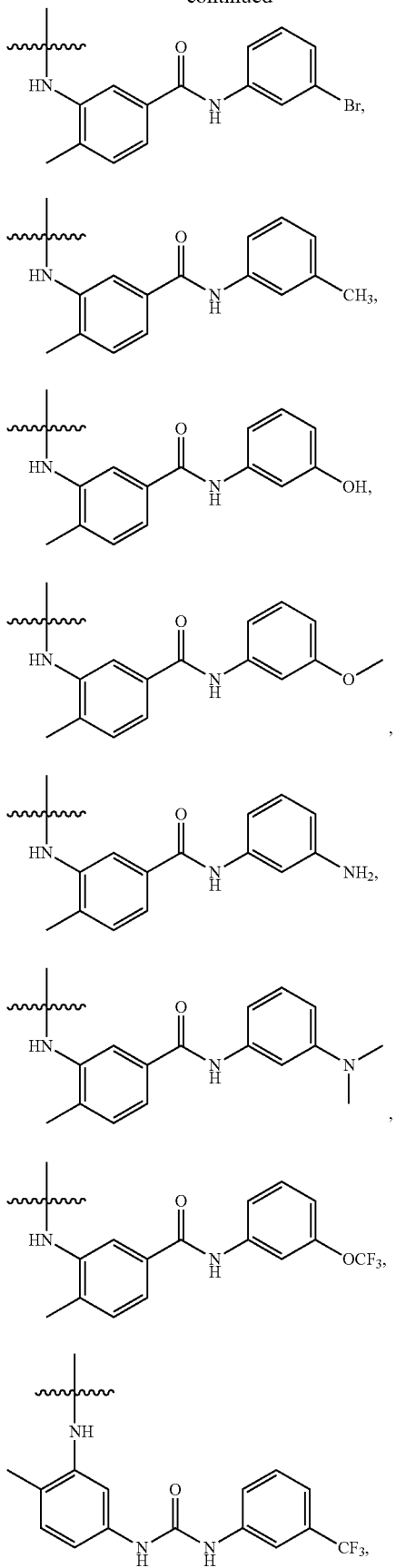

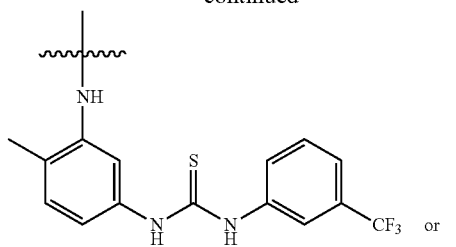

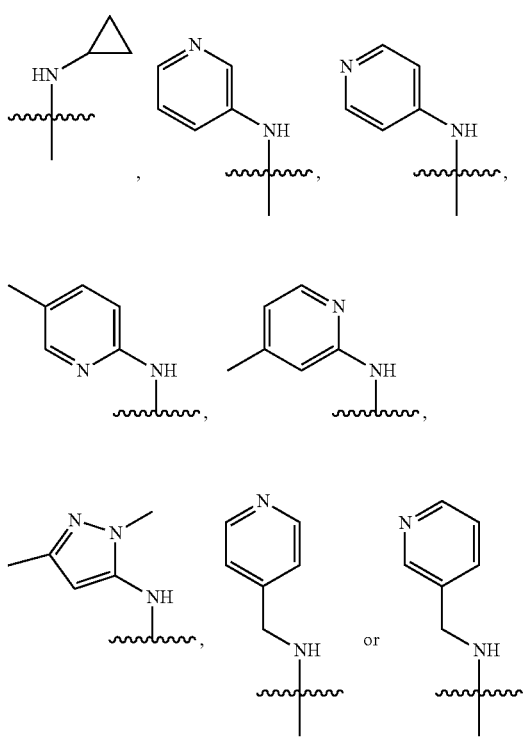

4) amino optionally substituted by C3-C7 cycloalkyl, amino substituted by optionally substituted heteroaryl, or amino substituted by C1-C6 alkyl optionally substituted by heteroaryl;

preferably amino substituted by the following groups: C3-C6 cycloalkyl, heteroaryl optionally substituted by C1-C6 alkyl or C1-C6 alkyl optionally substituted by heteroaryl;

most preferably selected from the following substituted amino:

5) optionally substituted heterocyclyl, preferably heterocyclyl substituted by di-(C1-C6 alkyl) amino or heterocyclyl substituted by C1-C6 alkyl-substituted heteroaryl, most preferably selected from:

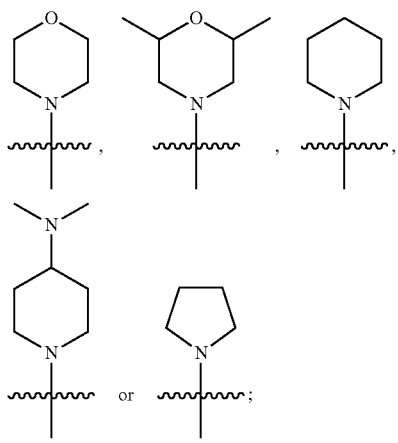

$R^3$ is selected from: —H or C1-C6 alkyl; preferably selected from: —H or —CH$_3$.

In the sixth aspect, according to a specific embodiment of the present invention, the compound, or a stereoisomer thereof, a prodrug thereof, a pharmaceutically acceptable salt thereof or a pharmaceutically acceptable solvate thereof has the following structure:

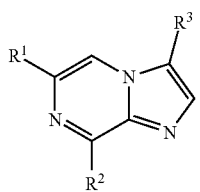

VI wherein,
$R^1$ is selected from: optionally substituted heteroaryl, preferably selected from:

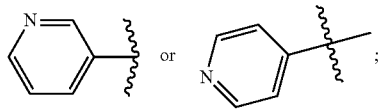 [SMILES: *c1cccnc1 ; *c1ccncc1]

$R^2$ is selected from:

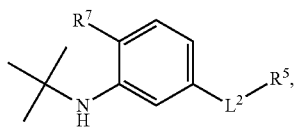

wherein,
$L^2$ is selected from NHCO, CONH, SO$_2$NH, NHSO$_2$, NHCONH or NHCSNH; preferably, $L^2$ is NHCO or CONH;
$R^5$ is selected from substituted or unsubstituted C6-C10 aryl, preferably substituted or unsubstituted phenyl;

$R^5$ is preferably

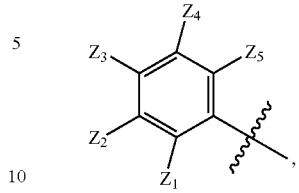

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C3 fluorine-containing alkoxy, optionally substituted heteroaryl, C1-C6 alkyl substituted by optionally substituted heterocyclyl;
$R^5$ is more preferably

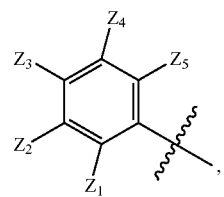

wherein one or two of $Z_1$, $Z_2$, $Z_3$, $Z_4$, $Z_5$ are independently selected from the following groups, the rest being H: H, fluoro, chloro, amino, hydroxy, trifluoromethyl, trifluoromethoxy, C1-C6 alkyl-substituted

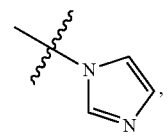 [SMILES: *n1ccnc1]

C1-C6 alkyl substituted by heterocyclyl that is optionally substituted by C1-C6 alkyl;
most preferably, $R^5$ is

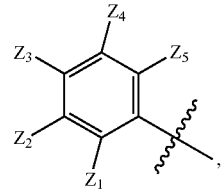

wherein, $Z_2$ or $Z_4$ is selected from the following groups, the rest being H: H, fluoro, trifluoromethyl, trifluoromethoxy; or $Z_2$ and $Z_3$ or $Z_2$ and $Z_4$, respectively, are independently selected from the following groups, the rest being H: trifluoromethyl,

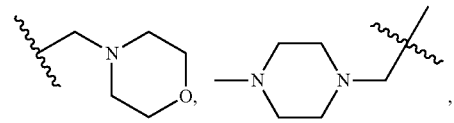

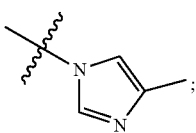

R⁷ is selected from H or C1-C6 alkyl; preferably, R⁷ is methyl;

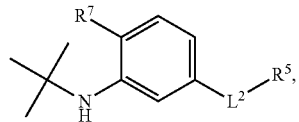

in its entirety, is most preferably selected from:

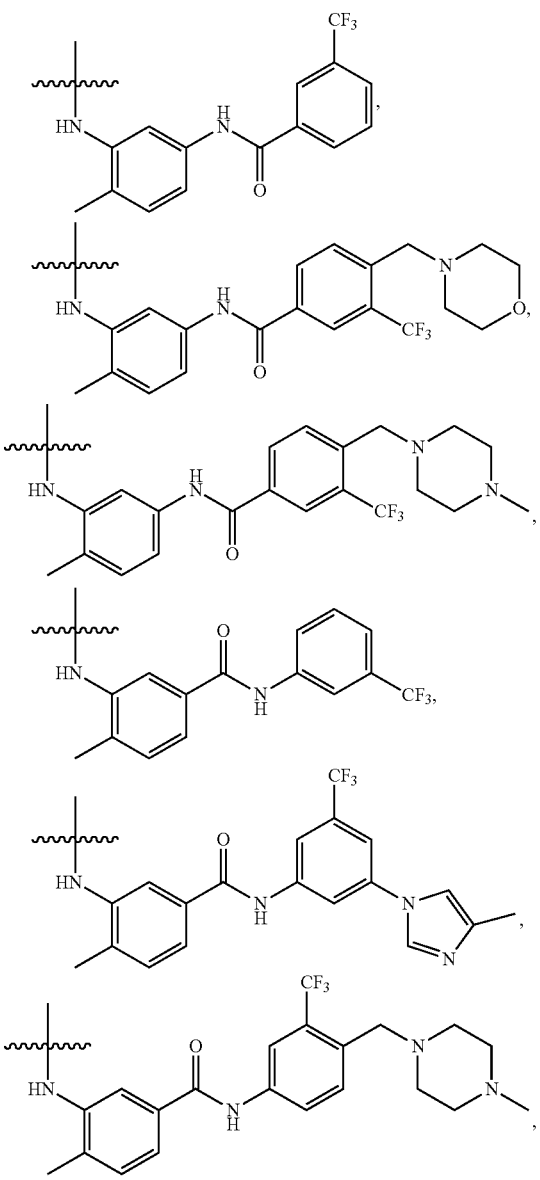

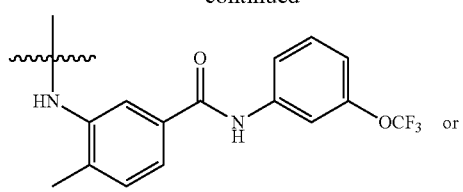

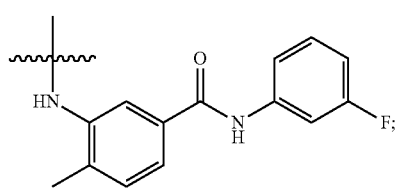

R³ is selected from: —H, halogen, C1-C6 alkyl or C3-C7 cycloalkyl; preferably selected from: —H, fluoro, chloro, C1-C3 alkyl or C3-C7 cycloalkyl; most preferably selected from: —H, —Br, —CH₃ or

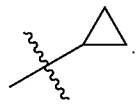 [SMILES: *C1CC1]

In the seventh aspect, according to a specific embodiment of the present invention, the compound, or a stereoisomer thereof, a prodrug thereof, a pharmaceutically acceptable salt thereof or a pharmaceutically acceptable solvate thereof has the following structure:

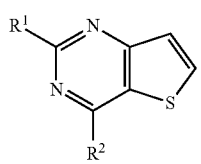

VII wherein,

R¹ is selected from:

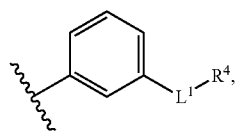

wherein,

L¹ is selected from NHCO or CONH; L¹ preferably NHCO;

R⁴ is selected from H, substituted or unsubstituted C6-C10 aryl, preferably substituted or unsubstituted phenyl, or substituted or unsubstituted heteroaryl, preferably substituted or unsubstituted pyridyl;

$R^4$ is preferably

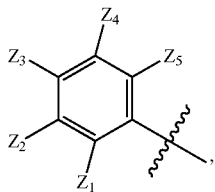

wherein one of $Z_1$, $Z_2$, $Z_3$, $Z_4$, $Z_5$ is selected from the following groups, the rest being H: H, halogen, amino, hydroxy, C1-C3 fluorine-containing alkyl; more preferably, $R^4$ is

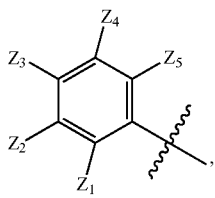

wherein $Z_2$ or $Z_4$ is selected from the following groups, the rest being H: H, chloro, amino, hydroxy, trifluoromethyl; most preferably, $R^4$ is

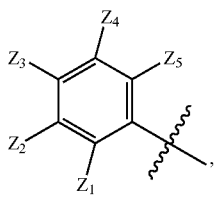

wherein $Z_2$ or $Z_4$ is trifluoromethyl, the rest being H; or $R^4$ is preferably

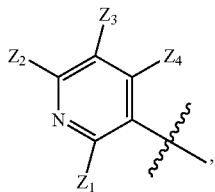

wherein one of $Z_1$, $Z_2$, $Z_3$, $Z_4$ is selected from the following groups, the rest being H: H, halogen, amino, hydroxy; more preferably, $R^4$ is

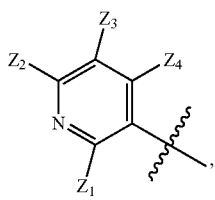

wherein $Z_2$ is selected from the following groups, the rest being H: H, chloro, amino, hydroxy; most preferably, $R^4$ is

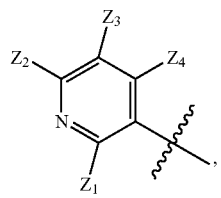

wherein $Z_2$ is amino, the rest being H;

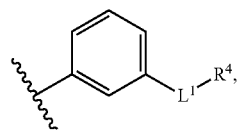

in its entirety, is most preferably selected from:

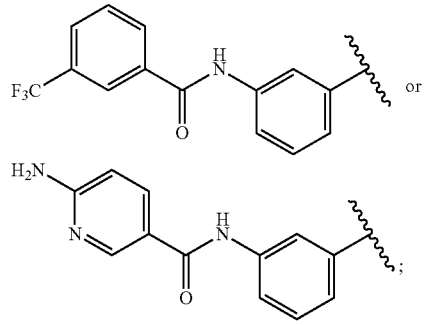

$R^2$ is selected from:
1) amino optionally substituted by C3-C7 cycloalkyl or amino substituted by optionally substituted heteroaryl;

preferably selected from amino substituted by cyclopropyl or amino substituted by heteroaryl that is optionally substituted by C1-C6 alkyl;

most preferably selected from the following substituted amino:

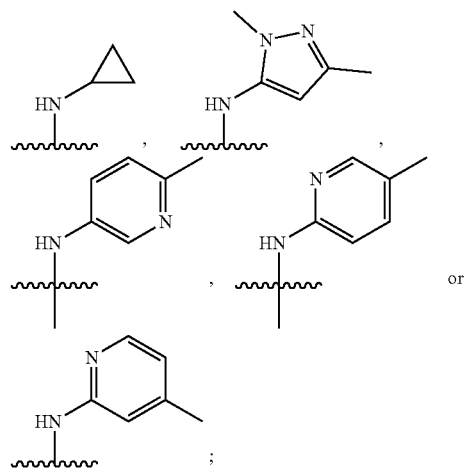

2) optionally substituted heterocyclyl,
preferably selected from heterocyclyl substituted by di-(C1-C6 alkyl)amino or heterocyclyl substituted by C1-C6 alkyl,
most preferably selected from:

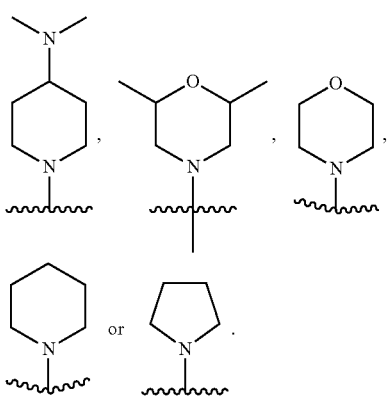

In the eighth aspect, according to a specific embodiment of the present invention, the compound, or a stereoisomer thereof, a prodrug thereof, a pharmaceutically acceptable salt thereof or a pharmaceutically acceptable solvate thereof has the following structure:

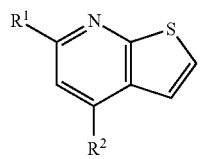

VIII wherein, $R^1$ is selected from: optionally substituted heteroaryl, preferably selected from:

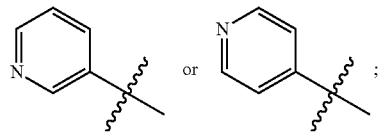 [SMILES: *c1cccnc1 ; *c1ccncc1]

$R^2$ is selected from:

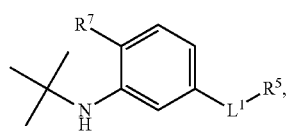

wherein, $L^2$ is selected from NHCO, CONH, SO$_2$NH, NHSO$_2$, NHCONH or NHCSNH; preferably, $L^2$ is NHCO or CONH;

$R^5$ is selected from substituted or unsubstituted C6-C10 aryl, preferably substituted or unsubstituted phenyl;

$R^5$ is preferably

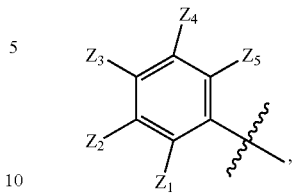

wherein one of $Z_1$, $Z_2$, $Z_3$, $Z_4$, $Z_5$ is selected from the following groups, the rest being H: H, halogen, amino, hydroxy, C1-C3 fluorine-containing alkyl;

most preferably, $R^5$ is

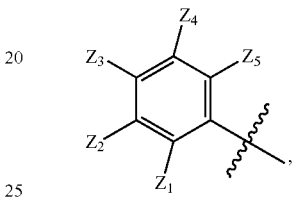

wherein $Z_2$ or $Z_4$ is selected from the following groups, the rest being H: H, trifluoromethyl;

$R^7$ is selected from H or C1-C6 alkyl; preferably, $R^7$ is H or methyl;

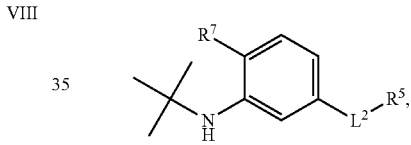

in its entirety, is most preferably selected from:

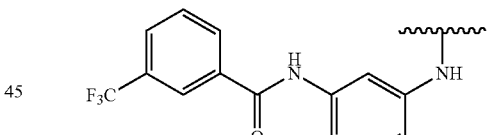

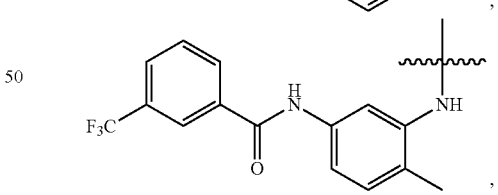

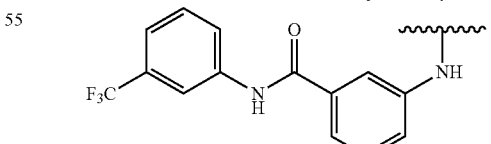

or

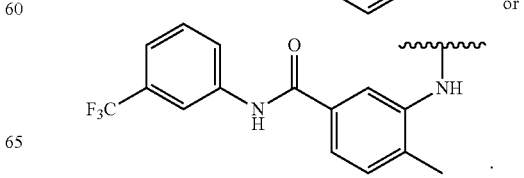

Unless otherwise indicated, the above groups and substituents have the ordinary meanings in the field of medicinal chemistry.

It should be noted that C1-C6 oxygen-containing alkyl refers to a group in which C1-C6 alkyl skeleton is substituted by one or more C1-C6 alkoxy groups, for example, methoxyethyl, methoxyethoxymethyl and the like. Similarly, C1-C3 oxygen-containing alkyl refers to a group in which C1-C3 alkyl skeleton is substituted by one or more C1-C6 alkoxy groups.

The term "aryl" or "C6-C10 aryl" refers to a C6-10 mono-, di- or poly-carbocyclic hydrocarbon having from 1 to 2 ring systems which are optionally further fused or attached to each other by a single bond, wherein at least one of the carbon rings is "aromatic", and the term "aromatic" refers to a fully conjugated π-electron bond system. The aryl ring may be optionally further fused or attached to aromatic or non-aromatic carbocyclic rings or heterocyclic rings. Non-limiting examples of the aryl group are phenyl, α- or β-naphthyl.

The term "heteroaryl" refers to an aromatic heterocyclic ring, which is usually a 5- to 8-membered heterocyclic ring having from 1 to 3 heteroatoms selected from N, O or S; a heteroaryl ring may be optionally further fused or attached to aromatic or non-aromatic carbocyclic rings or heterocyclic rings. Non-limiting examples of the heteroaryl group are, for example, pyridyl, pyrazinyl, pyrimidinyl, pyridazinyl, indolyl, imidazolyl, thiazolyl, isothiazolyl, thioxazolyl, pyrrolyl, phenyl-pyrrolyl, furyl, phenyl-furyl, oxazolyl, isoxazolyl, pyrazolyl, thienyl, benzofuryl, benzothienyl, benzo 1,3-dioxolane (benzodioxolane), isoindolinyl, benzoimidazolyl, indazolyl, quinolyl, isoquinolyl, 1,2,3-triazolyl, 1-phenyl-1,2,3-triazolyl, 2,3-indolinyl, 2,3-dihydrobenzofuryl, 2,3-dihydrobenzothienyl, benzopyranyl, 2,3-dihydrobenzoxazinyl, 2,3-dihydroquinoxalinyl and the like.

The term "C6-C10 arylamino" refers to a group formed by attaching a —NH- or nitrogen-containing group to the "aryl" or "C6-C10 aryl" defined above, the attaching position of the group to the rest of the compound being on the —NH- or nitrogen-containing group.

Similarly, the term "heteroarylamino" refers to a group formed by attaching a —NH- or nitrogen-containing group to the "heteroaryl" defined above, the attaching position of the group to the rest of the compound being on the —NH- or nitrogen-containing group.

The term "heterocyclyl" (also referred to as "heterocycloalkyl") refers to 3-, 4-, 5-, 6- and 7-membered saturated or partially unsaturated carbocyclic rings, wherein one or more carbon atoms are replaced by heteroatoms such as nitrogen, oxygen and sulfur. Non-limiting examples of the heterocyclic group are, for example, pyranyl, pyrrolidinyl, pyrrolinyl, imidazolinyl, imidazolidinyl, pyrazolidinyl, pyrazolinyl, thiazolinyl, thiazolidinyl, dihydrofuryl, tetrahydrofuryl, 1,3-dioxolanyl, piperidinyl, piperazinyl, morpholine, morpholinyl, tetrahydropyrrolyl, thiomorpholinyl and the like.

The term "optionally substituted heterocyclyl" refers to the group formed in the situation the above-mentioned "heterocyclyl" is substituted by one or more "C1-C6 alkyl", "C1-C3 alkyl", "C3-C6 cycloalkyl".

The term "C1-C6 alkyl" refers to any straight-chain or branched-chain group having 1 to 6 carbon atoms, such as methyl, ethyl, n-propyl, isopropyl, n-butyl, isobutyl, t-butyl, sec-butyl, n-pentyl, tert-amyl, n-hexyl and the like.

The term "C1-C3 alkyl" refers to any straight-chain or branched-chain group having 1 to 3 carbon atoms, such as methyl, ethyl, n-propyl, isopropyl and the like.

Unless otherwise indicated, the term "C3-C7 cycloalkyl" refers to a hydrocarbon of a 3-7 membered monocyclic system having a saturated ring, and the C3-C7 cycloalkyl may be cyclopropyl, cyclobutyl, cyclopentyl, cyclohexyl or cycloheptyl.

Similarly, the term "C3-C6 cycloalkyl" refers to a hydrocarbon of a 3-6 membered monocyclic system having a saturated ring, and the C3-C6 cycloalkyl may be cyclopropyl, cyclobutyl, cyclopentyl or cyclohexyl.

The term "C1-C6 fluorine-containing alkyl" refers to a group in which C1-C6 alkyl skeleton is substituted by one or more fluoro groups, for example, tetrafluoromethane, monofluoromethyl, difluoroethyl, trifluoromethyl, and the like.

Similarly, the term "C1-C3 fluorine-containing alkyl" refers to a group in which C1-C3 alkyl skeleton is substituted by one or more fluoro groups, for example, tetrafluoromethane, monofluoromethyl, difluoroethyl, trifluoromethyl, and the like.

The term "C1-C6 acyl" refers to —C($=$O)—H or —C($=$O)—C1-C5 alkyl, for example, formyl, acetyl, propionyl, butyryl, and the like.

The term "C1-C6 amido" refers to H—C($=$O)—NH— or —NH—C($=$O)—C1-C5 alkyl, for example, formamido, acetamido, propionamido, butyramido and the like.

The term "C1-C6 alkylsulfonylamino" refers to —NH—S($=$O) 2-C1-C6 alkyl, for example, methylsulfonylamino, ethylsulfonylamino, propylsulfonylamino, butylsulfonylamino and the like.

The terms "alkoxy", "cycloalkoxy" and derivatives thereof refer to any of the above-mentioned alkyl (for example, C1-C6 alkyl, C1-C3 alkyl and the like), cycloalkyl (for example, C3-C6 cycloalkyl), which is attached to the remainder of molecules through oxygen atom (—O—).

From all of the above description, it will be apparent to those skilled in the art that any group whose name is a compounded name, for example, "fluorine-containing oxygen-containing alkyl" shall mean to conventionally construct from the moiety that is derived, such as the oxygen-containing alkyl substituted by the fluoro, wherein the alkyl is as defined above. Similarly, "fluorine-containing alkoxy" is another example. For still another example, "arylamino" shall mean to conventionally construct from the moiety that is derived, such as the amino substituted by the aryl, wherein the aryl is as defined above. Similarly, the meaning of "heteroarylamino" can be understood.

Similarly, any term such as alkylamino, dialkylamino, alkoxycarbonyl, alkoxycarbonylamino, heterocyclylcarbonyl, heterocyclyl carbonylamino, cycloalkyloxycarbonyl, alkoxyformyl and the like includes groups, wherein alkyl, alkoxy, aryl, C3-C7 cycloalkyl and heterocyclyl moieties are as defined above.

According to the present invention and unless otherwise provided, any of the above groups may optionally be substituted at any of its free positions by one or more groups, for example by 1 to 6 groups, the groups being independently selected from: halogen atom, nitro, oxo ($=$O), cyano, C1-C6 alkyl, polyfluorinated alkyl, polyfluorinated alkoxy, alkenyl, alkynyl, hydroxy alkyl, hydroxyalkylamino, hydroxyheterocyclyl, aryl, aryl-alkyl, heteroaryl, heteroaryl-alkyl, heterocyclyl, heterocyclyl-alkyl, C3-C7 cycloalkyl, cycloalkyl-alkyl, alkyl-aryl, alkyl-heteroaryl, alkyl-heterocyclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkyl-amino, hydroxy, alkoxy, aryloxy, heterocyclyloxy, alkyl-heterocyclyloxy, methylenedioxy, alkylcarbonyloxy, arylcarbonyloxy, cycloalkenyloxy, heterocyclylcarbonyloxy, alkyleneaminooxy, carboxy, alkoxycarbonyl, aryloxycarbonyl, cycloalkyloxycarbonyl, heterocyclyloxycarbonyl, amino, ureido, alkylamino, aminoalkylamino, dialkylamino, dialkylamino-heterocyclyl, dialkylamino-alkylamino, arylamino, aryl alkylamino, diarylamino, heterocyclylamino, alkyl-heterocyclylamino, alkyl-heterocyclylcarbonyl, formylamino, alkylcarbonylamino, arylcarbonylamino, heterocyclylcarbonylamino, alkyl-heterocyclylcarbonylamino, aminocarbonyl, alkylaminocarbonyl, dialkylaminocarbonyl, arylaminocarbonyl, heterocyclylaminocarbonyl, alkoxycarbonylamino, alkoxycarbonylamino-alkylamino, alkoxycarbonylheterocyclyl-alkylamino, alkoxy-aryl-alkyl, hydroxyamino-carbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

Further, if appropriate, each of the above substituents may be further substituted by one or more of the above-exemplified groups.

In this respect, the term "halogen atom" refers to a fluorine (F), chlorine (Cl), bromine (Br) or iodine (I) atom.

The term "cyano" refers to —CN residue.

The term "nitro" refers to —NO$_2$ group.

As used herein, unless otherwise indicated, the term "prodrug" refers to a derivative that can be hydrolyzed, oxidized or otherwise reacted under biological conditions (in vitro or in vivo) to provide a compound of the invention. Prodrugs can become active compounds only by carrying out the reaction under biological conditions, or they are inactive in their non-reacted form. Prodrugs can be generally prepared using known methods, for example, those methods described in 1 Burger's Medicinal Chemistry and Drug Discovery (1995) 172-178, 949-982 (Manfred E. Wolff, ed. 5th edition).

Pharmaceutically acceptable salts can be obtained using standard procedures well known in the art, for example, by reacting a sufficient amount of a basic compound with a suitable acid that provides a pharmaceutically acceptable anion.

The term "treatment" as used herein generally refers to obtaining the desired pharmacological and/or physiological effect. The effect can be preventive according to complete or partial prevention of disease or its symptoms; and/or can be therapeutic according to partial or complete stabilization or cure of disease and/or side effects due to the disease. The term "treatment" as used herein encompasses any treatment on a patient's disease, including: (a) preventing the disease or symptom that occurs in a patient who is susceptible to the disease or symptom but not yet diagnosed to suffer from the disease; (b) suppressing symptoms of the disease, i.e., stopping its development; or (c) relieving symptoms of the disease, i.e., causing degeneration of the disease or symptom.

According to a specific embodiment of the present invention relating to the compound, a stereoisomer thereof, a prodrug thereof, or a pharmaceutically acceptable salt thereof or a pharmaceutically acceptable solvate thereof, the compound is one of the compounds described in the examples below.

In another aspect, the present invention provides a pharmaceutical composition comprising the compound, a stereoisomer thereof, a prodrug thereof, or a pharmaceutically acceptable salt thereof or pharmaceutically acceptable solvate thereof according to any one of the above embodiments, and a pharmaceutically acceptable carrier, diluent or excipient.

Methods for preparing a pharmaceutical composition comprising a certain amount of an active ingredient, are known or are obvious for a person skilled in the art according to the contents as disclosed in the invention. For example, as described in REMINGTON'S PHARMACEUTICAL SCIENCES, Martin, E. W., ed., Mack Publishing Company, 19th ed. (1995), methods for preparing a pharmaceutical composition comprise incorporating a suitable pharmaceutically acceptable excipient, carrier, diluent, etc.

The known methods for preparing a pharmaceutical preparation according to the invention include the conventional mixing, dissolving or freeze-drying methods. The compound according to the invention can be used to prepare into a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, or pressed into a tablet. For the treatment by oral administration, an active compound can be combined with one or more excipients, and be used in a form of a deglutible tablet, a buccal tablet, a troche, a capsule, an elixir, a suspension, a syrup, a wafer, etc. The composition and preparation shall comprise at least 0.1% of an active compound. The ratio of the composition to the preparation can be varied certainly, and the composition can account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc; a lubricant, such as magnesium stearate; and a sweeting agent, such as sucrose, fructose, lactose or aspartame; or a flavoring agent, such as peppermint, wintergreen oil or cherry flavor. When the unit dosage form is a capsule, in addition to the above types of materials, it may comprise a liquid carrier, such as vegetable oil or polyethylene glycol. Various other materials may be present as a coating or change the physical form of a solid unit dosage form in other manners. For example, a tablet, a pill or a capsule may be coated with gelatin, wax, shellac or sugar etc. A syrup or elixir can comprise an active compound, sucrose or fructose as a sweeting agent, methyl p-hydroxybenzoate or propyl p-hydroxybenzoate as preservative, a dye and a flavoring agent (such as a cherry flavor or an orange flavor). Certainly, any material for preparing any unit dosage form should be pharmaceutically acceptable and be substantively not toxic in its applied amount. In addition, an active compound can be incorporated into a sustained release preparation and a sustained release device.

An active compound can also be administered intravenously or intraperitoneally by infusion or injection. An aqueous solution of an active compound or a salt thereof can be prepared, optionally, by mixing it with a non-toxic surfactant. A dispersible formulation in glycerol, liquid polyethylene glycol, glycerin triacetate and a mixture thereof and in oil can also be prepared. Under the common conditions of storage and use, the preparations comprise a preservative in order to suppress the growth of microbes.

A pharmaceutical dosage form suitable for injection or infusion can include a sterile aqueous solution or a dispersible formulation or a sterile powder comprising an active ingredient (optionally encapsulated into a liposome) of an immediate preparation such as a solution or a dispersible formulation suitable for sterile injection or infusion. Under all the conditions, the final dosage form shall be sterile, liquid and stable under the production and storage conditions. A liquid carrier can be a solution or a liquid disperse medium, including, for example, water, ethanol, polyols (such as glycerol, propylene glycol, and liquid macrogol, etc), vegetable oil, a non-toxic glyceride and a suitable mixture thereof. A suitable fluidity can be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal, etc). In many conditions, an isotonizing agent, such as sugar, buffer agent or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation method is vacuum drying and freeze drying techniques, which will result in the production of the powder of the active ingredient and any other desired ingredient present in the previous sterile filtration solution.

A useful solid carrier includes crushed solid (such as talc, clay, microcrystalline cellulose, silicon dioxide, and aluminum oxide etc). A useful liquid carrier includes water, ethanol or ethylene glycol or water-ethanol/ethylene glycol mixture, in which the compound of the invention can be dissolved or dispersed in an effective amount, optionally, with the aid of a non-toxic surfactant. An adjuvant (such as a flavor) and an additional antimicrobial agent can be added to optimize the property for a given use.

A thickener (such as synthetic polymer, fatty acid, fatty acid salt and ester, fatty alcohol, modified cellulose or modified inorganic material) can also be used with a liquid carrier to form a coatable paste, gel, ointment, soap and the like, and be directly applied to the skin of a user.

As used herein, the term "subject" refers to a patient or other animal that receives a compound or pharmaceutical composition of the present invention to treat, prevent, ameliorate and/or alleviate the disease or condition mentioned in the present invention, particularly a mammal, for example, a human, a dog, a monkey, a cow, a horse and the like.

As used herein, the term "effective amount" or "required amount" refers to a dose that can achieve in a subject the treatment, prevention, amelioration and/or alleviation of the disease or condition mentioned in the present invention.

A therapeutically effective amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation can be present in a unit dosage form, which is a physical dispersion unit comprising a unit dose, suitable for administration to a human body and other mammalian body. A unit dosage form can be capsule(s) or tablet(s). Depending on the particular treatment involved, the amount of an active ingredient in a unit dose can be varied or adjusted between about 0.1 and about 1000 mg or more.

In addition, the present invention further includes use of various new drug dosage forms such as milk liposomes, microspheres and nanospheres, for example, medicaments prepared with the use of a particulate dispersion system including polymeric micelles, nanoemulsions, submicroemulsions, microcapsules, microspheres, liposomes and niosomes (also known as nonionic surfactant vesicles) and the like.

In another aspect, the present invention further provides a preparation method of the compound according to any of the above embodiments, comprising the following steps:

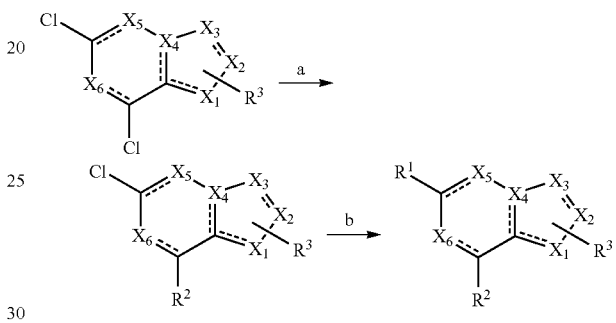

reaction conditions: (a) coupling reaction of carbon-carbon bond formation of heteroaryl chloride and boronic acid or boronic acid ester catalyzed by metal palladium, or coupling reaction of carbon-nitrogen bond formation of heteroaryl chloride and amine compound catalyzed by metal palladium, or nucleophilic substitution reaction of heteroaryl chloride with amine compound under alkaline condition, or nucleophilic substitution reaction of heteroaryl chloride with amine compound under acidic condition; (b) coupling reaction of carbon-carbon bond formation of heteroaryl chloride and boronic acid or boronic acid ester catalyzed by metal palladium, or coupling reaction of carbon-nitrogen bond formation of heteroaryl chloride and amine compound catalyzed by metal palladium, or nucleophilic substitution reaction of heteroaryl chloride with amine compound under acidic condition.

wherein, the heteroaryl chloride includes the following types:

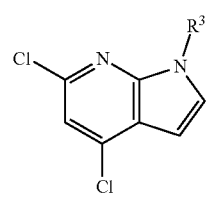

Ia

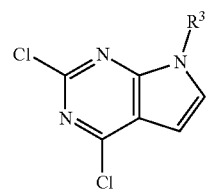

IIa

-continued

IIIa 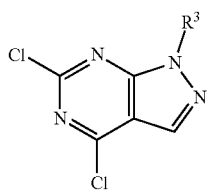

IVa 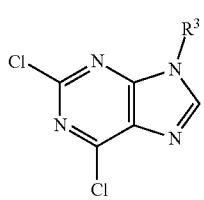

Va 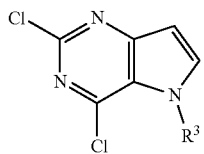

VIa 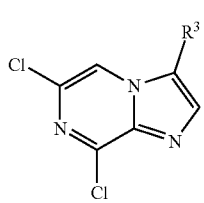

VIIa 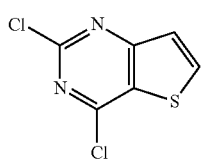

VIIIa 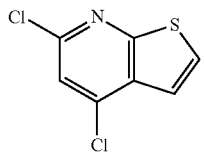

Ib 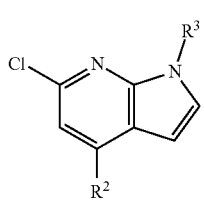

IIb 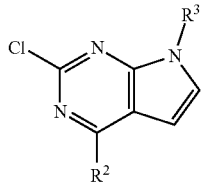

-continued

IIIb 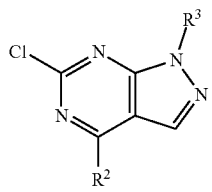

IVb 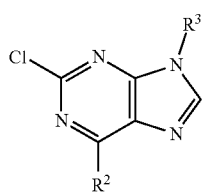

Vb 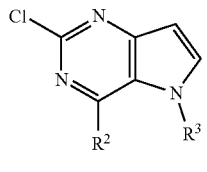

VIb 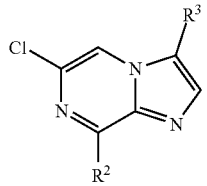

VIIb 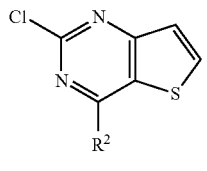

VIIIb 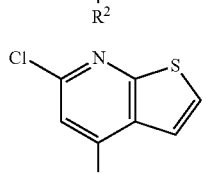

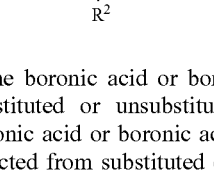

the boronic acid or boronic acid ester is selected from substituted or unsubstituted C6-C10 aryl or heteroaryl boronic acid or boronic acid ester; the amine compound is selected from substituted or unsubstituted C6-C10 arylamine, heteroarylamine, C1-C6 alkylamine, C3-C7 cycloalkylamine, C1-C6 oxygen-containing alkylamine or C3-C7 oxygen-containing cycloalkylamine. See above for details.

The metal palladium catalyst is selected from palladium acetate, tetrakis(triphenylphosphine) palladium, bistriphenylphosphine palladium dichloride, 1,1'-bis(diphenylphosphino)ferrocene] palladium dichloride or tris(dibenzylideneacetone) dipalladium; the alkaline condition refers to a condition in which any of the following substances exists: triethylamine, diisopropylethylamine, pyridine, sodium bicarbonate, sodium carbonate, potassium carbonate, cesium carbonate, lithium hydroxide, sodium hydroxide, potassium hydroxide, sodium hydride, potassium hydride; the acidic condition refers to a condition in which any of the following substances exists: acetic acid, trifluoroacetic acid, hydrochloric acid, methanesulfonic acid, p-toluene sulfonic acid, camphorsulfonic acid.

In another aspect, the present invention further provides use of the compound according to any one of the above embodiments, a stereoisomer thereof, a prodrug thereof, or a pharmaceutically acceptable salt thereof or a pharmaceutically acceptable solvate thereof, and a pharmaceutical composition comprising the compound in the manufacture of a medicament for preventing or treating PIKfyve-mediated cancers and other diseases.

Experimental Section

Regarding the examples described below, the compounds of the present invention are synthesized using the methods described herein or other methods well known in the art.

General Methods of Purification and Analysis

Thin layer chromatography was carried out on a silica gel GF254 precoated plate (Qingdao Marine Chemical Plant). Column chromatography was carried out by silica gel (300-400 mesh, Yantai Zhifu Huangwu Silica Gel Development Test Factory) under medium pressure or by a pre-packed silica gel cartridge (ISCO or Welch) with the use of an ISCO Combiflash Rf200 rapid purification system. The ingredient was visualized by UV light (λ: 254 nm) or iodine vapor. When necessary, the compound was prepared by preparative HPLC and purified by a Waters Symmetry C18 (19×50 mm, 5 μm) column or a Waters X Terra RP 18 (30×150 mm, 5 μm) column, wherein a Waters preparative HPLC 600 equipped with a 996 Waters PDA detector and Micromass mod. ZMD single quadrupole mass spectrometry (electrospray ionization, cationic mode) were used. Method 1: Phase A: 0.1% TFA/MeOH 95/5; Phase B: MeOH/H$_2$O 95/5. Gradient: proceeding at 10 to 90% B for 8 min, keeping at 90% B for 2 min; flow rate 20 mL/min. Method 2: Phase A: 0.05% NH$_4$OH/MeOH 95/5; Phase B: MeOH/H$_2$O 95/5. Gradient: proceeding at 10 to 100% B for 8 min, keeping at 100% B for 2 min. Flow rate 20 mL/min.

$^1$H-NMR spectra were recorded via a Bruker Avance 600 spectrometer (for $^1$H) operated at 600 MHz. Chemical shift (δ) was reported in parts per million (ppm) and coupling constant (J) in Hz. The tetramethylsilane signal was used as a reference (δ=0 ppm). The following abbreviations were used for peak splitting: s=singlet; br. s.=broad signal; d=doublet; t=triplet; m=multiplet; dd=doublet of doublets.

Electrospray (ESI) mass spectra were obtained via Finnigan LCQ ion trap.

Unless otherwise indicated, all final compounds were homogeneous (with purity not less than 95%), as determined by high performance liquid chromatography (HPLC). HPLC-UV-MS analysis for evaluation of compound purity was performed by combining an ion trap MS device and an HPLC system SSP4000 (Thermo Separation Products) equipped with an autosampler LC Pal (CTC Analytics) and a UV6000LP diode array detector (UV detection 215-400 nm). Device control, data acquisition and processing were performed with Xcalibur 1.2 software (Finnigan). HPLC chromatography was carried out at room temperature and a flow rate of 1 mL/min using a Waters X Terra RP 18 column (4.6×50 mm; 3.5 μm). Mobile phase A was ammonium acetate 5 mM buffer (pH 5.5 with acetic acid): acetonitrile 90:10, mobile phase B was ammonium acetate 5 mM buffer (pH 5.5 with acetic acid): acetonitrile 10:90; proceeding at a gradient of 0 to 100% B for 7 min and then keeping at 100% B for 2 min before rebalancing.

Reagent purification was carried out in accordance with the book Purification of Laboratory Chemicals (Perrin, D. D., Armarego, W. L. F. and Perrins Eds, D. R.; Pergamon Press: Oxford, 1980). Petroleum ether was 60-90° C. fraction, ethyl acetate, methanol and dichloromethane were all analytically pure.

MODE OF CARRYING OUT THE INVENTION

Some of the raw materials and intermediates involved in the synthesis process are described below:

1.

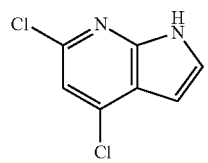 [SMILES: Clc1cc(Cl)c2cc[nH]c2n1]

CAS: 5912-18-5, Efe, Shanghai;

2.

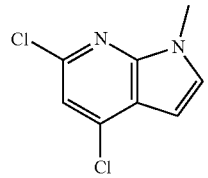

obtained from the reaction of 1 and methyl iodide (CAS: 74-AA-4 Xiya Reagent, Shandong);

3.

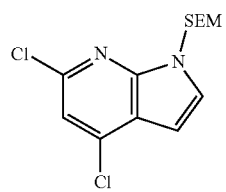 [SMILES: C[Si](C)(C)CCOCn1ccc2c(Cl)cc(Cl)nc21]

obtained from the reaction of 1 and 2-(trimethylsilyl)ethoxymethyl chloride (CAS: 76513-69-4, Efe, Shanghai);

4.

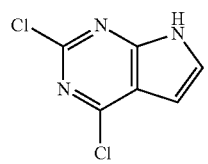 [SMILES: Clc1nc(Cl)c2cc[nH]c2n1]

CAS: 90213-66-4 Shuya, Shanghai;

5.

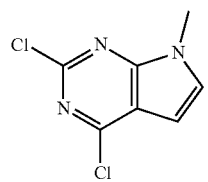

obtained from the reaction of 4 and methyl iodide (CAS: 74-88-4, Xiya Reagent, Shandong);

6.

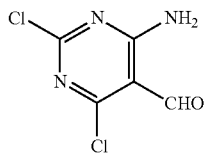

CAS: 50270-27-4, Bide, Shanghai;

7.

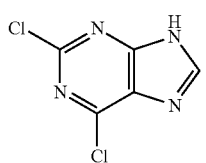 [SMILES: Clc1nc(Cl)c2nc[nH]c2n1]

CAS: 5451-40-1, Bide, Shanghai;

8.

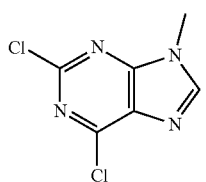

obtained from the reaction of 7 and methyl iodide (CAS: 74-88-4, Xiya Reagent, Shandong);

9.

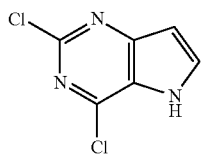 [SMILES: Clc1nc(Cl)c2[nH]ccc2n1]

CAS: 63200-54-4, PharmaBlock, Nanjing, Jiangsu;

10.

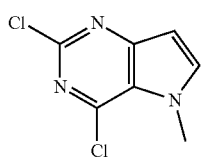

obtained from the reaction of 9 and methyl iodide (CAS: 74-88-4, Xiya Reagent, Shandong);

11.

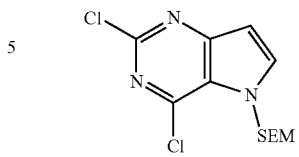

obtained from the reaction of 9 and 2-(trimethylsilyl)ethoxymethyl chloride (CAS: 76513-69-4, Efe, Shanghai);

12.

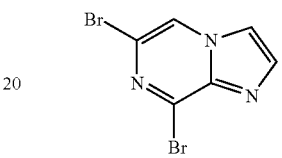

CAS: 63744-22-9, Shuya, Shanghai;

13.

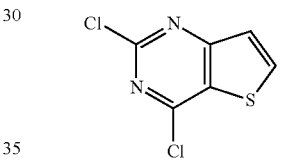

CAS: 16234-14-3, PharmaBlock, Nanjing, Jiangsu;

14

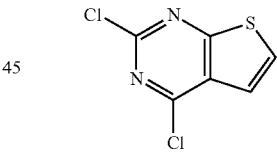

CAS: 18740-39-1, Chemlin, Jiangsu;

15.

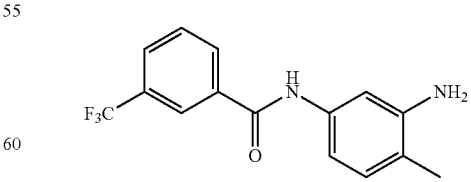

obtained by the steps of reacting 4-methyl-3-nitroaniline (CAS: 99-55-8, Energy, Shanghai) and m-trifluoromethyl-benzoyl chloride (CAS: 2251-65-2, Energy, Shanghai) to obtain

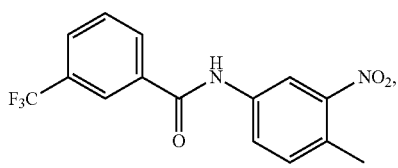 [SMILES: Cc1ccc(NC(=O)c2cccc(C(F)(F)F)c2)cc1[N+](=O)[O-]]

and then reducing nitro;

The following intermediates are obtained in a similar manner:

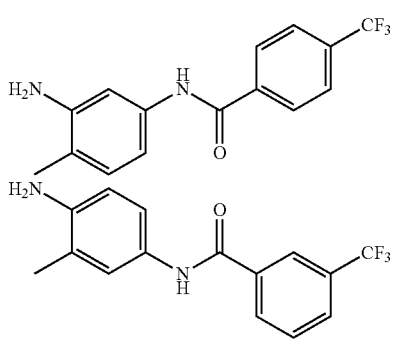
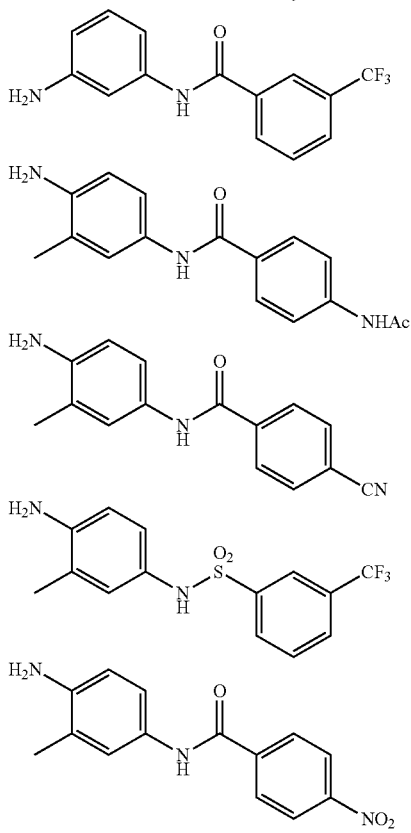

The involved raw materials are: p-trifluoromethylbenzoyl chloride (CAS: 329-15-7, Energy, Shanghai), 3-methyl-4-nitroaniline (CAS: 611-05-2, Energy, Shanghai), m-nitroaniline (CAS: 99-09-2, Energy, Shanghai), p-acetylaminobenzoyl chloride (CAS: 16331-48-9, Energy, Shanghai), p-cyanobenzoyl chloride (CAS: 6068-72-0, Energy, Shanghai), p-nitrobenzoyl chloride (CAS: 122-04-3, Energy, Shanghai), m-trifluoromethylphenylsulfonyl chloride (CAS: 777-44-6, Energy, Shanghai).

16.

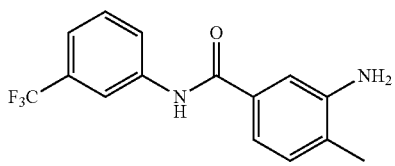 [SMILES: Cc1ccc(C(=O)Nc2cccc(C(F)(F)F)c2)cc1N]

obtained by the steps of reacting 3-nitro-4-methylbenzoic acid (CAS: 96-98-0, Energy, Shanghai) and m-trifluoromethylaniline (CAS: 98-16-8, Energy, Shanghai) to obtain

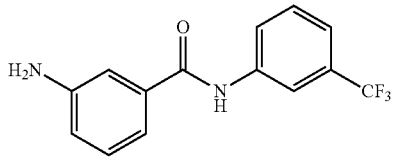

and then reducing nitro;

The following intermediates are obtained in a similar manner:

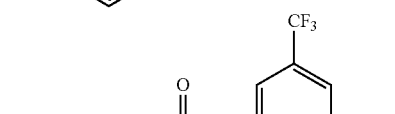
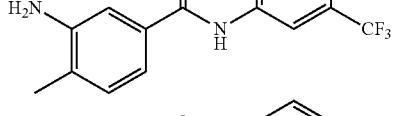

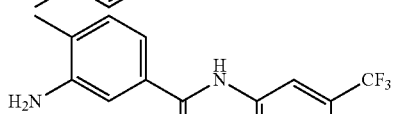
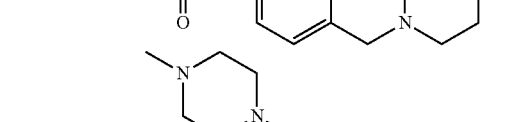
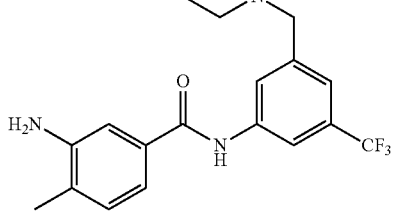

-continued

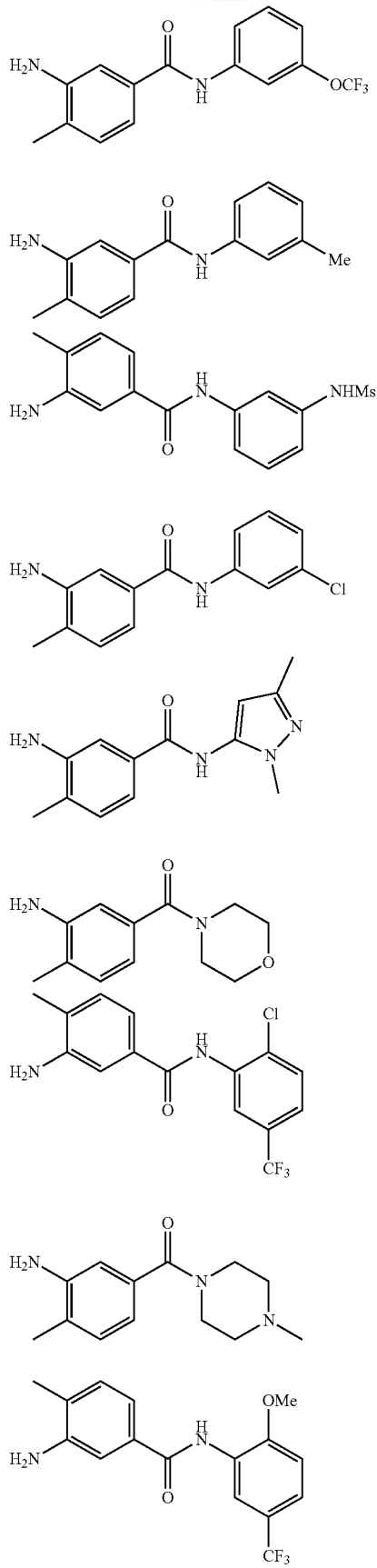

-continued

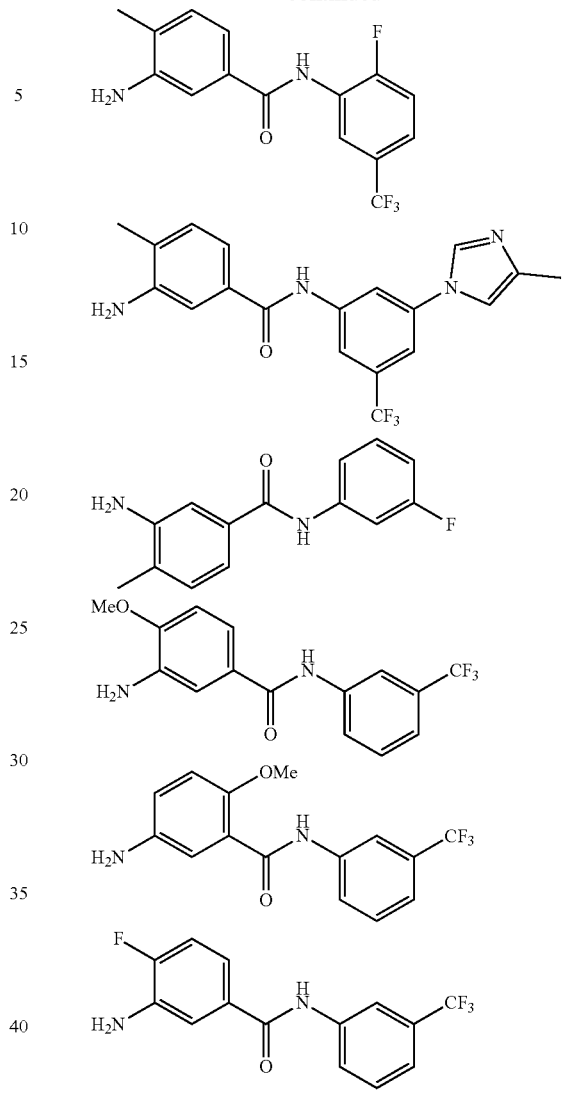

The involved raw materials are: m-nitrobenzoic acid (CAS: 121-92-6, Energy, Shanghai), m-bis(trifluoromethyl)aniline (CAS: 328-74-5, Energy, Shanghai), m-methoxyaniline (CAS: 536-90-3, Energy, Shanghai), m-trifluoromethoxyaniline (CAS: 1535-73-5, Energy, Shanghai), m-toluidine (CAS: 108-44-1, Energy, Shanghai), 3-methylsulfonylaminoaniline (CAS: 37045-73-1, Accela ChemBio, Shanghai), m-chloroaniline (CAS: 108-42-9, Energy, Shanghai), 3-amino-4-chlorotrifluorotoluene (CAS: 121-50-6, Energy, Shanghai), 2-fluoro-5-trifluoromethylaniline (CAS: 535-52-4, Energy, Shanghai), 2-methoxy-5-trifluoromethylaniline (CAS: 349-65-5, Energy, Shanghai), m-fluoroaniline (CAS: 372-19-0, Energy, Shanghai), 4-methoxy-3-nitrobenzoic acid (CAS: 89-41-8, Bidepharm, Shanghai), 2-methoxy-5-nitrobenzoic acid (CAS: 40751-89-1, Shuya, Shanghai), 4-fluoro-3-nitrobenzoic acid (CAS: 453-71-4, Shuya, Shanghai), 5-amino-1,3-dimethylpyrazole (CAS: 3524-32-1, J&K, Beijing), morpholine (CAS: 110-91-8, Aladdin, Shanghai), N-methylpiperazine (CAS: 109-01-3, Energy, Shanghai), 3-(4-methyl-1H-imidazol-1-yl)-5-(trifluoromethyl)aniline (CAS: 641571-11-1, Bidepharm, Shanghai),

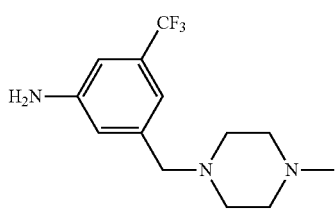 [SMILES: CN1CCN(Cc2cc(N)cc(C(F)(F)F)c2)CC1]

(CAS: 853296-94-3, Pharmlanch, Shanghai),

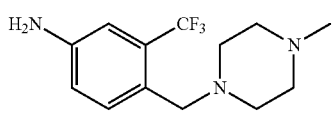 [SMILES: CN1CCN(Cc2ccc(N)cc2C(F)(F)F)CC1]

(CAS: 694499-26-8, Pharmlanch, Shanghai);

17.

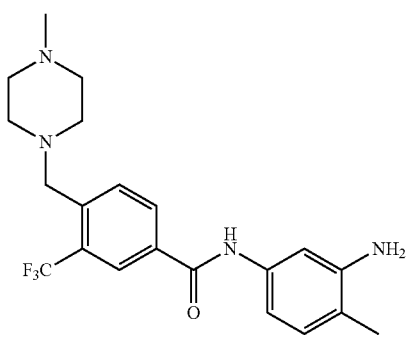 [SMILES: Cc1ccc(NC(=O)c2ccc(CN3CCN(C)CC3)c(C(F)(F)F)c2)cc1N]

obtained by the steps of reacting

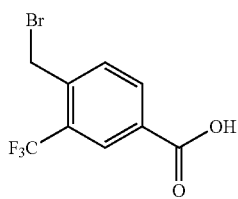 [SMILES: O=C(O)c1ccc(CBr)c(C(F)(F)F)c1]

(CAS: 859213-39-1, J&K, Beijing) and 2-amino-4-nitrotoluene (CAS: 99-55-8, Energy, Shanghai) to obtain

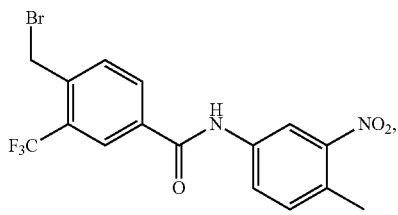

then reacting the above obtained product with N-methylpiperazine (CAS: 109-01-3, Energy, Shanghai) to obtain

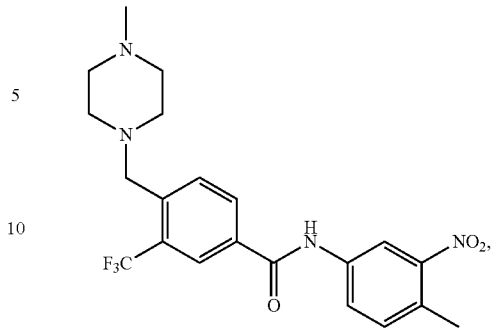

and finally reducing nitro;

18.

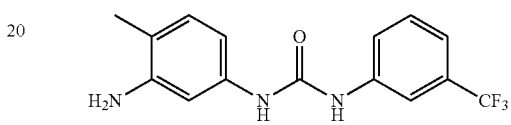

obtained by the steps of reacting m-trifluoromethylaniline (CAS: 98-16-8, Energy, Shanghai) and bis(trichloromethyl) carbonate (CAS: 32315-10-9, Energy, Shanghai) to obtain m-trifluoromethylphenyl thioisocyanate, then reacting the above obtained product with 4-methyl-3-nitroaniline (CAS: 99-55-8, Energy, Shanghai) to obtain

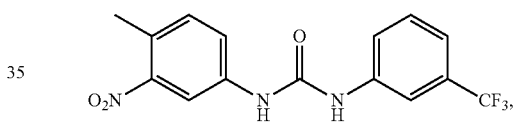

and finally reducing nitro;

The following intermediates are obtained in a similar manner:

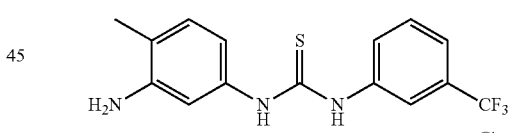

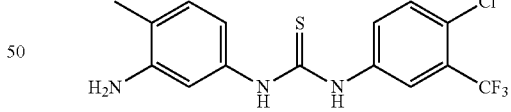

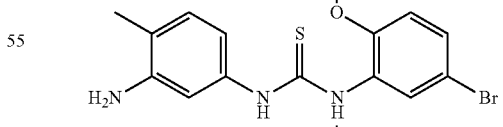


The involved raw materials are: 2-chloro-5-aminotrifluorotoluene (CAS: 320-51-4, Efe, Shanghai), 5-bromo-2- methoxyaniline (CAS: 6358-77-6, Bidepharm, Shanghai), thiophosgen (CAS: 463-71-8, Energy, Shanghai);

19. pyridine-3-boronic acid (CAS: 1692-25-7, Energy, Shanghai);
20. pyridine-4-boronic acid (CAS: 1692-15-5, Energy, Shanghai);
21. phenylboronic acid (CAS: 98-80-6, Adamas, Switzerland);
22. p-methylphenylboronic acid (CAS: 5720-05-8, Energy, Shanghai);
23. p-hydroxyphenylboronic acid (CAS: 71597-85-8, Bide, Shanghai);
24. m-hydroxyphenylboronic acid (CAS: 87199-18-6, Energy, Shanghai);
25. p-chlorophenylboronic acid (CAS: 1679-18-1, Energy, Shanghai);
26. m-chlorophenylboronic acid (CAS: 63503-60-6, Energy, Shanghai);
27. 3-furanboronic acid (CAS: 55552-70-0, Energy, Shanghai);
28. 3-thiopheneboronic acid (CAS: 6165-69-1, Energy, Shanghai);
29. 4-aminophenylboronic acid, Hydrochloride (CAS: 80460-73-7, Energy, Shanghai);
30. 3-aminophenylboronic acid, Hydrochloride (CAS: 80460-73-7, J&K, Beijing);
31. 4-methoxyphenylboronic acid (CAS: 5720-07-0, Energy, Shanghai);
32. 2-furanboronic acid (CAS: 13331-23-2, Energy, Shanghai);
33. 2-thiopheneboronic acid (CAS: 6165-68-0, Energy, Shanghai);
34. benzofuran-2-boronic acid (CAS: 13331-23-2, Energy, Shanghai);
35. benzothiophene-2-boronic acid (CAS: 6165-68-0, Energy, Shanghai);
36. 4-aminomethylpyridine (CAS: 3731-53-1, Energy, Shanghai);
37. 3-aminomethylpyridine (CAS: 3731-52-0, Energy, Shanghai);
38. 4-ethoxycarbonylphenylboronic acid (CAS: 4334-88-7, Energy, Shanghai);
39. 4-dimethylaminopiperidine (CAS: 50533-97-6, Accela ChemBio, Shanghai);
40. 2,6-dimethylmorpholine (CAS: 141-91-3, Energy, Shanghai);
41. cyclopropylamine (CAS: 765-30-0, Energy, Shanghai);
42. 4-aminopyridine (CAS: 504-24-5, Xiya, Shanghai);
43. 3-aminopyridine (CAS: 462-08-8, Energy, Shanghai);
44. 2-amino-5-methylpyridine (CAS: 1603-41-4, Shuya, Shanghai); 44. 2-amino-4-methylpyridine (CAS: 695-34-1, Accela ChemBio, Shanghai);
45. 3,4-(methylenedioxy)phenylboronic acid (CAS: 94839-07-3, Energy, Shanghai);
46. p-fluorophenylboronic acid (CAS: 1765-93-1, Adamas, Switzerland);
47. p-methylsulfonylphenylboronic acid (CAS: 149104-88-1, Energy, Shanghai).

The embodiments of the present invention are described in detail below by way of specific examples, but in any case they cannot be construed as limiting the present invention.

Synthetic route of compounds I-a-1, I-b-1, I-c-1:

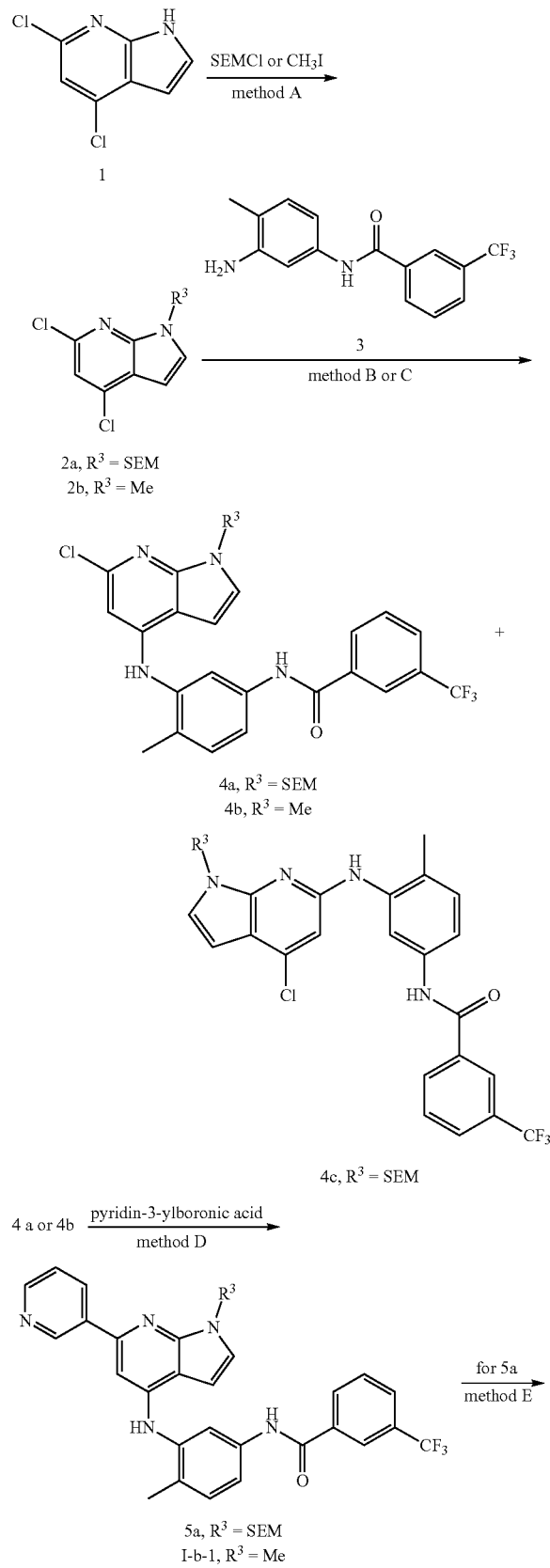

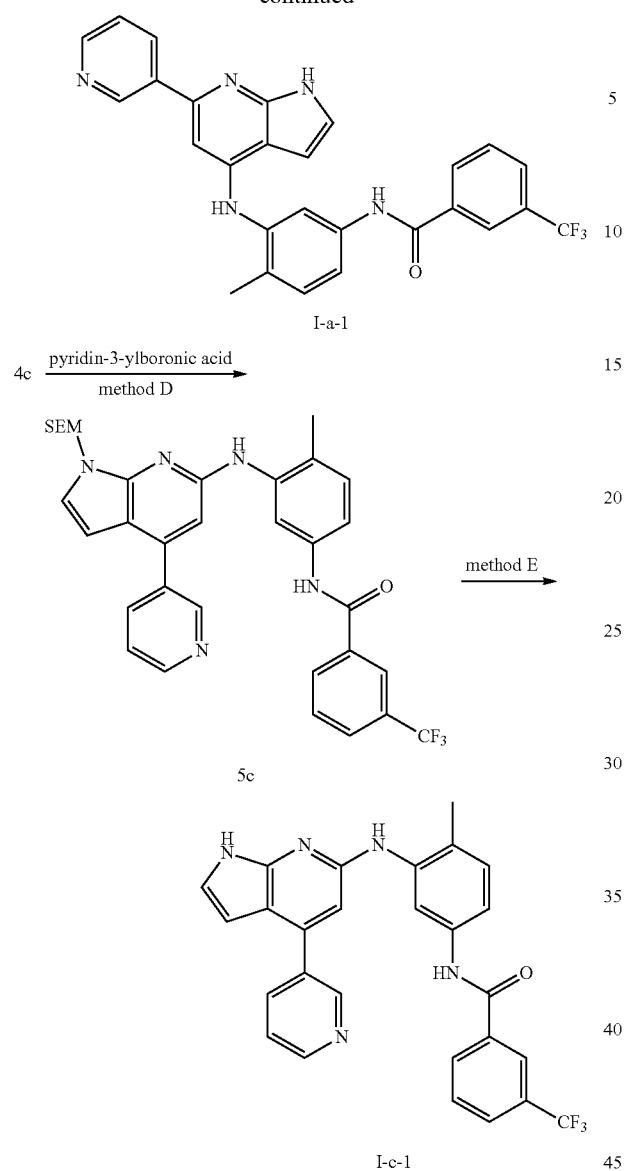

Synthesis of Compound 2a:

Method A: compound 1 (6 g, 32 mmol) was dissolved in 30 mL of dried N,N-dimethylformamide, and stirred in an ice-water bath for 10 min, to which was added sodium hydride (1.9 g, 48 mmol) in portions, followed by stirring for 15 min, then to the reaction system was added dropwise 2-(trimethylsilyl) ethoxymethyl chloride (6.8 mL, 38.4 mmol), followed by stirring at room temperature until complete reaction (monitored by LC-MS). After the reaction was stopped, 300 mL of water and 250 mL of ethyl acetate were added slowly to the reaction solution under low temperature conditions, the solution was separated, the organic phase was washed with water twice, dried with anhydrous sodium sulfate, filtered, concentrated and separated by silica gel column chromatography (petroleum ether), to obtain compound 2 (colorless liquid, 8.79 g, 87% yield).

MS (ESI) m/z: 318 [M+H]$^+$.

Synthesis of Compound 2b:

From compound 1 (187 mg, 1.0 mmol) and methyl iodide (124 μL, 2.0 mmol), through Method A, 2 (200 mg, 100% yield) was obtained.

MS (ESI) m/z: 202 [M+H]$^+$.

Synthesis of Compounds 4a, 4c:

Method B: compound 2a (500 mg, 1.58 mmol), arylamine compound 3 (465 mg, 1.58 mmol), tri(dibenzylideneacetone) dipalladium (72 mg, 0.08 mmol), 2-dicyclohexylphosphino-2',4',6'-triisopropylbiphenyl (57 mg, 0.12 mmol) and potassium carbonate (654 mg, 4.74 mmol) were dispersed in t-butanol, air was replaced with nitrogen, followed by heating in an oil bath preheated to 100° C. with stirring until complete reaction (monitored by TLC). After the reaction stopped, the system was cooled and filtered to remove solids, the filter cake was rinsed with MeOH, and the filtrate was collected, concentrated, and separated by silica gel column chromatography, to obtain compounds 4a (540 mg, 60% yield) and 4c (77 mg, 8.5% yield).

MS (ESI) m/z: 575 [M+H]$^+$.

Synthesis of Compound 4b:

Method C: compounds 2b (201 mg, 1 mmol) and 3 (294 mg, 1 mmol) were heated at 85° C. in t-butanol (5 mL) under the action of trifluoroacetic acid (89 μL, 1.2 mmol) until complete reaction (monitored by LC-MS). After cooling, ethyl acetate (50 mL) was added, the system was washed with saturated sodium bicarbonate twice, dried with anhydrous sodium sulfate, filtered, concentrated and separated by silica gel column chromatography (petroleum ether/ethyl acetate) to obtain compound 4b (280 mg, 61% yield).

MS (ESI) m/z: 459 [M+H]$^+$.

Synthesis of Compound 5a:

Method D: compound 4a (288 mg, 0.5 mmol), 3-pyridineboronic acid (73 mg, 0.6 mmol), PdCl$_2$ (dppf).CH$_2$Cl$_2$ (41 mg, 0.05 mmol) and Na$_2$CO$_3$ (265 mg, 2.5 mmol) were dispersed in 1,4-dioxane/H$_2$O (4/1 mL) in a reaction bottle, air was replaced with nitrogen, followed by heating at 100° C. until complete reaction (monitored by LC-MS). The reaction solution was filtered to remove insolubles, and the filtrate was concentrated, and purified by silica gel column chromatography to obtain the target product 5a (500 mg, 81% yield).

MS (ESI) m/z: 618 [M+H]$^+$.

Synthesis of Compound I-a-1:

Method E: compound 5a (200 mg, 0.32 mmol) was stirred in TFA (2 mL) at room temperature until complete reaction (monitored by LC-MS), concentrated, to which was added MeOH/THF/LiOH (1 M aq.) (2/2/2 mL), followed by stirring at room temperature until complete reaction (monitored by LC-MS). The precipitated solid was filtered, washed with water, and dried to obtain the target product 142 mg, in 91% yield.

Compound I-b-1 was synthesized from 4b through Method D; compound I-c-1 was synthesized from 4c through Method D, Method E.

Other such compounds could be synthesized by similar methods.

In the following table it lists the specific compounds and their structural characterization data.

| No. | Structure | ¹H NMR and/or MS data |
|---|---|---|
| I-a-1 | 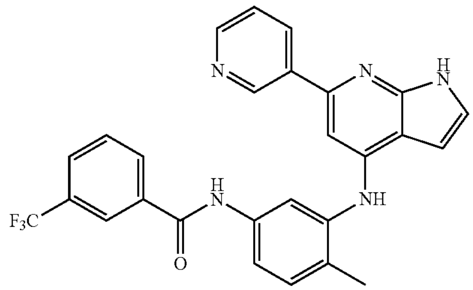 [SMILES: Cc1ccc(NC(=O)c2cccc(C(F)(F)F)c2)cc1Nc1cc(-c2cccnc2)nc2[nH]ccc12] | ¹H NMR (600 MHz, DMSO-d$_6$): δ 11.49 (s, 1H), 10.47 (s, 1H), 9.09 (d, J = 1.8 Hz, 1H), 8.52 (dd, J = 4.7, 1.6 Hz, 1H), 8.35 (s, 1H), 8.28 (s, 1H), 8.26-8.21 (m, 2H), 7.95 (d, J = 7.8 Hz, 1H), 7.88 (d, J = 2.0 Hz, 1H), 7.77 (t, J = 7.8 Hz, 1H), 7.57 (dd, J = 8.3, 2.1 Hz, 1H), 7.43 (dd, J = 7.9, 4.7 Hz, 1H), 7.34 (d, J = 8.4 Hz, 1H), 7.23 (dd, J = 3.3, 2.5 Hz, 1H), 6.78 (s, 1H), 6.54 (dd, J = 3.4, 2.0 Hz, 1H), 2.25 (s, 3H). MS (ESI) m/z: 488 [M + H]$^+$. |
| I-a-2 | 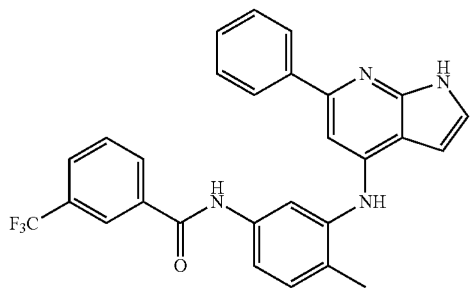 [SMILES: Cc1ccc(NC(=O)c2cccc(C(F)(F)F)c2)cc1Nc1cc(-c2ccccc2)nc2[nH]ccc12] | ¹H NMR (600 MHz, DMSO-d$_6$) δ 11.39 (s, 1H), 10.45 (s, 1H), 8.27 (s, 2H), 8.25 (d, J = 7.9 Hz, 1H), 7.95 (d, J = 7.8 Hz, 1H), 7.91 (d, J = 1.3 Hz, 1H), 7.89 (s, 1H), 7.85 (d, J = 2.0 Hz, 1H), 7.77 (t, J = 7.8 Hz, 1H), 7.58 (dd, J = 8.2, 2.1 Hz, 1H), 7.40 (t, J = 7.7 Hz, 2H), 7.32 (dd, J = 15.2, 7.9 Hz, 2H), 7.19 (dd, J = 3.3, 2.5 Hz, 1H), 6.73 (s, 1H), 6.50 (dd, J = 3.4, 2.0 Hz, 1H), 2.24 (s, 3H). MS (ESI) m/z: 487 [M + H]$^+$. |
| I-a-3 | 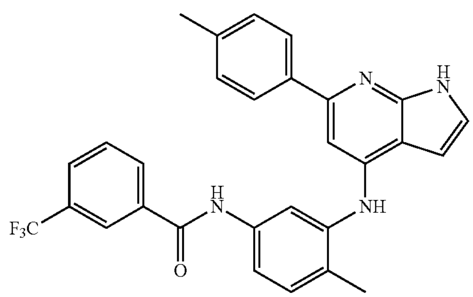 [SMILES: Cc1ccc(-c2cc(Nc3cc(NC(=O)c4cccc(C(F)(F)F)c4)ccc3C)c3cc[nH]c3n2)cc1] | ¹H NMR (600 MHz, DMSO-d$_6$) δ 12.14 (s, 1H), 10.62 (s, 1H), 10.10 (s, 1H), 8.29 (d, J = 2.1 Hz, 1H), 8.27 (d, J = 7.9 Hz, 1H), 7.98 (d, J = 7.8 Hz, 1H), 7.94 (d, J = 2.1 Hz, 1H), 7.79 (t, J = 7.8 Hz, 1H), 7.69-7.65 (m, 3H), 7.45 (d, J = 8.4 Hz, 1H), 7.42-7.31 (m, 3H), 6.55 (s, 1H), 2.38 (s, 3H), 2.24 (s, 3H). MS (ESI) m/z: 501 [M + H]$^+$. |
| I-a-4 | 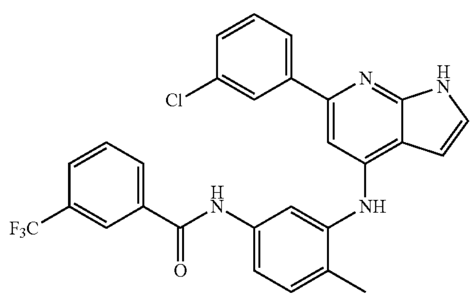 [SMILES: Cc1ccc(NC(=O)c2cccc(C(F)(F)F)c2)cc1Nc1cc(-c2cccc(Cl)c2)nc2[nH]ccc12] | ¹H NMR (600 MHz, DMSO-d$_6$) δ 11.44 (s, 1H), 10.47 (s, 1H), 8.30 (d, J = 6.5 Hz, 2H), 8.27 (d, J = 7.9 Hz, 1H), 8.03 (s, 1H), 7.95 (d, J = 7.6 Hz, 1H), 7.92 (s, 1H), 7.84 (d, J = 7.6 Hz, 1H), 7.78 (d, J = 7.9 Hz, 1H), 7.53 (d, J = 8.2 Hz, 1H), 7.43 (t, J = 7.9 Hz, 1H), 7.38 (d, J = 7.9 Hz, 1H), 7.33 (d, J = 8.3 Hz, 1H), 7.22 (s, 1H), 6.83 (s, 1H), 6.54 (s, 1H), 2.25 (s, 3H). MS (ESI) m/z: 521 [M + H]$^+$. |
| I-a-5 | 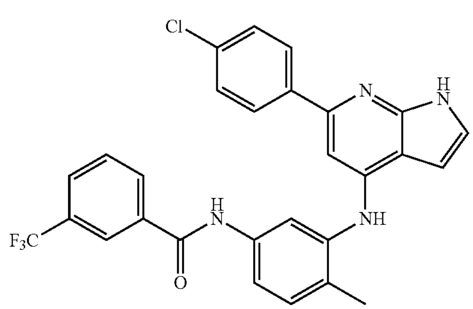 [SMILES: Cc1ccc(NC(=O)c2cccc(C(F)(F)F)c2)cc1Nc1cc(-c2ccc(Cl)cc2)nc2[nH]ccc12] | ¹H NMR (600 MHz, DMSO-d$_6$) δ 11.43 (s, 1H), 10.47 (s, 1H), 8.32 (s, 1H), 8.29 (s, 1H), 8.26 (d, J = 7.9 Hz, 1H), 7.96-7.91 (m, 3H), 7.87 (d, J = 2.0 Hz, 1H), 7.77 (t, J = 7.8 Hz, 1H), 7.59 (dd, J = 8.3, 2.1 Hz, 1H), 7.47-7.43 (m, 2H), 7.34 (d, J = 8.4 Hz, 1H), 7.23-7.19 (m, 1H), 6.75 (s, 1H), 6.53 (dd, J = 3.4, 2.0 Hz, 1H), 2.24 (s, 3H). MS (ESI) m/z: 521 [M + H]$^+$. |

-continued

| No. | Structure | ¹H NMR and/or MS data |
|---|---|---|
| I-a-6 | 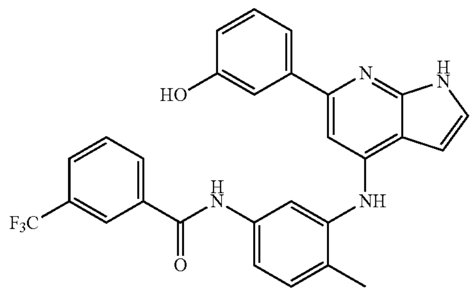 | ¹H NMR (600 MHz, DMSO-d$_6$) δ 11.35 (s, 1H), 10.45 (s, 1H), 9.36 (s, 1H), 8.27 (s, 2H), 8.24 (d, J = 8.0 Hz, 1H), 7.95 (d, J = 7.8 Hz, 1H), 7.82 (d, J = 2.1 Hz, 1H), 7.77 (t, J = 7.8 Hz, 1H), 7.61 (dd, J = 8.3, 2.1 Hz, 1H), 7.33 (dd, J = 6.0, 3.9 Hz, 2H), 7.30-7.27 (m, 1H), 7.19-7.16 (m, 2H), 6.70 (ddd, J = 8.0, 2.5, 0.9 Hz, 1H), 6.63 (s, 1H), 6.49 (dd, J = 3.4, 2.1 Hz, 1H), 2.23 (s, 3H). MS (ESI) m/z: 503 [M + H]⁺. |
| I-a-7 | TFA salt | ¹H NMR (600 MHz, DMSO-d$_6$) δ 12.18 (s, 1H), 10.64 (s, 1H), 10.38-10.17 (m, 1H), 10.05 (s, 1H), 8.30 (d, J = 2.0 Hz, 1H), 8.27 (d, J = 7.9 Hz, 1H), 7.98 (d, J = 7.8 Hz, 1H), 7.93 (d, J = 2.1 Hz, 1H), 7.79 (t, J = 7.8 Hz, 1H), 7.71 (dd, J = 8.3, 2.2 Hz, 1H), 7.66-7.61 (m, 2H), 7.45 (d, J = 8.3 Hz, 1H), 7.33 (s, 1H), 6.98-6.92 (m, 2H), 6.77-6.60 (m, 1H), 6.48 (s, 1H), 2.24 (s, 3H). MS (ESI) m/z: 503 [M + H]⁺. |
| I-a-8 | 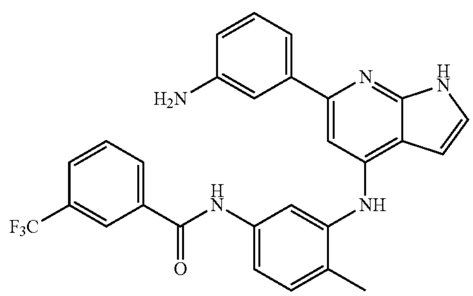 | ¹H NMR (600 MHz, DMSO-d$_6$) δ 11.30 (s, 1H), 10.44 (s, 1H), 8.27 (s, 1H), 8.24 (d, J = 8.2 Hz, 1H), 8.21 (s, 1H), 7.95 (d, J = 7.9 Hz, 1H), 7.80 (d, J = 2.0 Hz, 1H), 7.76 (t, J = 7.8 Hz, 1H), 7.60 (dd, J = 8.3, 2.1 Hz, 1H), 7.32 (d, J = 8.5 Hz, 1H), 7.15 (t, J = 2.9 Hz, 2H), 7.02 (dd, J = 12.2, 4.8 Hz, 2H), 6.62 (s, 1H), 6.51 (dt, J = 7.1, 2.1 Hz, 1H), 6.48 (dd, J = 3.4, 2.1 Hz, 1H), 2.23 (s, 3H). MS (ESI) m/z: 502 [M + H]⁺. |
| I-a-9 | 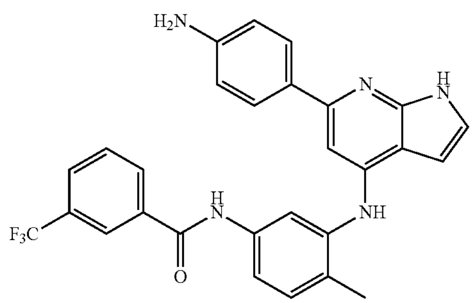 [SMILES: Cc1ccc(NC(=O)c2cccc(C(F)(F)F)c2)cc1Nc1cc(-c2ccc(N)cc2)nc2[nH]ccc12] | ¹H NMR (600 MHz, DMSO-d$_6$) δ 11.21 (s, 1H), 10.45 (s, 1H), 8.28 (s, 1H), 8.25 (d, J = 8.0 Hz, 1H), 8.11 (s, 1H), 7.95 (dd, J = 7.8, 0.7 Hz, 1H), 7.82 (d, J = 2.1 Hz, 1H), 7.77 (t, J = 7.8 Hz, 1H), 7.62-7.59 (m, 2H), 7.58 (dd, J = 8.3, 2.1 Hz, 1H), 7.32 (d, J = 8.5 Hz, 1H), 7.09 (dd, J = 3.4, 2.5 Hz, 1H), 6.60 (s, 1H), 6.59-6.55 (m, 2H), 6.44 (dd, J = 3.4, 2.0 Hz, 1H), 5.19 (s, 2H), 2.23 (s, 3H). MS (ESI) m/z: 502 [M + H]⁺. |
| I-a-10 | 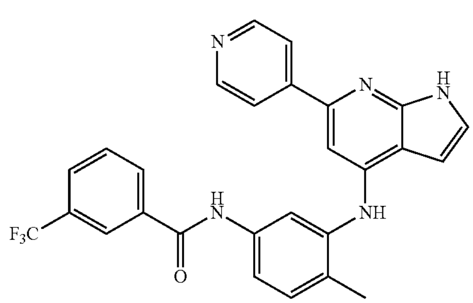 [SMILES: Cc1ccc(NC(=O)c2cccc(C(F)(F)F)c2)cc1Nc1cc(-c2ccncc2)nc2[nH]ccc12] | ¹H NMR (600 MHz, DMSO-d$_6$) δ 11.54 (s, 1H), 10.47 (s, 1H), 8.59 (d, J = 6.0 Hz, 2H), 8.40 (s, 1H), 8.28 (s, 1H), 8.26 (d, J = 7.9 Hz, 1H), 7.96 (d, J = 7.6 Hz, 1H), 7.89-7.84 (m, 3H), 7.78 (t, J = 7.8 Hz, 1H), 7.59 (d, J = 6.2 Hz, 1H), 7.35 (d, J = 8.3 Hz, 1H), 7.27 (d, J = 2.9 Hz, 1H), 6.87 (d, J = 5.6 Hz, 1H), 6.55 (s, 1H), 2.24 (s, 3H). MS (ESI) m/z: 488 [M + H]⁺. |

-continued

| No. | Structure | ¹H NMR and/or MS data |
|---|---|---|
| I-a-11 | 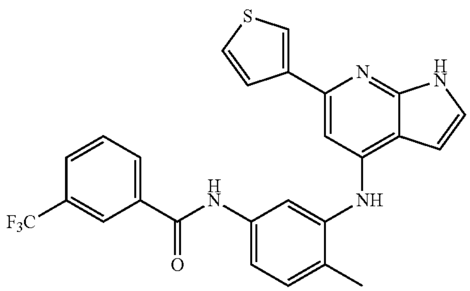 [SMILES: Cc1ccc(NC(=O)c2cccc(C(F)(F)F)c2)cc1Nc1cc(-c2ccsc2)nc2[nH]ccc12] | ¹H NMR (600 MHz, DMSO-$d_6$) δ 11.35 (s, 1H), 10.46 (s, 1H), 8.28 (s, 1H), 8.25 (d, J = 7.9 Hz, 1H), 8.21 (s, 1H), 7.95 (d, J = 7.8 Hz, 1H), 7.84-7.82 (m, 2H), 7.77 (t, J = 7.8 Hz, 1H), 7.58-7.55 (m, 2H), 7.54 (dd, J = 5.0, 3.0 Hz, 1H), 7.32 (d, J = 8.5 Hz, 1H), 7.15 (dd, J = 3.3, 2.5 Hz, 1H), 6.71 (s, 1H), 6.49 (dd, J = 3.2, 2.1 Hz, 1H), 2.24 (s, 3H). MS (ESI) m/z: 493 [M + H]⁺. |
| I-a-12 | 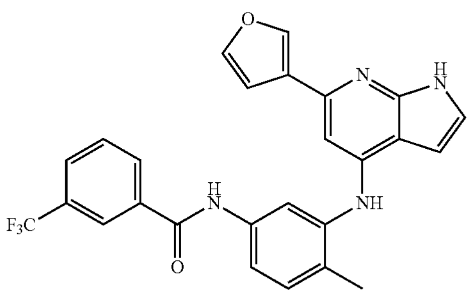 [SMILES: Cc1ccc(NC(=O)c2cccc(C(F)(F)F)c2)cc1Nc1cc(-c2ccoc2)nc2[nH]ccc12] | ¹H NMR (600 MHz, DMSO-$d_6$) δ 11.33 (s, 1H), 10.46 (s, 1H), 8.29 (s, 1H), 8.26 (d, J = 8.0 Hz, 1H), 8.18 (s, 1H), 8.07 (s, 1H), 7.95 (d, J = 7.9 Hz, 1H), 7.83 (s, 1H), 7.77 (t, J = 7.8 Hz, 1H), 7.68 (s, 1H), 7.55 (d, J = 8.0 Hz, 1H), 7.31 (d, J = 8.3 Hz, 1H), 7.14 (s, 1H), 6.87 (s, 1H), 6.64-6.59 (m, 1H), 6.49 (s, 1H), 2.24 (s, 3H). MS (ESI) m/z: 477 [M + H]⁺. |
| I-a-13 | 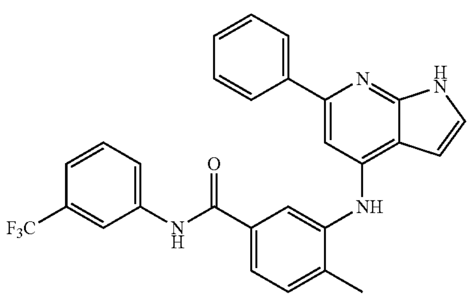 [SMILES: Cc1ccc(C(=O)Nc2cccc(C(F)(F)F)c2)cc1Nc1cc(-c2ccccc2)nc2[nH]ccc12] | ¹H NMR (600 MHz, DMSO-$d_6$) δ 11.43 (s, 1H), 10.48 (s, 1H), 8.44 (s, 1H), 8.22 (s, 1H), 8.05 (d, J = 8.9 Hz, 1H), 7.96 (d, J = 1.7 Hz, 1H), 7.86-7.82 (m, 3H), 7.57 (t, J = 8.0 Hz, 1H), 7.53 (d, J = 8.2 Hz, 1H), 7.43 (d, 1H), 7.40 (dd, J = 10.8, 4.5 Hz, 2H), 7.33-7.29 (m, 1H), 7.20 (dd, J = 3.4, 2.5 Hz, 1H), 6.65 (s, 1H), 6.40 (dd, J = 3.4, 2.0 Hz, 1H), 2.34 (s, 3H). MS (ESI) m/z: 487 [M + H]⁺. |
| I-a-14 | 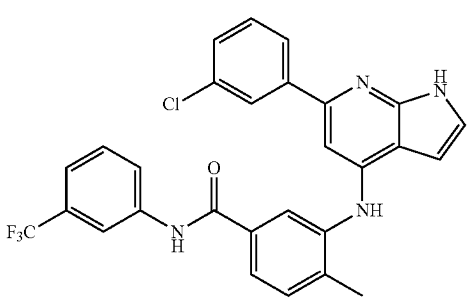 | ¹H NMR (600 MHz, DMSO-$d_6$) δ 11.48 (s, 1H), 10.48 (s, 1H), 8.48 (s, 1H), 8.22 (s, 1H), 8.04 (d, J = 9.2 Hz, 1H), 7.96 (d, J = 1.8 Hz, 1H), 7.95 (t, J = 1.9 Hz, 1H), 7.84 (dd, J = 7.9, 1.9 Hz, 1H), 7.77-7.72 (m, 1H), 7.57 (t, J = 8.0 Hz, 1H), 7.53 (d, J = 8.1 Hz, 1H), 7.45-7.41 (m, 2H), 7.38 (ddd, J = 8.0, 2.2, 1.1 Hz, 1H), 7.23 (dt, J = 5.4, 2.7 Hz, 1H), 6.68 (s, 1H), 6.39 (dd, J = 3.4, 2.1 Hz, 1H), 2.33 (s, 3H). MS (ESI) m/z: 521 [M + H]⁺. |
| I-a-15 | TFA salt | ¹H NMR (600 MHz, DMSO-$d_6$) δ 12.28 (s, 1H), 10.56 (s, 1H), 10.05 (s, 1H), 8.22 (s, 1H), 8.06 (d, J = 8.3 Hz, 1H), 8.02 (dd, J = 11.0, 3.1 Hz, 2H), 7.78 (d, J = 8.6 Hz, 2H), 7.62 (d, J = 8.5 Hz, 3H), 7.59 (t, J = 8.1 Hz, 1H), 7.44 (d, J = 7.7 Hz, 1H), 7.37 (s, 1H), 6.61 (s, 1H), 6.52 (s, 1H), 2.33 (s, 3H). MS (ESI) m/z: 521 [M + H]⁺. |

| No. | Structure | ¹H NMR and/or MS data |
|---|---|---|
| I-a-16 | 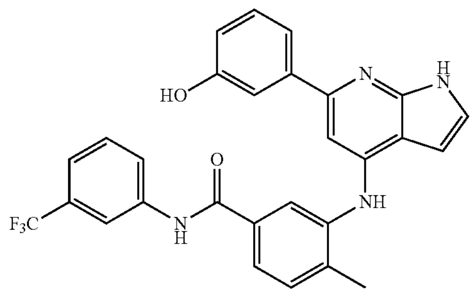 [SMILES: Cc1ccc(C(=O)Nc2cccc(C(F)(F)F)c2)cc1Nc1cc(-c2cccc(Cl)c2)nc2[nH]ccc12] | ¹H NMR (600 MHz, DMSO-d₆) δ 11.40 (s, 1H), 10.48 (s, 1H), 9.38 (s, 1H), 8.42 (s, 1H), 8.22 (s, 1H), 8.05 (d, J = 8.3 Hz, 1H), 7.95 (d, J = 1.3 Hz, 1H), 7.84 (dd, J = 7.9, 1.6 Hz, 1H), 7.57 (t, J = 8.0 Hz, 1H), 7.53 (d, J = 8.0 Hz, 1H), 7.43 (d, J = 7.6 Hz, 1H), 7.31 (s, 1H), 7.25 (d, J = 7.8 Hz, 1H), 7.20-7.15 (m, 2H), 6.71 (dd, J = 7.9, 1.8 Hz, 1H), 6.57 (s, 1H), 6.40 (dd, J = 3.2, 2.0 Hz, 1H), 2.33 (s, 3H). MS (ESI) m/z: 503 [M + H]⁺. |
| I-a-17 | 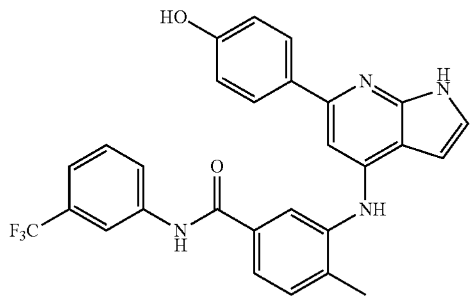 [SMILES: Cc1ccc(C(=O)Nc2cccc(C(F)(F)F)c2)cc1Nc1cc(-c2ccc(O)cc2)nc2[nH]ccc12] | ¹H NMR (600 MHz, DMSO-d₆) δ 11.33 (s, 1H), 10.48 (s, 1H), 9.51 (s, 1H), 8.35 (s, 1H), 8.23 (s, 1H), 8.05 (d, J = 8.2 Hz, 1H), 7.95 (d, J = 1.7 Hz, 1H), 7.83 (dd, J = 7.9, 1.8 Hz, 1H), 7.69-(m, 2H), 7.58 (t, J = 10.0, 6.0 Hz, 1H), 7.52 (d, J = 8.1 Hz, 1H), 7.43 (dd, J = 7.7, 0.8 Hz, 1H), 7.14 (dd, J = 3.4, 2.5 Hz, 1H), 6.79 (d, J = 8.8 Hz, 2H), 6.56 (s, 1H), 6.37 (dd, J = 3.4, 2.0 Hz, 1H), 2.33 (s, 3H). MS (ESI) m/z: 503 [M + H]⁺. |
| I-a-18 | 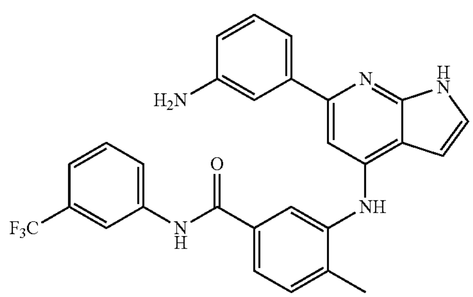 [SMILES: Cc1ccc(C(=O)Nc2cccc(C(F)(F)F)c2)cc1Nc1cc(-c2cccc(N)c2)nc2[nH]ccc12] | ¹H NMR (600 MHz, DMSO-d₆) δ 11.34 (s, 1H), 10.47 (s, 1H), 8.38 (s, 1H), 8.22 (s, 1H), 8.04 (d, J = 8.3 Hz, 1H), 7.93 (d, J = 1.6 Hz, 1H), 7.83 (dd, J = 7.9, 1.7 Hz, 1H), 7.57 (t, J = 8.0 Hz, 1H), 7.52 (d, J = 8.1 Hz, 1H), 7.43 (d, J = 7.8 Hz, 1H), 7.17 (dd, J = 3.3, 2.6 Hz, 1H), 7.12 (t, J = 1.8 Hz, 1H), 7.02 (t, J = 7.7 Hz, 1H), 6.95 (d, J = 7.8 Hz, 1H), 6.55 (s, 1H), 6.51 (dd, J = 7.8, 1.3 Hz, 1H), 6.37 (dd, J = 3.4, 2.0 Hz, 1H), 5.07 (s, 2H), 2.32 (s, 3H). MS (ESI) m/z: 502 [M + H]⁺. |
| I-a-19 | TFA salt | ¹H NMR (600 MHz, DMSO-d₆) δ 11.25 (s, 1H), 10.48 (s, 1H), 8.31 (s, 1H), 8.22 (s, 1H), 8.05 (d, J = 8.9 Hz, 1H), 7.93 (d, J = 1.7 Hz, 1H), 7.81 (dd, J = 7.9, 1.7 Hz, 1H), 7.58 (d, J = 7.9 Hz, 1H), 7.57-7.53 (m, 2H), 7.51 (d, J = 8.2 Hz, 1H), 7.43 (dd, J = 7.7, 0.8 Hz, 1H), 7.10 (dd, J = 3.4, 2.5 Hz, 1H), 6.59-6.54 (m, 2H), 6.52 (s, 1H), 6.33 (s, 1H), 5.22 (s, 2H), 2.33 (s, 3H). MS (ESI) m/z: 502 [M + H]⁺. |
| I-a-20 | 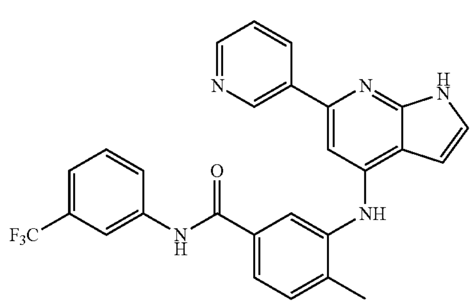 [SMILES: Cc1ccc(C(=O)Nc2cccc(C(F)(F)F)c2)cc1Nc1cc(-c2cccnc2)nc2[nH]ccc12] | ¹H NMR (600 MHz, DMSO-d₆): δ 11.52 (s, 1H), 10.48 (s, 1H), 9.04 (d, J = 2.1 Hz, 1H), 8.52 (t, J = 3.0 Hz, 2H), 8.22 (s, 1H), 8.17 (tt, J = 8.0, 1.9 Hz, 1H), 8.05 (d, J = 8.5 Hz, 1H), 7.97 (d, J = 1.5 Hz, 1H), 7.85 (dd, J = 7.9, 1.7 Hz, 1H), 7.57 (t, J = 8.0 Hz, 1H), 7.53 (d, J = 8.0 Hz, 1H), 7.43 (dd, J = 7.6, 5.0 Hz, 2H), 7.26-7.18 (m, 1H), 6.68 (s, 1H), 6.41 (dd, J = 3.3, 2.1 Hz, 1H), 2.34 (s, 3H). MS (ESI) m/z: 488 [M + H]⁺. |

-continued

| No. | Structure | ¹H NMR and/or MS data |
|---|---|---|
| I-a-21 | 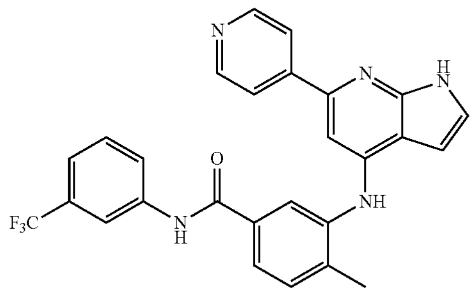 [SMILES: Cc1ccc(C(=O)Nc2cccc(C(F)(F)F)c2)cc1Nc1cc(-c2ccncc2)nc2[nH]ccc12] | ¹H NMR (600 MHz, DMSO-$d_6$) δ 11.58 (s, 1H), 10.49 (s, 1H), 8.59 (d, J = 4.6 Hz, 2H), 8.56 (s, 1H), 8.22 (s, 1H), 8.05 (d, J = 8.5 Hz, 1H), 7.97 (d, J = 1.6 Hz, 1H), 7.86 (dd, J = 7.9, 1.7 Hz, 1H), 7.81 (d, J = 5.4 Hz, 2H), 7.57 (t, J = 8.0 Hz, 1H), 7.54 (d, J = 8.0 Hz, 1H), 7.43 (d, J = 7.8 Hz, 1H), 7.29-7.26 (m, 1H), 6.76 (s, 1H), 6.43 (dd, J = 3.4, 2.0 Hz, 1H), 2.33 (s, 3H). MS (ESI) m/z: 488 [M + H]⁺. |
| I-a-22 | 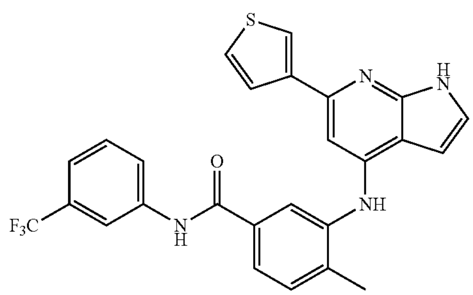 [SMILES: Cc1ccc(C(=O)Nc2cccc(C(F)(F)F)c2)cc1Nc1cc(-c2ccsc2)nc2[nH]ccc12] | ¹H NMR (600 MHz, DMSO-$d_6$) δ 11.39 (s, 1H), 10.47 (s, 1H), 8.37 (s, 1H), 8.22 (s, 1H), 8.05 (d, J = 8.3 Hz, 1H), 7.94 (d, J = 1.7 Hz, 1H), 7.83 (dd, J = 7.9, 1.8 Hz, 1H), 7.77 (dd, J = 2.5, 1.7 Hz, 1H), 7.58 (t, J = 8.0 Hz, 1H), 7.53 (t, 2H), 7.52 (d, J = 8.2 Hz, 1H), 7.43 (d, J = 7.7 Hz, 1H), 7.16 (dd, J = 3.4, 2.5 Hz, 1H), 6.61 (s, 1H), 6.37 (dd, J = 3.4, 2.0 Hz, 1H), 2.33 (s, 3H). MS (ESI) m/z: 493 [M + H]⁺. |
| I-a-23 | 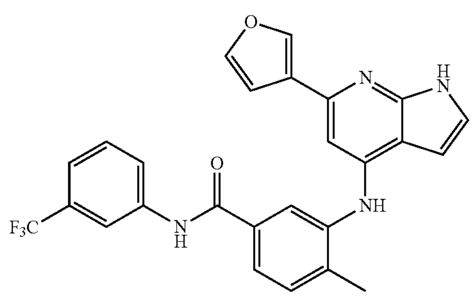 [SMILES: Cc1ccc(C(=O)Nc2cccc(C(F)(F)F)c2)cc1Nc1cc(-c2ccoc2)nc2[nH]ccc12] | ¹H NMR (600 MHz, DMSO-$d_6$) δ 11.36 (s, 1H), 10.47 (s, 1H), 8.34 (s, 1H), 8.22 (s, 1H), 8.05 (d, J = 8.2 Hz, 1H), 8.02 (s, 1H), 7.93 (d, J = 1.6 Hz, 1H), 7.82 (dd, J = 7.9, 1.7 Hz, 1H), 7.67 (t, J = 1.7 Hz, 1H), 7.58 (t, J = 8.1 Hz, 1H), 7.51 (d, J = 8.0 Hz, 1H), 7.43 (d, J = 7.7 Hz, 1H), 7.16-7.12 (m, 1H), 6.81 (d, J = 1.0 Hz, 1H), 6.47 (s, 1H), 6.34 (dd, J = 3.3, 2.0 Hz, 1H), 2.32 (s, 3H). MS (ESI) m/z: 477 [M + H]⁺. |
| I-a-24 | TFA salt | ¹H NMR (600 MHz, DMSO-$d_6$) δ 12.27 (s, 1H), 10.56 (s, 1H), 9.81 (s, 1H), 9.08 (d, J = 2.2 Hz, 1H), 8.79 (dd, J = 5.1, 1.4 Hz, 1H), 8.41 (d, J = 8.1 Hz, 1H), 8.22 (d, J = 2.2 Hz, 1H), 8.10 (dd, J = 8.5, 2.2 Hz, 1H), 8.04 (d, J = 1.8 Hz, 1H), 7.99 (dd, J = 8.0, 1.8 Hz, 1H), 7.75 (dd, J = 8.1, 5.1 Hz, 1H), 7.71 (d, J = 8.5 Hz, 1H), 7.61 (d, J = 8.1 Hz, 1H), 7.39 (t, J = 2.9 Hz, 1H), 6.66 (s, 1H), 6.60-6.46 (m, 1H), 3.73 (s, 2H), 3.46-3.37 (m, 2H), 3.15-3.01 (m, 2H), 3.01-2.87 (m, 2H), 2.82 (s, 3H), 2.53-2.42 (m, 2H), 2.35 (s, 3H). MS (ESI) m/z: 600 [M + H]⁺. |

-continued

| No. | Structure | ¹H NMR and/or MS data |
|---|---|---|
| I-a-25 | 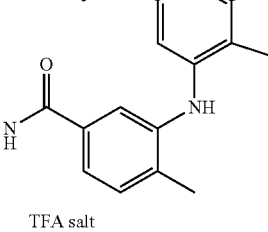 TFA salt | ¹H NMR (600 MHz, DMSO-d₆) δ 11.93 (s, 1H), 10.52 (s, 1H), 9.03 (s, 1H), 8.85 (d, J = 6.5 Hz, 2H), 8.32 (d, J = 6.5 Hz, 2H), 8.21 (d, J = 2.1 Hz, 1H), 8.09 (dd, J = 8.5, 1.8 Hz, 1H), 7.99 (d, J = 1.6 Hz, 1H), 7.92 (dd, J = 7.9, 1.7 Hz, 1H), 7.69 (d, J = 8.6 Hz, 1H), 7.57 (d, J = 8.2 Hz, 1H), 7.45-7.39 (m, 1H), 6.91 (s, 1H), 6.51 (s, 1H), 3.70 (s, 2H), 3.40 (s, 2H), 3.05 (s, 2H), 2.93 (s, 2H), 2.80 (s, 3H), 2.44 (s, 2H), 2.33 (s, 3H). MS (ESI) m/z: 600 [M + H]⁺. |
| I-a-26 | 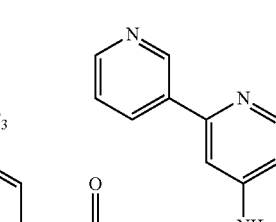 | ¹H NMR (600 MHz, Acetone) δ 7.71 (s, 1H), 7.31 (s, 1H), 7.00 (d, J = 8.0 Hz, 1H), 6.82 (s, 1H), 6.73 (s, 1H), 6.69 (s, 1H), 6.53 (d, J = 7.6 Hz, 1H), 6.33 (d, J = 8.6 Hz, 2H), 6.27 (dd, J = 14.7, 6.9 Hz, 3H), 6.14 (s, 2H), 6.00 (d, J = 3.5 Hz, 1H), 5.84 (s, 1H), 5.39 (d, J = 3.3 Hz, 1H), 2.39 (s, 2H), 2.09 (br. s, 8H), 1.59 (s, 3H). MS (ESI) m/z: 586 [M + H]⁺. |
| I-a-27 | 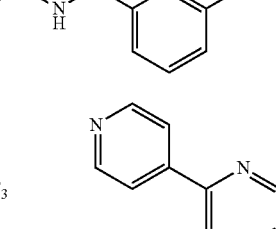 | ¹H NMR (600 MHz, DMSO-d₆) ¹H NMR (600 MHz, DMSO-d₆) δ 11.68 (s, 1H), 10.60 (s, 1H), 9.07 (s, 1H), 8.63 (d, J = 5.1 Hz, 1H), 8.18 (s, 1H), 8.05 (s, 1H), 7.96 (s, 1H), 7.94 (d, J = 5.2 Hz, 2H), 7.70 (d, J = 7.6 Hz, 1H), 7.63 (d, J = 8.1 Hz, 1H), 7.57 (t, J = 7.8 Hz, 1H), 7.42 (s, 1H), 7.37 (d, J = 5.1 Hz, 2H), 6.68-6.65 (m, 1H), 3.58 (s, 2H), 3.55-3.52 (m, 4H), 2.57 (br. s, 2H), 2.48-2.42 (m, 2H), 2.34 (s, 3H). MS (ESI) m/z: 586 [M + H]⁺. |
| I-a-28 | 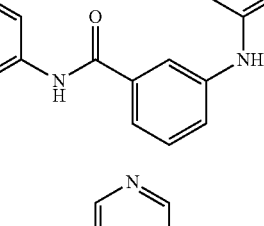 TFA salt | ¹H NMR (600 MHz, DMSO-d₆) δ 12.19 (s, 1H), 10.59 (s, 1H), 9.66 (s, 1H), 9.07 (s, 1H), 8.75 (s, 1H), 8.37 (d, J = 7.4 Hz, 1H), 8.13 (d, J = 6.2 Hz, 2H), 8.03 (d, J = 1.5 Hz, 1H), 8.00-7.95 (m, 1H), 7.72 (d, J = 7.1 Hz, 1H), 7.61 (d, J = 8.1 Hz, 1H), 7.46 (s, 1H), 7.39-7.35 (m, 1H), 6.67 (s, 1H), 6.48 (d, J = 3.6 Hz, 1H), 4.33 (s, 2H), 3.82 (s, 2H), 3.50 (s, 2H), 3.15 (s, 2H), 2.80 (s, 3H), 2.35 (s, 3H), 2.34 (s, 2H). MS (ESI) m/z: 479 [M + H]⁺. |
| I-a-29 | 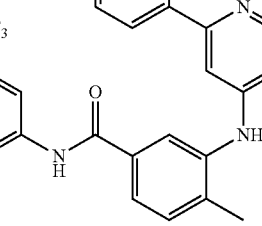 | ¹H NMR (600 MHz, DMSO-d₆) δ 11.58 (s, 1H), 10.54 (d, J = 28.0 Hz, 1H), 8.71-8.50 (m, 3H), 8.16 (s, 1H), 8.03-7.96 (m, 2H), 7.87 (dd, J = 8.0, 1.6 Hz, 1H), 7.84-7.81 (m, 2H), 7.53 (d, J = 8.1 Hz, 1H), 7.34 (s, 1H), 7.27 (dd, J = 8.6, 5.7 Hz, 1H), 6.85-6.68 (m, 1H), 6.47-6.44 (m, 1H), 3.54 (s, 2H), 3.49-3.40 (m, 8H) 2.34 (s, 3H), 2.30 (s, 3H). MS (ESI) m/z: 600 [M + H]⁺. |

-continued

| No. | Structure | ¹H NMR and/or MS data |
|---|---|---|
| I-a-30 | 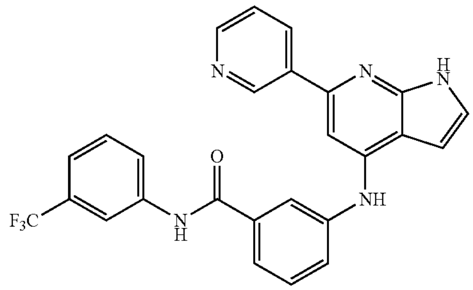 [SMILES: O=C(Nc1cccc(C(F)(F)F)c1)c1cccc(Nc2cc(-c3cccnc3)nc3[nH]ccc23)c1] | ¹H NMR (600 MHz, DMSO-d₆) δ 10.58 (s, 1H), 9.16 (s, 1H), 8.62 (s, 1H), 8.38 (d, J = 8.4 Hz, 1H), 8.25 (s, 1H), 8.06 (d, J = 8.7 Hz, 1H), 7.95 (s, 1H), 7.70 (d, J = 7.6 Hz, 1H), 7.66- 7.63 (m, 1H), 7.62-7.57 (m, 2H), 7.46 (d, J = 7.7 Hz, 1H), 7.35-7.33 (m, 1H), 7.31 (s, 1H), 7.18 (s, 1H), 7.10 (s, 1H), 7.01 (s, 1H), 6.67 (s, 1H). MS (ESI) m/z: 474 [M + H]⁺. |
| I-a-31 | 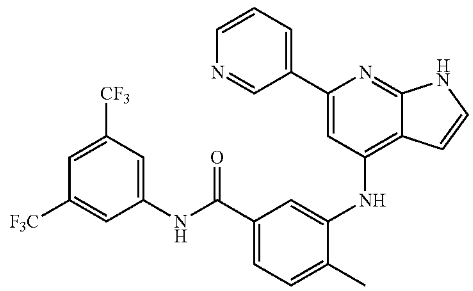 [SMILES: Cc1ccc(C(=O)Nc2cc(C(F)(F)F)cc(C(F)(F)F)c2)cc1Nc1cc(-c2cccnc2)nc2[nH]ccc12] | ¹H NMR (600 MHz, DMSO-d₆) δ 11.55 (s, 1H), 10.76 (s, 1H), 9.06 (d, J = 2.1 Hz, 1H), 8.54 (s, 1H), 8.50-8.52 (m, 3H), 8.21-8.16 (m, 1H), 8.01 (s, 1H), 7.87 (dd, J = 7.9, 1.8 Hz, 1H), 7.77 (s, 1H), 7.55 (d, J = 8.1 Hz, 1H), 7.42 (ddd, J = 8.0, 4.8, 0.7 Hz, 1H), 7.24 (dd, J = 3.3, 2.6 Hz, 1H), 6.70 (s, 1H), 6.42 (dd, J = 3.2, 2.1 Hz, 1H), 2.36 (s, 3H). (ESI) m/z: 556 [M + H]⁺. |
| I-a-32 | TFA salt | ¹H NMR (600 MHz, DMSO-d₆) δ 11.51 (s, 1H), 10.15 (s, 1H), 9.04 (d, J = 1.8 Hz, 1H), 8.51 (dd, J = 5.6, 2.4 Hz, 2H), 8.20-8.14 (m, 1H), 7.94 (d, J = 1.7 Hz, 1H), 7.81 (dd, J = 7.9, 1.8 Hz, 1H), 7.51 (d, J = 8.1 Hz, 1H), 7.45-7.41 (m, 2H), 7.37-7.34 (m, 1H), 7.23 (dt, J = 11.3, 4.9 Hz, 2H), 6.70-6.64 (m, 2H), 6.41 (dd, J = 3.4, 2.0 Hz, 1H), 3.73 (s, 3H), 2.33 (s, 3H). MS (ESI) m/z: 450 [M + H]⁺. |
| I-a-33 | TFA salt | ¹H NMR (600 MHz, DMSO-d₆) δ 12.06 (s, 1H), 10.47 (s, 1H), 9.65 (s, 1H), 9.05 (s, 1H), 8.76 (d, J = 4.9 Hz, 1H), 8.38 (d, J = 7.0 Hz, 1H), 7.99 (s, 1H), 7.96 (d, J = 7.9 Hz, 1H), 7.92 (s, 1H), 7.76 (d, J = 9.5 Hz, 1H), 7.73 (dd, J = 7.9, 5.1 Hz, 1H), 7.60 (d, 8.0 Hz, 1H), 7.47 (t, J = 8.3 Hz, 1H), 7.37 (s, 1H), 7.08 (d, J = 8.2 Hz, 1H), 6.63 (s, 1H), 6.52 (s, 1H), 2.34 (s, 3H). MS (ESI) m/z: 504 [M + H]⁺. |
| I-a-34 | 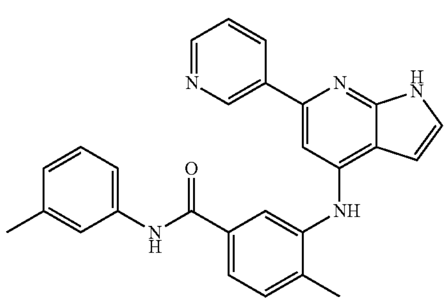 [SMILES: Cc1cccc(NC(=O)c2ccc(C)c(Nc3cc(-c4cccnc4)nc4[nH]ccc34)c2)c1] | ¹H NMR (600 MHz, DMSO-d₆) δ 11.52 (s, 1H), 10.11 (s, 1H), 9.05 (d, J = 1.8 Hz, 1H), 8.54-8.48 (m, 2H), 8.20-8.15 (m, 1H), 7.96 (d, J = 1.7 Hz, 1H), 7.82 (dd, J = 7.9, 1.8 Hz, 1H), 7.60 (s, 1H), 7.55 (d, J = 8.3 Hz, 1H), 7.50 (d, J = 8.1 Hz, 1H), 7.43 (ddd, J = 8.0, 4.7, 0.7 Hz, 1H), 7.25-7.18 (m, 2H), 6.91-6.87 (m, 1H), 6.68 (s, 1H), 6.43 (dd, J = 3.4, 2.0 Hz, 1H), 2.33 (s, 3H), 2.28 (s, 3H). MS (ESI) m/z: 434 [M + H]⁺. |

| No. | Structure | ¹H NMR and/or MS data |
|---|---|---|
| I-a-35 | 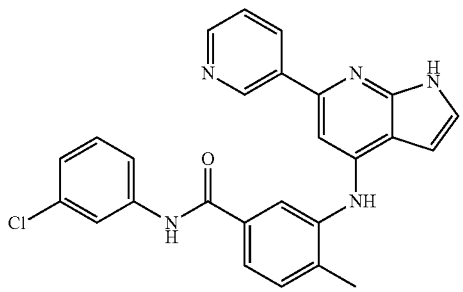 [SMILES: Cc1ccc(C(=O)Nc2cccc(Cl)c2)cc1Nc1cc(-c2cccnc2)nc2[nH]ccc12] | ¹H NMR (600 MHz, DMSO-d₆) δ 11.52 (s, 1H), 10.33 (s, 1H), 9.04 (d, J = 1.8 Hz, 1H), 8.52 (dd, J = 4.8, 1.6 Hz, 2H), 8.18-8.15 (m, 1H), 7.95 (dd, J = 5.5, 2.0 Hz, 2H), 7.82 (dd, J = 7.9, 1.8 Hz, 1H), 7.71-7.68 (m, 1H), 7.52 (d, J = 8.0 Hz, 1H), 7.43 (dd, J = 8.0, 4.7 Hz, 1H), 7.36 (t, J = 8.1 Hz, 1H), 7.23 (dd, J = 3.4, 2.5 Hz, 1H), 7.14 (ddd, J = 8.0, 2.1, 0.9 Hz, 1H), 6.67 (s, 1H), 6.41 (dd, J = 3.4, 2.0 Hz, 1H), 2.33 (s, 3H). MS (ESI) m/z: 455 [M + H]⁺. |
| I-a-36 | 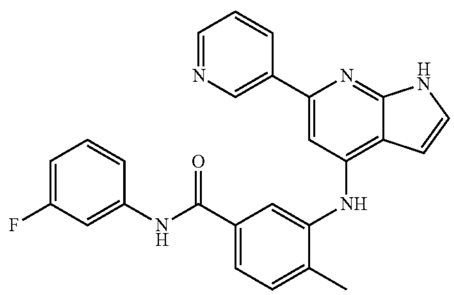 [SMILES: Cc1ccc(C(=O)Nc2cccc(F)c2)cc1Nc1cc(-c2cccnc2)nc2[nH]ccc12] | ¹H NMR (600 MHz, DMSO-d₆) δ 11.54 (s, 1H), 10.36 (s, 1H), 9.04 (d, J = 1.9 Hz, 1H), 8.57 (s, 1H), 8.53 (d, J = 3.6 Hz, 1H), 8.18 (d, J = 8.0 Hz, 1H), 7.94 (s, 1H), 7.82 (d, J = 8.1 Hz, 1H), 7.73 (d, J = 11.9 Hz, 1H), 7.54 (dd, J = 13.2, 8.6 Hz, 2H), 7.45 (dd, J = 8.0, 4.7 Hz, 1H), 7.36 (dd, J = 15.2, 8.1 Hz, 1H), 7.25-7.22 (m, 1H), 6.93-6.89 (m, 1H), 6.67 (s, 1H), 6.41 (s, 1H), 2.33 (s, 3H). MS (ESI) m/z: 438 [M + H]⁺. |
| I-a-37 | 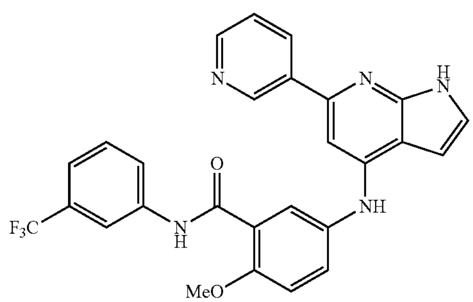 [SMILES: COc1ccc(Nc2cc(-c3cccnc3)nc3[nH]ccc23)cc1C(=O)Nc1cccc(C(F)(F)F)c1] | ¹H NMR (600 MHz, DMSO-d₆) δ 11.54 (d, J = 2.6 Hz, 1H), 10.52 (s, 1H), 9.10 (d, J = 2.2 Hz, 1H), 8.78 (s, 1H), 8.54 (dd, J = 4.8, 1.6 Hz, 1H), 8.25 (dt, J = 8.0, 2.0 Hz, 2H), 7.96 (d, J = 7.9 Hz, 1H), 7.63 (d, J = 2.8 Hz, 1H), 7.61-7.56 (m, 2H), 7.49-7.44 (m, 2H), 7.29-7.24 (m, 2H), 7.11 (s, 1H), 6.62 (dd, J = 3.5, 2.0 Hz, 1H), 3.94 (s, 3H). MS (ESI) m/z: 504 [M + H]⁺. |
| I-a-38 | 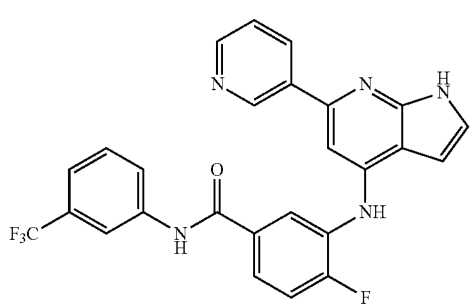 [SMILES: O=C(Nc1cccc(C(F)(F)F)c1)c1ccc(F)c(Nc2cc(-c3cccnc3)nc3[nH]ccc23)c1] | ¹H NMR (600 MHz, MeOD-d₄) δ 9.05 (s, 1H), 8.51 (s, 1H), 8.31 (d, J = 7.9 Hz, 1H), 8.15-8.07 (m, 2H), 7.91 (d, J = 7.6 Hz, 1H), 7.84 (s, 1H), 7.53 (dd, J = 16.0, 7.9 Hz, 2H), 7.41 (dd, J = 13.8, 8.6 Hz, 2H), 7.26 (d, J = 3.6 Hz, 1H), 6.96 (s, 1H), 6.53 (d, J = 3.4 Hz, 1H). MS (ESI) m/z: 492 [M + H]⁺. |
| I-a-39 | 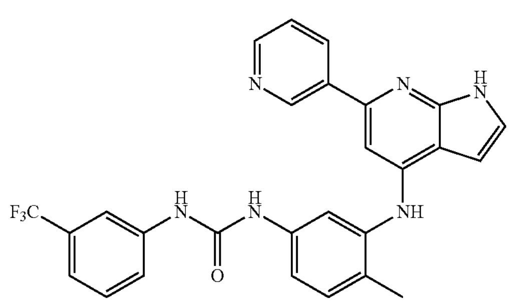 [SMILES: Cc1ccc(NC(=O)Nc2cccc(C(F)(F)F)c2)cc1Nc1cc(-c2cccnc2)nc2[nH]ccc12] | ¹H NMR (600 MHz, DMSO-d₆) δ 11.47 (s, 1H), 9.12-9.08 (m, 2H), 8.89 (s, 1H), 8.51 (dd, J = 4.7, 1.5 Hz, 1H), 8.28 (s, 1H), 8.25-8.21 (m, 1H), 7.99 (s, 1H), 7.60 (d, J = 2.1 Hz, 1H), 7.56 (d, J = 8.6 Hz, 1H), 7.48 (t, J = 7.9 Hz, 1H), 7.41 (dd, J = 7.9, 4.7 Hz, 1H), 7.28 (d, J = 7.2 Hz, 1H), 7.24 (d, J = 8.2 Hz, 1H), 7.23-7.21 (m, 1H), 7.18 (dd, J = 8.2, 2.2 Hz, 1H), 6.78 (s, 1H), 6.54 (dd, J = 3.4, 2.0 Hz, 1H), 2.20 (s, 3H). MS (ESI) m/z: 503 [M + H]⁺. |

| No. | Structure | ¹H NMR and/or MS data |
|---|---|---|
| I-a-40 | 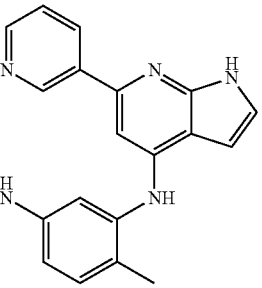 | ¹H NMR (600 MHz, DMSO-$d_6$) δ 11.48 (s, 1H), 10.05 (d, J = 14.1 Hz, 2H), 9.09 (s, 1H), 8.50 (d, J = 3.7 Hz, 1H), 8.28 (s, 1H), 8.22 (d, J = 7.8 Hz, 1H), 7.95 (s, 1H), 7.73 (d, J = 7.9 Hz, 1H), 7.53 (dd, J = 16.8, 8.8 Hz, 2H), 7.43 (d, J = 7.7 Hz, 1H), 7.37 (dd, J = 7.5, 4.8 Hz, 1H), 7.32 (d, J = 8.2 Hz, 1H), 7.23-7.18 (m, 2H), 6.84 (s, 1H), 6.61 (s, 1H), 2.25 (s, 3H). MS (ESI) m/z: 519 [M + H]⁺. |
| I-a-41 | 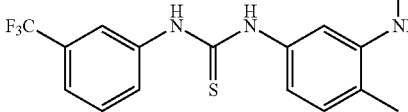 | ¹H NMR (600 MHz, DMSO-$d_6$) δ 11.87 (s, 1H), 10.31 (d, J = 6.3 Hz, 2H), 9.05 (s, 2H), 8.64 (d, J = 4.3 Hz, 1H), 8.28 (d, J = 8.1 Hz, 1H), 8.10 (d, J = 2.5 Hz, 1H), 7.75 (dd, J = 8.7, 2.4 Hz, 1H), 7.63 (d, J = 9.1 Hz, 2H), 7.54 (dd, J = 7.9, 4.9 Hz, 1H), 7.37 (d, J = 8.3 Hz, 1H), 7.33-7.30 (m, 1H), 7.25-7.22 (m, 1H), 6.82 (s, 1H), 6.70 (s, 1H), 2.26 (s, 3H). MS (ESI) m/z: 554 [M + H]⁺. |
| I-a-42 | 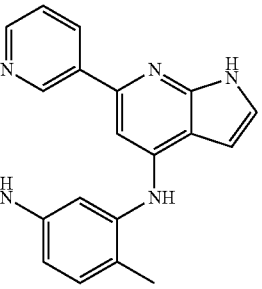 | ¹H NMR (600 MHz, DMSO-$d_6$) δ 11.61 (s, 1H), 9.06 (dd, J = 2.3, 0.8 Hz, 1H), 8.62 (s, 1H), 8.58 (dd, J = 4.8, 1.6 Hz, 1H), 8.24 (dt, J = 8.0, 1.9 Hz, 1H), 7.50 (ddd, J = 8.0, 4.8, 0.8 Hz, 1H), 7.44 (d, J = 7.8 Hz, 1H), 7.31 (d, J = 1.7 Hz, 1H), 7.27 (dd, J = 3.5, 2.5 Hz, 1H), 7.22 (dd, J = 7.7, 1.7 Hz, 1H), 6.73 (s, 1H), 6.46 (s, 1H), 3.67-3.25 (m, 8H), 2.31 (s, 3H). MS (ESI) m/z: 414 [M + H]⁺. |
| I-a-43 | 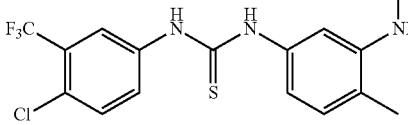 | ¹H NMR (600 MHz, DMSO-$d_6$) δ 11.52 (s, 1H), 9.04 (d, J = 1.8 Hz, 1H), 8.53 (dd, J = 4.7, 1.5 Hz, 1H), 8.37 (s, 1H), 8.20-8.15 (m, 1H), 7.44-7.39 (m, 2H), 7.23 (dd, J = 6.6, 3.4 Hz, 2H), 7.16-7.12 (m, 1H), 6.73 (s, 1H), 6.45 (dd, J = 3.3, 2.0 Hz, 1H), 2.30 (s, 3H), 2.18 (br. s, 4H), 2.11 (s, 3H), 1.77 (br. s, 4H). MS (ESI) m/z: 427 [M + H]⁺. |
| I-a-44 | 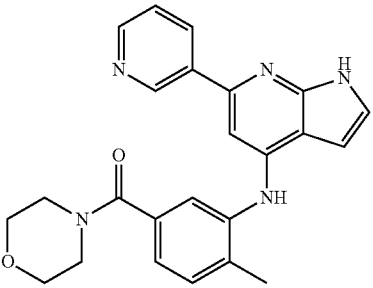 | ¹H NMR (600 MHz, DMSO-$d_6$) δ 11.53 (s, 1H), 10.46 (s, 1H), 9.05 (d, J = 1.9 Hz, 1H), 8.54 (dd, J = 4.7, 1.5 Hz, 1H), 8.40 (s, 1H), 8.23-8.20 (m, 1H), 7.65 (d, J = 1.9 Hz, 1H), 7.46 (dd, J = 7.9, 4.8 Hz, 1H), 7.35 (dd, J = 8.3, 2.1 Hz, 1H), 7.31 (d, J = 8.4 Hz, 1H), 7.23 (dd, J = 3.3, 2.1 Hz, 1H), 6.75 (s, 1H), 6.48 (d, J = 2.1 Hz, 1H), 3.78-3.75 (m, 2H), 2.22 (s, 3H). MS (ESI) m/z: 373 [M + H]⁺. |

-continued

| No. | Structure | ¹H NMR and/or MS data |
|---|---|---|
| I-a-45 | 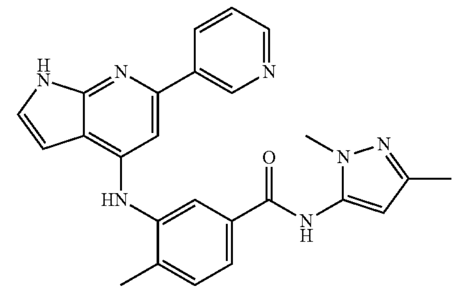 [SMILES: Cc1cc(NC(=O)c2ccc(C)c(Nc3cc(-c4cccnc4)nc4[nH]ccc34)c2)n(C)n1] | ¹H NMR (600 MHz, DMSO-d₆) δ 11.52 (s, 1H), 10.19 (s, 1H), 9.04 (dd, J = 2.3, 0.7 Hz, 1H), 8.52 (dd, J = 4.7, 1.6 Hz, 1H), 8.49 (s, 1H), 8.17 (ddd, J = 8.0, 2.2, 1.7 Hz, 1H), 7.94 (d, J = 1.3 Hz, 1H), 7.79 (d, J = 1.5 Hz, 1H), 7.51 (d, J = 8.1 Hz, 1H), 7.43 (ddd, J = 8.0, 4.8, 0.8 Hz, 1H), 7.23 (dd, J = 3.4, 2.5 Hz, 1H), 6.69 (s, 1H), 6.42 (dd, J = 3.4, 2.0 Hz, 1H), 5.98 (s, 1H), 3.56 (s, 3H), 2.33 (s, 3H), 2.10 (s, 3H). MS (ESI) m/z: 438 [M + H]⁺. |
| I-a-46 | 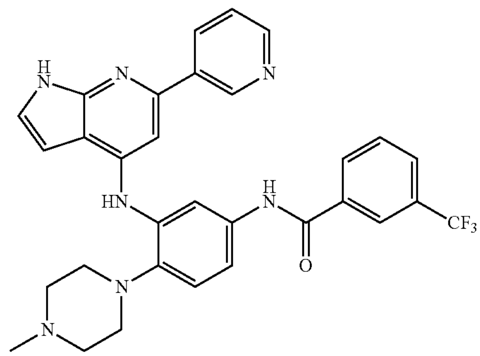 [SMILES: CN1CCN(c2ccc(NC(=O)c3cccc(C(F)(F)F)c3)cc2Nc2cc(-c3cccnc3)nc3[nH]ccc23)CC1] | ¹H NMR (600 MHz, MeOD) δ 9.17 (s, 1H), 8.80-8.76 (m, 1H), 8.57 (dt, J = 8.1, 1.9 Hz, 1H), 8.30-8.28 (m, 1H), 8.25 (d, J = 8.1 Hz, 1H), 8.17 (d, J = 2.5 Hz, 1H), 7.91 (d, J = 7.8 Hz, 1H), 7.79 (dd, J = 8.0, 5.0 Hz, 1H), 7.75 (t, J = 7.9 Hz, 1H), 7.57 (dd, J = 8.7, 2.5 Hz, 1H), 7.39 (d, J = 3.6 Hz, 1H), 7.35 (d, J = 8.7 Hz, 1H), 7.19 (s, 1H), 6.80 (d, J = 3.6 Hz, 1H), 3.60-3.51 (m, 2H), 3.45-3.38 (m, 2H), 3.22-3.08 (m, 4H), 2.92 (s, 3H). MS (ESI) m/z: 572 [M + H]⁺. |
| I-a-47 | 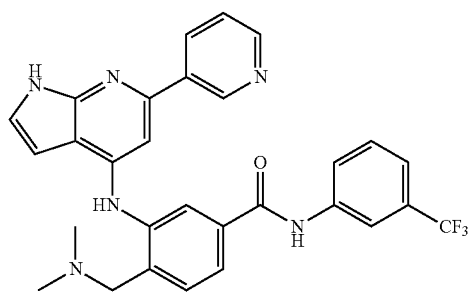 [SMILES: CN(C)Cc1ccc(C(=O)Nc2cccc(C(F)(F)F)c2)cc1Nc1cc(-c2cccnc2)nc2[nH]ccc12] | ¹H NMR (600 MHz, DMSO-d₆) δ 12.00 (s, 1H), 10.66-10.59 (m, 1H), 9.81 (br. s, 1H), 9.25 (s, 1H), 9.19 (br. s, 1H), 8.79 (s, 1H), 8.53-8.47 (m, 2H), 8.25-8.21 (m, 1H), 8.07 (d, J = 7.6 Hz, 1H), 7.90-7.86 (m, 1H), 7.84 (d, J = 8.0 Hz, 1H), 7.72 (d, J = 7.1 Hz, 1H), 7.67-7.63 (m, 1H), 7.61 (t, J = 8.0 Hz, 1H), 7.50-7.45 (m, 1H), 6.48 (dt, J = 2.7, 1.3 Hz, 1H), 4.53 (s, 2H), 2.79 (s, 6H). MS (ESI) m/z: 531 [M + H]⁺. |
| I-a-48 | 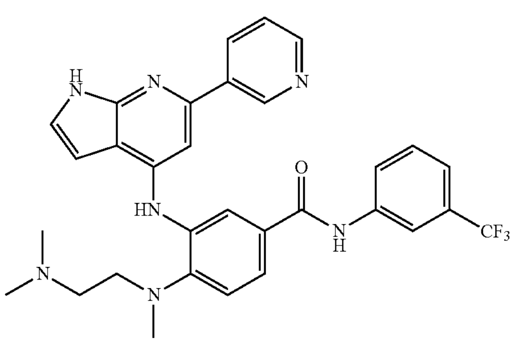 [SMILES: CN(C)CCN(C)c1ccc(C(=O)Nc2cccc(C(F)(F)F)c2)cc1Nc1cc(-c2cccnc2)nc2[nH]ccc12] | ¹H NMR (600 MHz, MeOD) δ 9.08 (s, 1H), 8.79-8.75 (m, 1H), 8.46 (dt, J = 8.1, 1.8 Hz, 1H), 8.17-8.15 (m, 1H), 8.08 (d, J = 2.2 Hz, 1H), 8.03 (dd, J = 8.6, 2.2 Hz, 1H), 7.92 (dd, J = 7.8, 1.9 Hz, 1H), 7.78 (dd, J = 8.1, 5.1 Hz, 1H), 7.55 (t, J = 8.1 Hz, 1H), 7.46-7.43 (m, 2H), 7.37 (d, J = 3.5 Hz, 1H), 6.97 (s, 1H), 6.58 (s, 1H), 3.57-3.52 (m, 2H), 2.94-2.90 (m, 5H), 2.81 (s, 6H). MS (ESI) m/z: 574 [M + H]⁺. |

| No. | Structure | ¹H NMR and/or MS data |
|---|---|---|
| I-a-49 | 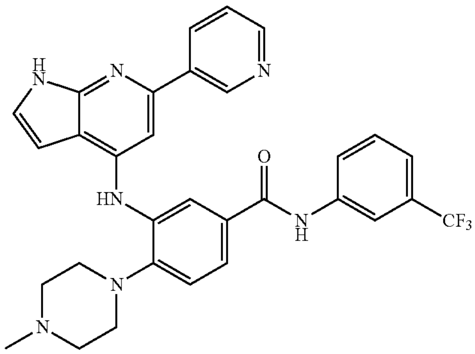 [SMILES: CN1CCN(c2ccc(C(=O)Nc3cccc(C(F)(F)F)c3)cc2Nc2cc(-c3cccnc3)nc3[nH]ccc23)CC1] | MS (ESI) m/z: 572 [M + H]⁺. |
| I-a-50 | 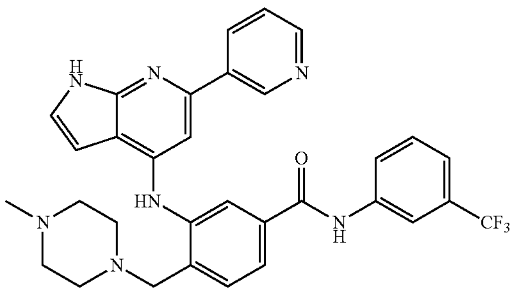 [SMILES: CN1CCN(Cc2ccc(C(=O)Nc3cccc(C(F)(F)F)c3)cc2Nc2cc(-c3cccnc3)nc3[nH]ccc23)CC1] | MS (ESI) m/z: 586 [M + H]⁺. |
| I-b-1 | 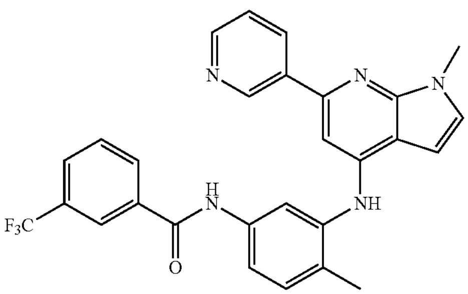 [SMILES: Cc1ccc(NC(=O)c2cccc(C(F)(F)F)c2)cc1Nc1cc(-c2cccnc2)nc2c1ccn2C] | ¹H NMR (600 MHz, DMSO-$d_6$) δ 10.47 (d, J = 6.3 Hz, 1H), 9.16 (s, 1H), 8.54 (d, J = 4.1 Hz, 1H), 8.43 (d, J = 5.0 Hz, 1H), 8.31 (dd, J = 5.1, 2.8 Hz, 1H), 8.28 (s, 1H), 8.25 (d, J = 7.6 Hz, 1H), 7.95 (d, J = 7.8 Hz, 1H), 7.89-7.85 (m, 1H), 7.77 (t, J = 7.8 Hz, 1H), 7.58 (s, 1H), 7.45 (dd, J = 7.8, 4.7 Hz, 1H), 7.34 (d, 8.3 Hz, 1H), 7.27 (d, J = 3.4 Hz, 1H), 6.80 (d, J = 6.7 Hz, 1H), 6.52 (dd, J = 5.6, 3.4 Hz, 1H), 3.83 (s, 3H), 2.24 (s, 3H). MS (ESI) m/z: 502 [M + H]⁺. |
| I-b-2 | 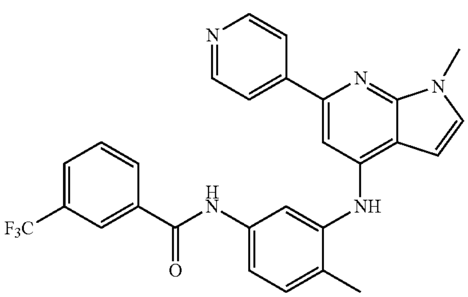 [SMILES: Cc1ccc(NC(=O)c2cccc(C(F)(F)F)c2)cc1Nc1cc(-c2ccncc2)nc2c1ccn2C] | ¹H NMR (600 MHz, DMSO-$d_6$) δ 10.47 (s, 1H), 8.63-8.59 (m, 2H), 8.45 (s, 1H), 8.28 (s, 1H), 8.25 (d, J = 8.0 Hz, 1H), 7.95 (d, J = 7.8 Hz, 1H), 7.95-7.92 (m, 2H), 7.85 (d, J = 2.1 Hz, 1H), 7.78 (t, J = 7.8 Hz, 1H), 7.59 (dd, J = 8.3, 2.1 Hz, 1H), 7.35 (d, J = 8.5 Hz, 1H), 7.31 (d, J = 3.5 Hz, 1H), 6.88 (s, 1H), 6.52 (d, J = 3.5 Hz, 1H), 3.83 (s, 3H), 2.23 (s, 3H). MS (ESI) m/z: 502 [M + H]⁺. |
| I-b-3 | 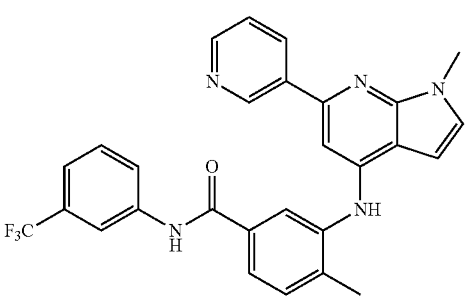 [SMILES: Cc1ccc(C(=O)Nc2cccc(C(F)(F)F)c2)cc1Nc1cc(-c2cccnc2)nc2c1ccn2C] | ¹H NMR (600 MHz, Acetone-$d_6$): δ 9.84 (s, 1H), 9.20 (s, 1H), 8.51 (d, J = 3.5 Hz, 1H), 8.33 (d, J = 8.0 Hz, 1H), 8.29 (s, 1H), 8.07 (s, 1H), 8.05 (d, J = 8.2 Hz, 1H), 7.88 (dd, J = 7.9, 1.6 Hz, 1H), 7.84 (s, 1H), 7.55 (t, J = 8.0 Hz, 1H), 7.51 (d, J = 7.9 Hz, 1H), 7.42 (d, J = 7.8 Hz, 1H), 7.38 (dd, J = 7.9, 4.8 Hz, 1H), 7.22 (d, J = 3.4 Hz, 1H), 6.88 (d, J = 4.2 Hz, 1H), 6.47-6.39 (m, 1H), 3.90 (s, 3H), 2.39 (s, 3H). MS (ESI) m/z: 502 [M + H]⁺. |

-continued

| No. | Structure | ¹H NMR and/or MS data |
|---|---|---|
| I-b-4 | 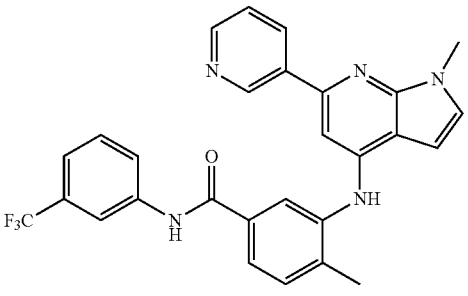<br>TFA salt | ¹H NMR (600 MHz, MeOD-d₄) δ 8.65-8.59 (m, 2H), 8.25-8.19 (m, 2H), 8.16 (d, J = 2.0 Hz, 1H), 7.97 (d, J = 1.9 Hz, 1H), 7.92 (dd, J = 8.3, 2.1 Hz, 1H), 7.84 (dd, J = 7.9, 2.0 Hz, 1H), 7.56-7.50 (m, 2H), 7.42 (d, J = 7.8 Hz, 1H), 7.25 (d, J = 3.5 Hz, 1H), 6.91 (s, 1H), 6.43 (d, J = 3.5 Hz, 1H), 3.89 (s, 3H), 2.36 (s, 3H). MS (ESI) m/z: 502 [M + H]⁺. |
| I-b-5 | 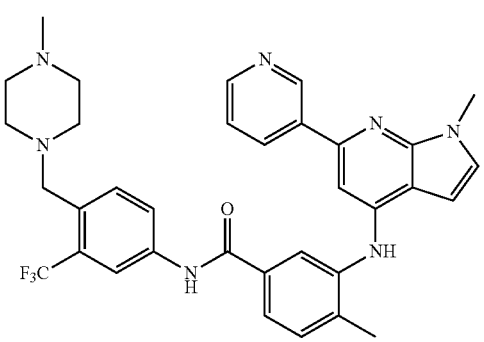 [SMILES: Cc1ccc(C(=O)Nc2ccc(CN3CCN(C)CC3)c(C(F)(F)F)c2)cc1Nc1cc(-c2cccnc2)nc2c1ccn2C] | ¹H NMR (600 MHz, CDCl₃) δ 9.12 (d, J = 2.2 Hz, 1H), 8.52 (dd, J = 4.8, 1.5 Hz, 1H), 8.41 (s, 1H), 8.27 (dt, J = 8.0, 2.0 Hz, 1H), 7.86 (dd, J = 8.7, 2.2 Hz, 1H), 7.84 (d, J = 1.8 Hz, 1H), 7.82 (d, J = 2.2 Hz, 1H), 7.72 (d, J = 8.5 Hz, 1H), 7.66 (dd, J = 7.9, 1.8 Hz, 1H), 7.39 (d, J = 8.0 Hz, 1H), 7.30 (dd, J = 8.0, 4.8 Hz, 1H), 7.06 (d, J = 3.5 Hz, 1H), 6.77 (s, 1H), 6.30 (s, 1H), 6.22 (d, J = 3.4 Hz, 1H), 3.89 (s, 3H), 3.59 (s, 2H), 2.33 (s, 3H), 2.27 (s, 3H), 2.04 (br. s, 4H), 1.26 (br. s, 4H). MS (ESI) m/z: 614 [M + H]⁺. |
| I-b-6 | 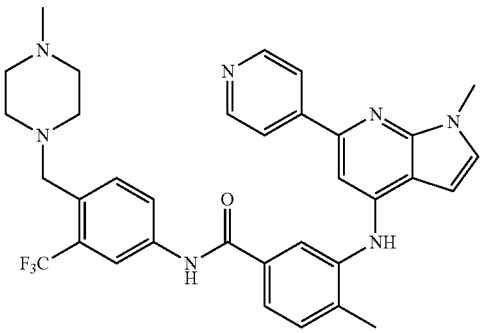 [SMILES: Cc1ccc(C(=O)Nc2ccc(CN3CCN(C)CC3)c(C(F)(F)F)c2)cc1Nc1cc(-c2ccncc2)nc2c1ccn2C] | ¹H NMR (600 MHz, CDCl₃) δ 8.86 (s, 1H), 8.53-8.46 (m, 2H), 7.88-7.82 (m, 3H), 7.81-7.77 (m, 2H), 7.73-7.65 (m, 2H), 7.36 (d, J = 7.9 Hz, 1H), 7.06 (d, J = 3.5 Hz, 1H), 6.77 (s, 1H), 6.42 (s, 1H), 6.22 (d, J = 3.5 Hz, 1H), 3.91 (s, 3H), 3.59 (s, 2H), 2.32 (s, 3H), 2.28 (s, 3H), 1.27 (s, 4H), 1.21 (d, J = 6.1 Hz, 4H). MS (ESI) m/z: 614 [M + H]⁺. |
| I-b-7 | 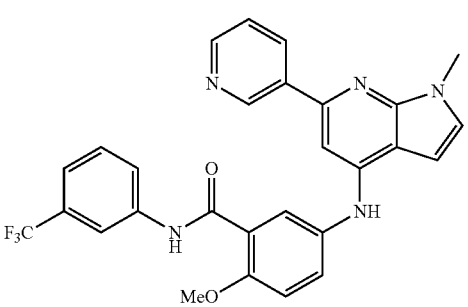 | ¹H NMR (600 MHz, DMSO-d₆) δ 10.51 (s, 1H), 9.15 (s, 1H), 8.80 (s, 1H), 8.55 (d, J = 3.4 Hz, 1H), 8.33-8.30 (m, 1H), 8.25 (s, 1H), 7.96 (d, J = 8.1 Hz, 1H), 7.63 (d, J = 2.7 Hz, 1H), 7.59-7.56 (m, 2H), 7.46 (dd, J = 10.4, 6.8 Hz, 2H), 7.31 (d, J = 3.5 Hz, 1H), 7.27 (d, J = 8.9 Hz, 1H), 7.13 (s, 1H), 6.60 (d, J = 3.5 Hz, 1H), 3.94 (s, 3H), 3.83 (s, 3H). MS (ESI) m/z: 518 [M + H]⁺. |
| I-b-8 | 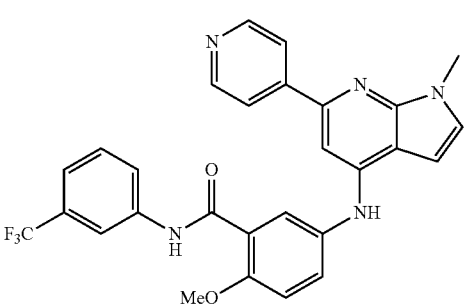 [SMILES: COc1ccc(Nc2cc(-c3ccncc3)nc3c2ccn3C)cc1C(=O)Nc1cccc(C(F)(F)F)c1] | ¹H NMR (600 MHz, DMSO-d₆) δ 10.52 (s, 1H), 8.84 (s, 1H), 8.62 (d, J = 5.7 Hz, 2H), 8.25 (s, 1H), 7.94-7.97 (m, 3H), 7.62-7.58 (m, 2H), 7.55 (dd, J = 8.8, 2.8 Hz, 1H), 7.45 (d, J = 7.8 Hz, 1H), 7.35 (d, J = 3.4 Hz, 1H), 7.27 (d, J = 8.9 Hz, 1H), 7.21 (s, 1H), 6.61 (d, J = 3.4 Hz, 1H), 3.94 (s, 3H), 3.84 (s, 3H). MS (ESI) m/z: 518 [M + H]⁺. |

| No. | Structure | ¹H NMR and/or MS data |
|---|---|---|
| I-c-1 | 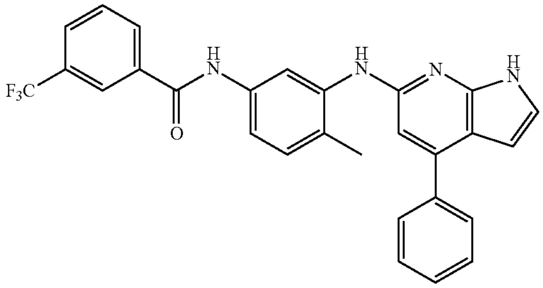 [SMILES: Cc1ccc(NC(=O)c2cccc(C(F)(F)F)c2)cc1Nc1cc(-c2ccccc2)c2cc[nH]c2n1] | ¹H NMR (600 MHz, DMSO-d$_6$) δ 11.25 (s, 1H), 10.36 (d, J = 7.4 Hz, 1H), 8.29 (s, 1H), 8.26 (d, J = 8.0 Hz, 1H), 8.07 (d, J = 2.2 Hz, 1H), 8.02 (s, 1H), 7.96 (d, J = 7.9 Hz, 1H), 7.78 (t, J = 7.8 Hz, 1H), 7.75 (d, J = 1.5 Hz, 1H), 7.74 (d, J = 1.3 Hz, 1H), 7.55 (t, J = 7.7 Hz, 2H), 7.48-7.44 (m, 1H), 7.41 (dd, J = 8.2, 2.2 Hz, 1H), 7.19 (d, J = 8.3 Hz, 1H), 7.12 (dd, J = 3.4, 2.4 Hz, 1H), 6.79 (s, 1H), 6.41 (dd, J = 3.5, 2.0 Hz, 1H), 2.26 (s, 2H). MS (ESI) m/z: 487 [M + H]⁺. |
| I-c-2 | 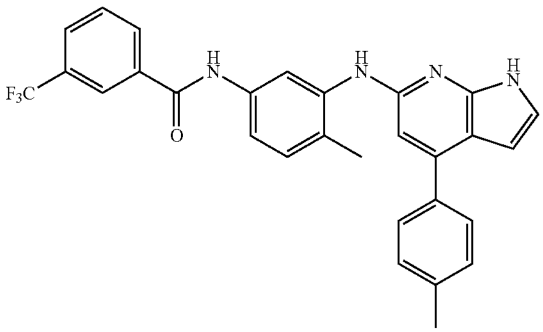 [SMILES: Cc1ccc(-c2cc(Nc3cc(NC(=O)c4cccc(C(F)(F)F)c4)ccc3C)nc3[nH]ccc23)cc1] | ¹H NMR (600 MHz, DMSO-d$_6$) δ 11.28 (s, 1H), 10.38 (d, J = 4.4 Hz, 1H), 8.30 (s, 1H), 8.26 (d, J = 7.9 Hz, 1H), 8.06 (d, J = 2.0 Hz, 1H), 7.96 (d, J = 7.5 Hz, 1H), 7.78 (t, J = 7.8 Hz, 1H), 7.65 (s, 1H), 7.64 (s, 1H), 7.43 (dd, J = 8.2, 2.0 Hz, 1H), 7.36 (s, 1H), 7.35 (s, 1H), 7.21 (d, J = 8.3 Hz, 1H), 7.13 (q, J = 4.3, 3.6 Hz, 1H), 7.06 (s, 1H), 6.78 (s, 1H), 6.43 (t, J = 2.6 Hz, 1H), 2.39 (s, 3H), 2.26 (s, 3H). MS (ESI) m/z: 501 [M + H]⁺. |
| I-c-3 | 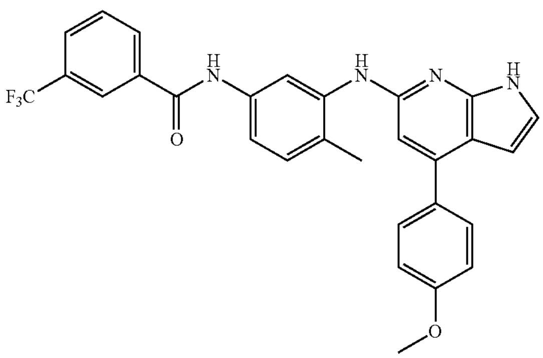 [SMILES: COc1ccc(-c2cc(Nc3cc(NC(=O)c4cccc(C(F)(F)F)c4)ccc3C)nc3[nH]ccc23)cc1] | ¹H NMR (600 MHz, DMSO-d$_6$) δ 11.29 (s, 1H), 10.40 (s, 1H), 8.30 (s, 1H), 8.26 (d, J = 7.8 Hz, 1H), 8.05 (d, J = 2.2 Hz, 1H), 7.96 (d, J = 7.8 Hz, 1H), 7.78 (t, J = 7.8 Hz, 1H), 7.72 (s, 1H), 7.71 (s, 1H), 7.45 (dd, J = 8.2, 2.2 Hz, 1H), 7.23 (d, J = 8.3 Hz, 1H), 7.14 (dd, J = 3.4, 2.4 Hz, 1H), 7.12 (s, 1H), 7.11 (s, 1H), 6.76 (s, 1H), 6.46 (dd, J = 3.5, 1.9 Hz, 1H), 3.84 (s, 3H), 2.26 (s, 3H). MS (ESI) m/z: 517 [M + H]⁺. |
| I-c-4 | 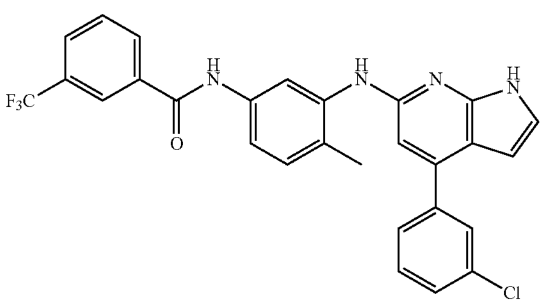 | ¹H NMR (600 MHz, CDCl$_3$) δ 10.53 (s, 1H), 8.56 (s, 1H), 8.38-8.34 (m, 1H), 8.27 (s, 1H), 7.93 (d, J = 7.6 Hz, 1H), 7.78 (d, J = 7.5 Hz, 1H), 7.72-7.68 (m, 1H), 7.66 (d, J = 7.5 Hz, 1H), 7.58 (dt, J = 6.5, 1.9 Hz, 1H), 7.45-7.37 (m, 2H), 7.21-7.16 (m, 2H), 6.71-6.67 (m, 1H), 6.63 (s, 1H), 6.42 (dd, J = 3.6, 1.9 Hz, 1H), 6.37-6.31 (m, 1H), 2.34 (s, 3H). MS (ESI) m/z: 522 [M + H]⁺. |
| I-c-5 | 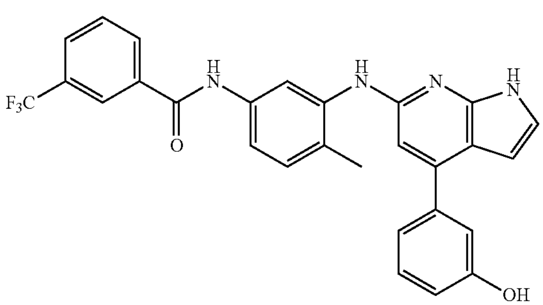 [SMILES: Cc1ccc(NC(=O)c2cccc(C(F)(F)F)c2)cc1Nc1cc(-c2cccc(O)c2)c2cc[nH]c2n1] | ¹H NMR (600 MHz, DMSO-d$_6$) δ 11.23 (t, J = 2.3 Hz, 1H), 10.36 (s, 1H), 9.60 (s, 1H), 8.30 (s, 1H), 8.26 (d, J = 7.9 Hz, 1H), 8.06 (d, J = 2.2 Hz, 1H), 8.03 (s, 1H), 7.96 (d, J = 7.7 Hz, 1H), 7.78 (t, J = 7.8 Hz, 1H), 7.42 (dd, J = 8.2, 2.2 Hz, 1H), 7.33 (t, J = 8.1 Hz, 1H), 7.19 (d, J = 8.3 Hz, 1H), 7.15 (dd, J = 6.7, 1.5 Hz, 2H), 7.13-7.10 (m, 1H), 6.87-6.84 (m, 1H), 6.75 (s, 1H), 6.40 (dd, J = 3.5, 1.9 Hz, 1H), 2.25 (s, 3H). MS (ESI) m/z: 503 [M + H]⁺. |

-continued

| No. | Structure | ¹H NMR and/or MS data |
|---|---|---|
| I-c-6 | 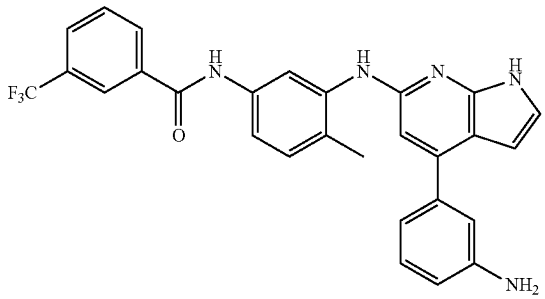 [SMILES: Cc1ccc(NC(=O)c2cccc(C(F)(F)F)c2)cc1Nc1cc(-c2cccc(N)c2)c2cc[nH]c2n1] | ¹H NMR (600 MHz, DMSO-d₆) δ 11.17 (t, J = 2.2 Hz, 1H), 10.35 (d, J = 5.9 Hz, 1H), 8.29 (t, J = 1.7 Hz, 1H), 8.26 (d, J = 8.0 Hz, 1H), 8.04 (d, J = 2.2 Hz, 1H), 7.98 (s, 1H), 7.97-7.94 (m, 1H), 7.78 (t, J = 7.8 Hz, 1H), 7.41 (dd, J = 8.2, 2.2 Hz, 1H), 7.19 (d, J = 8.4 Hz, 1H), 7.16 (t, J = 7.8 Hz, 1H), 7.09 (dd, J = 3.5, 2.4 Hz, 1H), 6.97 (t, J = 2.0 Hz, 1H), 6.86 (dt, J = 7.7, 1.2 Hz, 1H), 6.72 (s, 1H), 6.64 (ddd, J = 7.9, 2.3, 1.0 Hz, 1H), 6.41 (dd, J = 3.5, 2.0 Hz, 1H), 2.25 (s, 3H). MS (ESI) m/z: 502 [M + H]⁺. |
| I-c-7 | 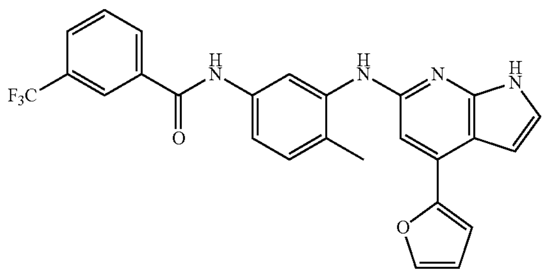 | ¹H NMR (600 MHz, DMSO-d₆) δ 11.30 (s, 1H), 10.38 (s, 1H), 8.29 (s, 1H), 8.26 (d, J = 7.9 Hz, 1H), 7.99 (d, J = 2.1 Hz, 1H), 7.96 (d, J = 7.8 Hz, 1H), 7.91 (d, J = 1.6 Hz, 1H), 7.78 (t, J = 7.8 Hz, 1H), 7.47 (dd, J = 8.3, 2.1 Hz, 1H), 7.22 (d, J = 3.3 Hz, 1H), 7.21 (s,1H), 7.16 (t, J = 2.9 Hz, 1H), 7.01 (s, 1H), 6.72 (dt, J = 5.1, 2.5 Hz, 2H), 2.24 (s, 3H). MS (ESI) m/z: 477 [M + H]⁺. |
| I-c-8 | 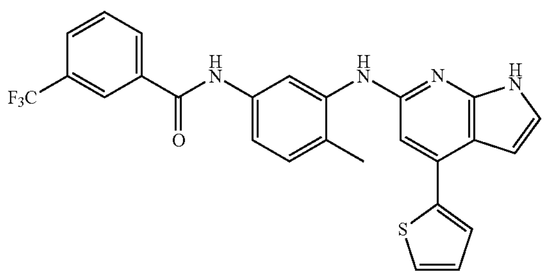 | ¹H NMR (600 MHz, DMSO-d₆) δ 11.29 (s, 1H), 10.36 (s, 1H), 8.29 (s, 1H), 8.26 (d, J = 7.9 Hz, 1H), 8.07 (s, 1H), 8.03 (d, J = 2.2 Hz, 1H), 7.96 (d, J = 7.9 Hz, 1H), 7.78 (t, J = 7.8 Hz, 1H), 7.71 (d, J = 5.5 Hz, 1H), 7.70 (d, J = 3.9 Hz, 1H), 7.42 (dd, J = 8.2, 2.2 Hz, 1H), 7.25 (dd, J = 5.0, 3.6 Hz, 1H), 7.19 (d, J = 8.4 Hz, 1H), 7.17-7.13 (m, 1H), 6.94 (s, 1H), 6.64 (dd, J = 3.6, 2.0 Hz, 1H), 2.25 (s, 3H). MS (ESI) m/z: 493 [M + H]⁺. |
| I-c-9 | 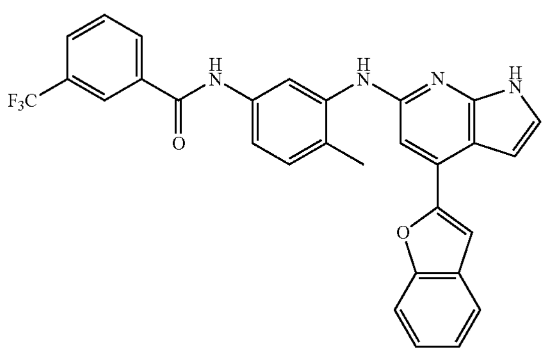 | ¹H NMR (600 MHz, DMSO-d₆) δ 11.39 (d, J = 2.3 Hz, 1H), 10.39 (s, 1H), 8.30 (s, 1H), 8.27 (d, J = 7.9 Hz, 1H), 8.04 (d, J = 2.1 Hz, 1H), 7.96 (d, J = 7.8 Hz, 1H), 7.80-7.75 (m, 2H), 7.72-7.69 (m, 2H), 7.47 (dd, J = 8.3, 2.1 Hz, 1H), 7.41 (t, J = 7.6 Hz, 1H), 7.33 (t, J = 7.5 Hz, 1H), 7.27 (s, 1H), 7.25-7.21 (m, 2H), 6.86 (dd, J = 3.4, 1.9 Hz, 1H), 2.27 (s, 3H). MS (ESI) m/z: 527 [M + H]⁺. |
| I-c-10 | 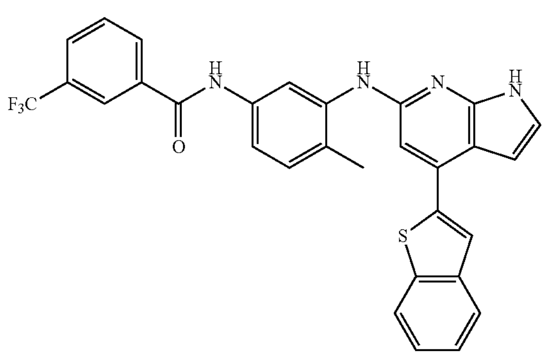 [SMILES: Cc1ccc(NC(=O)c2cccc(C(F)(F)F)c2)cc1Nc1cc(-c2cc3ccccc3s2)c2cc[nH]c2n1] | ¹H NMR (600 MHz, DMSO-d₆) δ 11.39 (t, J = 2.3 Hz, 1H), 10.38 (s, 1H), 8.30 (s, 1H), 8.27 (d, J = 8.0 Hz, 1H), 8.09 (s, 1H), 8.05 (dd, J = 6.8, 1.9 Hz, 2H), 7.98 (dd, J = 6.9, 1.9 Hz, 1H), 7.96 (d, J = 7.9 Hz, 1H), 7.78 (t, J = 7.8 Hz, 1H), 7.48-7.39 (m, 3H), 7.25-7.20 (m, 2H), 7.02 (s, 1H), 6.79 (dd, J = 3.6, 1.9 Hz, 1H), 2.27 (s, 3H). MS (ESI) m/z: 543 [M + H]⁺. |

| No. | Structure | ¹H NMR and/or MS data |
|---|---|---|
| I-c-11 | 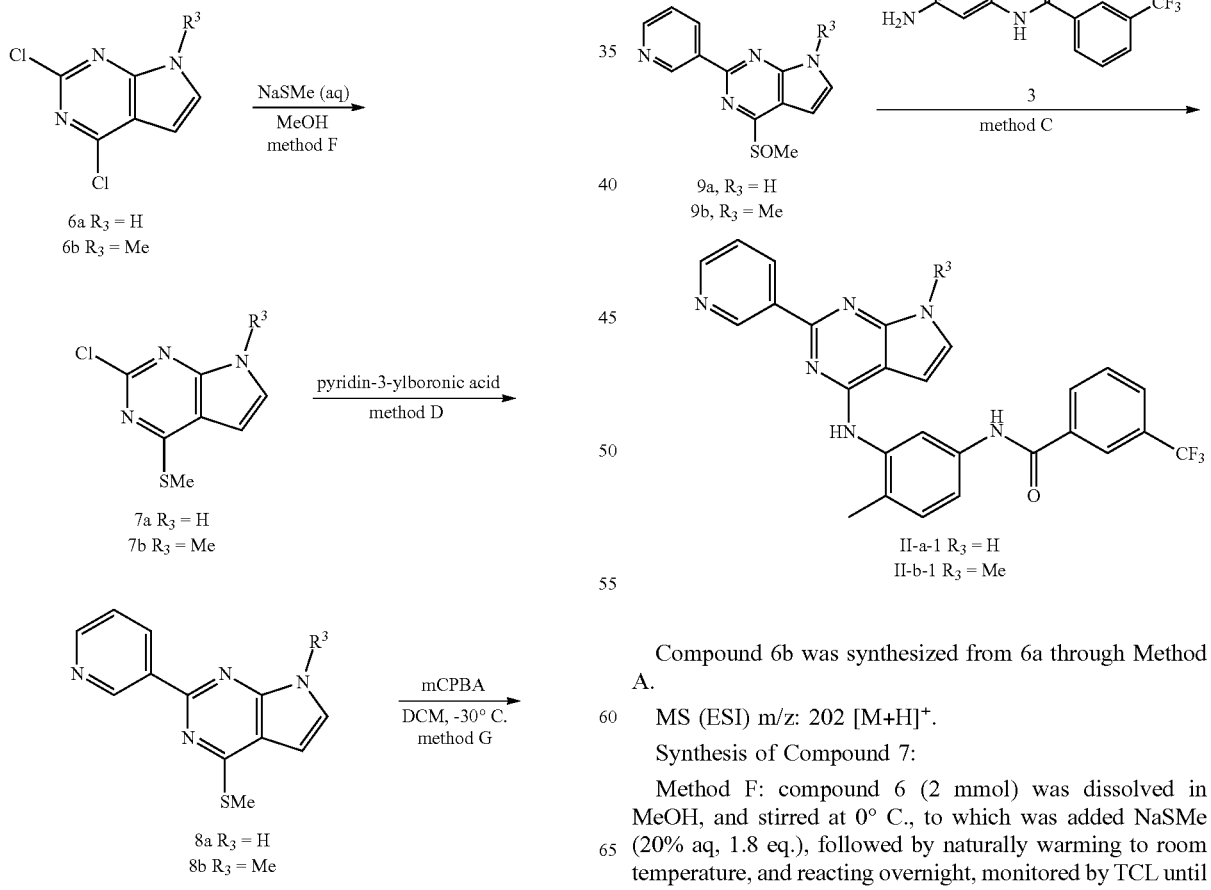 | ¹H NMR (600 MHz, DMSO-$d_6$) δ 11.34 (s, 1H), 10.35 (s, 1H), 8.74 (s, 1H), 8.73 (s, 1H), 8.30 (s, 1H), 8.26 (d, J = 7.8 Hz, 1H), 8.11 (s, 1H), 8.07 (d, J = 2.1 Hz, 1H), 7.95 (d, J = 7.8 Hz, 1H), 7.79 (dd, J = 7.8,7.8 Hz, 1H), 7.74 (d, J = 1.5 Hz, 1H), 7.73 (s, 1H), 7.41 (dd, J = 8.3, 2.1 Hz, 1H), 7.20 (d, J = 8.2 Hz, 1H), 7.18 (t, J = 3.0 Hz, 1H), 6.88 (s, 1H), 6.47 (dd, J = 3.5, 1.9 Hz, 1H), 2.26 (s, 3H). MS (ESI) m/z: 488 [M + H]⁺. |
| I-c-12 | 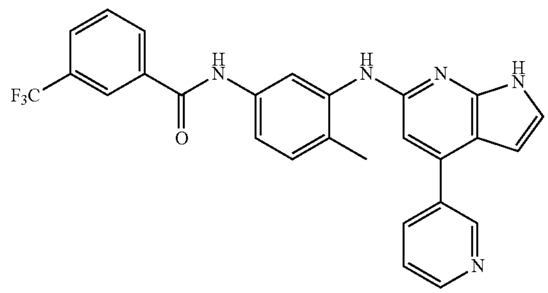 [SMILES: Cc1ccc(NC(=O)c2cccc(C(F)(F)F)c2)cc1Nc1cc(-c2cccnc2)c2cc[nH]c2n1] | ¹H NMR (600 MHz, DMSO-$d_6$) δ 11.34 (s, 1H), 10.37 (s, 1H), 8.94 (s, 1H), 8.67 (d, J = 4.8 Hz, 1H), 8.30 (s, 1H), 8.27 (d, J = 7.9 Hz, 1H), 8.15 (d, J = 8.1 Hz, 1H), 8.07-8.14 (m, 2H), 7.96 (d, J = 7.7 Hz, 1H), 7.79 (t, J = 7.8 Hz, 1H), 7.58 (dd, J = 7.7, 4.8 Hz, 1H), 7.41 (d, J = 8.2 Hz, 1H), 7.20 (d, J = 8.2 Hz, 1H), 7.17 (s, 1H), 6.84 (s, 1H), 6.42 (s, 1H), 2.26 (s, 3H). MS (ESI) m/z: 488 [M + H]⁺. |

Synthetic Route of Compounds II-a-1, II-b-1:

Compound 6b was synthesized from 6a through Method A.

MS (ESI) m/z: 202 [M+H]⁺.

Synthesis of Compound 7:

Method F: compound 6 (2 mmol) was dissolved in MeOH, and stirred at 0° C., to which was added NaSMe (20% aq, 1.8 eq.), followed by naturally warming to room temperature, and reacting overnight, monitored by TCL until complete conversion, to which was added DCM. The system was washed with water, and the organic phase was concentrated to obtain a while solid, which was directly used for the next step reaction.

7a: MS (ESI) m/z: 200 [M+H]$^+$; 7b: MS (ESI) m/z: 214 [M+H]$^+$.

compound 8 was synthesized from compound 7 and 3-pyridineboronic acid through Method D.

8a: MS (ESI) m/z: 243 [M+H]$^+$; 8b: MS (ESI) m/z: 257 [M+H]$^+$.

Synthesis of Compound 9:

Method G: compound 8 (1 mmol) was dissolved in DCM (5 mL), to which was slowly added dropwise a solution of mCPBA (1.5 eq.) in DCM (5 mL) at −30° C., followed by keeping at this temperature for 2-4 h, monitored by TLC until complete conversion, to which was added DCM for dilution. The system was washed with saturated NaHCO$_3$ aqueous solution, and the organic phase was concentrated, and purified by silica gel column chromatography, to obtain a yellowish solid.

9a: MS (ESI) m/z: 259 [M+H]$^+$; 9b: MS (ESI) m/z: 273 [M+H]$^+$.

Compounds II-a-1, II-b-1 were respectively synthesized from 9a, 9b and 3 through Method C.

Other such compounds could be synthesized by similar methods.

In the following table it lists the specific compounds and their structural characterization data.

| No. | Structure | $^1$H NMR and/or MS data |
|---|---|---|
| II-a-1 | 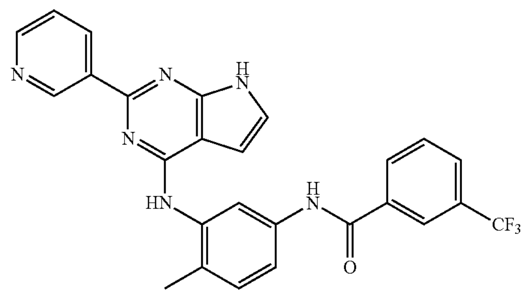 [SMILES: Cc1ccc(NC(=O)c2cccc(C(F)(F)F)c2)cc1Nc1nc(-c2cccnc2)nc2[nH]ccc12] | $^1$H NMR (600 MHz, DMSO-d$_6$) δ 11.83 (s, 1H), 10.49 (s, 1H), 9.39 (d, J = 2.0 Hz, 1H), 9.16 (s, 1H), 8.56 (dd, J = 4.7, 1.6 Hz, 1H), 8.54 (dt, J = 8.0, 1.9 Hz, 1H), 8.30 (s, 1H), 8.27 (d, J = 7.9 Hz, 1H), 8.06 (d, J = 1.8 Hz, 1H), 7.97 (d, J = 8.1 Hz, 1H), 7.79 (t, J = 7.9 Hz, 1H), 7.62 (dd, J = 8.3, 2.1 Hz, 1H), 7.43 (dd, J = 8.1, 4.8 Hz, 1H), 7.34 (d, J = 8.4 Hz, 1H), 7.24-7.22 (m, 1H), 6.45 (s, 1H), 2.25 (s, 3H). MS (ESI) m/z: 489 [M + H]$^+$. |
| II-a-2 | 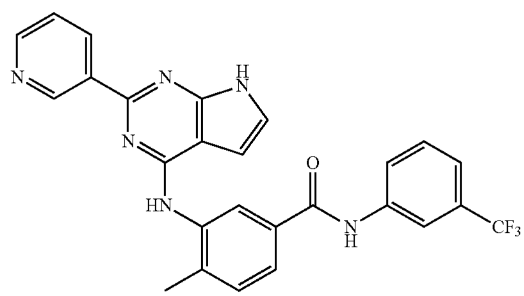 [SMILES: Cc1ccc(C(=O)Nc2cccc(C(F)(F)F)c2)cc1Nc1nc(-c2cccnc2)nc2[nH]ccc12] | $^1$H NMR (600 MHz, DMSO-d$_6$) δ 11.89 (s, 1H), 10.52 (s, 1H), 9.36 (d, J = 1.6 Hz, 1H), 9.28 (s, 1H), 8.55 (dd, J = 4.7, 1.7 Hz, 1H), 8.51 (dt, J = 8.0, 1.9 Hz, 1H), 8.27 (d, J = 1.6 Hz, 1H), 8.24 (s, 1H), 8.08 (d, J = 8.1 Hz, 1H), 7.87 (dd, J = 7.9, 1.8 Hz, 1H), 7.60 (t, J = 8.0 Hz, 1H), 7.54 (d, J = 8.1 Hz, 1H), 7.45 (d, J = 7.7 Hz, 1H), 7.41 (dd, J = 8.2, 4.5 Hz, 1H), 7.27 (dd, J = 3.2, 2.6 Hz, 1H), 6.55 (s, 1H), 2.38 (s, 3H). MS (ESI) m/z: 489 [M + H]$^+$. |
| II-a-3 | 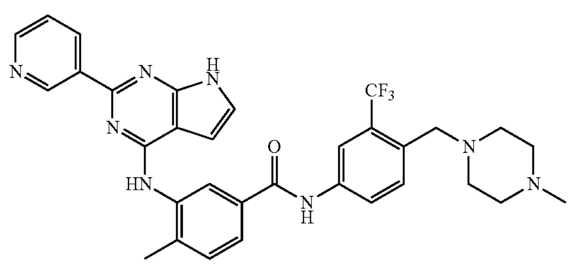 | $^1$H NMR (600 MHz, DMSO-d$_6$) δ 11.89 (s, 1H), 10.48 (s, 1H), 9.35 (d, J = 1.8 Hz, 1H), 9.27 (s, 1H), 8.55 (dd, J = 4.7, 1.7 Hz, 1H), 8.51 (dt, J = 8.0, 1.9 Hz, 1H), 8.27 (d, J = 1.8 Hz, 1H), 8.20 (d, J = 2.2 Hz, 1H), 8.08 (d, J = 8.4 Hz, 1H), 7.87 (dd, J = 7.9, 1.8 Hz, 1H), 7.70 (d, J = 8.7 Hz, 1H), 7.53 (d, J = 8.1 Hz, 1H), 7.41 (dd, J = 8.0, 5.3 Hz, 1H), 7.28-7.26 (m, 1H), 6.55 (s, 1H), 3.59 (s, 2H), 2.50-2.42 (m, 4H), 2.37 (s, 3H), 2.36-2.30 (m, 4H). MS (ESI) m/z: 601 [M + H]$^+$. |
| II-a-4 | 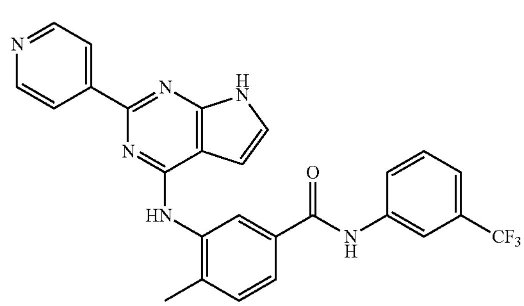 [SMILES: Cc1ccc(C(=O)Nc2cccc(C(F)(F)F)c2)cc1Nc1nc(-c2ccncc2)nc2[nH]ccc12] | $^1$H NMR (600 MHz, DMSO-d$_6$) δ 11.97 (s, 1H), 10.53 (s, 1H), 9.31 (s, 1H), 8.59 (d, J = 5.7 Hz, 2H), 8.30 (d, J = 1.7 Hz, 1H), 8.25 (s, 1H), 8.12-8.10 (m, 2H), 8.08 (s, 1H), 7.87 (dd, J = 8.0, 1.8 Hz, 1H), 7.61 (t, J = 8.1 Hz, 1H), 7.54 (d, J = 8.1 Hz, 1H), 7.46 (d, J = 7.0 Hz, 1H), 7.34-7.31 (m, 1H), 6.58-6.54 (m, 1H), 2.37 (s, 3H). MS (ESI) m/z: 489 [M + H]$^+$. |

| No. | Structure | ¹H NMR and/or MS data |
|---|---|---|
| II-a-5 | 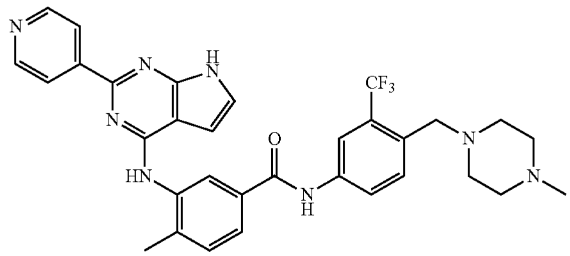 [SMILES: Cc1ccc(C(=O)Nc2ccc(CN3CCN(C)CC3)c(C(F)(F)F)c2)cc1Nc1nc(-c2ccncc2)nc2[nH]ccc12] | ¹H NMR (600 MHz, DMSO-d₆) δ 11.98 (s, 1H), 10.52 (s, 1H), 9.30 (s, 1H), 8.59 (d, J = 5.6 Hz, 2H), 8.32 (s, 1H), 8.22 (s, 1H), 8.13-8.10 (m, 3H), 7.86 (d, J = 9.3 Hz, 1H), 7.71 (d, J = 8.6 Hz, 1H), 7.54 (d, J = 8.3 Hz, 1H), 7.33 (s, 1H), 6.58 (s, 1H), 3.67 (s, 2H), 3.08-3.00 (m, 2H), 2.95-2.88 (m, 2H), 2.80 (s, 3H), 2.56-2.54 (m, 4H), 2.38 (s, 3H). MS (ESI) m/z: 601 [M + H]⁺. |
| II-b-1 | 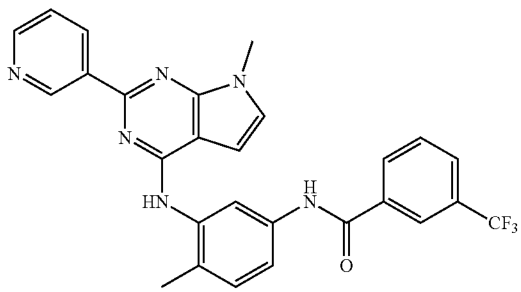 [SMILES: Cc1ccc(NC(=O)c2cccc(C(F)(F)F)c2)cc1Nc1nc(-c2cccnc2)nc2c1ccn2C] | ¹H NMR (600 MHz, DMSO-d₆) δ 10.49 (s, 1H), 9.44 (s, 1H), 9.21 (s, 1H), 8.60 (dt, J = 7.9, 1.9 Hz, 1H), 8.58 (d, J = 4.6 Hz, 1H), 8.30 (s, 1H), 8.27 (d, J = 7.8 Hz, 1H), 8.05 (d, J = 2.0 Hz, 1H), 7.97 (d, J = 7.8 Hz, 1H), 7.79 (t, J = 7.8 Hz, 1H), 7.63 (dd, J = 8.2, 2.1 Hz, 1H), 7.45 (dd, J = 7.8, 4.8 Hz, 1H), 7.35 (d, J = 8.4 Hz, 1H), 7.27 (d, J = 3.4 Hz, 1H), 6.43 (s, 1H), 3.83 (s, 3H), 2.24 (s, 3H). MS (ESI) m/z: 503 [M + H]⁺. |
| II-b-2 | 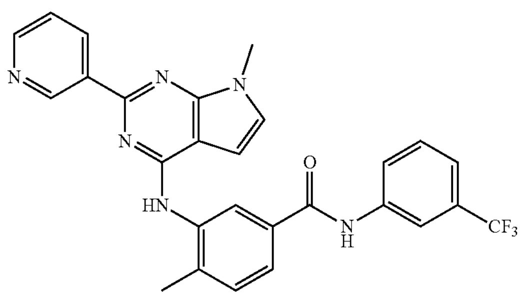 [SMILES: Cc1ccc(C(=O)Nc2cccc(C(F)(F)F)c2)cc1Nc1nc(-c2cccnc2)nc2c1ccn2C] | ¹H NMR (600 MHz, DMSO-d₆) δ 10.53 (s, 1H), 9.41 (d, J = 1.8 Hz, 1H), 9.33 (s, 1H), 8.58-8.55 (m, 2H), 8.27-8.23 (m, 2H), 8.09 (d, J = 9.1 Hz, 1H), 7.88 (dd, J = 7.9, 1.8 Hz, 1H), 7.60 (t, J = 8.0 Hz, 1H), 7.54 (d, J = 8.1 Hz, 1H), 7.45 (d, J = 7.7 Hz, 1H), 7.44-7.41 (m, 1H), 7.32 (d, J = 3.4 Hz, 1H), 6.53 (s, 1H), 3.85 (s, 3H), 2.37 (s, 3H). MS (ESI) m/z: 503 [M + H]⁺. |
| II-b-3 | 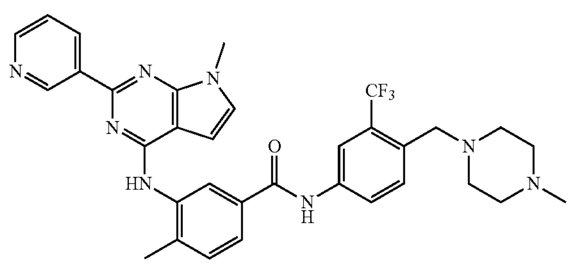 [SMILES: Cc1ccc(C(=O)Nc2ccc(CN3CCN(C)CC3)c(C(F)(F)F)c2)cc1Nc1nc(-c2cccnc2)nc2c1ccn2C] | ¹H NMR (600 MHz, DMSO-d₆) δ 10.49 (s, 1H), 9.40 (s, 1H), 9.33 (s, 1H), 8.59-8.55 (m, 2H), 8.25 (s, 1H), 8.20 (s, 1H), 8.08 (d, J = 8.6 Hz, 1H), 7.88 (d, J = 7.9 Hz, 1H), 7.70 (d, J = 8.5 Hz, 1H), 7.53 (d, J = 8.0 Hz, 1H), 7.42 (dd, J = 7.4, 5.2 Hz, 1H), 7.31 (d, J = 3.3 Hz, 1H), 6.53 (s, 1H), 3.85 (s, 3H), 3.58 (s, 2H), 2.56-2.54 (m, 4H), 2.48-2.39 (m, 4H), 2.36 (s, 3H), 2.29 (s, 3H). MS (ESI) m/z: 615 [M + H]⁺. |
| II-b-4 | 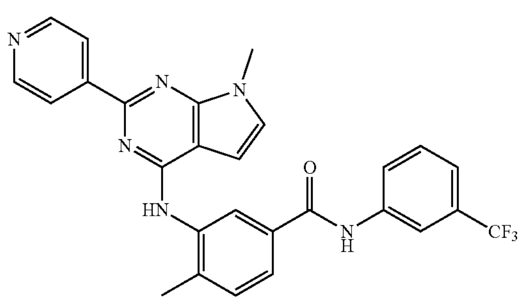 [SMILES: Cc1ccc(C(=O)Nc2cccc(C(F)(F)F)c2)cc1Nc1nc(-c2ccncc2)nc2c1ccn2C] | ¹H NMR (600 MHz, DMSO-d₆) δ 10.54 (s, 1H), 9.38 (s, 1H), 8.62 (d, J = 5.8 Hz, 2H), 8.28 (s, 1H), 8.25 (s, 1H), 8.19 (d, J = 5.9 Hz, 2H), 8.08 (d, J = 8.4 Hz, 1H), 7.89 (d, J = 8.2 Hz, 1H), 7.61 (t, J = 7.9 Hz, 1H), 7.54 (d, J = 7.9 Hz, 1H), 7.46 (d, J = 7.3 Hz, 1H), 7.37 (d, J = 3.3 Hz, 1H), 6.56 (s, 1H), 3.86 (s, 3H), 2.36 (s, 3H). MS (ESI) m/z: 503 [M + H]⁺. |

| No. | Structure | ¹H NMR and/or MS data |
|---|---|---|
| II-b-5 | 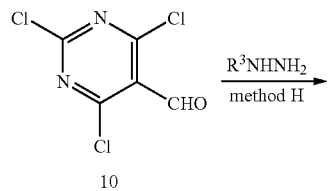 | ¹H NMR (600 MHz, DMSO-d₆) δ 10.53 (s, 1H), 9.51 (s, 1H), 8.79 (d, J = 5.5 Hz, 2H), 8.44 (d, J = 5.5 Hz, 2H), 8.26 (s, 1H), 8.23 (d, J = 2.1 Hz, 1H), 8.13-8.10 (m, 1H), 7.90 (d, J = 8.0 Hz, 1H), 7.71 (d, J = 8.6 Hz, 1H), 7.55 (d, J = 8.1 Hz, 1H), 7.45 (d, J = 3.4 Hz, 1H), 6.60 (s, 1H), 3.88 (s, 3H), 3.68 (s, 2H), 3.44-3.37 (m, 2H), 3.08-3.01 (m, 2H), 2.95-2.90 (m, 2H), 2.81 (s, 3H), 2.42-2.38 (m, 2H), 2.36 (s, 3H). MS (ESI) m/z: 615 [M + H]⁺. |

Synthetic Route of Compounds III-a-1, III-b-1:

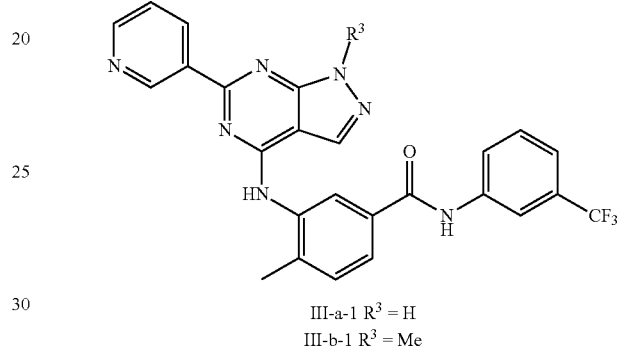

III-a-1 R³ = H
III-b-1 R³ = Me

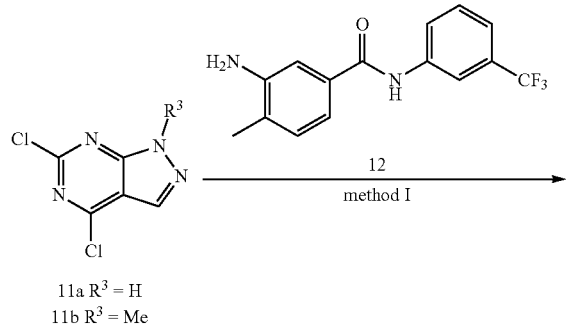

11a R³ = H
11b R³ = Me

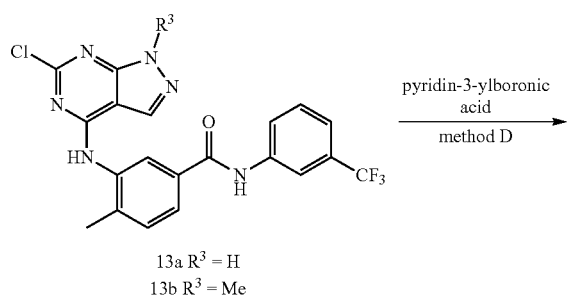

13a R³ = H
13b R³ = Me

Synthesis of Compound 11a:

Method H: compound 10 (211 mg, 1.0 mmol) was dissolved in ethanol (5 mL) and stirred at −78° C., to which was slowly added hydrazine hydrate (53 μL, 1.1 mmol), monitored by TLC until complete reaction, to which was added ethyl acetate (50 mL). The system washed with water once, and the organic phase was dried with anhydrous sodium sulfate, filtered, concentrated and separated by silica gel column chromatography to obtain compound 11a (127 mg, 67% yield).

MS (ESI) m/z: 190 [M+H]⁺.

compound 11b was synthesized from 10 and methylhydrazine through Method H.

MS (ESI) m/z: 204 [M+H]⁺.

Synthesis of compound 13:

Compound 11 (0.5 mmol) and 12 (0.5 mmol) were reacted in t-butanol (2 mL) in a microwave reactor at 150° C. for 4 h, concentrated and separated by silica gel column chromatography to obtain the compound.

13a: MS (ESI) m/z: 490 [M+H]⁺; 13b: MS (ESI) m/z: 504 [M+H]⁺.

Compounds III-a-1, III-a-2 were respectively synthesized from 13a, 13b and 3-pyridineboronic acid through Method D.

Other such compounds could be synthesized by similar methods.

In the following table it lists the specific compounds and their structural characterization data.

| No. | Structure | ¹H NMR and/or MS data |
|---|---|---|
| III-a-1 | 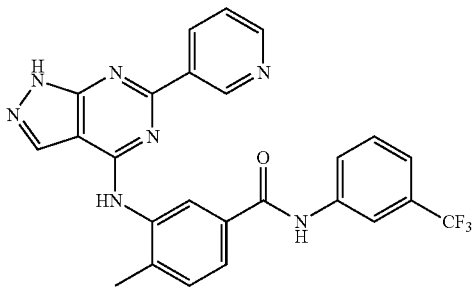 [SMILES: Cc1ccc(C(=O)Nc2cccc(C(F)(F)F)c2)cc1Nc1nc(-c2cccnc2)nc2[nH]ncc12] | ¹H NMR (600 MHz, DMSO-d$_6$) δ 10.53 (s, 1H), 10.09 (s, 1H), 9.38 (s, 1H), 8.66 (d, J = 27.9 Hz, 2H), 8.34 (s, 1H), 8.23 (s, 2H), 8.07 (d, J = 8.3 Hz, 1H), 7.95 (d, J = 8.0 Hz, 1H), 7.58 (d, J = 8.6 Hz, 3H), 7.45 (d, J = 7.8 Hz, 1H), 2.36 (s, 3H). MS (ESI) m/z: 490 [M + H]⁺. |
| III-b-1 | 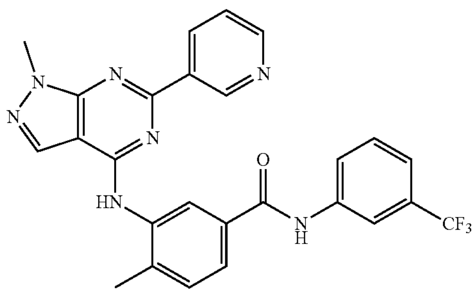 [SMILES: Cc1ccc(C(=O)Nc2cccc(C(F)(F)F)c2)cc1Nc1nc(-c2cccnc2)nc2c1cnn2C] | ¹H NMR (600 MHz, CDCl$_3$) δ 9.58 (s, 1H), 9.51 (s, 1H), 8.61 (dd, J = 7.9, 1.9 Hz, 1H), 8.49 (d, J = 4.8 Hz, 1H), 8.16 (s, 1H), 8.01 (s, 1H), 7.87 (dd, J = 21.7, 8.1 Hz, 2H), 7.44-7.32 (m, 3H), 7.28 (dt, J = 9.5, 3.0 Hz, 1H), 6.73 (s, 1H), 3.94 (d, J = 1.8 Hz, 3H), 2.24 (s, 3H). MS (ESI) m/z: 504 [M + H]⁺. |
| III-b-2 | 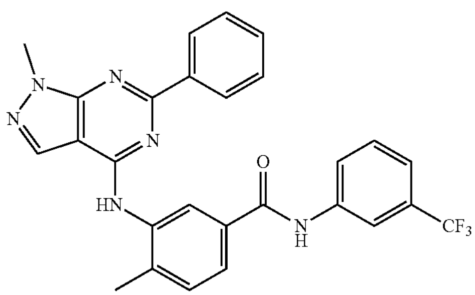 [SMILES: Cc1ccc(C(=O)Nc2cccc(C(F)(F)F)c2)cc1Nc1nc(-c2ccccc2)nc2c1cnn2C] | ¹H NMR (600 MHz, DMSO-d$_6$) δ 10.53 (s, 1H), 9.96 (s, 1H), 8.34 (d, J = 7.3 Hz, 2H), 8.23 (d, J = 2.0 Hz, 1H), 8.14-8.01 (m, 1H), 7.93 (d, J = 7.9 Hz, 1H), 7.59 (q, J = 7.9 Hz, 2H), 7.50-7.37 (m, 4H), 4.01 (s, 3H), 2.35 (s, 3H). MS (ESI) m/z: 503 [M + H]⁺. |
| III-b-3 | 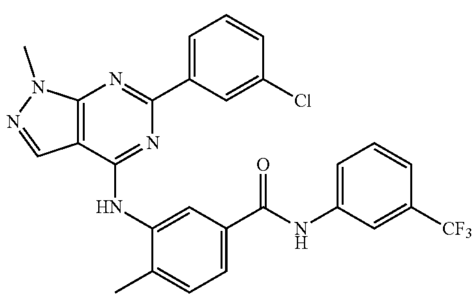 [SMILES: Cc1ccc(C(=O)Nc2cccc(C(F)(F)F)c2)cc1Nc1nc(-c2cccc(Cl)c2)nc2c1cnn2C] | ¹H NMR (600 MHz, DMSO-d$_6$) δ 10.53 (s, 1H), 10.03 (s, 1H), 8.32 (s, 1H), 8.28 (s, 3H), 8.25 (t, J = 1.9 Hz, 1H), 8.08-8.03 (m, 1H), 7.94 (d, J = 8.0 Hz, 1H), 7.58 (dd, J = 8.1, 4.5 Hz, 2H), 7.51 (d, J = 7.8 Hz, 1H), 7.49-7.42 (m, 2H), 4.02 (s, 3H), 2.36 (s, 3H). MS (ESI) m/z: 537 [M + H]⁺. |
| III-b-4 | 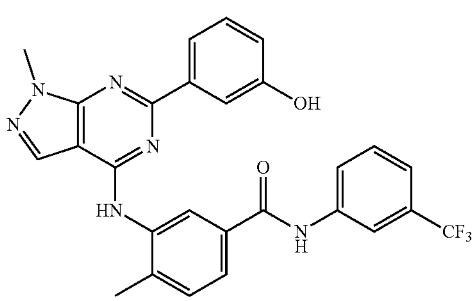 | ¹H NMR (600 MHz, DMSO-d$_6$) δ 10.51 (s, 1H), 9.94 (s, 1H), 9.47 (s, 1H), 8.23 (d, J = 2.1 Hz, 1H), 8.16 (s, 1H), 8.06 (d, J = 8.4 Hz, 1H), 7.97-7.90 (m, 1H), 7.76 (d, J = 9.3 Hz, 2H), 7.64-7.53 (m, 2H), 7.50-7.42 (m, 1H), 7.18 (t, J = 7.8 Hz, 1H), 6.83 (dd, J = 7.8, 2.3 Hz, 1H), 3.99 (s, 3H), 2.34 (s, 3H). MS (ESI) m/z: 519 [M + H]⁺. |

| No. | Structure | $^1$H NMR and/or MS data |
|---|---|---|
| III-b-5 | 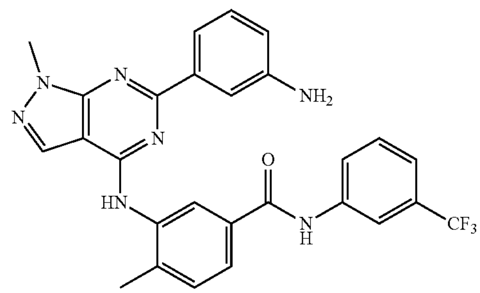 [SMILES: Cc1ccc(C(=O)Nc2cccc(C(F)(F)F)c2)cc1Nc1nc(-c2cccc(N)c2)nc2c1cnn2C] | $^1$H NMR (600 MHz, DMSO-d$_6$) 10.54 (s, 1H), 9.84 (s, 1H), 8.27 (s, 1H), 8.24 (d, J = 1.9 Hz, 1H), 8.09-8.05 (m, 1H), 7.92 (d, J = 7.9 Hz, 1H), 7.68 (t, J = 2.0 Hz, 1H), 7.61 (t, J = 8.0 Hz, 1H), 7.57 (d, J = 8.0 Hz, 1H), 7.50 (d, J = 7.6 Hz, 1H), 7.48-7.45 (m, 1H), 7.04 (t, J = 7.8 Hz, 1H), 6.66 (ddd, J = 7.9, 2.5, 1.0 Hz, 1H), 5.11 (s, 2H), 4.00 (s, 3H), 2.36 (s, 3H). MS (ESI) m/z: 518 [M + H]$^+$. |
| III-b-6 | 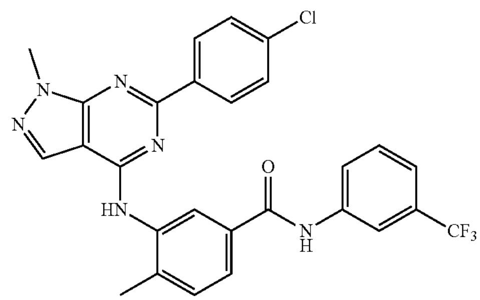 | $^1$H NMR (600 MHz, DMSO-d$_6$) δ 10.52 (s, 1H), 10.00 (s, 1H), 8.34 (d, J = 8.1 Hz, 2H), 8.23 (s, 2H), 8.09-8.04 (m, 1H), 7.93 (d, J = 7.9 Hz, 1H), 7.60-7.55 (m, 2H), 7.48 (d, J = 8.2 Hz, 2H), 7.45 (d, J = 7.7 Hz, 1H), 4.00 (s, 3H), 2.34 (s, 3H). MS (ESI) m/z: 537 [M + H]$^+$. |
| III-b-7 | 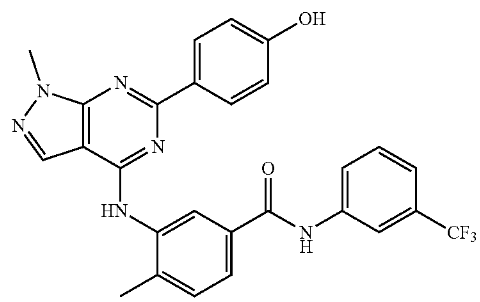 [SMILES: Cc1ccc(C(=O)Nc2cccc(C(F)(F)F)c2)cc1Nc1nc(-c2ccc(O)cc2)nc2c1cnn2C] | $^1$H NMR (600 MHz, DMSO-d$_6$) δ 10.52 (s, 1H), 9.82 (s, 1H), 9.81 (s, 1H), 8.23 (d, J = 7.1 Hz, 2H), 8.18 (d, J = 8.3 Hz, 2H), 8.07 (d, J = 8.2 Hz, 1H), 7.91 (d, J = 7.9 Hz, 1H), 7.59 (t, J = 8.0 Hz, 1H), 7.56 (d, J = 8.0 Hz, 1H), 7.45 (d, J = 7.7 Hz, 1H), 6.77 (d, J = 8.4 Hz, 2H), 3.97 (s, 3H), 2.34 (s, 3H). MS (ESI) m/z: 519 [M + H]$^+$. |
| III-b-8 | 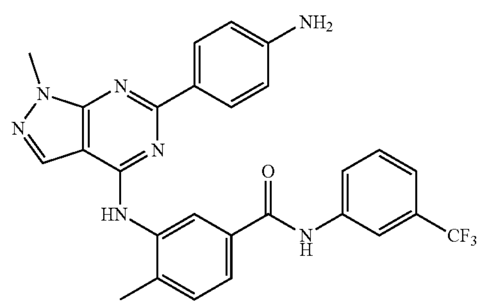 | $^1$H NMR (600 MHz, DMSO-d$_6$) δ 10.52 (s, 1H), 8.23 (d, J = 10.7 Hz, 2H), 8.07 (dd, J = 18.3, 8.3 Hz, 3H), 7.90 (d, J = 7.9 Hz, 1H), 7.59 (t, J = 8.0 Hz, 1H), 7.55 (d, J = 8.0 Hz, 1H), 7.45 (d, J = 7.8 Hz, 1H), 6.93 (s, 1H), 6.71-6.66 (m, 1H), 6.54 (d, J = 8.4 Hz, 2H), 5.53 (s, 2H), 3.95 (s, 3H), 2.34 (s, 3H). MS (ESI) m/z: 518 [M + H]$^+$. |
| III-b-9 | 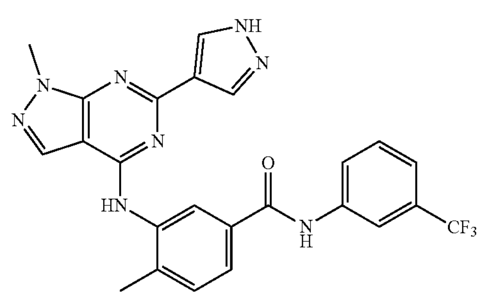 [SMILES: Cc1ccc(C(=O)Nc2cccc(C(F)(F)F)c2)cc1Nc1nc(-c2cn[nH]c2)nc2c1cnn2C] | $^1$H NMR (600 MHz, DMSO-d$_6$) δ 10.51 (s, 1H), 9.74 (s, 1H), 8.26 (s, 1H), 8.23 (d, J = 2.1 Hz, 1H), 8.09-8.04 (m, 1H), 8.03-7.95 (m, 1H), 7.90 (dd, J = 7.9, 1.9 Hz, 1H), 7.59 (t, J = 8.0 Hz, 1H), 7.54 (d, J = 8.0 Hz, 1H), 7.48-7.42 (m, 1H), 3.93 (s, 3H), 2.35 (s, 3H). MS (ESI) m/z: 493 [M + H]$^+$. |

-continued

| No. | Structure | ¹H NMR and/or MS data |
|---|---|---|
| III-b-10 | 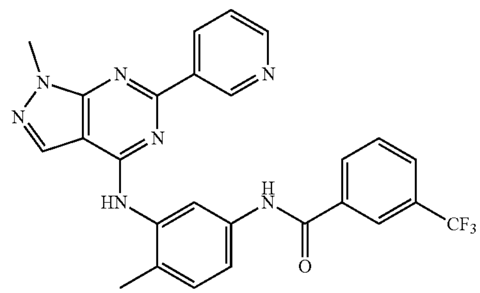 [SMILES: Cc1ccc(NC(=O)c2cccc(C(F)(F)F)c2)cc1Nc1nc(-c2cccnc2)nc2c1cnn2C] | ¹H NMR (600 MHz, DMSO-$d_6$) δ 10.53 (s, 1H), 9.99 (s, 1H), 9.46 (s, 1H), 8.72-8.53 (m, 2H), 8.29 (s, 1H), 8.26 (d, J = 7.9 Hz, 1H), 8.02 (d, J = 4.5 Hz, 1H), 7.96 (d, J = 7.8 Hz, 1H), 7.78 (t, J = 7.8 Hz, 1H), 7.68 (d, J = 8.3 Hz, 1H), 7.49 (dd, J = 7.9, 4.8 Hz, 1H), 7.40 (d, J = 8.3 Hz, 1H), 4.00 (s, 3H), 2.23 (s, 3H). MS (ESI) m/z: 504 [M + H]⁺. |
| III-b-11 | 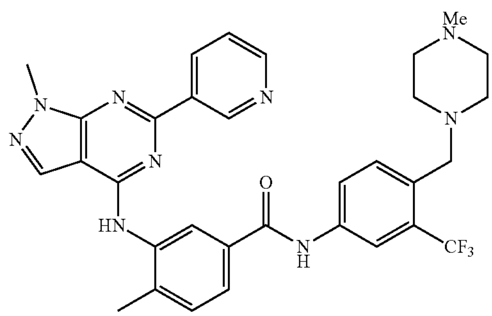 [SMILES: Cc1ccc(C(=O)Nc2ccc(CN3CCN(C)CC3)c(C(F)(F)F)c2)cc1Nc1nc(-c2cccnc2)nc2c1cnn2C] | ¹H NMR (600 MHz, DMSO-$d_6$) δ 10.48 (s, 1H), 10.09 (s, 1H), 9.42 (s, 1H), 8.63 (dd, J = 4.8, 1.7 Hz, 1H), 8.59 (d, J = 7.9 Hz, 1H), 8.21 (s, 1H), 8.18 (d, J = 2.2 Hz, 1H), 8.05 (dd, J = 8.6, 2.2 Hz, 1H), 7.94 (d, J = 8.1 Hz, 1H), 7.69 (d, J = 8.6 Hz, 1H), 7.57 (d, J = 8.1 Hz, 1H), 7.46 (dd, J = 8.1, 4.8 Hz, 1H), 4.02 (s, 3H), 3.55 (s, 2H), 2.45-2.31 (m, 8H), 2.35 (s, 3H), 2.16 (s, 3H). MS (ESI) m/z: 616 [M + H]⁺. |
| III-b-12 | 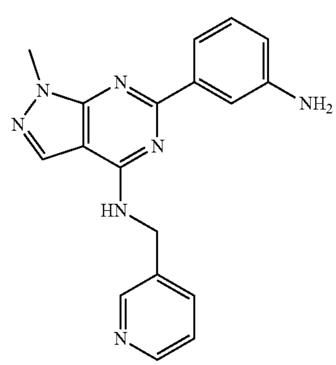 [SMILES: Cn1ncc2c(NCc3cccnc3)nc(-c3cccc(N)c3)nc21] | ¹H NMR (600 MHz, Methanol-$d_4$) δ 8.66 (d, J = 2.0 Hz, 1H), 8.40 (d, J = 4.8 Hz, 1H), 7.99 (s, 1H), 7.92 (d, J = 8.0 Hz, 1H), 7.82 (s, 1H), 7.75 (d, J = 7.7 Hz, 1H), 7.38 (dd, J = 7.9, 4.9 Hz, 1H), 7.18 (t, J = 7.8 Hz, 1H), 6.84 (dd, J = 7.9, 2.3 Hz, 1H), 4.90 (s, 2H), 3.99 (s, 3H). MS (ESI) m/z: 332 [M + H]⁺. |
| III-b-13 | 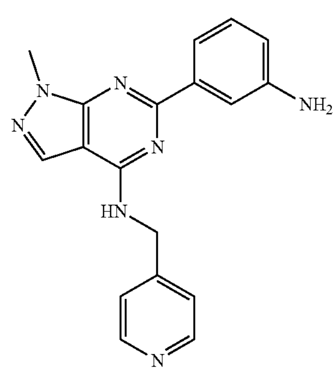 [SMILES: Cn1ncc2c(NCc3ccncc3)nc(-c3cccc(N)c3)nc21] | ¹H NMR (600 MHz, Methanol-$d_4$) δ 8.46 (d, J = 5.3 Hz, 2H), 8.04 (s, 1H), 7.77 (s, 1H), 7.69 (d, J = 7.7 Hz, 1H), 7.49 (d, J = 5.2 Hz, 2H), 7.15 (t, J = 7.8 Hz, 1H), 6.82 (dd, J = 7.9, 2.3 Hz, 1H), 4.95 (s, 2H), 4.02 (s, 3H). MS (ESI) m/z: 332 [M + H]⁺. |

| No. | Structure | ¹H NMR and/or MS data |
|---|---|---|
| III-b-14 | 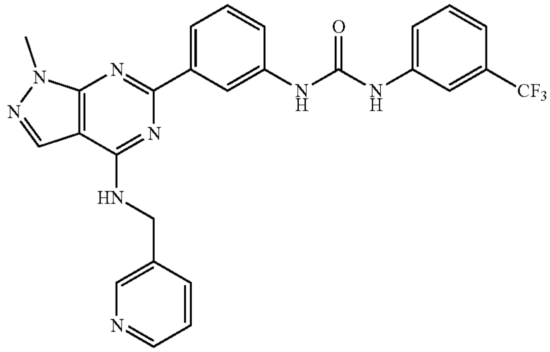 [SMILES: Cn1ncc2c(NCc3cccnc3)nc(-c3cccc(NC(=O)Nc4cccc(C(F)(F)F)c4)c3)nc21] | ¹H NMR (600 MHz, Methanol-d₄) δ 8.71 (d, J = 2.0 Hz, 1H), 8.54 (t, J = 1.9 Hz, 1H), 8.41 (dd, J = 4.9, 1.7 Hz, 1H), 8.13 (dt, J = 7.8, 1.3 Hz, 1H), 8.01 (d, J = 9.8 Hz, 2H), 7.93 (s, 1H), 7.63 (dd, J = 8.3, 2.1 Hz, 1H), 7.60 (ddd, J = 8.0, 2.3, 1.0 Hz, 1H), 7.47 (t, J = 8.0 Hz, 1H), 7.42-7.37 (m, 2H), 7.30-7.27 (m, 1H), 4.95 (s, 2H), 4.03 (s, 3H). MS (ESI) m/z: 519 [M + H]⁺. |
| III-b-15 | 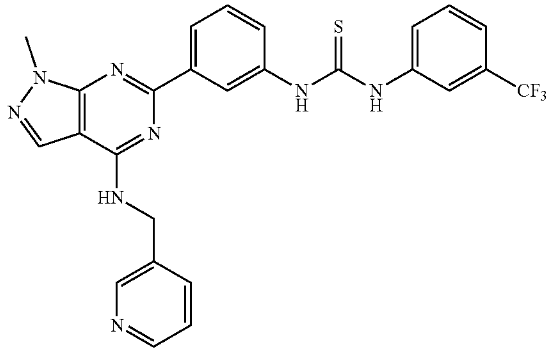 | ¹H NMR (600 MHz, DMSO-d₆) δ 10.18 (s, 1H), 10.09 (s, 1H), 8.86 (t, J = 5.9 Hz, 1H), 8.68 (d, J = 2.1 Hz, 1H), 8.55 (s, 1H), 8.46 (dd, J = 4.8, 1.5 Hz, 1H), 8.25 (d, J = 7.8 Hz, 1H), 8.11 (s, 1H), 7.98 (s, 1H), 7.83 (d, J = 7.9 Hz, 1H), 7.79-7.77 (m, 1H), 7.64-7.60 (m, 1H), 7.55 (t, J = 7.9 Hz, 1H), 7.46 (q, J = 8.0 Hz, 2H), 7.34 (dd, J = 7.9, 4.7 Hz, 1H), 4.87 (d, J = 5.6 Hz, 2H), 3.96 (s, 3H). MS (ESI) m/z: 535 [M + H]⁺. |
| III-b-16 | 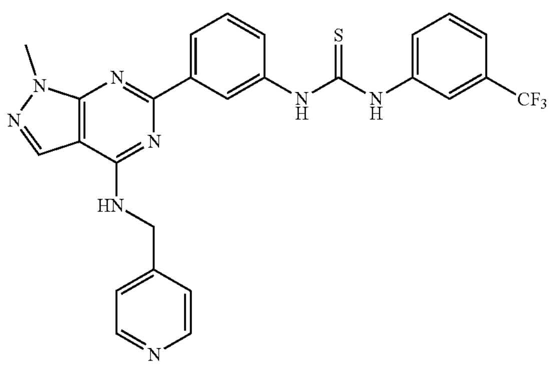 [SMILES: Cn1ncc2c(NCc3ccncc3)nc(-c3cccc(NC(=S)Nc4cccc(C(F)(F)F)c4)c3)nc21] | ¹H NMR (600 MHz, Methanol-d₄) δ 8.50 (s, 1H), 8.45-8.41 (m, 2H), 8.21 (d, J = 7.7 Hz, 1H), 8.04 (s, 1H), 7.91 (s, 1H), 7.70 (dd, J = 8.3, 1.9 Hz, 1H), 7.52-7.46 (m, 4H), 7.44-7.40 (m, 2H), 4.91 (s, 2H), 4.01 (s, 3H). MS (ESI) m/z: 535 [M + H]⁺. |
| III-b-17 TFA salt | | ¹H NMR (600 MHz, DMSO-d₆) δ 10.27 (s, 1H), 9.30 (s, 1H), 8.87 (t, J = 5.7 Hz, 1H), 8.70 (d, J = 2.2 Hz, 1H), 8.59 (s, 1H), 8.46 (dd, J = 4.8, 1.6 Hz, 1H), 8.30 (d, J = 2.5 Hz, 1H), 8.24 (d, J = 7.8 Hz, 1H), 8.12 (s, 1H), 7.85 (d, J = 7.9 Hz, 1H), 7.70 (d, J = 7.9 Hz, 1H), 7.46 (t, J = 7.9 Hz, 1H), 7.35 (dd, J = 7.9, 4.8 Hz, 1H), 7.30 (dd, J = 8.8, 2.5 Hz, 1H), 7.03 (d, J = 8.8 Hz, 1H), 4.90 (d, J = 5.6 Hz, 2H), 3.97 (s, 3H), 3.83 (s, 3H). MS (ESI) m/z: 576 [M + H]⁺. |

-continued

| No. | Structure | ¹H NMR and/or MS data |
|---|---|---|
| III-b-18 | 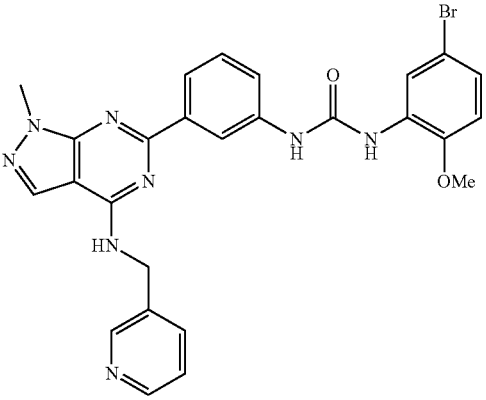 TFA salt | ¹H NMR (600 MHz, DMSO-d₆) δ 9.55 (s, 1H), 8.87 (d, J = 6.2 Hz, 1H), 8.72 (s, 1H), 8.47 (dt, J = 5.8, 1.7 Hz, 2H), 8.41 (d, J = 2.7 Hz, 2H), 8.12 (s, 1H), 8.08 (dd, J = 7.8, 1.4 Hz, 1H), 7.89 (d, J = 7.9 Hz, 1H), 7.72-7.69 (m, 1H), 7.42-7.36 (m, 2H), 7.11 (dd, J = 8.7, 2.5 Hz, 1H), 7.00 (d, J = 8.7 Hz, 1H), 4.91 (d, J = 5.9 Hz, 2H), 3.98 (s, 3H), 3.90 (s, 3H). MS (ESI) m/z: 560 [M + H]⁺. |
| III-c-1 | 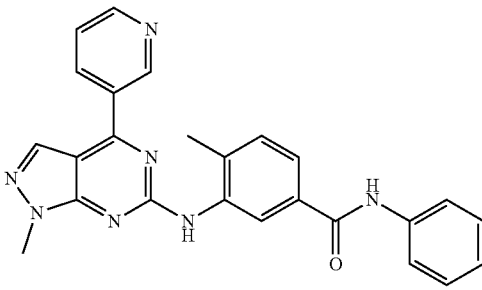 | ¹H NMR (600 MHz, DMSO-d₆) δ 10.49 (s, 1H), 9.37 (s, 1H), 9.35 (s, 1H), 8.78 (d, J = 4.7 Hz, 1H), 8.58 (d, J = 8.0 Hz, 1H), 8.48 (d, J = 1.5 Hz, 1H), 8.41 (s, 1H), 8.25 (s, 1H), 8.09 (d, J = 8.3 Hz, 1H), 7.77 (d, J = 8.0 Hz, 1H), 7.60 (t, J = 8.3 Hz, 2H), 7.45 (dd, J = 7.9, 3.3 Hz, 2H), 3.91-3.85 (m, 3H), 2.39 (s, 3H). MS (ESI) m/z: 504 [M + H]⁺. |

Synthetic Route of Compounds IV-a-1, IV-b-1:

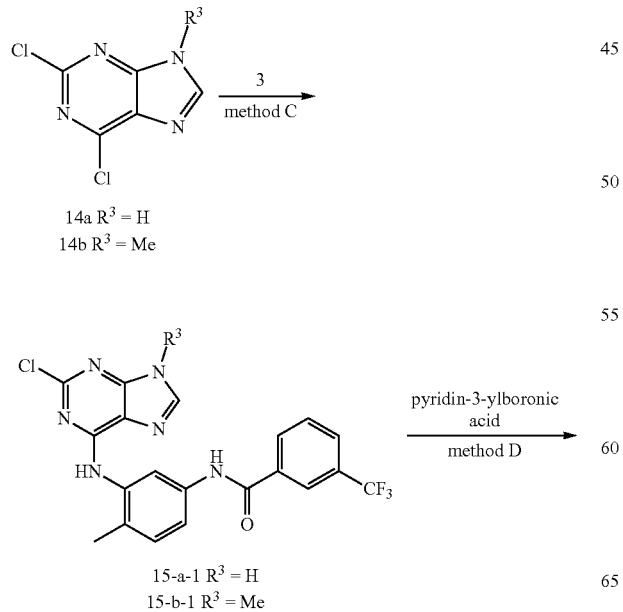

14a R³ = H
14b R³ = Me 15-a-1 R³ = H
15-b-1 R³ = Me

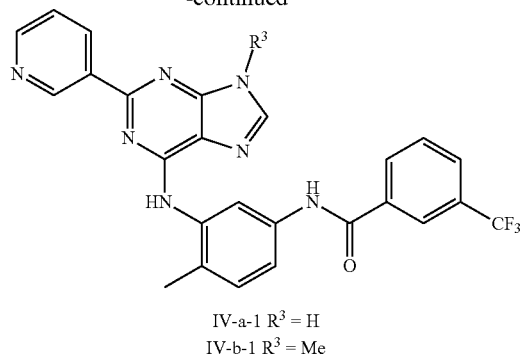

IV-a-1 R³ = H
IV-b-1 R³ = Me

Compounds IV-a-1, IV-b-1 were respectively synthesized from 14a, 14b through Method C, Method D in sequence.

Other such compounds could be synthesized by similar methods.

In the following table it lists the specific compounds and their structural characterization data.

| No. | Structure | ¹H NMR and/or MS data |
|---|---|---|
| IV-a-1 | 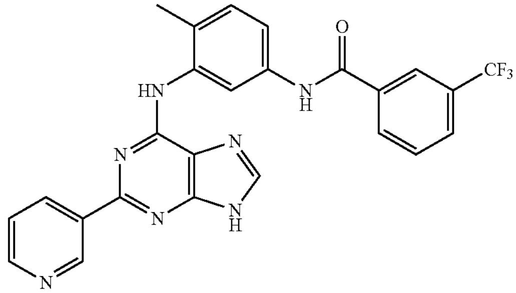 [SMILES: Cc1ccc(NC(=O)c2cccc(C(F)(F)F)c2)cc1Nc1nc(-c2cccnc2)nc2[nH]cnc12] | ¹H NMR (600 MHz, DMSO-d₆) δ 10.49 (s, 1H), 9.53-9.29 (m, 2H), 8.61-8.52 (m, 2H), 8.33-8.25 (m, 3H), 8.17 (s, 1H), 7.96 (d, J = 7.8 Hz, 1H), 7.79 (t, J = 7.9 Hz, 1H), 7.58 (d, J = 7.9 Hz, 1H), 7.43 (dd, J = 7.8, 4.8 Hz, 1H), 7.32 (d, J = 8.4 Hz, 1H), 2.27 (s, 3H). MS (ESI) m/z: 490 [M + H]⁺. |
| IV-a-2 | 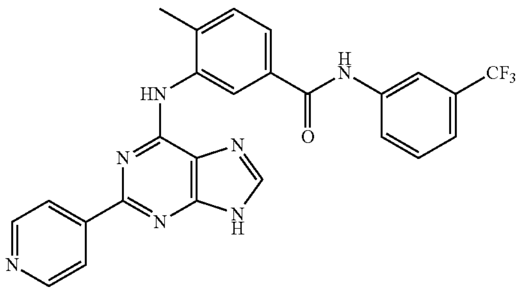 [SMILES: Cc1ccc(C(=O)Nc2cccc(C(F)(F)F)c2)cc1Nc1nc(-c2ccncc2)nc2[nH]cnc12] | ¹H NMR (600 MHz, MeOD) δ 8.91 (s, 1H), 8.54 (dd, J = 4.6, 1.6 Hz, 2H), 8.38 (dd, J = 4.6, 1.6 Hz, 2H), 8.30 (s, 1H), 8.20 (s, 1H), 7.97 (d, J = 8.7 Hz, 1H), 7.78 (dd, J = 7.9, 1.7 Hz, 1H), 7.58 (t, J = 8.0 Hz, 1H), 7.50 (d, J = 7.9 Hz, 1H), 7.46 (d, J = 7.7 Hz, 1H), 2.52 (s, 3H). MS (ESI) m/z: 490 [M + H]⁺. |
| IV-a-3 | 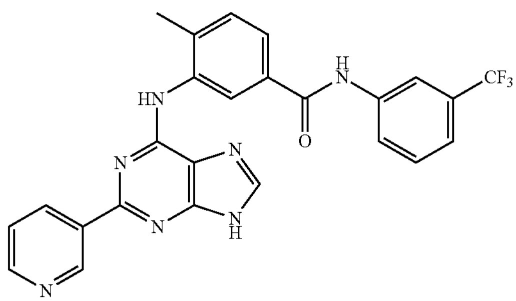 [SMILES: Cc1ccc(C(=O)Nc2cccc(C(F)(F)F)c2)cc1Nc1nc(-c2cccnc2)nc2[nH]cnc12] | ¹H NMR (600 MHz, DMSO-d₆) δ 10.59 (s, 1H), 9.63 (s, 1H), 9.34 (d, J = 1.7 Hz, 1H), 8.55 (dd, J = 4.7, 1.7 Hz, 1H), 8.51 (d, J = 8.0 Hz, 1H), 8.41 (s, 1H), 8.33 (s, 1H), 8.25 (s, 1H), 8.09 (d, J = 8.2 Hz, 1H), 7.86 (d, J = 8.1 Hz, 1H), 7.58 (t, J = 8.0 Hz, 1H), 7.49 (d, J = 8.1 Hz, 1H), 7.43 (d, J = 7.8 Hz, 1H), 7.39 (dd, J = 8.0, 4.8 Hz, 1H), 2.40 (s, 3H). MS (ESI) m/z: 490 [M + H]⁺. |
| IV-a-4 | 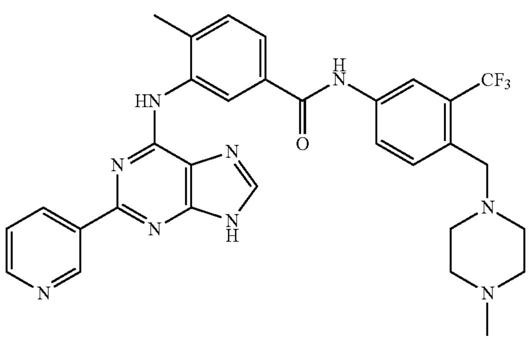 [SMILES: Cc1ccc(C(=O)Nc2ccc(CN3CCN(C)CC3)c(C(F)(F)F)c2)cc1Nc1nc(-c2cccnc2)nc2[nH]cnc12] | MS (ESI) m/z: 602 [M + H]⁺. |
| IV-a-5 | TFA salt | MS (ESI) m/z: 602 [M + H]⁺. |

| No. | Structure | ¹H NMR and/or MS data |
|---|---|---|
| IV-a-6 | 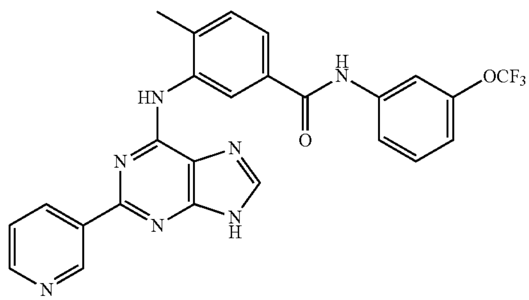 [SMILES: Cc1ccc(C(=O)Nc2cccc(OC(F)(F)F)c2)cc1Nc1nc(-c2cccnc2)nc2[nH]cnc12] | ¹H NMR (600 MHz, DMSO-d₆) δ 10.48 (s, 1H), 9.56 (s, 1H), 9.34 (s, 1H), 8.58 (d, J = 4.2 Hz, 1H), 8.50 (d, J = 8.3 Hz, 1H), 8.32 (d, J = 6.0 Hz, 1H), 7.94 (s, 1H), 7.86-7.72 (m, 2H), 7.57-7.46 (m, 2H), 7.45-7.35 (m, 1H), 7.09 (d, J = 7.3 Hz, 1H), 2.38 (s, 3H). MS (ESI) m/z: 506 [M + H]⁺. |
| IV-a-7 | 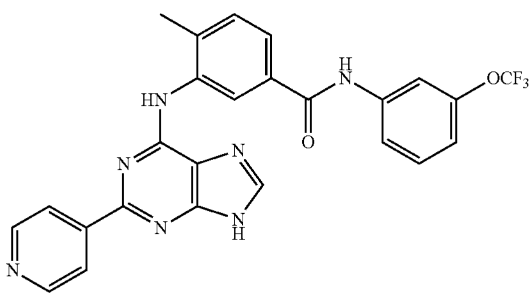 [SMILES: Cc1ccc(C(=O)Nc2cccc(OC(F)(F)F)c2)cc1Nc1nc(-c2ccncc2)nc2[nH]cnc12] | ¹H NMR (600 MHz, DMSO-d₆) δ 10.51 (s, 1H), 9.58 (s, 1H), 8.66-8.54 (m, 2H), 8.42-8.33 (m, 2H), 8.11 (s, 2H), 7.97 (s, 1H), 7.89-7.75 (m, 2H), 7.59-7.41 (m, 2H), 7.09 (d, J = 7.8 Hz, 1H), 2.39 (s, 3H). MS (ESI) m/z: 506 [M + H]⁺. |
| IV-b-1 | 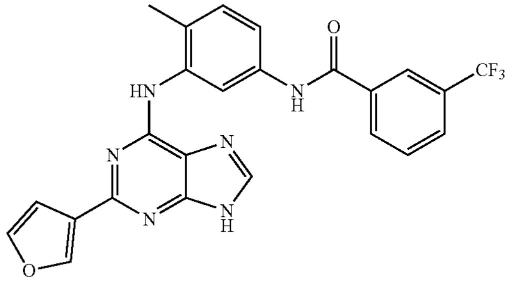 [SMILES: Cc1ccc(NC(=O)c2cccc(C(F)(F)F)c2)cc1Nc1nc(-c2ccoc2)nc2[nH]cnc12] | ¹H NMR (600 MHz, DMSO-d₆) δ 10.47 (s, 1H), 8.98 (s, 1H), 8.37 (s, 1H), 8.34-8.23 (m, 3H)), 8.20 (s, 1H), 7.97 (d, J = 7.5 Hz, 1H), 7.79 (t, J = 7.4 Hz, 1H), 7.69 (s, 1H), 7.47 (d, J = 7.8 Hz, 1H), 7.27 (d, J = 7.9 Hz, 1H), 6.92 (s, 1H), 2.28 (s, 3H). MS (ESI) m/z: 479 [M + H]⁺. |
| IV-b-2 | 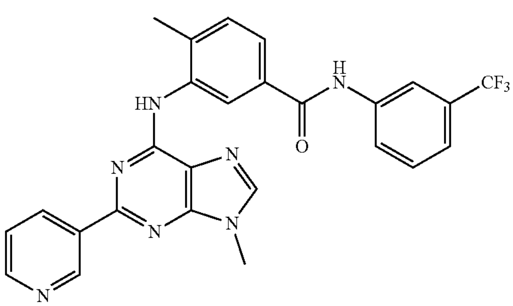 [SMILES: Cc1ccc(C(=O)Nc2cccc(C(F)(F)F)c2)cc1Nc1nc(-c2cccnc2)nc2c1ncn2C] | ¹H NMR (600 MHz, DMSO-d₆) δ 10.53 (s, 1H), 9.63 (s, 1H), 9.38 (d, J = 1.3 Hz, 1H), 8.59 (dd, J = 4.7, 1.5 Hz, 1H), 8.56-8.52 (m, 1H), 8.31 (d, J = 3.2 Hz, 2H), 8.25 (s, 1H), 8.09 (d, J = 8.3 Hz, 1H), 7.86 (dd, J = 7.9, 1.5 Hz, 1H), 7.60 (t, J = 8.0 Hz, 1H), 7.52 (d, J = 8.0 Hz, 1H), 7.47-7.39 (m, 2H), 3.88 (s, 3H), 2.37 (s, 3H). MS (ESI) m/z: 504 [M + H]⁺. |
| IV-b-3 | 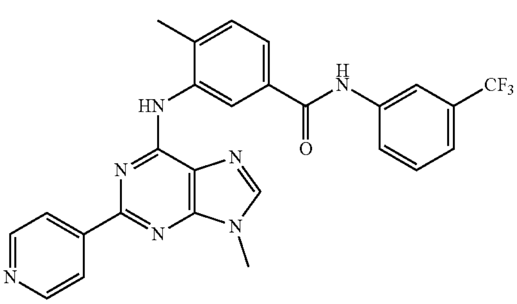 [SMILES: Cc1ccc(C(=O)Nc2cccc(C(F)(F)F)c2)cc1Nc1nc(-c2ccncc2)nc2c1ncn2C] | ¹H NMR (600 MHz, DMSO-d₆) δ 10.54 (s, 1H), 9.65 (s, 1H), 8.62 (s, 2H), 8.35 (d, J = 3.4 Hz, 2H), 8.26 (s, 1H), 8.19-8.05 (m, 3H), 7.87 (s, 1H), 7.68-7.38 (m, 3H), 3.88 (s, 3H), 2.37 (s, 3H). MS (ESI) m/z: 504 [M + H]⁺. |

| No. | Structure | ¹H NMR and/or MS data |
|---|---|---|
| IV-b-4 | 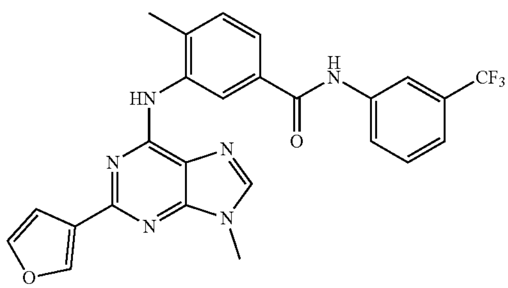 [SMILES: Cc1ccc(C(=O)Nc2cccc(C(F)(F)F)c2)cc1Nc1nc(-c2ccoc2)nc2c1ncn2C] | ¹H NMR (600 MHz, DMSO-d$_6$) δ 10.53 (s, 1H), 9.39 (s, 1H), 8.49 (s, 1H), 8.38 (s, 1H), 8.24 (s, 1H), 8.18 (d, J = 0.9 Hz, 1H), 8.08 (d, J = 8.3 Hz, 1H), 7.80 (dd, J = 7.9, 1.7 Hz, 1H), 7.70 (t, J = 1.6 Hz, 1H), 7.60 (t, J = 7.9 Hz, 1H), 7.46 (dd, J = 11.7, 8.0 Hz, 2H), 6.92 (d, J = 1.6 Hz, 1H), 3.83 (s, 3H), 2.38 (s, 3H). MS (ESI) m/z: 493 [M + H]⁺. |
| IV-b-5 | 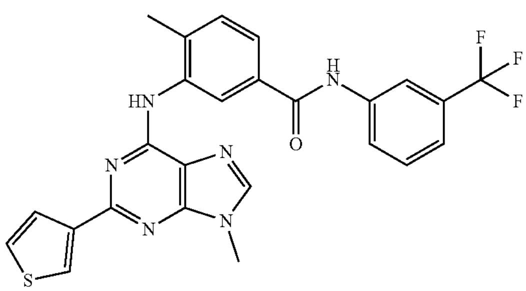 [SMILES: Cc1ccc(C(=O)Nc2cccc(C(F)(F)F)c2)cc1Nc1nc(-c2ccsc2)nc2c1ncn2C] | ¹H NMR (600 MHz, DMSO-d$_6$) δ 10.54 (s, 1H), 9.37 (s, 1H), 8.44 (d, J = 1.9 Hz, 1H), 8.28 (s, 1H), 8.26 (d, J = 2.0 Hz, 1H), 8.11 (dd, J = 3.1, 1.1 Hz, 1H), 8.09 (d, J = 7.5 Hz, 1H), 7.82 (dd, J = 7.9, 1.9 Hz, 1H), 7.70 (dd, J = 5.0, 1.2 Hz, 1H), 7.61 (t, J = 8.0 Hz, 1H), 7.52 (dd, J = 5.0, 3.0 Hz, 1H), 7.49 (d, J = 8.0 Hz, 1H), 7.46 (d, J = 7.7 Hz, 1H), 3.84 (s, 3H), 2.38 (s, 3H). MS (ESI) m/z: 509 [M + H]⁺ |
| IV-b-6 | 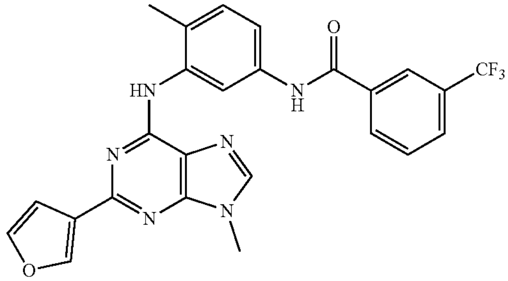 [SMILES: Cc1ccc(NC(=O)c2cccc(C(F)(F)F)c2)cc1Nc1nc(-c2ccoc2)nc2c1ncn2C] | ¹H NMR (600 MHz, DMSO-d$_6$) δ 10.47 (s, 1H), 9.04 (s, 1H), 8.35-8.24 (m, 4H), 8.20 (s, 1H), 7.97 (d, J = 7.6 Hz, 1H), 7.79 (t, J = 7.8 Hz, 1H), 7.69 (s, 1H), 7.49 (d, J = 8.1 Hz, 1H), 7.27 (d, J = 8.2 Hz, 1H), 6.95 (s, 1H), 3.80 (s, 3H), 2.27 (s, 3H). MS (ESI) m/z: 493 [M + H]⁺. |
| IV-b-7 | 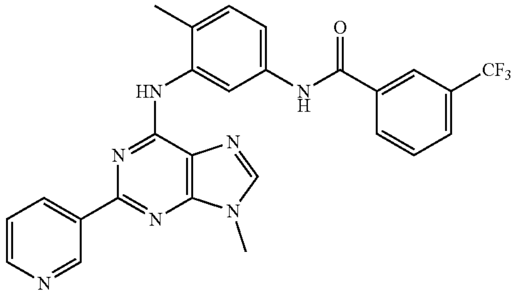 [SMILES: Cc1ccc(NC(=O)c2cccc(C(F)(F)F)c2)cc1Nc1nc(-c2cccnc2)nc2c1ncn2C] | ¹H NMR (600 MHz, DMSO-d$_6$) δ 10.49 (s, 1H), 9.45 (s, 1H), 9.40 (d, J = 1.9 Hz, 1H), 8.62-8.54 (m, 2H), 8.30 (s, 1H), 8.28-8.25 (m, 2H), 8.14 (d, J = 1.9 Hz, 1H), 7.96 (d, J = 7.8 Hz, 1H), 7.78 (t, J = 7.8 Hz, 1H), 7.59 (dd, J = 8.2, 2.1 Hz, 1H), 7.43 (dd, J = 7.5, 5.1 Hz, 1H), 7.31 (d, J = 8.4 Hz, 1H), 3.86 (s, 3H), 2.25 (s, 3H). MS (ESI) m/z: 504 [M + H]⁺. |
| IV-b-8 | 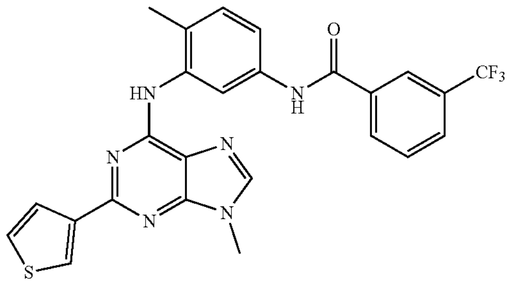 [SMILES: Cc1ccc(NC(=O)c2cccc(C(F)(F)F)c2)cc1Nc1nc(-c2ccsc2)nc2c1ncn2C] | ¹H NMR (600 MHz, DMSO-d$_6$) δ 10.48 (s, 1H), 9.15 (s, 1H), 8.31 (s, 1H), 8.28 (d, J = 7.9 Hz, 1H), 8.25 (s, 1H), 8.22 (s, 1H), 8.19 (d, J = 2.9 Hz, 1H), 7.96 (d, J = 7.7 Hz, 1H), 7.79 (t, J = 7.8 Hz, 1H), 7.73 (d, J = 5.0 Hz, 1H), 7.55-7.50 (m, 2H), 7.28 (d, J = 8.2 Hz, 1H), 3.81 (d, J = 9.9 Hz, 3H), 2.26 (s, 3H). MS (ESI) m/z: 509 [M + H]⁺. |

| No. | Structure | ¹H NMR and/or MS data |
|---|---|---|
| IV-b-9 | 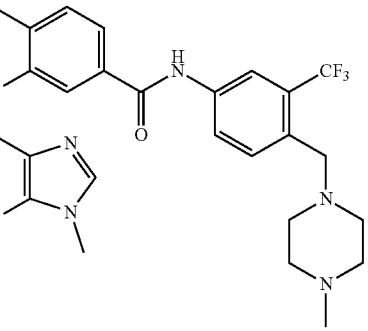 TFA salt | MS (ESI) m/z 616 [M + H]⁺. |
| IV-b-10 | 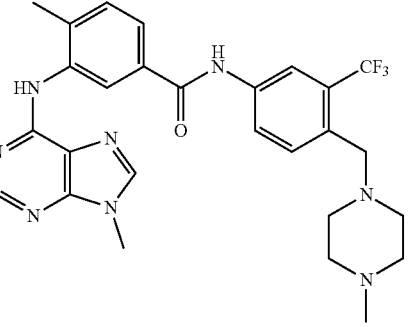 TFA salt | MS (ESI) m/z: 616 [M + H]⁺. |
| IV-b-11 | 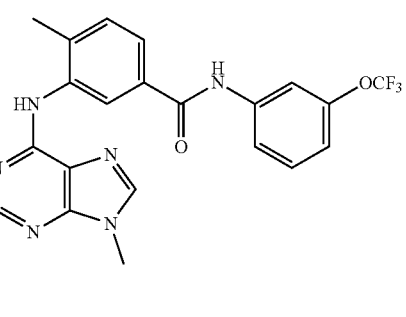 | ¹H NMR (600 MHz, DMSO-d₆) δ 10.49 (s, 1H), 9.62 (s, 1H), 9.38 (s, 1H), 8.56 (ddd, J = 11.7, 8.0, 3.2 Hz, 2H), 8.30 (s, 2H), 7.95 (s, 1H), 7.85 (dd, J = 7.9, 1.7 Hz, 1H), 7.81 (dd, J = 8.3, 1.1 Hz, 1H), 7.53-7.46 (m, 2H), 7.43 (dd, J = 7.9,4.8 Hz, 1H), 7.09 (d, J = 8.2 Hz, 1H), 3.88 (s, 3H), 2.37 (s, 3H). MS (ESI) m/z: 520 [M + H]⁺. |
| IV-b-12 | 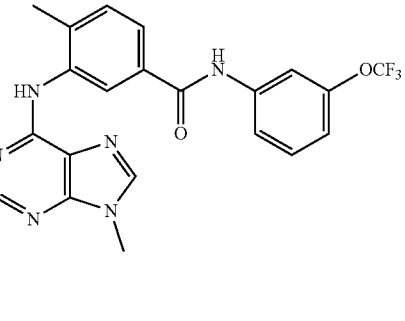 | ¹H NMR (600 MHz, DMSO-d₆) δ 10.50 (s, 1H), 9.64 (s, 1H), 8.63 (s, 2H), 8.35 (d, J = 6.6 Hz, 2H), 8.15 (s, 2H), 7.96 (s, 1H), 7.87-7.74 (m, 2H), 7.50 (dd, J = 19.4, 8.2 Hz, 2H), 7.09 (d, J = 8.1 Hz, 1H), 3.89 (s, 3H), 2.37 (s, 3H). MS (ESI) m/z: 520 [M + H]⁺. |

| No. | Structure | ¹H NMR and/or MS data |
|---|---|---|
| IV-b-13 | 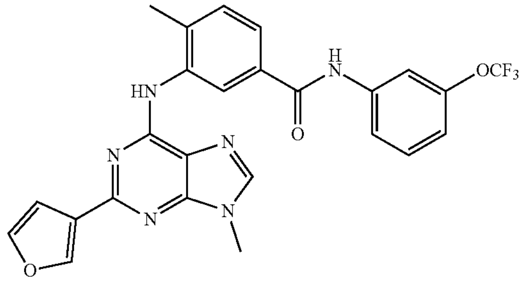 [SMILES: Cc1ccc(C(=O)Nc2cccc(OC(F)(F)F)c2)cc1Nc1nc(-c2ccoc2)nc2c1ncn2C] | ¹H NMR (600 MHz, DMSO-$d_6$) δ 10.48 (s, 1H), 9.26 (s, 1H), 8.49 (s, 1H), 8.23 (s, 1H), 8.17 (s, 1H), 7.95 (s, 1H), 7.85-7.77 (m, 2H), 7.70 (s, 1H), 7.57-7.40 (m, 2H), 7.09 (d, J = 8.1 Hz, 1H), 6.93 (s, 1H), 3.82 (s, 3H), 2.38 (s, 3H). MS (ESI) m/z: 509 [M + H]⁺. |

Synthetic Route of Compounds V-a-1, V-b-1:

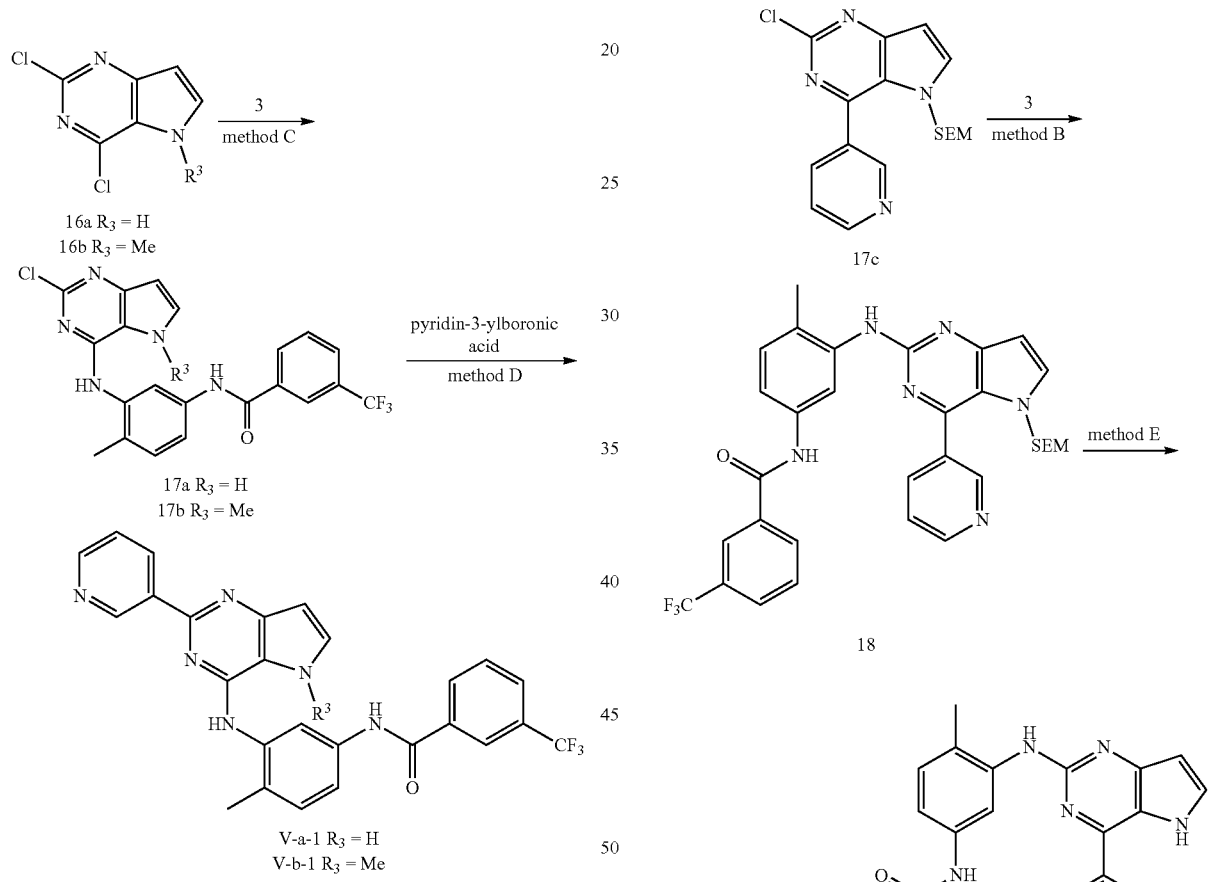

Compounds V-a-1, V-b-1 were respectively synthesized from 16a, 16b through Method C, Method D in sequence.

Synthetic route of compound V-c-1:

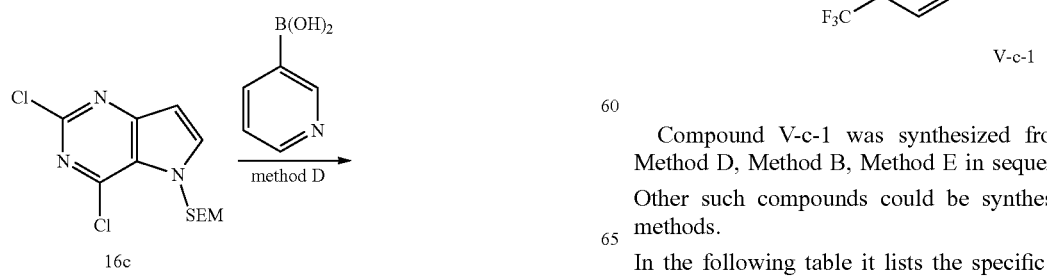

Compound V-c-1 was synthesized from 16c through Method D, Method B, Method E in sequence.

Other such compounds could be synthesized by similar methods.

In the following table it lists the specific compounds and their structural characterization data.

| No. | Structure | ¹H NMR and/or MS data |
|---|---|---|
| V-a-1 | 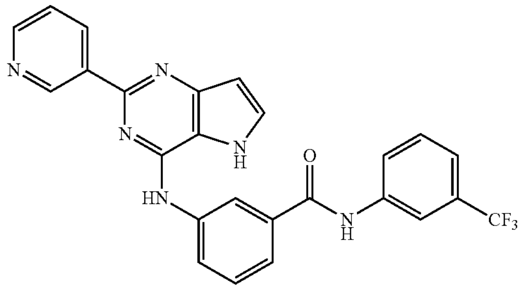 [SMILES: O=C(Nc1cccc(C(F)(F)F)c1)c1cccc(Nc2nc(-c3cccnc3)nc3cc[nH]c23)c1] | ¹H NMR (600 MHz, DMSO-d$_6$) δ 11.27 (s, 1H), 10.68 (s, 1H), 9.68 (s, 1H), 9.60 (s, 1H), 8.75 (d, J = 7.7 Hz, 1H), 8.67 (s, 1H), 8.61 (s, 1H), 8.30 (s, 1H), 8.23 (d, J = 7.9 Hz, 1H), 8.14 (d, J = 7.8 Hz, 1H), 7.77 (s, 1H), 7.73 (d, J = 7.4 Hz, 1H), 7.67-7.61 (m, 2H), 7.49 (d, J = 7.4 Hz, 1H), 7.45-7.40 (m, 1H), 6.63 (s, 1H). MS (ESI) m/z: 475 [M + H]⁺. |
| V-a-2 | 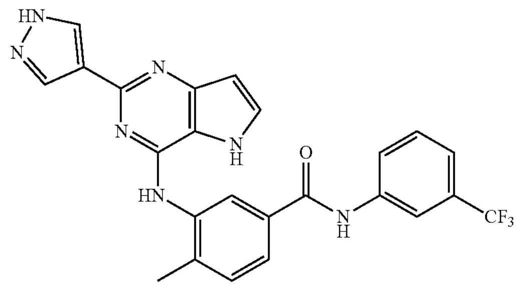 [SMILES: Cc1ccc(C(=O)Nc2cccc(C(F)(F)F)c2)cc1Nc1nc(-c2cn[nH]c2)nc2cc[nH]c12] | ¹H NMR (600 MHz, DMSO-d$_6$) δ 12.81 (s, 1H), 11.37 (s, 1H), 10.52 (s, 1H), 8.87 (d, J = 1.8 Hz, 1H), 8.48 (s, 1H), 8.26 (d, J = 2.0 Hz, 1H), 8.12 (dd, J = 8.2, 2.0 Hz, 1H), 8.06 (s, 2H), 7.76 (dd, J = 7.9, 1.9 Hz, 1H), 7.66 (t, J = 2.8 Hz, 1H), 7.61 (t, J = 8.0 Hz, 1H), 7.49-7.45 (m, 2H), 6.48 (dd, J = 3.1, 1.7 Hz, 1H), 2.47 (s, 3H). MS (ESI) m/z: 478 [M + H]⁺. |
| V-a-3 | 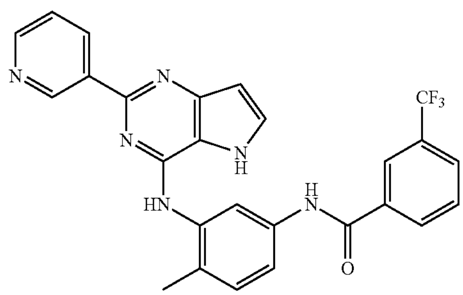 [SMILES: Cc1ccc(NC(=O)c2cccc(C(F)(F)F)c2)cc1Nc1nc(-c2cccnc2)nc2cc[nH]c12] | ¹H NMR (600 MHz, DMSO-d$_6$) δ 11.37 (s, 1H), 10.51 (s, 1H), 9.44 (d, J = 1.5 Hz, 1H), 8.72 (s, 1H), 8.62 (dt, J = 8.0, 1.9 Hz, 1H), 8.54 (dd, J = 4.7, 1.7 Hz, 1H), 8.43 (d, J = 2.0 Hz, 1H), 8.31 (s, 1H), 8.28 (d, J = 7.9 Hz, 1H), 7.97 (d, J = 7.8 Hz, 1H), 7.80 (t, J = 7.8 Hz, 1H), 7.73 (t, J = 2.9 Hz, 1H), 7.55 (dd, J = 8.2, 2.1 Hz, 1H), 7.39 (dd, J = 7.9, 4.7 Hz, 1H), 7.34 (d, J = 8.4 Hz, 1H), 6.60 (dd, J = 2.9, 1.9 Hz, 1H), 2.34 (s, 3H). MS (ESI) m/z: 489 [M + H]⁺. |
| V-a-4 | 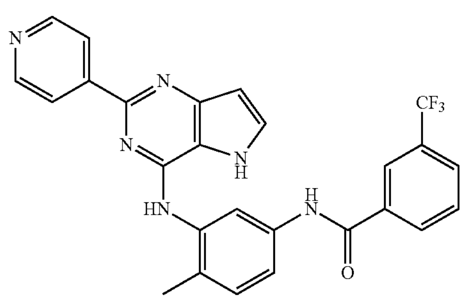 [SMILES: Cc1ccc(NC(=O)c2cccc(C(F)(F)F)c2)cc1Nc1nc(-c2ccncc2)nc2cc[nH]c12] | ¹H NMR (600 MHz, DMSO-d$_6$) δ 11.48 (s, 1H), 10.52 (s, 1H), 8.78 (s, 1H), 8.58 (d, J = 6.1 Hz, 2H), 8.43 (dd, J = 3.9, 2.2 Hz, 1H), 8.30 (s, 1H), 8.28 (d, J = 7.9 Hz, 1H), 8.24 (dd, J = 4.6, 1.5 Hz, 2H), 7.97 (d, J = 7.8 Hz, 1H), 7.80 (t, J = 7.8 Hz, 1H), 7.75 (t, J = 2.9 Hz, 1H), 7.52 (ddd, J = 8.1, 3.9, 2.2 Hz, 1H), 7.34 (d, J = 8.4 Hz, 1H), 6.63 (dd, J = 2.9, 2.0 Hz, 1H), 2.33 (s, 3H). MS (ESI) m/z: 489 [M + H]⁺. |
| V-a-5 | 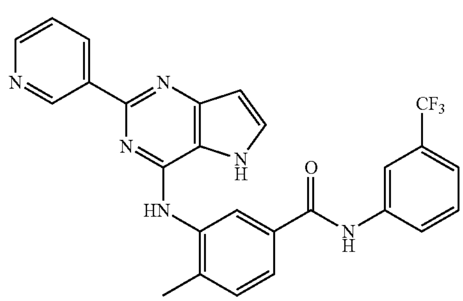 [SMILES: Cc1ccc(C(=O)Nc2cccc(C(F)(F)F)c2)cc1Nc1nc(-c2cccnc2)nc2cc[nH]c12] | ¹H NMR (600 MHz, DMSO-d$_6$) δ 11.47 (s, 1H), 10.53 (s, 1H), 9.41 (d, J = 1.6 Hz, 1H), 8.82 (s, 1H), 8.66 (d, J = 1.7 Hz, 1H), 8.59 (dt, J = 8.0, 1.9 Hz, 1H), 8.53 (dd, J = 4.7, 1.7 Hz, 1H), 8.24 (s, 1H), 8.09 (d, J = 8.4 Hz, 1H), 7.82 (dd, J = 7.9, 1.7 Hz, 1H), 7.75 (t, J = 2.5 Hz, 1H), 7.60 (t, J = 8.0 Hz, 1H), 7.52 (d, J = 8.0 Hz, 1H), 7.46 (d, J = 7.7 Hz, 1H), 7.36 (dd, J = 7.9, 4.7 Hz, 1H), 6.62 (s, 1H), 2.45 (s, 3H). MS (ESI) m/z: 489 [M + H]⁺. |

| No. | Structure | ¹H NMR and/or MS data |
|---|---|---|
| V-a-6 | 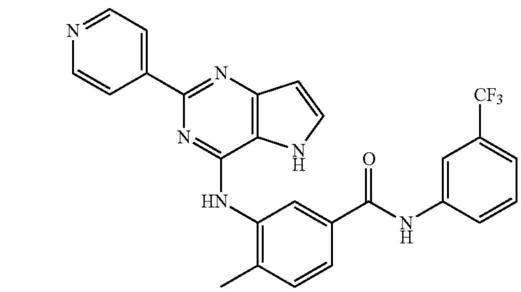 [SMILES: Cc1ccc(C(=O)Nc2cccc(C(F)(F)F)c2)cc1Nc1nc(-c2ccncc2)nc2cc[nH]c12] | ¹H NMR (600 MHz, DMSO-d₆) δ 11.54 (s, 1H), 10.56 (s, 1H), 8.82 (s, 1H), 8.75 (d, J = 1.6 Hz, 1H), 8.54 (dd, J = 4.5, 1.5 Hz, 2H), 8.26 (s, 1H), 8.20 (dd, J = 4.5, 1.5 Hz, 2H), 8.09 (d, J = 8.6 Hz, 1H), 7.81 (dd, J = 7.9, 1.8 Hz, 1H), 7.79 (t, J = 2.8 Hz, 1H), 7.61 (t, J = 8.0 Hz, 1H), 7.52 (d, J = 8.0 Hz, 1H), 7.46 (d, J = 7.7 Hz, 1H), 6.65 (dd, J = 2.8, 1.8 Hz, 1H), 2.46 (s, 3H). MS (ESI) m/z: 489 [M + H]⁺. |
| V-a-7 | 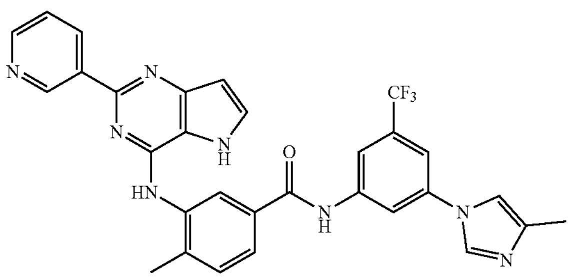 [SMILES: Cc1cn(-c2cc(NC(=O)c3ccc(C)c(Nc4nc(-c5cccnc5)nc5cc[nH]c45)c3)cc(C(F)(F)F)c2)cn1] | ¹H NMR (600 MHz, DMSO-d₆) δ 11.46 (s, 1H), 10.67 (s, 1H), 9.42 (s, 1H), 8.80 (s, 1H), 8.71 (s, 1H), 8.60 (d, J = 6.4 Hz, 1H), 8.54-8.50 (m, 1H), 8.31 (s, 1H), 8.21 (s, 1H), 8.17 (s, 1H), 7.83 (d, J = 7.7 Hz, 1H), 7.77 (s, 1H), 7.74 (s, 1H), 7.55 (d, J = 7.7 Hz, 1H), 7.49 (s, 1H), 7.39-7.34 (m, 1H), 6.62 (s, 1H), 2.47 (s, 3H), 2.19 (s, 3H). MS (ESI) m/z: 569 [M + H]⁺. |
| V-a-8 | 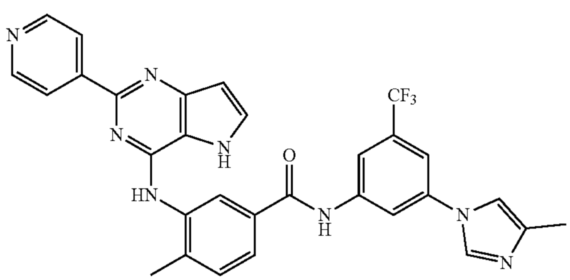 [SMILES: Cc1cn(-c2cc(NC(=O)c3ccc(C)c(Nc4nc(-c5ccncc5)nc5cc[nH]c45)c3)cc(C(F)(F)F)c2)cn1] | ¹H NMR (600 MHz, DMSO-d₆) δ 11.54 (s, 1H), 10.68 (s, 1H), 8.83 (s, 1H), 8.76 (d, J = 1.8 Hz, 1H), 8.55 (d, J = 6.0 Hz, 2H), 8.31 (s, 1H), 8.21 (s, 1H), 8.20 (dd, J = 4.5, 1.6 Hz, 2H), 8.18 (s, 1H), 7.83 (dd, J = 7.9, 1.8 Hz, 1H), 7.80 (t, J = 2.9 Hz, 1H), 7.74 (s, 1H), 7.55 (d, J = 8.4 Hz, 1H), 7.48 (s, 1H), 6.65 (dd, J = 3.0, 2.0 Hz, 1H), 2.47 (s, 3H), 2.19 (d, J = 0.8 Hz, 3H). MS (ESI) m/z: 569 [M + H]⁺. |
| V-a-9 | 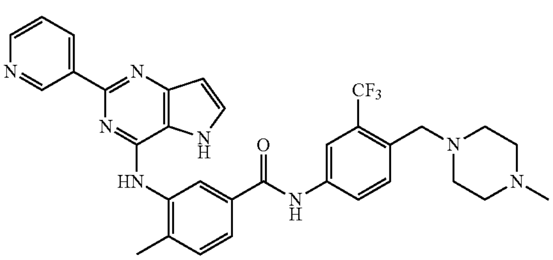 [SMILES: Cc1ccc(C(=O)Nc2ccc(CN3CCN(C)CC3)c(C(F)(F)F)c2)cc1Nc1nc(-c2cccnc2)nc2cc[nH]c12] | ¹H NMR (600 MHz, DMSO-d₆) δ 12.29 (s, 1H), 10.56 (s, 1H), 9.95 (s, 1H), 9.32 (s, 1H), 8.74 (s, 1H), 8.70 (d, J = 6.4 Hz, 1H), 8.47 (s, 1H), 8.22 (s, 1H), 8.13 (d, J = 8.4 Hz, 1H), 7.95-7.88 (m, 2H), 7.71 (d, J = 8.6 Hz, 1H), 7.67 (s, 1H), 7.57 (d, J = 8.0 Hz, 1H), 6.70 (s, 1H), 3.69 (s, 2H), 3.48-3.37 (m, 2H), 3.10-3.00 (m, 2H), 2.98-2.88 (m, 2H), 2.81 (s, 3H), 2.44 (s, 3H), 2.42-2.35 (m, 2H). MS (ESI) m/z: 601 [M + H]⁺. |
| V-a-10 | 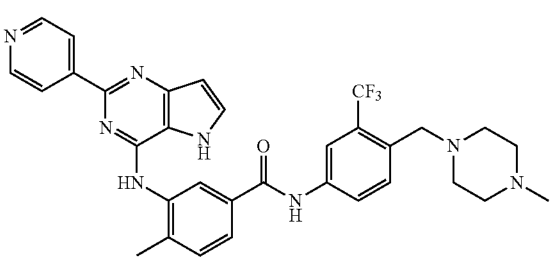 [SMILES: Cc1ccc(C(=O)Nc2ccc(CN3CCN(C)CC3)c(C(F)(F)F)c2)cc1Nc1nc(-c2ccncc2)nc2cc[nH]c12] | ¹H NMR (600 MHz, DMSO-d₆) δ 11.59 (s, 1H), 10.50 (s, 1H), 8.85 (s, 1H), 8.74 (d, J = 1.5 Hz, 1H), 8.54 (dd, J = 4.6, 1.5 Hz, 2H), 8.22 (d, J = 2.0 Hz, 1H), 8.20 (dd, J = 4.6, 1.5 Hz, 2H), 8.07 (dd, J = 8.5, 1.7 Hz, 1H), 7.80 (d, J = 7.9, 1.6 Hz, 1H), 7.78 (t, J = 2.5 Hz, 1H), 7.71 (d, J = 8.6 Hz, 1H), 7.51 (d, J = 8.1 Hz, 1H), 6.64 (d, J = 1.8 Hz, 1H), 3.57 (s, 2H), 2.46 (s, 3H), 2.44-2.27 (m, 8H), 2.18 (s, 3H). MS (ESI) m/z: 601 [M + H]⁺. |

| No. | Structure | ¹H NMR and/or MS data |
|---|---|---|
| V-a-11 | 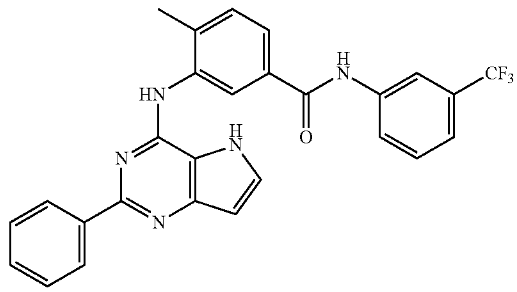 [SMILES: Cc1ccc(C(=O)Nc2cccc(C(F)(F)F)c2)cc1Nc1nc(-c2ccccc2)nc2cc[nH]c12] | ¹H NMR (600 MHz, DMSO-d₆) δ 11.76 (s, 1H), 10.54 (s, 1H), 9.07 (s, 1H), 8.70 (d, J = 2.1 Hz, 1H), 8.30 (t, J = 1.6 Hz, 1H), 8.29 (d, J = 2.2 Hz, 1H), 8.24 (d, J = 1.8 Hz, 1H), 8.08 (dt, J = 8.3, 1.3 Hz, 1H), 7.79 (dd, J = 7.9, 1.9 Hz, 1H), 7.73 (t, J = 2.9 Hz, 1H), 7.60 (t, J = 8.0 Hz, 1H), 7.50 (d, J = 8.0 Hz, 1H), 7.47-7.42 (m, 1H), 7.35-7.28 (m, 3H), 6.57 (dd, J = 3.0, 1.9 Hz, 1H), 2.46 (s, 3H). MS (ESI) m/z: 488 [M + H]⁺. |
| V-a-12 | 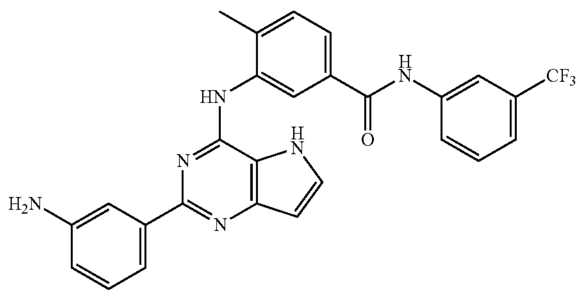 [SMILES: Cc1ccc(C(=O)Nc2cccc(C(F)(F)F)c2)cc1Nc1nc(-c2cccc(N)c2)nc2cc[nH]c12] | ¹H NMR (600 MHz, DMSO-d₆) δ 12.54 (s, 1H), 10.59 (s, 1H), 10.51 (s, 1H), 8.39 (s, 1H), 8.25 (d, J = 1.9 Hz, 1H), 8.09-8.04 (m, 1H), 7.97 (t, J = 2.9 Hz, 1H), 7.94 (dd, J = 8.0, 1.8 Hz, 1H), 7.60 (t, J = 8.0 Hz, 1H), 7.57 (d, J = 8.0 Hz, 1H), 7.46 (d, J = 7.3 Hz, 2H), 7.36 (s, 1H), 7.21 (t, J = 7.9 Hz, 1H), 6.93-6.83 (m, 1H), 6.67 (t, J = 2.3 Hz, 1 H), 2.43 (s, 3H). MS (ESI) m/z: 503 [M + H]⁺. |
| V-a-13 | 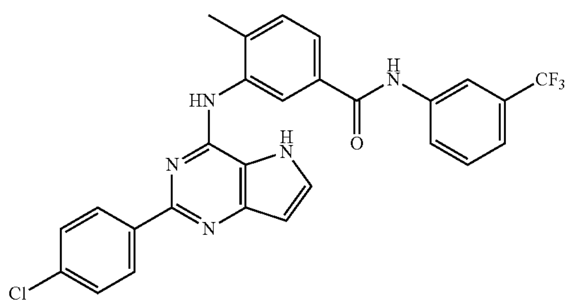 [SMILES: Cc1ccc(C(=O)Nc2cccc(C(F)(F)F)c2)cc1Nc1nc(-c2ccc(Cl)cc2)nc2cc[nH]c12] | ¹H NMR (600 MHz, DMSO-d₆) δ 11.44 (s, 1H), 10.54 (s, 1H), 8.74 (d, J = 1.9 Hz, 1H), 8.72 (s, 1H), 8.34-8.29 (m, 2H), 8.24 (d, J = 2.0 Hz, 1H), 8.10-8.04 (m, 1H), 7.77 (dd, J = 7.9, 1.9 Hz, 1H), 7.73 (t, J = 2.9 Hz, 1H), 7.61 (t, J = 8.0 Hz, 1H), 7.50 (d, J = 8.0 Hz, 1H), 7.46 (d, J = 7.7 Hz, 1H), 7.36-7.30 (m, 2H), 6.57 (dd, J = 3.0, 2.0 Hz, 1H), 2.44 (s, 3H). MS (ESI) m/z: 504 [M + H]⁺. |
| V-a-14 | 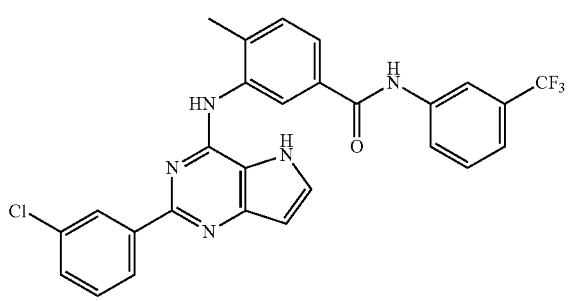 [SMILES: Cc1ccc(C(=O)Nc2cccc(C(F)(F)F)c2)cc1Nc1nc(-c2cccc(Cl)c2)nc2cc[nH]c12] | ¹H NMR (600 MHz, DMSO-d₆) δ 12.32 (s, 1H), 10.56 (s, 1H), 10.09 (s, 1H), 8.53 (d, J = 1.9 Hz, 1H), 8.28 (d, J = 2.0 Hz, 1H), 8.19 (d, J = 2.0 Hz, 1H), 8.13 (d, J = 7.8 Hz, 1H), 8.05 (dd, J = 8.3, 1.9 Hz, 1H), 7.94 (t, J = 3.0 Hz, 1H), 7.91 (dd, J = 7.9, 1.8 Hz, 1H), 7.59 (t, J = 8.0 Hz, 1H), 7.56 (dd, J = 8.7, 3.8 Hz, 2H), 7.49 (t, J = 7.9 Hz, 1H), 7.44 (d, J = 7.7 Hz, 1H), 6.68 (t, J = 2.4 Hz, 1H), 2.44 (s, 3H). MS (ESI) m/z: 522 [M + H]⁺. |

| No. | Structure | ¹H NMR and/or MS data |
|---|---|---|
| V-a-15 | 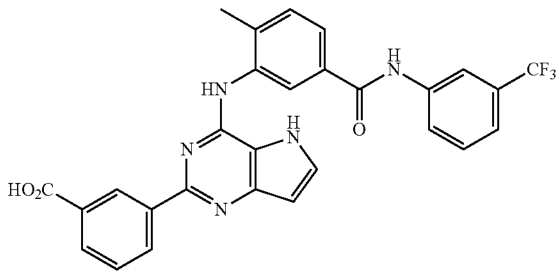 [SMILES: Cc1ccc(C(=O)Nc2cccc(C(F)(F)F)c2)cc1Nc1nc(-c2cccc(C(=O)O)c2)nc2cc[nH]c12] | ¹H NMR (600 MHz, DMSO-$d_6$) δ 11.41 (s, 1H), 10.48 (s, 1H), 8.89 (q, J = 3.2, 2.5 Hz, 1H), 8.78 (s, 1H), 8.67 (d, J = 1.8 Hz, 1H), 8.57 (dt, J = 7.7, 1.5 Hz, 1H), 8.20 (t, J = 2.0 Hz, 1H), 8.04 (d, J = 8.2 Hz, 1H), 7.90 (dt, J = 7.6, 1.5 Hz, 1H), 7.81 (dd, J = 8.0, 1.9 Hz, 1H), 7.74 (t, J = 2.9 Hz, 1H), 7.57 (t, J = 8.1 Hz, 1H), 7.51 (d, J = 8.2 Hz, 1H), 7.49-7.41 (m, 2H), 6.61 (dd, J = 3.0, 1.9 Hz, 1H), 2.45 (s, 3H). MS (ESI) m/z: 532 [M + H]⁺. |
| V-a-16 | 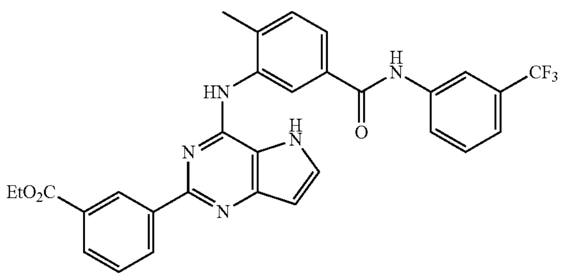 [SMILES: CCOC(=O)c1cccc(-c2nc(Nc3cc(C(=O)Nc4cccc(C(F)(F)F)c4)ccc3C)c3[nH]ccc3n2)c1] | ¹H NMR (600 MHz, DMSO-$d_6$) δ 12.34 (s, 1H), 10.52 (s, 1H), 10.21 (s, 1H), 8.75 (d, J = 1.8 Hz, 1H), 8.45 (s, 1H), 8.44 (dt, J = 7.8, 1.4 Hz, 1H), 8.22 (d, J = 2.0 Hz, 1H), 8.09-8.03 (m, 2H), 7.97-7.92 (m, 2H), 7.62 (t, J = 7.8 Hz, 1H), 7.58 (t, J = 8.1 Hz, 2H), 7.43 (d, J = 7.8 Hz, 1H), 6.70 (dd, J = 3.0, 1.9 Hz, 1H), 4.23 (q, J = 7.1 Hz, 2H), 2.44 (s, 3H), 1.25 (t, J = 7.1 Hz, 3H). MS (ESI) m/z: 560 [M + H]⁺. |
| V-a-17 | 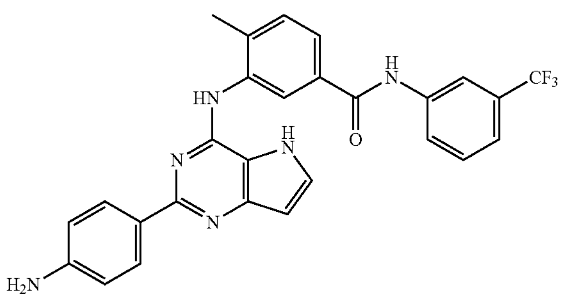 [SMILES: Cc1ccc(C(=O)Nc2cccc(C(F)(F)F)c2)cc1Nc1nc(-c2ccc(N)cc2)nc2cc[nH]c12] | ¹H NMR (600 MHz, DMSO-$d_6$) δ 11.31 (s, 1H), 10.51 (s, 1H), 8.66 (d, J = 1.8 Hz, 1H), 8.24 (d, J = 2.0 Hz, 1H), 8.10 (dd, J = 8.3, 1.9 Hz, 1H), 7.99 (d, J = 8.4 Hz, 2H), 7.76 (dd, J = 7.9, 1.8 Hz, 1H), 7.68-7.63 (m, 1H), 7.60 (t, J = 8.0 Hz, 1H), 7.49 (d, J = 7.9 Hz, 1H), 7.45 (d, J = 7.8 Hz, 1H), 6.53-6.42 (m, 3H), 5.32 (s, 2H), 2.43 (s, 3H). MS (ESI) m/z: 503 [M + H]⁺ |
| V-a-18 | 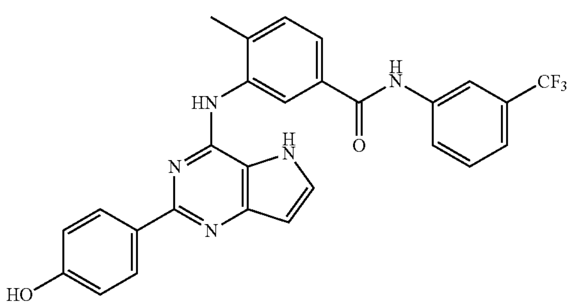 [SMILES: Cc1ccc(C(=O)Nc2cccc(C(F)(F)F)c2)cc1Nc1nc(-c2ccc(O)cc2)nc2cc[nH]c12] | ¹H NMR (600 MHz, DMSO-$d_6$) δ 12.44 (s, 1H), 10.57-10.35 (m, 2H), 9.85 (s, 1H), 8.31 (d, J = 1.8 Hz, 1H), 8.23 (d, J = 2.1 Hz, 1H), 8.06 (d, J = 8.5 Hz, 1H), 7.95 (d, J = 8.9 Hz, 2H), 7.62-7.57 (m, 2H), 7.55 (d, J = 7.8 Hz, 1H), 7.47 (t, J = 2.0 Hz, 1H), 7.45 (d, J = 7.7 Hz, 1H), 7.27 (t, J = 7.9 Hz, 1H), 6.97 (d, J = 8.1 Hz, 1H), 6.67 (q, J = 1.8 Hz, 1H), 2.41 (s, 3H). MS (ESI) m/z: 504 [M + H]⁺. |
| V-a-19 | 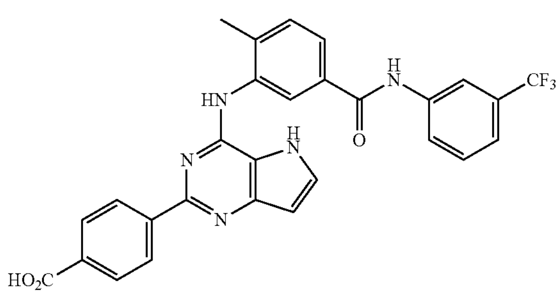 [SMILES: Cc1ccc(C(=O)Nc2cccc(C(F)(F)F)c2)cc1Nc1nc(-c2ccc(C(=O)O)cc2)nc2cc[nH]c12] | ¹H NMR (600 MHz, DMSO-$d_6$) δ 11.06 (s, 1H), 10.58 (s, 1H), 8.43 (s, 1H), 8.27 (d, J = 8.2 Hz, 2H), 8.24 (s, 1H), 8.08 (d, J = 8.3 Hz, 1H), 8.06-7.98 (m, 3H), 7.93 (dd, J = 7.9, 1.8 Hz, 1H), 7.60 (t, J = 8.0 Hz, 1H), 7.56 (d, J = 8.0 Hz, 1H), 7.45 (d, J = 7.7 Hz, 1H), 6.72 (t, J = 2.4 Hz, 1H), 1.21 (s, 3H). MS (ESI) m/z: 532 [M + H]⁺. |

| No. | Structure | ¹H NMR and/or MS data |
|---|---|---|
| V-a-20 | 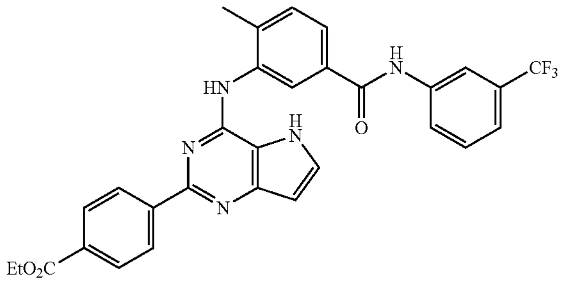 [SMILES: CCOC(=O)c1ccc(-c2nc(Nc3cc(C(=O)Nc4cccc(C(F)(F)F)c4)ccc3C)c3[nH]ccc3n2)cc1] | ¹H NMR (600 MHz, DMSO-d₆) δ 12.27 (s, 1H), 10.57 (s, 1H), 10.01 (s, 1H), 8.58 (s, 1H), 8.32 (d, J = 8.2 Hz, 2H), 8.26 (d, J = 1.9 Hz, 1H), 8.07 (dd, J = 8.2, 2.1 Hz, 1H), 8.00 (d, J = 8.2 Hz, 2H), 7.95 (t, J = 3.0 Hz, 1H), 7.90 (dd, J = 7.9, 1.8 Hz, 1H), 7.60 (t, J = 7.9 Hz, 1H), 7.55 (d, J = 8.0 Hz, 1H), 7.45 (d, J = 7.8 Hz, 1H), 6.70 (t, J = 2.4 Hz, 1H), 4.31 (q, J = 7.1 Hz, 2H), 2.44 (s, 3H), 1.31 (t, J = 7.1 Hz, 3H). MS (ESI) m/z: 560 [M + H]⁺. |
| V-a-21 | 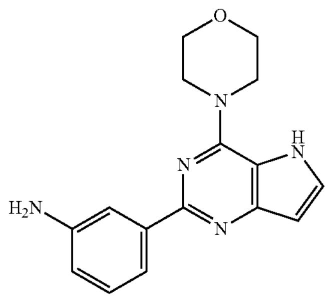 [SMILES: Nc1cccc(-c2nc(N3CCOCC3)c3[nH]ccc3n2)c1] | MS (ESI) m/z: 296 [M + H]⁺. |
| V-a-22 | TFA salt | ¹H NMR (600 MHz, DMSO-d₆) δ 12.55 (s, 1H), 10.56 (s, 1H), 8.67 (d, J = 2.1 Hz, 1H), 8.62 (s, 1H), 8.30 (dd, J = 9.2, 2.2 Hz, 1H), 7.98 (t, J = 8.5 Hz, 2H), 7.89 (t, J = 2.9 Hz, 1H), 7.62 (t, J = 8.0 Hz, 1H), 6.96 (d, J = 9.2 Hz, 1H), 6.67 (d, J = 2.1 Hz, 1H), 4.13-4.11 (m, 4H), 3.86-3.84 (m, 4H). MS (ESI) m/z: 416 [M + H]⁺. |
| V-a-23 | 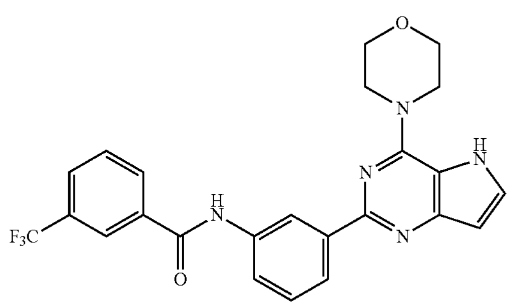 [SMILES: O=C(Nc1cccc(-c2nc(N3CCOCC3)c3[nH]ccc3n2)c1)c1cccc(C(F)(F)F)c1] | ¹H NMR (600 MHz, DMSO-d₄) δ 11.54 (s, 1H), 10.62 (s, 1H), 8.73 (t, J = 2.0 Hz, 1H), 8.37 (s, 1H), 8.33 (d, J = 7.8 Hz, 1H), 8.21-8.14 (m, 1H), 8.01-7.93 (m, 2H), 7.80 (t, J = 7.8 Hz, 1H), 7.61 (d, J = 3.1 Hz, 1H), 7.45 (t, J = 7.9 Hz, 1H), 6.55 (d, J = 3.1 Hz, 1H), 3.88-3.80 (m, 8H). MS (ESI) m/z: 416 [M + H]⁺. |
| V-a-24 | 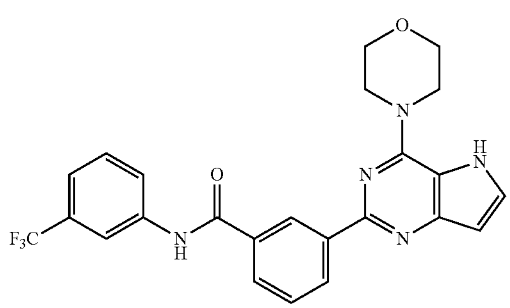 [SMILES: O=C(Nc1cccc(C(F)(F)F)c1)c1cccc(-c2nc(N3CCOCC3)c3[nH]ccc3n2)c1] | ¹H NMR (600 MHz, DMSO-d₆) δ 10.80 (s, 1H), 8.82 (s, 1H), 8.50 (d, J = 7.8 Hz, 1H), 8.28 (s, 1H), 8.21 (d, J = 7.5 Hz, 1H), 8.08 (d, J = 8.7 Hz, 1H), 7.86 (s, 1H), 7.78 (t, J = 7.8 Hz, 1H), 7.63 (t, J = 8.0 Hz, 1H), 7.49 (d, J = 7.8 Hz, 1H), 6.67 (s, 1H), 4.09 (s, 4H), 3.86-3.84 (m, 4H). MS (ESI) m/z: 468 [M + H]⁺. |

| No. | Structure | ¹H NMR and/or MS data |
|---|---|---|
| V-a-25 | 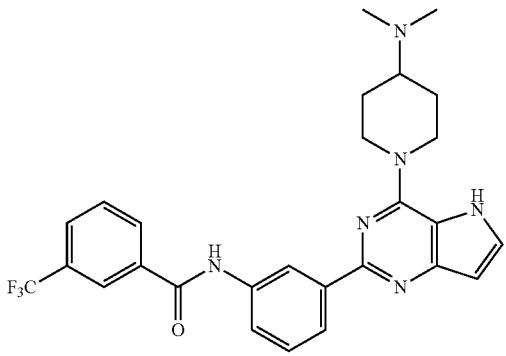<br>TFA salt | ¹H NMR (600 MHz, DMSO-d₆) δ 12.69 (s, 1H), 10.83 (s, 1H), 10.20 (s, 1H), 8.75 (t, J = 1.9 Hz, 1H), 8.34-8.30 (m, 2H), 8.02-8.00 (m, 2H), 7.92 (t, J = 3.0 Hz, 1H), 7.82 (t, J = 7.8 Hz, 1H), 7.66 (t, J = 8.0 Hz, 1H), 6.69 (dd, J = 2.9, 1.4 Hz, 1H), 5.00 (s, 2H), 3.65 (s, 1H), 3.42 (s, 2H), 2.79 (d, J = 1.8 Hz, 6H), 2.23 (d, J = 11.7 Hz, 2H), 1.83 (qd, J = 12.3, 4.1 Hz, 2H). MS (ESI) m/z: 509 [M + H]⁺. |
| V-a-26 | 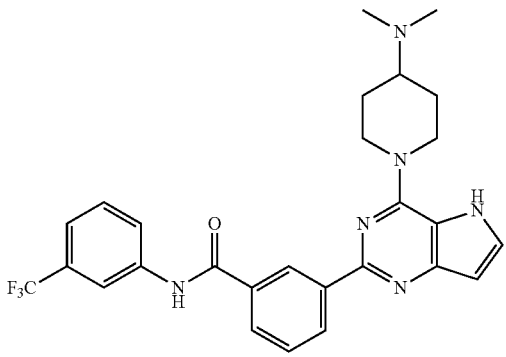 [SMILES: CN(C)C1CCN(c2nc(-c3cccc(C(=O)Nc4cccc(C(F)(F)F)c4)c3)nc3cc[nH]c23)CC1] | ¹H NMR (600 MHz, DMSO-d₆) δ 11.47 (s, 1H), 10.73 (s, 1H), 8.95 (s, 1H), 8.60 (d, J = 7.6 Hz, 1H), 8.30 (s, 1H), 8.09 (s, 1H), 7.99 (d, J = 7.5 Hz, 1H), 7.62 (d, J = 6.1 Hz, 2H), 7.57 (s, 1H), 7.47 (s, 1H), 6.56 (s, 1H), 4.63 (d, J = 13.0 Hz, 2H), 3.82-3.71 (m, 1H), 3.14 (s, 2H), 2.24 (s, 6H), 1.94 (d, J = 11.7 Hz, 2H), 1.53 (q, J = 10.7 Hz, 2H). MS (ESI) m/z: 509 [M + H]⁺. |
| V-a-27 | 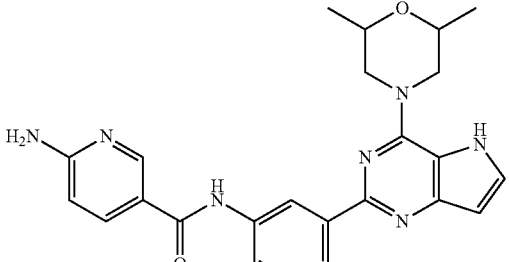<br>TFA salt | ¹H NMR (600 MHz, DMSO-d₆) δ 12.64 (s, 1H), 10.54 (d, J = 4.8 Hz, 1H), 8.74 (s, 1H), 8.68 (d, J = 2.0 Hz, 1H), 8.29 (dd, J = 9.2, 2.0 Hz, 1H), 7.99 (d, J = 7.9 Hz, 1H), 7.94 (d, J = 8.1 Hz, 1H), 7.90 (s, 1H), 7.62 (td, J = 8.0, 3.3 Hz, 1H), 6.95 (d, J = 9.1 Hz, 1H), 6.67 (d, J = 2.7 Hz, 1H), 4.73 (s, 2H), 3.79 (ddd, J = 10.4, 6.2, 2.5 Hz, 2H), 3.06 (s, 2H), 1.27 (d, J = 6.2 Hz, 6H). MS (ESI) m/z: 444 [M + H]⁺. |
| V-a-28 | 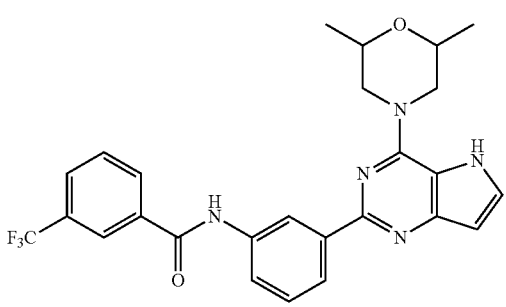 [SMILES: CC1CN(c2nc(-c3cccc(NC(=O)c4cccc(C(F)(F)F)c4)c3)nc3cc[nH]c23)CC(C)O1] | ¹H NMR (600 MHz, DMSO-d₆) δ 11.65 (s, 1H), 10.62 (s, 1H), 8.76 (t, J = 1.9 Hz, 1H), 8.37 (s, 1H), 8.32 (d, J = 7.9 Hz, 1H), 8.12 (d, J = 7.8 Hz, 1H), 7.98 (d, J = 7.8 Hz, 1H), 7.95-7.93 (m, 1H), 7.81 (t, J = 7.8 Hz, 1H), 7.66 (s, 1H), 7.48 (t, J = 7.8 Hz, 1H), 6.56 (s, 1H), 4.51 (s, 2H), 3.81-3.73 (m, 2H), 2.83 (t, J = 11.4 Hz, 2H), 1.25-1.23 (m, 6H). MS (ESI) m/z: 496 [M + H]⁺. |

-continued

| No. | Structure | ¹H NMR and/or MS data |
|---|---|---|
| V-a-29 | 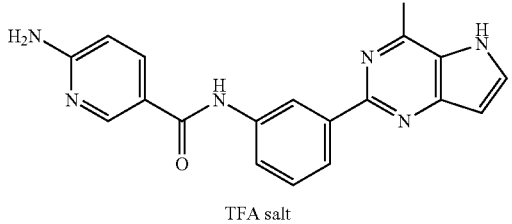 TFA salt | ¹H NMR (600 MHz, DMSO-$d_6$) δ 12.56 (s, 1H), 10.55 (s, 1H), 8.67 (d, J = 1.6 Hz, 1H), 8.63 (t, J = 1.7 Hz, 1H), 8.28 (dd, J = 9.2, 2.2 Hz, 1H), 7.98 (dd, J = 8.1, 1.4 Hz, 1H), 7.94 (d, J = 8.2 Hz, 1H), 7.84 (t, J = 2.8 Hz, 1H), 7.61 (t, J = 8.0 Hz, 1H), 6.94 (d, J = 9.1 Hz, 1H), 6.64 (d, J = 2.3 Hz, 1H), 4.13-4.09 (m, 4H), 1.79-1.75 (m, 6H). MS (ESI) m/z: 414 [M + H]⁺. |
| V-a-30 |  TFA salt | ¹H NMR (600 MHz, DMSO-$d_6$) δ 12.44 (s, 1H), 10.79 (s, 1H), 8.69 (t, J = 1.8 Hz, 1H), 8.33 (s, 1H), 8.31 (d, J = 7.9 Hz, 1H), 8.04-7.96 (m, 3H), 7.82 (dd, J = 9.7, 5.4 Hz, 2H), 7.64 (t, J = 7.9 Hz, 1H), 6.64 (d, J = 1.9 Hz, 1H), 4.12-4.09 (m, 4H), 1.78-1.73 (m, 6H). MS (ESI) m/z: 466 [M + H]⁺. |
| V-a-31 | 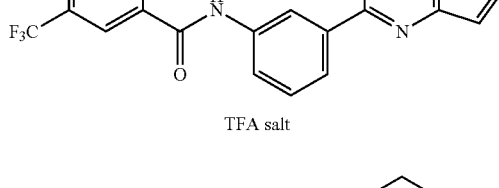 | ¹H NMR (600 MHz, DMSO-$d_6$) δ 11.43 (s, 1H), 10.73 (s, 1H), 8.95 (t, J = 1.7 Hz, 1H), 8.62-8.57 (m, 1H), 8.30 (s, 1H), 8.09 (d, J = 8.2 Hz, 1H), 8.00-7.95 (m, 1H), 7.62 (td, J = 7.9, 4.1 Hz, 2H), 7.55 (t, J = 2.9 Hz, 1H), 7.46 (d, J = 7.8 Hz, 1H), 6.55 (dd, J = 2.9, 1.2 Hz, 1H), 3.88-3.85 (m, 4H), 1.73-1.67 (m, 6H). MS (ESI) m/z: 466 [M + H]⁺. |
| V-a-32 | 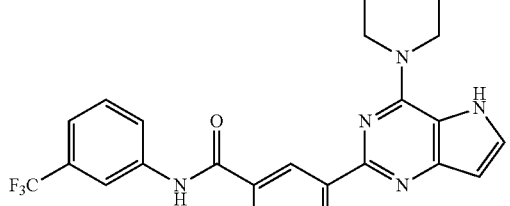 | ¹H NMR (600 MHz, DMSO-$d_6$) δ 11.27 (s, 1H), 10.02 (s, 1H), 8.68 (s, 1H), 8.65 (d, J = 2.3 Hz, 1H), 8.09 (d, J = 7.9 Hz, 1H), 7.99 (dd, J = 8.7, 2.5 Hz, 1H), 7.88 (dd, J = 8.0, 1.1 Hz, 1H), 7.49 (s, 1H), 7.40-7.35 (m, 1H), 6.60 (s, 2H), 6.50 (d, J = 8.7 Hz, 1H), 6.47 (d, J = 2.7 Hz, 1H), 3.88 (t, J = 6.5 Hz, 4H), 2.02 (t, J = 6.5 Hz, 4H). MS (ESI) m/z: 400 [M + H]⁺. |
| V-a-33 | 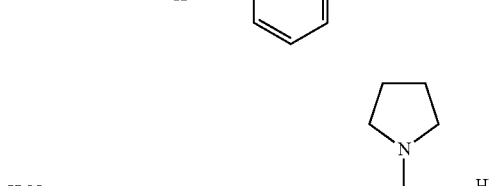 TFA salt | ¹H NMR (600 MHz, DMSO-$d_6$) δ 12.41 (s, 1H), 10.82 (s, 1H), 8.71 (t, J = 1.7 Hz, 1H), 8.34-8.29 (m, 2H), 8.02 (dd, J = 8.1, 1.3 Hz, 1H), 7.99-7.94 (m, 2H), 7.82-7.76 (m, 2H), 7.59 (t, J = 8.0 Hz, 1H), 6.59 (dd, J = 2.8, 1.7 Hz, 1H), 3.98-3.95 (m, 4H), 2.03-2.01 (m, 4H). MS (ESI) m/z: 452 [M + H]⁺. |

-continued

| No. | Structure | ¹H NMR and/or MS data |
|---|---|---|
| V-a-34 | 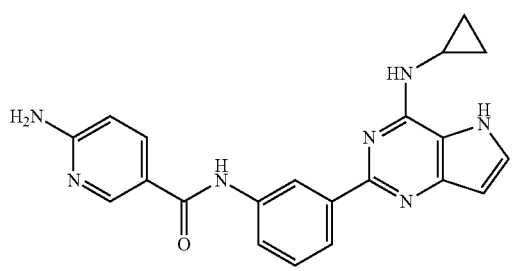 [SMILES: Nc1ccc(C(=O)Nc2cccc(-c3nc(NC4CC4)c4[nH]ccc4n3)c2)cn1] | ¹H NMR (600 MHz, DMSO-$d_6$) δ 12.32 (s, 1H), 10.60 (s, 1H), 9.34 (s, 1H), 8.74 (s, 1H), 8.68 (d, J = 1.8 Hz, 1H), 8.34 (dd, J = 9.2, 2.0 Hz, 1H), 7.98 (s, 1H), 7.94 (d, J = 7.4 Hz, 1H), 7.83 (s, 1H), 7.63 (t, J = 8.0 Hz, 1H), 7.01 (d, J = 9.2 Hz, 1H), 6.59 (s, 1H), 3.34 (s, 1H), 1.00 (d, J = 5.9 Hz, 2H), 0.78-0.76 (m, 2H). MS (ESI) m/z: 386 [M + H]⁺. |
| V-a-35 | 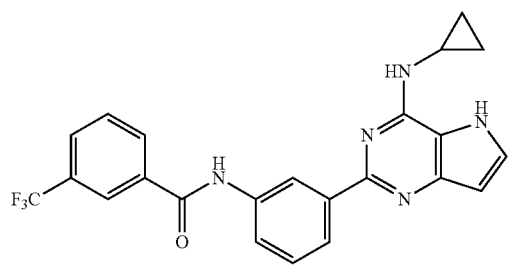 [SMILES: O=C(Nc1cccc(-c2nc(NC3CC3)c3[nH]ccc3n2)c1)c1cccc(C(F)(F)F)c1] | ¹H NMR (600 MHz, DMSO-$d_6$) δ 12.09 (s, 1H), 10.79 (s, 1H), 9.16 (s, 1H), 8.78 (s, 1H), 8.34 (s, 1H), 8.31 (d, J = 7.9 Hz, 1H), 8.03-7.97 (m, 3H), 7.82 (t, J = 7.7 Hz, 2H), 7.65 (t, J = 8.0 Hz, 1H), 6.61-6.58 (m, 1H), 3.32 (d, J = 3.7 Hz, 1H), 1.00 (q, J = 6.7 Hz, 2H), 0.78-0.74 (m, 2H). MS (ESI) m/z: 438 [M + H]⁺. |
| V-a-36 | 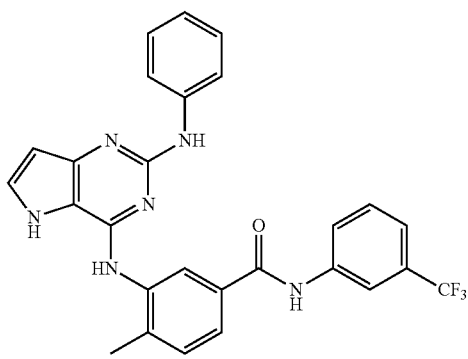 [SMILES: Cc1ccc(C(=O)Nc2cccc(C(F)(F)F)c2)cc1Nc1nc(Nc2ccccc2)nc2cc[nH]c12] | ¹H NMR (600 MHz, MeOD) δ 8.19 (d, J = 1.9 Hz, 1H), 8.15-8.13 (m, 1H), 7.93-7.89 (m, 2H), 7.60 (d, J = 3.0 Hz, 1H), 7.54 (t, J = 8.0 Hz, 1H), 7.51 (d, J = 8.1 Hz, 1H), 7.44 (d, J = 8.0 Hz, 1H), 7.35-7.32 (m, 2H), 7.18-7.13 (m, 2H), 6.99 (t, J = 7.4 Hz, 1H), 6.43 (d, J = 3.0 Hz, 1H), 2.43 (s, 3H). |
| V-a-37 | 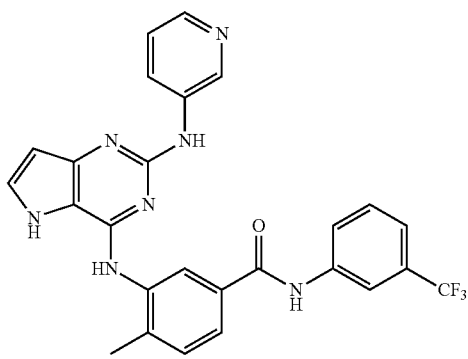 [SMILES: Cc1ccc(C(=O)Nc2cccc(C(F)(F)F)c2)cc1Nc1nc(Nc2cccnc2)nc2cc[nH]c12] | ¹H NMR (600 MHz, DMSO-$d_6$) δ 12.16 (brs, 1H), 10.60 (s, 1H), 9.68 (s, 1H), 9.30 (t, J = 2.0 Hz, 1H), 8.97 (dt, J = 5.7, 1.5 Hz, 1H), 8.52 (d, J = 1.8 Hz, 1H), 8.24-8.22 (m, 1H), 8.09-8.05 (m, 1H), 7.95 (t, J = 3.0 Hz, 1H), 7.88 (dd, J = 7.9, 1.9 Hz, 1H), 7.80-7.72 (m, 2H), 7.61 (t, J = 8.0 Hz, 1H), 7.55 (d, J = 8.0 Hz, 1H), 7.48 (d, J = 7.7 Hz, 1H), 6.79 (brs, 1H), 6.72 (dd, J = 3.1, 1.9 Hz, 1H), 2.45 (s, 3H). |

| No. | Structure | ¹H NMR and/or MS data |
|---|---|---|
| V-a-38 | 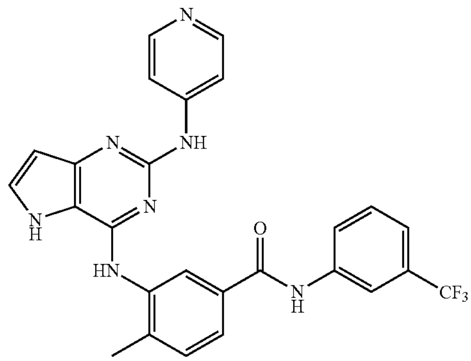 [SMILES: Cc1ccc(C(=O)Nc2cccc(C(F)(F)F)c2)cc1Nc1nc(Nc2ccncc2)nc2cc[nH]c12] | ¹H NMR (600 MHz, DMSO-d₆) δ 12.01-11.93 (m, 1H), 10.54 (s, 1H), 9.53 (s, 1H), 9.14-9.09 (m, 2H), 8.67-8.64 (m, 1H), 8.50 (d, J = 1.9 Hz, 1H), 8.21 (d, J = 1.9 Hz, 1H), 8.13 (dd, J = 8.3, 2.0 Hz, 1H), 7.89-7.85 (m, 2H), 7.61 (t, J = 8.0 Hz, 1H), 7.54 (d, J = 8.0 Hz, 1H), 7.47 (d, J = 7.7 Hz, 1H), 6.92-6.88 (m, 2H), 6.63 (dd, J = 3.0, 1.9 Hz, 1H), 2.44 (s, 3H). |
| V-a-39 | 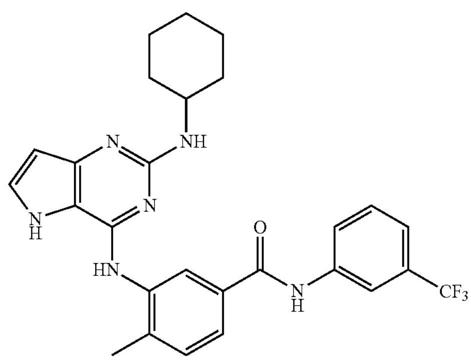 [SMILES: Cc1ccc(C(=O)Nc2cccc(C(F)(F)F)c2)cc1Nc1nc(NC2CCCCC2)nc2cc[nH]c12] | ¹H NMR (600 MHz, DMSO-d₆) δ 12.47 (brs, 1H), 11.92 (brs, 1H), 10.51 (s, 1H), 10.01 (s, 1H), 8.32 (brs, 1H), 8.26-8.22 (m, 1H), 8.09 (brs, 1H), 8.06 (dd, J = 8.9, 1.7 Hz, 1H), 7.86 (dd, J = 8.0, 1.9 Hz, 1H), 7.65 (t, J = 3.0 Hz, 1H), 7.61 (t, J = 8.0 Hz, 1H), 7.52 (d, J = 8.1 Hz, 1H), 7.48-7.44 (m, 1H), 6.32 (t, J = 2.5 Hz, 1H), 3.93 (h, J = 7.0 Hz, 1H), 2.40 (s, 3H), 1.87-1.75 (m, 2H), 1.60-1.48 (m, 2H), 1.47-1.29 (m, 4H) |
| V-a-40 | 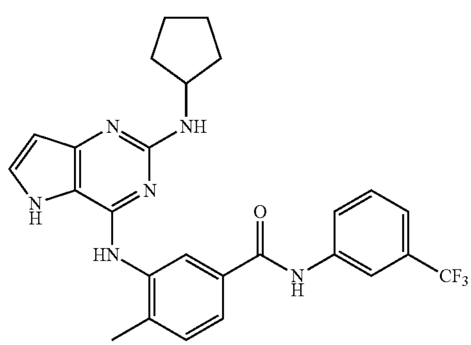 [SMILES: Cc1ccc(C(=O)Nc2cccc(C(F)(F)F)c2)cc1Nc1nc(NC2CCCC2)nc2cc[nH]c12] | ¹H NMR (600 MHz, DMSO-d₆) δ 12.47 (brs, 1H), 11.92 (brs, 1H), 10.51 (s, 1H), 10.01 (s, 1H), 8.32 (brs, 1H), 8.26-8.22 (m, 1H), 8.09 (brs, 1H), 8.06 (dd, J = 8.9, 1.7 Hz, 1H), 7.86 (dd, J = 8.0, 1.9 Hz, 1H), 7.65 (t, J = 3.0 Hz, 1H), 7.61 (t, J = 8.0 Hz, 1H), 7.52 (d, J = 8.1 Hz, 1H), 7.48-7.44 (m, 1H), 6.32 (t, J = 2.5 Hz, 1H), 3.93 (h, J = 7.0 Hz, 1H), 2.40 (s, 3H), 1.87-1.75 (m, 2H), 1.60-1.48 (m, 2H), 1.47-1.29 (m, 4H). MS (ESI) m/z: 495 [M + H]⁺. |
| V-a-41 | 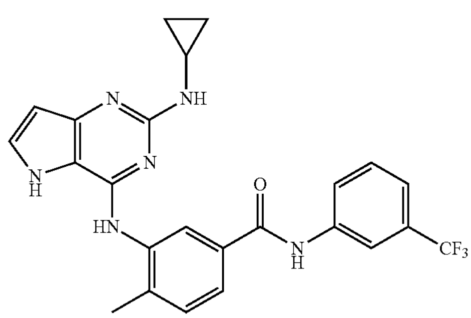 [SMILES: Cc1ccc(C(=O)Nc2cccc(C(F)(F)F)c2)cc1Nc1nc(NC2CC2)nc2cc[nH]c12] | ¹H NMR (600 MHz, DMSO-d₆) δ 12.43 (brs, 1H), 12.15 (s, 1H), 10.53 (s, 1H), 10.22 (s, 1H), 8.48 (d, J = 2.5 Hz, 1H), 8.26-8.23 (m, 1H), 8.12 (brs, 1H), 8.09-8.06 (m, 1H), 7.88 (dd, J = 7.9, 1.9 Hz, 1H), 7.66 (t, J = 3.0 Hz, 1H), 7.61 (t, J = 8.0 Hz, 1H), 7.52 (d, J = 8.0 Hz, 1H), 7.47-7.44 (m, 1H), 6.40 (t, J = 2.5 Hz, 1H), 2.60-2.54 (m, 1H), 2.36 (s, 3H), 0.84-0.67 (m, 2H), 0.62-0.51 (m, 2H). MS (ESI) m/z: 467 [M + H]⁺. |

| No. | Structure | ¹H NMR and/or MS data |
|---|---|---|
| V-a-42 | 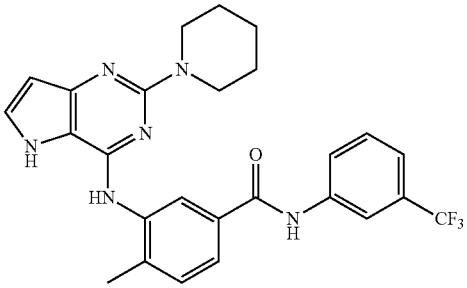 [SMILES: Cc1ccc(C(=O)Nc2cccc(C(F)(F)F)c2)cc1Nc1nc(N2CCOCC2)nc2cc[nH]c12] | ¹H NMR (600 MHz, DMSO-$d_6$) δ 12.40 (s, 1H), 12.17 (brs, 1H), 10.53 (s, 1H), 10.21 (s, 1H), 8.29 (d, J = 1.8 Hz, 1H), 8.24-8.22 (m, 1H), 8.10-8.07 (m, 1H), 7.88 (dd, J = 7.9, 1.9 Hz, 1H), 7.68 (t, J = 3.0 Hz, 1H), 7.60 (t, J = 8.0 Hz, 1H), 7.52 (d, J = 8.1 Hz, 1H), 7.47-7.44 (m, 1H), 6.35 (dd, J = 2.9, 2.1 Hz, 1H), 3.62-3.54 (m, 4H), 2.39 (s, 3H), 1.60-1.54 (m, 2H), 1.53-1.44 (m, 4H). MS (ESI) m/z: 495 [M + H]⁺. |
| V-a-43 | 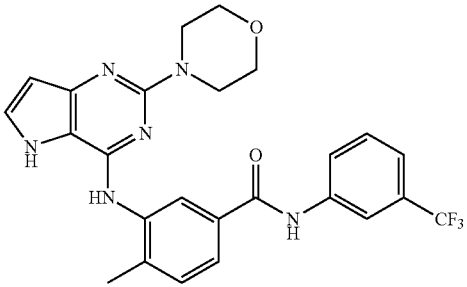 | ¹H NMR (600 MHz, DMSO-$d_6$) δ 12.61 (brs, 1H), 12.22 (brs, 1H), 10.55 (s, 1H), 10.28 (s, 1H), 8.28 (d, J = 1.8 Hz, 1H), 8.25-8.23 (m, 1H), 8.09-8.05 (m, 1H), 7.90 (dd, J = 7.9, 1.9 Hz, 1H), 7.71 (t, J = 3.0 Hz, 1H), 7.61 (t, J = 8.0 Hz, 1H), 7.52 (d, J = 8.1 Hz, 1H), 7.48-7.44 (m, 1H), 6.38 (dd, J = 2.9, 2.0 Hz, 1H), 3.67-3.62 (m, 4H), 3.62-3.57 (m, 4H), 2.39 (s, 3H). MS (ESI) m/z: 497 [M + H]⁺. |
| V-a-44 | 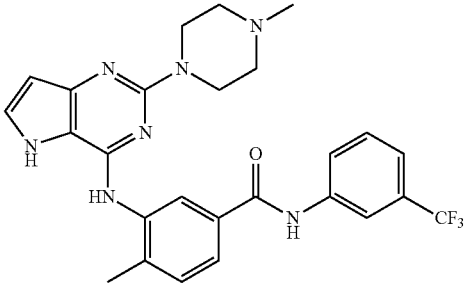 [SMILES: Cc1ccc(C(=O)Nc2cccc(C(F)(F)F)c2)cc1Nc1nc(N2CCN(C)CC2)nc2cc[nH]c12] | ¹H NMR (600 MHz, DMSO-$d_6$) δ 10.98-10.94 (m, 1H), 10.48 (s, 1H), 8.69 (d, J = 1.9 Hz, 1H), 8.33 (s, 1H), 8.24-8.21 (m, 1H), 8.09-8.05 (m, 1H), 7.66 (dd, J = 7.8, 1.9 Hz, 1H), 7.60 (t, J = 8.0 Hz, 1H), 7.47 (t, J = 2.9 Hz, 1H), 7.46-7.44 (m, 1H), 7.42 (dd, J = 7.8, 0.8 Hz, 1H), 6.17 (dd, J = 2.9, 2.0 Hz, 1H), 3.61-3.51 (m, 4H), 2.42 (s, 3H), 2.23-2.16 (m, 4H), 2.04 (s, 3H). MS (ESI) m/z: 510 [M + H]⁺. |
| V-a-45 | 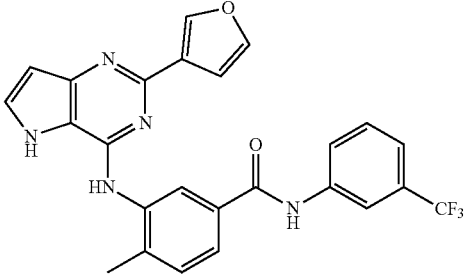 [SMILES: Cc1ccc(C(=O)Nc2cccc(C(F)(F)F)c2)cc1Nc1nc(-c2ccoc2)nc2cc[nH]c12] | ¹H NMR (600 MHz, DMSO-$d_6$) δ 12.08 (brs, 1H), 10.56 (s, 1H), 8.44 (s, 1H), 8.25-8.21 (m, 1H), 8.11-8.06 (m, 1H), 7.97 (s, 1H), 7.90-7.85 (m, 2H), 7.61 (t, J = 8.0 Hz, 1H), 7.54 (d, J = 8.0 Hz, 1H), 7.48-7.45 (m, 1H), 7.16-7.12 (m, 1H), 6.68 (s, 1H), 6.61 (t, J = 2.4 Hz, 1H), 2.42 (s, 3H). MS (ESI) m/z: 478 [M + H]⁺. |

| No. | Structure | ¹H NMR and/or MS data |
|---|---|---|
| V-a-46 | 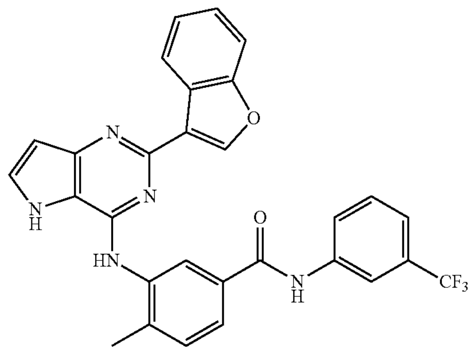 [SMILES: Cc1ccc(C(=O)Nc2cccc(C(F)(F)F)c2)cc1Nc1nc(-c2coc3ccccc23)nc2cc[nH]c12] | ¹H NMR (600 MHz, DMSO-d₆) δ 11.59-11.54 (m, 1H), 10.58 (s, 1H), 8.91 (d, J = 1.9 Hz, 1H), 8.74 (s, 1H), 8.35-8.33 (m, 1H), 8.10-8.06 (m, 1H), 7.80 (dd, J = 7.9, 1.9 Hz, 1H), 111 (t, J = 2.9 Hz, 1H), 7.61 (t, J = 8.0 Hz, 1H), 7.58 (d, J = 8.1 Hz, 1H), 7.53-7.49 (m, 2H), 7.48-7.45 (m, 2H), 7.31 (ddd, J = 8.3, 7.2, 1.3 Hz, 1H), 7.22 (td, J = 7.5, 1.0 Hz, 1H), 6.62 (dd, J = 3.0, 2.0 Hz, 1H), 2.48 (s, 3H). MS (ESI) m/z: 528 [M + H]⁺. |
| V-a-47 | 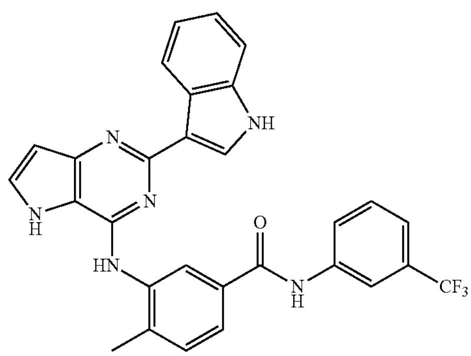 [SMILES: Cc1ccc(C(=O)Nc2cccc(C(F)(F)F)c2)cc1Nc1nc(-c2c[nH]c3ccccc23)nc2cc[nH]c12] | ¹H NMR (600 MHz, DMSO-d₆) δ 11.36-11.29 (m, 1H), 11.26-11.21 (m, 1H), 10.55 (s, 1H), 8.68 (d, J = 1.8 Hz, 1H), 8.59 (s, 1H), 8.40 (d, J = 8.0 Hz, 1H), 8.24-8.22 (m, 1H), 8.09-8.05 (m, 1H), 8.01 (d, J = 2.6 Hz, 1H), 7.83 (dd, J = 7.9, 1.9 Hz, 1H), 7.66 (t, J = 2.9 Hz, 1H), 7.59 (t, J = 8.0 Hz, 1H), 7.55-7.50 (m, 1H), 7.45 (ddt, J = 7.8, 1.7, 0.8 Hz, 1H), 7.34 (dt, J = 8.1, 1.0 Hz, 1H), 7.01 (ddd, J = 8.2, 7.0, 1.3 Hz, 1H), 6.91 (ddd, J = 8.0, 6.9, 1.1 Hz, 1H), 6.50 (dd, J = 3.0, 1.8 Hz, 1H), 2.47 (s, 3H). MS (ESI) m/z: 527 [M + H]⁺. |
| V-a-48 | 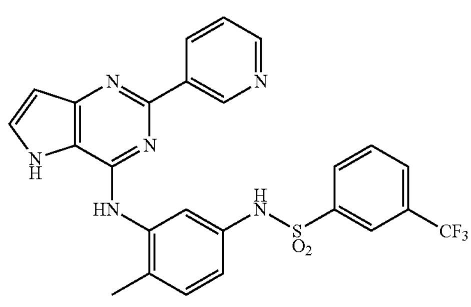 [SMILES: Cc1ccc(NS(=O)(=O)c2cccc(C(F)(F)F)c2)cc1Nc1nc(-c2cccnc2)nc2cc[nH]c12] | ¹H NMR (600 MHz, DMSO-d₆) δ 12.08 (s, 1H), 10.57 (s, 1H), 9.71 (brs, 1H), 9.31 (d, J = 2.2 Hz, 1H), 8.82 (dd, J = 5.0, 1.5 Hz, 1H), 8.70 (d, J = 8.1 Hz, 1H), 8.07 (d, J = 7.9 Hz, 1H), 8.03 (s, 1H), 7.97 (d, J = 7.9 Hz, 1H), 7.91 (t, J = 3.0 Hz, 1H), 7.80-7.74 (m, 2H), 7.56 (d, J = 2.2 Hz, 1H), 7.24 (d, J = 8.4 Hz, 1H), 6.93 (dd, J = 8.3, 2.3 Hz, 1H), 6.69 (dd, J = 3.0, 2.0 Hz, 1H), 2.22 (s, 3H). MS (ESI) m/z: 525 [M +H]⁺. |

| No. | Structure | ¹H NMR and/or MS data |
|---|---|---|
| V-a-49 | 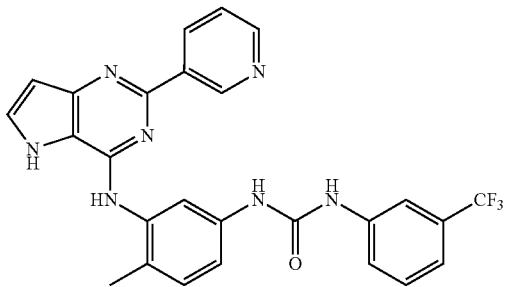 [SMILES: Cc1ccc(NC(=O)Nc2cccc(C(F)(F)F)c2)cc1Nc1nc(-c2cccnc2)nc2cc[nH]c12] | ¹H NMR (600 MHz, DMSO-d$_6$) δ 12.12 (brs, 1H), 9.87 (brs, 1H), 9.60 (s, 1H), 9.41 (s, 1H), 8.88-8.76 (m, 2H), 8.12 (d, J = 2.1 Hz, 1H), 8.09-8.07 (m, 1H), 7.93 (t, J = 3.0 Hz, 1H), 7.75 (s, 1H), 7.60-7.55 (m, 1H), 7.50 (t, J = 8.0 Hz, 1H), 7.30-7.27 (m, 2H), 7.24 (dd, J = 8.3, 2.2 Hz, 1H), 6.70 (dd, J = 3.0, 2.0 Hz, 1H), 2.28 (s, 3H). MS (ESI) m/z: 504 [M + H]⁺. |
| V-a-50 | 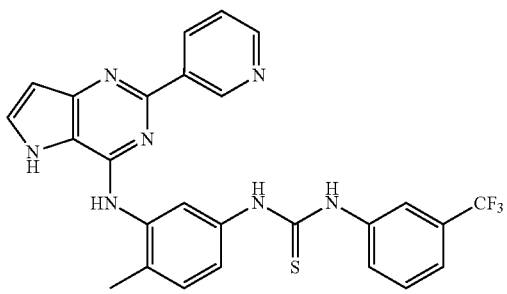 [SMILES: Cc1ccc(NC(=S)Nc2cccc(C(F)(F)F)c2)cc1Nc1nc(-c2cccnc2)nc2cc[nH]c12] | ¹H NMR (600 MHz, DMSO-d$_6$) δ 11.93 (brs, 1H), 10.20 (s, 1H), 10.17 (s, 1H), 9.88 (brs, 1H), 9.33 (d, J = 2.1 Hz, 1H), 8.80 (dd, J = 5.1, 1.5 Hz, 1H), 8.72 (d, J = 7.9 Hz, 1H), 7.99-7.95 (m, 1H), 7.94-7.89 (m, 2H), 7.75 (dd, J = 8.0, 1.9 Hz, 1H), 7.72 (dd, J = 8.1, 5.2 Hz, 1H), 7.55 (t, J = 8.0 Hz, 1H), 7.46 (d, J = 7.8 Hz, 1H), 7.37 (d, J = 8.3 Hz, 1H), 7.31 (dd, J = 8.2, 2.2 Hz, 1H), 6.71-6.67 (m, 1H), 2.31 (s, 3H). MS (ESI) m/z: 520 [M + H]⁺. |
| V-a-51 | 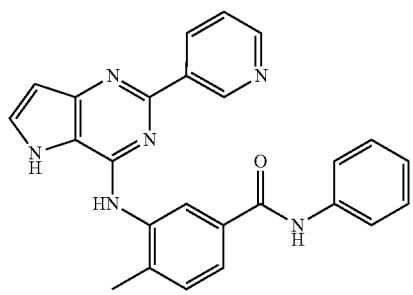 [SMILES: Cc1ccc(C(=O)Nc2ccccc2)cc1Nc1nc(-c2cccnc2)nc2cc[nH]c12] | ¹H NMR (600 MHz, DMSO-d$_6$) δ 12.25 (brs, 1H), 10.27 (s, 1H), 10.03 (brs, 1H), 9.33 (brs, 1H), 8.85-8.78 (m, 1H), 8.75 (d, J = 8.0 Hz, 1H), 8.44 (s, 1H), 7.98-7.94 (m, 1H), 7.90 (dd, J = 8.0, 1.8 Hz, 1H), 7.79 (d, J = 8.0 Hz, 2H), 7.76 (t, J = 6.7 Hz, 1H), 7.55 (d, J = 8.0 Hz, 1H), 7.36 (t, J = 7.8 Hz, 2H), 7.11 (t, J = 7.4 Hz, 1H), 6.74-6.68 (m, 1H), 2.43 (s, 3H). MS (ESI) m/z: 421 [M + H]⁺. |
| V-a-52 | 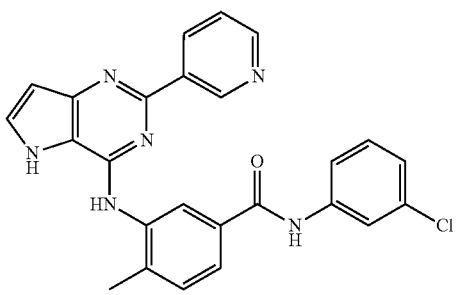 [SMILES: Cc1ccc(C(=O)Nc2cccc(Cl)c2)cc1Nc1nc(-c2cccnc2)nc2cc[nH]c12] | ¹H NMR (600 MHz, DMSO-d$_6$) δ 12.04 (s, 1H), 10.42 (s, 1H), 9.83 (s, 1H), 9.32 (d, J = 2.1 Hz, 1H), 8.79 (dd, J = 5.1, 1.6 Hz, 1H), 8.75 (d, J = 8.0 Hz, 1H), 8.49-8.44 (m, 1H), 7.98 (t, J = 2.1 Hz, 1H), 7.94 (t, J = 3.0 Hz, 1H), 7.88 (dd, J = 7.9, 1.9 Hz, 1H), 7.76-7.72 (m, 2H), 7.56 (d, J = 8.0 Hz, 1H), 7.39 (t, J = 8.1 Hz, 1H), 7.17 (ddd, J = 8.0, 2.1, 0.9 Hz, 1H), 6.71 (dd, J = 3.0, 1.9 Hz, 1H), 2.43 (s, 3H). MS (ESI) m/z: 455 [M + H]⁺. |

-continued

| No. | Structure | ¹H NMR and/or MS data |
|---|---|---|
| V-a-53 | 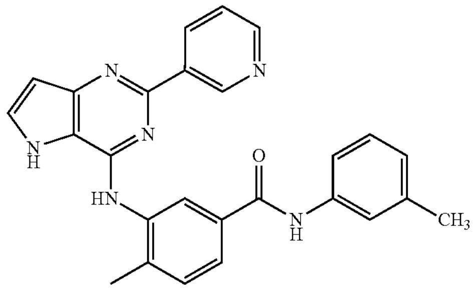 [SMILES: Cc1cccc(NC(=O)c2ccc(C)c(Nc3nc(-c4cccnc4)nc4cc[nH]c34)c2)c1] | ¹H NMR (600 MHz, DMSO-d₆) δ 12.13 (s, 1H), 10.20 (s, 1H), 10.11 (s, 1H), 9.26 (s, 1H), 8.79 (d, J = 5.1 Hz, 1H), 8.72 (d, J = 8.1 Hz, 1H), 8.37 (s, 1H), 7.93 (d, J = 3.0 Hz, 1H), 7.87 (d, J = 7.9 Hz, 1H), 7.77 (dd, J = 8.1, 5.2 Hz, 1H), 7.57-7.51 (m, 3H), 7.22 (t, J = 7.6 Hz, 1H), 6.93 (d, J = 7.5 Hz, 1H), 6.72 (t, J = 2.3 Hz, 1H), 2.40 (s, 3H), 2.28 (s, 3H). MS (ESI) m/z: 435 [M + H]⁺. |
| V-a-54 | 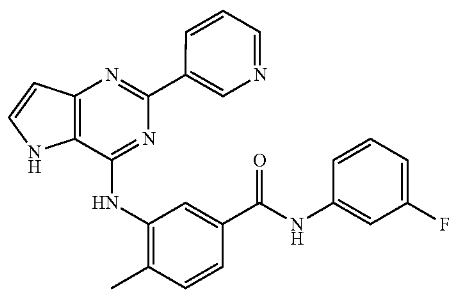 [SMILES: Cc1ccc(C(=O)Nc2cccc(F)c2)cc1Nc1nc(-c2cccnc2)nc2cc[nH]c12] | ¹H NMR (600 MHz, DMSO-d₆) δ 12.08 (brs, 1H), 10.45 (s, 1H), 9.85 (brs, 1H), 9.33 (s, 1H), 8.79 (d, J = 5.0 Hz, 1H), 8.75 (d, J = 8.1 Hz, 1H), 8.49-8.45 (m, 1H), 7.94 (t, J = 3.0 Hz, 1H), 7.88 (dd, J = 8.0, 1.9 Hz, 1H), 7.78 (dt, J = 11.8, 2.3 Hz, 1H), 7.74 (dd, J = 8.1, 5.1 Hz, 1H), 7.61-7.54 (m, 2H), 7.44-7.36 (m, 1H), 6.98-6.91 (m, 1H), 6.71 (dd, J = 3.0, 2.0 Hz, 1H), 2.44 (s, 3H). MS (ESI) m/z: 439 [M + H]⁺. |
| V-a-55 | 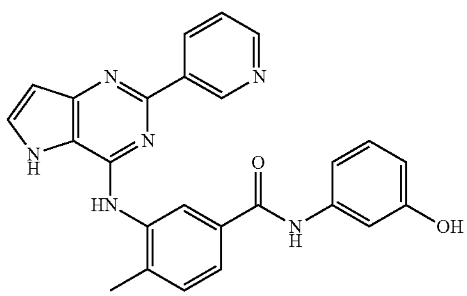 [SMILES: Cc1ccc(C(=O)Nc2cccc(O)c2)cc1Nc1nc(-c2cccnc2)nc2cc[nH]c12] | ¹H NMR (600 MHz, DMSO-d₆) δ 12.30 (brs, 1H), 10.14 (s, 1H), 10.10 (brs, 1H), 9.31 (d, J = 2.3 Hz, 1H), 8.80 (dd, J = 5.1, 1.5 Hz, 1H), 8.73 (d, J = 8.1 Hz, 1H), 8.40 (d, J = 1.9 Hz, 1H), 7.96 (t, J = 3.0 Hz, 1H), 7.88 (dd, J = 7.9, 1.9 Hz, 1H), 7.75 (dd, J = 8.1, 5.1 Hz, 1H), 7.54 (d, J = 8.1 Hz, 1H), 7.37 (t, J = 2.2 Hz, 1H), 7.18 (ddd, J = 8.1, 2.0, 1.1 Hz, 1H), 7.11 (t, J = 8.0 Hz, 1H), 6.72 (dd, J = 3.0, 1.9 Hz, 1H), 6.51 (ddd, J = 8.0, 2.4, 1.0 Hz, 1H), 2.42 (s, 3H). MS (ESI) m/z: 437 [M + H]⁺. |
| V-a-56 | 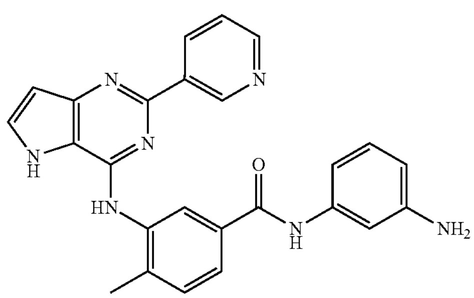 [SMILES: Cc1ccc(C(=O)Nc2cccc(N)c2)cc1Nc1nc(-c2cccnc2)nc2cc[nH]c12] | ¹H NMR (600 MHz, DMSO-d₆) δ 12.46 (brs, 1H), 10.51 (s, 1H), 10.21 (brs, 1H), 9.30 (d, J = 2.3 Hz, 1H), 8.79 (dd, J = 5.1, 1.6 Hz, 1H), 8.71 (dt, J = 8.2, 2.0 Hz, 1H), 8.41 (d, J = 1.8 Hz, 1H), 7.99-7.96 (m, 2H), 7.92 (dd, J = 8.0, 1.9 Hz, 1H), 7.74 (dd, J = 8.1, 5.1 Hz, 1H), 7.64 (ddd, J = 8.4, 2.0, 1.0 Hz, 1H), 7.57 (d, J = 8.1 Hz, 1H), 7.43 (t, J = 8.1 Hz, 1H), 7.03 (ddd, J = 7.9, 2.1, 1.0 Hz, 1H), 6.72 (dd, J = 3.0, 1.8 Hz, 1H), 2.43 (s, 3H). MS (ESI) m/z: 436 [M + H]⁺. |

-continued

| No. | Structure | ¹H NMR and/or MS data |
|---|---|---|
| V-a-57 | 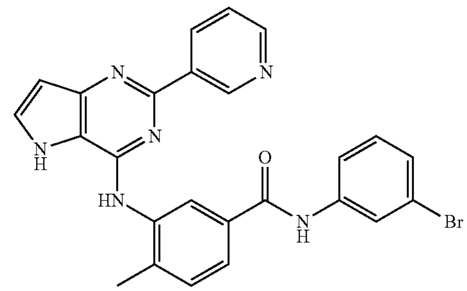 [SMILES: Cc1ccc(C(=O)Nc2cccc(Br)c2)cc1Nc1nc(-c2cccnc2)nc2cc[nH]c12] | MS (ESI) m/z: 499 [M + H]⁺. |
| V-a-58 | 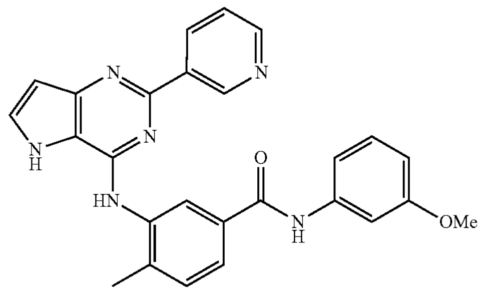 [SMILES: COc1cccc(NC(=O)c2ccc(C)c(Nc3nc(-c4cccnc4)nc4cc[nH]c34)c2)c1] | MS (ESI) m/z: 451 [M + H]⁺. |
| V-a-59 | 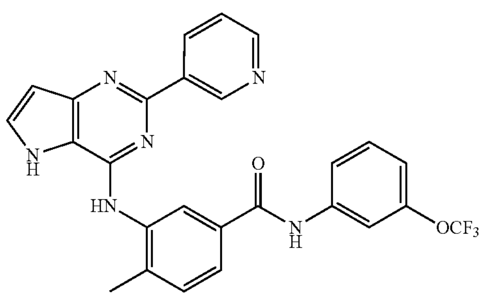 [SMILES: Cc1ccc(C(=O)Nc2cccc(OC(F)(F)F)c2)cc1Nc1nc(-c2cccnc2)nc2cc[nH]c12] | ¹H NMR (600 MHz, DMSO-$d_6$) δ 12.13 (s, 1H), 10.51 (s, 1H), 9.88 (s, 1H), 9.32 (s, 1H), 8.77 (d, J = 5.0 Hz, 1H), 8.73 (d, J = 8.2 Hz, 1H), 8.47 (d, J = 1.9 Hz, 1H), 7.95-7.92 (m, 2H), 7.90 (dd, J = 8.0, 1.9 Hz, 1H), 7.82-7.79 (m, 1H), 7.70 (dd, J = 8.1, 5.0 Hz, 1H), 7.56 (d, J = 8.1 Hz, 1H), 7.49 (t, J = 8.2 Hz, 1H), 7.09 (ddt, J = 8.2, 2.2, 1.0 Hz, 1H), 6.70 (dd, J = 3.0, 1.9 Hz, 1H), 2.44 (s, 3H). MS (ESI) m/z: 505 [M + H]⁺. |
| V-a-60 | 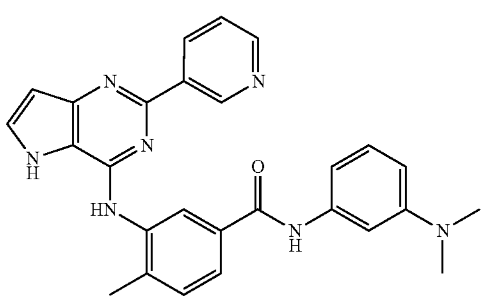 [SMILES: Cc1ccc(C(=O)Nc2cccc(N(C)C)c2)cc1Nc1nc(-c2cccnc2)nc2cc[nH]c12] | ¹H NMR (600 MHz, DMSO-$d_6$) δ 12.17 (s, 1H), 10.12 (s, 1H), 9.98 (s, 1H), 9.31 (d, J = 2.2 Hz, 1H), 8.79 (dd, J = 5.1, 1.6 Hz, 1H), 8.73 (d, J = 8.1 Hz, 1H), 8.43 (d, J = 1.9 Hz, 1H), 7.95 (t, J = 3.0 Hz, 1H), 7.89 (dd, J = 7.9, 1.9 Hz, 1H), 7.73 (dd, J = 8.1, 5.1 Hz, 1H), 7.54 (d, J = 8.1 Hz, 1H), 7.33 (s, 1H), 7.29-7.25 (m, 1H), 7.20 (t, J = 8.1 Hz, 1H), 6.71 (dd, J = 3.0, 1.9 Hz, 1H), 6.63 (dd, J = 8.6, 2.3 Hz, 1H), 2.93 (s, 6H), 2.43 (s, 3H). MS (ESI) m/z: 464 [M + H]⁺. |
| V-b-1 | 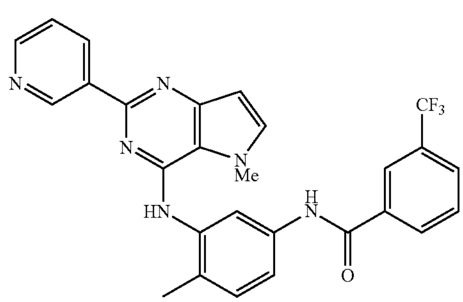 [SMILES: Cc1ccc(NC(=O)c2cccc(C(F)(F)F)c2)cc1Nc1nc(-c2cccnc2)nc2ccn(C)c12] | ¹H NMR (600 MHz, DMSO-$d_6$) δ 10.50 (s, 1H), 9.28 (s, 1H), 8.53 (d, J = 3.7 Hz, 1H), 8.49 (d, J = 7.9 Hz, 1H), 8.40 (s, 1H), 8.31 (s, 1H), 8.28 (d, J = 7.8 Hz, 1H), 8.18 (s, 1H), 7.97 (d, J = 7.7 Hz, 1H), 7.79 (t, J = 7.8 Hz, 1H), 7.61 (d, J = 2.9 Hz, 1H), 7.55 (d, J = 8.1 Hz, 1H), 7.38 (dd, J = 7.6, 4.8 Hz, 1H), 7.34 (d, J = 8.3 Hz, 1H), 6.53 (d, J = 2.9 Hz, 1H), 4.20 (s, 3H), 2.25 (S, 3H). MS (ESI) m/z: 503 [M + H]⁺. |

| No. | Structure | ¹H NMR and/or MS data |
|---|---|---|
| V-b-2 | 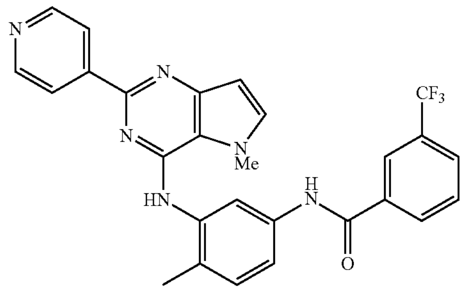 [SMILES: Cc1ccc(NC(=O)c2cccc(C(F)(F)F)c2)cc1Nc1nc(-c2ccncc2)nc2ccn(C)c12] | ¹H NMR (600 MHz, DMSO-d₆) δ 10.50 (s, 1H), 8.56 (dd, J = 4.5, 1.6 Hz, 2H), 8.40 (s, 1H), 8.31 (s, 1H), 8.28 (d, J = 7.9 Hz, 1H), 8.22 (d, J = 2.1 Hz, 1H), 8.08 (dd, J = 4.5, 1.6 Hz, 2H), 7.98 (d, J = 7.8 Hz, 1H), 7.80 (t, J = 7.8 Hz, 1H), 7.64 (d, J = 3.1 Hz, 1H), 7.54 (dd, J = 8.2, 2.1 Hz, 1H), 7.35 (d, J = 8.4 Hz, 1H), 6.56 (d, J = 3.1 Hz, 1H), 4.21 (s, 3H), 2.25 (s, 3H). MS (ESI) m/z: 503 [M + H]⁺. |
| V-b-3 | 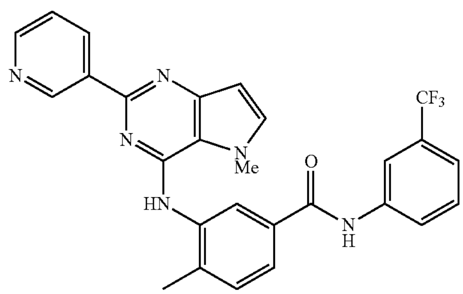 [SMILES: Cc1ccc(C(=O)Nc2cccc(C(F)(F)F)c2)cc1Nc1nc(-c2cccnc2)nc2ccn(C)c12] | ¹H NMR (600 MHz, DMSO-d₆) δ 10.57 (s, 1H), 9.24 (dd, J = 2.2, 0.8 Hz, 1H), 8.54-8.51 (m, 2H), 8.47-8.44 (m, 1H), 8.32 (d, J = 1.8 Hz, 1H), 8.25 (s, 1H), 8.09 (d, J = 8.3 Hz, 1H), 7.86 (dd, J = 7.9, 1.9 Hz, 1H), 7.63 (d, J = 3.0 Hz, 1H), 7.61 (t, J = 8.1 Hz, 1H), 7.54 (d, J = 8.1 Hz, 1H), 7.46 (d, J = 7.7 Hz, 1H), 7.36 (ddd, J = 8.0, 4.7, 0.8 Hz, 1H), 6.55 (d, J = 3.1 Hz, 1H), 4.23 (s, 3H), 2.35 (s, 3H). MS (ESI) m/z: 503 [M + H]⁺. |
| V-b-4 | 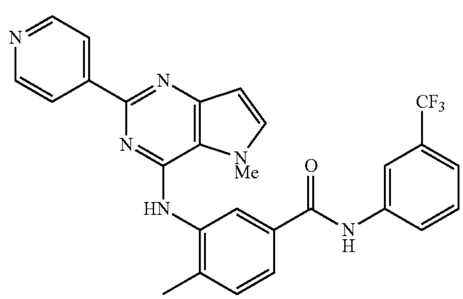 [SMILES: Cc1ccc(C(=O)Nc2cccc(C(F)(F)F)c2)cc1Nc1nc(-c2ccncc2)nc2ccn(C)c12] | ¹H NMR (600 MHz, DMSO-d₆) δ 10.59 (s, 1H), 8.55 (d, J = 5.9 Hz, 2H), 8.53 (s, 1H), 8.42 (d, J = 1.2 Hz, 1H), 8.27 (s, 1H), 8.10 (d, J = 8.3 Hz, 1H), 8.06 (d, J = 5.9 Hz, 2H), 7.86 (dd, J = 7.9, 1.5 Hz, 1H), 7.66 (d, J = 3.0 Hz, 1H), 7.61 (t, J = 8.0 Hz, 1H), 7.54 (d, J = 8.0 Hz, 1H), 7.46 (d, J = 7.7 Hz, 1H), 6.59 (d, J = 3.0 Hz, 1H), 4.25 (s, 3H), 2.36 (s 3H). MS (ESI) m/z: 503 [M + H]⁺. |
| V-b-5 | 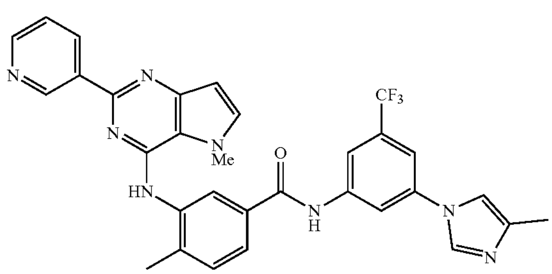 | ¹H NMR (600 MHz, DMSO-d₆) δ 10.71 (s, 1H), 9.26 (s, 1H), 8.54-8.50 (m, 2H), 8.46 (d, J = 7.9 Hz, 1H), 8.37 (s, 1H), 8.31 (s, 1H), 8.21 (s, 1H), 8.18 (s, 1H), 7.88 (d, J = 7.8 Hz, 1H), 7.73 (s, 1H), 7.64 (d, J = 2.9 Hz, 1H), 7.57 (d, J = 8.0 Hz, 1H), 7.49 (s, 1H), 7.37 (dd, J = 7.8, 4.7 Hz, 1H), 6.55 (d, J = 3.0 Hz, 1H), 4.24 (s, 3H), 2.37 (s, 3H), 2.19 (s, 3H). MS (ESI) m/z: 583 [M + H]⁺. |

| No. | Structure | ¹H NMR and/or MS data |
|---|---|---|
| V-b-6 | (TFA salt) | ¹H NMR (600 MHz, DMSO-d₆) δ 10.59 (s, 1H), 9.19 (s, 1H), 9.07 (s, 1H), 8.72 (s, 1H), 8.60 (d, J = 6.8 Hz, 1H), 8.27 (s, 1H), 8.23 (s, 1H), 8.13 (d, J = 8.4 Hz, 1H), 7.94 (d, J = 7.9 Hz, 1H), 7.79 (s, 1H), 7.72 (d, J = 8.7 Hz, 1H), 7.67-7.63 (m, 1H), 7.57 (d, J = 8.3 Hz, 1H), 6.64-6.61 (m, 1H), 4.28 (s, 3H), 3.70 (s, 2H), 3.45-3.37 (m, 2H), 3.08-3.00 (m, 2H), 2.97-2.90 (m, 2H), 2.80 (s, 3H), 2.46-2.39 (m, 2H), 2.36 (s, 3H). MS (ESI) m/z: 615 [M + H]⁺. |
| V-b-7 | 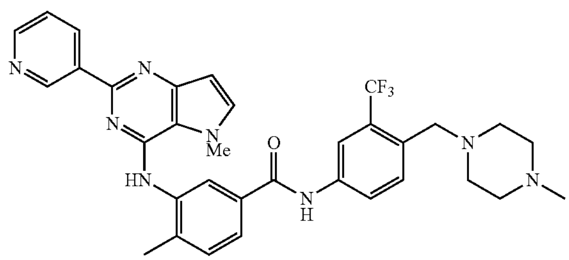 | ¹H NMR (600 MHz, DMSO-d₆) δ 10.57 (s, 1H), 8.54 (d, J = 6.0 Hz, 2H), 8.51 (s, 1H), 8.44 (d, J = 1.3 Hz, 1H), 8.24 (d, J = 1.9 Hz, 1H), 8.12 (d, J = 8.6 Hz, 1H), 8.05 (dd, J = 4.6, 1.4 Hz, 2H), 7.85 (dd, J = 7.9, 1.6 Hz, 1H), 7.71 (d, J = 8.6 Hz, 1H), 7.67 (d, J = 3.0 Hz, 1H), 7.54 (d, J = 8.0 Hz, 1H), 6.58 (d, J = 3.0 Hz, 1H), 4.25 (s, 3H), 3.66 (s, 2H), 3.18-2.93 (m, 4H), 2.74-2.66 (m, 4H), 2.55 (s, 3H), 2.36 (s, 3H). MS (ESI) m/z: 615 [M + H]⁺. |
| V-b-8 | (TFA salt) | ¹H NMR (600 MHz, DMSO-d₆) δ 9.40 (s, 2H), 9.28 (s, 1H), 9.05 (s, 1H), 8.59-8.53 (m, 2H), 8.44 (s, 1H), 8.13 (s, 1H), 7.84 (d, J = 7.6 Hz, 1H), 7.79 (s, 1H), 7.76 (s, 1H), 7.60 (d, J = 8.2 Hz, 1H), 7.55 (d, J = 7.8 Hz, 1H), 7.48 (d, J = 7.8 Hz, 1H), 7.42 (d, J = 7.7 Hz, 1H), 7.33 (d, J = 7.3 Hz, 1H), 6.62 (d, J = 2.8 Hz, 1H), 4.23 (s, 3H). MS (ESI) m/z: 504 [M + H]⁺. |
| V-b-9 | 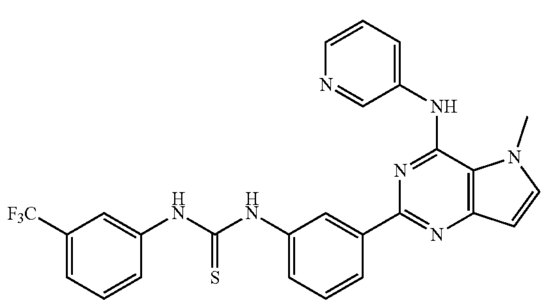 [SMILES: Cn1ccc2nc(-c3cccc(NC(=S)Nc4cccc(C(F)(F)F)c4)c3)nc(Nc3cccnc3)c21] | ¹H NMR (600 MHz, DMSO-d₆) δ 10.25 (s, 1H), 10.19 (s, 1H), 9.46 (s, 1H), 9.08 (s, 1H), 8.49 (t, J = 6.5 Hz, 2H), 8.39 (s, 1H), 7.99 (d, J = 9.9 Hz, 2H), 7.81 (d, J = 3.0 Hz, 1H), 7.77 (t, J = 7.6 Hz, 2H), 7.58 (t, J = 8.1 Hz, 2H), 7.48 (t, J = 7.9 Hz, 2H), 6.62 (d, J = 3.0 Hz, 1H), 4.23 (s, 3H). MS (ESI) m/z: 520 [M + H]⁺. |

| No. | Structure | ¹H NMR and/or MS data |
|---|---|---|
| V-b-10 | 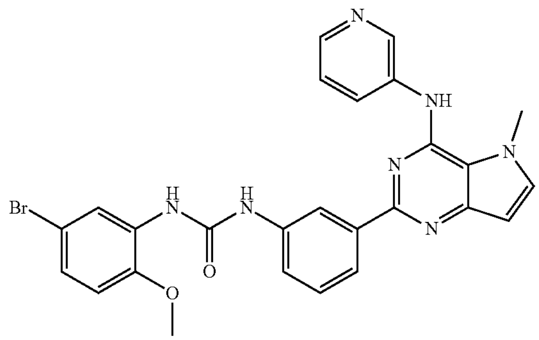 [SMILES: COc1ccc(Br)cc1NC(=O)Nc1cccc(-c2nc(Nc3cccnc3)c3c(ccn3C)n2)c1] | ¹H NMR (600 MHz, DMSO-d$_6$) δ 9.51 (s, 1H), 8.89 (d, J = 2.4 Hz, 1H), 8.64 (dd, J = 4.2, 2.4 Hz, 2H), 8.48 (d, J = 2.5 Hz, 1H), 8.41-8.37 (m, 2H), 8.32-8.28 (m, 1H), 7.92 (d, J = 7.5 Hz, 1H), 7.63 (d, J = 3.0 Hz, 1H), 7.50 (dd, J = 8.3, 4.7 Hz, 1H), 7.39-7.32 (m, 2H), 7.12 (dd, J = 8.6, 2.5 Hz, 1H), 7.00 (d, J = 8.7 Hz, 1H), 6.55 (d, J = 3.0 Hz, 1H), 4.20 (s, 3H), 3.90 (s, 3H). MS (ESI) m/z: 545 [M + H]⁺. |
| V-b-11 | 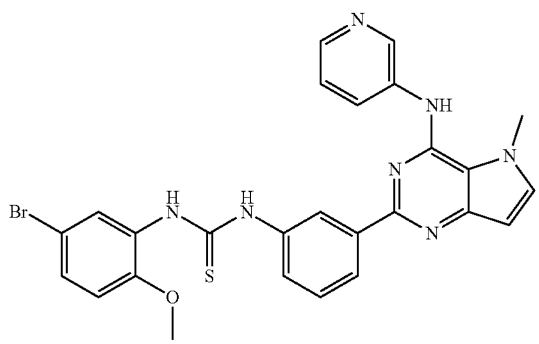 [SMILES: COc1ccc(Br)cc1NC(=S)Nc1cccc(-c2nc(Nc3cccnc3)c3c(ccn3C)n2)c1] | ¹H NMR (600 MHz, DMSO-d$_6$) δ 10.32 (s, 1H), 9.55 (s, 1H), 9.38 (s, 1H), 9.10 (d, J = 2.1 Hz, 1H), 8.55 (d, J = 8.3 Hz, 1H), 8.52 (d, J = 5.0 Hz, 1H), 8.46 (s, 1H), 8.26 (d, J = 2.3 Hz, 1H), 7.98 (d, J = 7.8 Hz, 1H), 7.83-7.79 (m, 2H), 7.65 (d, J = 8.3 Hz, 1H), 7.48 (t, J = 7.9 Hz, 1H), 7.33 (dd, J = 8.7, 2.4 Hz, 1H), 7.04 (d, J = 8.9 Hz, 1H), 6.63 (d, J = 3.0 Hz, 1H), 4.23 (s, 3H), 3.83 (s, 3H). MS (ESI) m/z: 561 [M + H]⁺. |
| V-b-12 | TFA salt | ¹H NMR (600 MHz, DMSO-d$_6$) δ 10.66 (s, 1H), 9.22 (s, 1H), 9.16 (s, 1H), 8.62 (s, 1H), 8.60 (s, 1H), 8.58 (s, 1H), 8.02 (s, 1H), 7.99 (s, 1H), 7.97 (s, 1H), 7.96 (s, 1H), 7.88 (d, J = 3.1 Hz, 1H), 7.65 (d, J = 7.2 Hz, 1H), 7.55-7.51 (m, 2H), 7.41 (t, J = 7.9 Hz, 1H), 7.33 (d, J = 7.8 Hz, 1H), 6.73 (d, J = 3.1 Hz, 1H), 4.12 (s, 3H). MS (ESI) m/z: 504 [M + H]⁺. |
| V-b-13 | 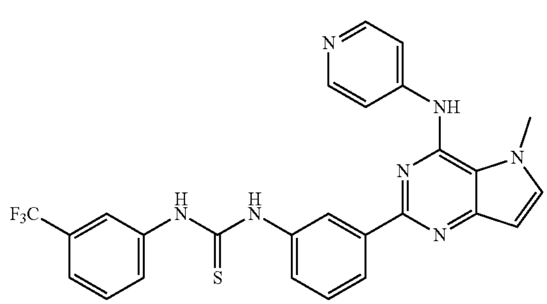 [SMILES: Cn1ccc2nc(-c3cccc(NC(=S)Nc4cccc(C(F)(F)F)c4)c3)nc(Nc3ccncc3)c21] | ¹H NMR (600 MHz, DMSO-d$_6$) δ 10.72 (s, 1H), 10.30 (s, 1H), 10.24 (s, 1H), 8.56 (d, J = 7.2 Hz, 2H), 8.53 (s, 1H), 8.14 (d, J = 7.9 Hz, 1H), 7.98-7.93 (m, 3H), 7.88 (d, J = 3.1 Hz, 1H), 7.80 (d, J = 8.4 Hz, 1H), 7.63-7.55 (m, 2H), 7.47 (t, J = 7.8 Hz, 2H), 6.71 (d, J = 3.1 Hz, 1H), 4.12 (s, 3H). MS (ESI) m/z: 520 [M + H]⁺. |

| No. | Structure | ¹H NMR and/or MS data |
|---|---|---|
| V-b-14 | 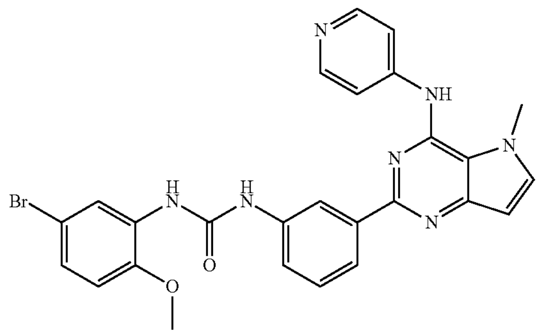 | ¹H NMR (600 MHz, DMSO-$d_6$) δ 10.56 (s, 1H), 10.18 (s, 1H), 8.68 (s, 1H), 8.63 (d, J = 7.1 Hz, 2H), 8.46 (s, 1H), 8.39 (d, J = 2.5 Hz, 1H), 8.11 (d, J = 6.9 Hz, 2H), 7.96 (d, J = 7.8 Hz, 1H), 7.86 (d, J = 3.1 Hz, 1H), 7.68 (d, J = 8.0 Hz, 1H), 7.38 (t, J = 7.9 Hz, 1H), 7.10 (dd, J = 8.6, 2.5 Hz, 1H), 6.97 (d, J = 8.7 Hz, 1H), 6.70 (d, J = 3.0 Hz, 1H), 4.23 (s, 3H), 3.86 (s, 3H). MS (ESI) m/z: 545 [M + H]⁺. |
| V-b-15 | 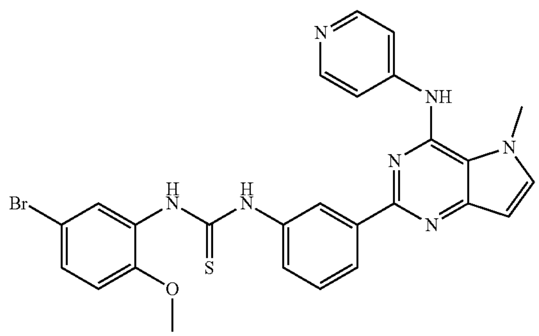 [SMILES: COc1ccc(Br)cc1NC(=O)Nc1cccc(-c2nc(Nc3ccncc3)c3c(ccn3C)n2)c1] | ¹H NMR (600 MHz, DMSO-$d_6$) δ 10.73 (s, 1H), 10.32 (s, 1H), 9.34 (s, 1H), 8.59 (s, 1H), 8.56 (d, J = 7.2 Hz, 2H), 8.26 (d, J = 2.3 Hz, 1H), 8.14 (d, J = 7.9 Hz, 1H), 7.95 (d, J = 6.9 Hz, 2H), 7.88 (d, J = 3.1 Hz, 1H), 7.67 (d, J = 8.1 Hz, 1H), 7.47 (t, J = 7.9 Hz, 1H), 7.32 (dd, J = 8.7, 2.5 Hz, 1H), 7.04 (d, J = 8.8 Hz, 1H), 6.71 (d, J = 3.1 Hz, 1H), 4.12 (s, 3H), 3.84 (s, 3H). MS (ESI) m/z: 561 [M + H]⁺. |
| V-b-16 | 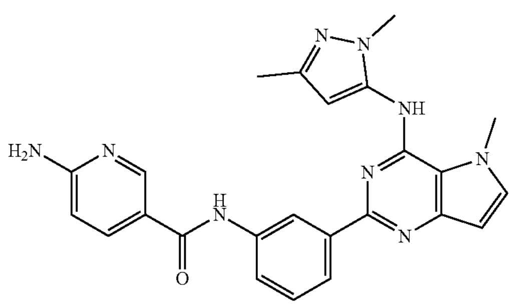 [SMILES: Cc1cc(Nc2nc(-c3cccc(NC(=O)c4ccc(N)nc4)c3)nc3ccn(C)c23)n(C)n1] | ¹H NMR (600 MHz, DMSO-$d_6$) δ 10.02 (s, 1H), 8.72 (s, 1H), 8.65 (dd, J = 2.5, 0.5 Hz, 1H), 8.55 (s, 1H), 8.00 (dd, J = 8.7, 2.5 Hz, 1H), 7.83 (d, J = 7.8 Hz, 1H), 7.77 (ddd, J = 8.1, 2.1, 1.0 Hz, 1H), 7.60 (s, 1H), 7.35 (t, J = 7.8 Hz, 1H), 6.64 (s, 2H), 6.51 (dd, J = 8.7, 0.5 Hz, 2H), 6.23 (s, 1H), 4.15 (s, 3H), 3.65 (s, 3H), 2.20 (s, 3H). MS (ESI) m/z: 454 [M + H]⁺. |
| V-b-17 | 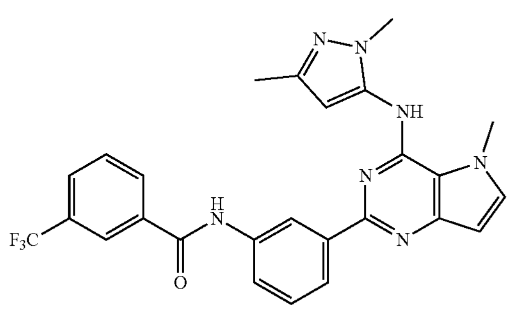 [SMILES: Cc1cc(Nc2nc(-c3cccc(NC(=O)c4cccc(C(F)(F)F)c4)c3)nc3ccn(C)c23)n(C)n1] | ¹H NMR (600 MHz, DMSO-$d_6$) δ 10.64 (s, 1H), 8.77 (s, 1H), 8.39 (s, 1H), 8.32 (t, J = 9.8 Hz, 1H), 7.98 (d, J = 7.8 Hz, 1H), 7.91 (d, J = 7.8 Hz, 1H), 7.85 (dd, J = 8.0, 1.2 Hz, 1H), 7.81 (t, J = 7.8 Hz, 1H), 7.66 (s, 1H), 7.45 (s, 1H), 6.53 (s, 1H), 6.25 (s, 1H), 4.18 (s, 3H), 3.67 (s, 3H), 2.22 (s, 3H). MS (ESI) m/z: 506 [M + H]⁺. |
| V-b-18 | 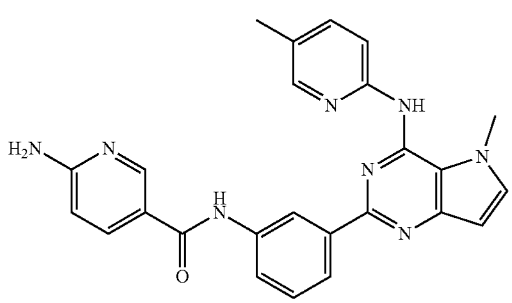 [SMILES: Cc1ccc(Nc2nc(-c3cccc(NC(=O)c4ccc(N)nc4)c3)nc3ccn(C)c23)nc1] | ¹H NMR (600 MHz, DMSO-$d_6$) δ 10.09 (s, 1H), 8.82 (t, J = 1.8 Hz, 1H), 8.68-8.66 (m, 1H), 8.16 (s, 1H), 8.04 (dd, J = 8.7, 2.5 Hz, 2H), 7.83 (ddd, J = 8.1, 2.1, 0.9 Hz, 1H), 7.71 (dd, J = 8.5, 1.9 Hz, 1H), 7.63 (d, J = 2.9 Hz, 1H), 7.42 (t, J = 7.9 Hz, 1H), 6.73 (s, 2H), 6.56-6.52 (m, 2H), 4.14 (s, 3H), 2.29 (s, 3H). MS (ESI) m/z: 451 [M + H]⁺. |

| No. | Structure | ¹H NMR and/or MS data |
|---|---|---|
| V-b-19 | 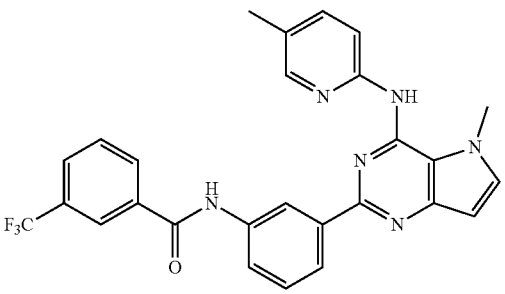 [SMILES: Cc1ccc(Nc2nc(-c3cccc(NC(=O)c4cccc(C(F)(F)F)c4)c3)nc3ccn(C)c23)nc1] | ¹H NMR (600 MHz, DMSO-$d_6$) δ 10.64 (s, 1H), 8.99 (s, 1H), 8.86 (t, J = 1.9 Hz, 1H), 8.41 (d, J = 1.7 Hz, 1H), 8.37-8.33 (m, 1H), 8.17 (d, J = 2.2 Hz, 1H), 8.11 (d, J = 7.7 Hz, 1H), 8.02-7.97 (m, 1H), 7.91 (ddd, J = 8.0, 2.2, 1.0 Hz, 1H), 7.82 (t, J = 7.8 Hz, 1H), 7.72 (dd, J = 8.6, 2.4 Hz, 1H), 7.65 (d, J = 3.0 Hz, 1H), 7.48 (t, J = 7.9 Hz, 1H), 6.55 (d, J = 3.0 Hz, 1H), 4.16 (s, 3H), 2.29 (s, 3H). MS (ESI) m/z: 503 [M + H]⁺. |
| V-b-20 | TFA salt | ¹H NMR (600 MHz, DMSO-$d_6$) δ 10.47 (s, 1H), 8.79 (s, 1H), 8.66 (d, J = 2.2 Hz, 1H), 8.32 (d, J = 9.2 Hz, 1H), 8.24 (d, J = 5.8 Hz, 1H), 7.98 (s, 1H), 7.96 (S, 1H), 7.81 (d, J = 9.4 Hz, 1H), 7.75 (s, 1H), 7.56 (t, J = 7.9 Hz, 1H), 7.21 (s, 1H), 7.12 (s, 1H), 7.07 (d, J = 5.9 Hz, 1H), 7.04 (s, 1H), 6.97 (d, J = 9.0 Hz, 1H), 6.56 (s, 1H), 4.19 (s, 3H), 2.46 (s, 3H). MS (ESI) m/z: 451 [M + H]⁺. |
| V-b-21 | 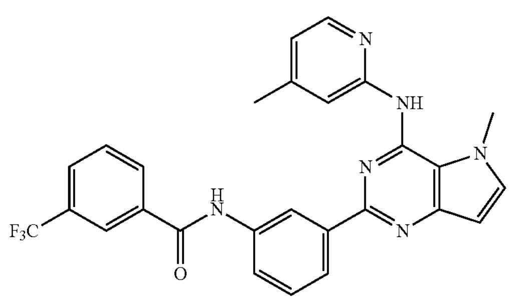 [SMILES: Cc1ccnc(Nc2nc(-c3cccc(NC(=O)c4cccc(C(F)(F)F)c4)c3)nc3ccn(C)c23)c1] | ¹H NMR (600 MHz, DMSO-$d_6$) δ 10.63 (s, 1H), 9.00 (s, 1H), 8.82 (s, 1H), 8.39 (s, 1H), 8.33 (d, J = 8.0 Hz, 1H), 8.17-8.13 (m, 2H), 8.09 (s, 1H), 7.99 (d, J = 7.8 Hz, 1H), 7.88 (d, J = 8.0 Hz, 1H), 7.81 (t, J = 7.7 Hz, 1H), 7.67 (d, J = 2.8 Hz, 1H), 7.49 (t, J = 7.9 Hz, 1H), 6.89 (d, J = 4.8 Hz, 1H), 6.55 (d, J = 2.9 Hz, 1H), 4.13 (s, 3H), 2.38 (s, 3H). MS (ESI) m/z: 503 [M + H]⁺. |
| V-b-22 | 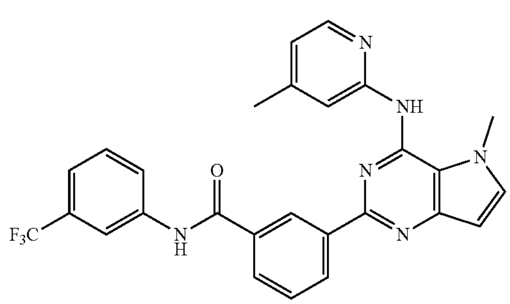 [SMILES: Cc1ccnc(Nc2nc(-c3cccc(C(=O)Nc4cccc(C(F)(F)F)c4)c3)nc3ccn(C)c23)c1] | ¹H NMR (600 MHz, DMSO-$d_6$) δ 10.75 (s, 1H), 8.97 (d, J = 1.8 Hz, 1H), 8.60 (dt, J = 7.8, 1.4 Hz, 1H), 8.27 (d, J = 1.9 Hz, 1H), 8.17 (d, J = 5.0 Hz, 1H), 8.14-8.09 (m, 2H), 8.03 (dt, J = 7.7, 1.5 Hz, 1H), 7.69-7.65 (m, 2H), 7.63 (t, J = 8.0 Hz, 1H), 7.48 (d, J = 7.7 Hz, 1H), 6.89 (dd, J = 5.2, 1.5 Hz, 1H), 6.60 (d, J = 3.0 Hz, 1H), 4.15 (s, 3H), 2.35 (s, 3H). MS (ESI) m/z: 503 [M + H]⁺. |

-continued

| No. | Structure | ¹H NMR and/or MS data |
|---|---|---|
| V-b-23 | 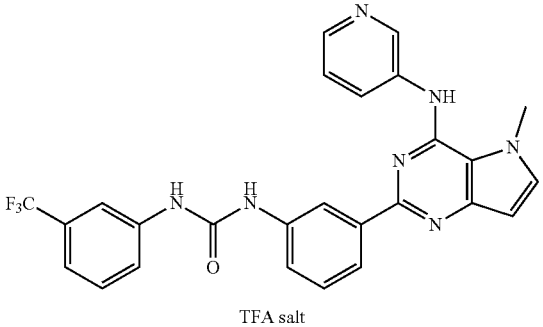<br>TFA salt | ¹H NMR (600 MHz, DMSO-d₆) δ 9.87 (s, 1H), 9.74 (s, 1H), 8.97 (s, 1H), 8.75 (d, J = 5.5 Hz, 2H), 8.40 (s, 1H), 8.08 (s, 1H), 8.05 (d, J = 5.8 Hz, 2H), 7.84 (d, J = 3.0 Hz, 1H), 7.67-7.62 (m, 3H), 7.55 (t, J = 7.9 Hz, 1H), 7.47 (t, J = 7.9 Hz, 1H), 7.33 (d, J = 8.3 Hz, 1H), 6.58 (d, J = 3.0 Hz, 1H), 5.14 (d, J = 5.7 Hz, 2H), 4.24 (s, 3H). MS (ESI) m/z: 518 [M + H]⁺. |
| V-b-24 | 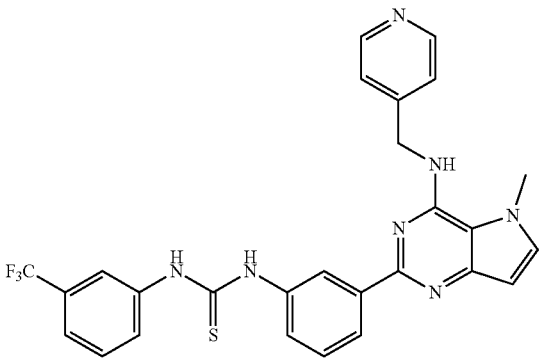 [SMILES: Cn1ccc2nc(-c3cccc(NC(=S)Nc4cccc(C(F)(F)F)c4)c3)nc(NCc3ccncc3)c21] | ¹H NMR (600 MHz, DMSO-d₆) δ 10.11 (s, 1H), 10.05 (s, 1H), 8.51-8.44 (m, 2H), 8.33 (t, J = 1.9 Hz, 1H), 8.03-7.98 (m, 2H), 7.80 (dd, J = 8.1, 2.0 Hz, 1H), 7.62-7.55 (m, 2H), 7.51-7.44 (m, 5H), 7.36 (t, J = 7.9 Hz, 1H), 6.41 (d, J = 3.0 Hz, 1H), 4.83 (d, J = 5.7 Hz, 2H), 4.14 (s, 3H). MS (ESI) m/z: 534 [M + H]⁺. |
| V-b-25 | 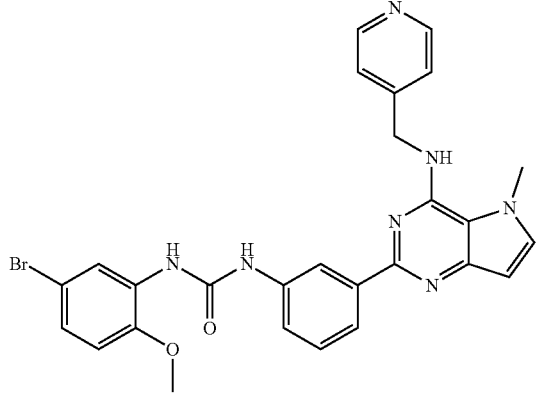<br>TFA salt | ¹H NMR (600 MHz, DMSO-d₆) δ 9.70 (s, 1H), 8.88 (s, 1H), 8.71 (d, J = 5.0 Hz, 2H), 8.50 (s, 1H), 8.44 (s, 1H), 8.40 (d, J =2.4 Hz, 1H), 7.94 (d, J = 4.9 Hz, 2H), 7.81 (d, J = 2.9 Hz, 1H), 7.66 (d, J = 7.4 Hz, 1H), 7.50-7.43 (m, 2H), 7.14 (dd, J = 8.7, 2.5 Hz, 1H), 7.00 (d, J = 8.7 Hz, 1H), 6.57 (d, J = 3.0 Hz, 1H), 5.11 (d, J = 5.7 Hz, 2H), 4.23 (s, 3H), 3.89 (s, 3H). MS (ESI) m/z: 559 [M + H]⁺. |
| V-b-26 | 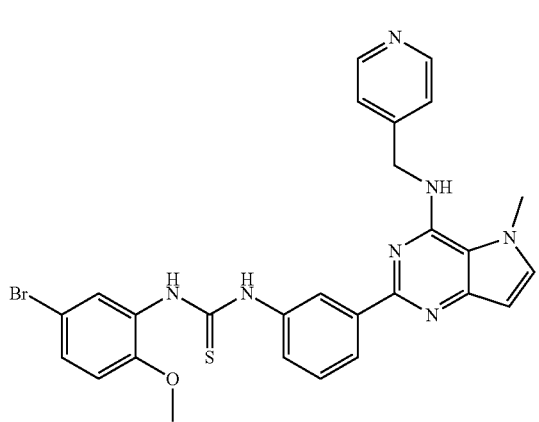 [SMILES: COc1ccc(Br)cc1NC(=S)Nc1cccc(-c2nc(NCc3ccncc3)c3c(ccn3C)n2)c1] | ¹H NMR (600 MHz, DMSO-d₆) δ 10.20 (s, 1H), 9.24 (s, 1H), 8.47 (dd, J = 4.5, 1.5 Hz, 2H), 8.37 (t, J = 1.8 Hz, 1H), 8.34 (d, J = 2.5 Hz, 1H), 8.01-7.98 (m, 1H), 7.55 (dd, J = 7.9, 1.1 Hz, 1H), 7.51 (t, J = 5.8 Hz, 1H), 7.48 (d, J = 6.0 Hz, 2H), 7.45 (d, J = 3.0 Hz, 1H), 7.34 (t, J = 7.9 Hz, 1H), 7.30 (dd, J = 8.8, 2.5 Hz, 1H), 7.03 (d, J = 8.8 Hz, 1H), 6.40 (d, J = 3.0 Hz, 1H), 4.83 (d, J = 5.7 Hz, 2H), 4.13 (s, 3H), 3.82 (s, 3H). MS (ESI) m/z: 575 [M + H]⁺. |

| No. | Structure | ¹H NMR and/or MS data |
|---|---|---|
| V-b-27 | 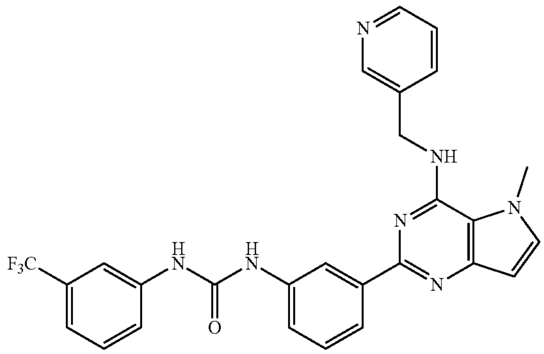 [SMILES: Cn1ccc2nc(-c3cccc(NC(=O)Nc4cccc(C(F)(F)F)c4)c3)nc(NCc3cccnc3)c21] | ¹H NMR (600 MHz, DMSO-d₆) δ 9.69 (s, 1H), 9.60 (s, 1H), 8.91 (S, 1H), 8.88 (s, 1H), 8.58 (d, J = 4.0 Hz, 1H), 8.50 (t, J = 1.9 Hz, 1H), 8.29 (d, J = 7.9 Hz, 1H), 8.09 (s, 1H), 7.79 (d, J = 3.0 Hz, 1H), 7.75 (d, J = 7.8 Hz, 1H), 7.65 (dd, J = 13.1, 4.9 Hz, 2H), 7.60 (dd, J = 7.9, 5.1 Hz, 1H), 7.52 (dt, J = 11.5, 7.9 Hz, 2H), 7.32 (d, J = 7.6 Hz, 1H), 6.55 (d, J = 3.0 Hz, 1H), 5.05 (d, J = 5.8 Hz, 2H), 4.20 (s, 3H). MS (ESI) m/z: 518 [M + H]⁺. |
| V-b-28 | 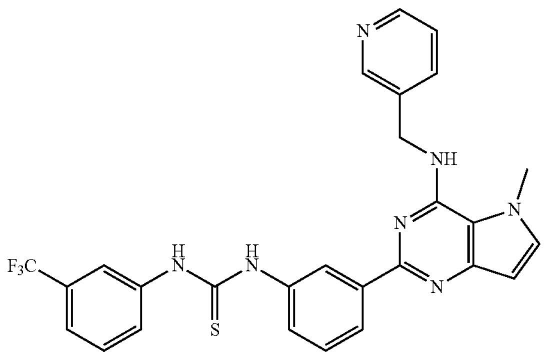 | ¹H NMR (600 MHz, DMSO-d₆) δ 10.46-10.42 (m, 2H), 8.87 (d, J = 13.6 Hz, 2H), 8.61 (d, J = 4.8 Hz, 1H), 8.43 (s, 1H), 8.28 (d, J = 8.0 Hz, 1H), 7.99 (s, 1H), 7.92 (d, J = 8.0 Hz, 1H), 7.78 (dd, J = 12.3, 5.5 Hz, 2H), 7.68-7.62 (m, 2H), 7.57 (t, J = 7.9 Hz, 2H), 7.48 (d, J = 7.6 Hz, 1H), 6.55 (d, J = 3.0 Hz, 1H), 5.05 (d, J = 5.8 Hz, 2H), 4.19 (s, 3H). MS (ESI) m/z: 534 [M + H]⁺. |
| V-b-29 | 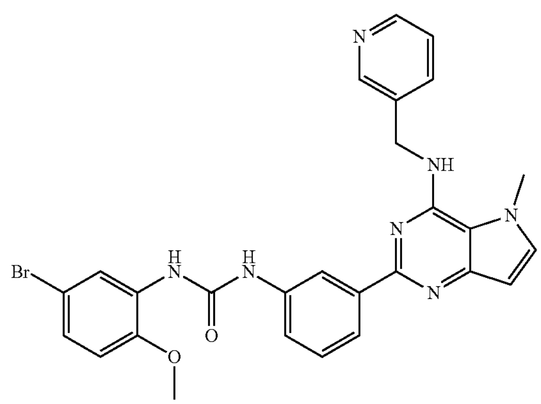 [SMILES: COc1ccc(Br)cc1NC(=O)Nc1cccc(-c2nc(NCc3cccnc3)c3c(ccn3C)n2)c1] | ¹H NMR (600 MHz, DMSO-d₆) δ 9.75 (s, 1H), 8.97-8.94 (m, 2H), 8.65 (s, 1H), 8.51 (d, J = 2.5 Hz, 2H), 8.39 (d, J = 2.4 Hz, 2H), 7.81 (d, J = 3.0 Hz, 1H), 7.77-7.68 (m, 2H), 7.51 (d, J = 5.1 Hz, 2H), 7.13 (dd, J = 8.7, 2.5 Hz, 1H), 7.00 (d, J = 8.7 Hz, 1H), 6.56 (d, J = 3.0 Hz, 1H), 5.08 (d, J = 5.7 Hz, 2H), 4.21 (s, 3H), 3.89 (s, 3H). MS (ESI) m/z: 559 [M + H]⁺. |
| V-b-30 | 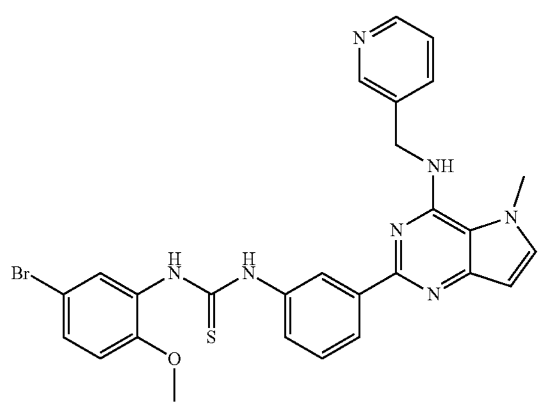 [SMILES: COc1ccc(Br)cc1NC(=S)Nc1cccc(-c2nc(NCc3cccnc3)c3c(ccn3C)n2)c1] | ¹H NMR (600 MHz, DMSO-d₆) δ 10.43 (s, 1H), 9.54 (s, 1H), 8.90 (d, J = 10.6 Hz, 2H), 8.63 (d, J = 4.9 Hz, 1H), 8.52 (t, J = 1.9 Hz, 1H), 8.32 (d, J = 7.7 Hz, 1H), 8.18 (d, J = 2.4 Hz, 1H), 7.94-7.91 (m, 1H), 7.81 (d, J = 3.0 Hz, 1H), 7.68 (d, J = 6.4 Hz, 2H), 7.57 (t, J = 7.9 Hz, 1H), 7.33 (dd, J = 8.8, 2.5 Hz, 1H), 7.05 (d, J = 8.9 Hz, 1H), 6.56 (d, J = 3.0 Hz, 1H), 5.08 (d, J = 5.8 Hz, 2H), 4.20 (s, 3H), 3.83 (s, 3H). MS (ESI) m/z: 575 [M + H]⁺. |

-continued

| No. | Structure | ¹H NMR and/or MS data |
|---|---|---|
| V-b-31 | 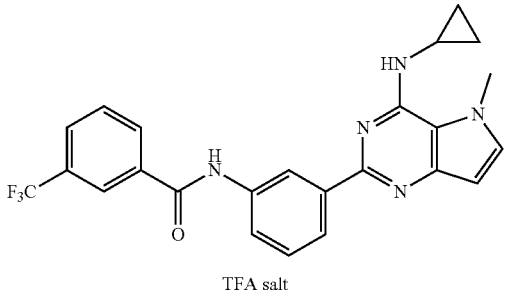 [SMILES: Cn1ccc2nc(-c3cccc(NC(=O)c4cccc(C(F)(F)F)c4)c3)nc(NC3CC3)c21]<br>TFA salt | ¹H NMR (600 MHz, DMSO-d₆) δ 10.77 (s, 1H), 8.86 (t, J = 1.8 Hz, 1H), 8.33 (s, 1H), 8.30 (d, J = 7.9 Hz, 1H), 8.07 (d, J = 7.9 Hz, 1H), 7.99 (d, J = 7.7 Hz, 2H), 7.95 (d, J = 8.0 Hz, 1H), 7.81 (t, J = 7.8 Hz, 1H), 7.70 (d, J = 2.7 Hz, 1H), 7.62 (t, J = 7.9 Hz, 1H), 6.52 (d, J = 3.0 Hz, 1H), 4.10 (s, 3H), 3.20-3.17 (m, 1H), 1.01-0.97 (m, 2H), 0.84-0.80 (m, 2H). MS (ESI) m/z: 452 [M + H]⁺. |
| V-b-32 | 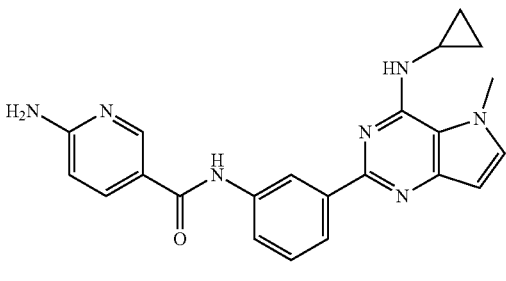<br>TFA salt | ¹H NMR (600 MHz, DMSO-d₆) δ 10.57 (s, 1H), 8.82 (s, 1H), 8.67 (d, J = 2.0 Hz, 1H), 8.31 (dd, J = 9.2, 2.0 Hz, 1H), 8.21 (d, J = 12.7 Hz, 1H), 8.01 (t, J = 9.3 Hz, 1H), 7.90 (dt, J = 8.0, 3.9 Hz, 1H), 7.74 (d, J = 2.9 Hz, 1H), 7.62 (t, J = 8.0 Hz, 1H), 6.98 (d, J = 9.2 Hz, 1H), 6.53 (t, J = 4.7 Hz, 1H), 4.11 (s 3H), 3.22-3.19 (m, 1H), 1.02-0.98 (m, 2H), 0.86-0.83 (m, 2H). MS (ESI) m/z: 400 [M + H]⁺. |
| V-b-33 | 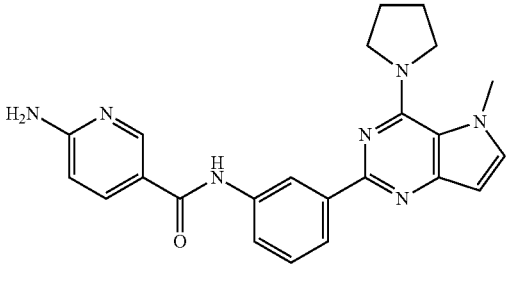 [SMILES: Cn1ccc2nc(-c3cccc(NC(=O)c4ccc(N)nc4)c3)nc(N3CCCC3)c21] | ¹H NMR (600 MHz, DMSO-d₆) δ 10.10 (s, 1H), 8.68 (d, J = 1.7 Hz, 1H), 8.65 (d, J = 2.0 Hz, 1H), 8.03-7.98 (m, 2H), 7.90 (dd, J = 8.1, 1.1 Hz, 1H), 7.63 (d, J = 3.0 Hz, 1H), 7.45 (t, J = 7.9 Hz, 1H), 6.69 (s, 2H), 6.52 (t, J = 6.2 Hz, 2H), 4.00 (s, 3H), 3.84 (t, J = 6.5 Hz, 4H), 1.95 (t, J = 6.6 Hz, 4H). MS (ESI) m/z: 414 [M + H]⁺. |
| V-b-34 | 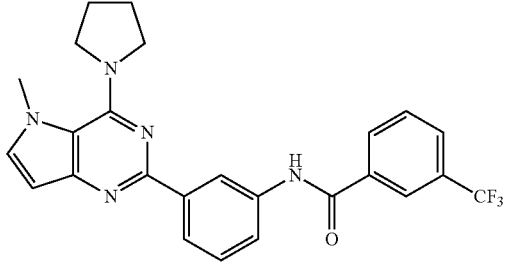 [SMILES: Cn1ccc2nc(-c3cccc(NC(=O)c4cccc(C(F)(F)F)c4)c3)nc(N3CCCC3)c21] | ¹H NMR (600 MHz, DMSO-d₆) δ 10.59 (s, 1H), 8.72 (t, J = 1.8 Hz, 1H), 8.36 (s, 1H), 8.32 (d, J = 7.8 Hz, 1H), 8.17-8.15 (m, 1H), 7.97 (d, J = 7.8 Hz, 1H), 7.94 (dd, J = 8.0, 1.1 Hz, 1H), 7.80 (t, J = 7.8 Hz, 1H), 7.55 (d, J = 3.1 Hz, 1H), 7.44 (t, J = 7.9 Hz, 1H), 6.49 (d, J = 3.1 Hz, 1H), 3.98 (s, 3H), 3.78 (t, J = 6.6 Hz, 4H), 1.94-1.91 (m, 4H). MS (ESI) m/z: 466 [M + H]⁺. |
| V-b-35 | 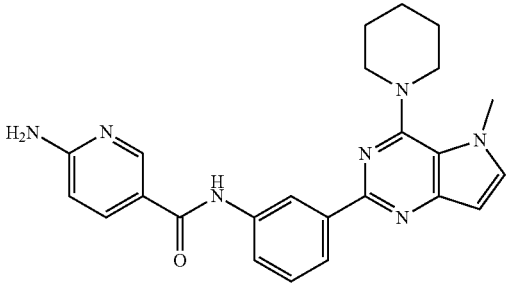 [SMILES: Cn1ccc2nc(-c3cccc(NC(=O)c4ccc(N)nc4)c3)nc(N3CCCCC3)c21] | ¹H NMR (600 MHz, DMSO-d₆) δ 10.08 (s, 1H), 8.69 (t, J = 1.9 Hz, 1H), 8.64 (dd, J = 2.4, 0.5 Hz, 1H), 8.11-8.09 (m, 1H), 8.02 (dd, J = 8.8, 2.5 Hz, 1H), 7.88 (ddd, J = 8.1, 2.2, 1.0 Hz, 1H), 7.64 (d, J = 3.1 Hz, 1H), 7.41 (t, J = 7.9 Hz, 1H), 6.74 (s, 2H), 6.56 (d, J = 3.1 Hz, 1H), 6.54 (dd, J = 8.8, 0.5 Hz, 1H), 3.97 (s, 3H), 3.45-3.40 (m, 4H), 1.79-1.72 (m, 4H), 1.68-1.61 (m, 2H). MS (ESI) m/z: 428 [M + H]⁺. |

| No. | Structure | ¹H NMR and/or MS data |
|---|---|---|
| V-b-36 | 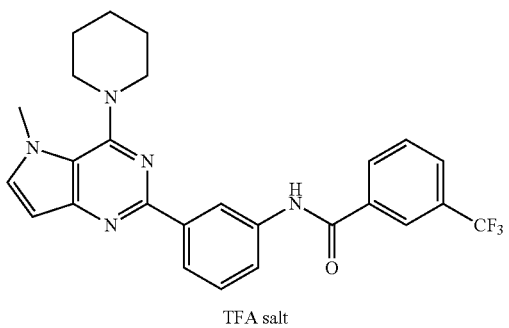<br>TFA salt | ¹H NMR (600 MHz, DMSO-$d_6$) δ 10.61 (s, 1H), 8.74 (t, J = 1.7 Hz, 1H), 8.36 (s, 1H), 8.32 (d, J = 7.8 Hz, 1H), 8.18 (s, 1H), 7.98 (d, J = 7.8 Hz, 1H), 7.96-7.93 (m, 1H), 7.81 (d, J = 7.8 Hz, 1H), 7.65 (d, J = 3.1 Hz, 1H), 7.46 (t, J = 7.9 Hz, 1H), 6.57 (d, J = 3.1 Hz, 1H), 3.97 (s, 3H), 3.43-3.38 (m, 4H), 1.78-1.73 (m, 4H), 1.66 (d, J = 4.8 Hz, 2H). MS (ESI) m/z: 496 [M + H]⁺. |
| V-b-37 | 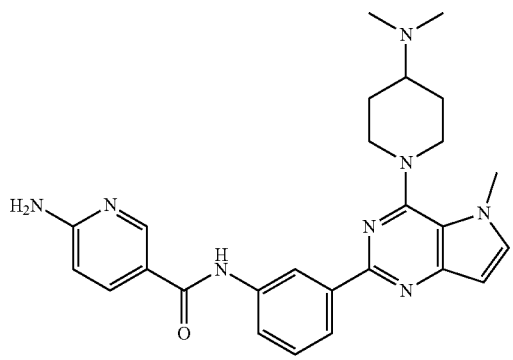 [SMILES: CN(C)C1CCN(c2nc(-c3cccc(NC(=O)c4ccc(N)nc4)c3)nc3ccn(C)c23)CC1] | ¹H NMR (600 MHz, DMSO-$d_6$) δ 10.05 (s, 1H), 8.72 (s, 1H), 8.66 (d, J = 2.5 Hz, 1H), 8.10 (d, J = 7.8 Hz, 1H), 8.00 (dd, J = 8.7, 2.4 Hz, 1H), 7.90-7.87 (m, 1H), 7.62 (d, J = 3.1 Hz, 1H), 7.40 (t, J = 7.9 Hz, 1H), 6.61 (s, 2H), 6.56 (dd, J = 3.1, 0.7 Hz, 1H), 6.51 (d, J = 8.7 Hz, 1H), 3.96 (s, 3H), 3.85 (d, J = 12.6 Hz, 2H), 2.98 (t, J = 12.0 Hz, 2H), 2.50-2.43 (m, 1H), 2.30 (s, 6H), 1.96 (d, J = 11.2 Hz, 2H), 1.67 (qd, J = 12.2, 3.2 Hz, 2H). MS (ESI) m/z: 471 [M + H]⁺. |
| V-b-38 | 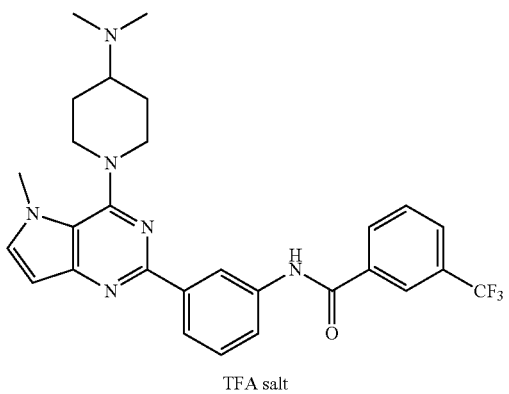 [SMILES: CN(C)C1CCN(c2nc(-c3cccc(NC(=O)c4cccc(C(F)(F)F)c4)c3)nc3ccn(C)c23)CC1]<br>TFA salt | ¹H NMR (600 MHz, DMSO-$d_6$) δ 10.76 (s, 1H), 8.82 (t, J = 1.8 Hz, 1H), 8.36 (s, 1H), 8.32 (d, J = 7.9 Hz, 1H), 8.09 (d, J = 8.0 Hz, 1H), 7.98 (t, J = 7.5 Hz, 1H), 7.96 (dd, J = 8.1, 1.2 Hz, 1H), 7.84 (d, J = 3.1 Hz, 1H), 7.81 (t, J = 7.8 Hz, 1H), 7.57 (t, J = 7.9 Hz, 1H), 6.66 (d, J = 3.1 Hz, 1H), 4.28 (d, J = 12.8 Hz, 2H), 4.01 (s, 3H), 3.54 (dd, J = 11.8, 8.6 Hz, 1H), 3.26 (t, J = 12.4 Hz, 2H), 2.81 (d, J = 4.3 Hz, 6H), 2.18 (d, J = 10.8 Hz, 2H), 1.90 (qd, J = 12.2, 3.7 Hz, 2H). MS (ESI) m/z: 523 [M + H]⁺. |
| V-b-39 | 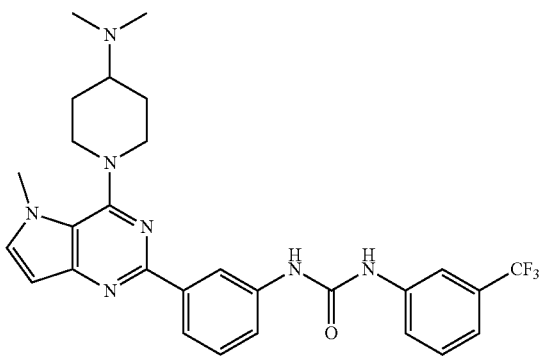 [SMILES: CN(C)C1CCN(c2nc(-c3cccc(NC(=O)Nc4cccc(C(F)(F)F)c4)c3)nc3ccn(C)c23)CC1] | ¹H NMR (600 MHz, DMSO-$d_6$) δ 9.05 (s, 1H), 8.96 (s, 1H), 8.46 (t, J = 1.7 Hz, 1H), 8.06-8.01 (m, 2H), 7.63 (d, J = 3.1 Hz, 1H), 7.61-7.57 (m, 2H), 7.52 (t, J = 7.9 Hz, 1H), 7.37 (t, J = 7.9 Hz, 1H), 7.31 (d, J = 7.7 Hz, 1H), 6.58 (d, J = 3.1 Hz, 1H), 3.96 (s, 3H), 3.85 (d, J = 12.8 Hz, 2H), 2.99 (t, J = 11.8 Hz, 2H), 2.36 (t, J = 11.1 Hz, 1H), 2.24 (s, 6H), 1.93 (d, J = 11.1 Hz, 2H), 1.65 (qd, J = 12.3, 3.5 Hz, 2H). MS (ESI) m/z: 538 [M + H]⁺. |

| No. | Structure | ¹H NMR and/or MS data |
|---|---|---|
| V-b-40 | (structure) | ¹H NMR (600 MHz, DMSO-d$_6$) δ 10.51 (s, 1H), 8.72-8.66 (m, 2H), 8.36 (dd, J = 9.3, 2.1 Hz, 1H), 8.07 (d, J = 7.8 Hz, 1H), 7.94-7.91 (m, 1H), 7.79 (d, J = 3.0 Hz, 1H), 7.52 (t, J = 7.9 Hz, 1H), 7.03 (d, J = 9.3 Hz, 1H), 6.62 (d, J = 3.1 Hz, 1H), 3.98 (s, 3H), 3.85-3.81 (m, 4H), 3.64-3.61 (m, 4H). MS (ESI) m/z: 430 [M + H]⁺. |
| V-b-41 | (structure) TFA salt | ¹H NMR (600 MHz, DMSO-d$_6$) δ 10.67 (s, 1H), 8.75 (s, 1H), 8.35 (s, 1H), 8.32 (d, J = 7.9 Hz, 1H), 8.11 (d, J = 7.9 Hz, 1H), 7.98 (dd, J = 16.1, 4.5 Hz, 2H), 7.81 (t, J = 7.8 Hz, 1H), 7.78 (d, J = 3.0 Hz, 1H), 7.53 (t, J = 8.0 Hz, 1H), 6.63 (d, J = 3.1 Hz, 1H), 3.99 (s, 3H), 3.85-3.83 (m, 4H), 3.62-3.58 (m, 4H). MS (ESI) m/z: 482 [M + H]⁺. |
| V-b-42 | (structure) TFA salt | ¹H NMR (600 MHz, DMSO-d$_6$) δ 10.55 (s, 1H), 8.78 (s, 1H), 8.68 (d, J = 1.9 Hz, 1H), 8.36 (dd, J = 9.3, 2.2 Hz, 1H), 8.03 (d, J = 7.8 Hz, 1H), 7.87 (dd, J = 8.1, 1.2 Hz, 1H), 7.84 (d, J = 3.0 Hz, 1H), 7.57 (t, J = 7.9 Hz, 1H), 7.05 (d, J = 9.3 Hz, 1H), 6.64 (d, J = 3.1 Hz, 1H), 4.10 (d, J = 12.5 Hz, 2H), 3.98 (s, 3H), 3.83-3.79 (m, 2H), 3.02-2.97 (m, 2H), 1.20 (d, J = 6.2 Hz, 6H). MS (ESI) m/z: 458 [M + H]⁺. |
| V-b-43 | (structure) TFA salt | ¹H NMR (600 MHz, DMSO-d$_6$) δ 10.71 (s, 1H), 8.83 (s, 1H), 8.35 (s, 1H), 8.31 (d, J = 7.8 Hz, 1H), 8.06 (d, J = 7.8 Hz, 1H), 7.98 (d, J = 7.7 Hz, 1H), 7.95-7.92 (m, 1H), 7.81 (t, J = 7.6 Hz, 2H), 7.56 (t, J = 7.9 Hz, 1H), 6.63 (d, J = 3.0 Hz, 1H), 4.03 (d, J = 12.5 Hz, 2H), 3.98 (s, 3H), 3.83 (dd, J = 8.5, 6.3 Hz, 2H), 2.95 (t, J = 11.6 Hz, 2H), 1.20 (d, J = 6.2 Hz, 6H). MS (ESI) m/z: 510 [M + H]⁺. |

| No. | Structure | ¹H NMR and/or MS data |
|---|---|---|
| V-b-44 | 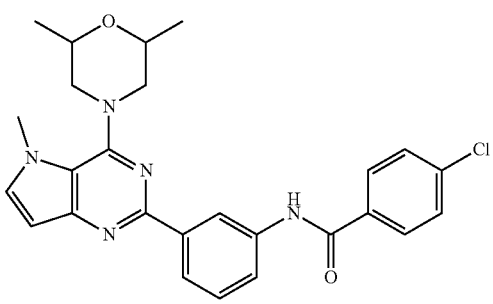 | ¹H NMR (600 MHz, DMSO-d₆) δ 10.60 (s, 1H), 8.86 (s, 1H), 8.03 (d, J = 8.2 Hz, 2H), 7.99 (d, J = 7.5 Hz, 1H), 7.91 (dd, J = 14.8, 6.0 Hz, 2H), 7.63 (d, J = 8.2 Hz, 2H), 7.59 (t, J = 7.8 Hz, 1H), 6.66 (s, 1H), 4.21 (d, J = 12.6 Hz, 2H), 3.98 (s, 3H), 3.79 (s, 2H), 3.07 (t, J = 11.6 Hz, 2H), 1.20 (d, J = 5.9 Hz, 6H). MS (ESI) m/z: 488 [M + H]⁺. |
| V-b-45 | 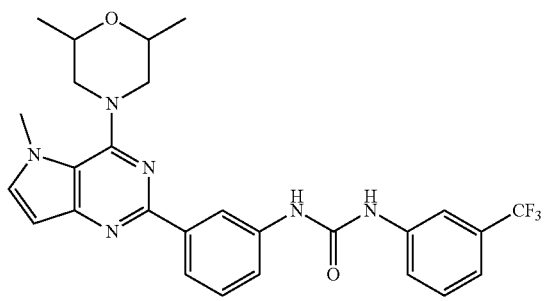<br>TFA salt | ¹H NMR (600 MHz, DMSO-d₆) δ 9.49 (s, 1H), 9.40 (s, 1H), 8.67 (s, 1H), 8.15 (s, 1H), 7.91 (d, J = 7.5 Hz, 1H), 7.82 (d, J = 2.8 Hz, 1H), 7.57-7.50 (m, 4H), 7.31 (d, J = 7.6 Hz, 1H), 6.64 (d, J = 3.1 Hz, 1H), 4.07 (s, 2H), 3.98 (s, 3H), 3.82 (s, 2H), 2.99 (t, J = 11.3 Hz, 2H), 1.20 (d, J = 6.2 Hz, 6H). MS (ESI) m/z: 525 [M + H]⁺. |
| V-c-1 | 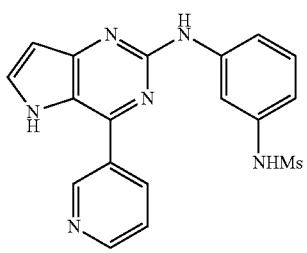 | ¹H NMR (600 MHz, DMSO-d₆) δ 11.93-11.74 (m, 1H), 9.69 (s, 1H), 9.41 (s, 1H), 9.29 (d, J = 2.3 Hz, 1H), 8.79 (dd, J = 4.8, 1.6 Hz, 1H), 8.51 (dt, J = 7.9, 2.0 Hz, 1H), 7.92 (t, J = 2.1 Hz, 1H), 7.82 (t, J = 3.0 Hz, 1H), 7.68 (dd, J = 7.9, 4.8 Hz, 1H), 7.54 (dd, J = 8.0, 2.0 Hz, 1H), 7.21 (t, J = 8.1 Hz, 1H), 6.76-6.71 (m, 1H), 6.47 (dd, J = 3.0, 1.7 Hz, 1H), 3.03 (s, 3H). MS (ESI) m/z: 381 [M + H]⁺. |
| V-c-2 | 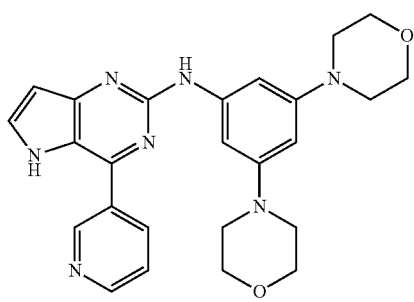 [SMILES: c1cncc(-c2nc(Nc3cc(N4CCOCC4)cc(N4CCOCC4)c3)nc3cc[nH]c23)c1] | ¹H NMR (600 MHz, DMSO-d₆) δ 11.82-11.65 (m, 1H), 9.29 (dd, J = 2.4, 0.8 Hz, 1H), 8.97 (s, 1H), 8.78 (dd, J = 4.8, 1.6 Hz, 1H), 8.47 (dt, J = 7.9, 2.0 Hz, 1H), 7.79 (t, J = 3.0 Hz, 1H), 7.65 (ddd, J = 7.9, 4.8, 0.9 Hz, 1H), 7.17 (d, J = 2.1 Hz, 2H), 6.45 (dd, J = 3.0, 1.7 Hz, 1H), 6.10 (t, J = 2.1 Hz, 1H), 3.79-3.71 (m, 8H), 3.14-3.05 (m, 6H). MS (ESI) m/z: 458 [M + H]⁺. |

| No. | Structure | ¹H NMR and/or MS data |
|---|---|---|
| V-c-3 | 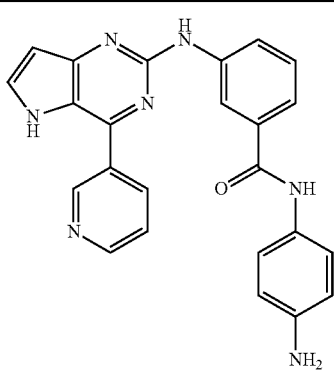 | ¹H NMR (600 MHz, DMSO-d₆) δ 11.85 (t, J = 2.4 Hz, 1H), 10.22 (s, 1H), 9.54 (s, 1H), 9.30 (d, J = 2.3 Hz, 1H), 8.77 (dd, J = 4.8, 1.7 Hz, 1H), 8.51 (dt, J = 7.9, 1.9 Hz, 1H), 8.47 (q, J = 1.4 Hz, 1H), 8.08 (dt, J = 6.5, 2.4 Hz, 1H), 7.82 (t, J = 3.0 Hz, 1H), 7.74-7.69 (m, 2H), 7.63 (dd, J = 8.3, 5.2 Hz, 1H), 7.45-7.39 (m, 2H), 7.05 (d, J = 8.6 Hz, 2H), 6.50 (dd, J = 3.0, 1.6 Hz, 1H). MS (ESI) m/z: 422 [M + H]⁺. |
| V-c-4 | 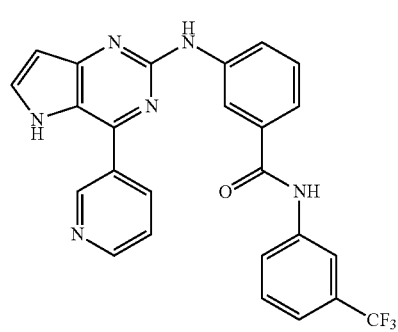 [SMILES: O=C(Nc1cccc(C(F)(F)F)c1)c1cccc(Nc2nc(-c3cccnc3)c3[nH]ccc3n2)c1] | ¹H NMR (600 MHz, DMSO-d₆) δ 11.83-11.76 (m, 1H), 10.56 (s, 1H), 9.53 (s, 1H), 9.30 (d, J = 2.4 Hz, 1H), 8.76 (dd, J = 4.8, 1.6 Hz, 1H), 8.53 (d, J = 1.9 Hz, 1H), 8.50 (dt, J = 8.0, 2.0 Hz, 1H), 8.28 (d, J = 1.9 Hz, 1H), 8.13-8.05 (m, 2H), 7.81 (t, J = 3.0 Hz, 1H), 7.65-7.58 (m, 2H), 7.50-7.43 (m, 3H), 6.50 (dd, J = 3.1, 1.7 Hz, 1H). MS (ESI) m/z: 475 [M + H]⁺. |
| V-c-5 | 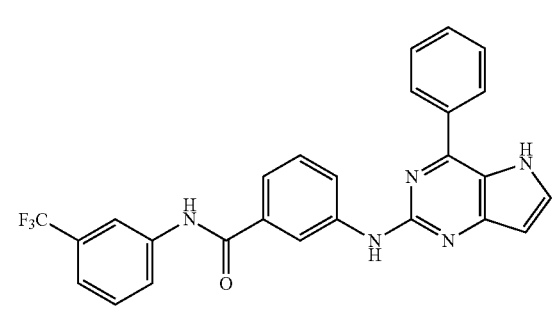 [SMILES: O=C(Nc1cccc(C(F)(F)F)c1)c1cccc(Nc2nc(-c3ccccc3)c3[nH]ccc3n2)c1] | ¹H NMR (600 MHz, DMSO-d₆) δ 11.65 (s, 1H), 10.59 (s, 1H), 9.48 (s, 1H), 8.61 (t, J = 2.0 Hz, 1H), 8.31 (s, 1H), 8.16 (dd, J = 6.6, 2.9 Hz, 2H), 8.12-8.06 (m, 2H), 7.76 (t, J = 2.6 Hz, 1H), 7.62 (t, J = 8.0 Hz, 1H), 7.60-7.52 (m, 5H), 7.50-7.41 (m, 1H), 6.48 (d, J = 2.9 Hz, 1H). MS (ESI) m/z: 474 [M + H]⁺. |
| V-c-6 | 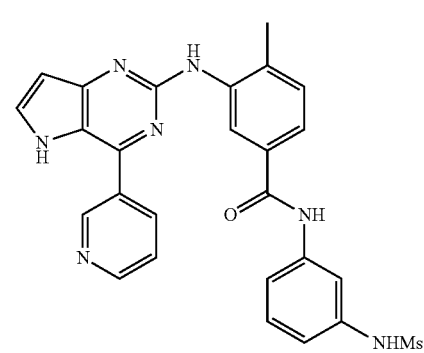 | ¹H NMR (600 MHz, DMSO-d₆) δ 11.74 (s, 1H), 10.25 (s, 1H), 9.79 (s, 1H), 9.25 (dd, J = 2.4, 0.8 Hz, 1H), 8.74 (dd, J = 4.8, 1.6 Hz, 1H), 8.49 (d, J = 1.9 Hz, 1H), 8.46 (dt, J = 7.9, 1.9 Hz, 1H), 8.40 (s, 1H), 7.79-7.76 (m, 2H), 7.60 (dd, J = 7.9, 1.9 Hz, 1H), 7.58 (ddd, J = 7.9, 4.8, 0.9 Hz, 1H), 7.53 (ddd, J = 8.2, 2.1, 0.9 Hz, 1H), 7.36 (d, J = 8.0 Hz, 1H), 7.29 (t, J = 8.1 Hz, 1H), 6.94 (ddd, J = 8.1, 2.3, 0.9 Hz, 1H), 6.41 (dd, J = 3.1, 1.7 Hz, 1H), 3.02 (s, 3H), 2.37 (s, 3H). MS (ESI) m/z: 514 [M + H]⁺. |

| No. | Structure | ¹H NMR and/or MS data |
|---|---|---|
| V-c-7 | 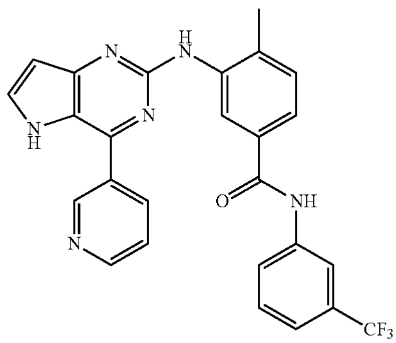 [SMILES: Cc1ccc(C(=O)Nc2cccc(C(F)(F)F)c2)cc1Nc1nc(-c2cccnc2)c2[nH]ccc2n1] | ¹H NMR (600 MHz, DMSO-d₆) δ 11.74 (s, 1H), 10.48 (s, 1H), 9.26 (dd, J = 2.3, 0.9 Hz, 1H), 8.74 (dd, J = 4.8, 1.6 Hz, 1H), 8.54 (d, J = 1.9 Hz, 1H), 8.46 (ddd, J = 7.9, 2.3, 1.7 Hz, 1H), 8.42 (s, 1H), 8.26 (d, J = 2.0 Hz, 1H), 8.10-8.06 (m, 1H), 7.78 (t, J = 3.0 Hz, 1H), 7.63 (dd, J = 7.9, 1.9 Hz, 1H), 7.60 (t, J = 8.0 Hz, 1H), 7.57 (ddd, J = 8.0, 4.8, 0.9 Hz, 1H), 7.47-7.43 (m, 1H), 7.38 (d, J = 7.9 Hz, 1H), 6.42 (dd, J = 3.0, 1.6 Hz, 1H), 2.38 (s, 3H). MS (ESI) m/z: 489 [M + H]⁺. |
| V-c-8 | 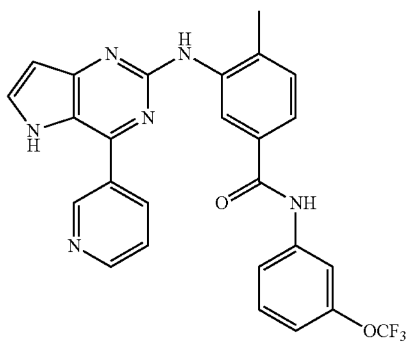 [SMILES: Cc1ccc(C(=O)Nc2cccc(OC(F)(F)F)c2)cc1Nc1nc(-c2cccnc2)c2[nH]ccc2n1] | ¹H NMR (600 MHz, DMSO-d₆) δ 11.72 (s, 1H), 10.42 (s, 1H), 9.25 (dd, J = 2.3, 0.9 Hz, 1H), 8.73 (dd, J = 4.8, 1.6 Hz, 1H), 8.52 (d, J = 1.9 Hz, 1H), 8.46 (dt, J = 8.0, 1.9 Hz, 1H), 8.38 (s, 1H), 7.95 (s, 1H), 7.80 (ddd, J = 8.2, 2.0, 0.9 Hz, 1H), 7.77 (t, J = 3.0 Hz, 1H), 7.61 (dd, J = 7.8, 1.9 Hz, 1H), 7.56 (ddd, J = 7.9, 4.8, 0.9 Hz, 1H), 7.48 (t, J = 8.2 Hz, 1H), 7.37 (d, J = 7.9 Hz, 1H), 7.10-7.06 (m, 1H), 6.41 (dd, J = 3.0, 1.6 Hz, 1H), 2.38 (s, 3H). MS (ESI) m/z: 505 [M + H]⁺. |
| V-c-9 | 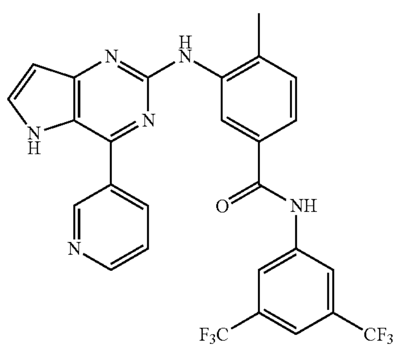 [SMILES: Cc1ccc(C(=O)Nc2cc(C(F)(F)F)cc(C(F)(F)F)c2)cc1Nc1nc(-c2cccnc2)c2[nH]ccc2n1] | ¹H NMR (600 MHz, DMSO-d₆) δ 11.74 (d, J = 2.6 Hz, 1H), 10.76 (s, 1H), 9.26 (dd, J = 2.3, 0.9 Hz, 1H), 8.73 (dd, J = 4.8, 1.6 Hz, 1H), 8.58 (d, J = 1.8 Hz, 1H), 8.56-8.54 (m, 2H), 8.46 (dt, J = 8.0, 1.9 Hz, 1H), 8.42 (s, 1H), 7.81 (s, 1H), 7.78 (t, J = 3.0 Hz, 1H), 7.65 (dd, J = 7.8, 1.9 Hz, 1H), 7.57 (ddd, J = 7.8, 4.9, 0.9 Hz, 1H), 7.41 (d, J = 7.9 Hz, 1H), 6.42 (dd, J = 3.1, 1.6 Hz, 1H), 2.39 (s, 3H). MS (ESI) m/z: 557 [M + H]⁺. |
| V-c-10 | 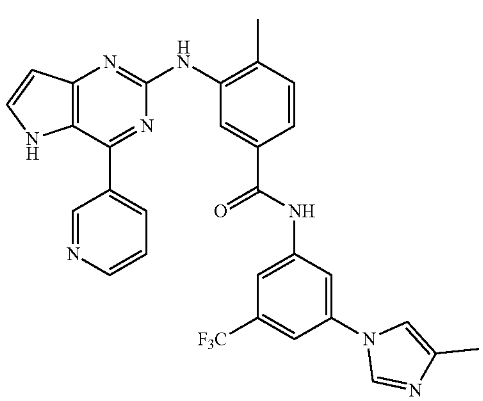 [SMILES: Cc1cn(-c2cc(NC(=O)c3ccc(C)c(Nc4nc(-c5cccnc5)c5[nH]ccc5n4)c3)cc(C(F)(F)F)c2)cn1] | ¹H NMR (600 MHz, DMSO-d₆) δ 11.76-11.71 (m, 1H), 10.61 (s, 1H), 9.27 (dd, J = 2.3, 0.8 Hz, 1H), 8.72 (dd, J = 4.8, 1.7 Hz, 1H), 8.59 (d, J = 1.9 Hz, 1H), 8.46 (dt, J = 7.9, 1.9 Hz, 1H), 8.42-8.39 (m, 1H), 8.32 (t, J = 2.0 Hz, 1H), 8.21 (d, J = 1.5 Hz, 1H), 8.20-8.16 (m, 1H), 7.77 (t, J = 3.0 Hz, 1H), 7.72 (s, 1H), 7.65 (dd, J = 7.8, 2.0 Hz, 1H), 7.57 (ddd, J = 7.9, 4.9, 0.9 Hz, 1H), 7.51-7.48 (m, 1H), 7.40 (d, J = 8.0 Hz, 1H), 6.42 (dd, J = 3.1, 1.6 Hz, 1H), 2.39 (s, 3H), 2.19 (s, 3H). MS (ESI) m/z: 569 [M + H]⁺. |

| No. | Structure | ¹H NMR and/or MS data |
|---|---|---|
| V-c-11 | 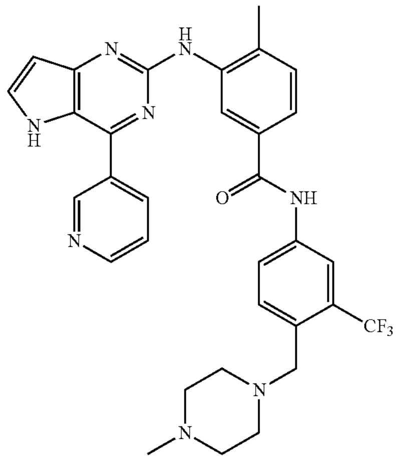 [SMILES: Cc1ccc(C(=O)Nc2ccc(CN3CCN(C)CC3)c(C(F)(F)F)c2)cc1Nc1nc(-c2cccnc2)c2[nH]ccc2n1] | ¹H NMR (600 MHz, DMSO-d₆) δ 11.73 (s, 1H), 10.42 (s, 1H), 9.26 (d, J = 2.2 Hz, 1H), 8.72 (dd, J = 4.8, 1.7 Hz, 1H), 8.53 (d, J = 1.8 Hz, 1H), 8.46 (dt, J = 7.9, 1.9 Hz, 1H), 8.38 (s, 1H), 8.21 (d, J = 2.2 Hz, 1H), 8.06 (dd, J = 8.6, 2.2 Hz, 1H), 7.77 (d, J = 3.1 Hz, 1H), 7.70 (d, J = 8.6 Hz, 1H), 7.62 (dd, J = 7.9, 1.9 Hz, 1H), 7.56 (ddd, J = 7.9, 4.8, 0.9 Hz, 1H), 7.37 (d, J = 7.9 Hz, 1H), 6.41 (d, J = 3.0 Hz, 1H), 3.57 (s, 2H), 2.45-2.30 (m, 8H), 2.37 (s, 3H), 2.16 (s, 3H). MS (ESI) m/z: 601 [M + H]⁺. |
| V-c-12 | 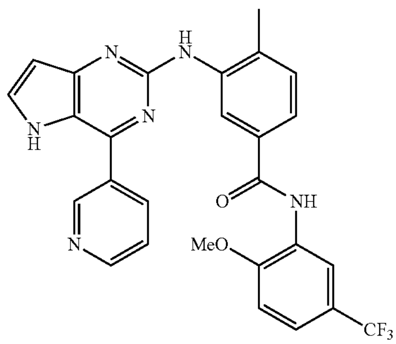 [SMILES: COc1ccc(C(F)(F)F)cc1NC(=O)c1ccc(C)c(Nc2nc(-c3cccnc3)c3[nH]ccc3n2)c1] | ¹H NMR (600 MHz, DMSO-d₆) δ 11.89-11.62 (m, 1H), 9.44 (s, 1H), 9.27 (d, J = 2.2 Hz, 1H), 8.74 (dd, J = 4.8, 1.6 Hz, 1H), 8.55 (d, J = 1.9 Hz, 1H), 8.46 (dt, J = 8.0, 2.0 Hz, 1H), 8.39 (s, 1H), 8.31 (d, J = 2.2 Hz, 1H), 7.78 (t, J = 3.1 Hz, 1H), 7.61-7.56 (m, 2H), 7.54 (dd, J = 8.7, 2.3 Hz, 1H), 7.37 (d, J = 7.9 Hz, 1H), 7.28 (d, J = 8.6 Hz, 1H), 6.43 (dd, J = 3.1, 1.6 Hz, 1H), 3.89 (s, 3H), 2.38 (s, 3H). MS (ESI) m/z: 519 [M + H]⁺. |
| V-c-13 | 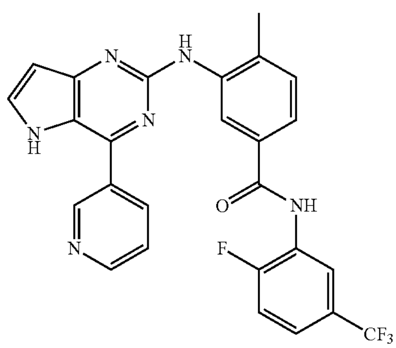 [SMILES: Cc1ccc(C(=O)Nc2cc(C(F)(F)F)ccc2F)cc1Nc1nc(-c2cccnc2)c2[nH]ccc2n1] | ¹H NMR (600 MHz, DMSO-d₆) δ 11.74 (t, J = 2.4 Hz, 1H), 10.26 (s, 1H), 9.27 (d, J = 2.2 Hz, 1H), 8.74 (dd, J = 4.8, 1.7 Hz, 1H), 8.59 (d, J = 1.9 Hz, 1H), 8.46 (dt, J = 8.0, 2.0 Hz, 1H), 8.41 (s, 1H), 8.11 (dd, J = 6.9, 2.4 Hz, 1H), 7.78 (t, J = 3.0 Hz, 1H), 7.68-7.62 (m, 2H), 7.60-7.54 (m, 2H), 7.38 (d, J = 7.9 Hz, 1H), 6.42 (dd, J = 3.1, 1.6 Hz, 1H), 2.39 (s, 3H); MS (ESI) m/z: 507 [M + H]⁺. |
| V-c-14 | 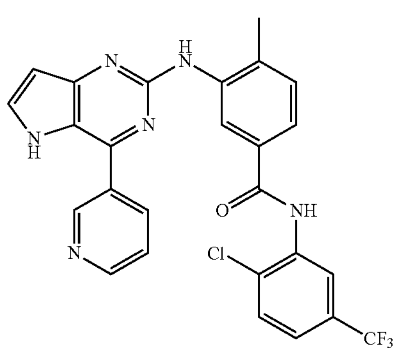 | ¹H NMR (600 MHz, DMSO-d₆) δ 12.06 (s, 1H), 10.13 (s, 1H), 9.26 (d, J = 2.3 Hz, 1H), 8.99-8.84 (m, 1H), 8.79 (dd, J = 4.9, 1.7 Hz, 1H), 8.53-8.44 (m, 2H), 8.07 (d, J = 2.2 Hz, 1H), 7.88 (t, J = 3.0 Hz, 1H), 7.82 (d, J = 8.4 Hz, 1H), 7.72 (d, J = 7.8 Hz, 1H), 7.68-7.64 (m, 2H), 7.44 (d, J = 7.9 Hz, 1H), 6.46 (dd, J = 3.0, 1.6 Hz, 1H), 2.39 (s, 3H). MS (ESI) m/z: 523 [M + H]⁺. |

| No. | Structure | ¹H NMR and/or MS data |
|---|---|---|
| V-c-15 | 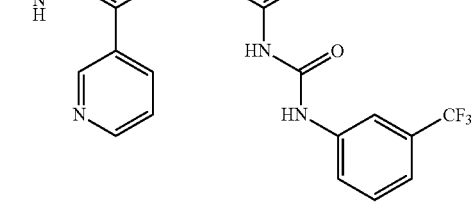 | ¹H NMR (600 MHz, DMSO-d$_6$) δ 11.69 (t, J = 2.3 Hz, 1H), 9.26 (d, J = 2.2 Hz, 1H), 8.97 (s, 1H), 8.73 (dd, J = 4.8, 1.6 Hz, 1H), 8.67 (s, 1H), 8.50 (dt, J = 7.9, 2.0 Hz, 1H), 8.09 (s, 1H), 8.06-8.02 (m, 2H), 7.75 (t, J = 3.1 Hz, 1H), 7.59 (dd, J = 7.9, 4.8 Hz, 1H), 7.57-7.54 (m, 1H), 7.51 (t, J = 7.9 Hz, 1H), 7.30 (d, J = 7.6 Hz, 1H), 7.15-7.06 (m, 2H), 6.40 (dd, J = 3.1, 1.7 Hz, 1H), 2.23 (s, 3H). MS (ESI) m/z: 504 [M + H]⁺. |
| V-c-16 | 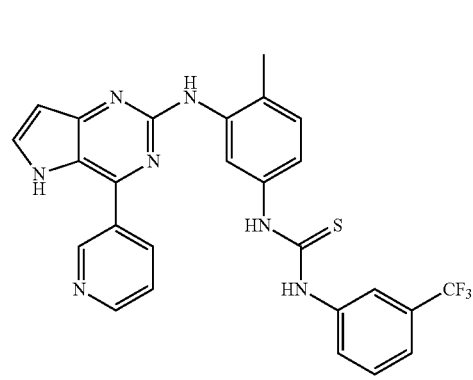 | ¹H NMR (600 MHz, DMSO-d$_6$) δ 11.70 (s, 1H), 10.01 (s, 1H), 9.87 (s, 1H), 9.27-9.22 (m, 1H), 8.75 (dt, J = 4.9, 1.4 Hz, 1H), 8.47-8.42 (m, 1H), 8.16 (s, 1H), 8.07 (d, J = 2.0 Hz, 1H), 7.99 (s, 1H), 7.78 (d, J = 8.1 Hz, 1H), 7.76-7.71 (m, 1H), 7.63-7.58 (m, 1H), 7.54 (t, J = 8.0 Hz, 1H), 7.44 (d, J = 7.6 Hz, 1H), 7.17 (d, J = 8.1 Hz, 1H), 7.06 (d, J = 8.1 Hz, 1H), 6.33-6.29 (m, 1H), 2.29 (s, 3H). MS (ESI) m/z: 520 [M + H]⁺. |
| V-c-17 | 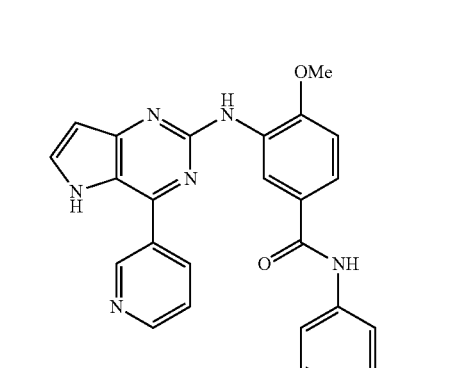 | ¹H NMR (600 MHz, DMSO-d$_6$) δ 11.87 (s, 1H), 10.48 (s, 1H), 9.33 (d, J = 2.2 Hz, 1H), 9.30 (d, J = 2.2 Hz, 1H), 8.76 (dd, J = 4.8, 1.6 Hz, 1H), 8.55 (dt, J = 7.9, 2.0 Hz, 1H), 8.31 (s, 1H), 8.12 (dd, J = 8.1, 2.0 Hz, 1H), 7.88 (s, 1H), 7.84 (t, J = 3.0 Hz, 1H), 7.65 (dd, J = 8.4, 2.2 Hz, 1H), 7.61 (t, J = 7.9 Hz, 1H), 7.56 (dd, J = 7.9, 4.8 Hz, 1H), 7.45 (d, J = 7.8 Hz, 1H), 7.18 (d, J = 8.4 Hz, 1H), 6.52 (dd, J = 3.0, 1.6 Hz, 1H), 4.01 (s, 3H). MS (ESI) m/z: 505 [M + H]⁺. |
| V-c-18 | 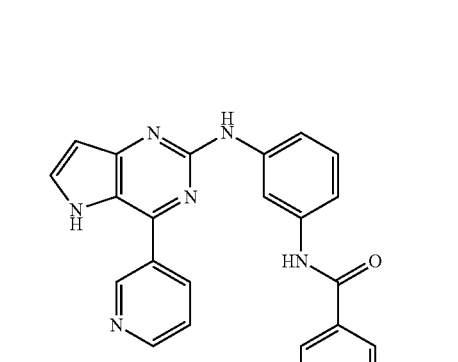 | ¹H NMR (600 MHz, DMSO-d$_6$) δ 11.79-11.73 (m, 1H), 10.46 (s, 1H), 9.35 (s, 1H), 9.31 (d, J = 2.2 Hz, 1H), 8.77 (dd, J = 4.8, 1.7 Hz, 1H), 8.53 (dt, J = 7.9, 2.0 Hz, 1H), 8.39-8.36 (m, 1H), 8.34 (s, 1H), 8.31 (d, J = 7.8 Hz, 1H), 7.99-7.96 (m, 1H), 7.82-7.78 (m, 2H), 7.68-7.65 (m, 1H), 7.63 (ddd, J = 7.9, 4.8, 0.8 Hz, 1H), 7.31-7.24 (m, 2H), 6.49 (dd, J = 3.1, 1.6 Hz, 1H). MS (ESI) m/z: 475 [M + H]⁺. |

| No. | Structure | ¹H NMR and/or MS data |
|---|---|---|
| V-c-19 | 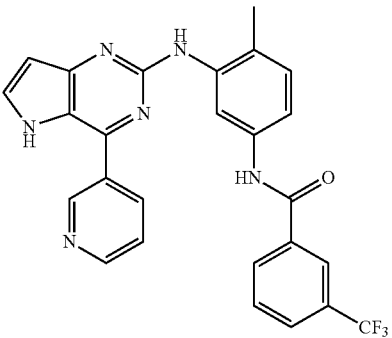 [SMILES: Cc1ccc(NC(=O)c2cccc(C(F)(F)F)c2)cc1Nc1nc(-c2cccnc2)c2[nH]ccc2n1] | ¹H NMR (600 MHz, DMSO-d$_6$) δ 11.68 (s, 1H), 10.41 (s, 1H), 9.30-9.25 (m, 1H), 8.74 (dd, J = 4.8, 1.7 Hz, 1H), 8.48 (dt, J = 8.0, 2.0 Hz, 1H), 8.31 (s, 1H), 8.30-8.27 (m, 2H), 8.21 (s, 1H), 7.97 (d, J = 7.8 Hz, 1H), 7.80 (t, J = 7.8 Hz, 1H), 7.75 (t, J = 3.0 Hz, 1H), 7.60 (ddd, J = 7.9, 4.9, 1.0 Hz, 1H), 7.41 (dd, J = 8.2, 2.2 Hz, 1H), 7.19 (d, J = 8.2 Hz, 1H), 6.40 (dd, J = 3.0, 1.7 Hz, 1H), 2.27 (s, 3H). MS (ESI) m/z: 489 [M + H]⁺. |
| V-c-20 | 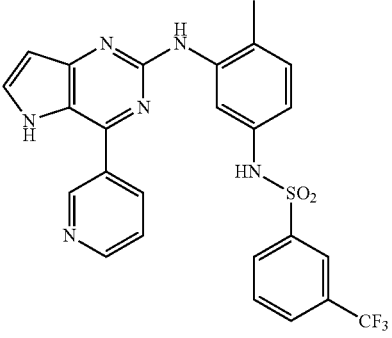 [SMILES: Cc1ccc(NS(=O)(=O)c2cccc(C(F)(F)F)c2)cc1Nc1nc(-c2cccnc2)c2[nH]ccc2n1] | ¹H NMR (600 MHz, DMSO-d$_6$) δ 11.75-11.70 (m, 1H), 10.32 (s, 1H), 9.26 (dd, J = 2.3, 0.9 Hz, 1H), 8.77 (dd, J = 4.8, 1.6 Hz, 1H), 8.44 (dt, J = 7.9, 2.0 Hz, 1H), 8.11-8.08 (m, 2H), 8.07 (s, 1H), 7.99-7.95 (m, 1H), 7.89 (d, J = 2.2 Hz, 1H), 7.79-7.74 (m, 2H), 7.62 (ddd, J = 7.9, 4.8, 0.9 Hz, 1H), 7.05-7.01 (m, 1H), 6.67 (dd, J = 8.2, 2.3 Hz, 1H), 6.39 (dd, J = 3.1, 1.7 Hz, 1H), 2.19 (s, 3H). MS (ESI) m/z: 525 [M + H]⁺. |
| V-c-21 | 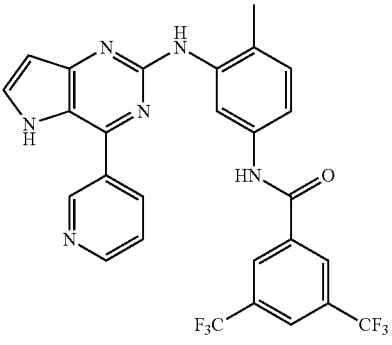 [SMILES: Cc1ccc(NC(=O)c2cc(C(F)(F)F)cc(C(F)(F)F)c2)cc1Nc1nc(-c2cccnc2)c2[nH]ccc2n1] | ¹H NMR (600 MHz, DMSO-d$_6$) δ 11.69 (s, 1H), 10.60 (s, 1H), 9.27 (dd, J = 2.3, 0.9 Hz, 1H), 8.74 (dd, J = 4.8, 1.6 Hz, 1H), 8.65-8.62 (m, 2H), 8.48 (ddd, J = 7.9, 2.4, 1.7 Hz, 1H), 8.37 (s, 1H), 8.32 (d, J = 2.2 Hz, 1H), 8.22-8.20 (m, 1H), 7.75 (t, J = 3.0 Hz, 1H), 7.60 (ddd, J = 7.9, 4.8, 0.9 Hz, 1H), 7.41 (dd, J = 8.1, 2.3 Hz, 1H), 7.21 (d, J = 8.2 Hz, 1H), 6.40 (dd, J = 3.1, 1.7 Hz, 1H), 2.28 (s, 3H). MS (ESI) m/z: 557 [M + H]⁺. |
| V-c-22 | 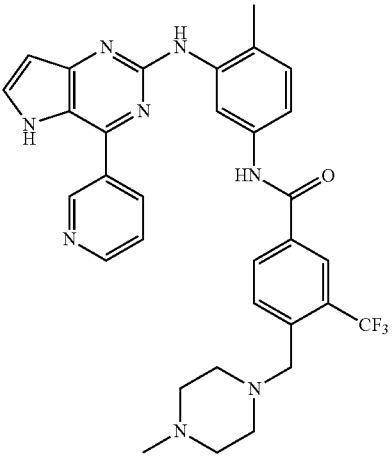 [SMILES: Cc1ccc(NC(=O)c2ccc(CN3CCN(C)CC3)c(C(F)(F)F)c2)cc1Nc1nc(-c2cccnc2)c2[nH]ccc2n1] | ¹H NMR (600 MHz, DMSO-d$_6$) δ 10.39 (s, 1H), 9.28 (dt, J = 2.2, 1.1 Hz, 1H), 8.73 (dd, J = 4.8, 1.7 Hz, 1H), 8.50 (dt, J = 7.9, 2.0 Hz, 1H), 8.30 (d, J = 2.2 Hz, 1H), 8.26 (d, J = 1.8 Hz, 1H), 8.24 (dd, J = 8.1, 1.9 Hz, 1H), 8.18 (d, J = 2.0 Hz, 1H), 7.92 (d, J = 8.1 Hz, 1H), 7.74 (d, J = 3.1 Hz, 1H), 7.59 (ddd, J = 7.9, 4.8, 0.9 Hz, 1H), 7.40 (dd, J = 8.1, 2.2 Hz, 1H), 7.21-7.15 (m, 1H), 6.39 (d, J = 3.0 Hz, 1H), 3.67 (s, 2H), 2.48-2.30 (m, 8H), 2.27 (s, 3H), 2.16 (s, 3H). MS (ESI) m/z: 601 [M + H]⁺. |

| No. | Structure | ¹H NMR and/or MS data |
|---|---|---|
| V-c-23 | 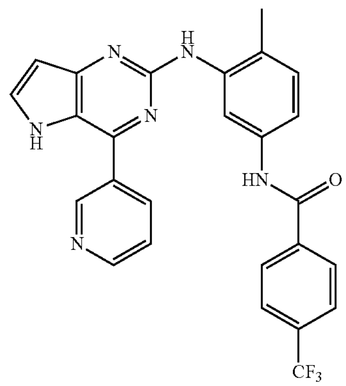 [SMILES: Cc1ccc(NC(=O)c2ccc(C(F)(F)F)cc2)cc1Nc1nc(-c2cccnc2)c2[nH]ccc2n1] | ¹H NMR (600 MHz, DMSO-d₆) δ 11.68 (d, J = 2.6 Hz, 1H), 10.40 (s, 1H), 9.26 (dd, J = 2.3, 0.9 Hz, 1H), 8.74 (dd, J = 4.8, 1.7 Hz, 1H), 8.48 (dt, J = 7.9, 1.9 Hz, 1H), 8.30 (d, J = 2.1 Hz, 1H), 8.20 (s, 1H), 8.16 (d, J = 8.1 Hz, 2H), 7.92 (d, J = 8.1 Hz, 2H), 7.75 (t, J = 3.0 Hz, 1H), 7.60 (ddd, J = 7.9, 4.8, 0.9 Hz, 1H), 7.40 (dd, J = 8.1, 2.2 Hz, 1H), 7.21-7.17 (m, 1H), 6.39 (dd, J = 3.1, 1.7 Hz, 1H), 2.27 (s, 3H). MS (ESI) m/z: 489 [M + H]⁺. |
| V-c-24 | 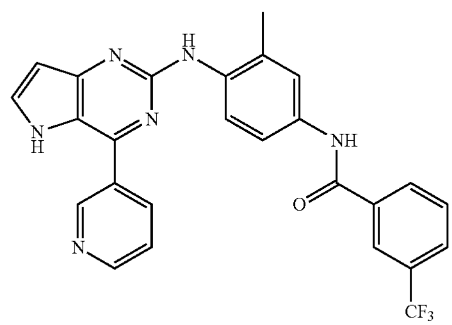 [SMILES: Cc1cc(NC(=O)c2cccc(C(F)(F)F)c2)ccc1Nc1nc(-c2cccnc2)c2[nH]ccc2n1] | ¹H NMR (600 MHz, DMSO-d₆) δ 11.69-11.63 (m, 1H), 10.37 (s, 1H), 9.24 (dd, J = 2.3, 0.9 Hz, 1H), 8.75 (dd, J = 4.8, 1.7 Hz, 1H), 8.42 (dt, J = 7.9, 1.9 Hz, 1H), 8.33 (s, 1H), 8.30 (d, J = 8.0 Hz, 1H), 8.20 (s, 1H), 7.99-7.95 (m, 1H), 7.81-7.77 (m, 2H), 7.74 (t, J = 3.0 Hz, 1H), 7.64-7.61 (m, 2H), 7.60 (dd, J = 8.6, 2.5 Hz, 1H), 6.39 (dd, J = 3.0, 1.7 Hz, 1H), 2.31 (s, 3H). MS (ESI) m/z: 489 [M + H]⁺. |
| V-c-25 | TFA salt | ¹H NMR (600 MHz, DMSO-d₆) δ 12.62 (s, 1H), 10.10 (s, 1H), 9.82 (s, 1H), 9.23 (d, J = 2.2 Hz, 1H), 8.87 (dd, J = 4.8, 1.6 Hz, 1H), 8.47 (dt, J = 8.0, 2.0 Hz, 1H), 7.99 (t, J = 3.0 Hz, 1H), 7.76 (d, J = 2.4 Hz, 1H), 7.74 (dd, J = 8.0, 4.9 Hz, 1H), 7.69-7.65 (m, 2H), 7.52 (d, J = 8.6 Hz, 1H), 7.25 (ddd, J = 8.5, 7.1, 1.5 Hz, 1H), 6.81 (dd, J = 8.4, 1.2 Hz, 1H), 6.68-6.64 (m, 1H), 6.50 (dd, J = 2.9, 1.6 Hz, 1H), 2.29 (s, 3H). MS (ESI) m/z: 436 [M + H]⁺. |
| V-c-26 | TFA salt | ¹H NMR (600 MHz, DMSO-d₆) δ 12.68 (s, 1H), 10.57 (s, 1H), 10.30 (s, 1H), 9.93 (s, 1H), 9.26-9.21 (m, 1H), 8.88 (dd, J = 5.0, 1.7 Hz, 1H), 8.48 (dt, J = 8.0, 1.9 Hz, 1H), 8.02 (t, J = 3.0 Hz, 1H), 7.92 (dd, J = 7.8, 1.5 Hz, 1H), 7.78-7.74 (m, 2H), 7.67 (dd, J = 8.6, 2.5 Hz, 1H), 7.63-7.57 (m, 3H), 7.32 (ddd, J = 8.3, 6.9, 1.7 Hz, 1H), 6.52 (dd, J = 2.9, 1.5 Hz, 1H), 3.16 (s, 3H), 2.31 (s, 3H). MS (ESI) m/z: 514 [M + H]⁺. |

-continued

| No. | Structure | ¹H NMR and/or MS data |
|---|---|---|
| V-c-27 | 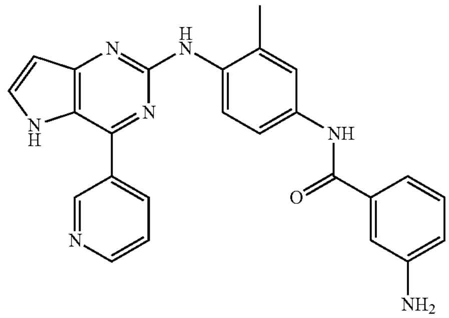 [SMILES: Cc1cc(NC(=O)c2cccc(N)c2)ccc1Nc1nc(-c2cccnc2)c2[nH]ccc2n1] | ¹H NMR (600 MHz, DMSO-d₆) δ 12.22 (s, 1H), 10.12 (s, 1H), 9.26-9.19 (m, 1H), 9.14 (s, 1H), 8.81 (dd, J = 4.8, 1.6 Hz, 1H), 8.47-8.39 (m, 1H), 7.88 (t, J = 3.0 Hz, 1H), 7.71 (d, J = 2.3 Hz, 1H), 7.69 (ddd, J = 7.9, 4.9, 0.8 Hz, 1H), 7.64 (dd, J = 8.5, 2.4 Hz, 1H), 7.59 (d, J = 8.6 Hz, 1H), 7.26-7.20 (m, 3H), 6.87 (dt, J = 7.4, 2.1 Hz, 1H), 6.44 (dd, J = 3.1, 1.4 Hz, 1H), 2.28 (s, 3H). MS (ESI) m/z: 437 [M + H]⁺. |
| V-c-28 | TFA salt | ¹H NMR (600 MHz, DMSO-d₆) δ 12.62 (s, 1H), 10.36 (s, 1H), 10.00 (s, 1H), 9.83 (s, 1H), 9.25-9.22 (m, 1H), 8.87 (dd, J = 4.9, 1.6 Hz, 1H), 8.47 (dt, J = 8.1, 1.9 Hz, 1H), 8.00 (t, J = 3.0 Hz, 1H), 7.80-7.76 (m, 2H), 7.76-7.70 (m, 3H), 7.55 (d, J = 8.6 Hz, 1H), 7.52 (t, J = 7.8 Hz, 1H), 7.44 (ddd, J = 8.1, 2.3, 1.0 Hz, 1H), 6.51 (dd, J = 3.0, 1.6 Hz, 1H), 3.07 (s, 3H), 2.30 (s, 3H). MS (ESI) m/z: 514 [M + H]⁺. |
| V-c-29 | TFA salt | ¹H NMR (600 MHz, DMSO-d₆) δ 12.65 (s, 1H), 10.33 (s, 1H), 10.19 (s, 1H), 9.89 (s, 1H), 9.24 (d, J = 2.2 Hz, 1H), 8.87 (dd, J = 4.9, 1.6 Hz, 1H), 8.47 (dt, J = 8.0, 1.9 Hz, 1H), 8.15 (t, J = 2.0 Hz, 1H), 8.00 (t, J = 3.0 Hz, 1H), 7.83-7.81 (m, 1H), 7.80 (d, J = 2.4 Hz, 1H), 7.76-7.71 (m, 2H), 7.65 (dt, J = 7.8, 1.3 Hz, 1H), 7.54 (d, J = 8.5 Hz, 1H), 7.47 (t, J = 7.9 Hz, 1H), 6.51 (dd, J = 2.9, 1.5 Hz, 1H), 2.30 (s, 3H), 2.09 (s, 3H). MS (ESI) m/z: 478 [M + H]+. |
| V-c-30 | 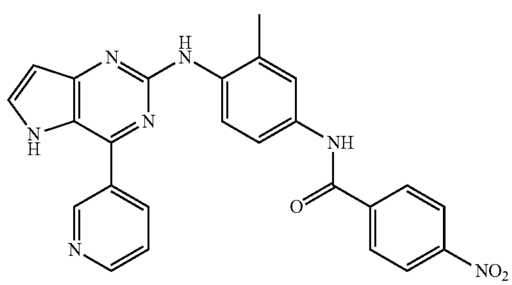 | ¹H NMR (600 MHz, DMSO-d₆) δ 11.67 (s, 1H), 10.47 (s, 1H), 9.23 (d, J = 2.2 Hz, 1H), 8.76 (dd, J = 4.8, 1.6 Hz, 1H), 8.43-8.36 (m, 3H), 8.25-8.18 (m, 3H), 7.77 (d, J = 8.6 Hz, 1H), 7.74 (t, J = 3.0 Hz, 1H), 7.65-7.62 (m, 2H), 7.58 (d, J = 8.6 Hz, 1H), 6.39 (t, J = 2.3 Hz, 1H), 2.30 (s, 3H). MS (ESI) m/z: 466 [M + H]⁺. |
| V-c-31 | 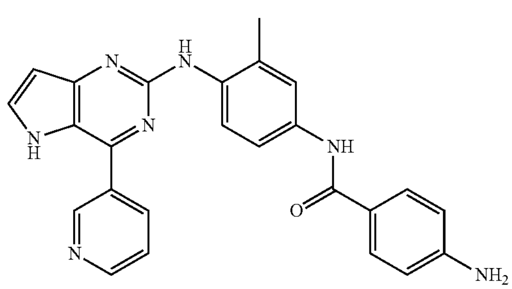 | ¹H NMR (600 MHz, DMSO-d₆) δ 11.67 (s, 1H), 9.67 (s, 1H), 9.24-9.21 (m, 1H), 8.75 (dd, J = 4.8, 1.7 Hz, 1H), 8.41 (dt, J = 7.9, 2.0 Hz, 1H), 8.19 (s, 1H), 7.76-7.72 (m, 3H), 7.65-7.60 (m, 3H), 7.54 (dd, J = 8.7, 2.5 Hz, 1H), 6.64-6.60 (m, 2H), 6.38 (dd, J = 3.1, 1.6 Hz, 1H), 5.76 (br. s, 2H), 2.27 (s, 3H). MS (ESI) m/z: 436 [M + H]⁺. |

| No. | Structure | ¹H NMR and/or MS data |
|---|---|---|
| V-c-32 | (TFA salt) | ¹H NMR (600 MHz, DMSO-$d_6$) δ 12.53 (s, 1H), 10.22 (s, 1H), 10.21 (s, 1H), 9.70 (s, 1H), 9.23 (d, J = 2.5 Hz, 1H), 8.86 (dd, J = 4.8, 1.6 Hz, 1H), 8.45 (dt, J = 8.0, 1.9 Hz, 1H), 8.01-7.95 (m, 3H), 7.78 (d, J = 2.4 Hz, 1H), 7.75-7.69 (m, 2H), 7.54 (d, J = 8.6 Hz, 1H), 7.36-7.31 (m, 2H), 6.49 (dd, J = 2.9, 1.6 Hz, 1H), 3.11 (s, 3H), 2.29 (s, 3H). MS (ESI) m/z: 514 [M + H]⁺. |
| V-c-33 | (TFA salt) | ¹H NMR (600 MHz, DMSO-$d_6$) δ 12.51 (s, 1H), 10.25 (s, 1H), 10.17 (s, 1H), 9.66 (s, 1H), 9.23 (d, J = 2.3 Hz, 1H), 8.86 (dd, J = 5.0, 1.6 Hz, 1H), 8.45 (dt, J = 7.9, 2.0 Hz, 1H), 7.98-7.94 (m, 3H), 7.78 (d, J = 2.4 Hz, 1H), 7.75-7.69 (m, 4H), 7.53 (d, J = 8.5 Hz, 1H), 6.49 (dd, J = 3.0, 1.7 Hz, 1H), 2.29 (s, 3H), 2.10 (s, 3H). MS (ESI) m/z: 478 [M + H]⁺. MS (ESI) m/z: 478 [M + H]⁺. |
| V-c-34 | 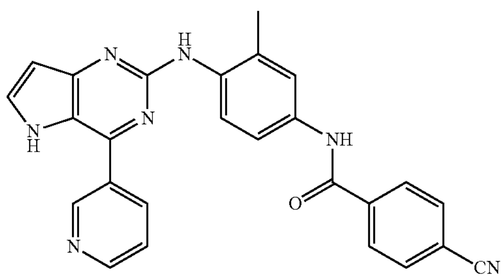 [SMILES: Cc1cc(NC(=O)c2ccc(C#N)cc2)ccc1Nc1nc(-c2cccnc2)c2[nH]ccc2n1] | ¹H NMR (600 MHz, DMSO-$d_6$) δ 11.66 (t, J = 2.3 Hz, 1H), 10.38 (s, 1H), 9.24-9.21 (m, 1H), 8.75 (dd, J = 4.8, 1.6 Hz, 1H), 8.41 (dt, J = 7.9, 2.0 Hz, 1H), 8.19 (s, 1H), 8.15-8.11 (m, 2H), 8.06-8.01 (m, 2H), 7.77 (d, J = 8.6 Hz, 1H), 7.74 (t, J = 3.0 Hz, 1H), 7.65-7.62 (m, 2H), 7.57 (dd, J = 8.6, 2.5 Hz, 1H), 6.39 (dd, J = 3.1, 1.7 Hz, 1H), 2.30 (s, 3H). MS (ESI) m/z: 446 [M + H]⁺. |
| V-c-35 | (TFA salt) | ¹H NMR (600 MHz, DMSO-$d_6$) δ 12.49 (s, 1H), 10.36 (s, 1H), 9.48 (s, 1H), 9.18 (d, J = 2.2 Hz, 1H), 8.88-8.81 (m, 1H), 8.41 (dt, J = 8.1, 2.0 Hz, 1H), 7.96 (t, J = 3.1 Hz, 1H), 7.86-7.80 (m, 2H), 7.72 (dd, J = 8.0, 5.0 Hz, 1H), 7.66-7.61 (m, 1H), 7.61-7.57 (m, 2H), 7.45 (d, J = 8.5 Hz, 1H), 7.05 (d, J = 2.4 Hz, 1H), 7.01 (dd, J = 8.6, 2.5 Hz, 1H), 6.46 (dd, J = 2.9, 1.6 Hz, 1H), 2.17 (s, 3H). MS (ESI) m/z: 457 [M + H]⁺. |
| V-c-36 | 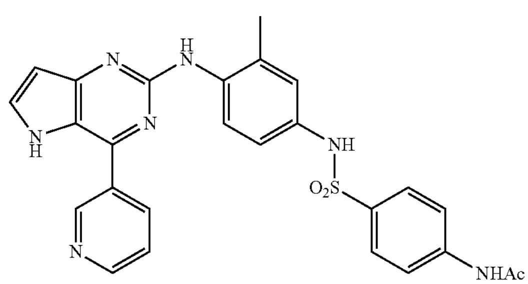 [SMILES: CC(=O)Nc1ccc(S(=O)(=O)Nc2ccc(Nc3nc(-c4cccnc4)c4[nH]ccc4n3)c(C)c2)cc1] | ¹H NMR (600 MHz, DMSO-$d_6$) δ 12.56 (s, 1H), 10.35 (s, 1H), 10.24 (s, 1H), 9.59 (s, 1H), 9.19 (dd, J = 2.3, 0.8 Hz, 1H), 8.85 (dd, J = 4.9, 1.6 Hz, 1H), 8.42 (dt, J = 8.0, 1.9 Hz, 1H), 7.97 (t, J = 3.0 Hz, 1H), 7.77-7.70 (m, 5H), 7.45 (d, J = 8.5 Hz, 1H), 7.05 (d, J = 2.5 Hz, 1H), 7.01 (dd, J = 8.5, 2.6 Hz, 1H), 6.48 (dd, J = 2.9, 1.5 Hz, 1H), 2.18 (s, 3H), 2.07 (s, 3H). MS (ESI) m/z: 514 [M + H]⁺. |

| No. | Structure | ¹H NMR and/or MS data |
|---|---|---|
| V-c-37 | 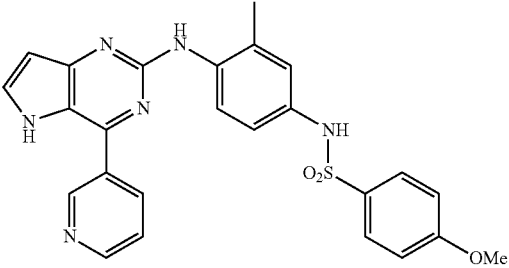 [SMILES: COc1ccc(S(=O)(=O)Nc2ccc(Nc3nc(-c4cccnc4)c4[nH]ccc4n3)c(C)c2)cc1] | ¹H NMR (600 MHz, DMSO-d$_6$) δ 12.65 (s, 1H), 10.33 (s, 1H), 10.19 (s, 1H), 9.89 (s, 1H), 9.24 (d, J = 2.2 Hz, 1H), 8.87 (dd, J = 4.9, 1.6 Hz, 1H), 8.47 (dt, J = 8.0, 1.9 Hz, 1H), 8.15 (t, J = 2.0 Hz, 1H), 8.00 (t, J = 3.0 Hz, 1H), 7.83-7.81 (m, 1H), 7.80 (d, J = 2.4 Hz, 1H), 7.76-7.71 (m, 2H), 7.65 (dt, J = 7.8, 1.3 Hz, 1H), 7.54 (d, J = 8.5 Hz, 1H), 7.47 (t, J = 7.9 Hz, 1H), 6.51 (dd, J = 2.9, 1.5 Hz, 1H), 2.30 (s, 3H), 2.09 (s, 3H). MS (ESI) m/z: 487 [M + H]⁺. |
| V-c-38 | 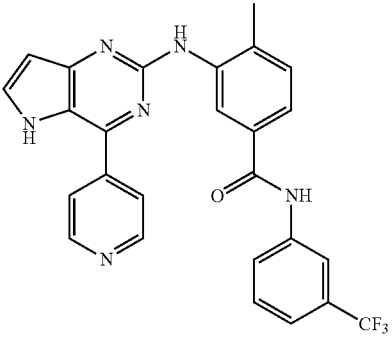 | ¹H NMR (600 MHz, DMSO-d$_6$) δ 11.73 (s, 1H), 10.50 (s, 1H), 8.78-8.73 (m, 2H), 8.57 (d, J = 1.9 Hz, 1H), 8.46 (s, 1H), 8.27 (d, J = 2.2 Hz, 1H), 8.11-8.07 (m, 1H), 8.07-8.04 (m, 2H), 7.82 (t, J = 3.0 Hz, 1H), 7.65-7.59 (m, 2H), 7.49-7.44 (m, 1H), 7.39 (d, J = 7.9 Hz, 1H), 6.44 (dd, J = 3.0, 1.7 Hz, 1H), 2.38 (s, 3H). MS (ESI) m/z: 489 [M + H]⁺. MS (ESI) m/z: 489 [M + H]⁺. |
| V-c-39 | 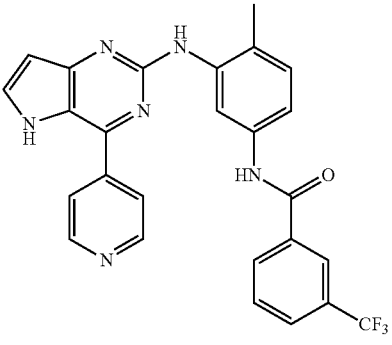 [SMILES: Cc1ccc(NC(=O)c2cccc(C(F)(F)F)c2)cc1Nc1nc(-c2ccncc2)c2[nH]ccc2n1] | ¹H NMR (600 MHz, DMSO-d$_6$) δ 11.72-11.69 (m, 1H), 10.44 (s, 1H), 8.82-8.75 (m, 2H), 8.36-8.24 (m, 4H), 8.10-8.05 (m, 2H), 7.97 (d, J = 7.4 Hz, 1H), 7.84-7.75 (m, 2H), 7.41 (dd, J = 8.1, 2.2 Hz, 1H), 7.20 (d, J = 8.3 Hz, 1H), 6.42 (dd, J = 3.1, 1.7 Hz, 1H), 2.27 (s, 3H). MS (ESI) m/z: 489 [M + H]⁺. |
| V-c-40 | 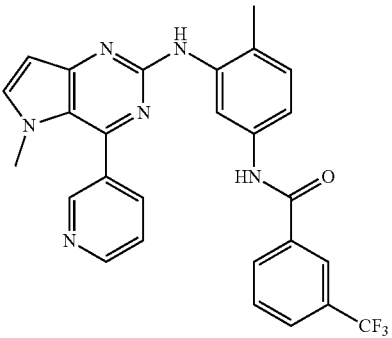 [SMILES: Cc1ccc(NC(=O)c2cccc(C(F)(F)F)c2)cc1Nc1nc(-c2cccnc2)c2c(ccn2C)n1] | ¹H NMR (600 MHz, DMSO-d$_6$) δ 10.39 (s, 1H), 8.89 (dd, J = 2.3, 0.9 Hz, 1H), 8.73 (dd, J = 4.8, 1.6 Hz, 1H), 8.32-8.26 (m, 3H), 8.19 (d, J = 2.2 Hz, 1H), 8.14 (dt, J = 7.8, 1.9 Hz, 1H), 7.99-7.95 (m, 1H), 7.79 (t, J = 7.8 Hz, 1H), 7.68 (d, J = 3.1 Hz, 1H), 7.56 (ddd, J = 7.8, 4.8, 0.9 Hz, 1H), 7.40 (dd, J = 8.1, 2.2 Hz, 1H), 7.18 (d, J = 8.3 Hz, 1H), 6.35 (d, J = 3.1 Hz, 1H), 3.42 (s, 3H), 2.24 (s, 3H). MS (ESI) m/z: 503 [M + H]⁺. |

| No. | Structure | ¹H NMR and/or MS data |
|---|---|---|
| V-c-41 | 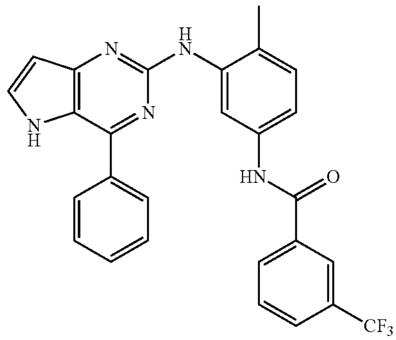 | ¹H NMR (600 MHz, DMSO-d₆) δ 11.52 (s, 1H), 10.42 (s, 1H), 8.34-8.31 (m, 2H), 8.29 (d, J = 7.9 Hz, 1H), 8.14-8.08 (m, 3H), 7.96 (dt, J = 7.8, 1.2 Hz, 1H), 7.79 (t, J = 7.8 Hz, 1H), 7.70 (d, J = 3.1 Hz, 1H), 7.59-7.53 (m, 3H), 7.40 (dd, J = 8.2, 2.1 Hz, 1H), 7.21-7.17 (m, 1H), 6.38 (d, J = 3.0 Hz, 1H), 2.28 (s, 3H). MS (ESI) m/z: 488 [M + H]⁺. |
| V-c-42 | 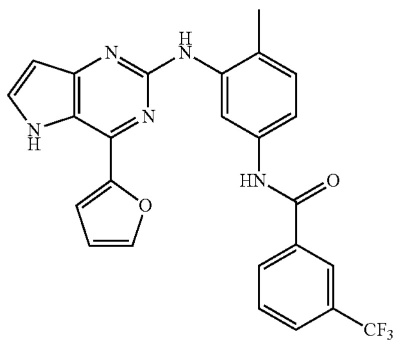 | ¹H NMR (600 MHz, DMSO-d₆) δ 11.45 (s, 1H), 10.43 (s, 1H), 8.34-8.30 (m, 2H), 8.28 (d, J = 7.9 Hz, 1H), 8.04 (s, 1H), 8.01 (d, J = 1.6 Hz, 1H), 7.96 (d, J = 7.8 Hz, 1H), 7.78 (t, J = 7.8 Hz, 1H), 7.69 (d, J = 3.0 Hz, 1H), 7.47 (d, J = 3.4 Hz, 1H), 7.40 (dd, J = 8.2, 2.2 Hz, 1H), 7.18 (d, J = 8.2 Hz, 1H), 6.78 (dd, J = 3.5, 1.8 Hz, 1H), 6.33 (d, J = 3.0 Hz, 1H), 2.27 (s, 3H). MS (ESI) m/z: 478 [M + H]⁺. |
| V-c-43 | 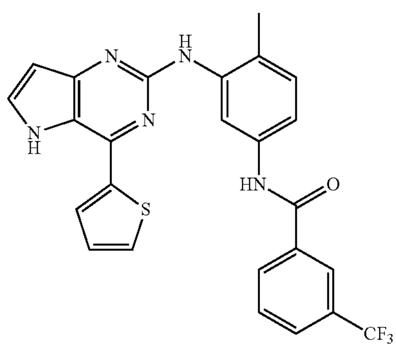 | ¹H NMR (600 MHz, DMSO-d₆) δ 12.23 (s, 1H), 10.52 (s, 1H), 9.32 (s, 1H), 8.30 (s, 1H), 8.28 (d, J = 7.9 Hz, 1H), 8.17 (d, J = 2.2 Hz, 1H), 8.15-8.11 (m, 2H), 7.97 (d, J = 7.8 Hz, 1H), 7.90 (t, J = 3.1 Hz, 1H), 7.80 (t, J = 7.8 Hz, 1H), 7.68 (s, 1H), 7.67 (s, 1H), 7.54 (dd, J = 8.3, 2.2 Hz, 1H), 7.30 (d, J = 8.2 Hz, 1H), 6.47 (t, J = 2.2 Hz, 1H), 2.26 (a, 3H). MS (ESI) m/z: 494 [M + H]⁺. |
| V-c-44 | 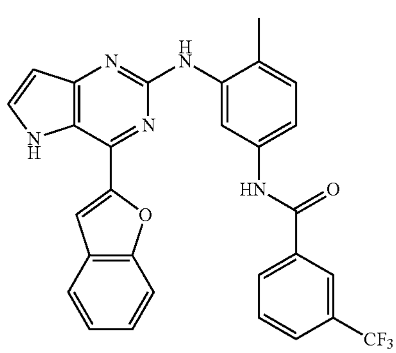 | ¹H NMR (600 MHz, DMSO-d₆) δ 11.66 (s, 1H), 10.45 (s, 1H), 8.43 (d, J = 2.1 Hz, 1H), 8.35 (s, 1H), 8.32 (d, J = 7.9 Hz, 1H), 8.15 (d, J = 4.6 Hz, 1H), 7.97 (d, J = 7.9 Hz, 1H), 7.95 (s, 1H), 7.83 (d, J = 3.0 Hz, 1H), 7.82-7.75 (m, 3H), 7.48 (t, J = 7.9 Hz, 1H), 7.41-7.34 (m, 2H), 7.20 (d, J = 8.2 Hz, 1H), 6.40 (d, J = 3.0 Hz, 1H), 2.30 (s, 3H). MS (ESI) m/z: 528 [M + H]⁺. |

| No. | Structure | ¹H NMR and/or MS data |
|---|---|---|
| V-c-45 | 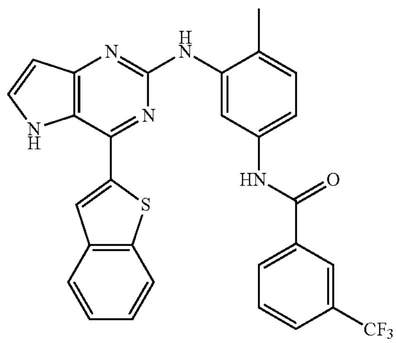 [SMILES: Cc1ccc(NC(=O)c2cccc(C(F)(F)F)c2)cc1Nc1nc(-c2cc3ccccc3s2)c2[nH]ccc2n1] | ¹H NMR (600 MHz, DMSO-d$_6$) δ 11.74 (s, 1H), 10.44 (s, 1H), 8.55 (s, 1H), 8.31 (d, J = 1.9 Hz, 1H), 8.28 (d, J = 7.8 Hz, 1H), 8.22 (s, 1H), 8.18 (d, J = 2.2 Hz, 1H), 7.99-7.93 (m, 2H), 7.92-7.88 (m, 1H), 7.82 (d, J = 3.1 Hz, 1H), 7.78 (t, J = 7.8 Hz, 1H), 7.48-7.40 (m, 3H), 7.22 (d, J = 8.3 Hz, 1H), 6.41 (d, J = 3.1 Hz, 1H), 2.28 (s, 3H). MS (ESI) m/z: 544 [M + H]⁺. |
| V-c-46 | 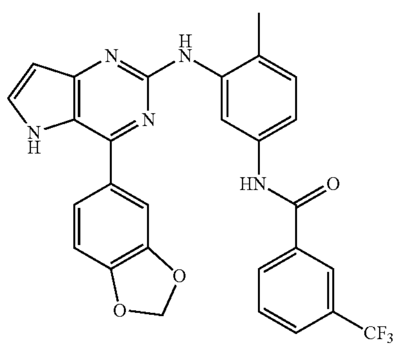 [SMILES: Cc1ccc(NC(=O)c2cccc(C(F)(F)F)c2)cc1Nc1nc(-c2ccc3c(c2)OCO3)c2[nH]ccc2n1] | ¹H NMR (600 MHz, DMSO-d$_6$) δ 11.51 (s, 1H), 10.42 (s, 1H), 8.40 (d, J = 2.1 Hz, 1H), 8.33 (d, J = 2.1 Hz, 1H), 8.29 (d, J = 7.8 Hz, 1H), 8.04 (s, 1H), 7.96 (d, J = 7.8 Hz, 1H), 7.79 (t, J = 7.8 Hz, 1H), 7.71 (d, J = 1.7 Hz, 1H), 7.70-7.67 (m, 2H), 7.38 (dd, J = 8.2, 2.2 Hz, 1H), 7.18 (d, J = 8.2 Hz, 1H), 7.09 (d, J = 8.0 Hz, 1H), 6.36 (d, J = 3.0 Hz, 1H), 6.12 (s, 2H), 2.28 (s, 3H). MS (ESI) m/z: 532 [M + H]⁺. |
| V-c-47 | TFA salt | ¹H NMR (600 MHz, DMSO-d$_6$) δ 12.23 (s, 1H), 10.52 (s, 1H), 9.32 (s, 1H), 8.30 (s, 1H), 8.28 (d, J = 7.9 Hz, 1H), 8.17 (d, J = 2.2 Hz, 1H), 8.13 (d, J = 8.3 Hz, 2H), 7.97 (d, J = 7.8 Hz, 1H), 7.90 (t, J = 3.1 Hz, 1H), 7.80 (t, J = 7.8 Hz, 1H), 7.67 (d, J = 8.4 Hz, 2H), 7.54 (dd, J = 8.3, 2.2 Hz, 1H), 7.30 (d, J = 8.2 Hz, 1H), 6.47 (t, J = 2.2 Hz, 1H), 2.26 (s, 3H). MS (ESI) m/z: 522 [M + H]⁺. |
| V-c-48 | 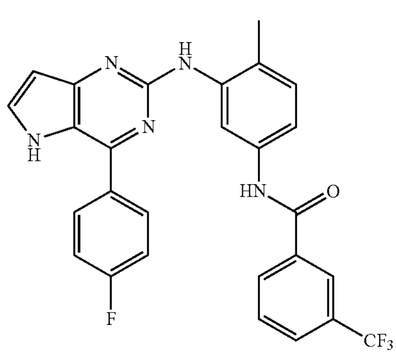 [SMILES: Cc1ccc(NC(=O)c2cccc(C(F)(F)F)c2)cc1Nc1nc(-c2ccc(F)cc2)c2[nH]ccc2n1] | ¹H NMR (600 MHz, DMSO-d$_6$) δ 11.58 (s, 1H), 10.43 (s, 1H), 8.33-8.30 (m, 2H), 8.28 (d, J = 7.9 Hz, 1H), 8.22-8.17 (m, 2H), 8.11 (s, 1H), 7.96 (dt, J = 7.9, 1.2 Hz, 1H), 7.79 (t, J = 7.8 Hz, 1H), 7.71 (d, J = 3.1 Hz, 1H), 7.43-7.35 (m, 3H), 7.19 (d, J = 8.3 Hz, 1H), 6.38 (d, J = 3.1 Hz, 1H), 2.27 (s, 3H). MS (ESI) m/z: 506 [M + H]⁺. |

| No. | Structure | ¹H NMR and/or MS data |
|---|---|---|
| V-c-49 | 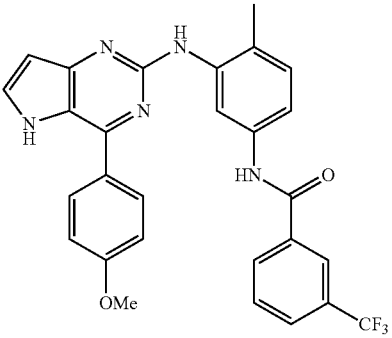 [SMILES: COc1ccc(-c2nc(Nc3cc(NC(=O)c4cccc(C(F)(F)F)c4)ccc3C)nc3cc[nH]c23)cc1] | ¹H NMR (600 MHz, DMSO-$d_6$) δ 10.43 (s, 1H), 8.35 (d, J = 2.2 Hz, 1H), 8.32 (d, J = 1.8 Hz, 1H), 8.30-8.28 (m, 1H), 8.15-8.11 (m, 2H), 8.02 (s, 1H), 7.96 (ddd, J = 8.6, 1.8, 0.9 Hz, 1H), 7.79 (t, J = 7.8 Hz, 1H), 7.67 (d, J = 3.0 Hz, 1H), 7.39 (dd, J = 8.1, 2.2 Hz, 1H), 7.18 (dd, J = 8.1, 0.8 Hz, 1H), 7.12-7.08 (m, 2H), 6.36 (d, J = 3.1 Hz, 1H), 3.84 (s, 3H), 2.28 (s, 3H). MS (ESI) m/z: 518 [M + H]⁺. |
| V-c-50 | 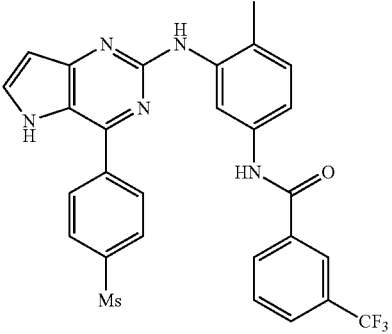 [SMILES: Cc1ccc(NC(=O)c2cccc(C(F)(F)F)c2)cc1Nc1nc(-c2ccc(S(C)(=O)=O)cc2)c2[nH]ccc2n1] | ¹H NMR (600 MHz, DMSO-$d_6$) δ 11.64 (br. s, 1H), 10.42 (s, 1H), 8.38-8.33 (m, 2H), 8.31 (d, J = 2.3 Hz, 1H), 8.30 (d, J = 2.2 Hz, 1H), 8.29-8.27 (m, 1H), 8.22 (s, 1H), 8.13-8.09 (m, 2H), 7.96 (dt, J = 7.8, 1.2 Hz, 1H), 7.80 (d, J = 7.9 Hz, 1H), 7.77 (d, J = 3.1 Hz, 1H), 7.40 (dd, J = 8.1, 2.3 Hz, 1H), 7.20 (d, J = 8.3 Hz, 1H), 6.41 (d, J = 3.1 Hz, 1H), 3.30 (s, 3H), 2.27 (s, 3H). MS (ESI) m/z: 566 [M + H]⁺. |
| V-c-51 | 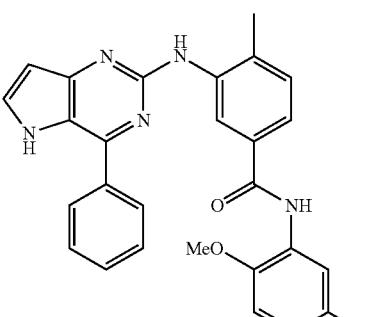 | ¹H NMR (600 MHz, DMSO-$d_6$) δ 11.60 (s, 1H), 9.43 (s, 1H), 8.63 (d, J = 1.8 Hz, 1H), 8.33 (d, J = 2.3 Hz, 1H), 8.27 (s, 1H), 8.14-8.09 (m, 2H), 7.73 (d, J = 3.0 Hz, 1H), 7.60-7.51 (m, 5H), 7.36 (d, J = 7.9 Hz, 1H), 7.28 (d, J = 8.6 Hz, 1H), 6.41 (d, J = 3.1 Hz, 1H), 3.88 (s, 3H), 2.39 (s, 3H). MS (ESI) m/z: 518 [M + H]⁺. |
| V-c-52 | 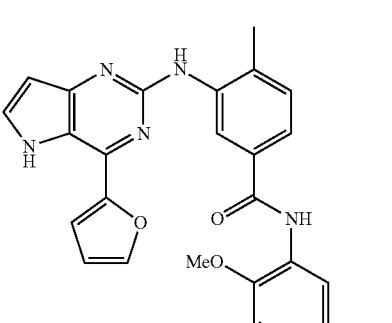 | ¹H NMR (600 MHz, DMSO-$d_6$) δ 11.53 (t, J = 2.4 Hz, 1H), 9.42 (s, 1H), 8.66 (d, J = 1.8 Hz, 1H), 8.34 (d, J = 2.4 Hz, 1H), 8.24 (s, 1H), 8.00 (d, J = 1.7 Hz, 1H), 7.73 (t, J = 3.0 Hz, 1H), 7.58 (dd, J = 7.8, 1.9 Hz, 1H), 7.52 (dd, J = 8.7, 2.3 Hz, 1H), 7.43-7.42 (m, 1H), 7.35 (d, J = 7.9 Hz, 1H), 7.27 (d, J = 8.6 Hz, 1H), 6.78 (dd, J = 3.5, 1.7 Hz, 1H), 6.37 (dd, J = 3.1, 1.7 Hz, 1H), 3.89 (s, 3H), 2.38 (s, 3H). MS (ESI) m/z: 508 [M + H]⁺. |

| No. | Structure | ¹H NMR and/or MS data |
|---|---|---|
| V-c-53 | 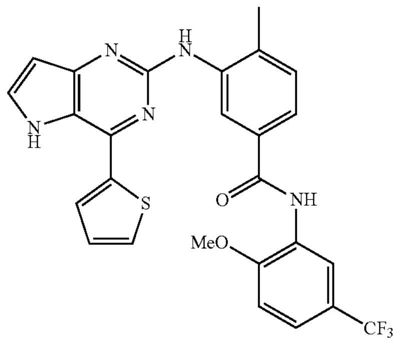 | ¹H NMR (600 MHz, DMSO-$d_6$) δ 11.63 (s, 1H), 9.39 (s, 1H), 8.49 (d, J = 1.8 Hz, 1H), 8.34 (d, J = 2.3 Hz, 1H), 8.27 (s, 1H), 8.22 (d, J = 3.8 Hz, 1H), 7.77 (d, J = 3.1 Hz, 1H), 7.74 (d, J = 5.0 Hz, 1H), 7.59 (dd, J = 7.9, 1.9 Hz, 1H), 7.52 (dd, J = 8.6, 2.3 Hz, 1H), 7.36 (d, J = 7.9 Hz, 1H), 7.31 (dd, J = 5.0, 3.7 Hz, 1H), 7.26 (d, J = 8.7 Hz, 1H), 6.39 (d, J = 3.0 Hz, 1H), 3.84 (s, 3H), 2.38 (s, 3H). MS (ESI) m/z: 524 [M + H]⁺. |
| V-c-54 | 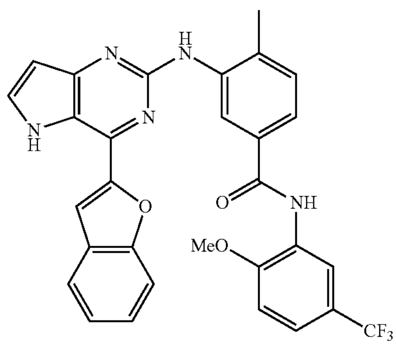 [SMILES: COc1ccc(C(F)(F)F)cc1NC(=O)c1ccc(C)c(Nc2nc(-c3cc4ccccc4o3)c3[nH]ccc3n2)c1] | ¹H NMR (600 MHz, DMSO-$d_6$) δ 11.71 (s, 1H), 9.42 (s, 1H), 8.71 (s, 1H), 8.40 (d, J = 2.2 Hz, 1H), 8.35 (s, 1H), 7.86 (d, J = 3.1 Hz, 1H), 7.83 (s, 1H), 7.77 (d, J = 8.3 Hz, 1H), 7.73 (d, J = 7.8 Hz, 1H), 7.60 (dd, J = 7.9, 1.8 Hz, 1H), 7.53 (dd, J = 8.7, 2.2 Hz, 1H), 7.48 (t, J = 7.7 Hz, 1H), 7.40-7.34 (m, 2H), 7.26 (d, J = 8.6 Hz, 1H), 6.43 (d, J = 3.0 Hz, 1H), 2.40 (s, 3H). MS (ESI) m/z: 558 [M + H]⁺. |
| V-c-55 | 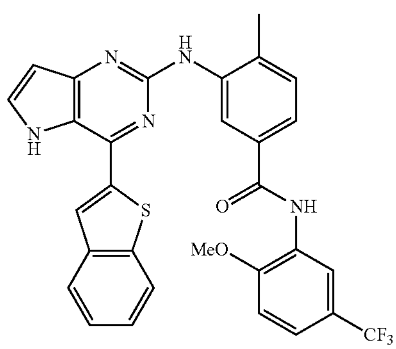 | ¹H NMR (600 MHz, DMSO-$d_6$) δ 11.83 (s, 1H), 9.39 (s, 1H), 8.61-8.58 (m, 1H), 8.56 (d, J = 1.8 Hz, 1H), 8.39 (d, J = 2.3 Hz, 1H), 8.34 (s, 1H), 7.95 (d, J = 7.9 Hz, 1H), 7.86 (t, J = 3.1 Hz, 1H), 7.80 (d, J = 7.9 Hz, 1H), 7.60 (dd, J = 7.8, 1.7 Hz, 1H), 7.51 (dd, J = 8.7, 2.2 Hz, 1H), 7.47-7.43 (m, 1H), 7.43-7.37 (m, 2H), 7.22 (d, J = 8.6 Hz, 1H), 6.45 (dd, J = 3.1, 1.5 Hz, 1H), 3.77 (s, 3H), 2.40 (s, 3H). MS (ESI) m/z: 574 [M + H]⁺. |
| V-c-56 | 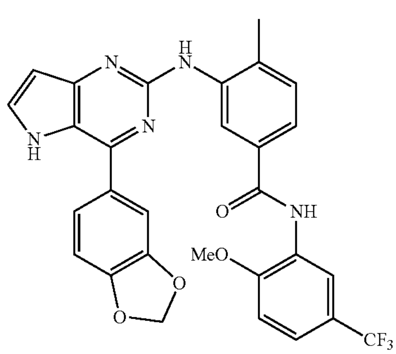 [SMILES: COc1ccc(C(F)(F)F)cc1NC(=O)c1ccc(C)c(Nc2nc(-c3ccc4c(c3)OCO4)c3[nH]ccc3n2)c1] | ¹H NMR (600 MHz, DMSO-$d_6$) δ 11.62 (s, 1H), 9.42 (s, 1H), 8.64 (d, J = 1.8 Hz, 1H), 8.34 (d, J = 2.2 Hz, 1H), 8.21 (s, 1H), 7.72-7.68 (m, 2H), 7.66 (d, J = 1.7 Hz, 1H), 7.56 (dd, J = 7.8, 1.8 Hz, 1H), 7.54-7.50 (m, 1H), 7.35 (d, J = 7.9 Hz, 1H), 7.27 (d, J = 8.6 Hz, 1H), 7.06 (d, J = 8.0 Hz, 1H), 6.38 (d, J = 2.9 Hz, 1H), 6.10 (s, 2H), 3.88 (s, 3H), 2.38 (s, 3H). MS (ESI) m/z: 562 [M + H]⁺. |

| No. | Structure | ¹H NMR and/or MS data |
|---|---|---|
| V-c-57 | 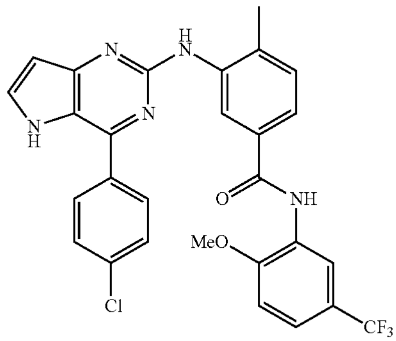 [SMILES: COc1ccc(C(F)(F)F)cc1NC(=O)c1ccc(C)c(Nc2nc(-c3ccc(Cl)cc3)c3[nH]ccc3n2)c1] | ¹H NMR (600 MHz, DMSO-d₆) δ 11.68 (s, 1H), 9.44 (s, 1H), 8.59 (d, J = 1.8 Hz, 1H), 8.35 (s, 1H), 8.31 (d, J = 2.3 Hz, 1H), 8.16-8.12 (m, 2H), 7.76 (t, J = 3.1 Hz, 1H), 7.62-7.57 (m, 3H), 7.54 (dd, J = 8.7, 2.3 Hz, 1H), 7.36 (d, J = 7.9 Hz, 1H), 7.28 (d, J = 8.6 Hz, 1H), 6.41 (dd, J = 3.1, 1.6 Hz, 1H), 3.88 (s, 3H), 2.38 (s, 3H). MS (ESI) m/z: 552 [M + H]⁺. |
| V-c-58 | 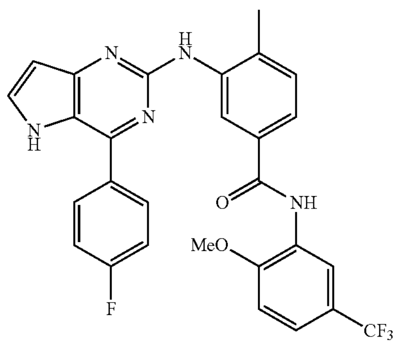 | ¹H NMR (600 MHz, DMSO-d₆) δ 11.76 (s, 1H), 9.45 (s, 1H), 8.60 (d, J = 1.8 Hz, 1H), 8.35 (s, 1H), 8.31 (d, J = 2.3 Hz, 1H), 8.21-8.17 (m, 2H), 7.75 (t, J = 3.1 Hz, 1H), 7.58 (dd, J = 7.8, 1.9 Hz, 1H), 7.53 (dd, J = 8.6, 2.3 Hz, 1H), 7.39-7.34 (m, 3H), 7.28 (d, J = 8.7 Hz, 1H), 6.41 (dd, J = 3.1, 1.6 Hz, 1H), 3.88 (s, 3H), 2.38 (s, 3H). MS (ESI) m/z: 536 [M + H]⁺. |
| V-c-59 | 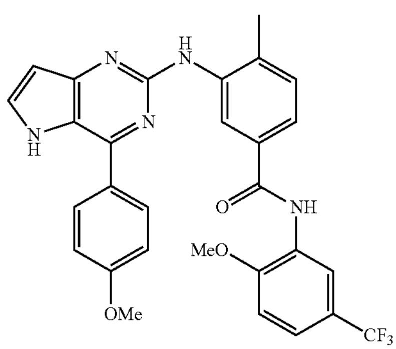 [SMILES: COc1ccc(-c2nc(Nc3cc(C(=O)Nc4cc(C(F)(F)F)ccc4OC)ccc3C)nc3cc[nH]c23)cc1] | ¹H NMR (600 MHz, DMSO-d₆) δ 11.54 (s, 1H), 9.42 (s, 1H), 8.67 (d, J = 1.8 Hz, 1H), 8.35 (d, J = 2.3 Hz, 1H), 8.21 (s, 1H), 8.14-8.10 (m, 2H), 7.71 (d, J = 3.1 Hz, 1H), 7.56 (dd, 7.8, 1.9 Hz, 1H), 7.53 (dd, J = 8.8, 2.3 Hz, 1H), 7.35 (d, J = 7.9 Hz, 1H), 7.28 (d, J = 8.6 Hz, 1H), 7.10-7.05 (m, 2H), 6.39 (d, J = 3.0 Hz, 1H), 3.88 (s, 3H), 3.84 (s, 3H), 2.39 (s, 3H). MS (ESI) m/z: 548 [M + H]⁺. |
| V-c-60 | 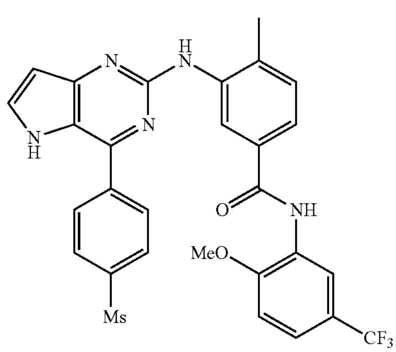 [SMILES: COc1ccc(C(F)(F)F)cc1NC(=O)c1ccc(C)c(Nc2nc(-c3ccc(S(C)(=O)=O)cc3)c3[nH]ccc3n2)c1] | ¹H NMR (600 MHz, DMSO-d₆) δ 11.91 (br.. s, 1H), 9.47 (s, 1H), 8.56 (s, 1H), 8.42-8.35 (m, 3H), 8.29 (s, 1H), 8.11-8.05 (m, 2H), 7.79 (d, J = 3.0 Hz, 1H), 7.60 (d, J = 7.8 Hz, 1H), 7.53 (d, J = 8.6 Hz, 1H), 7.36 (d, J = 7.8 Hz, 1H), 7.28 (d, J = 8.6 Hz, 1H), 6.42 (d, J = 3.1 Hz, 1H), 3.88 (s, 3H), 3.29 (s, 3H), 2.38 (s, 3H). MS (ESI) m/z: 596 [M + H]⁺. |

| No. | Structure | ¹H NMR and/or MS data |
|---|---|---|
| V-c-61 | 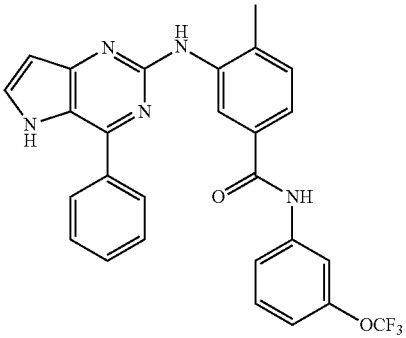 [SMILES: Cc1ccc(C(=O)Nc2cccc(OC(F)(F)F)c2)cc1Nc1nc(-c2ccccc2)c2[nH]ccc2n1] | ¹H NMR (600 MHz, DMSO-d₆) δ 11.64 (s, 1H), 10.50 (s, 1H), 8.63 (d, J = 1.8 Hz, 1H), 8.29 (s, 1H), 8.15-8.11 (m, 2H), 7.99 (s, 1H), 7.83 (dd, J = 8.2, 1.9 Hz, 1H), 7.72 (t, J = 3.0 Hz, 1H), 7.62 (dd, J = 7.8, 1.8 Hz, 1H), 7.54-7.50 (m, 3H), 7.48 (t, J = 8.2 Hz, 1H), 7.36 (d, J = 7.9 Hz, 1H), 7.12-7.05 (m, 1H), 6.39 (dd, J = 3.1, 1.6 Hz, 1H), 2.39 (s, 3H). MS (ESI) m/z: 504 [M + H]⁺. |
| V-c-62 | 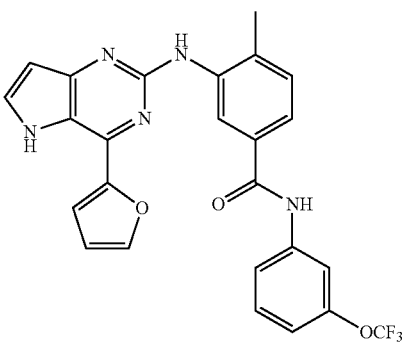 | ¹H NMR (600 MHz, DMSO-d₆) δ 11.64 (s, 1H), 10.48 (s, 1H), 8.59 (d, J = 1.9 Hz, 1H), 8.50-8.43 (m, 1H), 8.03 (d, J = 1.7 Hz, 1H), 7.99-7.94 (m, 1H), 7.84-7.80 (m, 1H), 7.76 (t, J = 3.0 Hz, 1H), 7.64 (dd, J = 7.8, 1.9 Hz, 1H), 7.48 (t, J = 8.2 Hz, 1H), 7.46 (d, J = 3.4 Hz, 1H), 7.37 (d, J = 7.9 Hz, 1H), 7.08 (ddt, J = 8.2, 2.3, 1.0 Hz, 1H), 6.80 (dd, J = 3.5, 1.8 Hz, 1H), 6.38 (dd, J = 3.0, 1.8 Hz, 1H), 2.38 (s, 3H). MS (ESI) m/z: 494 [M + H]⁺. |
| V-c-63 | 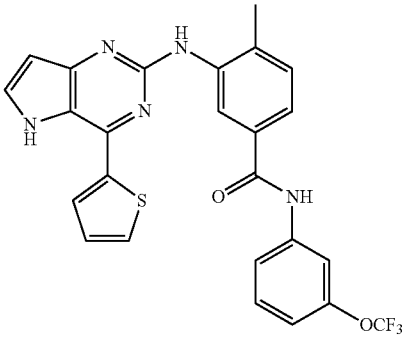 | ¹H NMR (600 MHz, DMSO-d₆) δ 12.01 (s, 1H), 10.54 (s, 1H), 8.55-8.45 (m, 2H), 8.37 (d, J = 3.7 Hz, 1H), 7.98 (s, 1H), 7.82 (dd, J = 8.3, 1.9 Hz, 1H), 7.78 (t, J = 3.0 Hz, 1H), 7.75 (d, J = 5.0 Hz, 1H), 7.68 (dd, J = 7.8, 1.9 Hz, 1H), 7.47 (t, J = 8.2 Hz, 1H), 7.37 (d, J = 7.9 Hz, 1H), 7.30 (dd, J = 5.0, 3.8 Hz, 1H), 7.11-7.02 (m, 1H), 6.40 (dd, J = 3.0, 1.5 Hz, 1H), 2.38 (s, 3H). MS (ESI) m/z: 510 [M + H]⁺. |
| V-c-64 | 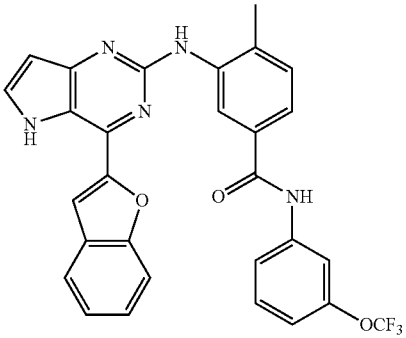 | ¹H NMR (600 MHz, DMSO-d₆) δ 11.75 (t, J = 2.4 Hz, 1H), 10.51 (s, 1H), 8.70 (d, J = 1.8 Hz, 1H), 8.39 (s, 1H), 8.02 (q, J = 1.4 Hz, 1H), 7.86 (t, J = 3.0 Hz, 1H), 7.84 (d, J = 0.9 Hz, 1H), 7.82 (dd, J = 8.0, 1.9 Hz, 1H), 7.79 (d, J = 8.3 Hz, 1H), 7.72 (dt, J = 7.8, 0.9 Hz, 1H), 7.64 (dd, J = 7.8, 1.9 Hz, 1H), 7.51-7.45 (m, 2H), 7.38 (d, J = 7.9 Hz, 1H), 7.37-7.33 (m, 1H), 7.11-7.07 (m, 1H), 6.42 (dd, J = 3.1, 1.8 Hz, 1H), 2.40 (s, 3H). MS (ESI) m/z: 544 [M + H]⁺. |

| No. | Structure | ¹H NMR and/or MS data |
|---|---|---|
| V-c-65 | 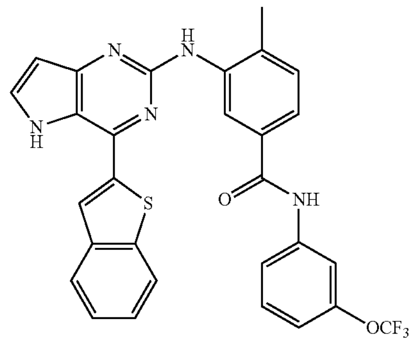 [SMILES: Cc1ccc(C(=O)Nc2cccc(OC(F)(F)F)c2)cc1Nc1nc(-c2cc3ccccc3s2)c2[nH]ccc2n1] | ¹H NMR (600 MHz, DMSO-d₆) δ 12.37 (s, 1H), 10.59 (s, 1H), 8.90-8.74 (m, 2H), 8.59 (d, J = 1.8 Hz, 1H), 8.00 (d, J = 2.4 Hz, 1H), 7.94 (d, J = 7.9 Hz, 1H), 7.91 (t, J = 3.0 Hz, 1H), 7.82 (dd, J = 8.0, 1.9 Hz, 1H), 7.72-7.66 (m, 2H), 7.50-7.37 (m, 4H), 7.10-7.06 (m, 1H), 6.48 (dd, J = 3.1, 1.5 Hz, 1H), 2.41 (s, 3H). MS (ESI) m/z: 560 [M + H]⁺. |
| V-c-66 | 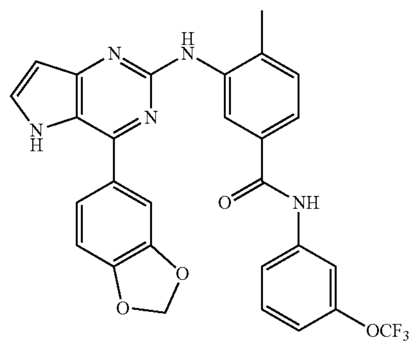 [SMILES: Cc1ccc(C(=O)Nc2cccc(OC(F)(F)F)c2)cc1Nc1nc(-c2ccc3c(c2)OCO3)c2[nH]ccc2n1] | ¹H NMR (600 MHz, DMSO-d₆) δ 11.54 (t, J = 2.3 Hz, 1H), 10.43 (s, 1H), 8.60 (d, J = 1.8 Hz, 1H), 8.24 (s, 1H), 7.99-7.96 (m, 1H), 7.79 (ddd, J = 8.3, 2.0, 0.9 Hz, 1H), 7.71-7.67 (m, 2H), 7.65 (d, J = 1.7 Hz, 1H), 7.59 (dd, J = 7.8, 1.9 Hz, 1H), 7.48 (t, J = 8.2 Hz, 1H), 7.38-7.34 (m, 1H), 7.08 (ddt, J = 8.2, 2.3, 1.0 Hz, 1H), 7.05 (d, J = 8.1 Hz, 1H), 6.37 (dd, J = 3.0, 1.7 Hz, 1H), 6.11 (s, 2H), 2.38 (s, 3H). MS (ESI) m/z: 548 [M + H]⁺. |
| V-c-67 | 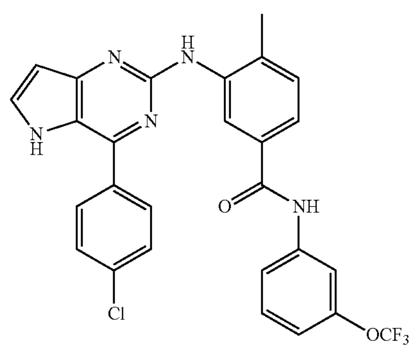 | ¹H NMR (600 MHz, DMSO-d₆) δ 11.86 (s, 1H), 10.55 (s, 1H), 8.62 (d, J = 1.9 Hz, 1H), 8.42 (s, 1H), 8.22-8.15 (m, 2H), 8.01 (d, J = 2.8 Hz, 1H), 7.87-7.81 (m, 1H), 7.77 (t, J = 3.1 Hz, 1H), 7.66 (dd, J = 7.8, 1.9 Hz, 1H), 7.59-7.55 (m, 2H), 7.48 (t, J = 8.2 Hz, 1H), 7.36 (d, J = 8.0 Hz, 1H), 7.08 (ddd, J = 8.3, 2.3, 1.2 Hz, 1H), 6.41 (dd, J = 3.1, 1.6 Hz, 1H), 2.38 (s, 3H). MS (ESI) m/z: 538 [M + H]⁺. |
| V-c-68 | 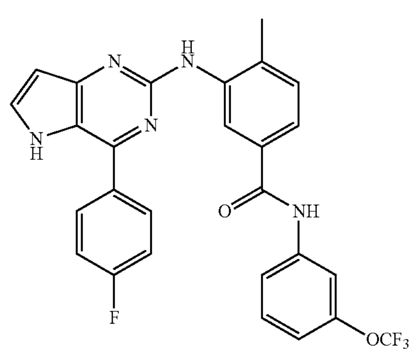 | ¹H NMR (600 MHz, DMSO-d₆) δ 11.74 (d, J = 6.0 Hz, 1H), 10.56-10.50 (m, 1H), 8.61 (s, 1H), 8.29 (s, 1H), 8.24-8.15 (m, 2H), 7.99 (s, 1H), 7.83 (d, J = 8.3 Hz, 1H), 7.73 (t, J = 3.1 Hz, 1H), 7.67-7.61 (m, 1H), 7.48 (t, J = 8.2 Hz, 1H), 7.39-7.29 (m, 3H), 7.08 (dd, J = 8.2, 2.3 Hz, 1H), 6.39 (dd, J = 3.0, 1.6 Hz, 1H), 2.38 (s, 3H). MS (ESI) m/z: 522 [M + H]⁺. |

| No. | Structure | ¹H NMR and/or MS data |
|---|---|---|
| V-c-69 | 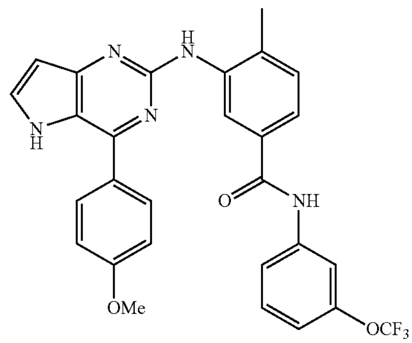 | ¹H NMR (600 MHz, DMSO-d₆) δ 11.78 (s, 1H), 10.56 (s, 1H), 8.66 (d, J = 1.9 Hz, 1H), 8.40 (d, J = 9.0 Hz, 1H), 8.18-8.13 (m, 2H), 8.01 (s, 1H), 7.83 (dd, J = 8.2, 1.9 Hz, 1H), 7.73 (t, J = 3.0 Hz, 1H), 7.64 (dd, J = 7.9, 1.9 Hz, 1H), 7.48 (t, J = 8.2 Hz, 1H), 7.36 (d, J = 8.0 Hz, 1H), 7.09-7.07 (m, 1H), 7.06-7.04 (m, 2H), 6.39 (dd, J = 3.0, 1.6 Hz, 1H), 3.82 (s, 3H), 2.39 (s, 3H). MS (ESI) m/z: 534 [M + H]⁺. |
| V-c-70 | 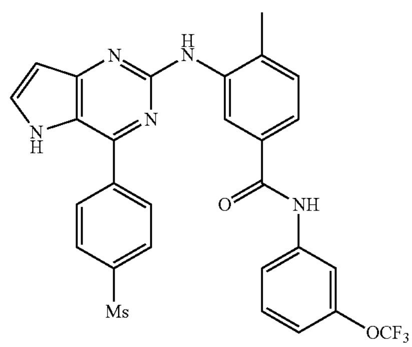 | ¹H NMR (600 MHz, DMSO-d₆) δ 11.78 (s, 1H), 10.48 (s, 1H), 8.55 (d, J = 1.9 Hz, 1H), 8.42 (s, 1H), 8.38-8.33 (m, 2H), 8.10-8.06 (m, 2H), 7.99 (dq, J = 2.3, 1.2 Hz, 1H), 7.82 (ddd, J = 8.4, 2.0, 0.9 Hz, 1H), 7.80 (t, J = 2.9 Hz, 1H), 7.64 (dd, J = 7.8, 2.0 Hz, 1H), 7.48 (t, J = 8.2 Hz, 1H), 7.39-7.35 (m, 1H), 7.08 (ddt, J = 8.3, 2.2, 1.0 Hz, 1H), 6.43 (dd, J = 3.1, 1.2 Hz, 1H), 3.30 (s, 3H), 2.38 (s, 3H). MS (ESI) m/z: 582 [M + H]+. |
| V-c-71 | 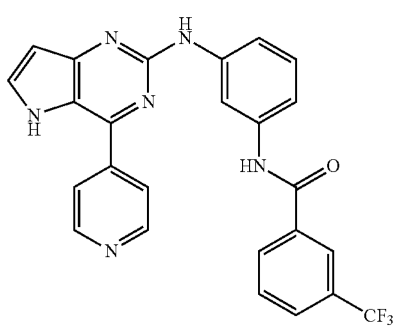 | ¹H NMR (600 MHz, DMSO-d₆) δ 11.92 (s, 1H), 10.56 (d, J = 2.3 Hz, 1H), 9.40 (s, 1H), 8.84-8.78 (m, 2H), 8.41 (d, J = 1.8 Hz, 1H), 8.38-8.32 (m, 2H), 8.18-8.12 (m, 2H), 7.97 (d, J = 7.8 Hz, 1H), 7.84-7.78 (m, 2H), 7.63 (dt, J = 7.7, 1.8 Hz, 1H), 7.32-7.23 (m, 2H), 6.49 (dd, J = 3.1, 1.6 Hz, 1H). MS (ESI) m/z: 475 [M + H]⁺. |
| V-c-72 | 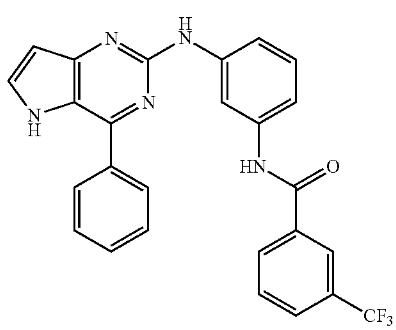 [SMILES: O=C(Nc1cccc(Nc2nc(-c3ccccc3)c3[nH]ccc3n2)c1)c1cccc(C(F)(F)F)c1] | MS (ESI) m/z: 474 [M + H]⁺. |

| No. | Structure | ¹H NMR and/or MS data |
|---|---|---|
| V-c-73 | 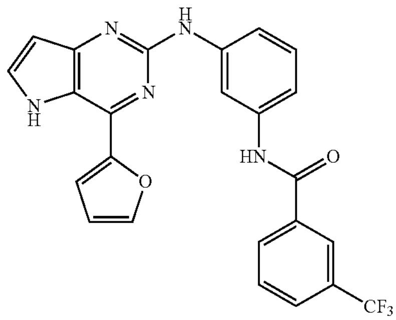 [SMILES: O=C(Nc1cccc(Nc2nc(-c3cccs3)c3[nH]ccc3n2)c1)c1cccc(C(F)(F)F)c1] | MS (ESI) m/z: 464 [M + H]⁺. |
| V-c-74 | 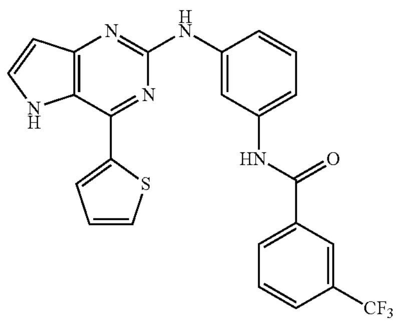 | ¹H NMR (600 MHz, DMSO-$d_6$) δ 12.00 (s, 1H), 10.51 (s, 1H), 9.69 (s, 1H), 8.34-8.27 (m, 3H), 8.11 (t, J = 2.1 Hz, 1H), 7.98 (d, J = 7.8 Hz, 1H), 7.95 (d, J = 5.0 Hz, 1H), 7.89 (t, J = 3.0 Hz, 1H), 7.81 (t, J = 7.8 Hz, 1H), 7.70 (dt, J = 8.0, 1.5 Hz, 1H), 7.42-7.37 (m, 2H), 7.34 (t, J = 8.0 Hz, 1H), 6.50 (dd, J = 3.0, 1.7 Hz, 1H). MS (ESI) m/z: 480 [M + H]⁺. |
| V-c-75 | 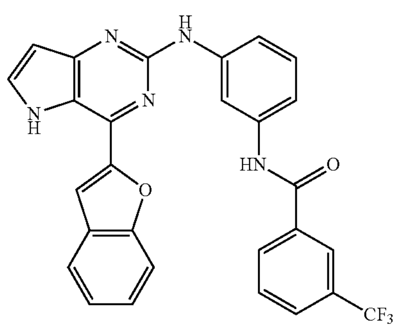 [SMILES: O=C(Nc1cccc(Nc2nc(-c3cc4ccccc4s3)c3[nH]ccc3n2)c1)c1cccc(C(F)(F)F)c1] | ¹H NMR (600 MHz, DMSO-$d_6$) δ 11.84 (s, 1H), 10.54 (s, 1H), 9.49 (s, 1H), 8.59 (t, J = 2.0 Hz, 1H), 8.39 (s, 1H), 8.37 (d, J = 7.9 Hz, 1H), 8.12 (s, 1H), 8.00 (d, J = 7.9 Hz, 1H), 7.90 (t, J = 3.0 Hz, 1H), 7.86-7.78 (m, 3H), 7.58 (dt, J = 7.9, 1.8 Hz, 1H), 7.50 (ddd, J = 8.3, 7.1, 1.4 Hz, 1H), 7.38 (t, J = 7.8 Hz, 1H), 7.32-7.24 (m, 2H), 6.48 (dd, J = 3.0, 1.8 Hz, 1H). MS (ESI) m/z: 514 [M + H]⁺. |
| V-c-76 | 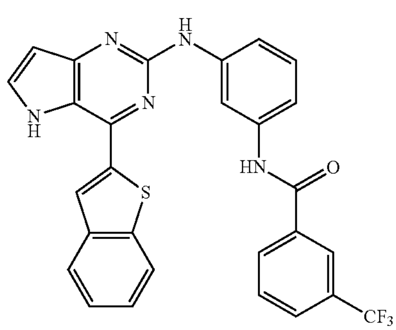 | ¹H NMR (600 MHz, DMSO-$d_6$) δ 11.85 (s, 1H), 10.48 (s, 1H), 9.30 (s, 1H), 8.61 (s, 1H), 8.36-8.30 (m, 2H), 8.21 (t, J = 1.9 Hz, 1H), 8.01-7.95 (m, 3H), 7.87 (t, J = 3.0 Hz, 1H), 7.84-7.77 (m, 2H), 7.49-7.45 (m, 2H), 7.33-7.28 (m, 2H), 6.49 (dd, J = 3.1, 1.6 Hz, 1H). MS (ESI) m/z: 530 [M + H]⁺. |

| No. | Structure | ¹H NMR and/or MS data |
|---|---|---|
| V-c-77 | 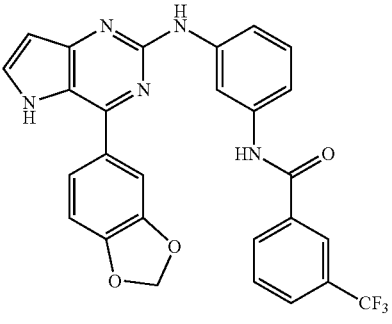<br>TFA salt | ¹H NMR (600 MHz, DMSO-$d_6$) δ 11.60 (d, J = 3.0 Hz, 1H), 10.49 (s, 1H), 9.23 (s, 1H), 8.40 (d, J = 2.3 Hz, 1H), 8.35 (s, 1H), 8.33 (d, J = 7.9 Hz, 1H), 7.98 (d, J = 7.7 Hz, 1H), 7.80 (t, J = 7.8 Hz, 1H), 7.76-7.70 (m, 3H), 7.62-7.58 (m, 1H), 7.28-7.22 (m, 2H), 7.12 (d, J = 8.0 Hz, 1H), 6.42 (dd, J = 3.1, 1.7 Hz, 1H), 6.14 (s, 2H). MS (ESI) m/z: 518 [M + H]⁺. |
| V-c-78 | 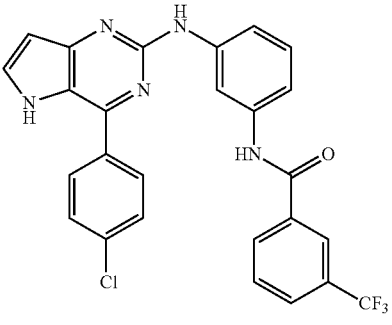 [SMILES: O=C(Nc1cccc(Nc2nc(-c3ccc(Cl)cc3)c3[nH]ccc3n2)c1)c1cccc(C(F)(F)F)c1] | ¹H NMR (600 MHz, DMSO-$d_6$) δ 12.07 (s, 1H), 10.52 (s, 1H), 9.83 (s, 1H), 8.33 (t, J = 2.0 Hz, 2H), 8.31 (d, J = 7.9 Hz, 1H), 8.22-8.17 (m, 2H), 7.99 (d, J = 7.8 Hz, 1H), 7.90 (d, J = 3.0 Hz, 1H), 7.81 (t, J = 7.8 Hz, 1H), 7.72-7.65 (m, 2H), 7.55 (d, J = 7.9 Hz, 1H), 7.40-7.30 (m, 2H), 6.52 (dd, J = 2.9, 1.6 Hz, 1H). MS (ESI) m/z: 508 [M + H]+. MS (ESI) m/z: 508 [M + H]⁺. |
| V-c-79 | 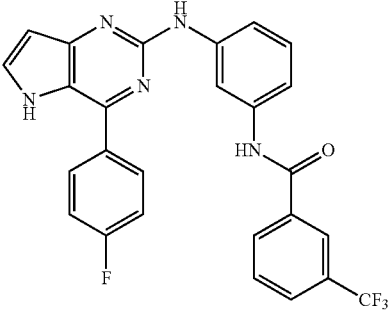 | ¹H NMR (600 MHz, DMSO-$d_6$) δ 11.73 (s, 1H), 10.52 (s, 1H), 9.28 (s, 1H), 8.40-8.31 (m, 3H), 8.25 (dd, J = 8.4, 5.5 Hz, 2H), 7.97 (d, J = 7.8 Hz, 1H), 7.80 (t, J = 7.8 Hz, 1H), 7.75 (d, J = 3.0 Hz, 1H), 7.65 (d, J = 7.8 Hz, 1H), 7.46-7.38 (m, 2H), 7.32-7.22 (m, 2H), 6.45 (d, J = 3.0 Hz, 1H). MS (ESI) m/z: 492 [M + H]⁺. |
| V-c-80 | 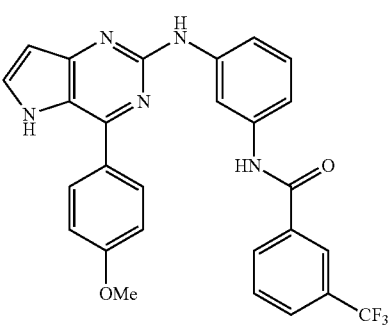 [SMILES: COc1ccc(-c2nc(Nc3cccc(NC(=O)c4cccc(C(F)(F)F)c4)c3)nc3cc[nH]c23)cc1] | ¹H NMR (600 MHz, DMSO-$d_6$) δ 11.64 (s, 1H), 10.52 (s, 1H), 9.19 (s, 1H), 8.39-8.32 (m, 3H), 8.22-8.16 (m, 2H), 7.97 (d, J = 7.7 Hz, 1H), 7.80 (t, J = 7.8 Hz, 1H), 7.70 (t, J = 3.0 Hz, 1H), 7.65 (dt, J = 7.3, 1.9 Hz, 1H), 7.28-7.22 (m, 2H), 7.15-7.10 (m, 2H), 6.42 (dd, J = 3.0, 1.6 Hz, 1H), 3.86 (s, 3H). MS (ESI) m/z: 504 [M + H]⁺. |

| No. | Structure | ¹H NMR and/or MS data |
|---|---|---|
| V-c-81 | 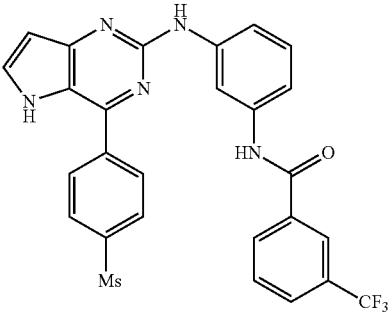 [SMILES: CS(=O)(=O)c1ccc(-c2nc(Nc3cccc(NC(=O)c4cccc(C(F)(F)F)c4)c3)nc3cc[nH]c23)cc1] | ¹H NMR (600 MHz, DMSO-d₆) δ 11.80 (s, 1H), 10.49 (s, 1H), 9.37 (s, 1H), 8.44-8.40 (m, 2H), 8.39-8.34 (m, 3H), 8.32 (d, J = 7.9 Hz, 1H), 8.19-8.12 (m, 2H), 7.98 (d, J = 7.8 Hz, 1H), 7.86-7.76 (m, 2H), 7.66 (dt, J = 7.0, 2.1 Hz, 1H), 7.31-7.23 (m, 2H), 6.49 (dd, J = 3.1, 1.6 Hz, 1H), 3.32 (s, 3H). MS (ESI) m/z: 552 [M + H]⁺. |
| V-c-82 | 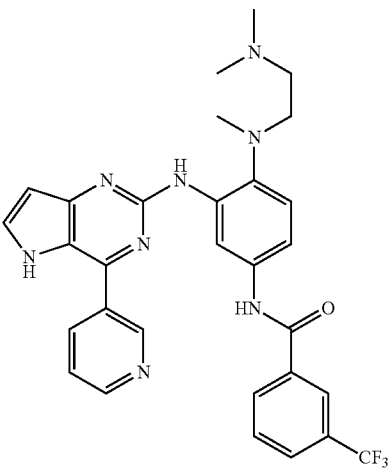 [SMILES: CN(C)CCN(C)c1ccc(NC(=O)c2cccc(C(F)(F)F)c2)cc1Nc1nc(-c2cccnc2)c2[nH]ccc2n1] | MS (ESI) m/z: 575 [M + H]⁺. |
| V-c-83 | 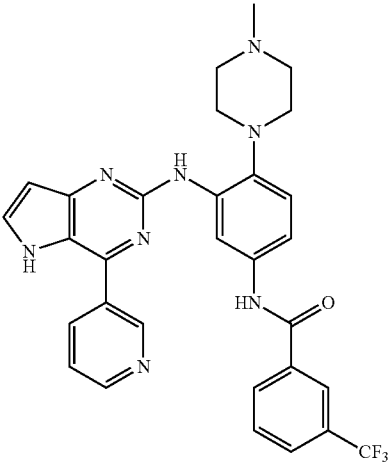 [SMILES: CN1CCN(c2ccc(NC(=O)c3cccc(C(F)(F)F)c3)cc2Nc2nc(-c3cccnc3)c3[nH]ccc3n2)CC1] | MS (ESI) m/z: 573 [M + H]⁺. |

| No. | Structure | ¹H NMR and/or MS data |
|---|---|---|
| V-c-84 | 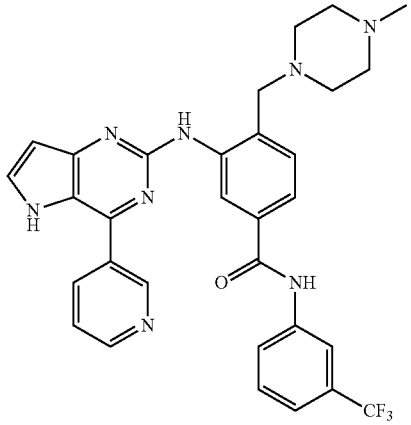 [SMILES: CN1CCN(Cc2ccc(C(=O)Nc3cccc(C(F)(F)F)c3)cc2Nc2nc(-c3cccnc3)c3[nH]ccc3n2)CC1] | MS (ESI) m/z: 587 [M + H]⁺. |
| V-c-85 | 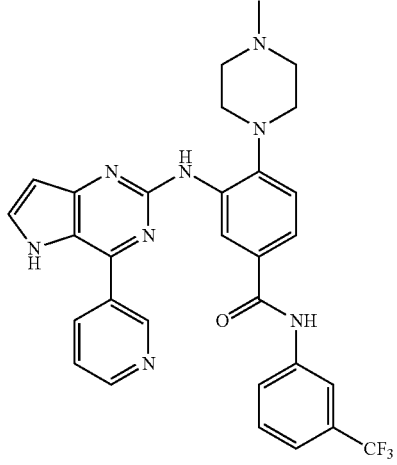 [SMILES: CN1CCN(c2ccc(C(=O)Nc3cccc(C(F)(F)F)c3)cc2Nc2nc(-c3cccnc3)c3[nH]ccc3n2)CC1] | MS (ESI) m/z: 573 [M + H]⁺. |
| V-c-86 | 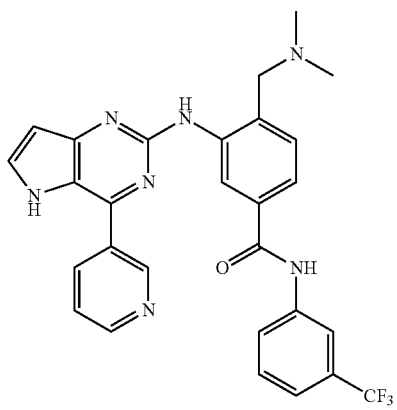 [SMILES: CN(C)Cc1ccc(C(=O)Nc2cccc(C(F)(F)F)c2)cc1Nc1nc(-c2cccnc2)c2[nH]ccc2n1] | MS (ESI) m/z: 532 [M + H]⁺. |

-continued

| No. | Structure | ¹H NMR and/or MS data |
|---|---|---|
| V-c-87 | 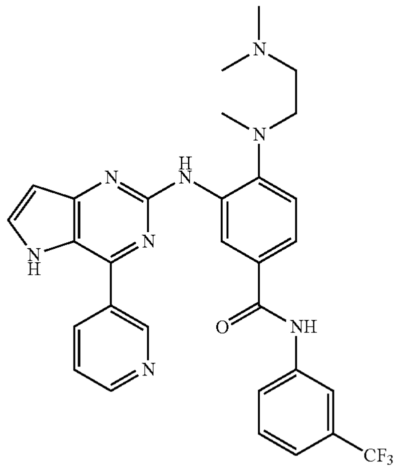 [SMILES: CN(C)CCN(C)c1ccc(C(=O)Nc2cccc(C(F)(F)F)c2)cc1Nc1nc(-c2cccnc2)c2[nH]ccc2n1] | MS (ESI) m/z: 575 [M + H]⁺. |

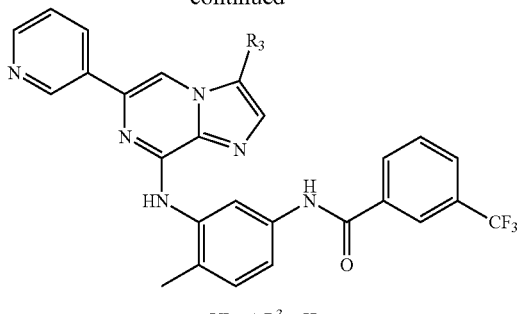

Synthetic Route of Compounds VI-a-1, VI-b-1:

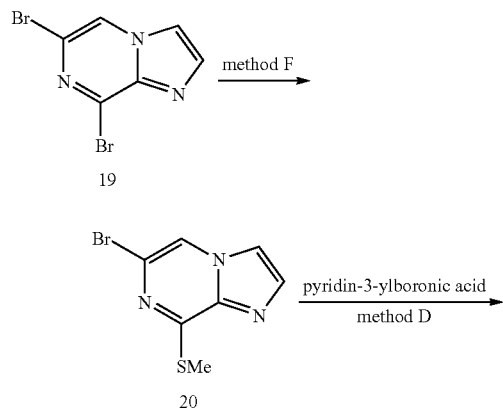

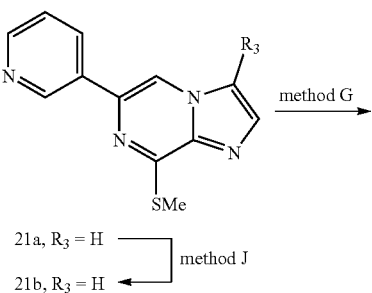

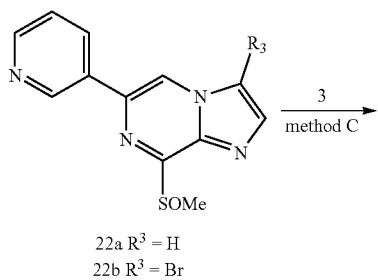

Compound 21a was synthesized from 19 through Method F, Method D in sequence, MS (ESI) m/z: 243 [M+H]⁺.

Synthesis of Compound 21b:

Method J: compound 21a (484 mg, 2 mmol) and NBS (427 mg, 2.4 mmol) were stirred in ethanol (10 mL) at room temperature for 3 h, concentrated, and dissolved with ethyl acetate. The system was washed with water, dried with anhydrous sodium sulfate, filtered, concentrated, and purified by silica gel column chromatography to obtain the target product 591 mg, as a white solid, in 92% yield.

MS (ESI) m/z: 321 [M+H]⁺.

Compounds VI-a-1, VI-a-1 were respectively synthesized from 21a, 21b through Method G, Method C in sequence.

Other such compounds could be synthesized by similar methods.

In the following table it lists the specific compounds and their structural characterization data.

| No. | Structure | ¹H NMR and/or MS data |
|---|---|---|
| VI-a-1 | 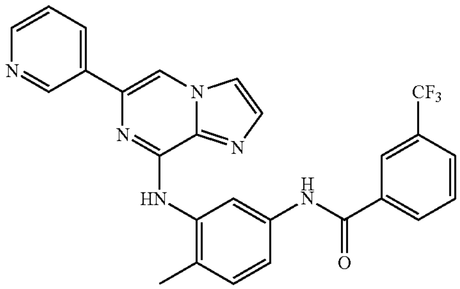 [SMILES: Cc1ccc(NC(=O)c2cccc(C(F)(F)F)c2)cc1Nc1nc(-c2cccnc2)cn2ccnc12] | ¹H NMR (600 MHz, DMSO-d$_6$) δ 10.51 (s, 1H), 9.15 (d, J = 2.0 Hz, 1H), 8.98 (s, 1H), 8.75 (s, 1H), 8.62 (d, J = 1.9 Hz, 1H), 8.52 (dd, J = 4.7, 1.4 Hz, 1H), 8.39 (dt, J = 8.0, 1.8 Hz, 1H), 8.35 (s, 1H), 8.31 (d, J = 7.9 Hz, 1H), 8.03 (d, J = 0.7 Hz, 1H), 7.98 (d, J = 7.8 Hz, 1H), 7.81 (t, J = 7.8 Hz, 1H), 7.70 (d, J = 0.8 Hz, 1H), 7.47 (dd, J = 8.2, 2.1 Hz, 1H), 7.41 (dd, J = 7.9, 4.7 Hz, 1H), 7.31 (d, J = 8.3 Hz, 1H), 2.33 (s, 3H). MS (ESI) m/z: 489 [M + H]⁺. |
| VI-a-2 | 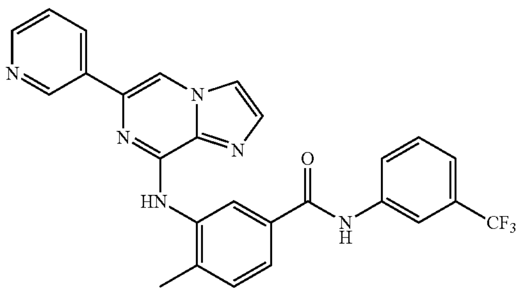 [SMILES: Cc1ccc(C(=O)Nc2cccc(C(F)(F)F)c2)cc1Nc1nc(-c2cccnc2)cn2ccnc12] | ¹H NMR (600 MHz, DMSO-d$_6$) δ 10.55 (s, 1H), 9.18 (s, 1H), 9.10 (s, 1H), 8.78 (s, 1H), 8.68 (s, 1H), 8.51 (d, J = 4.6 Hz, 1H), 8.28-8.25 (m, 2H), 8.11 (d, J = 8.3 Hz, 1H), 8.05 (s, 1H), 7.80 (d, J = 7.8 Hz, 1H), 7.72 (s, 1H), 7.61 (d, J = 8.0 Hz, 1H), 7.51 (d, J = 8.0 Hz, 1H), 7.46 (d, J = 7.8 Hz, 1H), 7.37 (dd, J = 7.8, 4.9 Hz, 1H), 2.43 (s, 3H) MS (ESI) m/z: 489 [M + H]⁺. |
| VI-a-3 | TFA salt | ¹H NMR (600 MHz, DMSO-d$_6$) δ 10.86 (s, 1H), 9.39 (s, 1H), 9.23 (s, 1H), 9.13 (s, 1H), 8.80 (s, 1H), 8.69 (s, 1H), 8.57 (s, 1H), 8.52 (d, J = 4.8 Hz, 1H), 8.31 (d, J = 8.1 Hz, 1H), 8.26 (s, 1H), 8.07 (s, 1H), 7.97 (s, 1H), 7.90 (s, 1H), 7.83 (d, J = 7.8 Hz, 1H), 7.73 (s, 1H), 7.54 (d, J = 8.0 Hz, 1H), 7.44 (dd, J = 8.1, 4.9 Hz, 1H), 2.44 (s, 3H), 2.34 (s, 3H). MS (ESI) m/z: 569 [M + H]⁺. |
| VI-a-4 | TFA salt | ¹H NMR (600 MHz, DMSO-d$_6$) δ 10.56 (s, 1H), 9.36 (s, 1H), 9.16 (s, 1H), 8.91 (s, 1H), 8.70 (d, J = 4.5 Hz, 1H), 8.62 (d, J = 8.2 Hz, 1H), 8.58 (s, 1H), 8.25 (d, J = 1.7 Hz, 1H), 8.15 (d, J = 8.5 Hz, 1H), 8.11 (d, J = 0.9 Hz, 1H), 7.86-7.82 (m, 1H), 7.78 (d, J = 0.8 Hz, 1H), 7.75-7.70 (m, 2H), 7.51 (d, J = 8.1 Hz, 1H), 3.73 (s, 2H), 3.49-3.38 (m, 2H), 3.12-3.02 (m, 2H), 3.02-2.92 (m, 2H), 2.82 (s, 3H), 2.49-2.43 (m, 2H), 2.42 (s, 3H). MS (ESI) m/z: 601 [M + H]⁺. |
| VI-a-5 | 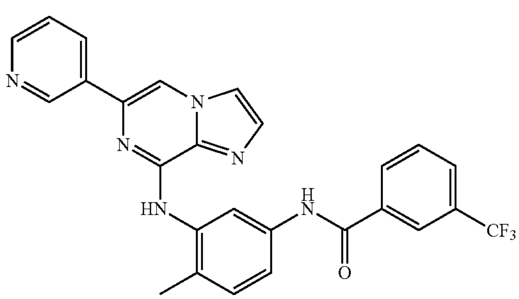 [SMILES: Cc1ccc(NC(=O)c2cccc(C(F)(F)F)c2)cc1Nc1nc(-c2cccnc2)cn2ccnc12] | ¹H NMR (600 MHz, DMSO-d$_6$) δ 10.52 (s, 1H), 8.95 (s, 1H), 8.89 (s, 1H), 8.69 (d, J = 2.1 Hz, 1H), 8.58 (dd, J = 4.6, 1.5 Hz, 2H), 8.36 (s, 1H), 8.33 (d, J = 7.9 Hz, 1H), 8.06 (d, J = 1.0 Hz, 1H), 8.00 (dd, J = 4.5, 1.6 Hz, 2H), 7.99 (s, 1H), 7.83 (t, J = 7.8 Hz, 1H), 7.72 (d, J = 1.1 Hz, 1H), 7.46 (dd, J = 8.2, 2.1 Hz, 1H), 7.32 (d, J = 8.3 Hz, 1H), 2.34 (s, 3H). MS (ESI) m/z: 489 [M + H]⁺. |

-continued

| No. | Structure | ¹H NMR and/or MS data |
|---|---|---|
| VI-a-6 | 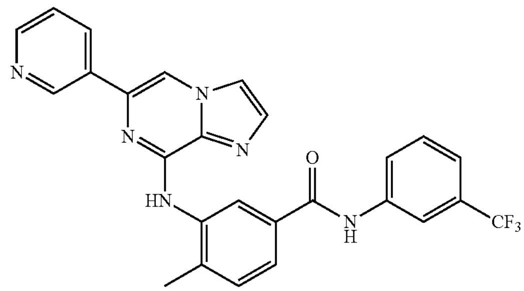 [SMILES: Cc1ccc(C(=O)Nc2cccc(C(F)(F)F)c2)cc1Nc1nc(-c2cccnc2)cn2ccnc12] | ¹H NMR (600 MHz, DMSO-d₆) δ 10.59 (s, 1H), 9.16 (s, 1H), 8.91 (s, 1H), 8.76 (d, J = 1.8 Hz, 1H), 8.52 (dd, J = 4.6, 1.6 Hz, 2H), 8.28 (s, 1H), 8.11 (d, J = 8.2 Hz, 1H), 8.08 (d, J = 1.1 Hz, 1H), 7.89 (dd, J = 4.6, 1.6 Hz, 2H), 7.80 (dd, J = 7.8, 1.8 Hz, 1H), 7.74 (d, J = 1.1 Hz, 1H), 7.62 (t, J = 8.0 Hz, 1H), 7.51 (d, J = 8.1 Hz, 1H), 7.47 (d, J = 7.8 Hz, 1H), 2.43 (s, 3H). MS (ESI) m/z: 489 [M + H]⁺. |
| VI-a-7 | 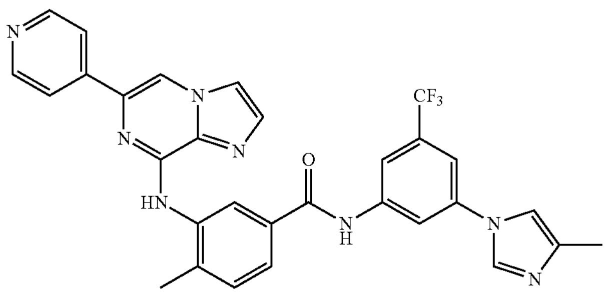 [SMILES: Cc1cn(-c2cc(NC(=O)c3ccc(C)c(Nc4nc(-c5ccncc5)cn5ccnc45)c3)cc(C(F)(F)F)c2)cn1] | ¹H NMR (600 MHz, DMSO-d₆) δ 10.72 (s, 1H), 9.21 (s, 1H), 8.92 (s, 1H), 8.76 (d, J = 1.8 Hz, 1H), 8.54 (dd, J = 4.5, 1.6 Hz, 2H), 8.35 (s, 1H), 8.23 (d, J = 1.3 Hz, 1H), 8.19 (s, 1H), 8.08 (d, J = 1.1 Hz, 1H), 7.89 (dd, J = 4.5, 1.6 Hz, 2H), 7.82 (dd, J = 7.9, 1.9 Hz, 1H), 7.75 (s, 1H), 7.74 (d, J = 1.1 Hz, 1H), 7.54 (d, J = 8.1 Hz, 1H), 7.50 (s, 1H), 2.44 (s, 3H), 2.19 (d, J = 0.7 Hz, 3H). MS (ESI) m/z: 569 [M + H]⁺. |
| VI-a-8 | TFA salt | ¹H NMR (600 MHz, DMSO-d₆) δ 10.57 (s, 1H), 9.53 (s, 1H), 9.25 (s, 1H), 8.85 (d, J = 6.7 Hz, 2H), 8.51 (d, J = 1.6 Hz, 1H), 8.36 (d, J = 6.8 Hz, 2H), 8.25 (d, J = 2.1 Hz, 1H), 8.16-8.13 (m, 2H), 7.87 (dd, J = 7.9, 1.8 Hz, 1H), 7.81 (d, J = 1.2 Hz, 1H), 7.72 (d, J = 8.5 Hz, 1H), 7.53 (d, J = 8.2 Hz, 1H), 3.73 (s, 3H), 3.48-3.38 (m, 2H), 3.12-3.02 (m, 2H), 3.00-2.91 (m, 2H), 2.82 (s, 3H), 2.48-2.43 (m, 2H), 2.41 (s, 3H). MS (ESI) m/z: 601 [M + H]⁺. |
| VI-a-9 | 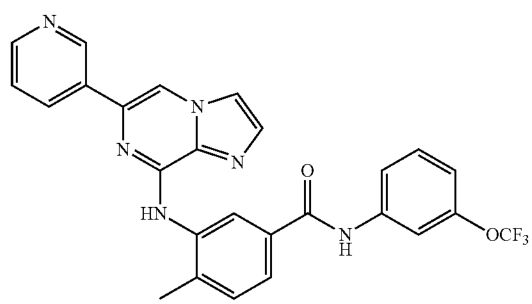 [SMILES: Cc1ccc(C(=O)Nc2cccc(OC(F)(F)F)c2)cc1Nc1nc(-c2cccnc2)cn2ccnc12] | ¹H NMR (600 MHz, DMSO-d₆) δ 10.49 (s, 1H), 9.16 (s, 1H), 9.11-9.07 (m, 1H), 8.76 (s, 1H), 8.66 (d, J = 1.7 Hz, 1H), 8.50 (dd, J = 4.7, 1.6 Hz, 1H), 8.26 (ddd, J = 8.0, 2.2, 1.7 Hz, 1H), 8.04 (d, J = 1.1 Hz, 1H), 7.95 (s, 1H), 7.81 (dd, J = 8.3, 1.1 Hz, 1H), 7.77 (dd, J = 7.9, 1.8 Hz, 1H), 7.70 (d, J = 1.1 Hz, 1H), 7.49 (dd, J = 11.6, 4.8 Hz, 2H), 7.35 (ddd, J = 8.0, 4.7, 0.8 Hz, 1H), 7.09 (dd, J = 8.9, 1.6 Hz, 1H), 2.42 (s, 3H). MS (ESI) m/z: 505 [M + H]⁺. |
| VI-a-10 | TFA salt | ¹H NMR (600 MHz, DMSO-d₆) δ 10.59 (s, 1H), 9.26 (s, 1H), 9.07 (s, 1H), 8.87 (s, 1H), 8.67-8.65 (m, 3H), 8.39-8.37 (m, 2H), 8.08 (s, 2H), 7.75 (s, 1H), 7.72-7.67 (m, 1H), 7.46 (dd, J = 8.2, 2.1 Hz, 1H), 7.32 (d, J = 8.4 Hz, 1H), 4.35 (s, 2H), 3.80 (br. s, 4H), 3.06 (br. s, 4H), 2.33 (s, 3H). MS (ESI) m/z: 588 [M + H]⁺. |

-continued

| No. | Structure | ¹H NMR and/or MS data |
|---|---|---|
| VI-b-1 | 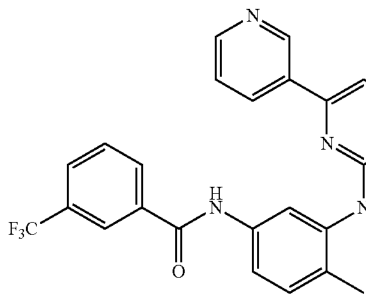 | ¹H NMR (600 MHz, DMSO-d₆) δ 10.51 (s, 1H), 9.21 (s, 2H), 8.54 (d, J = 3.6 Hz, 1H), 8.46 (t, J = 5.0 Hz, 2H), 8.38 (s, 1H), 8.33 (s, 1H), 8.30 (d, J = 7.8 Hz, 1H), 7.98 (d, J = 7.8 Hz, 1H), 7.86 (s, 1H), 7.81 (t, J = 7.8 Hz, 1H), 7.51 (dd, J = 8.1, 2.0 Hz, 1H), 7.42 (dd, J = 7.9.4.7 Hz, 1H), 7.32 (d, J = 8.3 Hz, 1H), 2.30 (s, 3H). MS (ESI) m/z: 568 [M + H]⁺. |
| VI-b-2 | 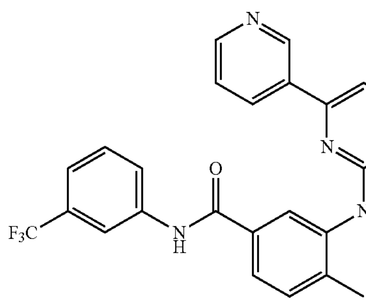 | ¹H NMR (600 MHz, DMSO-d₆) δ 10.55 (s, 1H), 9.40 (s, 1H), 9.16 (d, J = 2.2 Hz, 1H), 8.55 (d, J = 1.7 Hz, 1H), 8.53 (dd, J = 4.7, 1.6 Hz, 1H), 8.40 (s, 1H), 8.38-8.34 (m, 1H), 8.26 (s, 1H), 8.10 (d, J = 8.3 Hz, 1H), 7.87 (s, 1H), 7.83 (dd, J = 7.9, 1.8 Hz, 1H), 7.61 (t, J = 8.0 Hz, 1H), 7.52 (d, J = 8.0 Hz, 1H), 7.45 (t, J = 7.3 Hz, 1H), 7.37 (dd, J = 8.0, 4.8 Hz, 1H), 2.40 (s, 3H). MS (ESI) m/z: 568 [M + H]⁺. |
| VI-b-3 | TFA salt | ¹H NMR (600 MHz, DMSO-d₆) δ 10.88 (s, 1H), 10.60 (s, 1H), 9.39 (s, 1H), 9.15 (d, J = 1.7 Hz, 1H), 8.57-8.48 (m, 2H), 8.40 (s, 1H), 8.38-8.34 (m, 1H), 8.24 (d, J = 2.1 Hz, 1H), 8.16-8.12 (m, 1H), 7.88-7.84 (m, 2H), 7.71 (d, J = 8.1 Hz, 1H), 7.51 (d, J = 8.2 Hz, 1H), 7.38 (dd, J = 7.9, 4.7 Hz, 1H), 3.67 (s, 2H), 3.07-2.98 (m, 4H), 2.92-2.84 (m, 4H), 2.73 (s, 3H), 2.40 (s, 3H). MS (ESI) m/z: 680 [M + H]⁺. |
| VI-b-4 | 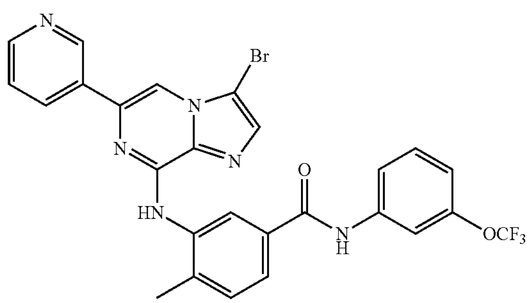 [SMILES: Cc1ccc(C(=O)Nc2cccc(OC(F)(F)F)c2)cc1Nc1nc(-c2cccnc2)cn2c(Br)cnc12] | ¹H NMR (600 MHz, DMSO-d₆) δ 10.50 (s, 1H), 9.39 (s, 1H), 9.16 (d, J = 1.6 Hz, 1H), 8.53 (d, J = 2.1 Hz, 2H), 8.40 (s, 1H), 8.36 (d, J = 8.0 Hz, 1H), 7.95 (s, 1H), 7.87 (s, 1H), 7.81 (d, J = 8.1 Hz, 2H), 7.50 (dd, J = 15.9, 7.9 Hz, 2H), 7.37 (dd, J = 8.0, 4.7 Hz, 1H), 7.09 (d, J = 7.8 Hz, 1H), 2.41 (s, 3H). MS (ESI) m/z: 584 [M + H]⁺. |
| VI-b-5 | 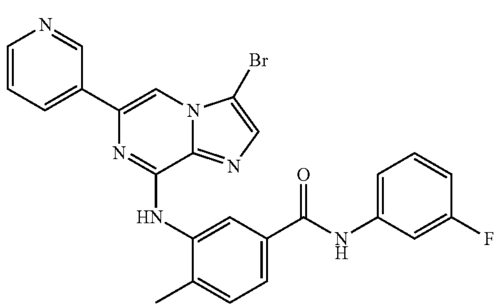 [SMILES: Cc1ccc(C(=O)Nc2cccc(F)c2)cc1Nc1nc(-c2cccnc2)cn2c(Br)cnc12] | ¹H NMR (600 MHz, DMSO-d₆) δ 10.43 (s, 1H), 9.39 (s, 1H), 9.17 (d, J = 1.6 Hz, 1H), 8.57-8.49 (m, 2H), 8.41 (s, 1H), 8.36 (d, J = 8.0 Hz, 1H), 7.87 (s, 1H), 7.79 (t, J = 11.9 Hz, 2H), 7.60 (d, J = 9.2 Hz, 1H), 7.51 (d, J = 8.0 Hz, 1H), 7.39 (d, J = 6.6 Hz, 2H), 6.94 (t, J = 8.5 Hz, 1H), 2.41 (s, 3H). MS (ESI) m/z: 518 [M + H]⁺. |

| No. | Structure | ¹H NMR and/or MS data |
|---|---|---|
| VI-b-6 | 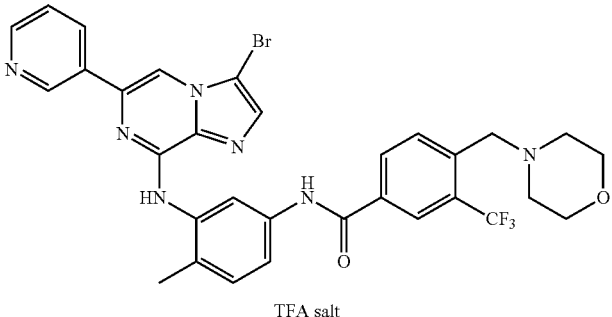 [SMILES: Cc1ccc(NC(=O)c2ccc(CN3CCOCC3)c(C(F)(F)F)c2)cc1Nc1nc(-c2cccnc2)cn2c(Br)cnc12] TFA salt | ¹H NMR (600 MHz, DMSO-d₆) δ 10.56 (s, 1H), 9.31 (s, 1H), 9.28 (s, 1H), 8.72 (s, 1H), 8.65 (d, J = 4.1 Hz, 1H), 8.49 (s, 1H), 8.47 (d, J = 2.0 Hz, 1H), 8.37 (d, J = 15.6 Hz, 2H), 8.05 (d, J = 8.1 Hz, 1H), 7.88 (s, 1H), 7.64 (s, 1H), 7.52-7.47 (m, 1H), 7.33 (d, J = 8.5 Hz, 1H), 3.88-3.71 (m, 4H), 3.13-2.83 (m, 4H), 2.31 (s, 3H). MS (ESI) m/z: 667 [M + H]⁺. |
| VI-b-7 | 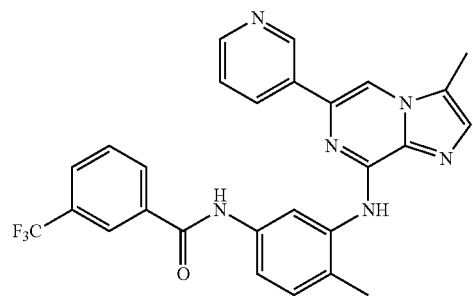 TFA salt | ¹H NMR (600 MHz, DMSO-d₆) δ 10.44 (s, 1H), 8.94 (s, 1H), 8.83 (s, 1H), 8.66 (d, J = 4.9 Hz, 1H), 8.57 (d, J = 2.2 Hz, 1H), 8.35 (d, J = 7.9 Hz, 1H), 8.32 (s, 1H), 8.29 (d, J = 7.7 Hz, 1H), 8.16 (d, J = 1.2 Hz, 1H), 7.98 (d, J = 7.7 Hz, 1H), 7.83-7.80 (m, 2H), 7.65 (dd, J = 7.9, 5.1 Hz, 1H), 7.38 (dd, J = 8.2, 2.2 Hz, 1H), 7.25 (d, J = 8.7 Hz, 1H), 2.62 (s, 3H), 2.31 (s, 3H). MS (ESI) m/z: 503 [M + H]⁺. |
| VI-b-8 | 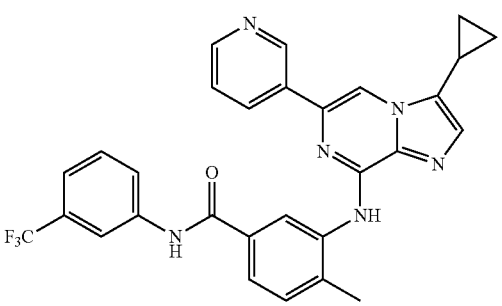 [SMILES: Cc1ccc(C(=O)Nc2cccc(C(F)(F)F)c2)cc1Nc1nc(-c2cccnc2)cn2c(C3CC3)cnc12] | ¹H NMR (600 MHz, DMSO-d₆) δ 10.56 (s, 1H), 9.21 (d, J = 2.2 Hz, 1H), 9.05 (s, 1H), 8.71 (d, J = 1.5 Hz, 1H), 8.64 (s, 1H), 8.51 (dd, J = 4.7, 1.5 Hz, 1H), 8.38 (dt, J = 8.0, 1.9 Hz, 1H), 8.26 (s, 1H), 8.11 (d, J = 8.5 Hz, 1H), 7.78 (dd, J = 7.9, 1.7 Hz, 1H), 7.61 (t, J = 8.0 Hz, 1H), 7.49 (d, J = 8.0 Hz, 1H), 7.46 (d, J = 7.7 Hz, 1H), 7.41 (s, 1H), 7.36 (dd, J = 8.0, 4.7 Hz, 1H), 2.42 (s, 3H), 2.24-2.16 (m, 1H), 1.13-1.06 (m, 2H), 0.84-0.78 (m, 2H). MS (ESI) m/z: 529 [M + H]⁺. |
| VI-b-9 | 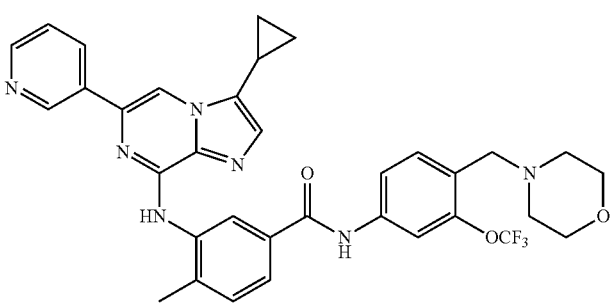 | ¹H NMR (600 MHz, DMSO-d₆) δ 10.46 (s, 1H), 9.24 (dd, J = 2.3, 0.7 Hz, 1H), 8.87 (s, 1H), 8.62 (s, 1H), 8.58 (d, J = 2.1 Hz, 1H), 8.52 (dd, J = 4.7, 1.6 Hz, 1H), 8.49-8.46 (m, 1H), 8.29 (s, 1H), 8.26 (d, J = 8.1 Hz, 1H), 7.96 (d, J = 8.2 Hz, 1H), 7.44 (dd, J = 8.2, 2.2 Hz, 1H), 7.42-7.40 (m, 1H), 7.39 (d, J = 0.8 Hz, 1H), 7.28 (d, J = 8.6 Hz, 1H), 3.71 (s, 2H), 2.46-2.38 (m, 8H), 2.31 (s, 3H), 2.25-2.17 (m, 1H), 1.13-1.09 (m, 2H), 0.84-0.79 (m, 2H). MS (ESI) m/z: 628 [M + H]⁺. |

Synthetic Route of Compound VII-a-1:

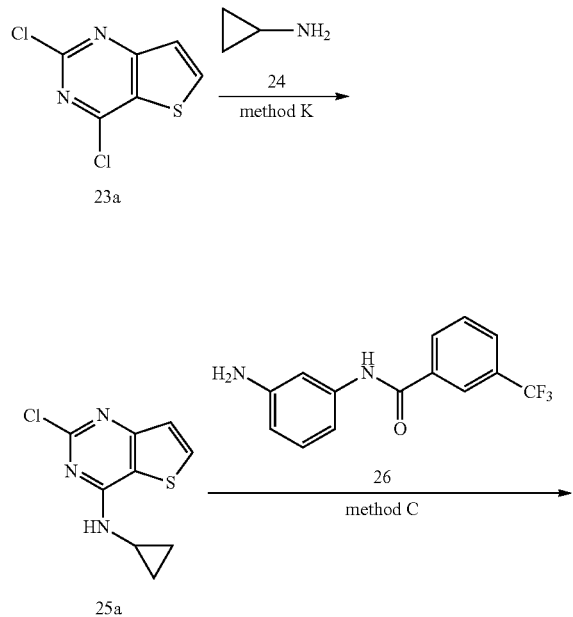

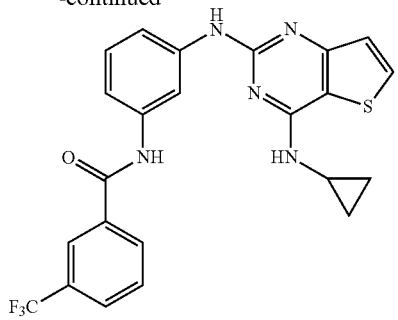

Preparation of Compound 25a:

Method K: compound 23a (410 mg, 2 mmol), cyclopropylamine (166 μL, 2.4 mmol) and diisopropylethylamine (0.5 mL, 3 mmol) were reacted in 2-butanol at 75° C., monitored by TLC until complete reaction. The system was concentrated, and purified by column chromatography to obtain the target product 347 mg, in 77% yield.

MS (ESI) m/z: 226 [M+H]$^+$.

Compound VII-a-1 was prepared from 25a and 26 though above Method.

Other such compounds could be synthesized by a similar method.

In the following table it lists the specific compounds and their structural characterization data.

| No. | Structure | $^1$H NMR and/or MS data |
|---|---|---|
| VII-a-1 | 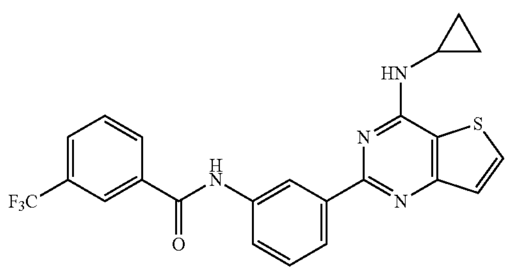 [SMILES: O=C(Nc1cccc(-c2nc(NC3CC3)c3sccc3n2)c1)c1cccc(C(F)(F)F)c1] | $^1$H NMR (600 MHz, DMSO-d$_6$) δ 10.63 (s, 1H), 8.80 (s, 1H), 8.37 (s, 1H), 8.32 (d, J = 7.8 Hz, 1H), 8.24 (d, J = 8.0 Hz, 1H), 8.16 (d, J = 5.4 Hz, 1H), 8.05 (d, J = 3.4 Hz, 1H), 7.98 (t, J = 7.7 Hz, 2H), 7.80 (t, J = 7.8 Hz, 1H), 7.49 (t, J = 7.9 Hz, 1H), 7.45 (d, J = 5.4 Hz, 1H), 1.23 (s, 1H), 0.91-0.85 (m, 2H), 0.71 (m, 2H). MS (ESI) m/z: 455 [M + H]$^+$. |
| VII-a-2 | 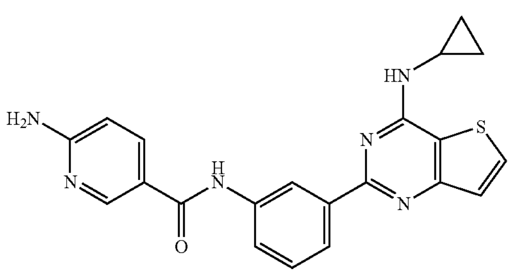 [SMILES: Nc1ccc(C(=O)Nc2cccc(-c3nc(NC4CC4)c4sccc4n3)c2)cn1] | $^1$H NMR (600 MHz, Chloroform-d) δ 8.63 (s, 1H), 8.43 (s, 1H), 8.23 (d, J = 7.6 Hz, 1H), 8.00 (s, 2H), 7.87 (s, 1H), 7.80 (d, J = 5.5 Hz, 1H), 7.48 (d, J = 5.4 Hz, 2H), 6.55 (d, J = 8.6 Hz, 1H), 5.64 (s, 1H), 4.88 (s, 2H), 3.11 (s, 1H), 1.03 (m, J = 6.6 Hz, 2H), 0.83 (m, 2H). MS (ESI) m/z: 403 [M + H]$^+$. |
| VII-a-3 | 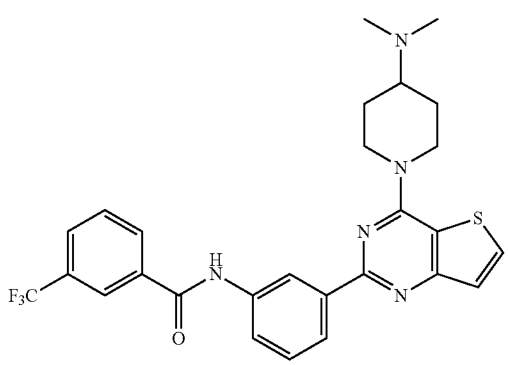 [SMILES: CN(C)C1CCN(c2nc(-c3cccc(NC(=O)c4cccc(C(F)(F)F)c4)c3)nc3ccsc23)CC1] | $^1$H NMR (600 MHz, Methanol-d$_4$) δ 8.72 (t, J = 1.9 Hz, 1H), 8.28 (s, 1H), 8.23 (d, J = 7.8 Hz, 1H), 8.16 (dt, J = 7.8, 1.3 Hz, 1H), 7.98 (d, J = 5.6 Hz, 1H), 7.89 (ddd, J = 7.8, 1.9, 1.0 Hz, 1H), 7.85 (ddd, J = 8.0, 2.3, 1.1 Hz, 1H), 7.72 (t, J = 7.8 Hz, 1H), 7.47 (t, J = 7.9 Hz, 1H), 7.43 (d, J = 5.6 Hz, 1H), 5.03 (dp, J = 14.2, 2.5 Hz, 2H), 3.22-3.14 (m, 2H), 2.79 (tt, J = 11.5, 3.9 Hz, 1H), 2.42 (s, 6H), 2.14-2.07 (m, 2H), 1.59 (qd, J = 12.4, 4.0 Hz, 2H). MS (ESI) m/z: 526 [M + H]$^+$. |

-continued

| No. | Structure | ¹H NMR and/or MS data |
|---|---|---|
| VII-a-4 | 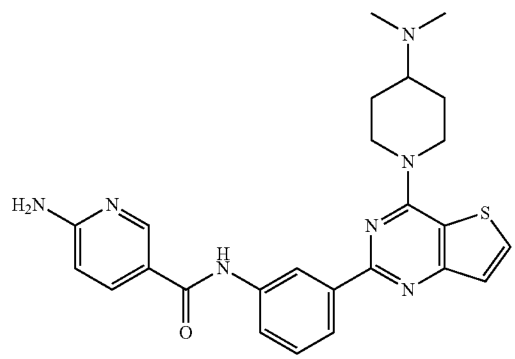 [SMILES: CN(C)C1CCN(c2nc(-c3cccc(NC(=O)c4ccc(N)nc4)c3)nc3ccsc23)CC1] | ¹H NMR (600 MHz, Methanol-d₄) δ 8.66-8.56 (m, 2H), 8.10 (dt, J = 7.8, 1.4 Hz, 1H), 8.00 (dd, J = 8.8, 2.5 Hz, 1H), 7.93 (d, J = 5.5 Hz, 1H), 7.83-7.77 (m, 1H), 7.44-7.37 (m, 2H), 6.60 (d, J = 8.8 Hz, 1H), 5.01-4.93 (m, 2H), 3.11 (td, J = 13.2, 2.4 Hz, 2H), 2.63 (tt, J = 11.5, 3.9 Hz, 1H), 2.33 (s, 6H), 2.08-2.00 (m, 2H), 1.53 (qd, J = 12.3, 3.8 Hz, 2H). MS (ESI) m/z: 474 [M + H]⁺. |
| VII-a-5 | 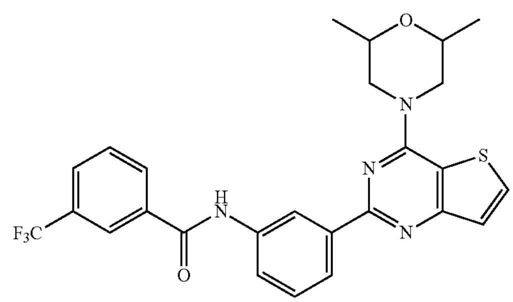 [SMILES: CC1CN(c2nc(-c3cccc(NC(=O)c4cccc(C(F)(F)F)c4)c3)nc3ccsc23)CC(C)O1] | ¹H NMR (600 MHz, Chloroform-d) δ 8.54 (t, J = 1.9 Hz, 1H), 8.32 (s, 1H), 8.23 (dt, J = 7.8, 1.3 Hz, 1H), 8.09 (d, J = 2.1 Hz, 1H), 8.05 (d, J = 7.4 Hz, 1H), 7.98 (d, J = 7.8 Hz, 1H), 7.75 (d, J = 6.8 Hz, 1H), 7.72 (d, J = 5.5 Hz, 1H), 7.55 (t, J = 7.8 Hz, 1H), 7.50 (t, J = 7.9 Hz, 1H), 7.45 (d, J = 5.5 Hz, 1H), 4.74 (dq, J = 13.0, 1.4 Hz, 2H), 3.78 (dqd, J = 10.4, 6.2, 2.3 Hz, 2H), 2.92 (dd, J = 13.2, 10.5 Hz, 2H), 1.32 (d, J = 6.3 Hz, 6H). MS (ESI) m/z: 513 [M + H]⁺. |
| VII-a-6 | 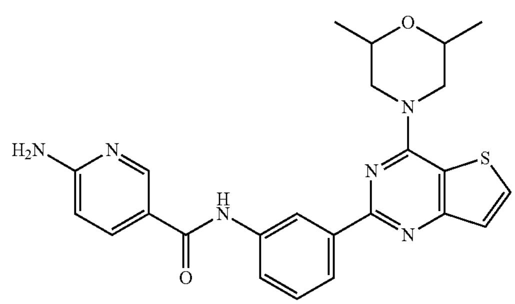 [SMILES: CC1CN(c2nc(-c3cccc(NC(=O)c4ccc(N)nc4)c3)nc3ccsc23)CC(C)O1] | ¹H NMR (600 MHz, Methanol-d₄) δ 8.66 (t, J = 1.9 Hz, 1H), 8.61 (d, J = 2.4 Hz, 1H), 8.15 (dt, J = 7.8, 1.3 Hz, 1H), 8.07-8.03 (m, 2H), 7.82 (ddd, J = 8.0, 2.3, 1.1 Hz, 1H), 7.50-7.46 (m, 2H), 6.65 (d, J = 8.7 Hz, 1H), 4.84 (dd, J = 14.0, 1.7 Hz, 2H), 4.60 (s, 1H), 3.81 (dqd, J = 10.6, 6.2, 2.3 Hz, 2H), 2.96 (dd, d= 13.3, 10.5 Hz, 2H), 1.32 (d, J = 6.2 Hz, 6H). MS (ESI) m/z: 461 [M + H]⁺. |
| VII-a-7 | 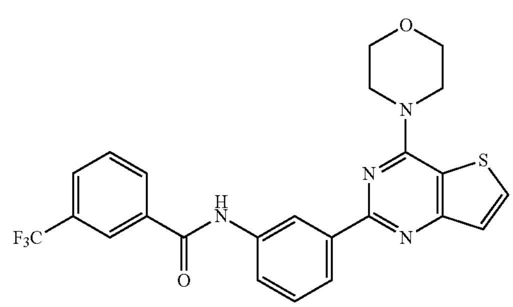 [SMILES: O=C(Nc1cccc(-c2nc(N3CCOCC3)c3sccc3n2)c1)c1cccc(C(F)(F)F)c1] | ¹H NMR (600 MHz, DMSO-d₆) δ 10.64 (s, 1H), 8.76 (t, J = 1.9 Hz, 1H), 8.36 (s, 1H), 8.32 (d, J = 7.8 Hz, 1H), 8.28 (d, J = 5.5 Hz, 1H), 8.20 (dt, J = 7.8, 1.4 Hz, 1H), 8.02-7.97 (m, 2H), 7.81 (t, J = 7.8 Hz, 1H), 7.54 (d, J = 5.5 Hz, 1H), 7.50 (t, J = 7.9 Hz, 1H), 4.07-4.01 (m, 4H), 3.85-3.80 (m, 4H). MS (ESI) m/z: 485 [M + H]⁺. |
| VII-a-8 | 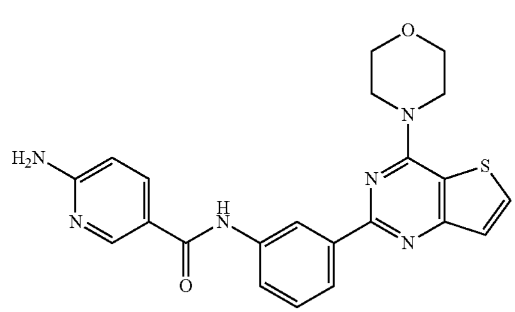 [SMILES: Nc1ccc(C(=O)Nc2cccc(-c3nc(N4CCOCC4)c4sccc4n3)c2)cn1] | ¹H NMR (600 MHz, Chloroform-d) δ 8.62 (d, J = 2.2 Hz, 1H), 8.42 (t, J = 1.9 Hz, 1H), 8.22 (dt, J = 7.8, 1.4 Hz, 1H), 8.06-7.92 (m, 3H), 7.75 (d, J = 5.5 Hz, 1H), 7.52-7.45 (m, 2H), 6.54 (d, J = 8.6 Hz, 1H), 4.92 (s, 2H), 4.11-4.06 (m, 4H), 3.93-3.87 (m, 4H). MS (ESI) m/z: 433 [M + H]⁺. |

| No. | Structure | ¹H NMR and/or MS data |
|---|---|---|
| VII-a-9 | 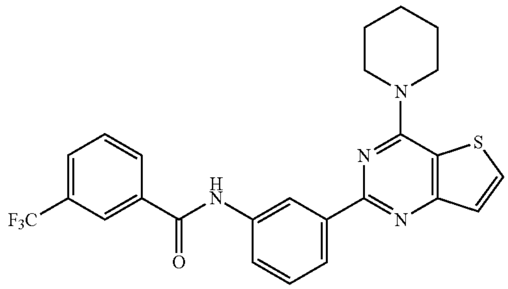 [SMILES: O=C(Nc1cccc(-c2nc(N3CCCCC3)c3sccc3n2)c1)c1cccc(C(F)(F)F)c1] | ¹H NMR (600 MHz, Chloroform-d) δ 8.50 (s, 1H), 8.35 (s, 1H), 8.26 (d, J = 7.8 Hz, 1H), 8.12 (d, J = 11.9 Hz, 2H), 7.99 (d, J = 7.8 Hz, 1H), 7.75 (d, J = 7.8 Hz, 1H), 7.70 (d, J = 5.6 Hz, 1H), 7.56 (t, J = 7.8 Hz, 1H), 7.50 (t, J = 7.9 Hz, 1H), 7.44 (d, J = 5.5 Hz, 1H), 4.04 (t, J = 4.9 Hz, 4H), 1.83-1.70 (m, 6H). MS (ESI) m/z: 483 [M + H]⁺. |
| VII-a-10 | 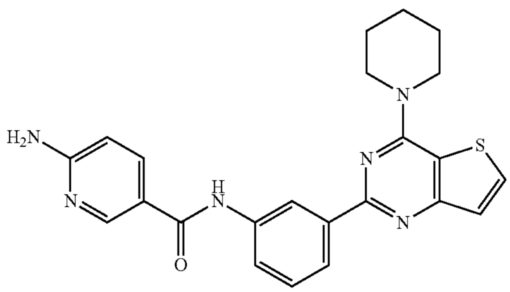 [SMILES: Nc1ccc(C(=O)Nc2cccc(-c3nc(N4CCCCC4)c4sccc4n3)c2)cn1] | ¹H NMR (600 MHz, DMSO-d₆) δ 10.07 (s, 1H), 8.71 (t, J = 2.0 Hz, 1H), 8.64 (d, J = 2.4 Hz, 1H), 8.21 (d, J = 5.5 Hz, 1H), 8.12 (dt, J = 7.7, 1.4 Hz, 1H), 7.98 (dd, J = 8.7, 2.5 Hz, 1H), 7.94 (ddd, J = 8.1, 2.2, 1.1 Hz, 1H), 7.50 (d, J = 5.5 Hz, 1H), 7.43 (t, J = 7.9 Hz, 1H), 6.61 (s, 2H), 6.49 (dd, J = 8.7, 0.8 Hz, 1H), 4.04 (t, J = 5.3 Hz, 4H), 1.77-1.65 (m, 6H). MS (ESI) m/z: 431 [M + H]⁺. |
| VII-a-11 | 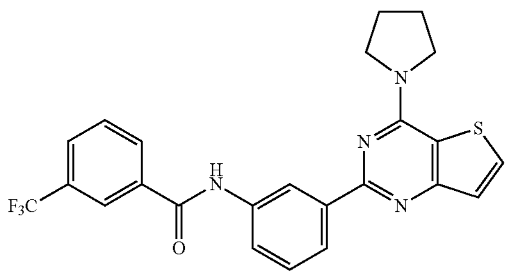 [SMILES: O=C(Nc1cccc(-c2nc(N3CCCC3)c3sccc3n2)c1)c1cccc(C(F)(F)F)c1] | ¹H NMR (600 MHz, DMSO-d₆) δ 10.63 (s, 1H), 8.77 (t, J = 1.9 Hz, 1H), 8.36 (s, 1H), 8.32 (d, J = 7.9 Hz, 1H), 8.23-8.19 (m, 2H), 7.98 (ddd, J = 7.9, 2.1, 1.0 Hz, 2H), 7.81 (t, J = 7.8 Hz, 1H), 7.50-7.45 (m, 2H), 3.94 (s, 4H), 2.05 (s, 4H). MS (ESI) m/z: 469 [M + H]⁺. |
| VII-a-12 | 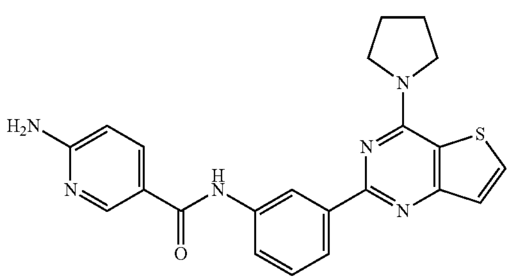 [SMILES: Nc1ccc(C(=O)Nc2cccc(-c3nc(N4CCCC4)c4sccc4n3)c2)cn1] | ¹H NMR (600 MHz, Methanol-d₄) δ 8.61-8.57 (m, 2H), 8.12 (ddd, J = 7.8,1.7,1.1 Hz, 1H), 8.02 (dd, J = 8.8, 2.5 Hz, 1H), 7.96 (d, J = 5.5 Hz, 1H), 7.82 (ddd, J = 8.0, 2.3, 1.1 Hz, 1H), 7.43 (t, J = 7.9 Hz, 1H), 7.39 (d, J = 5.5 Hz, 1H), 6.63 (dd, J = 8.8, 0.8 Hz, 1H), 3.97 (s, 4H), 2.08 (s, 4H). MS (ESI) m/z: 417 [M + H]⁺. |
| VII-a-13 | 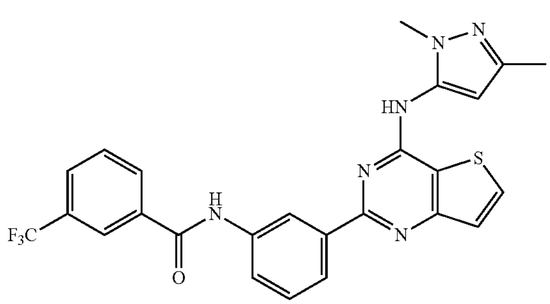 | ¹H NMR (600 MHz, Methanol-d₄) δ 8.73 (t, J = 1.9 Hz, 1H), 8.31 (d, J = 1.8 Hz, 1H), 8.25 (d, J = 7.8 Hz, 1H), 8.15-8.11 (m, 2H), 7.91 (d, J = 7.8 Hz, 1H), 7.81 (ddd, J = 8.0, 2.3, 1.1 Hz, 1H), 7.75 (t, J = 7.8 Hz, 1H), 7.67-7.62 (m, 1H), 7.52-7.48 (m, 2H), 6.25 (s, 1H), 3.71 (s, 3H), 2.30 (s, 3H). MS (ESI) m/z: 506 [M + H]⁺. |

| No. | Structure | ¹H NMR and/or MS data |
| --- | --- | --- |
| VII-a-14 | 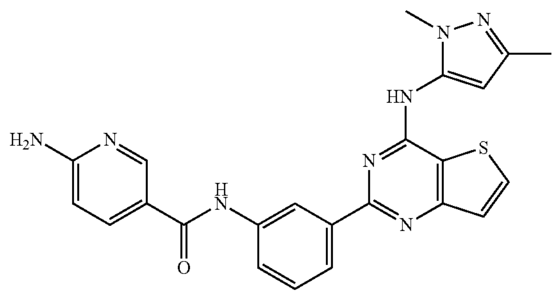 [SMILES: Cc1cc(Nc2nc(-c3cccc(NC(=O)c4ccc(N)nc4)c3)nc3ccsc23)n(C)n1] | ¹H NMR (600 MHz, DMSO-d₆) δ 10.08 (s, 1H), 9.73 (s, 1H), 8.78 (d, J = 1.9 Hz, 1H), 8.65 (d, J = 2.4 Hz, 1H), 8.23 (d, J = 5.4 Hz, 1H), 8.04-7.95 (m, 2H), 7.86 (d, J = 8.0 Hz, 1H), 7.51 (d, J = 5.3 Hz, 1H), 7.43 (t, J = 7.9 Hz, 1H), 6.61 (s, 2H), 6.49 (d, J = 8.7 Hz, 1H), 6.19 (s, 1H), 3.61 (s, 3H), 2.21 (s, 3H). MS (ESI) m/z: 458 [M + H]⁺. |
| VII-a-15 | 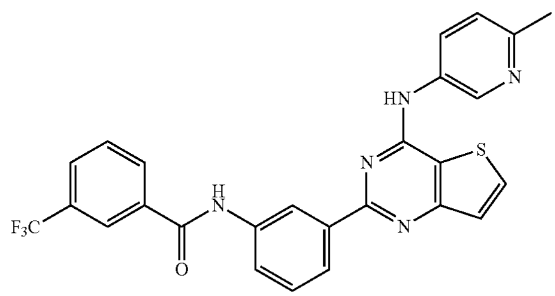 [SMILES: Cc1ccc(Nc2nc(-c3cccc(NC(=O)c4cccc(C(F)(F)F)c4)c3)nc3ccsc23)cn1] | ¹H NMR (600 MHz, DMSO-d₆) δ 10.67 (s, 1H), 9.93 (s, 1H), 8.92 (s, 1H), 8.86 (t, J = 2.0 Hz, 1H), 8.39 (s, 1H), 8.34 (d, J = 8.0 Hz, 2H), 8.30 (d, J = 5.4 Hz, 1H), 8.13 (dt, J = 7.7, 1.3 Hz, 1H), 7.99 (d, J = 7.8 Hz, 1H), 7.98-7.94 (m, 1H), 7.82 (t, J = 7.8 Hz, 1H), 7.56 (d, J = 5.3 Hz, 1H), 7.52 (t, J = 7.9 Hz, 1H), 7.39 (d, J = 8.3 Hz, 1H), 3.17 (s, 3H). MS (ESI) m/z: 507 [M + H]⁺. |
| VII-a-16 | 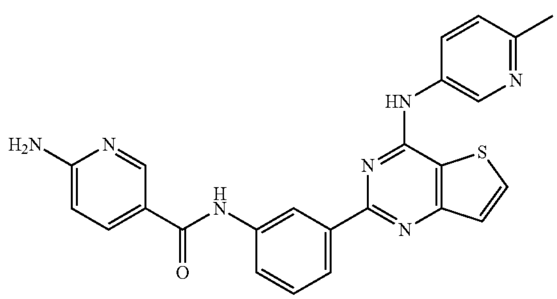 [SMILES: Cc1ccc(Nc2nc(-c3cccc(NC(=O)c4ccc(N)nc4)c3)nc3ccsc23)cn1] | ¹H NMR (600 MHz, DMSO-d₆) δ 10.09 (s, 1H), 9.88 (s, 1H), 8.90 (d, J = 2.7 Hz, 1H), 8.82 (t, J = 1.9 Hz, 1H), 8.68-8.64 (m, 1H), 8.32 (dd, J = 8.4, 2.7 Hz, 1H), 8.29 (d, J = 5.4 Hz, 1H), 8.06 (dt, J = 7.8, 1.4 Hz, 1H), 8.00 (dd, J = 8.7, 2.5 Hz, 1H), 7.88 (ddd, J = 8.1, 2.2, 1.1 Hz, 1H), 7.56 (d, J = 5.3 Hz, 1H), 7.46 (t, J = 7.9 Hz, 1H), 7.36 (d, J = 8.4 Hz, 1H), 6.62 (s, 2H), 6.50 (dd, J = 8.7, 0.7 Hz, 1H), 1.04 (d, J = 6.1 Hz, 3H). MS (ESI) m/z: 454 [M + H]⁺. |
| VII-a-17 | 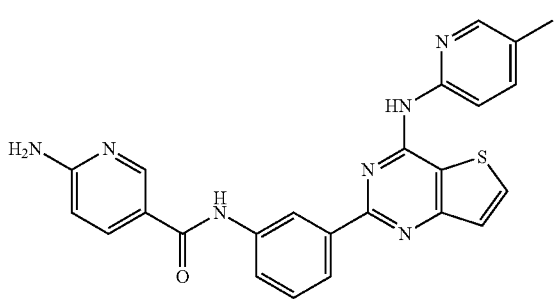 [SMILES: Cc1ccc(Nc2nc(-c3cccc(NC(=O)c4ccc(N)nc4)c3)nc3ccsc23)nc1] | ¹H NMR (600 MHz, DMSO-d₆) δ 10.40 (s, 1H), 10.10 (s, 1H), 8.90 (t, J = 2.0 Hz, 1H), 8.69-8.64 (m, 1H), 8.30-8.22 (m, 3H), 8.12 (dt, J = 7.9, 1.4 Hz, 1H), 8.01 (dd, J = 8.7, 2.5 Hz, 1H), 7.87 (ddd, J = 8.1, 2.2, 1.1 Hz, 1H), 7.77 (dd, J = 8.6, 2.4 Hz, 1H), 7.53 (d, J = 5.4 Hz, 1H), 7.47 (t, J = 7.9 Hz, 1H), 6.63 (s, 2H), 6.51 (dd, J = 8.8, 0.8 Hz, 1H), 2.32 (d, J = 1.0 Hz, 3H). MS (ESI) m/z: 454 [M + H]⁺. |
| VII-a-18 | 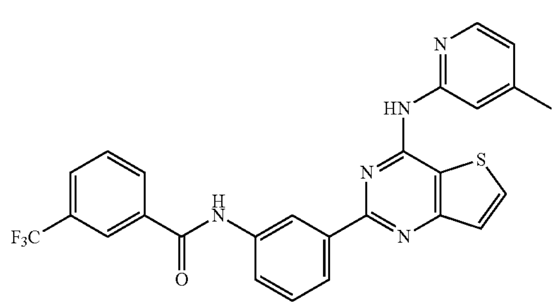 [SMILES: Cc1ccnc(Nc2nc(-c3cccc(NC(=O)c4cccc(C(F)(F)F)c4)c3)nc3ccsc23)c1] | ¹H NMR (600 MHz, DMSO-d₆) δ 10.68 (s, 1H), 10.42 (s, 1H), 8.89 (t, J = 1.9 Hz, 1H), 8.39 (d, J = 2.1 Hz, 1H), 8.34 (d, J = 7.8 Hz, 1H), 8.29 (d, J = 5.4 Hz, 1H), 8.25 (d, J = 5.1 Hz, 1H), 8.23 (dt, J = 7.8, 1.4 Hz, 1H), 8.17 (s, 1H), 8.01-7.97 (m, 1H), 7.94 (ddd, J = 8.1, 2.2, 1.1 Hz, 1H), 7.81 (t, J = 7.8 Hz, 1H), 7.58-7.51 (m, 2H), 6.99 (dd, J = 5.1, 1.3 Hz, 1H), 2.41 (s, 3H). MS (ESI) m/z: 506 [M + H]⁺. |

-continued

| No. | Structure | $^1$H NMR and/or MS data |
|---|---|---|
| VII-a-19 | 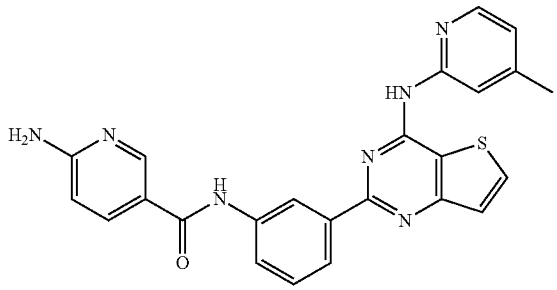 [SMILES: Cc1ccnc(Nc2nc(-c3cccc(NC(=O)c4ccc(N)nc4)c3)nc3ccsc23)c1] | $^1$H NMR (600 MHz, DMSO-$d_6$) δ 10.40 (s, 1H), 10.10 (s, 1H), 8.86 (q, J = 2.8, 1.8 Hz, 1H), 8.66 (d, J = 2.5 Hz, 1H), 8.27 (dd, J = 18.4, 5.2 Hz, 2H), 8.22-8.12 (m, 2H), 7.99 (dd, J = 8.7, 2.5 Hz, 1H), 7.89-7.81 (m, 1H), 7.54 (d, J = 5.4 Hz, 1H), 7.49 (t, J = 7.9 Hz, 1H), 6.99 (d, J = 5.0 Hz, 1H), 6.62 (s, 2H), 6.50 (d, J = 8.7 Hz, 1H), 2.41 (s, 3H). MS (ESI) m/z: 454 [M + H]$^+$. |

Synthetic Route of Compound VIII-a-1:

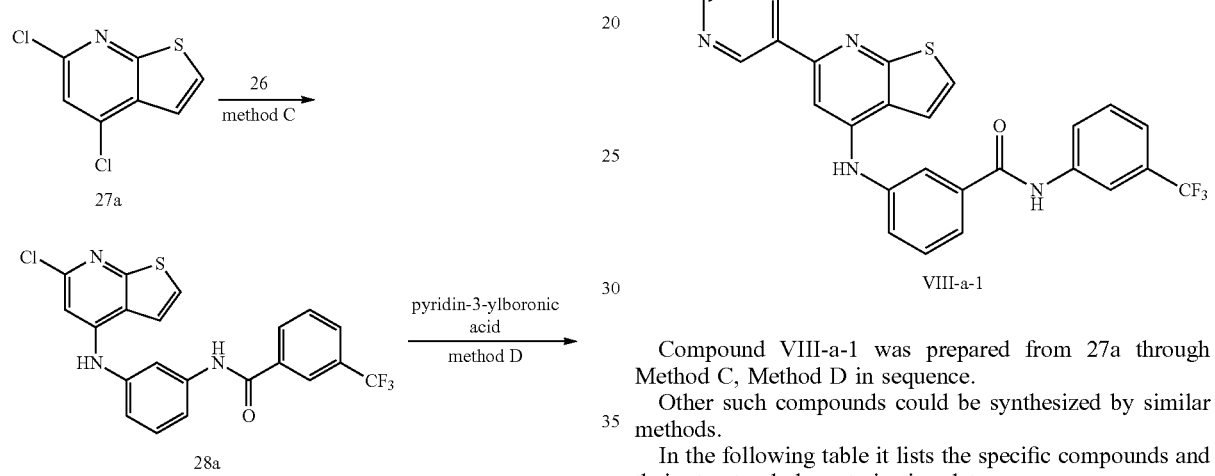

Compound VIII-a-1 was prepared from 27a through Method C, Method D in sequence.

Other such compounds could be synthesized by similar methods.

In the following table it lists the specific compounds and their structural characterization data.

| No. | Structure | $^1$H NMR and/or MS data |
|---|---|---|
| VIII-a-1 | TFA salt | $^1$H NMR (600 MHz, DMSO-$d_6$) δ 10.62 (s, 1H), 9.38 (s, 2H), 8.87-8.76 (m, 2H), 8.35-8.27 (m, 2H), 8.10 (d, J = 2.1 Hz, 1H), 7.98 (d, J = 7.7 Hz, 1H), 7.85 (d, J = 6.0 Hz, 2H), 7.80 (t, J = 7.8 Hz, 1H), 7.77 (d, J = 6.0 Hz, 1H), 7.67 (s, 1H), 7.52-7.42 (m, 2H), 7.19 (dt, J = 6.5, 2.3 Hz, 1H). MS (ESI) m/z: 491 [M + H]$^+$. |
| VIII-a-2 | 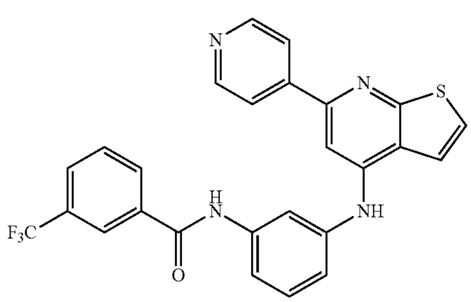 [SMILES: O=C(Nc1cccc(Nc2cc(-c3ccncc3)nc3sccc23)c1)c1cccc(C(F)(F)F)c1] | $^1$H NMR (600 MHz, DMSO-$d_6$) δ 10.60 (s, 1H), 9.23 (s, 1H), 8.68-8.63 (m, 2H), 8.32 (s, 1H), 8.29 (d, J = 8.0 Hz, 1H), 8.08 (t, J = 2.1 Hz, 1H), 8.04-8.01 (m, 2H), 7.99-7.95 (m, 1H), 7.82 (d, J = 6.1 Hz, 1H), 7.80 (s, 1H), 7.74 (d, J = 6.0 Hz, 1H), 7.67 (s, 1H), 7.50-7.42 (m, 2H), 7.18 (dt, J = 7.7, 1.6 Hz, 1H). MS (ESI) m/z: 491 [M + H]$^+$. |

| No. | Structure | ¹H NMR and/or MS data |
|---|---|---|
| VIII-a-3 | 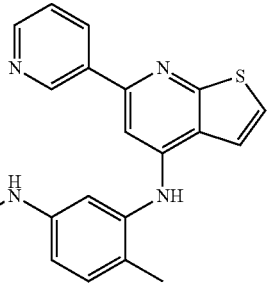 TFA salt | ¹H NMR (600 MHz, DMSO-$d_6$) δ 10.56 (s, 1H), 9.20 (s, 1H), 9.04 (s, 1H), 8.72 (d, J = 5.0 Hz, 1H), 8.56 (d, J = 8.0 Hz, 1H), 8.28 (s, 1H), 8.26 (d, J = 8.0 Hz, 1H), 7.96 (d, J = 7.8 Hz, 1H), 7.91 (d, J = 2.2 Hz, 1H), 7.81 (d, J = 6.1 Hz, 1H), 7.78 (t, J = 7.8 Hz, 1H), 7.73 (dd, J = 6.8, 3.4 Hz, 2H), 7.62 (dd, J = 8.3, 2.2 Hz, 1H), 7.40 (d, J = 8.4 Hz, 1H), 6.91 (s, 1H), 2.24 (s, 3H). MS (ESI) m/z: 505 [M + H]⁺. |
| VIII-a-4 | 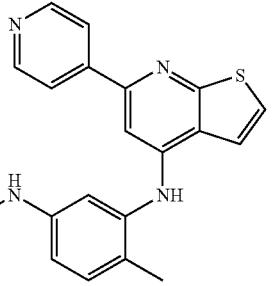 | ¹H NMR (600 MHz, DMSO-$d_6$) δ 10.53 (s, 1H), 8.87 (s, 1H), 8.63-8.61 (m, 2H), 8.30-8.28 (m, 1H), 8.27-8.24 (m, 1H), 7.95 (ddd, J = 8.6, 1.9, 0.9 Hz, 1H), 7.89 (d, J = 2.2 Hz, 1H), 7.87-7.85 (m, 2H), 7.78 (d, J = 6.3 Hz, 2H), 7.71 (d, J = 6.1 Hz, 1H), 7.64 (dd, J = 8.3, 2.3 Hz, 1H), 7.40 (dd, J = 8.2, 0.8 Hz, 1H), 6.91 (s, 1H), 2.23 (s, 3H). MS (ESI) m/z: 505 [M + H]⁺. |
| VIII-a-5 | 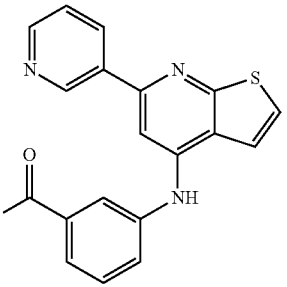 | ¹H NMR (600 MHz, DMSO-$d_6$) δ 10.59 (s, 1H), 9.31 (s, 1H), 9.14 (d, J = 2.3 Hz, 1H), 8.60 (dd, J = 4.7, 1.6 Hz, 1H), 8.33 (dt, J = 8.0, 1.9 Hz, 1H), 8.25 (d, J = 2.0 Hz, 1H), 8.08-8.05 (m, 1H), 7.99 (t, J = 2.0 Hz, 1H), 7.78 (t, J = 5.7 Hz, 2H), 7.74 (d, J = 6.1 Hz, 1H), 7.72-7.69 (m, 1H), 7.61 (q, J = 7.8 Hz, 2H), 7.50 (s, 1H), 7.50-7.48 (m, 1H), 7.47-7.45 (m, 1H). MS (ESI) m/z: 491 [M + H]⁺. |
| VIII-a-6 | 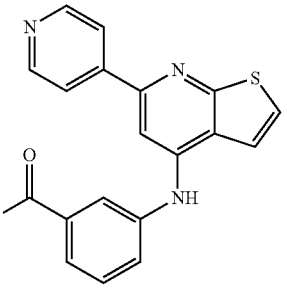 | ¹H NMR (600 MHz, DMSO-$d_6$) δ 10.60 (s, 1H), 9.35 (s, 1H), 8.76-8.58 (m, 2H), 8.25 (d, J = 1.9 Hz, 1H), 8.07 (dd, J = 8.2, 1.9 Hz, 1H), 7.99 (t, J = 2.0 Hz, 1H), 7.97-7.93 (m, 2H), 7.82-7.76 (m, 3H), 7.70 (dd, J = 7.8, 2.2 Hz, 1H), 7.62 (dt, J = 10.9, 7.9 Hz, 2H), 7.56 (s, 1H), 7.46 (d, J = 7.8 Hz, 1H). MS (ESI) m/z: 491 [M + H]⁺. |
| VIII-a-7 | 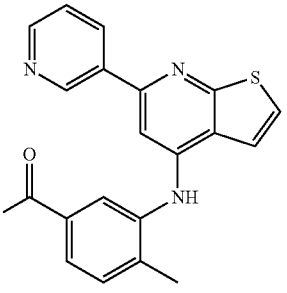 TFA salt | ¹H NMR (600 MHz, DMSO-$d_6$) δ 10.51 (s, 1H), 9.24 (s, 2H), 8.80 (s, 1H), 8.71 (d, J = 8.1 Hz, 1H), 8.23 (s, 1H), 8.07-8.02 (m, 2H), 7.97 (d, J = 7.9 Hz, 1H), 7.88 (s, 1H), 7.83-7.77 (m, 2H), 7.64-7.55 (m, 2H), 7.44 (d, J = 7.7 Hz, 1H), 6.80 (s, 1H), 2.33 (s, 3H). MS (ESI) m/z: 505 [M + H]⁺. |

| No. | Structure | ¹H NMR and/or MS data |
|---|---|---|
| VIII-a-8 | 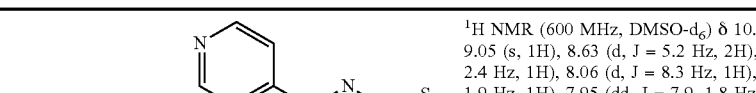<br>TFA salt | ¹H NMR (600 MHz, DMSO-$d_6$) δ 10.52 (s, 1H), 9.05 (s, 1H), 8.63 (d, J = 5.2 Hz, 2H), 8.22 (d, J = 2.4 Hz, 1H), 8.06 (d, J = 8.3 Hz, 1H), 8.02 (d, J = 1.9 Hz, 1H), 7.95 (dd, J = 7.9, 1.8 Hz, 1H), 7.86 (d, J = 5.3 Hz, 2H), 7.76 (s, 2H), 7.64-7.55 (m, 2H), 7.44 (d, J = 7.8 Hz, 1H), 6.76 (s, 1H), 2.32 (s, 3H). MS (ESI) m/z: 505 [M + H]⁺. |

Biological Activity Assay.

I. Determination of Vacuolation of MDA-MB-231 Cells Caused by Inhibition of Compounds on PIKfyve When the activity of pikfyve kinase is inhibited, vacuoles will be produced in cytoplasm. By observing the number of vacuoles under a microscope, the ability of compounds to inhibit the activity of pikfyve kinase can be known.

Experimental Method:

1. Cell plating: cells in logarithmic growth phase were made into a single cell suspension, counted with a cell counter and diluted to a cell concentration of about $2\times10^5$/mL. Then, the cells were inoculated into a 12-well plate, and cultured in a 37° C., 5% $CO_2$ incubator.

2. Administrating agent to cell: after cell adherence, drug samples (each drug sample had two concentration gradients 1 μmol/L, 10 μmol/L) diluted with culture medium were added to cells, with DMSO as negative control.

3. Vacuolation test: after 24 and 48 hours of culture, photos were taken under an electron microscope to observe the degree of vacuolation.

In the following table it lists the vacuolation test results of some compounds. (In the table, "+" represents the degree of vacuolation; more "+" indicates more obvious vacuolation; "−" represents no vacuolation)

| No. | 1 μM, 24 h | 10 μM, 24 h | 1 μM, 48 h | 10 μM, 48 h |
|---|---|---|---|---|
| I-a-1 | +++ | +++ | +++ | +++ |
| I-a-10 | − | ++ | − | ++ |
| I-a-20 | +++ | ++++ | +++ | ++++ |
| I-a-21 | − | − | − | − |
| I-a-24 | − | − | − | − |
| I-a-25 | + | + | + | + |
| I-a-26 | − | − | − | − |
| I-a-27 | + | + | − | − |
| I-a-30 | + | + | + | + |
| I-a-31 | − | − | − | − |
| I-a-32 | + | + | ++ | ++ |
| I-a-33 | + | + | ++ | ++ |
| I-a-34 | + | + | ++ | ++ |
| I-a-35 | + | + | ++ | ++ |
| I-a-38 | + | ++ | + | ++ |
| I-a-40 | + | + | + | + |
| I-a-45 | − | + | + | + |
| I-b-1 | ++ | +++ | ++ | +++ |
| I-b-2 | − | ++ | − | ++ |
| I-b-3 | + | ++ | + | ++ |
| I-b-4 | − | +/2 | − | +/2 |
| I-b-5 | − | + | − | + |
| I-c-11 | ++ | ++ | ++ | ++ |
| I-c-12 | +++ | +++ | +++ | +++ |
| II-a-1 | +/2 | +/2 | + | + |
| II-a-2 | + | + | + | + |
| II-a-4 | − | + | − | + |
| II-b-2 | + | + | + | + |
| III-b-1 | + | + | ++ | ++ |
| III-b-2 | − | − | − | − |
| III-b-3 | − | − | +/2 | +/2 |
| III-b-10 | − | − | + | + |
| III-b-14 | + | + | + | + |
| III-b-15 | − | + | − | + |
| IV-a-1 | + | + | ++ | ++ |
| IV-a-2 | + | + | ++ | ++ |
| IV-a-3 | +/2 | +/2 | + | + |
| IV-a-5 | + | + | − | − |
| IV-a-7 | − | + | − | ++ |
| IV-b-2 | + | + | + | + |
| IV-b-7 | + | + | + | + |
| IV-b-9 | +/2 | +/2 | − | − |
| IV-b-10 | +/2 | +/2 | − | − |
| IV-b-11 | + | +/2 | + | + |
| V-a-1 | − | + | − | + |
| V-a-3 | ++ | + | ++ | + |
| V-a-4 | − | − | − | − |
| V-a-5 | +++ | ++ | +++ | ++ |
| V-a-6 | ++ | ++ | ++ | ++ |
| V-a-7 | − | + | − | + |
| V-a-8 | + | ++ | + | ++ |
| V-a-10 | ++ | − | ++ | − |
| V-b-1 | ++ | ++ | ++ | ++ |
| V-b-2 | − | ++ | − | ++ |
| V-b-3 | + | ++ | + | ++ |
| V-b-4 | ++ | ++ | ++ | ++ |
| V-b-7 | + | − | + | − |
| V-b-29 | + | − | − | − |
| V-b-30 | − | + | − | + |
| V-c-1 | − | ++ | − | ++ |
| V-c-2 | − | − | − | − |
| V-c-3 | + | ++ | + | ++ |
| V-c-4 | ++ | +++ | ++ | +++ |
| V-c-6 | + | +++ | ++ | +++ |
| V-c-7 | ++ | + | ++ | + |
| V-c-8 | +++ | +++ | +++ | +++ |
| V-c-10 | − | ++ | − | ++ |
| V-c-11 | − | − | − | − |
| V-c-12 | +++ | +++ | +++ | +++ |
| V-c-13 | ++ | ++ | − | ++ |
| V-c-14 | ++ | ++ | − | ++ |
| V-c-15 | ++ | ++ | ++ | ++ |
| V-c-16 | ++ | ++ | ++ | ++ |
| V-c-17 | ++ | ++ | − | + |
| V-c-18 | +++ | +++ | +++ | +++ |
| V-c-19 | +++ | +++ | +++ | +++ |
| V-c-20 | − | − | ++ | ++ |
| V-c-23 | ++ | ++ | − | − |
| V-c-25 | − | − | − | − |
| V-c-35 | − | + | − | + |

-continued

| No. | 1 μM, 24 h | 10 μM, 24 h | 1 μM, 48 h | 10 μM, 48 h |
|---|---|---|---|---|
| V-c-40 | + | + | +++ | +++ |
| VI-a-2 | + | + | + | + |
| VI-a-5 | − | − | + | + |
| VI-a-6 | − | − | +/2 | +/2 |
| VI-a-8 | +/2 | +/2 | − | − |
| VI-b-4 | − | + | − | + |
| VI-b-6 | − | − | − | − |
| VI-b-7 | − | + | − | + |
| VII-a-15 | + | + | + | + |
| VII-a-16 | + | + | + | + |
| VII-a-17 | − | − | − | − |
| VII-a-18 | + | + | + | + |
| VII-a-19 | − | − | − | − |
| VIII-a-1 | ++ | ++ | ++ | ++ |
| VIII-a-2 | ++ | ++ | ++ | ++ |
| VIII-a-3 | ++ | ++ | ++ | ++ |
| VIII-a-4 | + | + | + | + |
| VIII-a-5 | − | + | + | + |
| VIII-a-6 | + | + | + | + |
| VIII-a-7 | ++ | +++ | ++ | +++ |
| VIII-a-8 | − | − | ++ | ++ |

II. Determination of Dissociation Equilibrium Constant (Kd Value) of Compound and PIKfyve Protein The Kd value was determined by DiscoverX's KINOMEscan™ technology according to the following steps:

1. Preparation of magnetic beads: biotin-labeled small molecule ligand and avidin-coated magnetic beads were allowed to interact at room temperature for 30 minutes, and then added with excess biotin, followed by washing with a blocking solution (1% BSA, 0.05% Tween 20, 1 mM DTT) to remove unbound ligand.

2. Binding reaction: in a 384 plate, 0.02 mL system, DNA-labeled protein, small molecule ligand-bound magnetic beads, and different concentrations of compound to be tested were mixed in a reaction solution (0.17×PBS, 0.05% Tween 20, 6 mM DTT) at room temperature with shaking for 1 hr, to which was added an eluant (1×PBS, 0.05% Tween 20) for elution. Magnetic beads were resuspended by an eluant (1×PBS, 0.05% Tween 20, 0.5 μM non-biotin-labeled small molecule ligand), and shaken at room temperature for 30 min before separating out the eluant.

3. Determination of Kd value: the content of protein in the above eluate was determined by qPCR. Eleven 3-fold dilution concentrations were determined for the compound to be tested, with 3 DMSO controls for each concentration, and the Kd value was obtained by curve fitting.

In the following table it lists the Kd values of some compounds.

| No. | $K_d$ value (μM) |
|---|---|
| V-c-1 | 130 |
| V-c-2 | 2000 |
| V-c-10 | 3500 |
| V-c-11 | 700 |
| V-c-12 | >30000 |
| V-c-13 | 16 |
| V-c-14 | 20 |
| V-c-15 | 140 |
| V-c-16 | 110 |
| V-c-17 | 640 |
| V-c-18 | 6.4 |
| V-c-19 | 16 |
| V-c-19 | 15 |
| V-c-20 | 1000 |
| V-c-21 | 910 |
| V-c-22 | 21000 |
| V-c-23 | 33 |
| V-c-24 | >30000 |
| V-c-38 | >30000 |
| V-c-39 | >30000 |
| V-c-4 | 33 |
| V-c-40 | 380 |
| V-c-41 | >30000 |
| V-c-42 | >30000 |
| V-c-43 | >30000 |
| V-c-51 | >30000 |
| V-c-52 | >30000 |
| V-c-53 | >30000 |
| V-c-6 | 16 |
| V-c-61 | >30000 |
| V-c-62 | >30000 |
| V-c-63 | >30000 |
| V-c-8 | 13 |
| V-c-9 | 29 |

III. Determination of $IC_{50}$ Value of Compound for Inhibiting Tumor Cell Growth by MTS Method Experimental Method:

1. Cell plating: cells in logarithmic growth phase were counted and inoculated in a 96-well plate (20000 cells per well).

2. Administrating agent to cell: 10 mM compound mother solution in DMSO was subjected to 3 fold-gradient dilution, to set 8 concentrations, which were then added to various wells, with three replicates for each concentration, and three blank wells (only culture medium) and three negative controls (containing 0.1% DMSO) on each plate.

3. Determination of $IC_{50}$ value: after 5 days of culture, 20 μL of MTS reaction solution was added, followed by uniform mixing, and incubation in a cell culture incubator (37° C.; 5% $CO_2$) for 1-4 hr. The OD value at 490 nm was measured with microplate reader $OD_{490}$. The cell growth inhibition rate was calculated by the following formula:

Cell growth inhibition rate %=1−
($OD_{experimental\ group}$−$OD_{blank\ group}$)/
($OD_{negative\ group}$−$OD_{blank\ group}$)×100%

The semi-inhibitory concentration $IC_{50}$ of the compound acting on cell growth was calculated using GradPad Prism 5 software according to the measured cell growth inhibition rate.

In the following table it lists the $IC_{50}$ value or the inhibition rates of some compounds at 10 μM against JeKo-1 cells

| No. | $IC_{50}$ value (μM) |
|---|---|
| I-a-1 | 2.04 |
| I-a-20 | 2.54 |
| I-a-25 | 2.13 |
| I-b-1 | 2.77 |
| I-b-2 | 1.60 |
| I-b-3 | 2.68 |
| I-b-4 | 1.33 |
| I-c-11 | 6.13 |
| I-c-12 | 1.10 |
| II-a-1 | 17.3%[a] |
| II-a-2 | 43.4%[a] |
| II-a-4 | 18.7%[a] |
| II-b-2 | 2.85 |
| III-b-1 | 0.939 |
| III-b-10 | 1.88 |
| III-b-14 | 6.78 |
| III-b-15 | 24.1%[a] |

-continued

| No. | IC$_{50}$ value (μM) |
|---|---|
| III-b-3 | 4.86 |
| III-c-1 | 2.00 |
| IV-a-1 | 18.3%$^a$ |
| IV-a-2 | 19.0%$^a$ |
| IV-a-3 | 16.2%$^a$ |
| IV-b-2 | 7.12 |
| IV-b-7 | 19.1%$^a$ |
| V-a-5 | 3.08 |
| V-a-6 | 0.987 |
| V-b-1 | 12.3%$^a$ |
| V-b-4 | 17.2%$^a$ |
| V-c-12 | 2.79 |
| V-c-13 | 34.3%$^a$ |
| V-c-14 | 46.6%$^a$ |
| V-c-15 | 35.1%$^a$ |
| V-c-16 | 6.22 |
| V-c-17 | 0.743 |
| V-c-18 | 0.862 |
| V-c-19 | 2.09 |
| V-c-20 | 9.41 |
| V-c-22 | 1.54 |
| V-c-23 | 15.8%$^a$ |
| V-c-4 | 5.94 |
| V-c-6 | 4.95 |
| V-c-7 | 3.28 |
| V-c-8 | 39.0%$^a$ |
| VI-a-1 | 7.49 |
| VI-a-2 | 38.6%$^a$ |
| VI-a-6 | 11.3%$^a$ |
| VI-b-1 | 17.5%$^a$ |
| VI-b-2 | 14.7%$^a$ |
| VI-b-5 | 16.9%$^a$ |
| VI-b-7 | 16.5%$^a$ |
| VI-b-9 | 37.0%$^a$ |
| VII-a-15 | 2.67 |
| VII-a-16 | 0.824 |
| VII-a-17 | 1.15 |
| VII-a-18 | 2.56 |
| VII-a-19 | 1.52 |
| VIII-a-1 | 2.71 |
| VIII-a-2 | 3.26 |
| VIII-a-3 | 2.01 |
| VIII-a-4 | 17.3%$^a$ |
| VIII-a-5 | 5.14 |
| VIII-a-6 | 6.32 |
| VIII-a-7 | 3.17 |
| VIII-a-8 | 2 |

$^a$represents the cell growth inhibition rate of compounds at 10 μM.

In the following table it lists the inhibition rates of compound I-a-1 at 3.3 μM against multiple tumor cells.

| Cell Lines | Inhibition rate % |
|---|---|
| A375 | 93.97 |
| SK-MEL-28 | 64.03 |
| SK-MEL-30 | 61.87 |
| A549 | 65.3 |
| MDA-MB-231 | 48.39 |
| MDA-MB-435S | 56.23 |
| MCF-7 | 44.23 |
| HCT116 | 55.83 |
| BGC823 | 53.95 |
| HepG2 | 64.85 |

IV. Determination of Growth Inhibition Rates of Compounds Against PIKfyve-Mediated Tumor Cells by Cell Titer Glo Method Experimental Method:

1. Cell plating: cells in logarithmic growth phase were counted and inoculated in 384-well plate.

2. Administrating agent to cell: compound (3.3 μM DMSO solution) or blank control (DMSO) was added to various wells, with two replicates for each well.

3. Determination of growth inhibition rate: after 5 days of culture (37° C.; 5% $CO_2$), CellTiter-Glo® was added, followed by shaking for 2 min, centrifugation (90×g) for 30 sec, and then standing at room temperature for 10 min. RLU was measured on PHERAstar Plus. The cell growth inhibition rate was calculated by the following formula:

Cell growth inhibition rate %=1−
    $RLU_{experimental\ group}/RLU_{DMSO}$×100%

In the following table it lists the inhibition rates of some compounds against Toledo and ST486 cells (3.3 10 μM).

| No. | Inhibition rate % (Toledo) | Inhibition rate % (ST486) |
|---|---|---|
| I-a-1 | 99.52 | 98.42 |
| V-c-1 | 43.06 | 35.20 |
| V-c-2 | <10% | 18.01 |
| V-c-4 | 99.55 | 76.17 |
| V-c-6 | 93.93 | 69.86 |
| V-c-7 | 95.82 | 91.34 |
| V-c-8 | 96.33 | 50.96 |
| V-c-9 | 19.27 | 37.67 |
| V-c-10 | 94.84 | 92.98 |
| V-c-11 | 95.35 | 96.15 |
| V-c-12 | 95.57 | 72.33 |
| V-c-13 | 99.65 | 85.25 |
| V-c-14 | 99.56 | 52.24 |
| V-c-15 | 99.60 | 57.54 |
| V-c-16 | 99.55 | 60.33 |
| V-c-17 | 99.65 | 95.67 |
| V-c-18 | 95.21 | 95.98 |
| V-c-19 | 97.26 | 70.63 |
| V-c-20 | 99.66 | 33.29 |
| V-c-21 | 99.51 | 23.77 |
| V-c-22 | 64.25 | 57.14 |
| V-c-23 | 94.89 | 27.23 |
| V-c-24 | 97.30 | 55.78 |
| V-c-38 | 53.31 | 29.96 |
| v-c-39 | 49.11 | 9.57 |
| V-c-40 | 98.83 | 57.10 |

Figure 3:
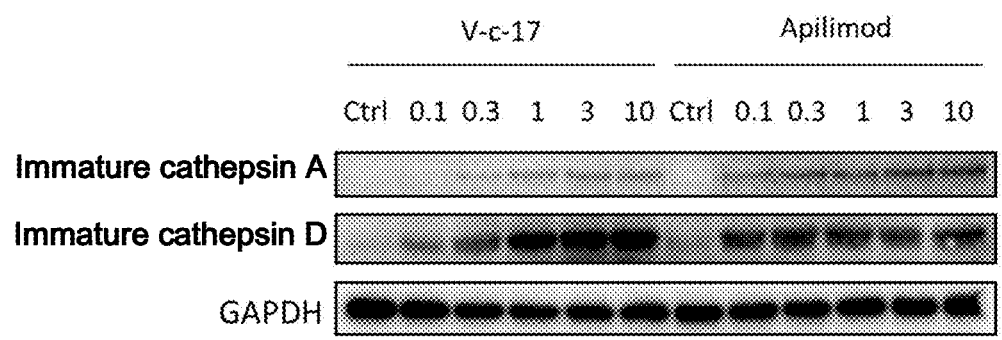
FIG. 3 shows that the representative compound V-c-17 which inhibits PIKfyve causes lysosomal dysfunction. Under the action of V-c-17 or the control compound apilimod, immature cathepsins A and D gradually increase, with good dose dependence.

V. Lysosomal Dysfunction Caused by Inhibition of Compound V-c-17 on PIKfyve (FIG. 3)

After treatment with V-c-17 for 24 hr, JeKo-1 cells were lysed and tested by Western Blot. It showed that immature cathepsin A and cathepsin D increased, and had good concentration dependence. This was similar to the treatment result with the known PIKfyve inhibitor apilimod.

Figure 4:
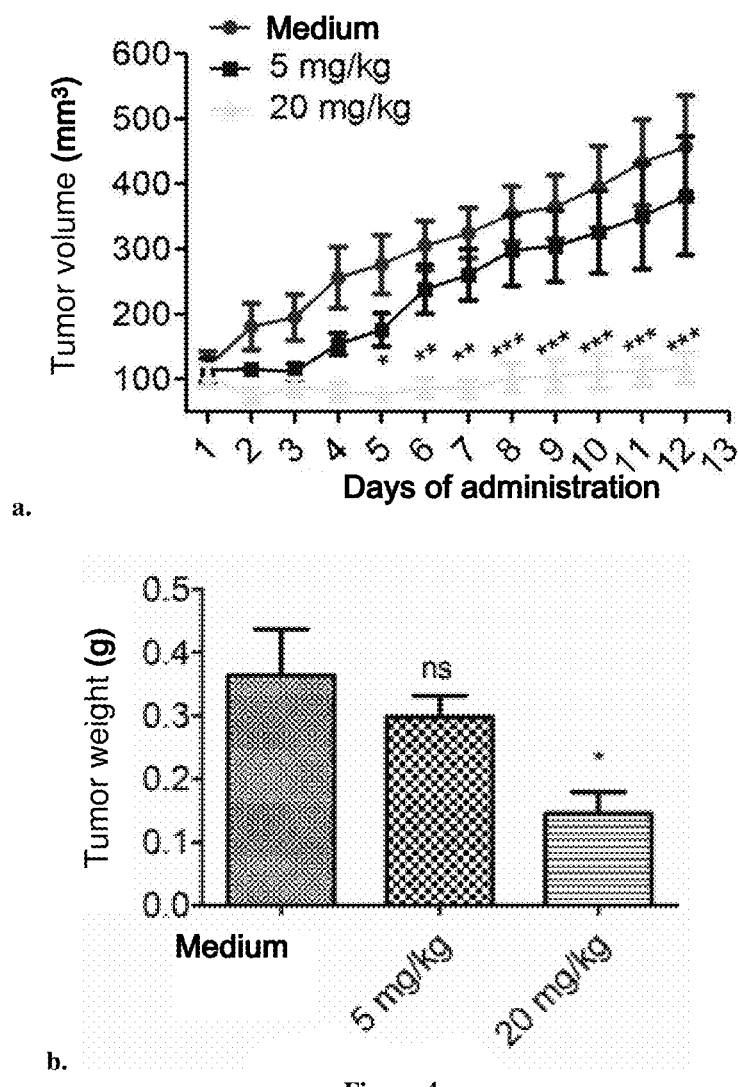
FIG. 4 shows that the representative compound I-a-1 can effectively inhibit tumor growth in a xenograft model of triple negative breast cancer cells (MDA-MB-231). In the MDA-MB-231 xenograft mice model, the drug is administered via tail vein at doses 5 mg/kg, 20 mg/kg every day. a) The administration group can effectively inhibit the increase of tumor volume, with good dose dependence; b) the final tumor weight in the administration group is significantly smaller than that in the control group, with good dose dependence.

VI. Compound I-a-1 Effectively Inhibited Tumor Growth in a Xenograft Model of Triple Negative Breast Cancer Cells, with Good Dose Dependence (FIG. 4).

1. 4-6 weeks old female nude mice were injected subcutaneously with about 5×10$^6$ MDA-MB-231 cells;

2. When tumor volume (length×width×height×0.5) reached about 100 mm$^3$, the mice were randomly divided into three groups: control group, group with a dose of 5 mg/kg once a day, and group with a dose of 20 mg/kg once a day, and the initial tumor volume was recorded.

3. The drug or the control solvent was administered intravenously on time every day, the tumor volume was measured every day, and the procedures were continued for 12 days;

4. In the last day, the mice were killed 6 hours after administration, the tumor grown under skin was completely peeled off, and the tumor weight was recorded.

Figure 5:
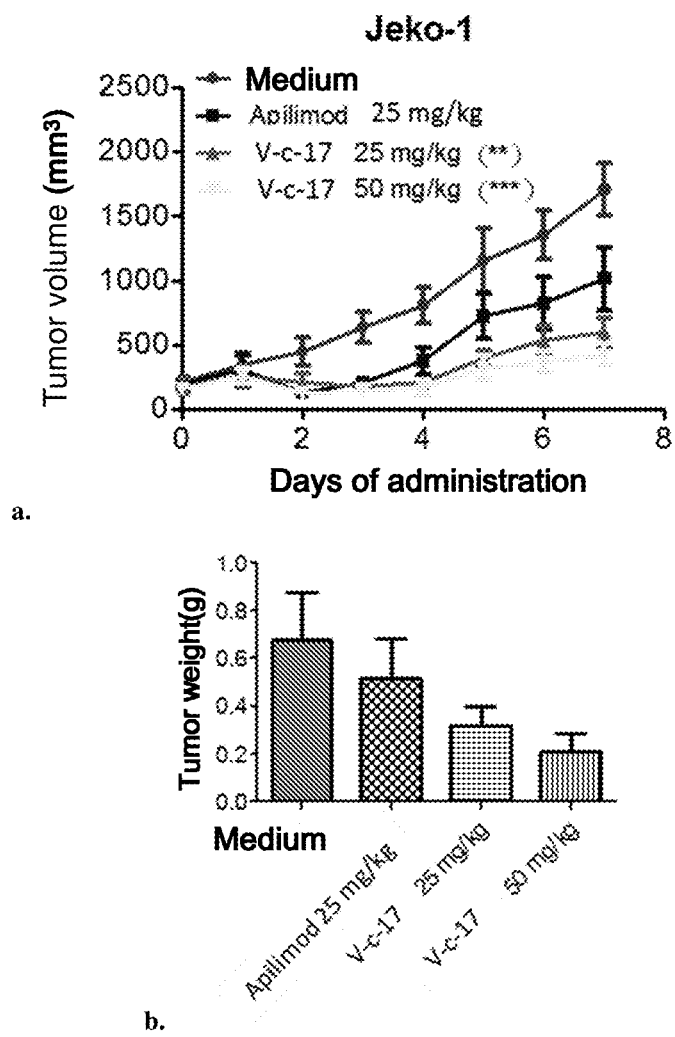
FIG. 5 shows that the representative compound V-c-17 can effectively inhibit tumor growth in a xenograft model of non-Hodgkin's lymphoma cells (Jeko-1). In the JeKo-1 xenograft mice model, the drug is administered via tail vein at doses 25 mg/kg once a day or twice a day. a) The administration group can effectively inhibit the increase of tumor volume, with good dose dependence; b) the final tumor weight in the administration group is significantly smaller than that in the control group, with good dose dependence.

VII. Compound V-c-17 Effectively Inhibited Tumor Growth in a Xenograft Model of Non-Hodgkin's Lymphoma Cells (Jeko-1), with Good Dose Dependence (FIG. 5).

1. 4-6 weeks old female nude mice were injected subcutaneously with about $1 \times 10^7$ JeKo-1 cells;

2. When tumor volume (length×width×height×π/4) reached about 100 mm³, the mice were randomly divided into four groups: control group, V-c-17 group with a dose of 25 mg/kg once a day, V-c-17 group with a dose of 25 mg/kg twice a day, and apilimod group with a dose of 25 mg/kg once a day, and the initial tumor volume was recorded.

3. The drug or the control solvent was administered intravenously on time every day, the tumor volume was measured every day, and the procedures were continued for 7 days;

4. In the last day, the mice were killed 6 hours after administration, the tumor grown under skin was completely peeled off, and the tumor weight was recorded.

The invention claimed is:

1. A compound having the general formula:

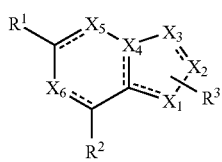

or a stereoisomer thereof, a prodrug thereof, a pharmaceutically acceptable salt thereof or a pharmaceutically acceptable solvate thereof, wherein, $X_1$, $X_2$, $X_3$, $X_4$, $X_5$, $X_6$ and their adjacent carbon atoms form a general formula selected from the group consisting of:

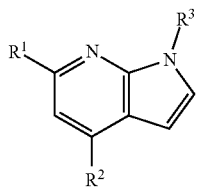

I

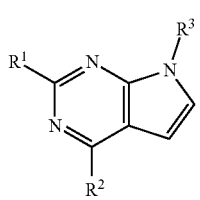

II

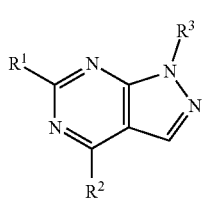

III

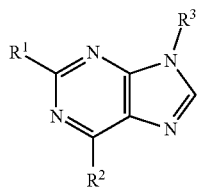

IV

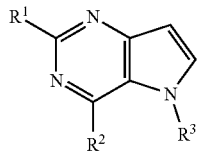

V

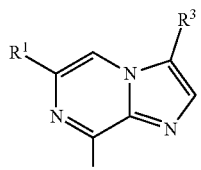

VI

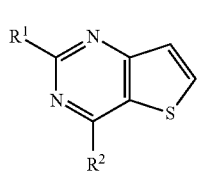

VII

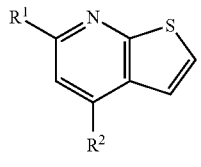

VIII wherein,
in formula I

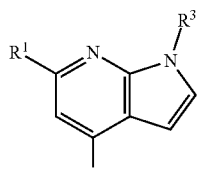

I $R^1$ is selected from:

1)

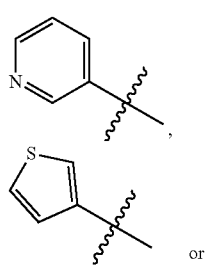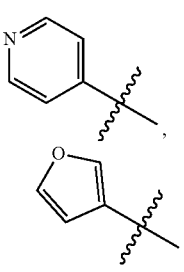

2)

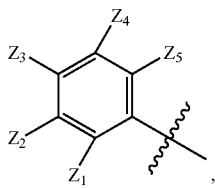

wherein one of $Z_1, Z_2, Z_3, Z_4, Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano;

3)

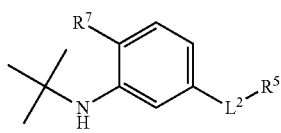

wherein,
$L^2$ is NHCO or CONH;
$R^5$ is

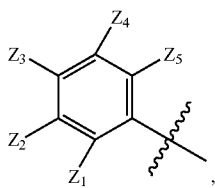

wherein one of $Z_1, Z_2, Z_3, Z_4, Z_5$ is selected from the following groups, the rest being H: H, halogen, amino, hydroxy, C1-C3 fluorine-containing alkyl;
$R^7$ is selected from H or C1-C6 alkyl;
$R^2$ is selected from:
1)

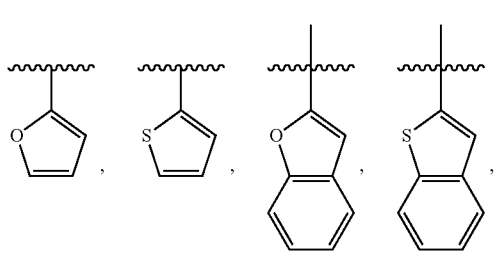

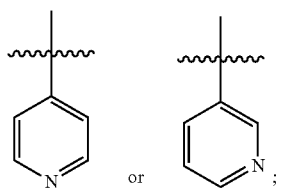

2)

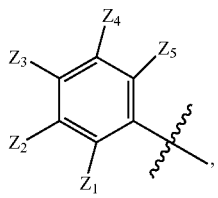

wherein one of $Z_1, Z_2, Z_3, Z_4, Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano;

3)

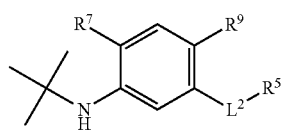

wherein,
$L^2$ is NHCO, CONH, NHCONH, NHCSNH or CO;
$R^5$ is selected from:
when $L^2$ is NHCO, CONH, NHCONH or NHCSNH, $R^5$ is

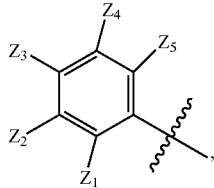

wherein one or two of $Z_1, Z_2, Z_3, Z_4, Z_5$ are independently selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano, C1-C6 alkyl substituted by optionally substituted heterocyclyl; or
when $L^2$ is NHCO, $R^5$ is amino-substituted C1-C6 alkyl, wherein the C1-C6 alkyl is methyl, ethyl or propyl; or
when $L^2$ is CONH, $R^5$ is substituted heteroaryl, wherein the substituted heteroaryl is pyrazolyl substituted by multiple C1-C6 alkyl groups; or
when $L^2$ is CO, $R^5$ is

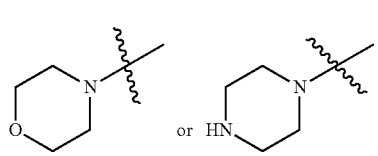 [SMILES: *N1CCOCC1 ; *N1CCNCC1]

optionally substituted by C1-C6 alkyl;

R⁷ is selected from H, C1-C6 alkyl, halogen;
R⁹ is selected from H or C1-C6 alkoxy;
wherein, when R⁷ and R⁹ both are non-hydrogen groups, they don't exist at the same time;
R³ is selected from: —H or C1-C6 alkyl;
in formula II

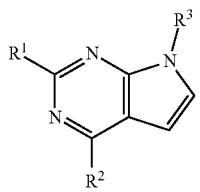

R¹ is selected from:

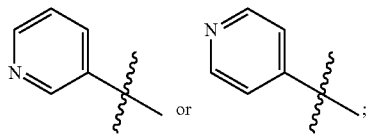 [SMILES: *c1cccnc1 ; *c1ccncc1]

R² is

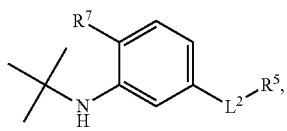

wherein,
L² is NHCO or CONH;
R⁵ is

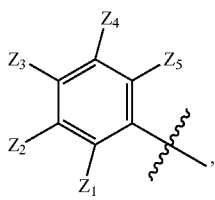

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C6 alkyl substituted by optionally substituted heterocyclyl;
R⁷ is selected from H or C1-C6 alkyl;
R³ is selected from: —H or C1-C6 alkyl;
in formula III

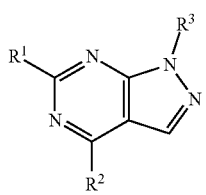

R¹ is selected from:
1)

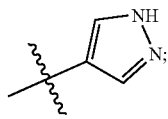 [SMILES: *c1cn[nH]c1]

2)

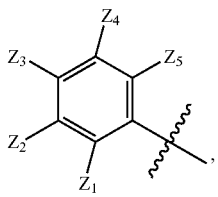

wherein one of $Z_1$, $Z_2$, $Z_3$, $Z_4$, $Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro or cyano;
3)

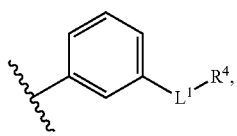

wherein,
L¹ is NHCONH or NHCSNH,
R⁴ is

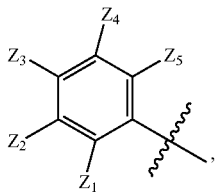

wherein one or two of $Z_1$, $Z_2$, $Z_3$, $Z_4$, $Z_5$ are independently selected from the following groups, the rest being H: halogen, amino, hydroxy, C1-C3 fluorine-containing alkyl;
4)

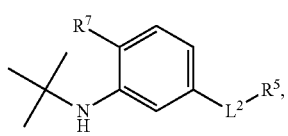

wherein,
L² is NHCO or CONH;

$R^5$ is

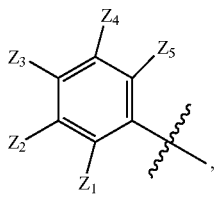

wherein one of $Z_1, Z_2, Z_3, Z_4, Z_5$ is selected from the following groups, the rest being H: H, halogen, amino, hydroxy, C1-C3 fluorine-containing alkyl;
$R^7$ is selected from H or C1-C6 alkyl;
$R^2$ is selected from:
1)

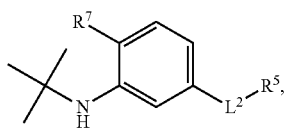

wherein,
$L^2$ is CONH;
$R^5$ is

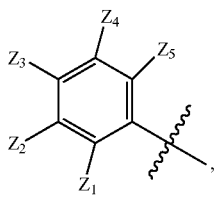

wherein one or two of $Z_1, Z_2, Z_3, Z_4, Z_5$ are independently selected from the following groups, the rest being H: H, halogen, amino; hydroxy, C1-C3 fluorine-containing alkyl, C1-C6 alkyl substituted by optionally substituted heterocyclyl;
$R^7$ is selected from H or C1-C6 alkyl;
2) amino substituted by pyridyl-methyl;
3)

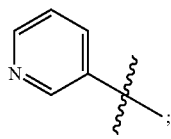

$R^3$ is selected from: —H or C1-C6 alkyl;
in formula IV

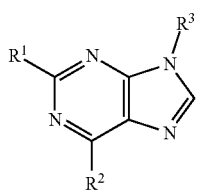

IV $R^1$ is selected from:

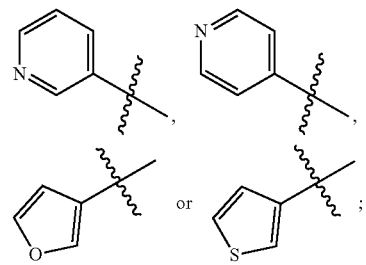

$R^2$ is

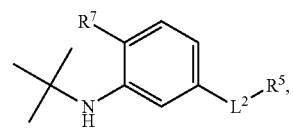

wherein,
$L^2$ is NHCO or CONH;
$R^5$ is

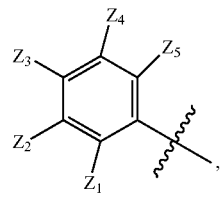

wherein one or two of $Z_1, Z_2, Z_3, Z_4, Z_5$ are independently selected from the following groups, the rest being H: H, halogen, amino, hydroxy, C1-C3 fluorine-containing alkyl, C1-C3 fluorine-containing alkoxy, C1-C6 alkyl substituted by optionally substituted heterocyclyl;
$R^7$ is selected from H or C1-C6 alkyl;
$R^3$ is selected from: —H or C1-C6 alkyl;
in formula V

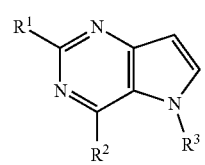

V $R^1$ is selected from:
1)

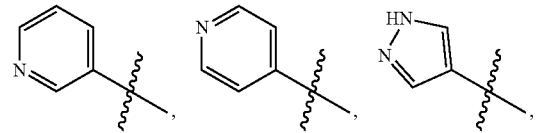

-continued

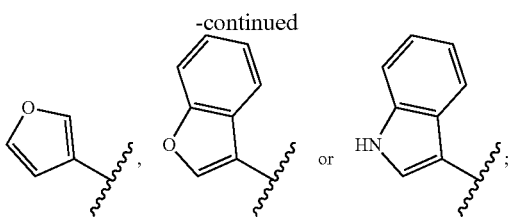 ;

2)

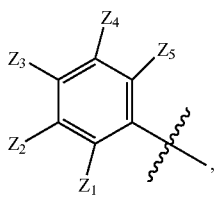

wherein one of $Z_1$, $Z_2$, $Z_3$, $Z_4$, $Z_5$ is selected from the following groups, the rest being H: H, C1-C6 alkyl, C1-C3 alkoxy, C1-C3 fluorine-containing alkyl, C1-C3 fluorine-containing alkoxy, halogen, amino, hydroxy, HOOC—, C1-C6 alkoxyformyl;

3)

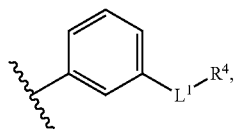

wherein,
$L^1$ is NHCO, CONH, NHCONH or NHCSNH;
$R^4$ is

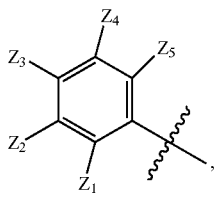

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C3 alkoxy; or
$R^4$ is

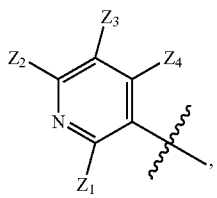

wherein one of $Z_1$, $Z_2$, $Z_3$, $Z_4$ is selected from the following groups, the rest being H: H, halogen, amino, hydroxy;

4)

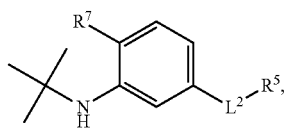

wherein,
$L^2$ is selected from NHCO, CONH, NHSO$_2$, NHCONH or NHCSNH;
$R^5$ is

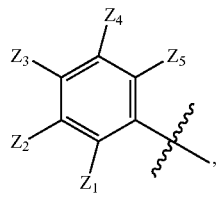

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C3 alkoxy, C1-C6 amino, C1-C6 alkylsulfamido, C1-C3 fluorine-containing alkoxy, nitro, cyano, C1-C6 alkyl substituted by optionally substituted heterocyclyl, optionally substituted heteroaryl;

$R^7$ is H, methyl, fluoro,

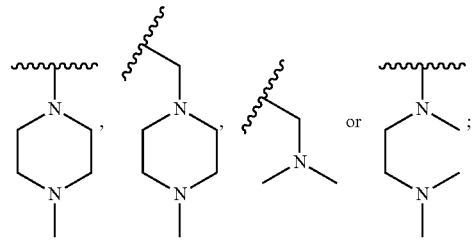 ;

5) amino substituted by unsubstituted phenyl or amino substituted by the following substituted phenyl: phenyl mono-substituted by methylsulfonylamino, phenyl di-substituted by heterocyclyl;

6) pyridylamino;

7) C3-C6 cycloalkylamino;

8)

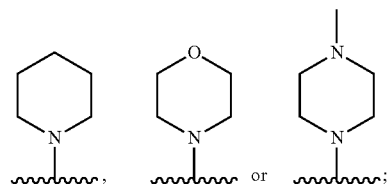 ;

$R^2$ is selected from:
1) selected from:

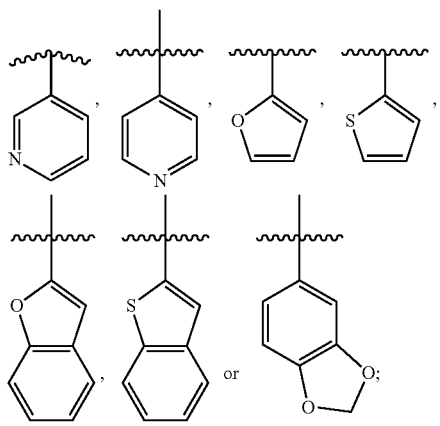

2)

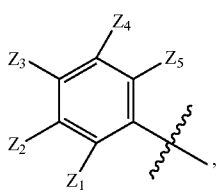

wherein one of $Z_1, Z_2, Z_3, Z_4, Z_5$ is selected from the following groups, the rest being H: H, C1-C6 alkyl, C1-C3 alkoxy, C1-C3 fluorine-containing alkyl, C1-C3 fluorine-containing alkoxy, halogen, amino, hydroxy, nitro, cyano, C1-C3 alkylsulfonyl;

3)

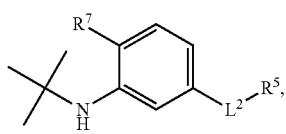

wherein,
$L^2$ is NHCO, CONH, NHSO$_2$, NHCONH or NHCSNH;
$R^5$ is

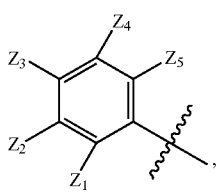

wherein one or two of $Z_1, Z_2, Z_3, Z_4, Z_5$ are independently selected from the following groups, the rest being H: H, halogen, amino, di-C1-C3 alkyl-substituted amino, hydroxy, C1-C3 alkyl, C1-C3 alkoxy, C1-C3 fluorine-containing alkyl, C1-C3 fluorine-containing alkoxy, optionally substituted heteroaryl, C1-C6 alkyl substituted by optionally substituted heterocyclyl;

$R^7$ is selected from or C1-C6 alkyl;

4) selected from the following substituted amino:

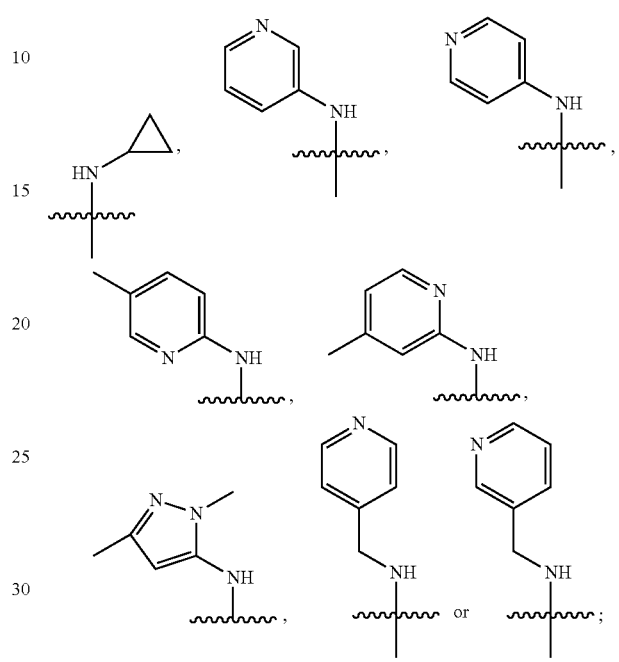

5) selected from:

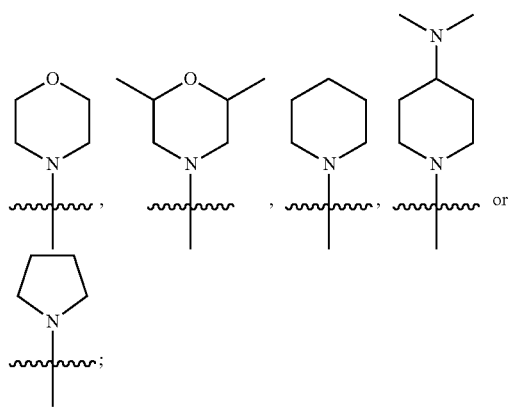

$R^3$ is selected from: —H or C1-C6 alkyl;
in formula VI

VI

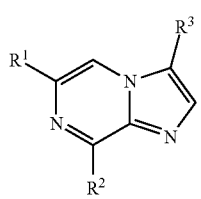

$R^1$ is

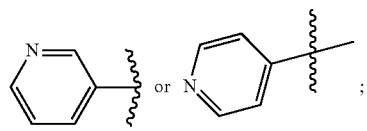

$R^2$ is

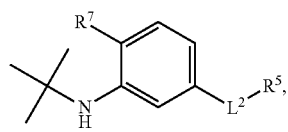

wherein,
$L^2$ is NHCO or CONH;
$R^5$ is

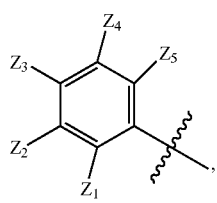

wherein one or two of $Z_1$, $Z_2$, $Z_3$, $Z_4$, $Z_5$ are independently selected from the following groups, the rest being H: halogen, amino, hydroxy, C1-C3 fluorine-containing alkyl, C1-C3 fluorine-containing alkoxy, optionally substituted heteroaryl, C1-C6 alkyl substituted by optionally substituted heterocyclyl;

$R^7$ is C1-C6 alkyl;
$R^3$ is selected from: —H, halogen, C1-C6 alkyl or C3-C7 cycloalkyl;

in formula VII

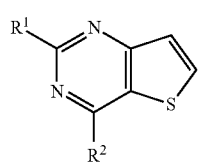

$R^1$ is selected from:

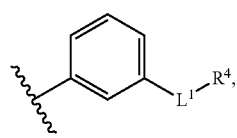

wherein,
$L^1$ is selected from NHCO or CONH;

$R^4$ is

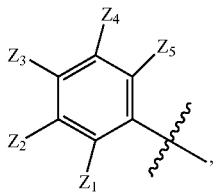

wherein one of $Z_1$, $Z_2$, $Z_3$, $Z_4$, $Z_5$ is selected from the following groups, the rest being H: H, halogen, amino, hydroxy, C1-C3 fluorine-containing alkyl; or $R^4$ is

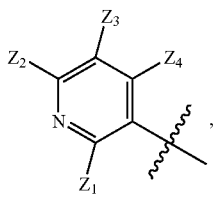

wherein one of $Z_1$, $Z_2$, $Z_3$, $Z_4$ is selected from the following groups, the rest being H: H, halogen, amino, hydroxy;

$R^2$ is selected from:
1) selected from the following substituted amino:

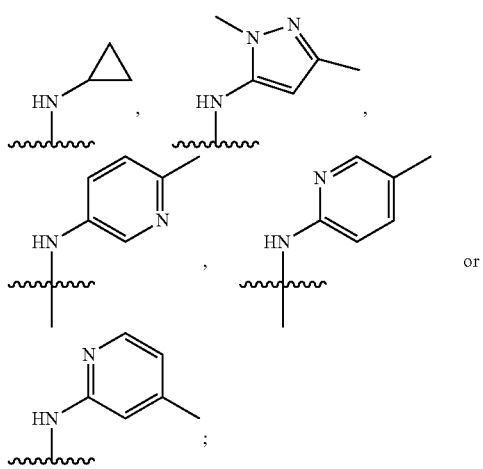

2) selected from:

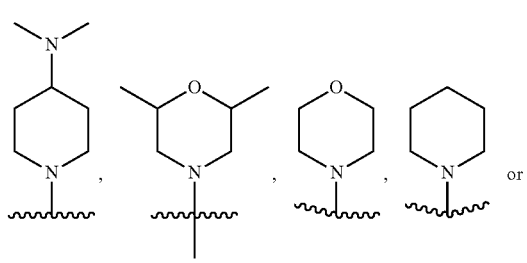

-continued

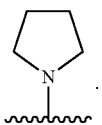

in formula VIII

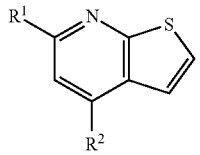

$R^1$ is

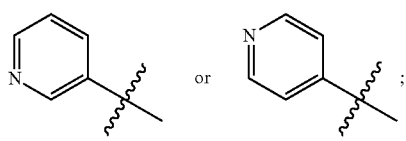 [SMILES: *c1cccnc1 ; *c1ccncc1]

$R^2$ is

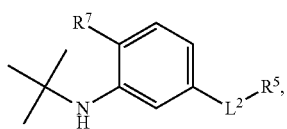

wherein,
$L^2$ is NHCO or CONH;
$R^5$ is

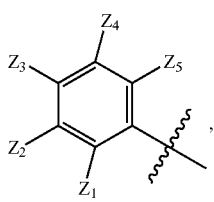

wherein one of $Z_1$, $Z_2$, $Z_3$, $Z_4$, $Z_5$ is selected from the following groups, the rest being H: H, halogen, amino, hydroxy, C1-C3 fluorine-containing alkyl;
$R^7$ is selected from H or C1-C6 alkyl.

2. The compound according to claim 1 or a stereoisomer thereof, a prodrug thereof, a pharmaceutically acceptable salt thereof or a pharmaceutically acceptable solvate thereof, wherein, the compound has the following structure:

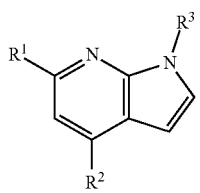

wherein,
$R^1$ is selected from:
1)

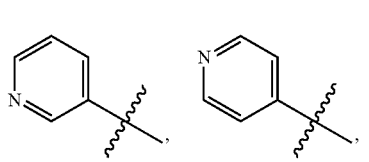

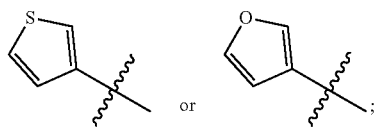

2)

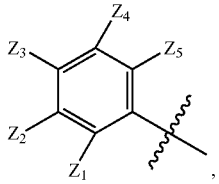

wherein one of $Z_1$, $Z_2$, $Z_3$, $Z_4$, $Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyan;

3)

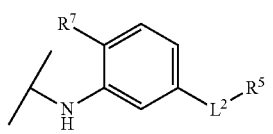

wherein,
$L^2$ is NHCO or CONH;
$R^5$ is

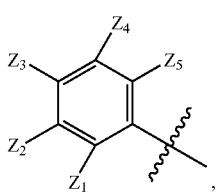

wherein one of $Z_1$, $Z_2$, $Z_3$, $Z_4$, $Z_5$ is selected from the following groups, the rest being H: H; halogen, amino, hydroxy, C1-C3 fluorine-containing alkyl;
$R^7$ is selected from H or C1-C6 alkyl;

$R^2$ is selected from:

1)

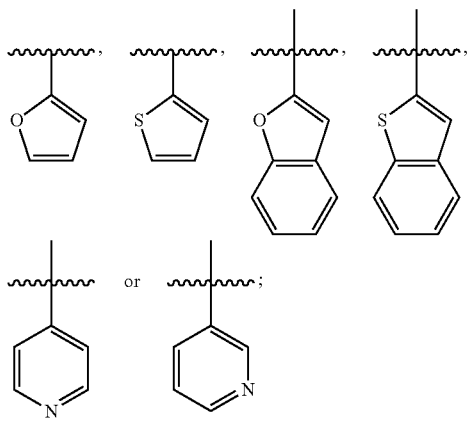

2)

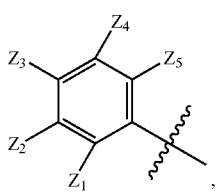

wherein one of $Z_1$, $Z_2$, $Z_3$, $Z_4$, $Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano;

3)

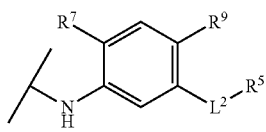

wherein,
$L^2$ is NHCO, CONH, NHCONH, NHCSNH or CO;
$R^5$ is selected from:
when $L^2$ is NHCO, CONH, NHCONH or NHCSNH, $R^5$ is

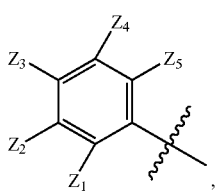

wherein one or two of $Z_1$, $Z_2$, $Z_3$, $Z_4$, $Z_5$ are independently selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro, cyano, C1-C6 alkyl substituted by optionally substituted heterocyclyl; or when $L^2$ is NHCO, $R^5$ is amino-substituted C1-C6 alkyl, wherein the C1-C6 alkyl is methyl, ethyl or propyl; or when $L^2$ is CONH, $R^5$ is substituted heteroaryl, wherein the substituted heteroaryl is pyrazolyl substituted by multiple C1-C6 alkyl groups; or when $L^2$ is CO, $R^5$ is

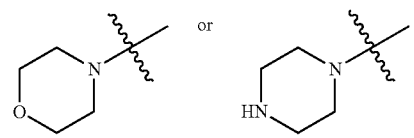 [SMILES: *N1CCOCC1 ; *N1CCNCC1]

optionally substituted by C1-C6 alkyl;

$R^7$ is selected from H, C1-C6 alkyl, halogen;

$R^9$ is selected from H or C1-C6 alkoxy;

wherein, when $R^7$ and $R^9$ both are non-hydrogen groups, they don't exist at the same time;

$R^3$ is selected from: —H or C1-C6 alkyl.

3. The compound according to claim 1 or a stereoisomer thereof, a prodrug thereof, a pharmaceutically acceptable salt thereof or a pharmaceutically acceptable solvate thereof, wherein, the compound has the following structure:

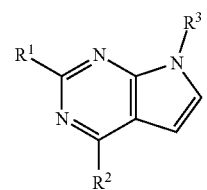

II wherein,
$R^1$ is selected from:

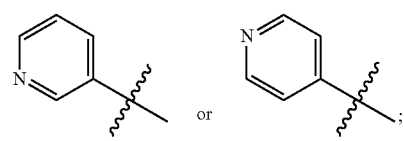 [SMILES: *c1cccnc1 ; *c1ccncc1]

$R^2$ is

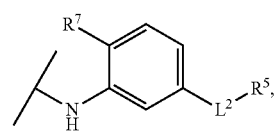

wherein,
$L^2$ is NHCO or CONH;

R⁵ is

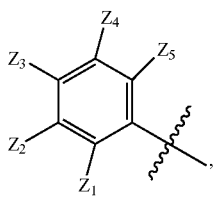

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C6 alkyl substituted by optionally substituted heterocyclyl;

R⁷ is selected from H or C1-C6 alkyl;

R³ is selected from: —H or C1-C6 alkyl.

4. The compound according to claim 1 or a stereoisomer thereof, a prodrug thereof, a pharmaceutically acceptable salt thereof or a pharmaceutically acceptable solvate thereof, wherein, the compound has the following structure:

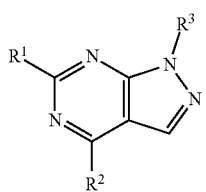

III wherein,
R¹ is selected from:
1)

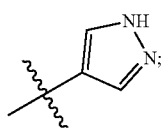 [SMILES: *c1cn[nH]c1]

2)

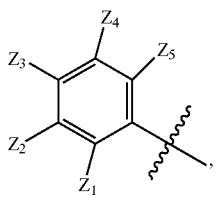

wherein one of $Z_1$, $Z_2$, $Z_3$, $Z_4$, $Z_5$ is selected from the following groups, the rest being H: H, C1-C6 alkyl, C1-C3 alkoxy, C1-C3 oxygen-containing alkyl, C1-C3 fluorine-containing alkyl, C1-C3 fluorine-containing alkoxy, halogen, amino, hydroxy, nitro or cyano;

3)

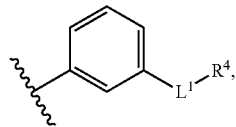

wherein,
L¹ is NHCONH or NHCSNH,
R⁴ is

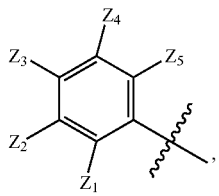

wherein one or two of $Z_1$, $Z_2$, $Z_3$, $Z_4$, $Z_5$ are independently selected from the following groups, the rest being H: halogen, amino, hydroxy, C1-C3 fluorine-containing alkyl;

4)

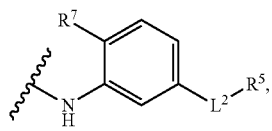

wherein,
L² is NHCO or CONH;
R⁵ is

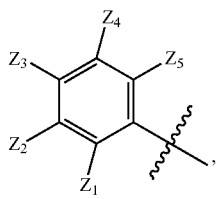

wherein one of $Z_1$, $Z_2$, $Z_3$, $Z_4$, $Z_5$ is selected from the following groups, the rest being H: H, halogen, amino, hydroxy, C1-C3 fluorine-containing alkyl;

R⁷ is selected from H or C1-C6 alkyl;
R² is selected from:
1)

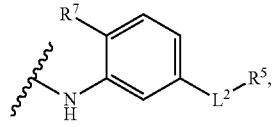

wherein,
L² is CONH;

$R^5$ is

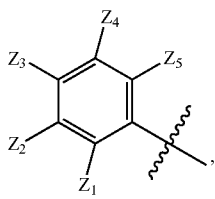

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C6 alkyl substituted by optionally substituted heterocyclyl;

$R^7$ is selected from H or C1-C6 alkyl;

2) amino substituted by pyridyl-methyl;

3)

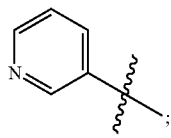 [SMILES: *c1cccnc1]

$R^3$ is selected from: —H or C1-C6 alkyl.

5. The compound according to claim 1 or a stereoisomer thereof, a prodrug thereof, a pharmaceutically acceptable salt thereof or a pharmaceutically acceptable solvate thereof, wherein, the compound has the following structure:

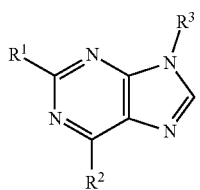

IV wherein,
$R^1$ is selected from:

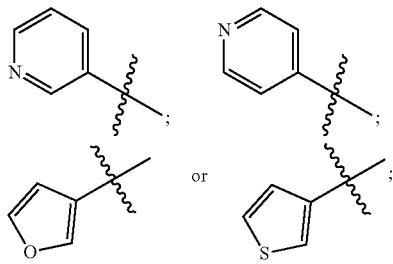

$R^2$ is

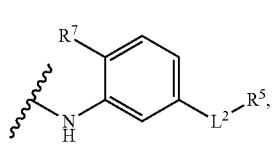

wherein,
$L^2$ is NHCO or CONH;

$R^5$ is

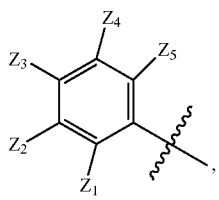

wherein one or two of $Z_1$, $Z_2$, $Z_3$, $Z_4$, $Z_5$ are independently selected from the following groups, the rest being H: H, halogen, amino, hydroxy, C1-C3 fluorine-containing alkyl, C1-C3 fluorine-containing alkoxy, C1-C6 alkyl substituted by optionally substituted heterocyclyl;

$R^7$ is selected from H or C1-C6 alkyl;

$R^3$ is selected from: —H or C1-C6 alkyl.

6. The compound according to claim 1 or a stereoisomer thereof, a prodrug thereof, a pharmaceutically acceptable salt thereof or a pharmaceutically acceptable solvate thereof, wherein, the compound has the following structure:

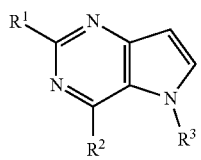

V wherein,
$R^1$ is selected from:

1)

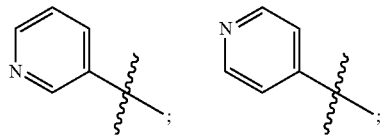

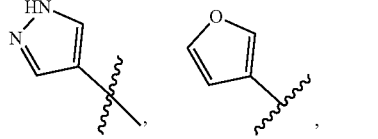

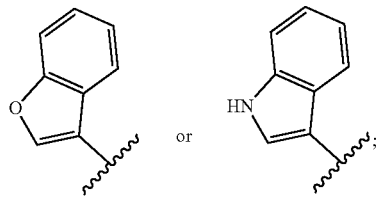

2)

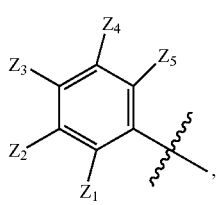

wherein one of $Z_1, Z_2, Z_3, Z_4, Z_5$ is selected from the following groups, the rest being H: H, C1-C6 alkyl, C1-C3 alkoxy, C1-C3 fluorine-containing alkyl, C1-C3 fluorine-containing alkoxy, halogen, amino, hydroxy, HOOC—, C1-C6 alkoxyformyl;

3)

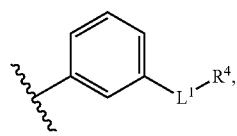

wherein,
$L^1$ is NHCO, CONH, NHCONH or NHCSNH;
$R^4$ is

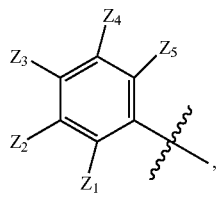

wherein one or two of $Z_1, Z_2, Z_3, Z_4, Z_5$ are independently selected from the following groups, the rest being H: H, halogen, amino, hydroxy, C1-C3 fluorine-containing alkyl, C1-C3 alkoxy; or
$R^4$ is

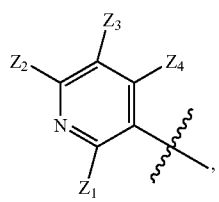

wherein one of $Z_1, Z_2, Z_3, Z_4$ is selected from the following groups, the rest being H: H, halogen, amino, hydroxy;

4)

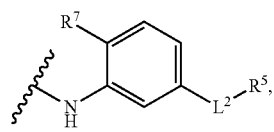

wherein,
$L^2$ is selected from NHCO, CONH, NHSO$_2$, NHCONH or NHCSNH,
$R^5$ is

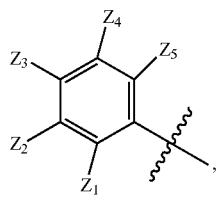

wherein one or two of $Z_1, Z_2, Z_3, Z_4, Z_5$ are independently selected from the following groups, the rest being H: H, halogen, amino, hydroxy, C1-C3 fluorine-containing alkyl, C1-C3 alkoxy, C1-C6 amido, C1-C6 alkylsulfamido, C1-C3 fluorine-containing alkoxy, nitro, cyano, C1-C6 alkyl substituted by optionally substituted heterocyclyl, optionally substituted heteroaryl;

$R^7$ is H, methyl, fluoro,

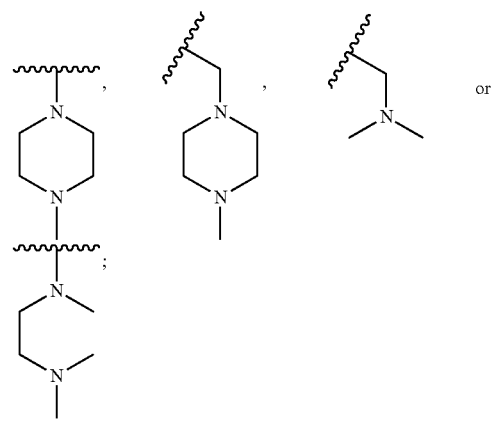

5) amino substituted by unsubstituted phenyl or amino substituted by the following substituted phenyl: phenyl mono-substituted by methylsulfonylamino, phenyl di-substituted by heterocyclyl;

6) pyridylamino;

7) C3-C6 cycloalkylamino;

8)

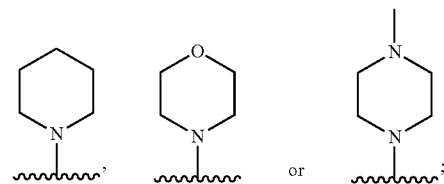

$R^2$ is selected from:

1) selected from:

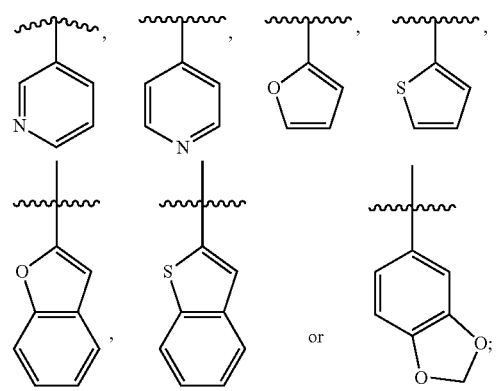

2)

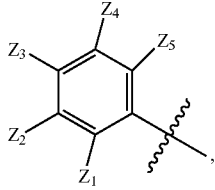

wherein one of $Z_1$, $Z_2$, $Z_3$, $Z_4$, $Z_5$ is selected from the following groups, the rest being H: H, C1-C6 alkyl, C1-C3 alkoxy, C1-C3 fluorine-containing alkyl, C1-C3 fluorine-containing alkoxy, halogen, amino, hydroxy, nitro, cyano, C1-C3 alkylsulfonyl;

3)

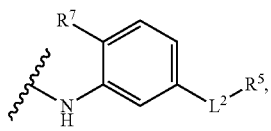

wherein,
$L^2$ is NHCO, CONH, NHSO$_2$, NHCONH or NHCSNH;
$R^5$ is

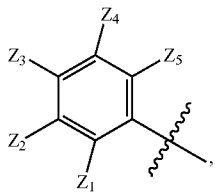

wherein one or two of $Z_1$, $Z_2$, $Z_3$, $Z_4$, $Z_5$ are independently selected from the following groups, the rest being H: H, halogen, amino, di-C1-C3 alkyl-substituted amino, hydroxy, C1-C3 alkyl, C1-C3 alkoxy, C1-C3 fluorine-containing alkyl, C1-C3 fluorine-containing alkoxy, optionally substituted heteroaryl, C1-C6 alkyl substituted by optionally substituted heterocyclyl;
$R^7$ is selected from H or C1-C6 alkyl;
4) selected from the following substituted amino:

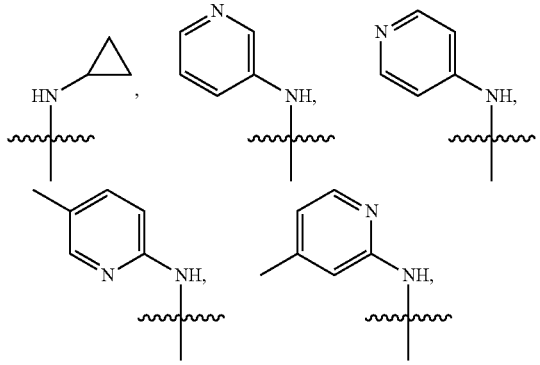

-continued

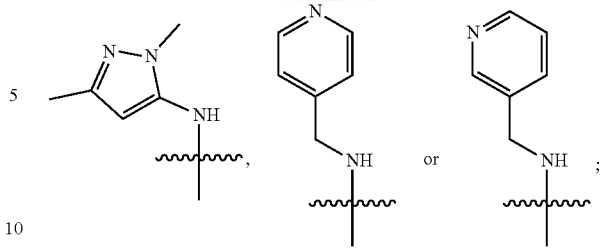

5) selected from:

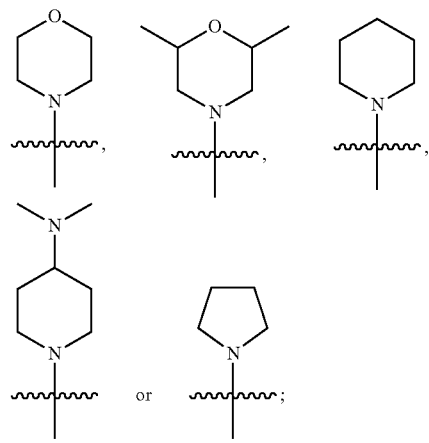

$R^3$ is selected from: —H or C1-C6 alkyl.

7. The compound according to claim 1 or a stereoisomer thereof, a prodrug thereof, a pharmaceutically acceptable salt thereof or a pharmaceutically acceptable solvate thereof, wherein, the compound has the following structure:

VI

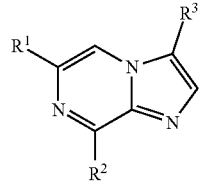

wherein,
$R^1$ is

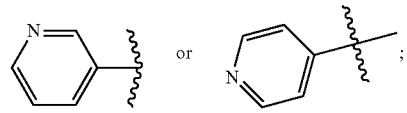 [SMILES: *c1cccnc1 ; *c1ccncc1]

$R^2$ is

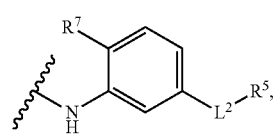

wherein,
$L^2$ is NHCO or CONH;

$R^5$ is

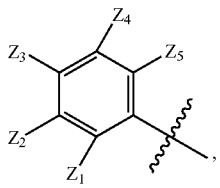

wherein one or two of $Z_1$, $Z_2$, $Z_3$, $Z_4$, $Z_5$ are independently selected from the following groups, the rest being H: halogen, amino, hydroxy, C1-C3 fluorine-containing alkyl, C1-C3 fluorine-containing alkoxy, optionally substituted heteroaryl, C1-C6 alkyl substituted by optionally substituted heterocyclyl;

$R^7$ is C1-C6 alkyl;

$R^3$ is selected from: —H, halogen, C1-C6 alkyl or C3-C7 cycloalkyl.

8. The compound according to claim 1 or a stereoisomer thereof, a prodrug thereof, a pharmaceutically acceptable salt thereof or a pharmaceutically acceptable solvate thereof, wherein, the compound has the following structure:

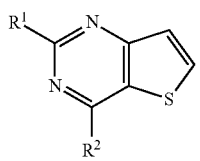
VII wherein,
$R^1$ is

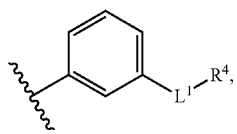

wherein,
$L^1$ is selected from NHCO or CONH;
$R^4$ is

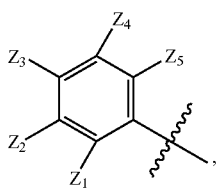

wherein one of $Z_1$, $Z_2$, $Z_3$, $Z_4$, $Z_5$ is selected from the following groups, the rest being H: H, halogen, amino, hydroxy, C1-C3 fluorine-containing alkyl; or $R^4$ is

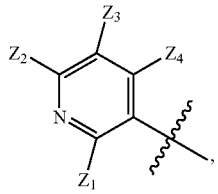

wherein one of $Z_1$, $Z_2$, $Z_3$, $Z_4$ is selected from the following groups, the rest being H: H, halogen, amino, hydroxy;

$R^2$ is selected from:

1) selected from the following substituted amino:

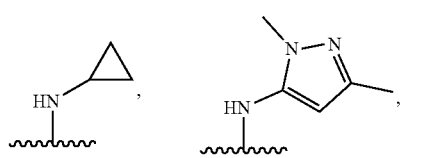

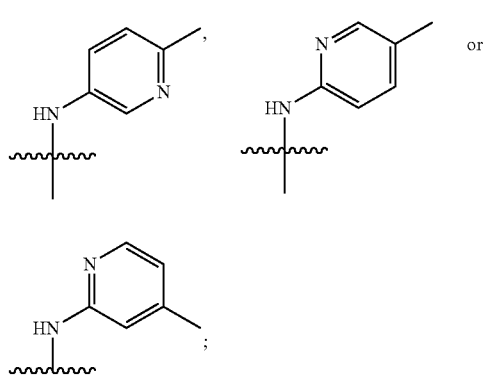

2) selected from:

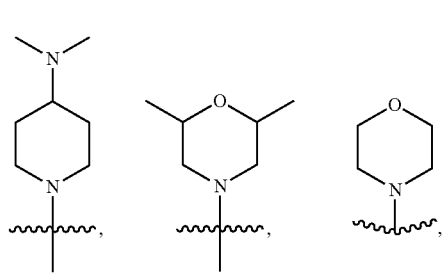

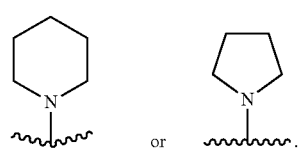

9. The compound according to claim 1 or a stereoisomer thereof, a prodrug thereof, a pharmaceutically acceptable salt thereof or a pharmaceutically acceptable solvate thereof, wherein, the compound has the following structure:

VIII

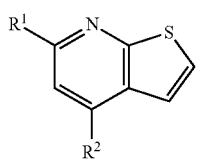

wherein,
R¹ is

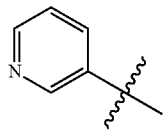 or 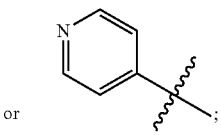;

R² is

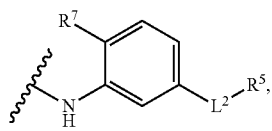

wherein,
L² is NHCO or CONH;
R⁵ is

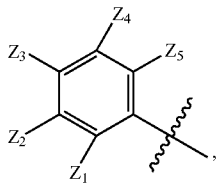, wherein one of $Z_1, Z_2, Z_3, Z_4, Z_5$ is selected from the following groups, the rest being H: H, halogen, amino, hydroxy, C1-C3 fluorine-containing alkyl;
R⁷ is selected from H or C1-C6 alkyl.

10. The compound according to claim 1 or a stereoisomer thereof, a prodrug thereof, a pharmaceutically acceptable salt thereof or a pharmaceutically acceptable solvate thereof, wherein, the compound is selected from:

I-a-1

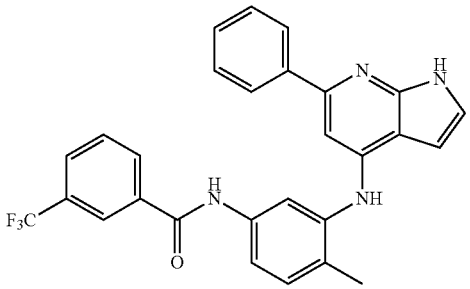

I-a-2

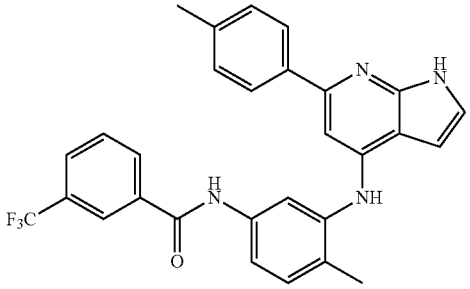

I-a-3

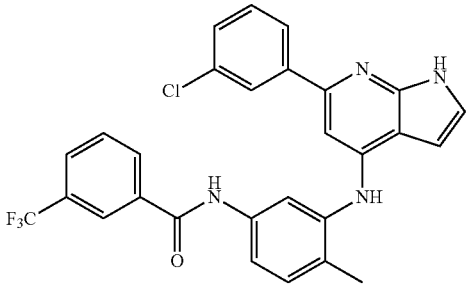

I-a-4

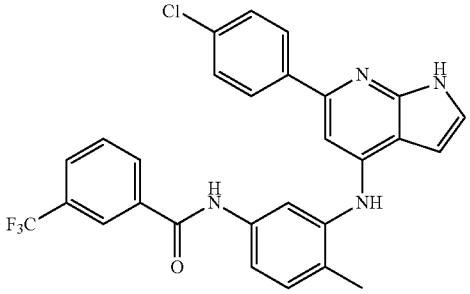

I-a-5

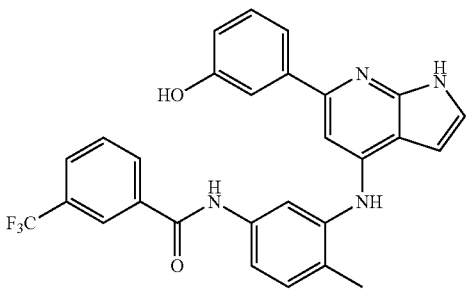

I-a-6

-continued
I-a-7
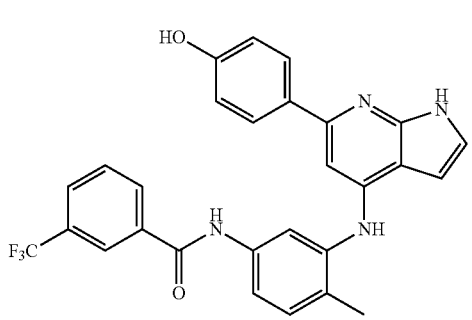
I-a-8
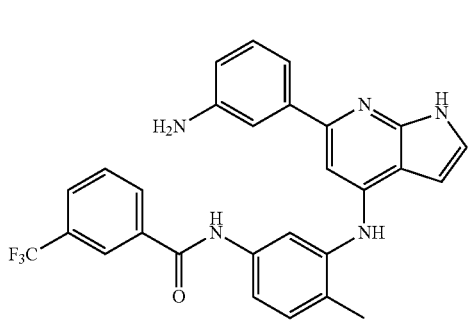
I-a-9
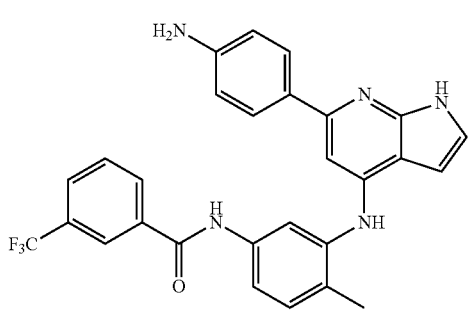
I-a-10
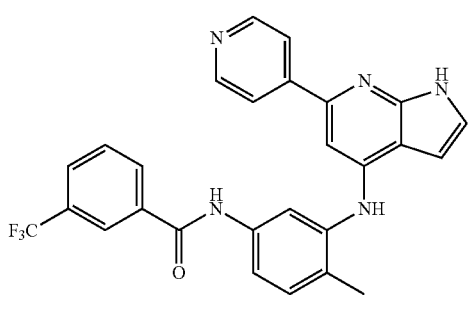
I-a-11
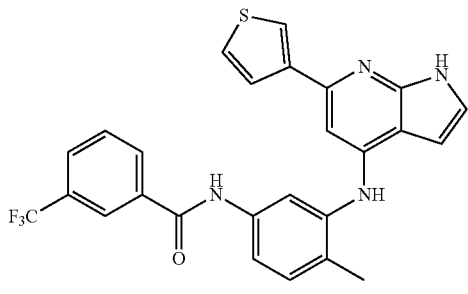
-continued
I-a-12
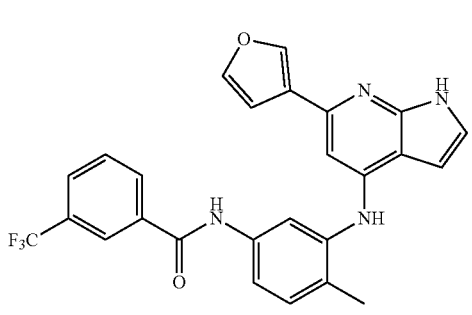
I-a-13
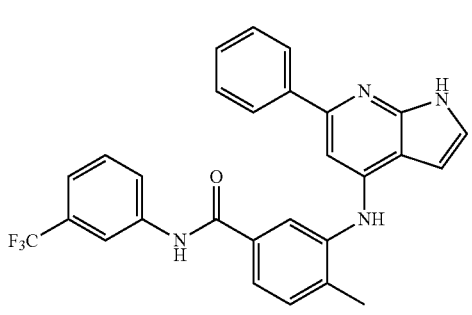
I-a-14
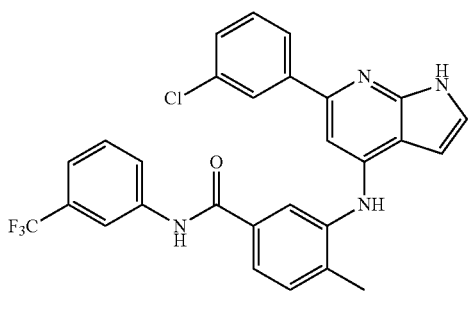
I-a-15
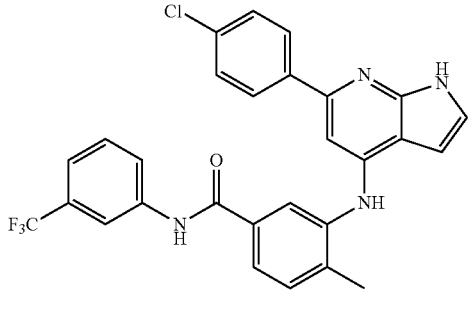
I-a-16

283
-continued
I-a-17
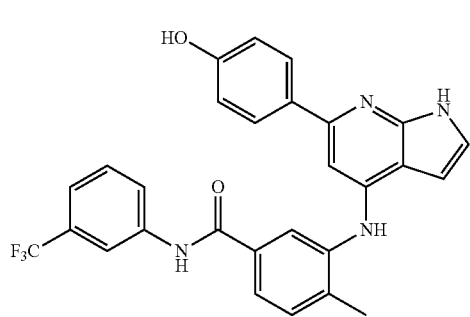
I-a-18
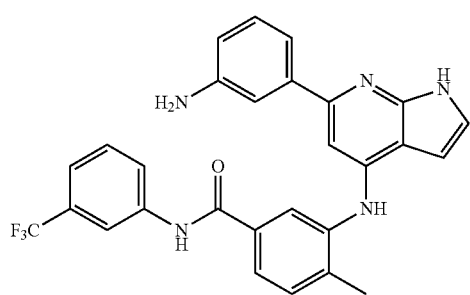
I-a-19
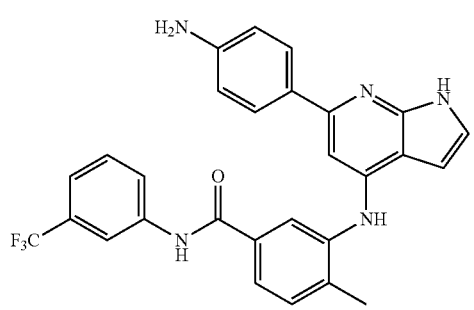
I-a-20
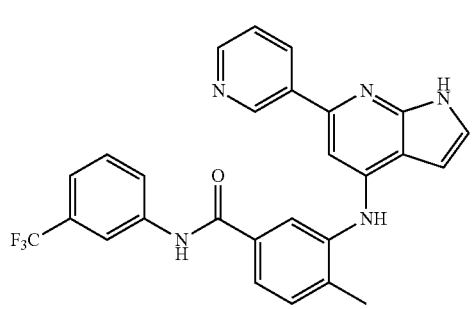
I-a-21
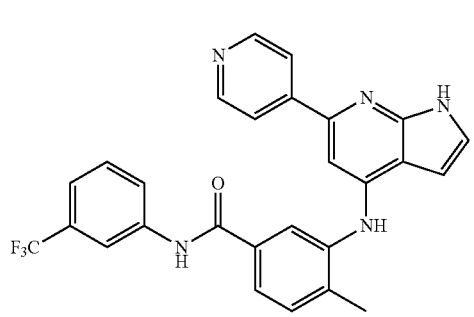
284
-continued
I-a-22
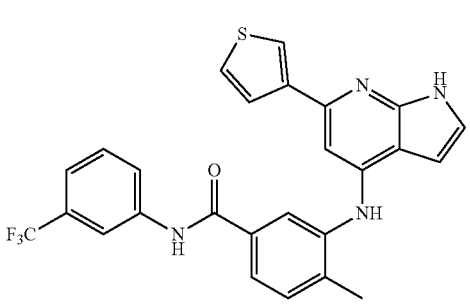
I-a-23
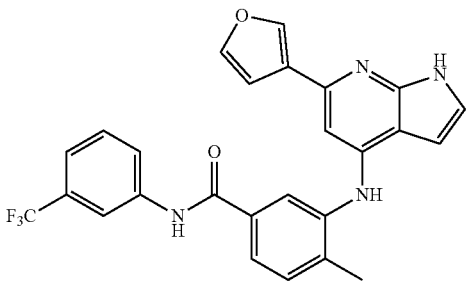
I-a-24
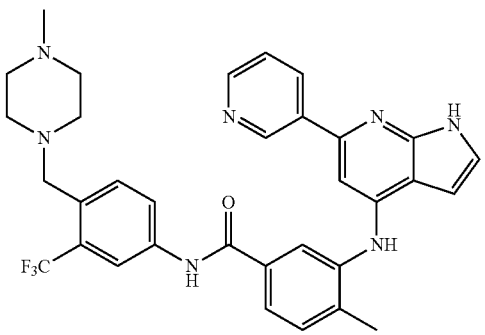
I-a-25
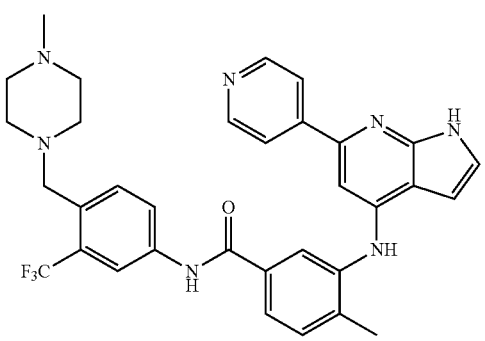
I-a-26

285
-continued
I-a-27
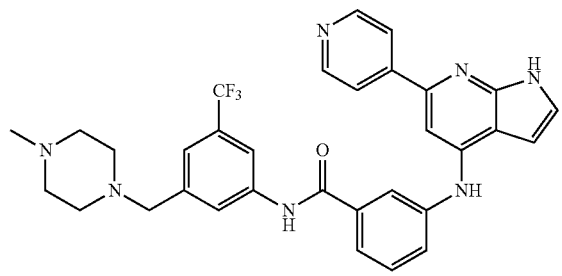
I-a-28
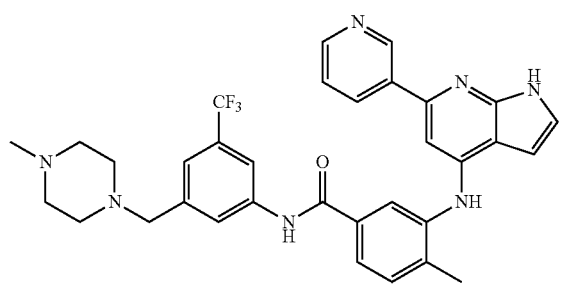
I-a-29
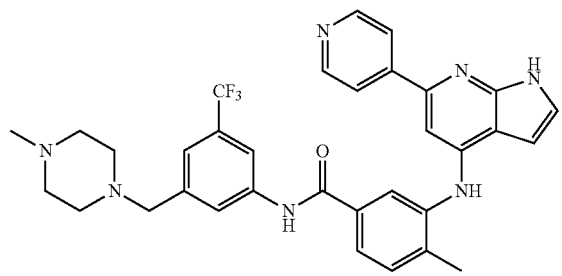
I-a-30
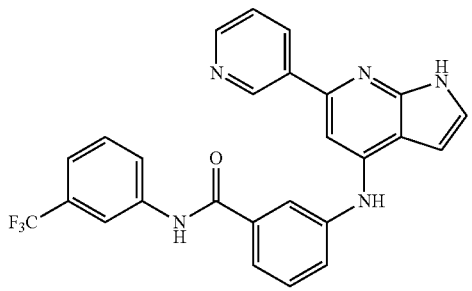
I-a-31
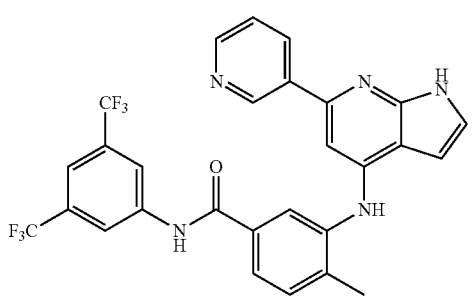
286
-continued
I-a-32
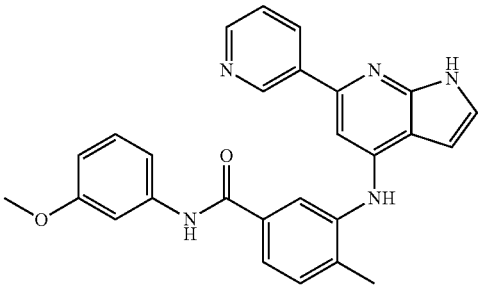
I-a-33
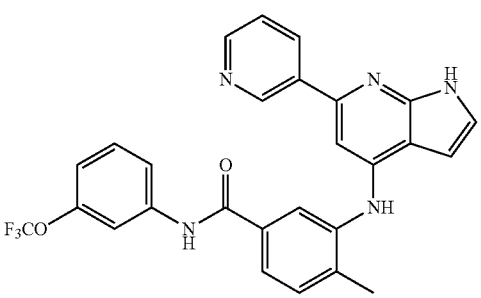
I-a-34
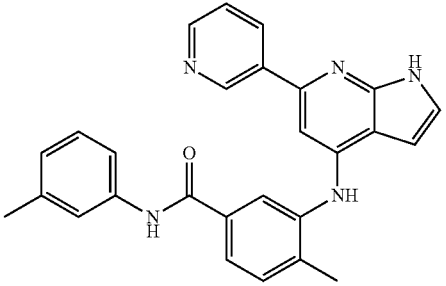
I-a-35
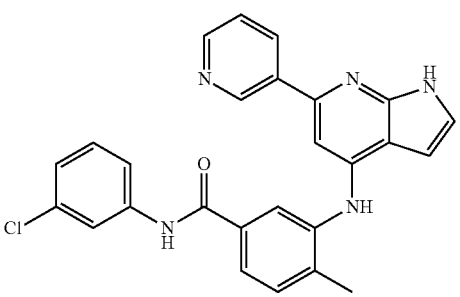
I-a-36
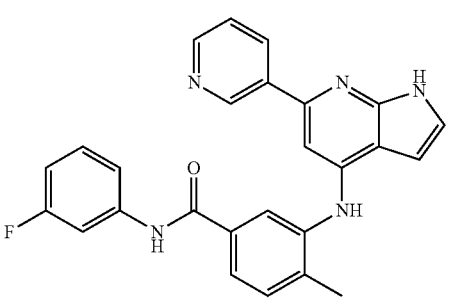

I-a-37
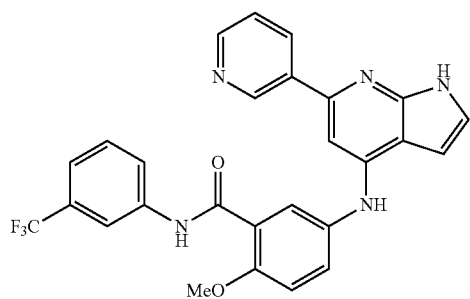
I-a-38
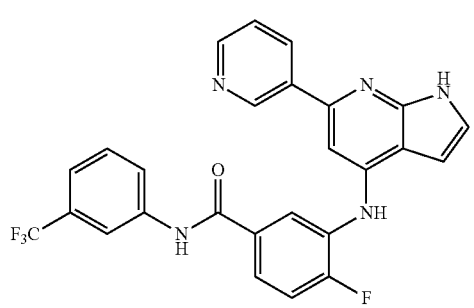
I-a-39
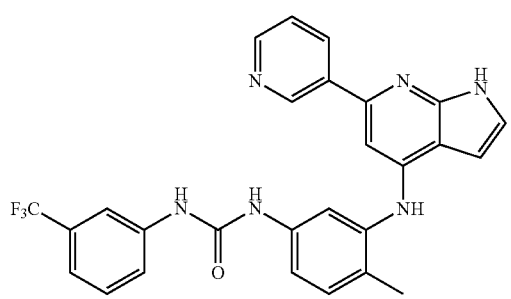
I-a-40
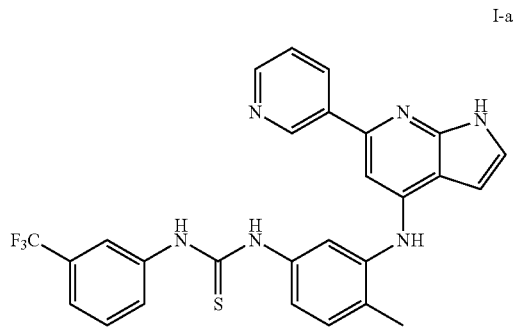
I-a-41
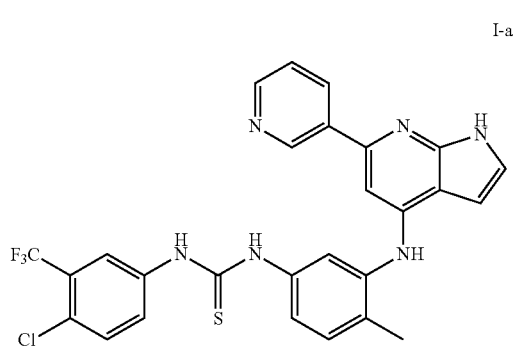
I-a-42
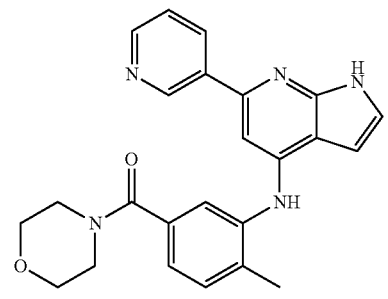
I-a-43
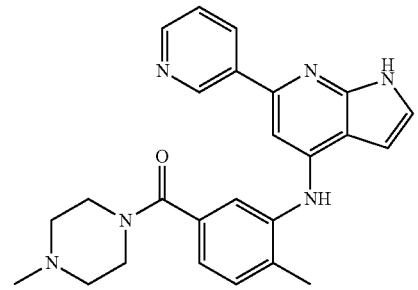
I-a-44
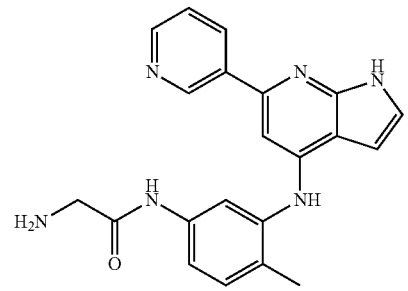
I-a-45
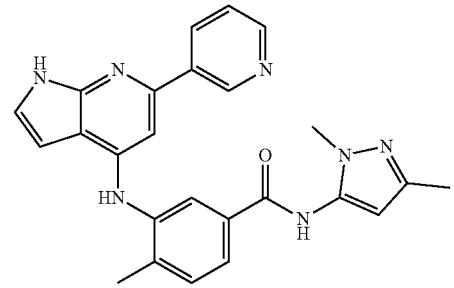
I-a-46
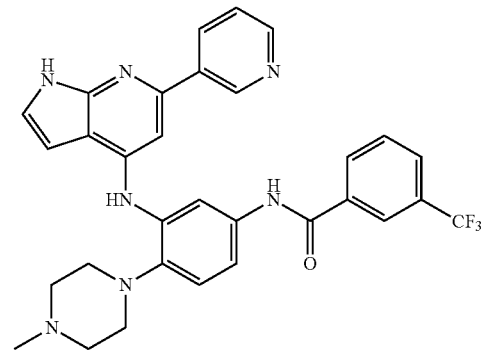

I-a-47
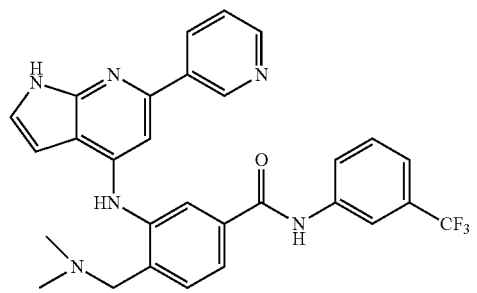
I-a-48
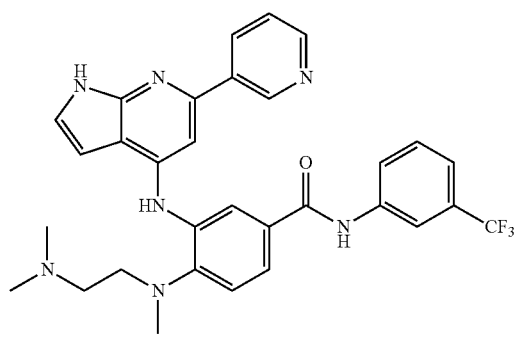
I-a-49
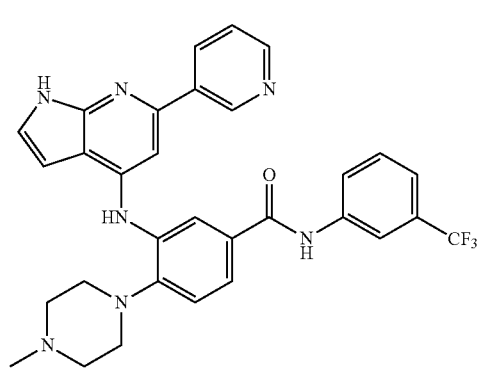
I-a-50
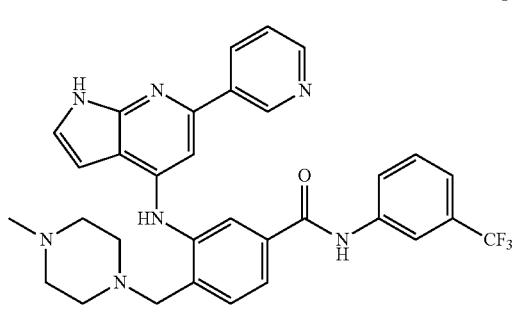
I-b-1
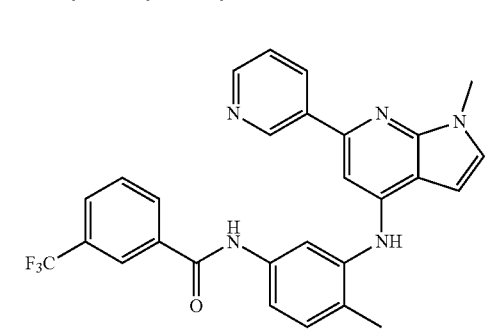
I-b-2
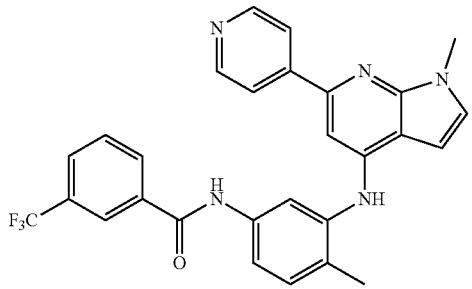
I-b-3
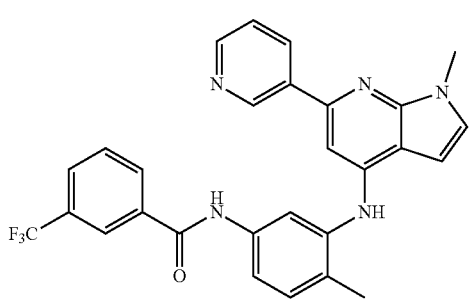
I-b-4
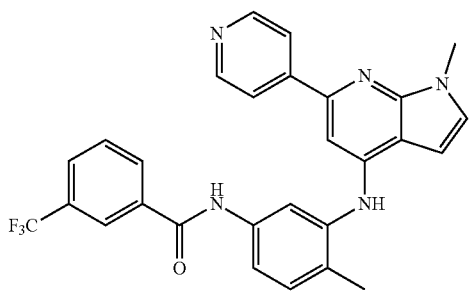
I-b-5
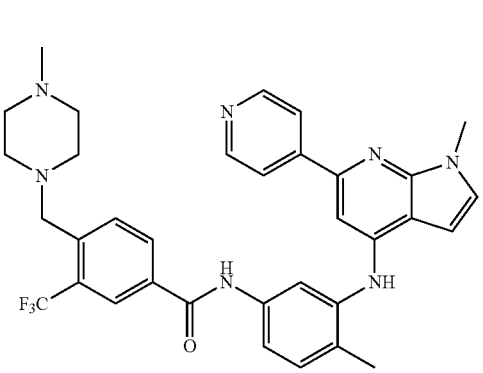
I-b-6
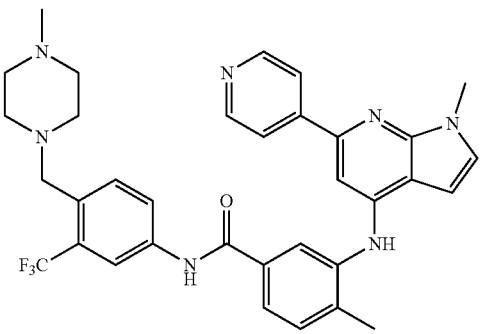

-continued
I-b-7
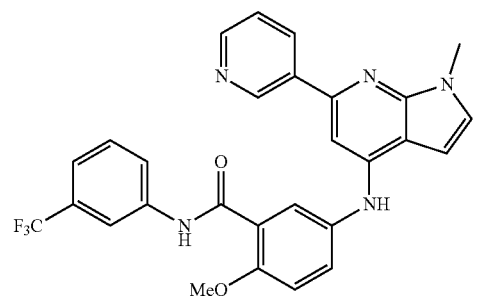
I-b-8
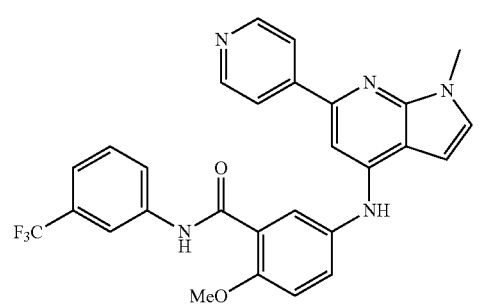
I-c-1
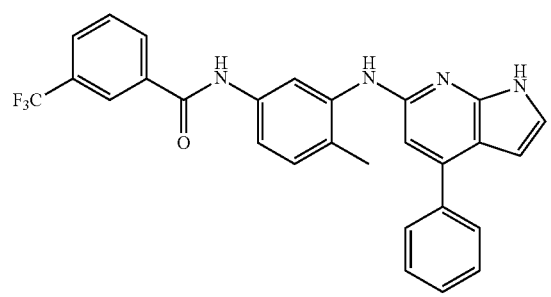
I-c-2
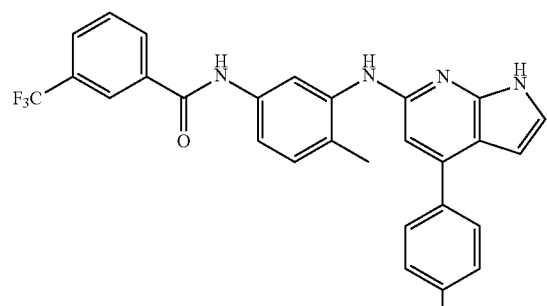
I-c-3
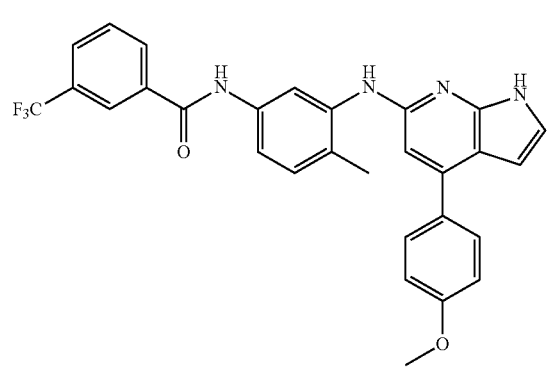
-continued
I-c-4
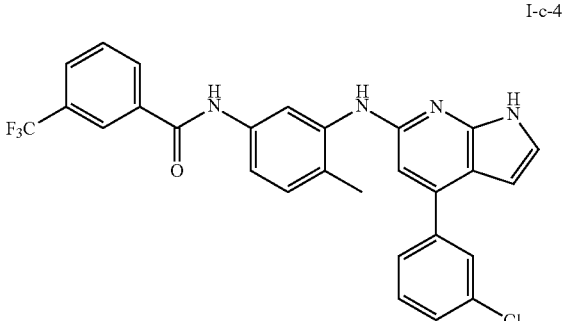
I-c-5
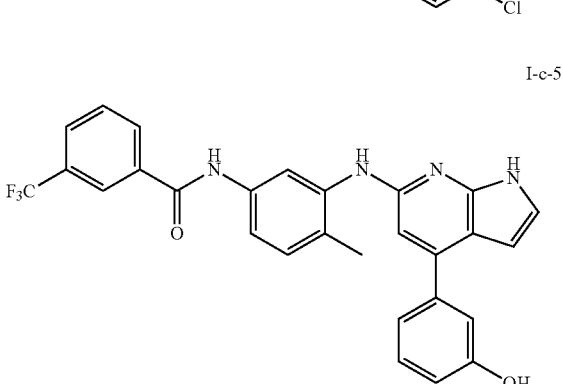
I-c-6
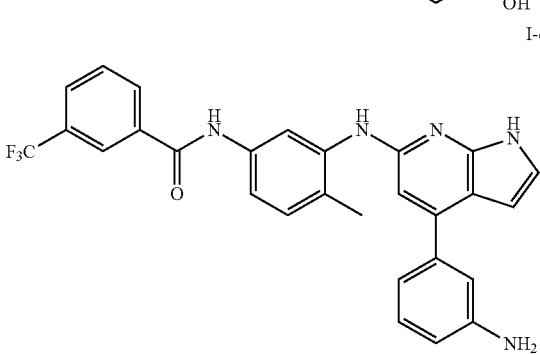
I-c-7
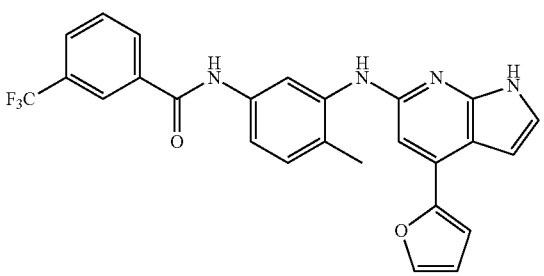
I-c-8
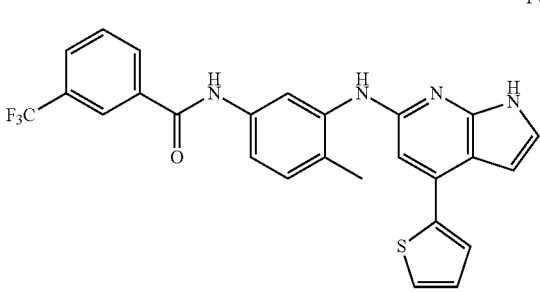

I-c-9
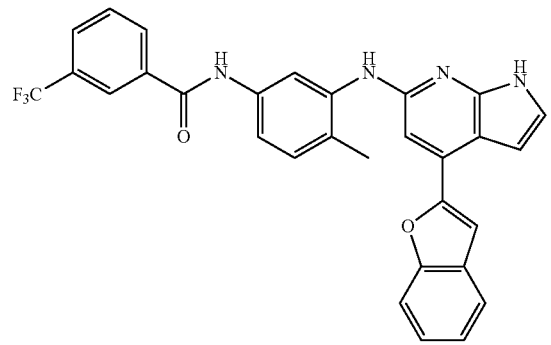
II-a-1
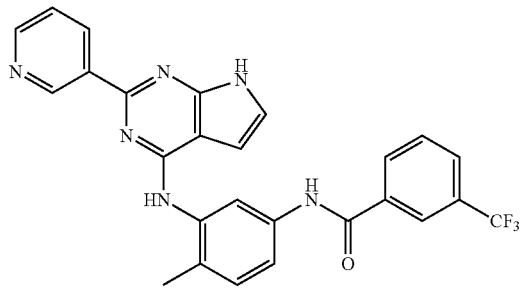
I-c-10
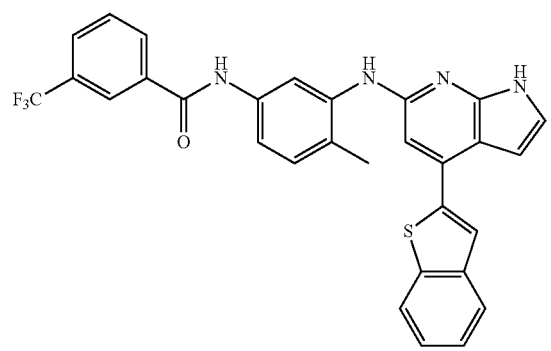
II-a-2
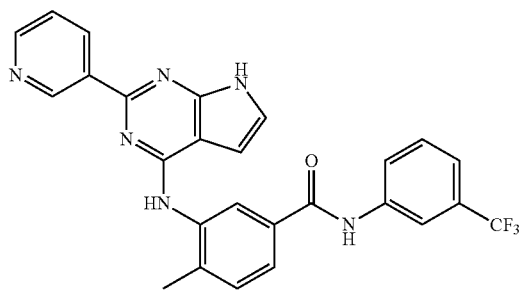
II-a-3
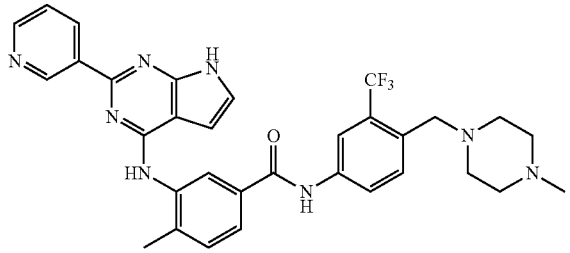
I-c-11
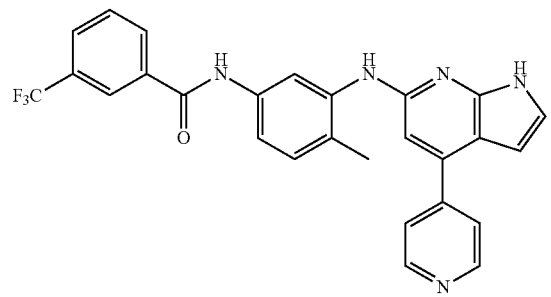
II-a-4
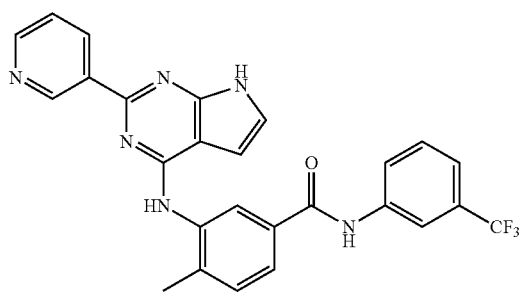
I-c-12
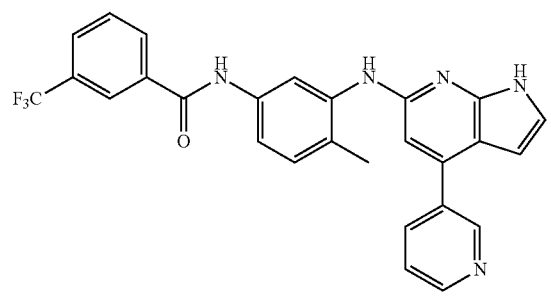
II-a-5
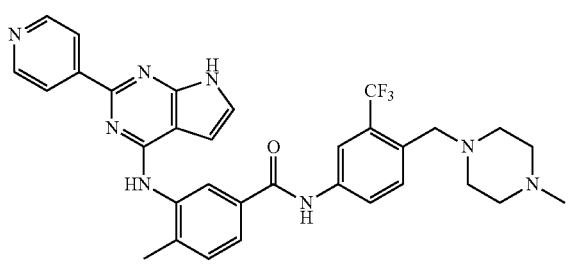

II-b-1
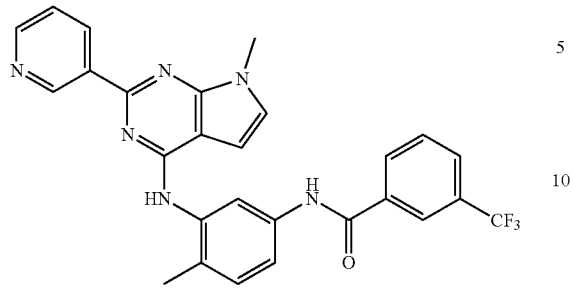
II-b-2
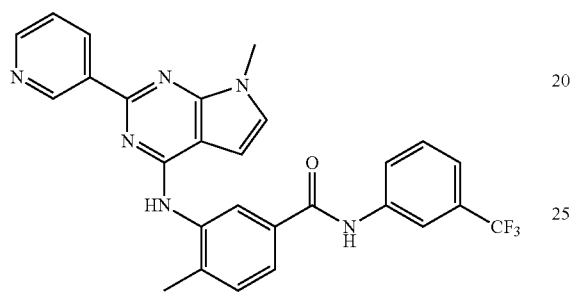
II-b-3
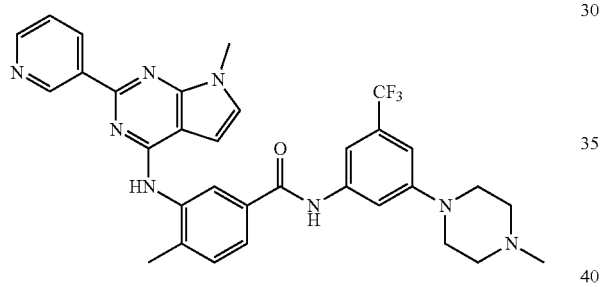
II-b-4
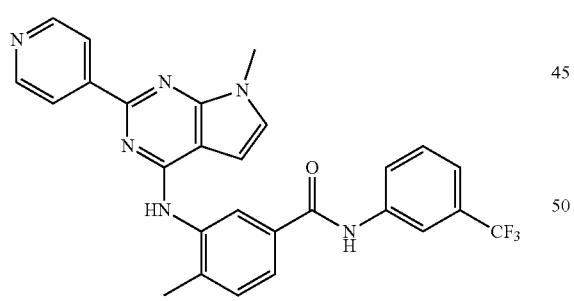
II-b-5
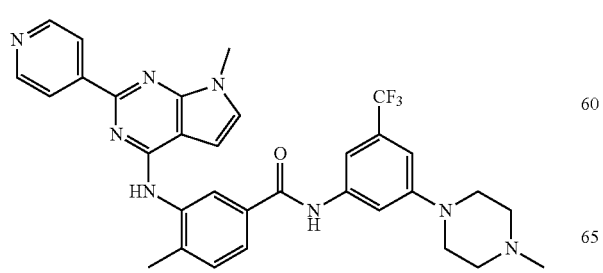
III-a-1
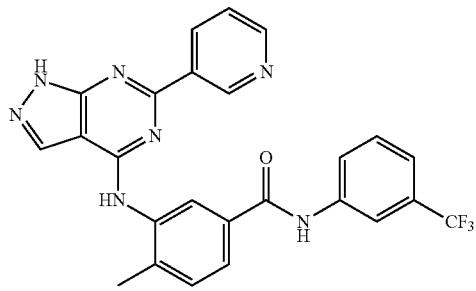
III-b-2
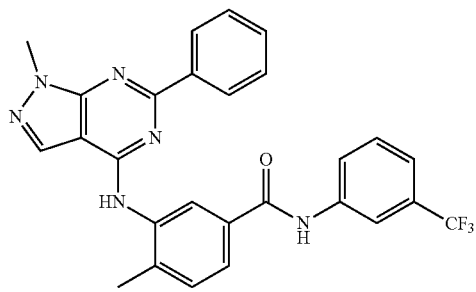
III-b-3
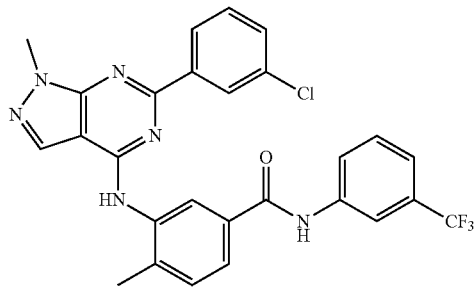
III-b-4
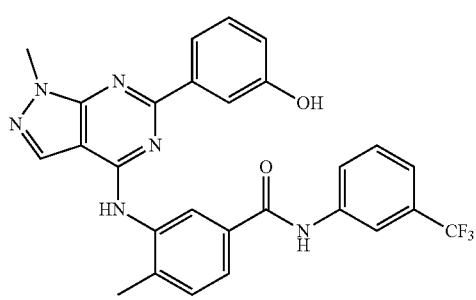
III-b-5
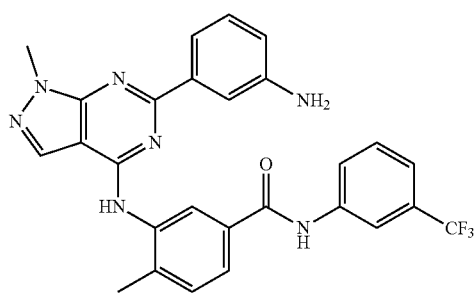

III-b-6
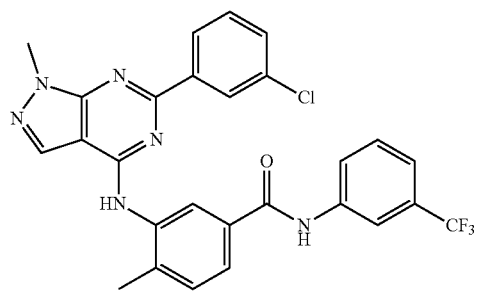
III-b-7
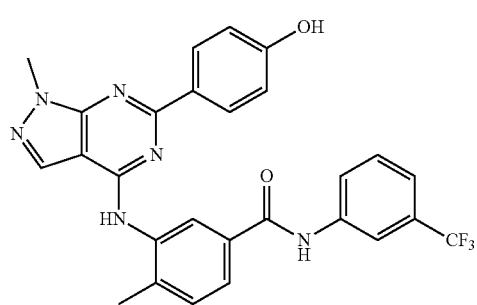
III-b-8
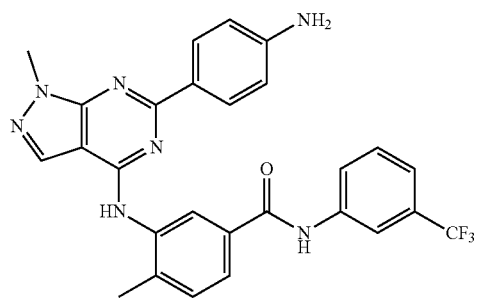
III-b-9
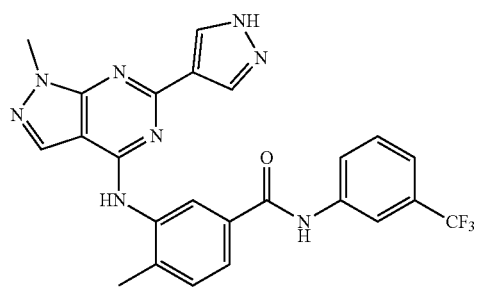
III-b-10
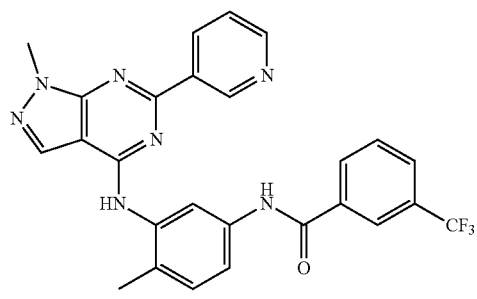
III-b-11
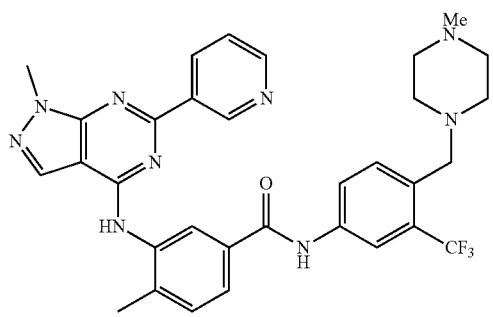
III-b-12
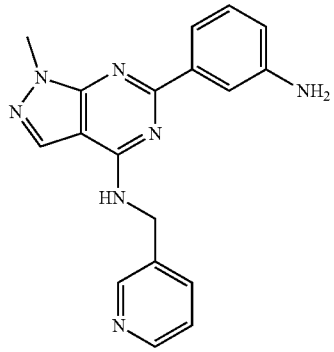
III-b-13
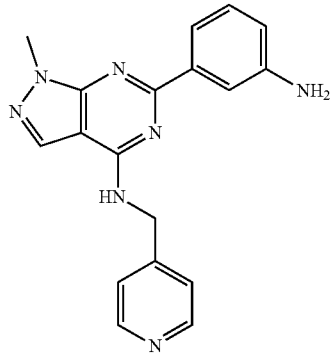
III-b-14
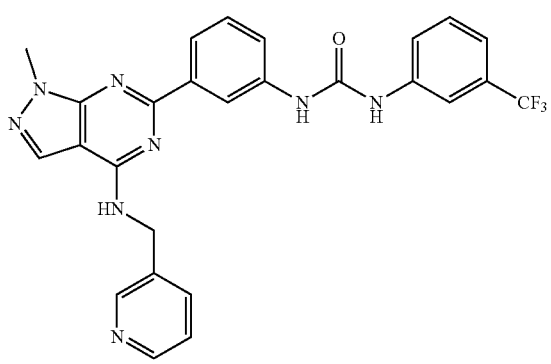

III-b-15
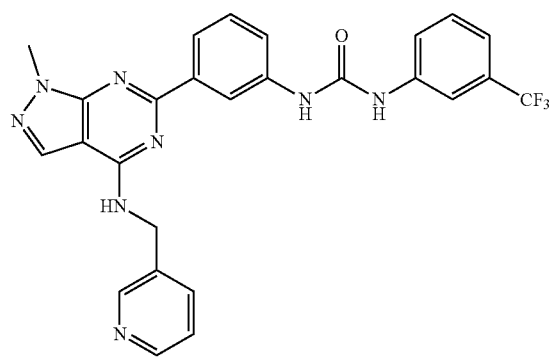
III-b-16
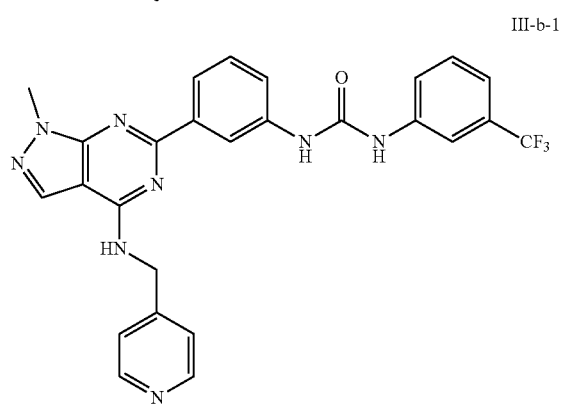
III-b-17
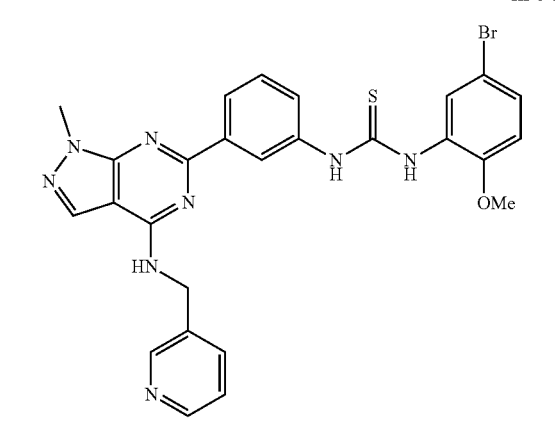
III-b-18
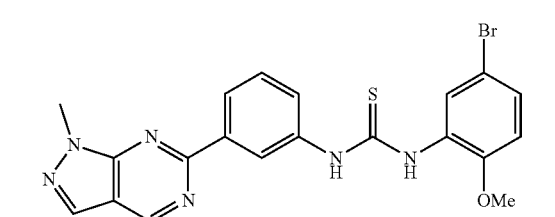
III-c-1
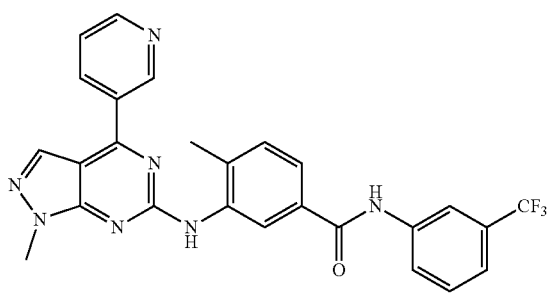
IV-a-1
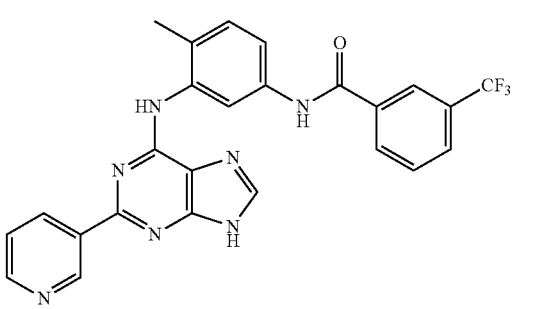
IV-a-2
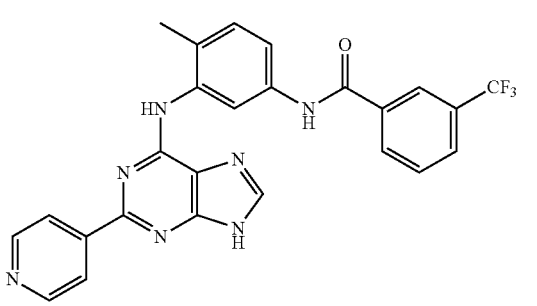
IV-a-3
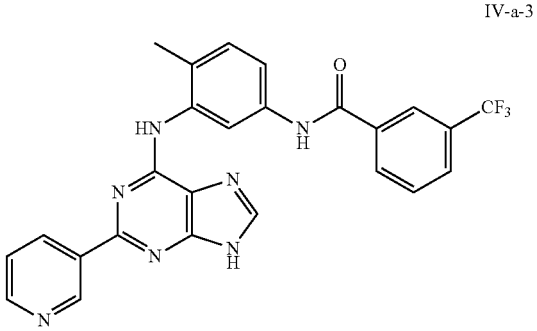
IV-a-4
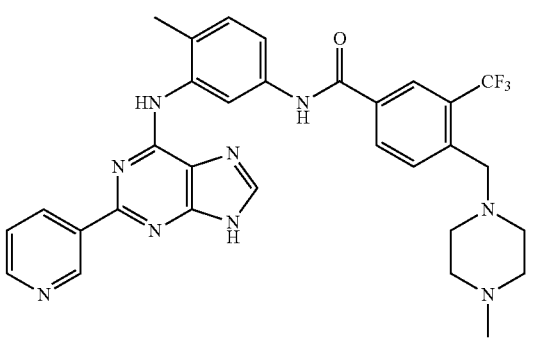

IV-a-5
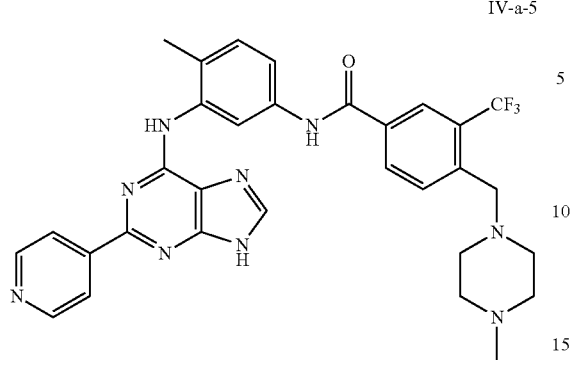
IV-a-6
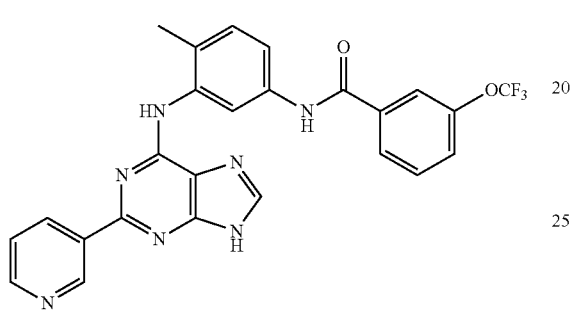
IV-a-7
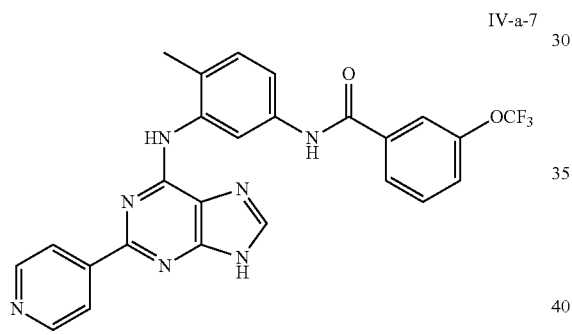
IV-b-1
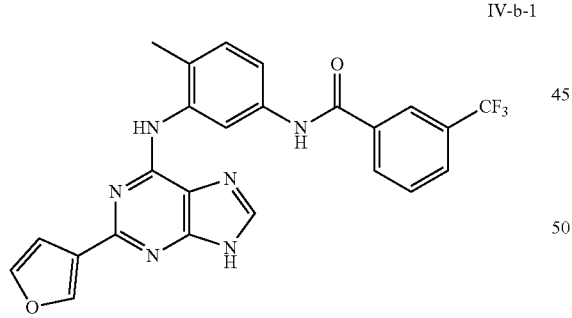
IV-b-2
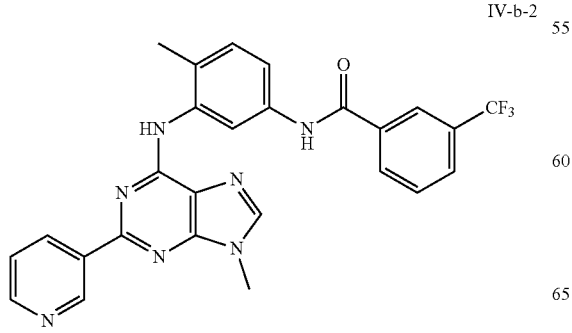
IV-b-3
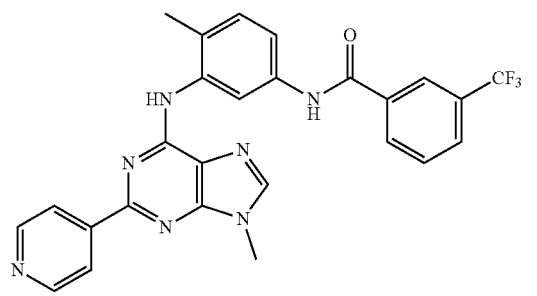
IV-b-4
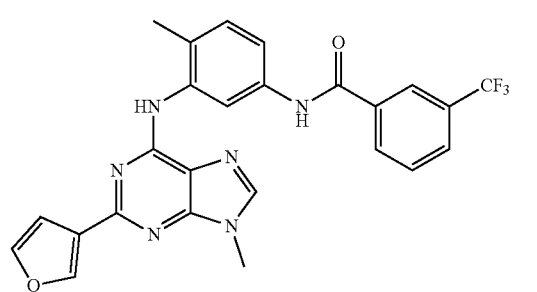
IV-b-5
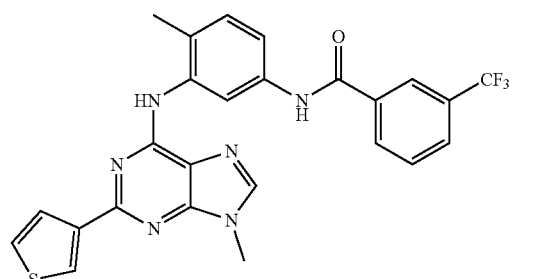
IV-b-6
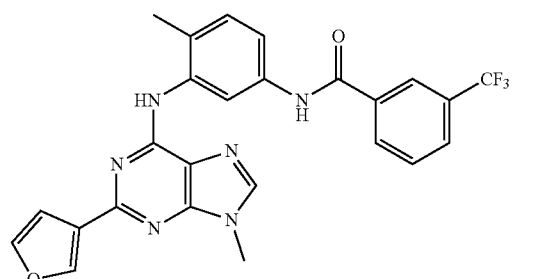
IV-b-7
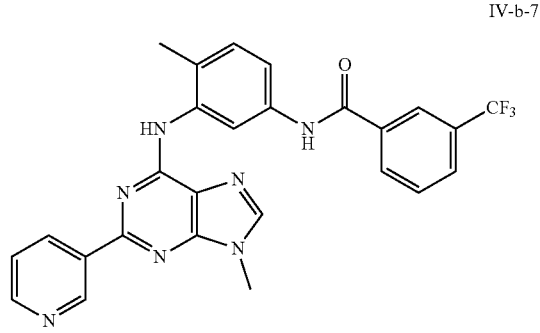

IV-b-8
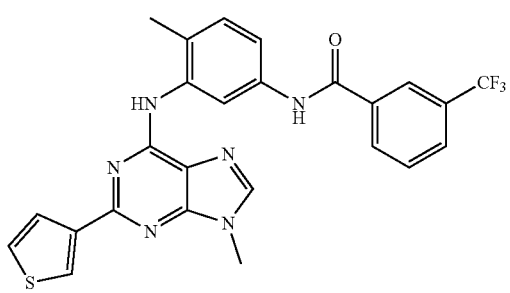
IV-b-9
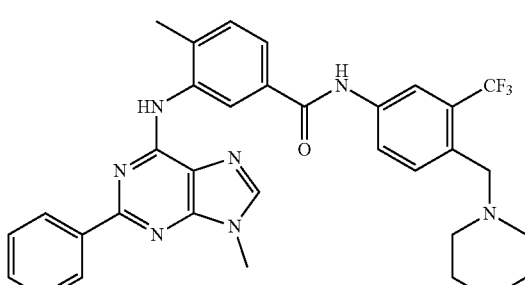
IV-b-10
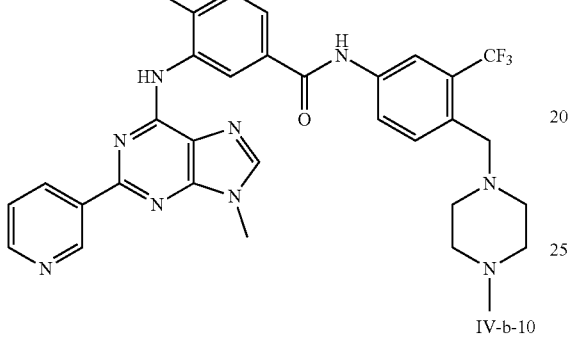
IV-b-11
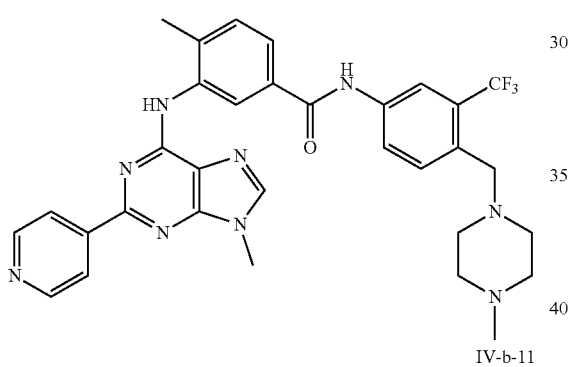
IV-b-12
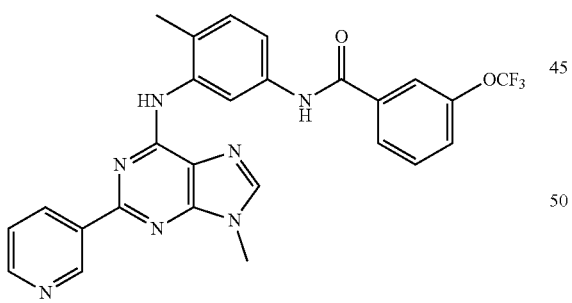
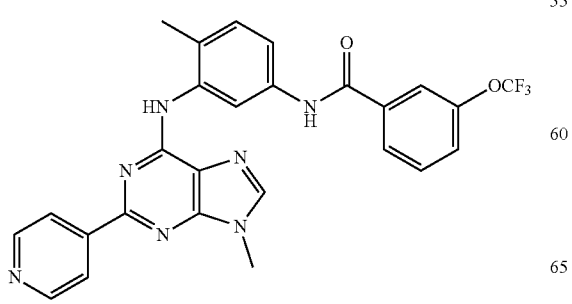
IV-b-13
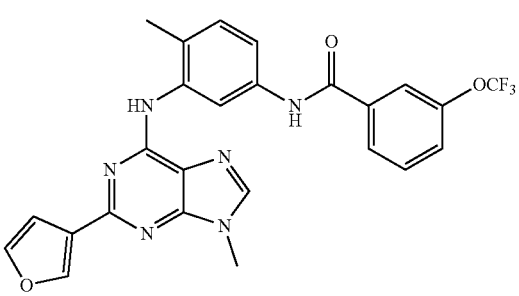
V-a-1
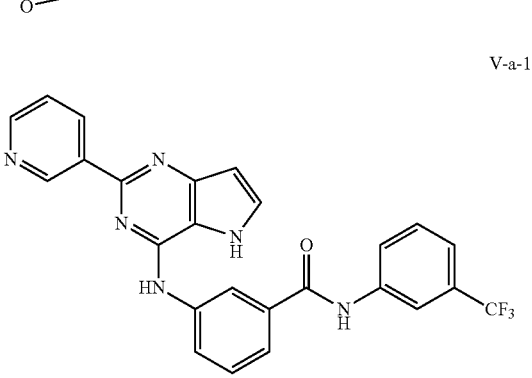
V-a-2
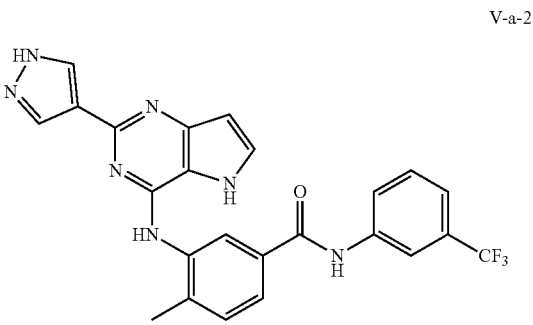
V-a-3
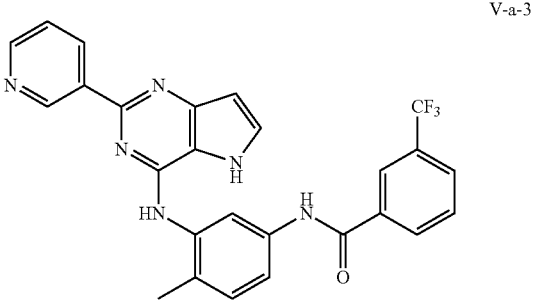
V-a-4
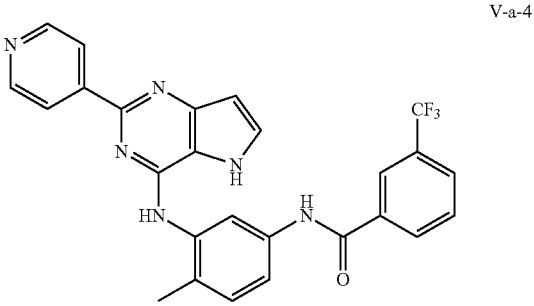

-continued
V-a-5
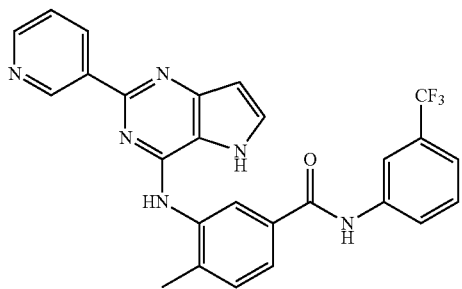
V-a-6
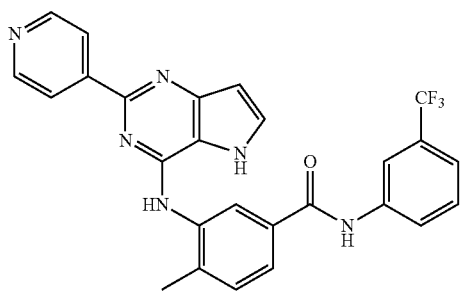
V-a-7
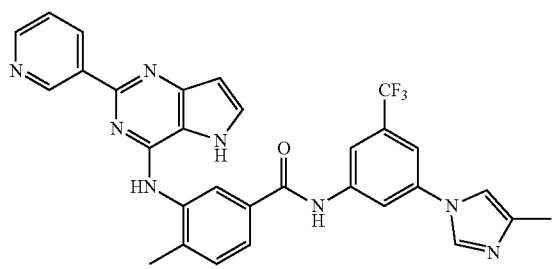
V-a-8
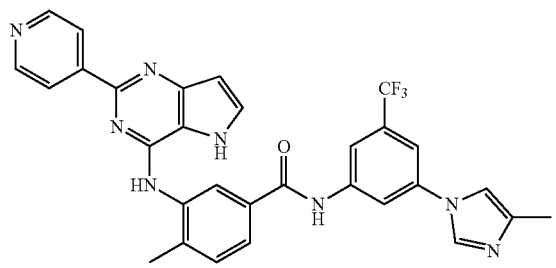
V-a-9
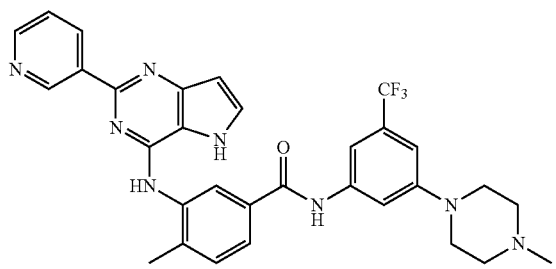
-continued
V-a-10
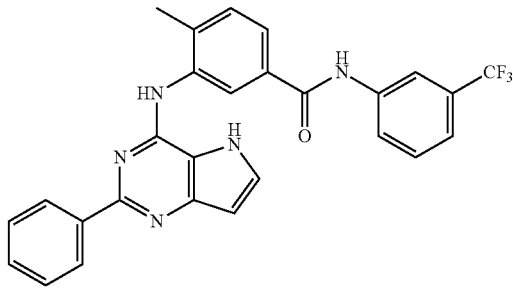
V-a-11
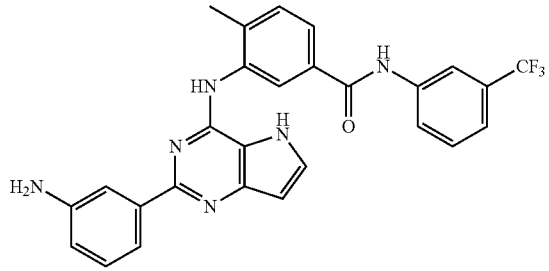
V-a-12
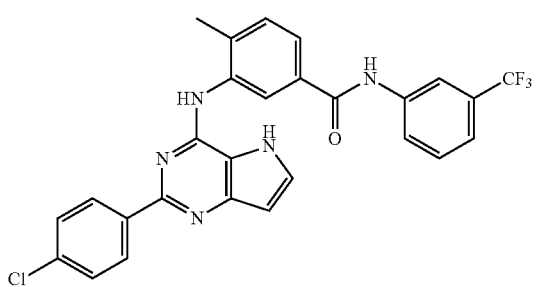
V-a-13
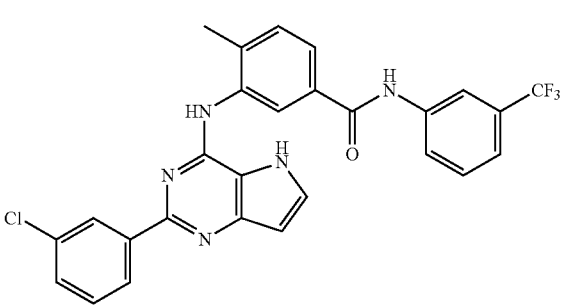
V-a-14

V-a-15
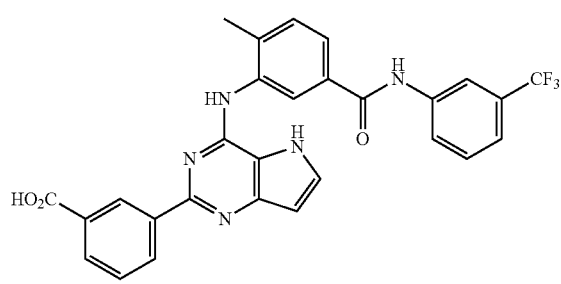
V-a-16
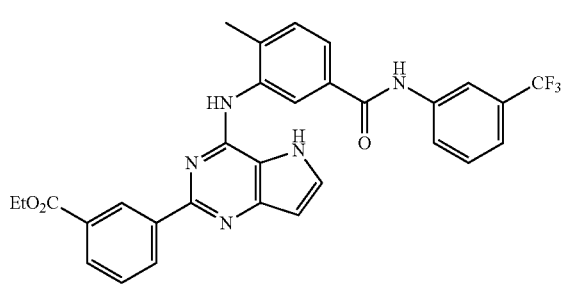
V-a-17
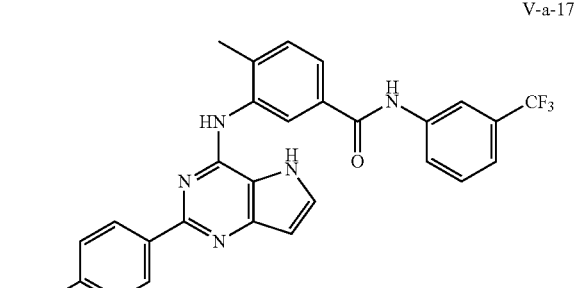
V-a-18
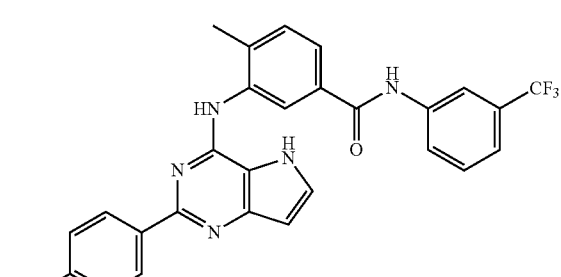
V-a-19
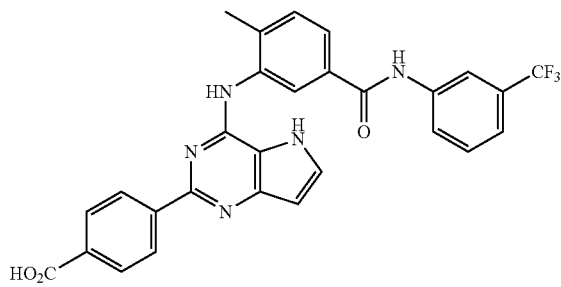
V-a-20
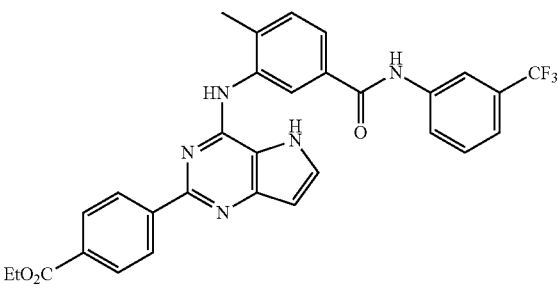
V-a-21
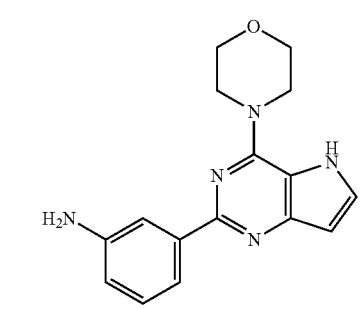
V-a-22
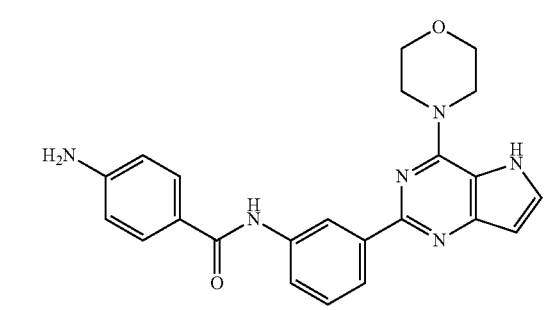
V-a-23
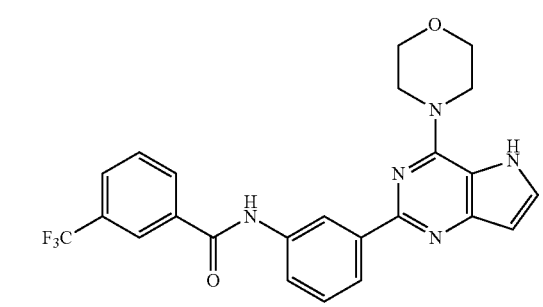
V-a-24
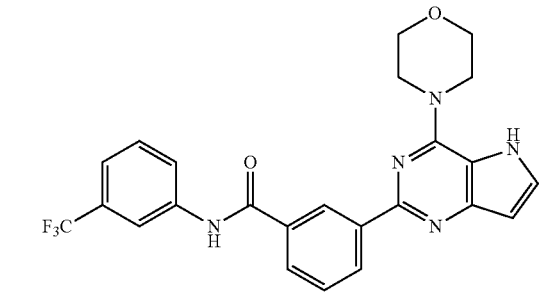

V-a-25
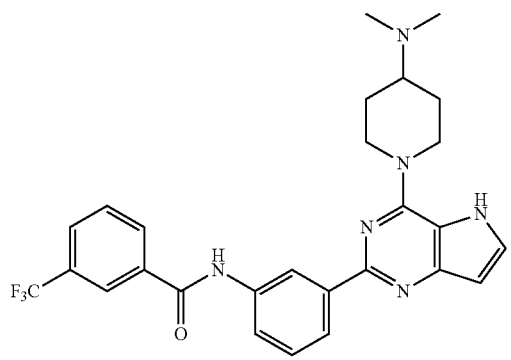
V-a-26
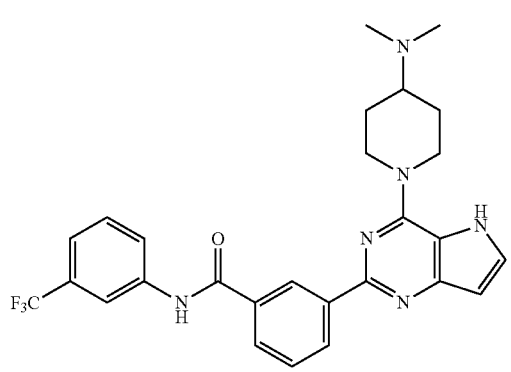
V-a-27
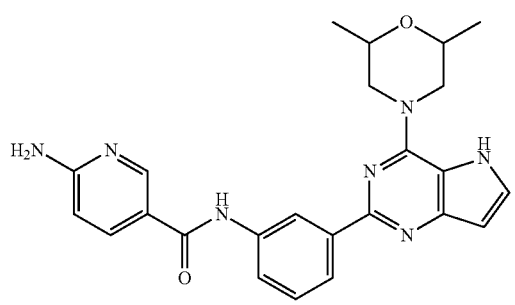
V-a-28
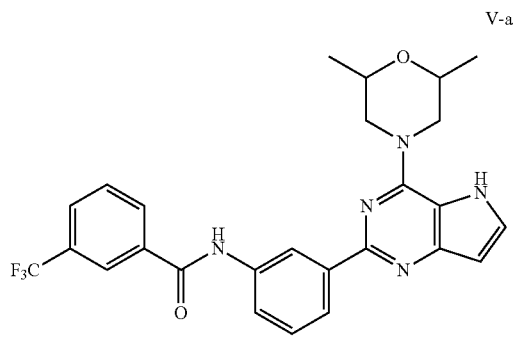
V-a-29
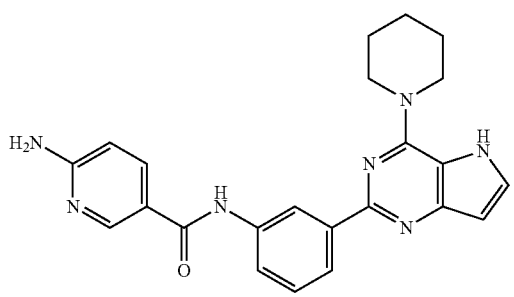
V-a-30
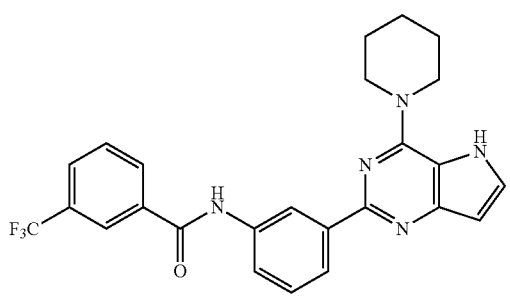
V-a-31
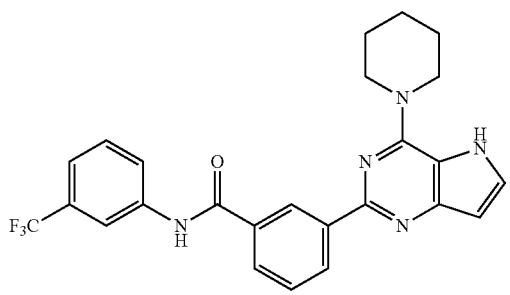
V-a-32
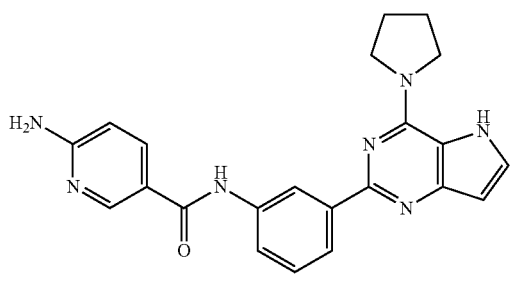
V-a-33
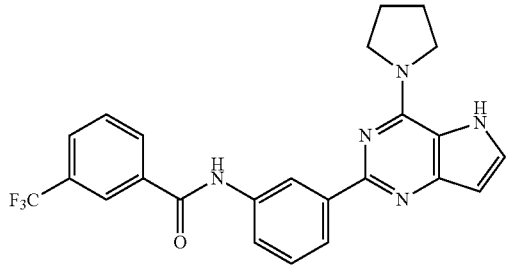

V-a-34
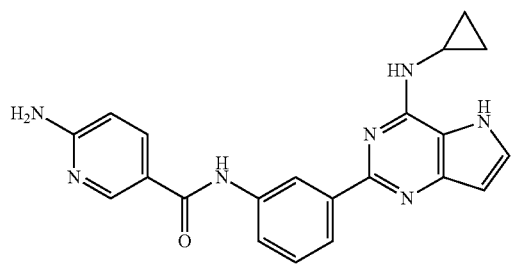
V-a-35
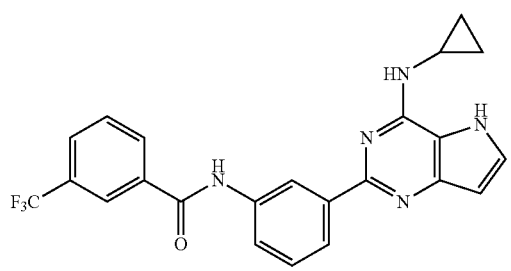
V-a-36
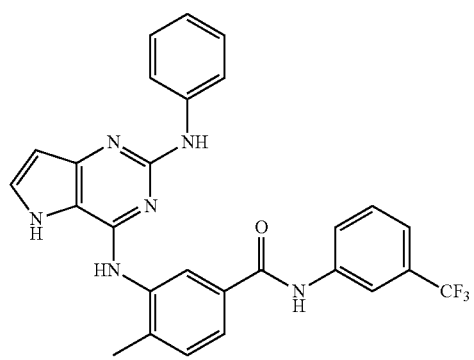
V-a-37
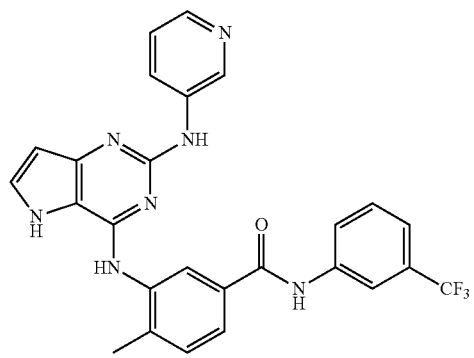
V-a-38
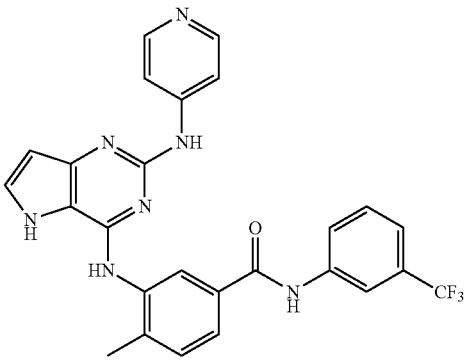
V-a-39
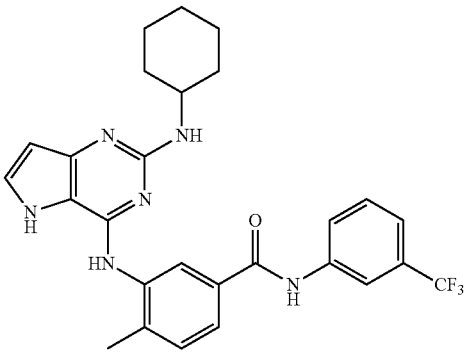
V-a-40
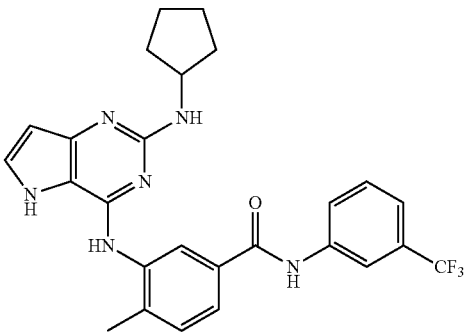
V-a-41
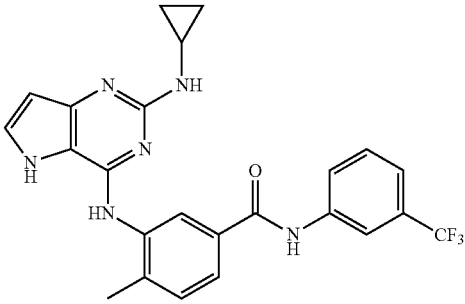

V-a-42
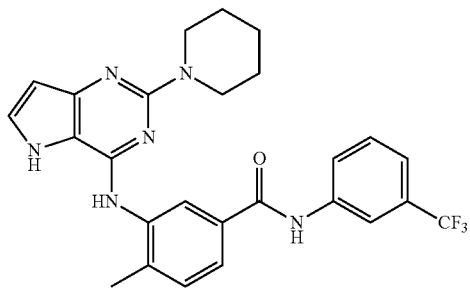
V-a-43
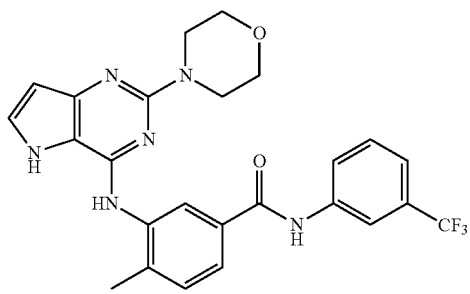
V-a-44
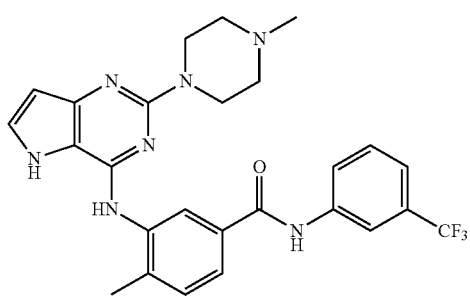
V-a-45
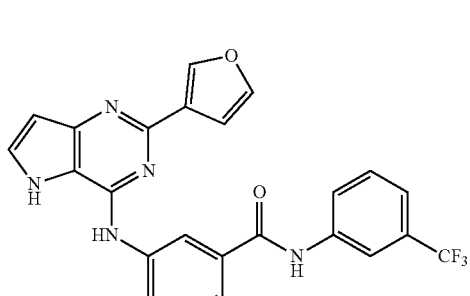
V-a-46
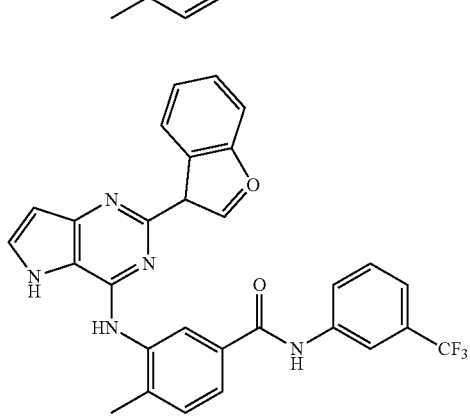
V-a-47
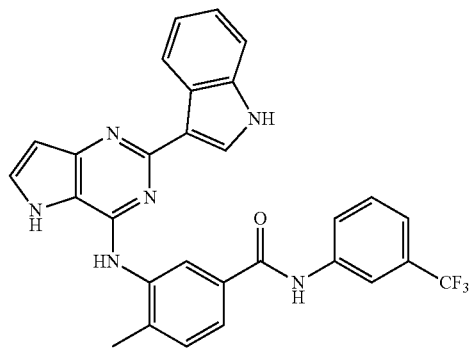
V-a-48
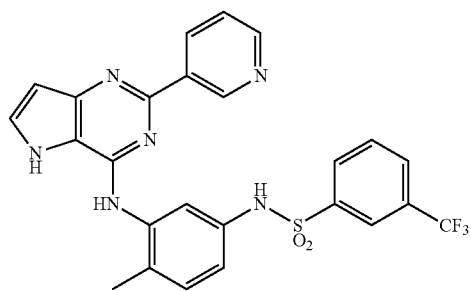
V-a-49
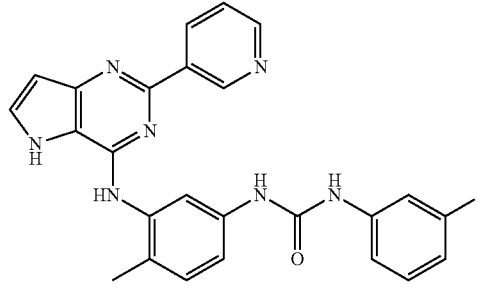
V-a-50
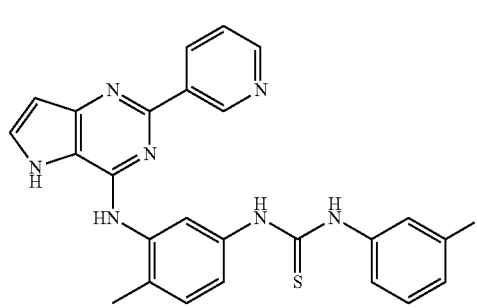
V-a-51
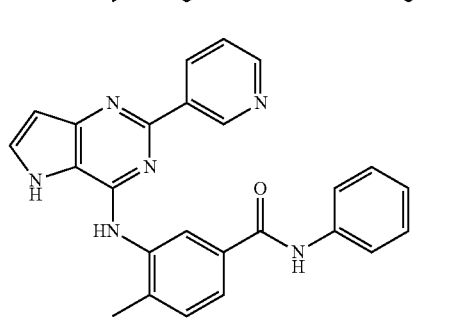

315
-continued
V-a-52
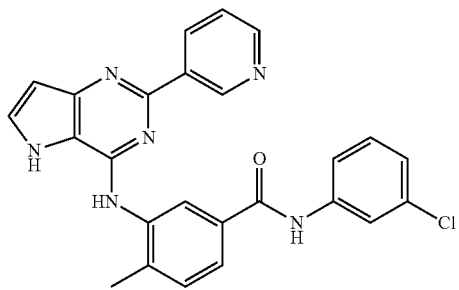
V-a-53
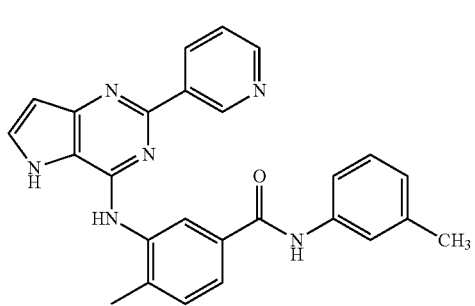
V-a-54
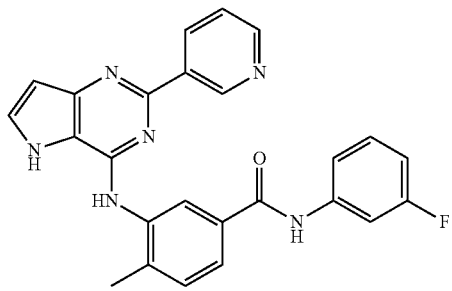
V-a-55
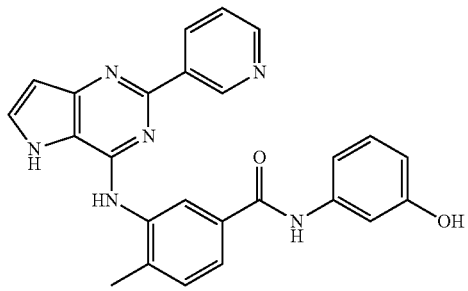
V-a-56
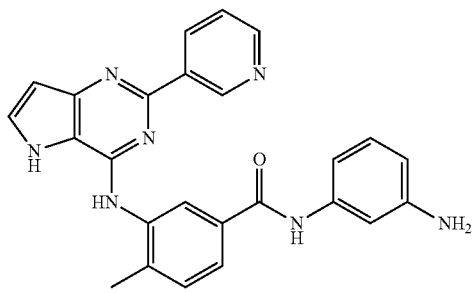
316
-continued
V-a-57
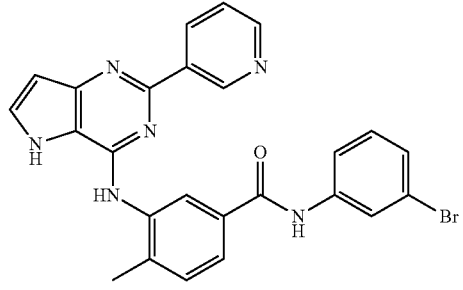
V-a-58
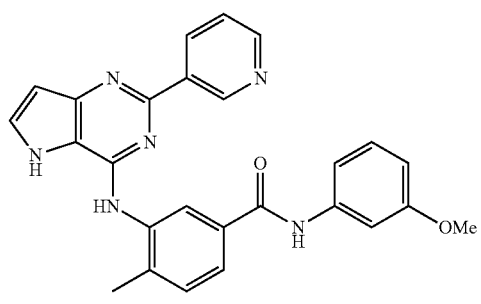
V-a-59
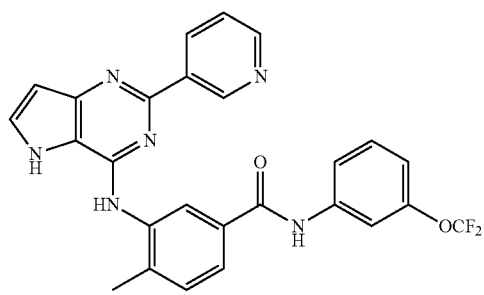
V-a-60
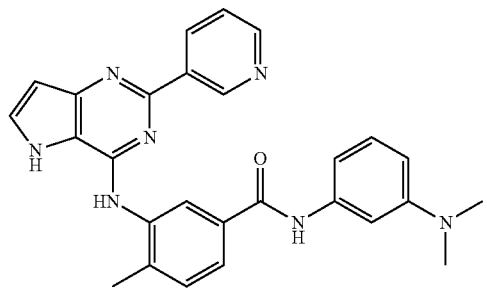
V-b-1
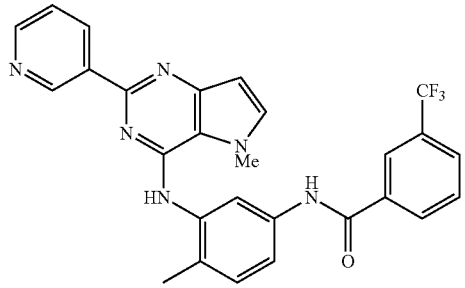

V-b-2
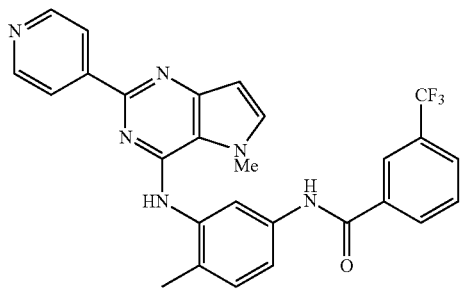
V-b-3
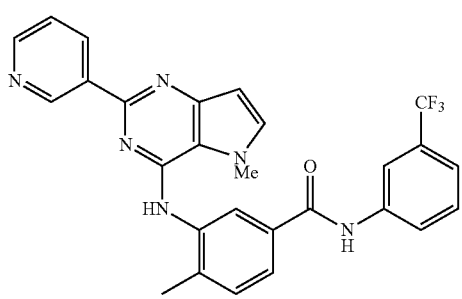
V-b-4
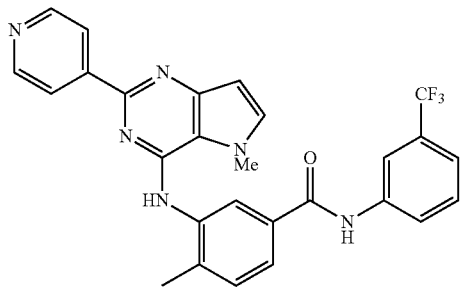
V-b-5
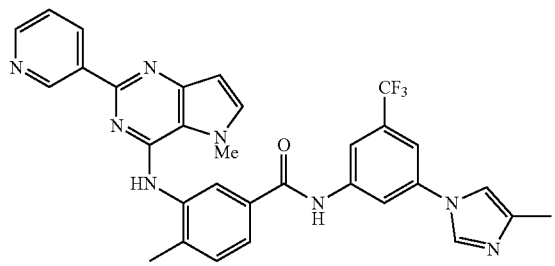
V-b-6
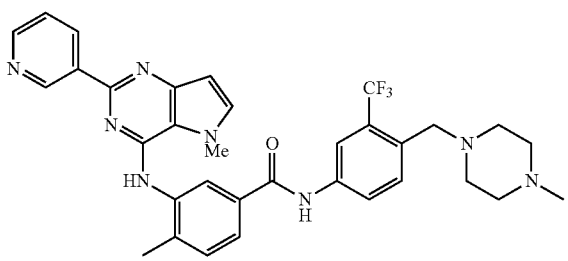
V-b-7
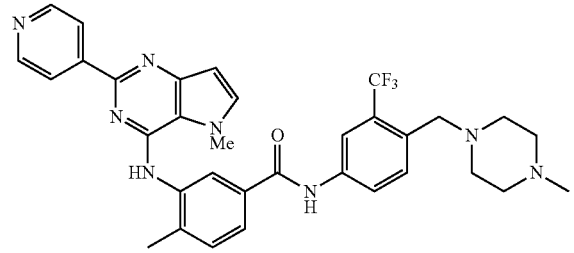
V-b-8
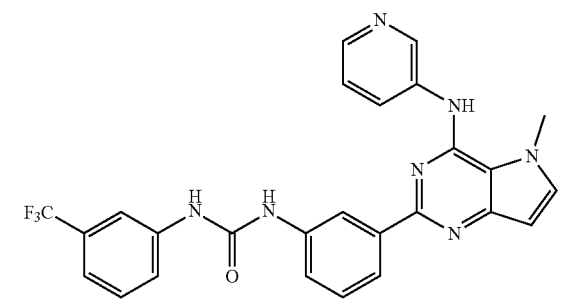
V-b-9
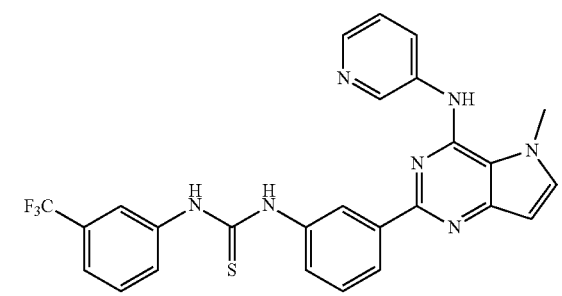
V-b-10
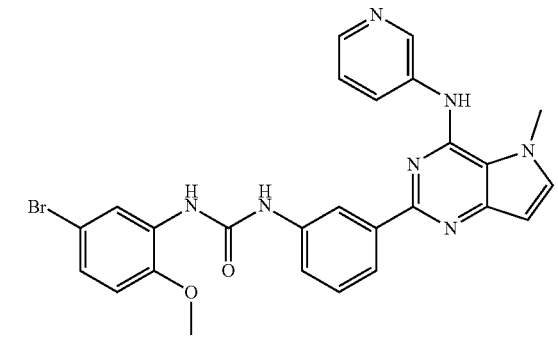
V-b-11
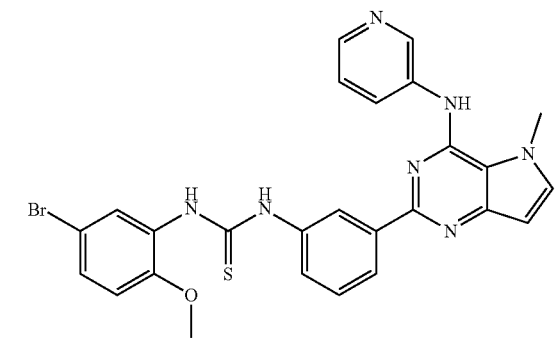

V-b-12
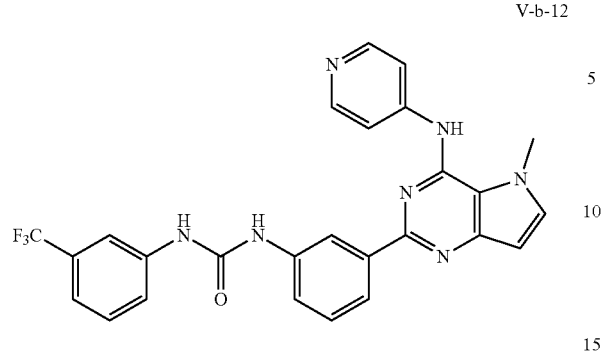
V-b-16
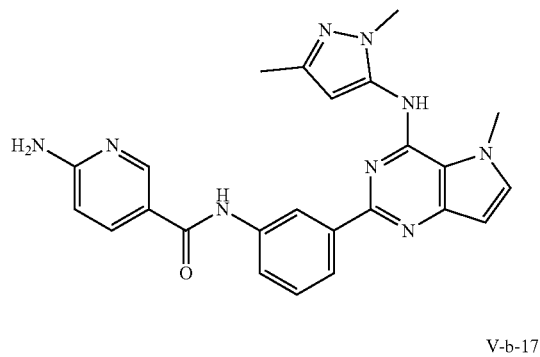
V-b-13
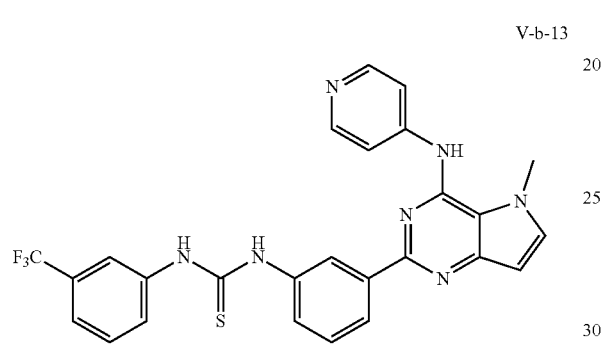
V-b-17
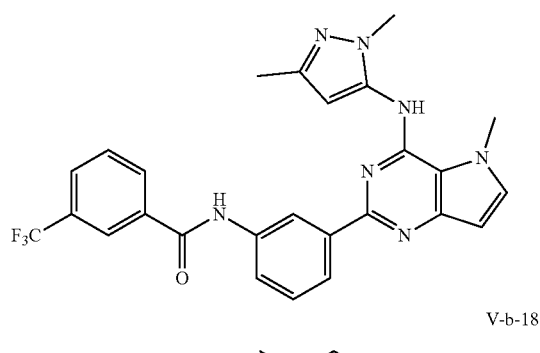
V-b-14
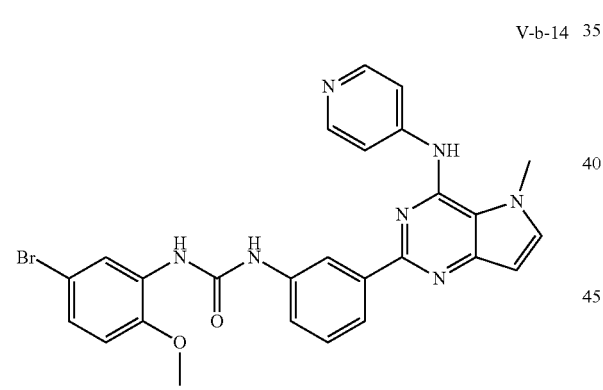
V-b-18
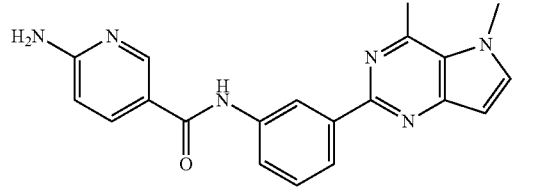
V-b-15
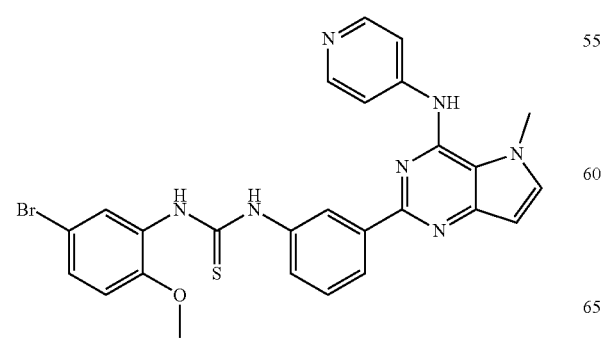
V-b-19
V-b-20
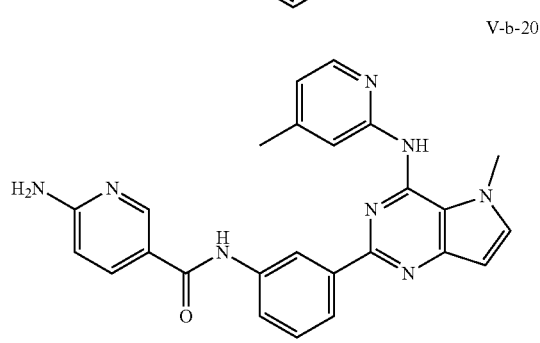

V-b-21
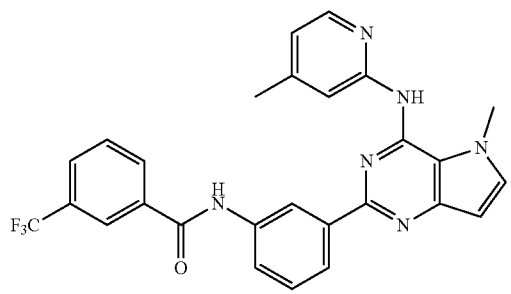
V-b-22
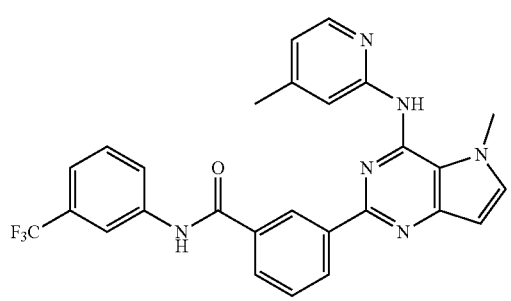
V-b-23
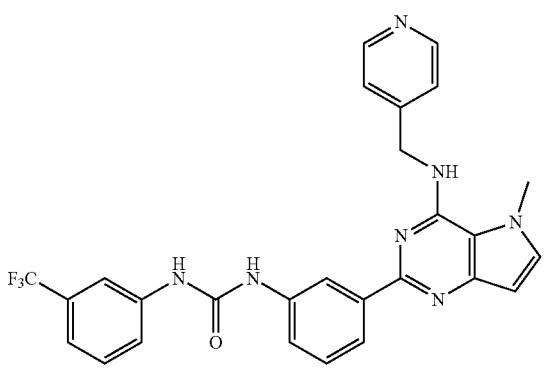
V-b-24
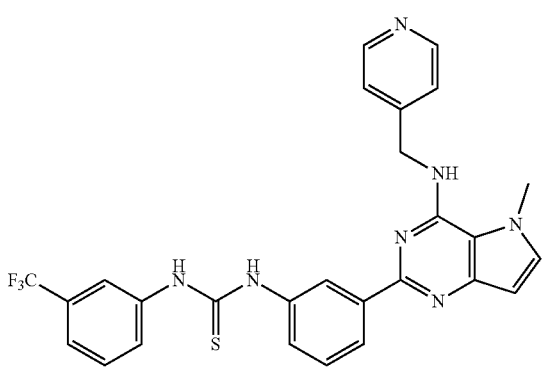
V-b-25
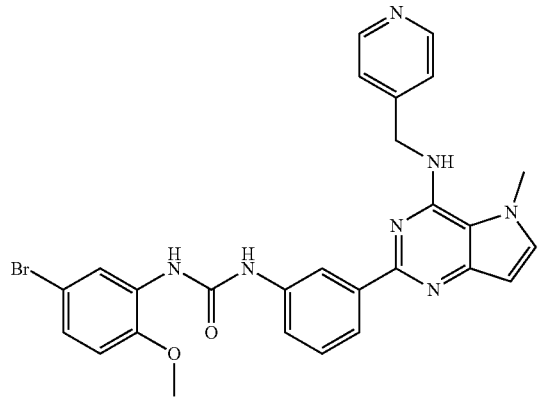
V-b-26
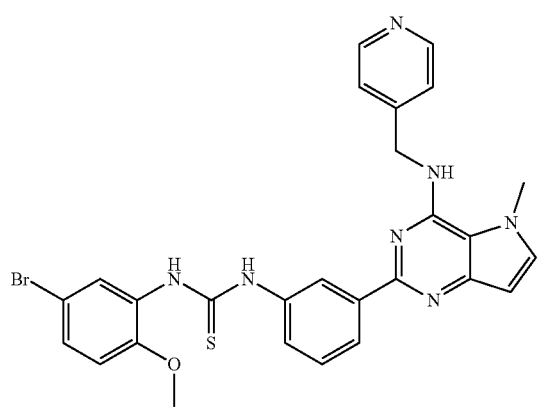
V-b-27
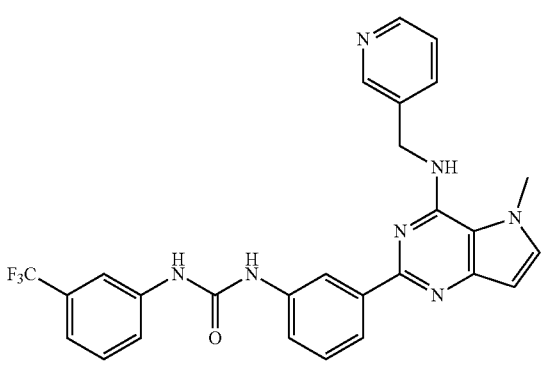
V-b-28
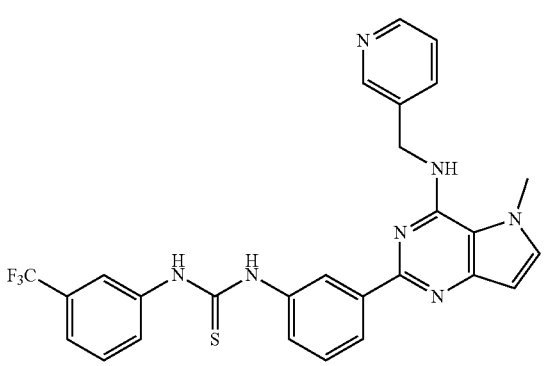

-continued
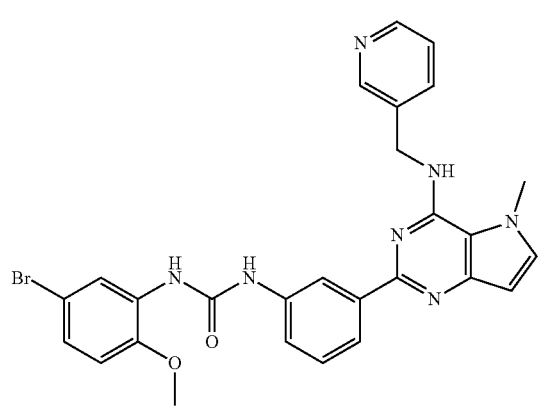
V-b-29
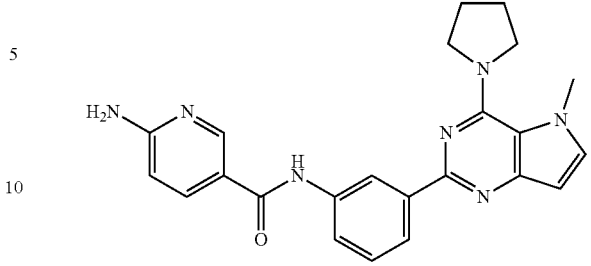
V-b-33
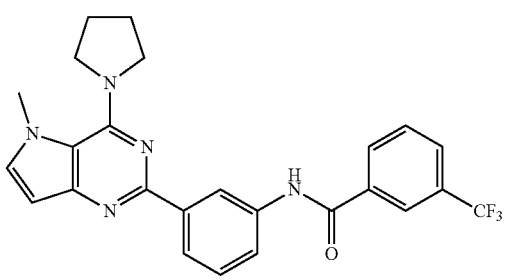
V-b-34
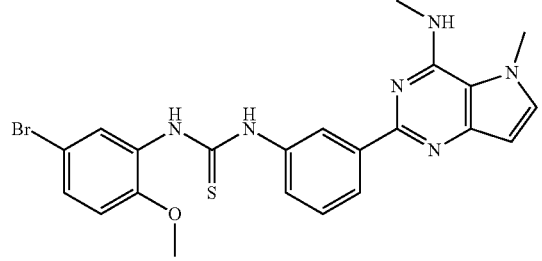
V-b-30
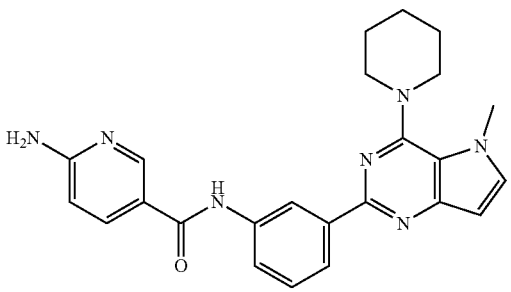
V-b-35
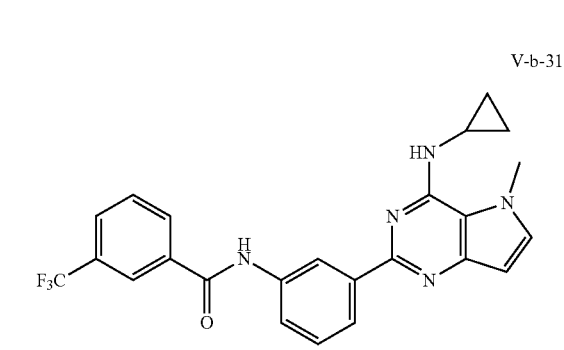
V-b-31
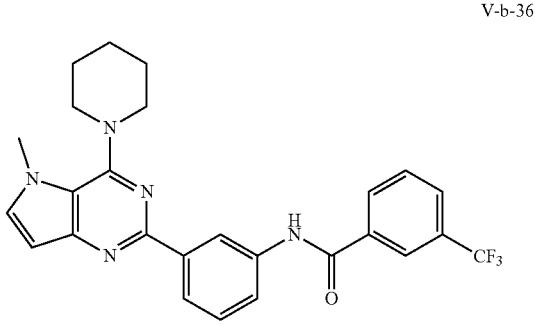
V-b-36
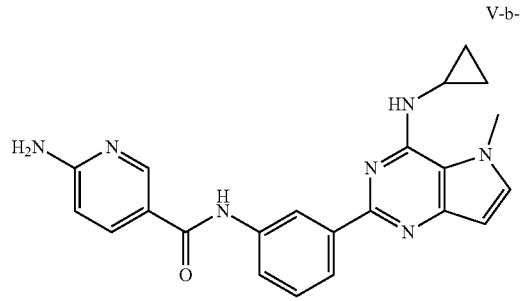
V-b-32
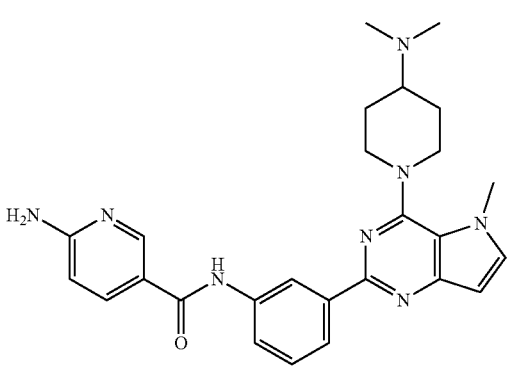
V-b-37

V-b-38
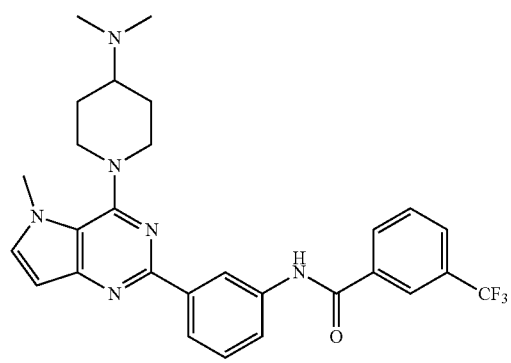
V-b-39
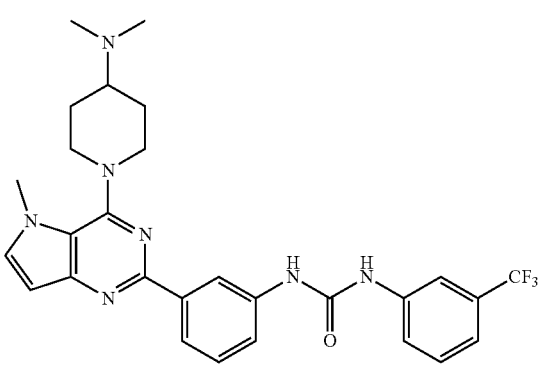
V-b-40
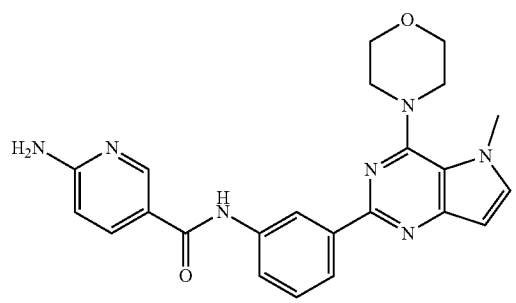
V-b-41
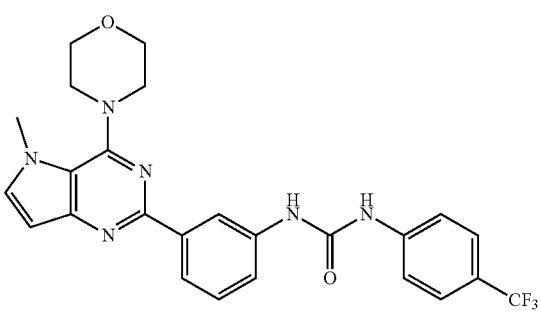
V-b-42
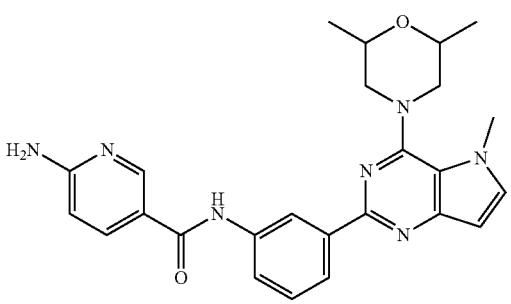
V-b-43
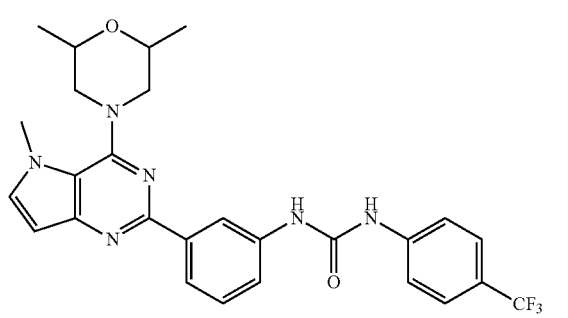
V-b-44
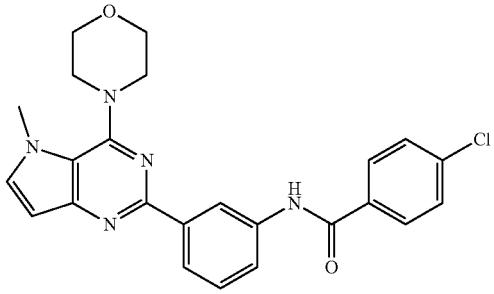
V-b-45
V-c-1
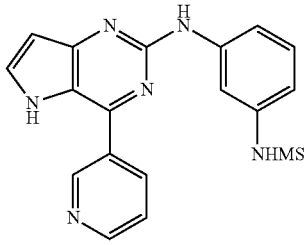

V-c-2
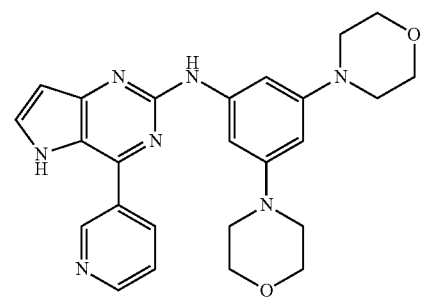
V-c-3
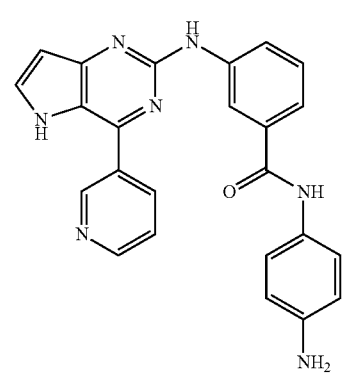
V-c-4
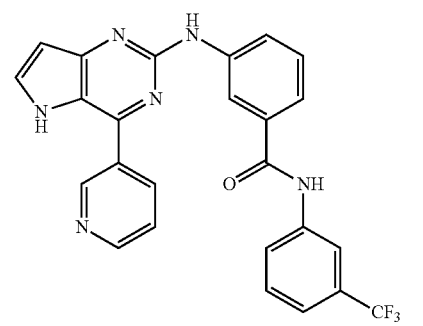
V-c-5
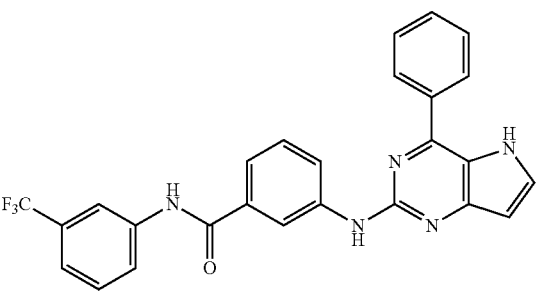
V-c-6
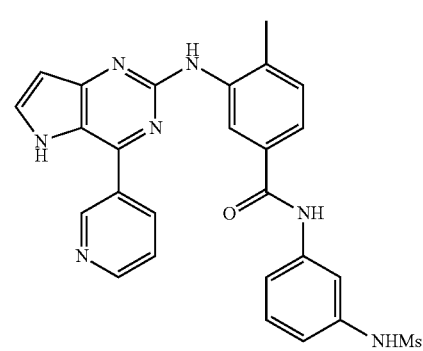
V-c-7
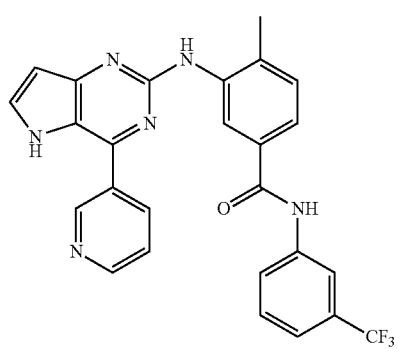
V-c-8
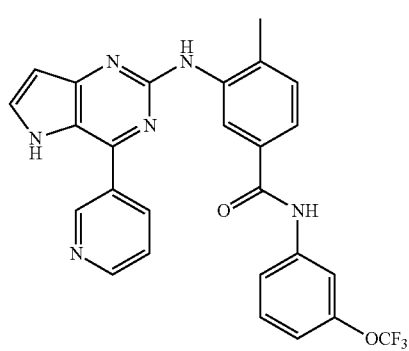
V-c-9
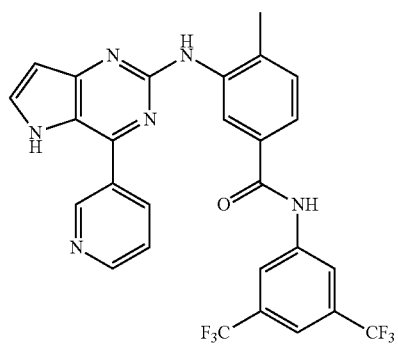
V-c-10
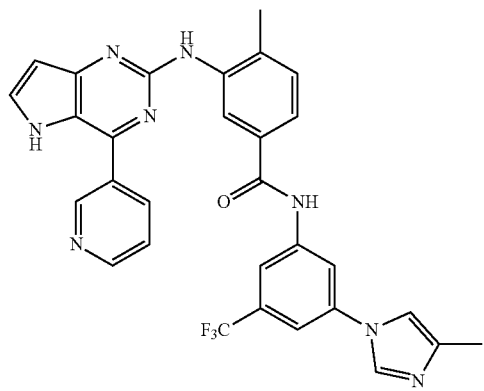

V-c-11
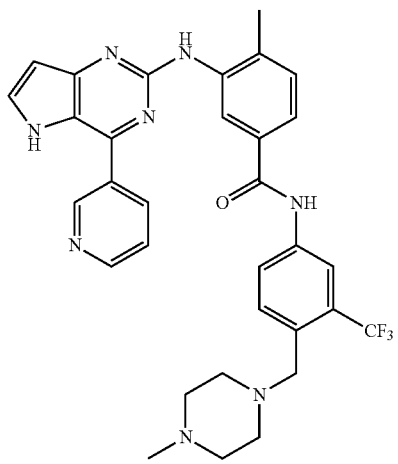
V-c-15
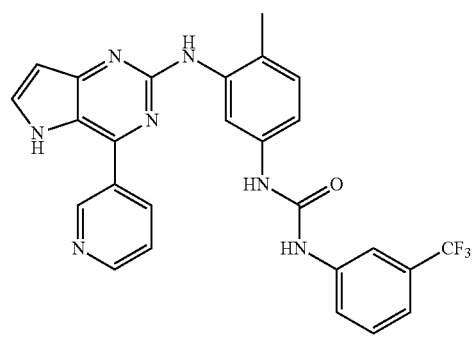
V-c-12
V-c-16
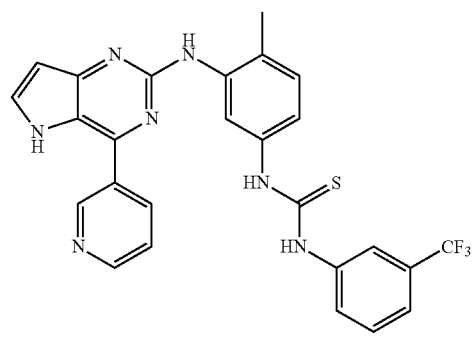
V-c-13
V-c-17
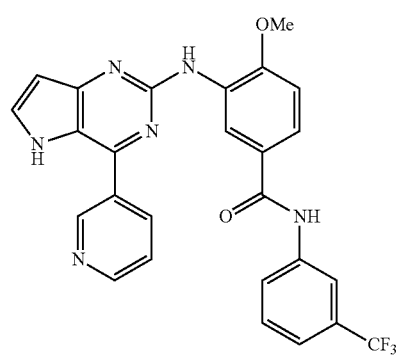
V-c-14
V-c-18
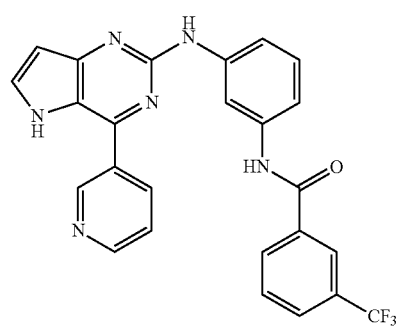

V-c-19 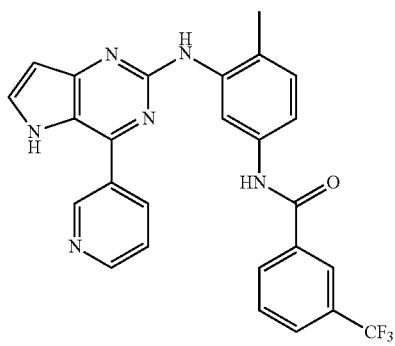
V-c-20 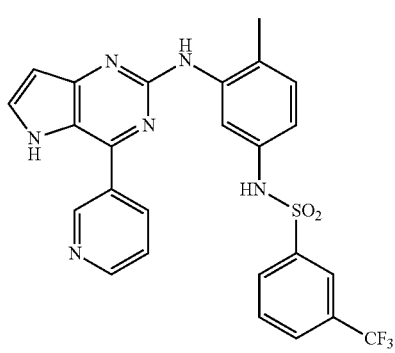
V-c-21 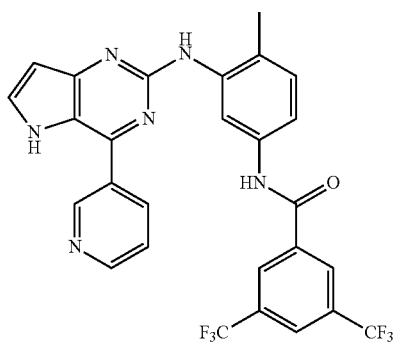
V-c-22 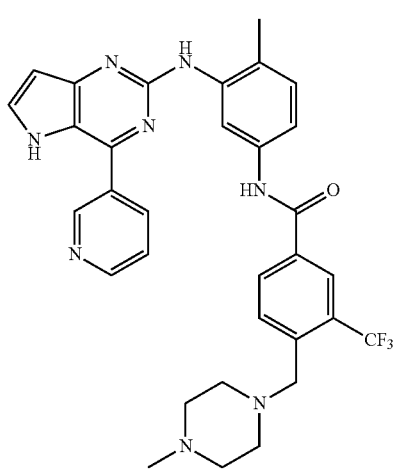
V-c-23 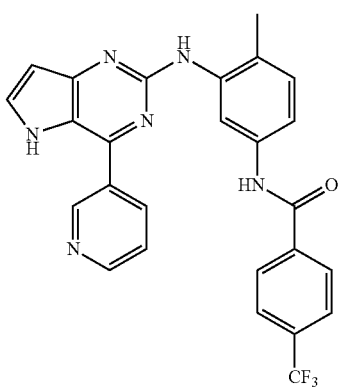
V-c-24 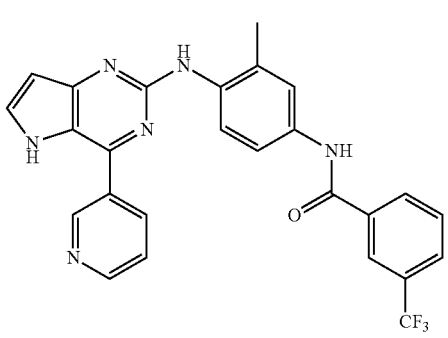
V-c-25 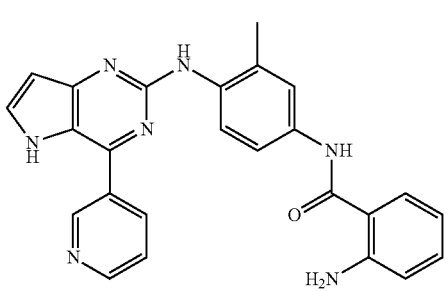
V-c-26 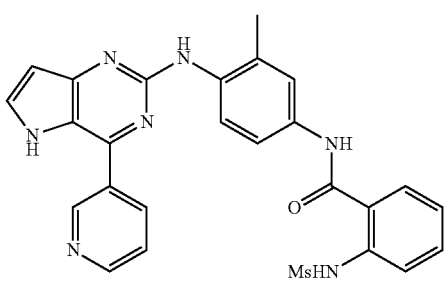
V-c-27 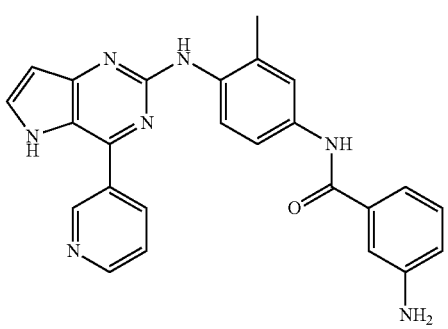

V-c-28
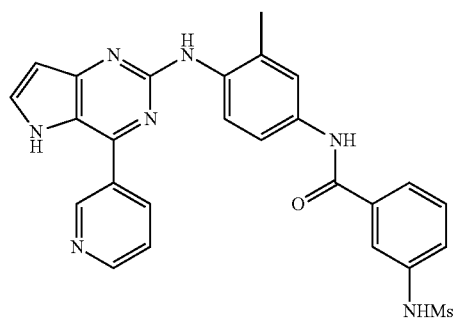
V-c-29
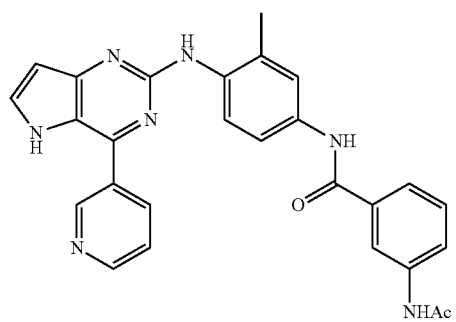
V-c-30
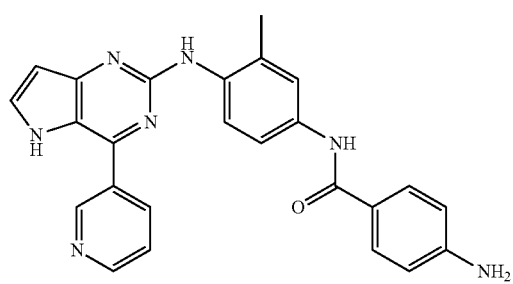
V-c-31
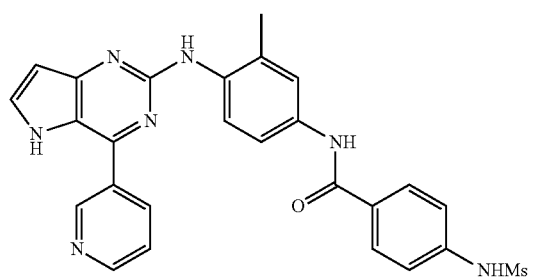
V-c-32
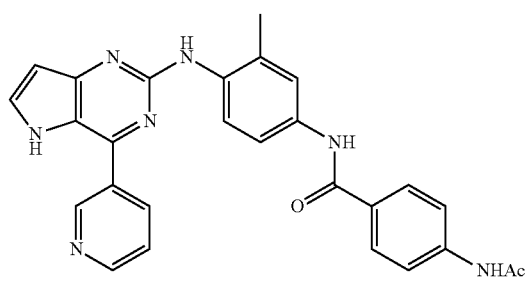
V-c-33
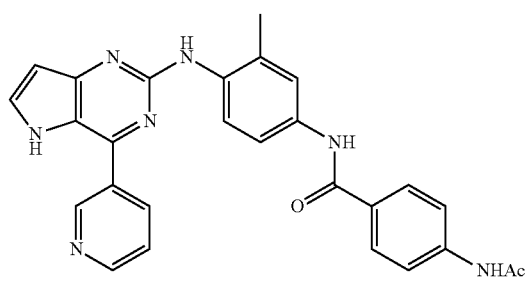
V-c-34
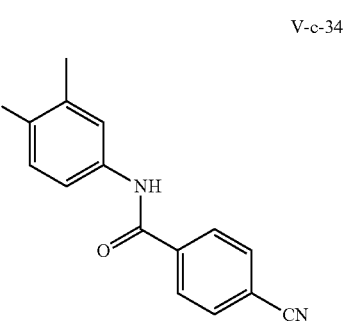
V-c-35
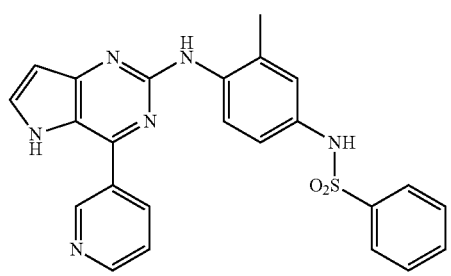
V-c-36
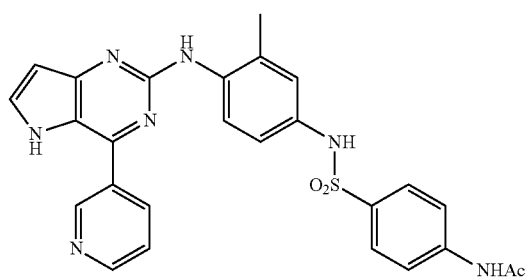
V-c-37
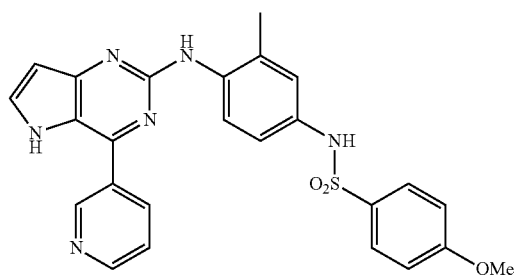

V-c-38
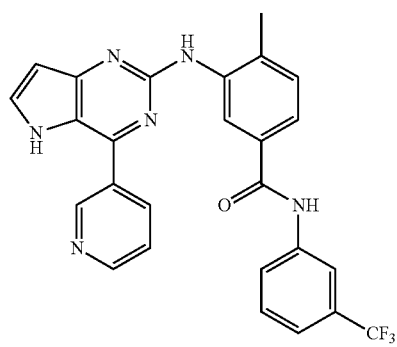
V-c-39
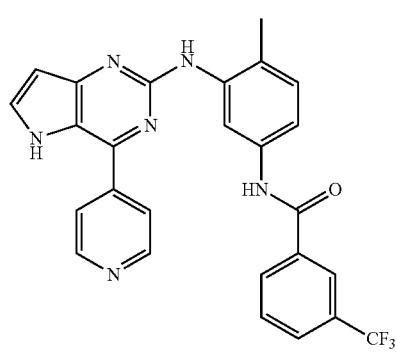
V-c-40
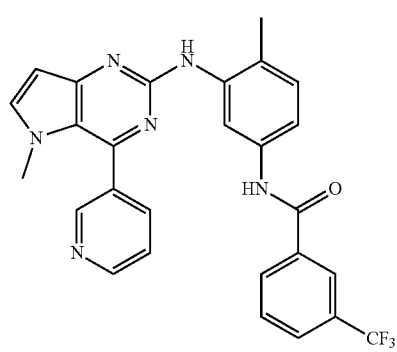
V-c-41
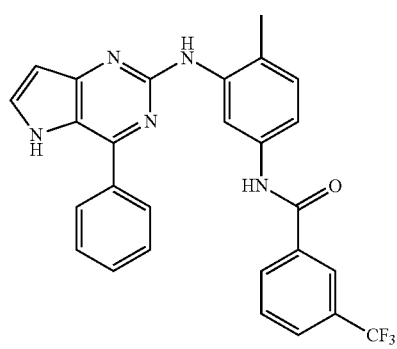
V-c-42
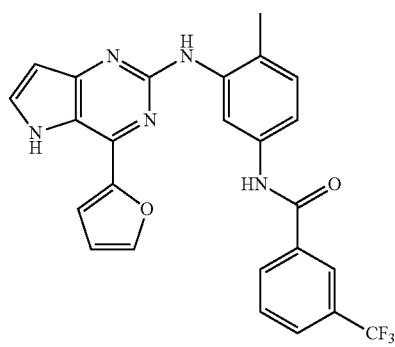
V-c-43
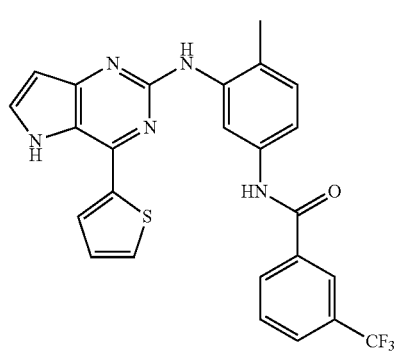
V-c-44
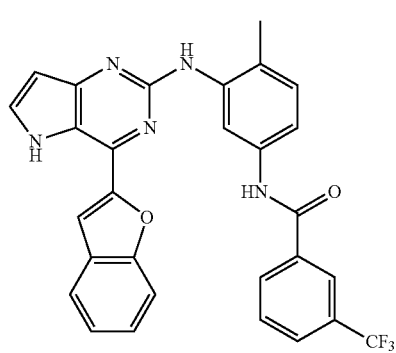
V-c-45
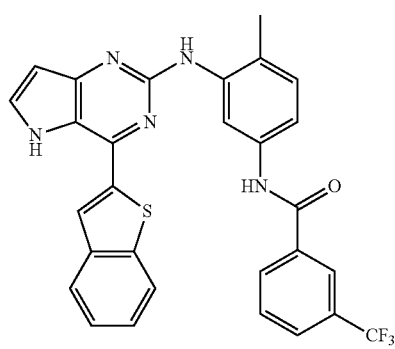

V-c-46
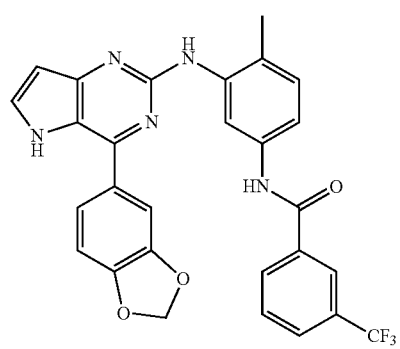
V-c-47
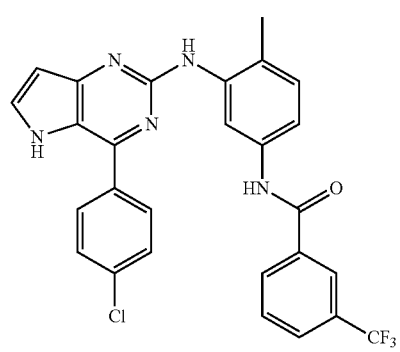
V-c-48
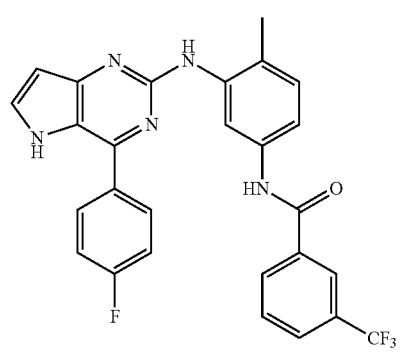
V-c-49
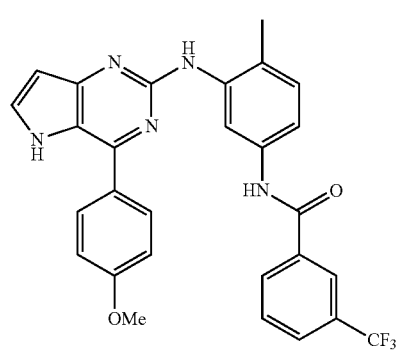
V-c-50
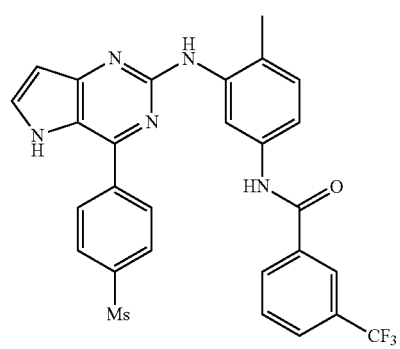
V-c-51
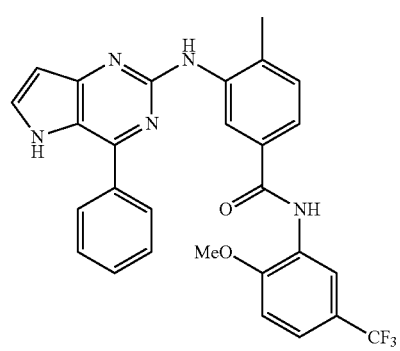
V-c-52
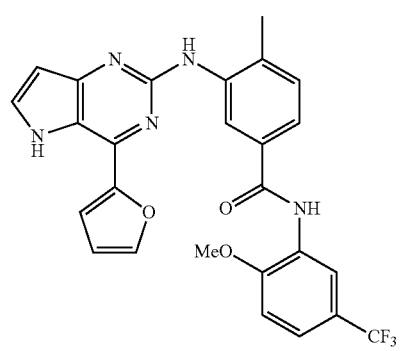
V-c-53
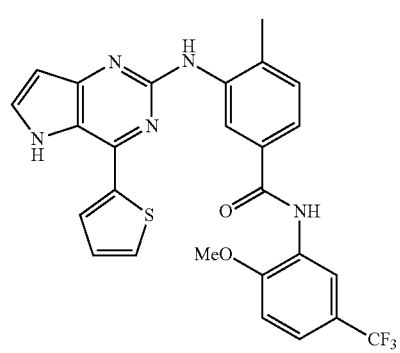

-continued
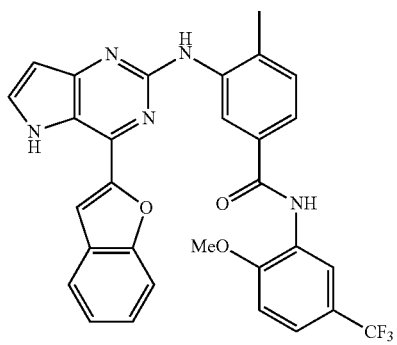 V-c-54
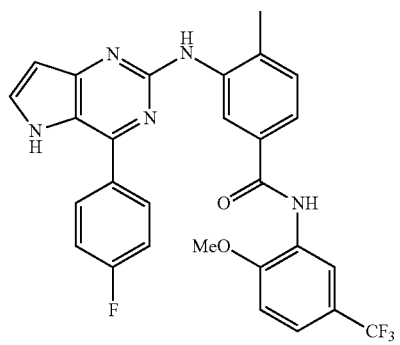 V-c-58
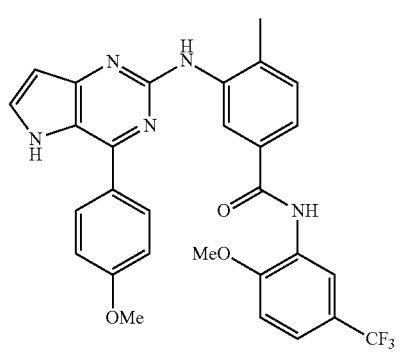 V-c-59
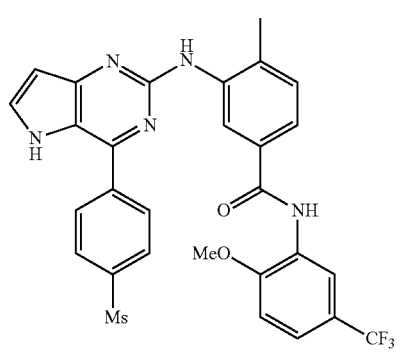 V-c-60
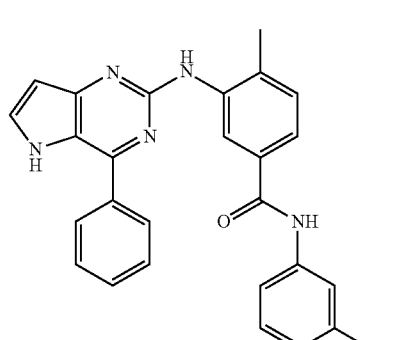 V-c-61
V-c-55
V-c-56
V-c-57

V-c-62
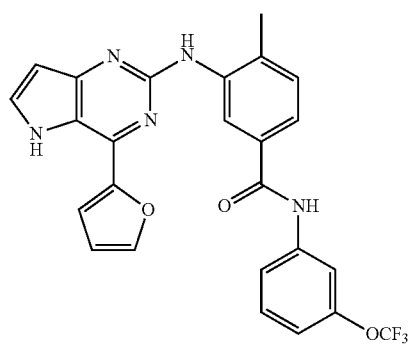
V-c-66
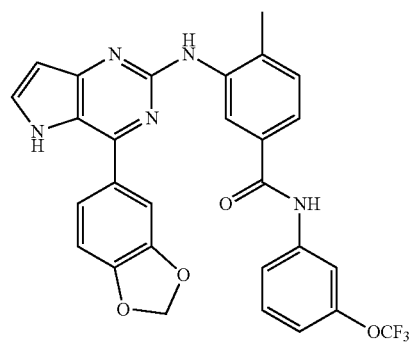
V-c-63
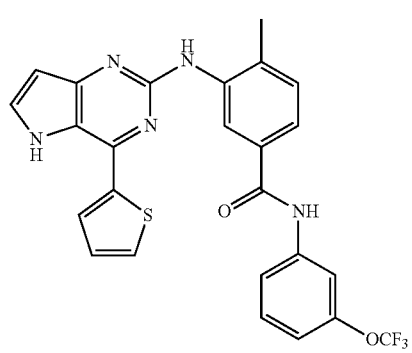
V-c-67
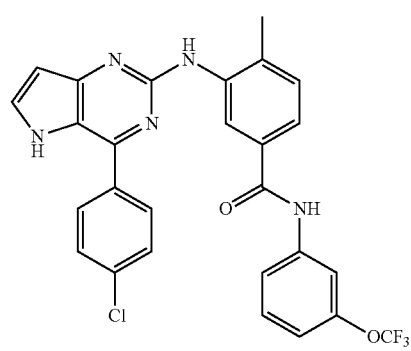
V-c-64
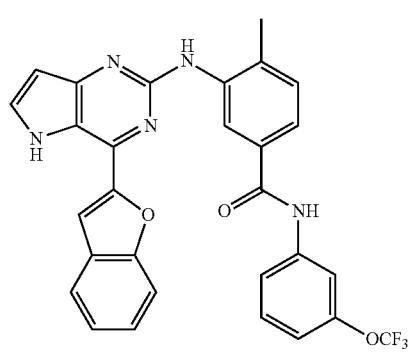
V-c-68
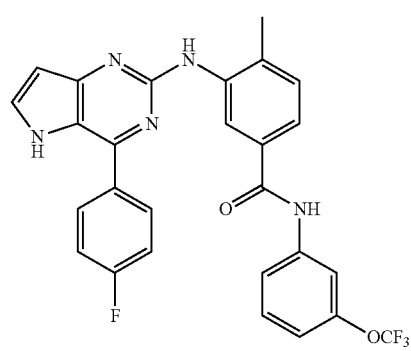
V-c-65
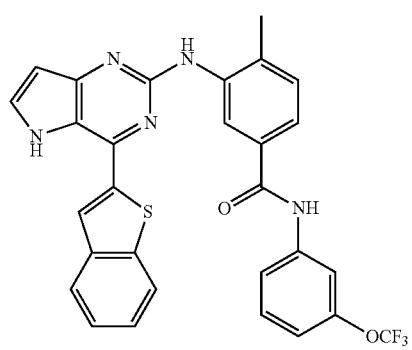
V-c-69
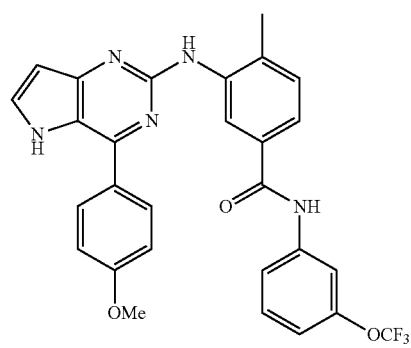

V-c-70
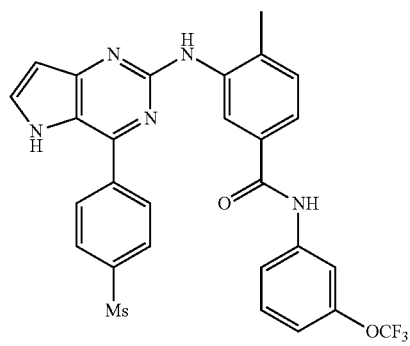
V-c-75
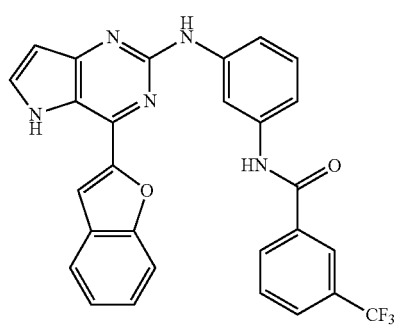
V-c-71
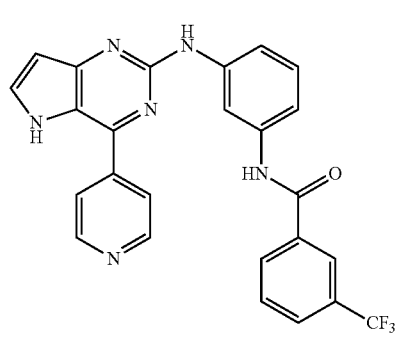
V-c-76
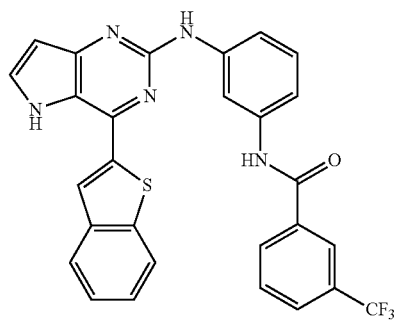
V-c-72
V-c-77
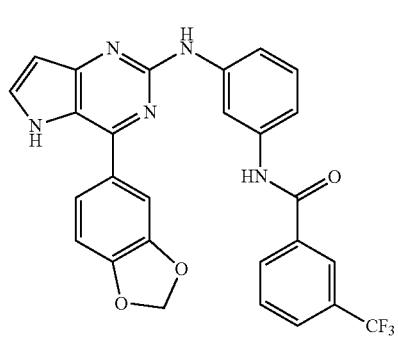
V-c-73
V-c-78
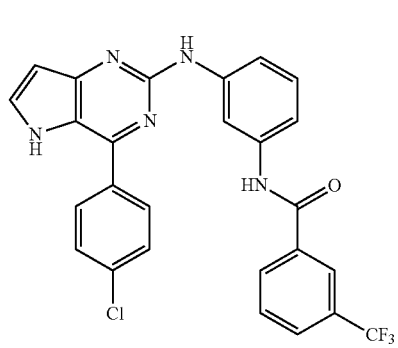
V-c-74
V-c-79
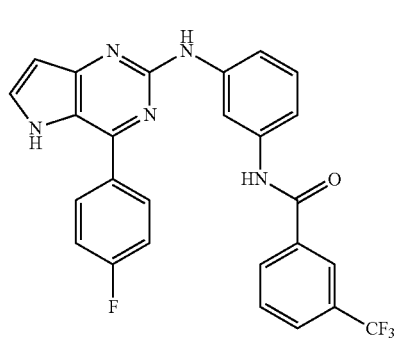

V-c-80
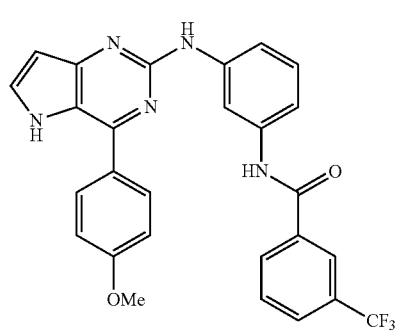
V-c-81
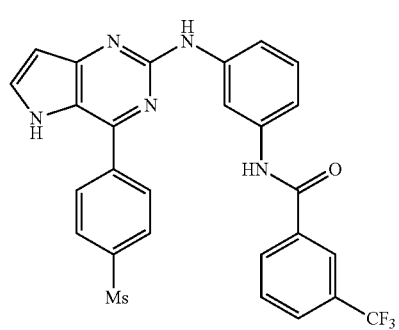
V-c-82
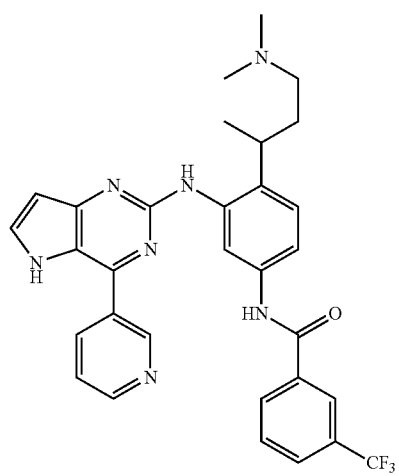
V-c-83
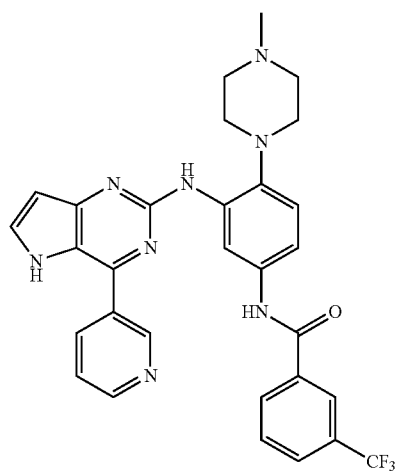
V-c-84
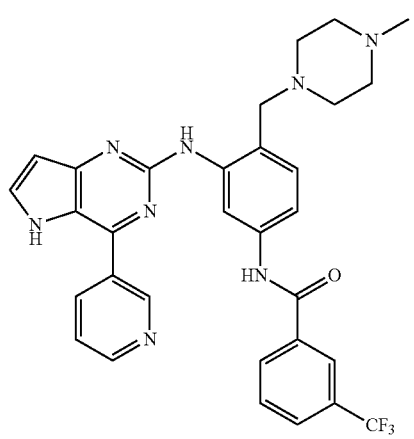
V-c-85
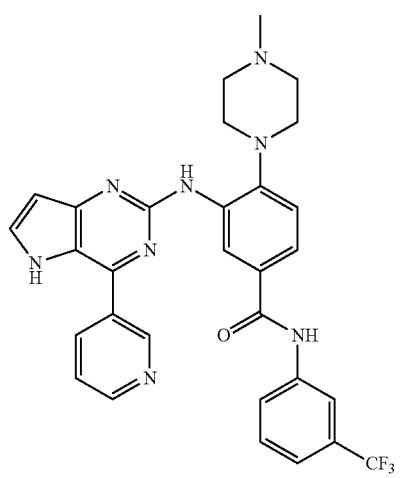
V-c-86
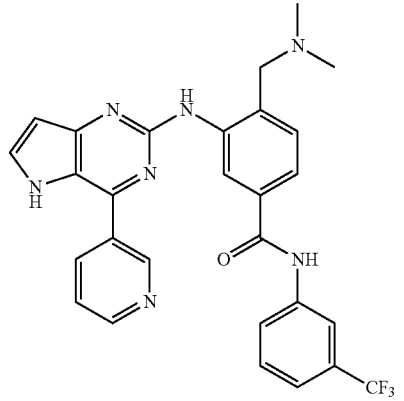

V-c-87
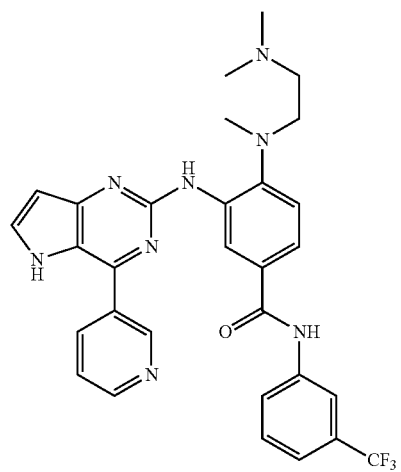
VI-a-1
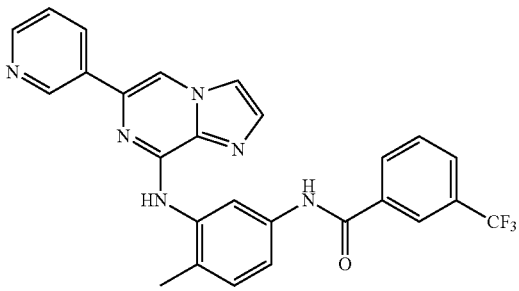
VI-a-5
VI-a-6
VI-a-2
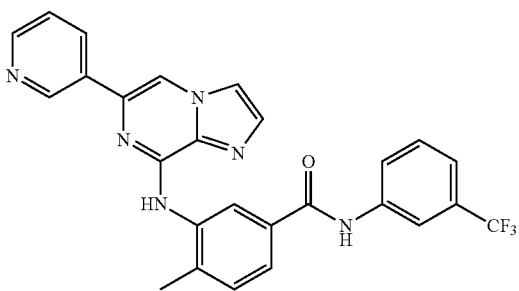
VI-a-7
VI-a-8
VI-a-3
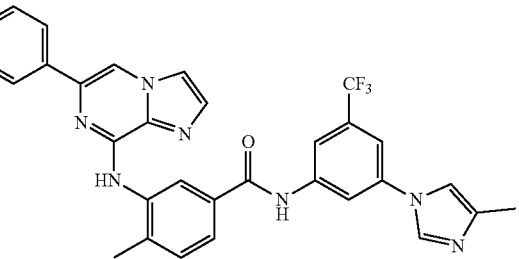
VI-a-9
VI-a-4
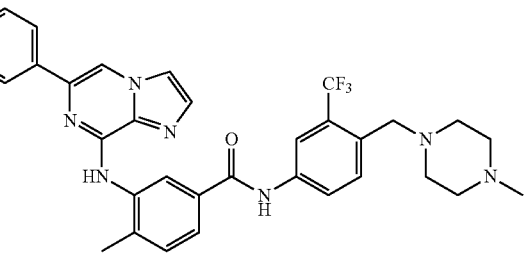
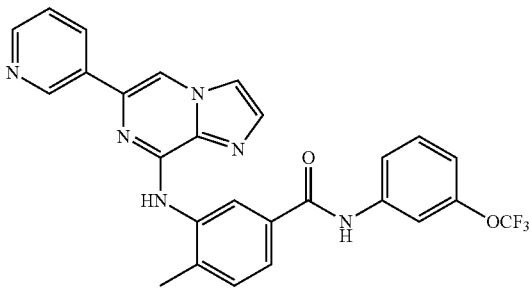

VI-a-10
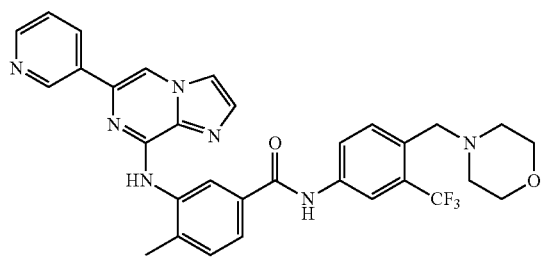
VI-b-1
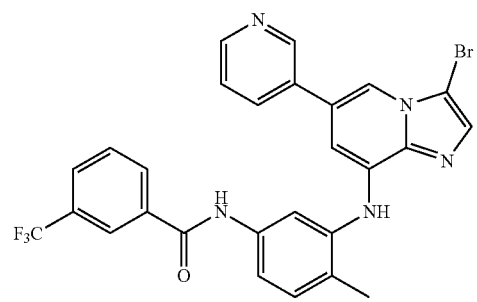
VI-b-2
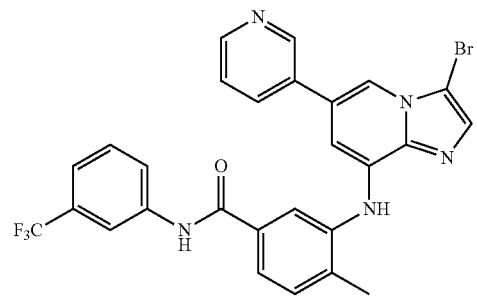
VI-b-3
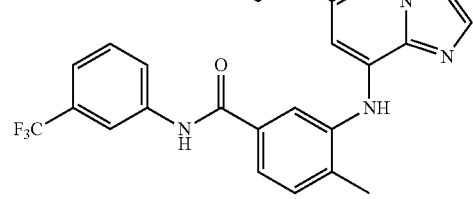
VI-b-4
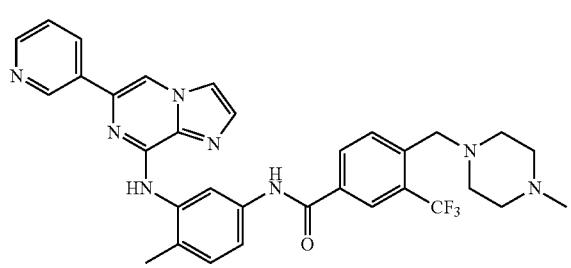
VI-b-5
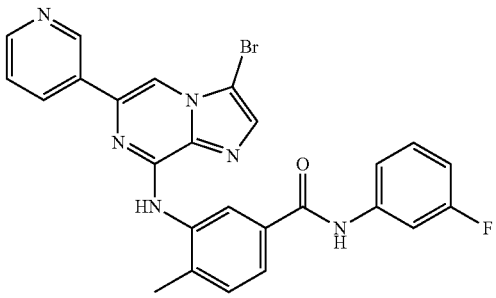
VI-b-6
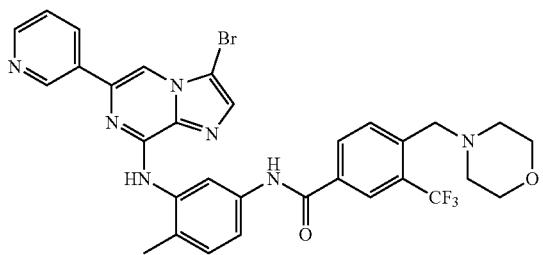
VI-b-7
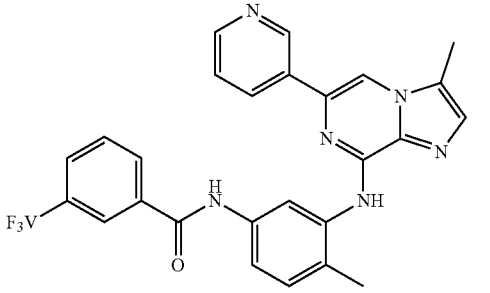
VIb-8
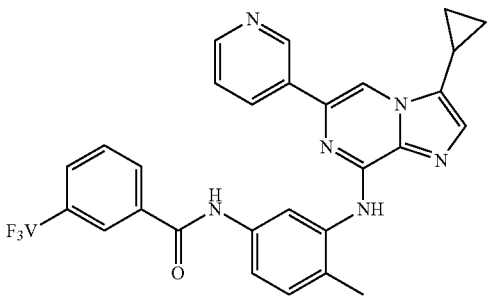
VI-b-9
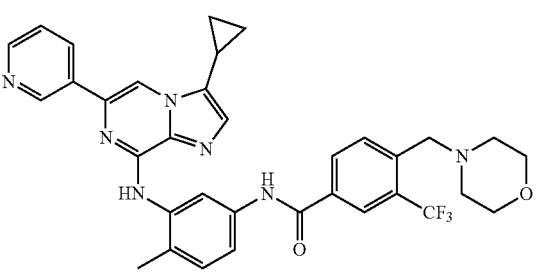

-continued
VII-a-1
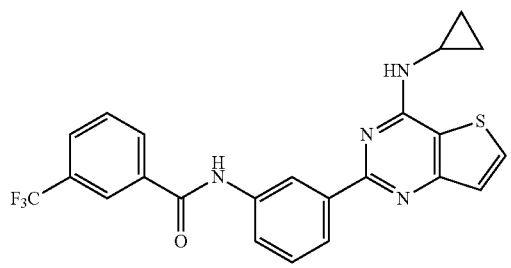
VII-a-2
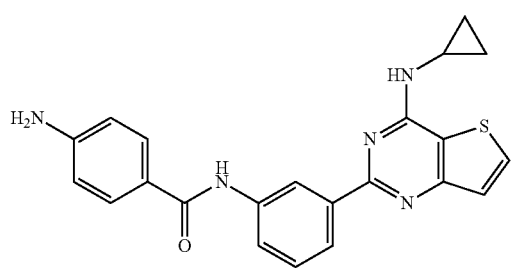
VII-a-3
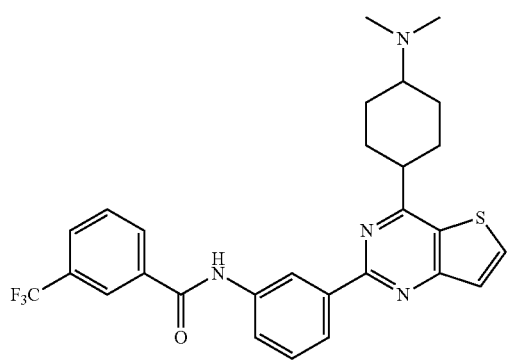
VII-a-4
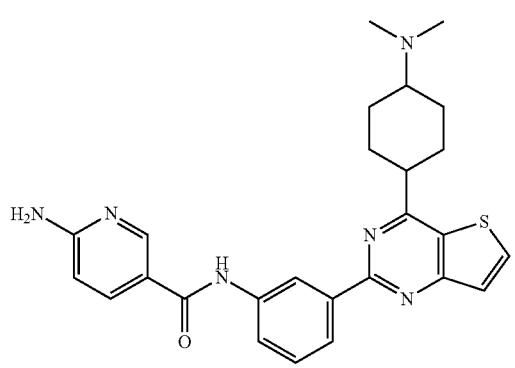
VII-a-5
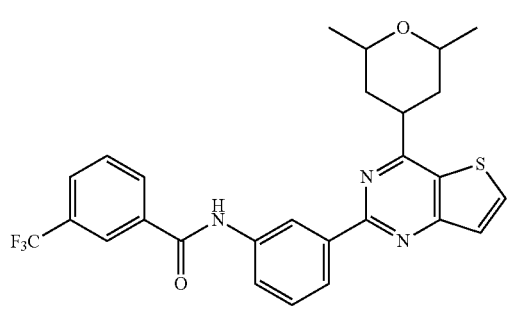
-continued
VII-a-6
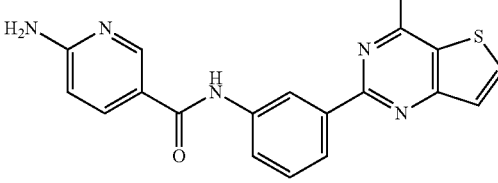
VII-a-7
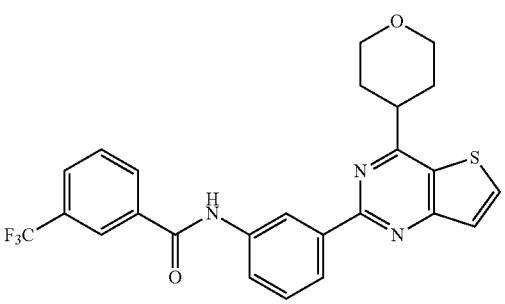
VII-a-8
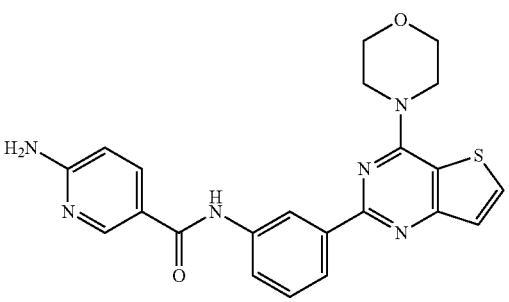
VII-a-9
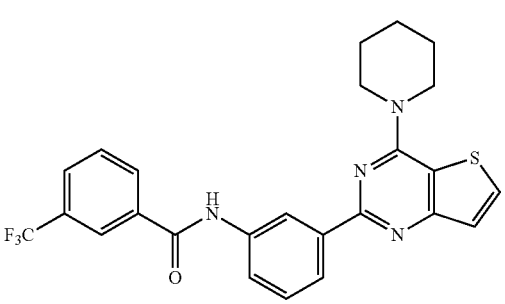
VII-a-10
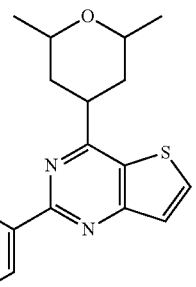

VII-a-11
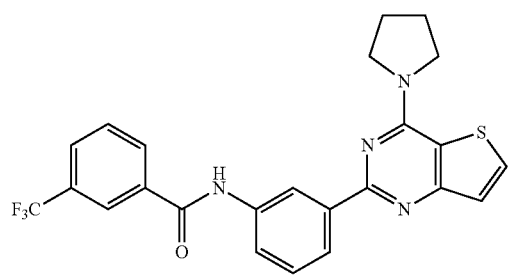
VII-a-16
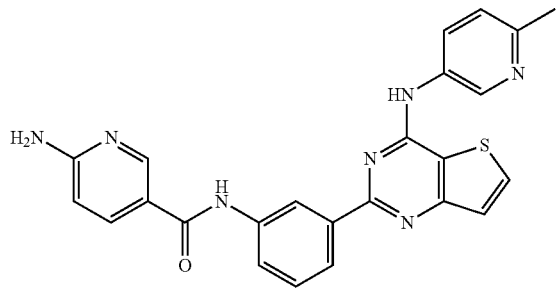
VII-a-12
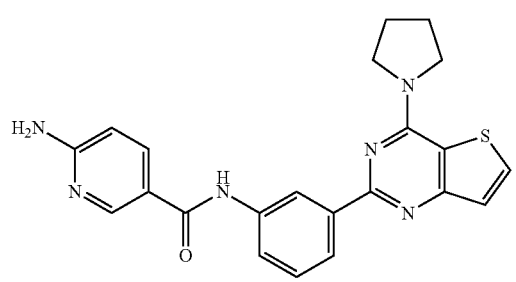
VII-a-17
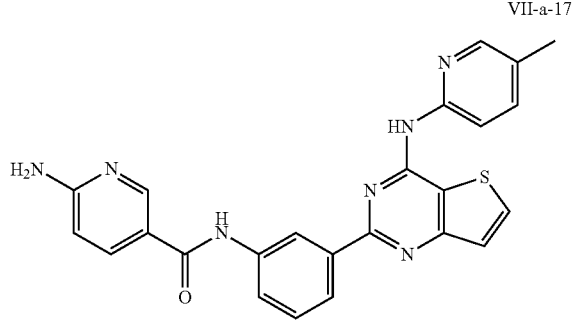
VII-a-13
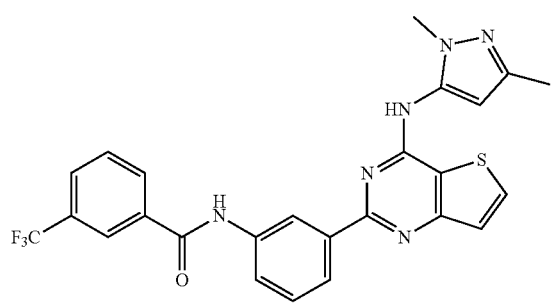
VIIa-18
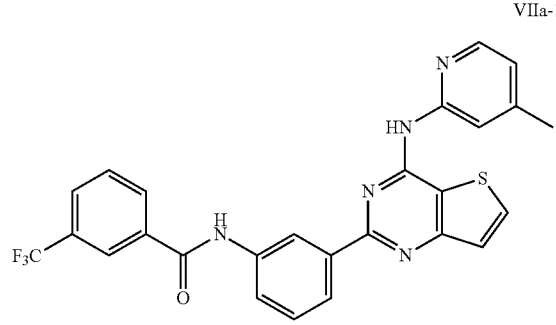
VII-a-14
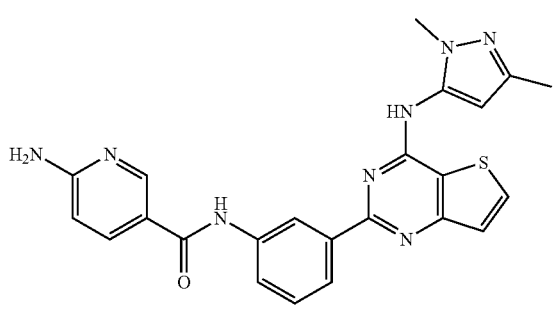
VII-a-19
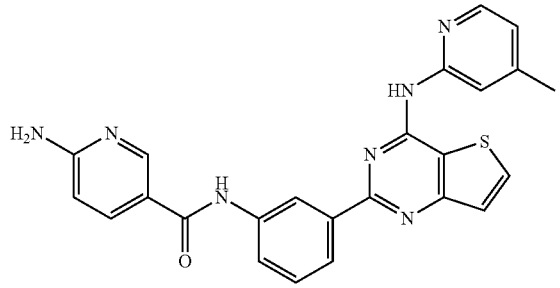
VII-a-15
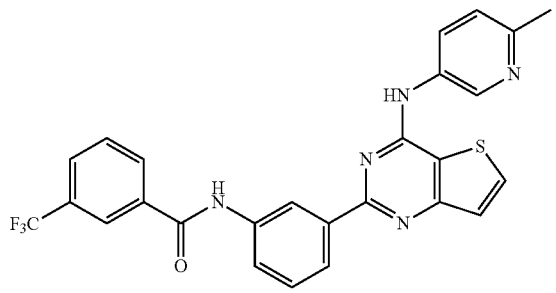
VIII-a-1
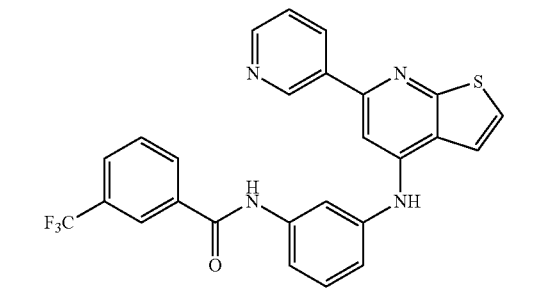

11. The compound according to claim 1 or a stereoisomer thereof, a prodrug thereof, a pharmaceutically acceptable salt thereof or a pharmaceutically acceptable solvate thereof, wherein, the compound is

12. The compound according to claim 1 or a stereoisomer thereof, a prodrug thereof, a pharmaceutically acceptable salt thereof or a pharmaceutically acceptable solvate thereof, wherein, the compound is

13. A pharmaceutical composition, comprising the compound according to claim 1 or a stereoisomer thereof, a prodrug thereof, a pharmaceutically acceptable salt thereof or a pharmaceutically acceptable solvate thereof and optionally a pharmaceutically acceptable excipient.

14. A preparation method of the compound according to claim 1, comprising the following steps:

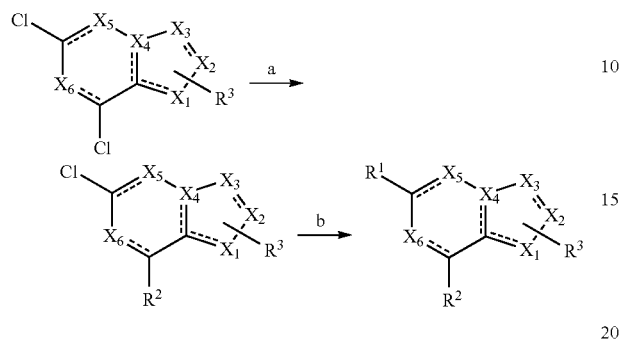

reaction conditions: (a) coupling reaction of carbon-carbon bond formation of heteroaryl chloride and boronic acid or boronic acid ester catalyzed by metal palladium, or coupling reaction of carbon-nitrogen bond formation of heteroaryl chloride and amine compound catalyzed by metal palladium, or nucleophilic substitution reaction of heteroaryl chloride with amine compound under alkaline condition, or nucleophilic substitution reaction of heteroaryl chloride with amine compound under acidic condition; (b) coupling reaction of carbon-carbon bond formation of heteroaryl chloride and boronic acid or boronic acid ester catalyzed by metal palladium, or coupling reaction of carbon-nitrogen bond formation of heteroaryl chloride and amine compound catalyzed by metal palladium, or nucleophilic substitution reaction of heteroaryl chloride with amine compound under acidic condition;

wherein, the heteroaryl chloride includes the following types:

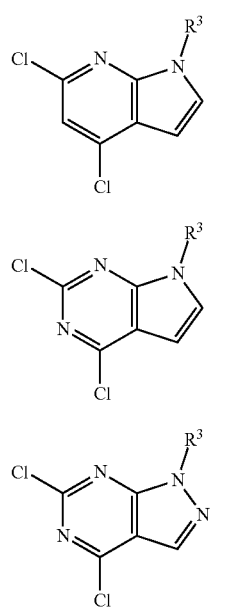

Ia

IIa

IIIa

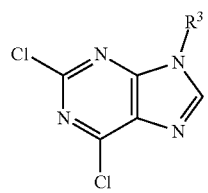

IVa

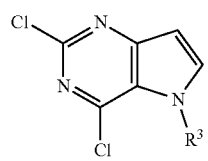

Va

VIa

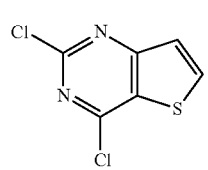

VIIa

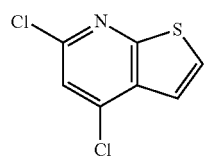

VIIIa

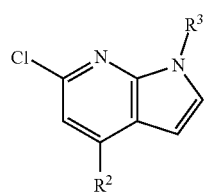

Ib

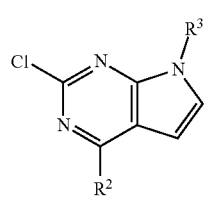

IIb

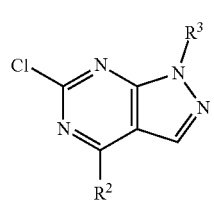

IIIb

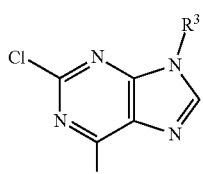 IVb

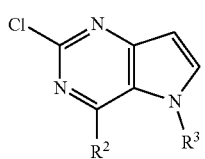 Vb

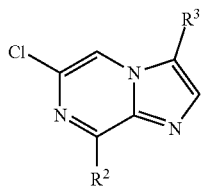 VIb

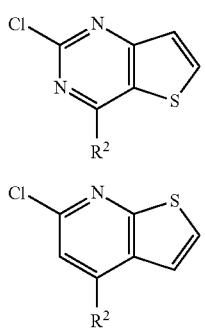 VIIb

VIIIb the boronic acid or boronic acid ester is selected from substituted or unsubstituted C6-C10 aryl or heteroaryl boronic acid or boronic acid ester; the amine compound is selected from substituted or unsubstituted C6-C10 arylamine, heteroarylamine, C1-C6 alkylamine, C3-C7 cycloalkylamine, C1-C6 oxygen-containing alkylamine or C3-C7 oxygen-containing, cycloalkylamine;

the metal palladium catalyst is selected from palladium acetate, tetrakis(triphenylphosphine) palladium, bistriphenylphosphine palladium dichloride, 1,1'-bis(diphenylphosphino)ferrocene] palladium dichloride or tris (dibenzylideneacetone) dipalladium; the alkaline condition refers to a condition in which any of the following substances exists: triethylamine, diisopropylethylamine, pyridine, sodium bicarbonate, sodium carbonate, potassium carbonate, cesium carbonate, lithium hydroxide, sodium hydroxide, potassium hydroxide, sodium hydride, potassium hydride; the acidic condition refers to a condition in which any of the following substances exists: acetic acid, trifluoroacetic acid, hydrochloric acid, methanesulfonic acid, p-toluene sulfonic acid, camphorsulfonic acid.

15. A method of treating a PIKfyve-mediated disease in vivo comprising administering to a subject an effective amount of the compound according to claim 1 or a stereoisomer thereof, a prodrug thereof, a pharmaceutically acceptable salt thereof or a pharmaceutically acceptable solvate thereof, wherein the treating refers to suppressing or relieving symptoms of a PIKfyve-mediated disease.

16. A method of treating a PIKfyve-mediated disease in vivo comprising administering to a subject an effective amount of the pharmaceutical composition according to claim 13, wherein the treating refers to suppressing or relieving symptoms of a PIKfyve-mediated disease.

17. The method according to claim 15, wherein the compound according to claim 1 or a stereoisomer thereof, a prodrug thereof, a pharmaceutically acceptable salt thereof or a pharmaceutically acceptable solvate thereof causes vacuolation of cells, optionally, the compound according to claim 1 or a stereoisomer thereof, a prodrug thereof, a pharmaceutically acceptable salt thereof or a pharmaceutically acceptable solvate thereof causes vacuolation of cells by inhibiting PIKfyve.

18. The method according to claim 16, wherein the pharmaceutical composition according to claim 11 causes vacuolation of cells, optionally, the pharmaceutical composition according to claim 11 causes vacuolation of cells by inhibiting PIKfyve.

* * * * *

UNITED STATES PATENT AND TRADEMARK OFFICE
CERTIFICATE OF CORRECTION

PATENT NO. : 11,352,354 B2  
APPLICATION NO. : 16/636333  
DATED : June 7, 2022  
INVENTOR(S) : Xianming Deng et al.

Page 1 of 26

It is certified that error appears in the above-identified patent and that said Letters Patent is hereby corrected as shown below:

In the Specification

At Column 21, Lines 55-64, the formula: 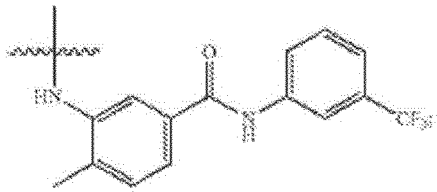

Should be replaced with the formula: 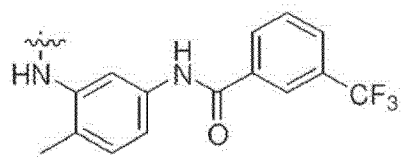 .

At Column 27, Lines 5-11, the formulae and text: 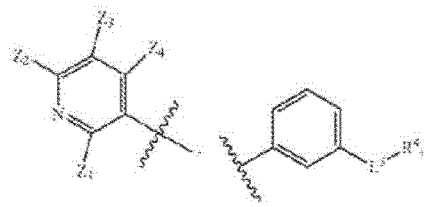 wherein $Z_9$ is amino, the rest being H; in its entirety Should be replaced with the formulae and text: 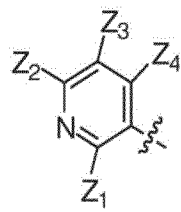 , wherein $Z_2$ is amino, the rest being H; 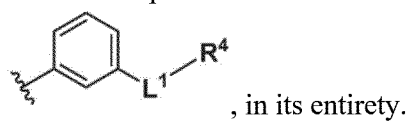 , in its entirety.

Signed and Sealed this  
Twenty-fifth Day of June, 2024

Katherine Kelly Vidal  
*Director of the United States Patent and Trademark Office*

At Column 29, Lines 52-67, the formula:
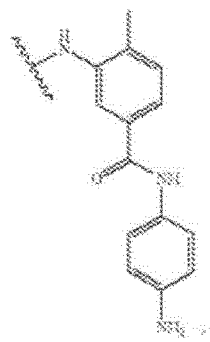
Should be replaced with the formula:
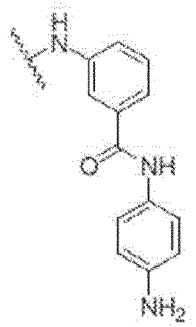
At Column 97, the formula I-b-4:
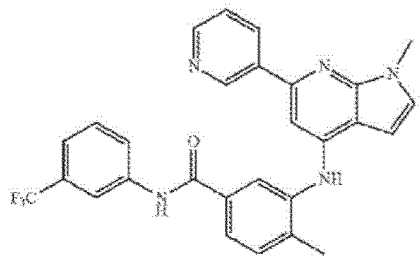
Should be replaced with the formula:
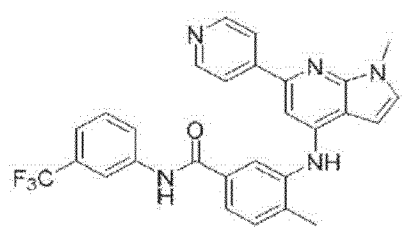
At Column 169, the formula V-b-23:
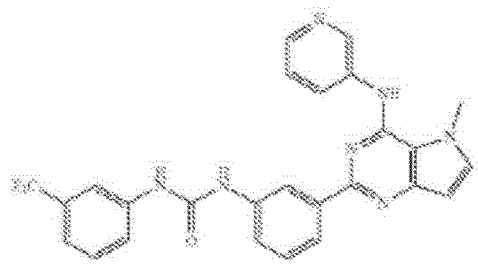

CERTIFICATE OF CORRECTION (continued)
U.S. Pat. No. 11,352,354 B2

Should be replaced with the formula: 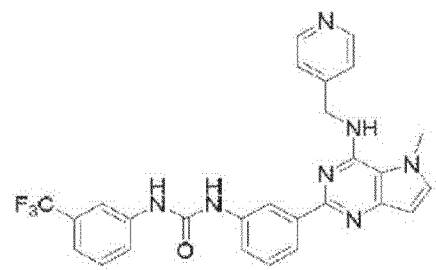

At Column 225, the formula VI-a-5: 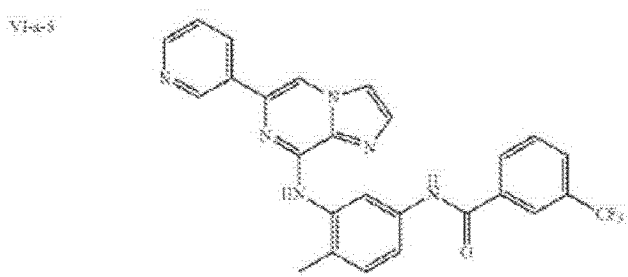

Should be replaced with the formula: 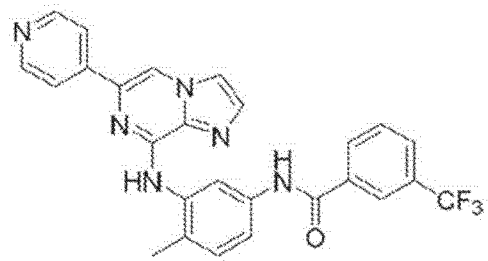 .

At Column 227, the formula VI-a-10: 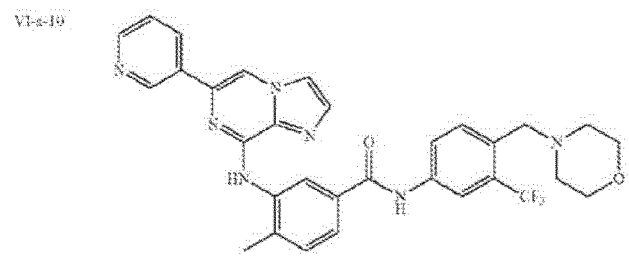

Should be replaced with the formula: 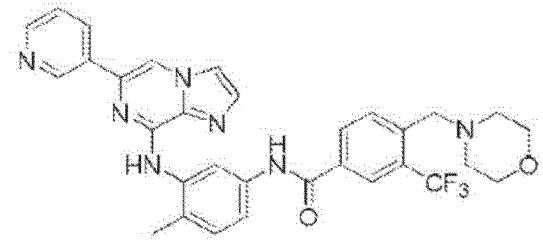 .

CERTIFICATE OF CORRECTION (continued)
U.S. Pat. No. 11,352,354 B2

At Column 231, the formula VI-b-9:

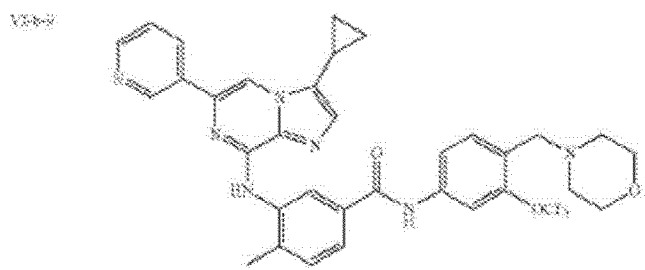

Should be replaced with the formula:

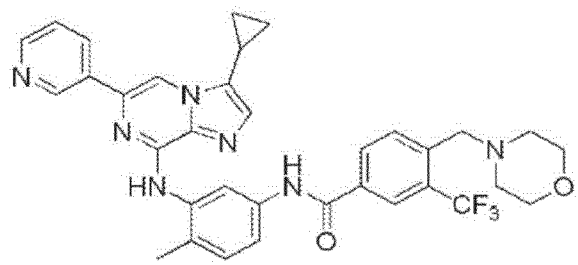

In the Claims

In Claim 1, at Column 253, Lines 21-27, the formula:

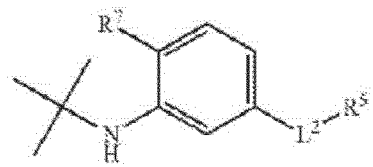

Should be replaced with the formula:

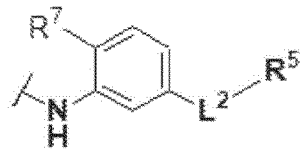

In Claim 1, at Column 254, Lines 21-27, the formula:

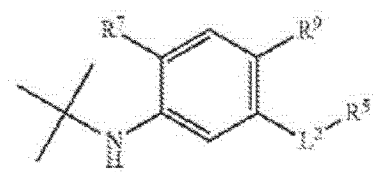

Should be replaced with the formula:

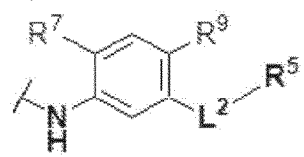

In Claim 1, at Column 255, Lines 29-34, the formula:

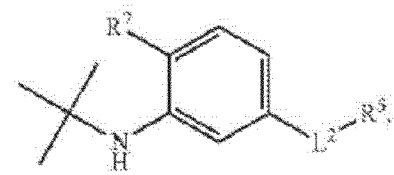

In Claim 1, at Column 256, Lines 58-64, the formula: 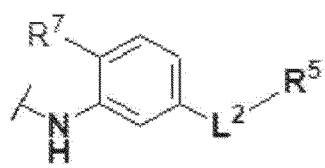
Should be replaced with the formula: 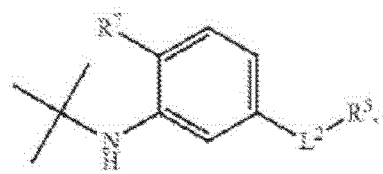 .
In Claim 1, at Column 257, Lines 18-25, the formula: 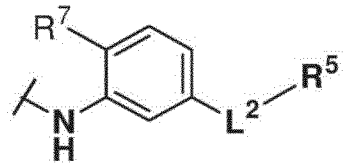
Should be replaced with the formula: 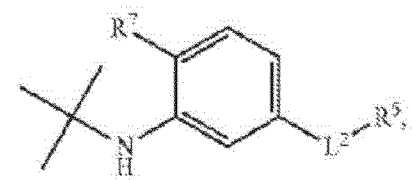 .
In Claim 1, at Column 258, Lines 17-22, the formula: 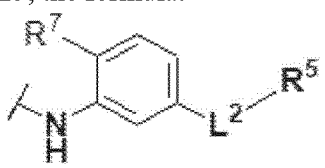
Should be replaced with the formula: 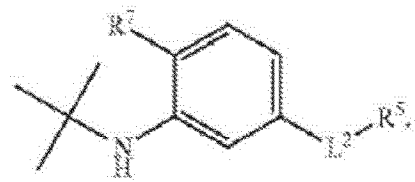 .
In Claim 1, at Column 260, Lines 3-8, the formula: 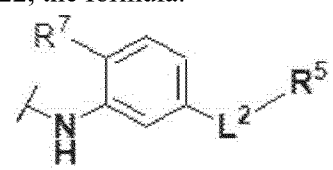
Should be replaced with the formula: 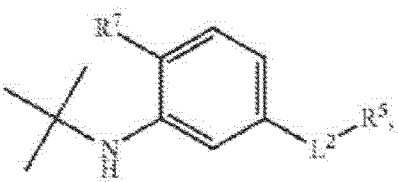 .

Should be replaced with the formula: 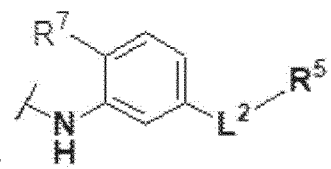 .
In Claim 1, at Column 261, Lines 41-46, the formula: 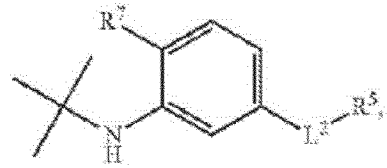
Should be replaced with the formula: 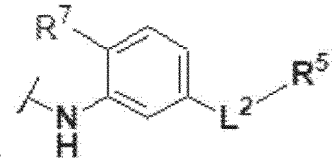 .
In Claim 1, at Column 263, Lines 12-18, the formula: 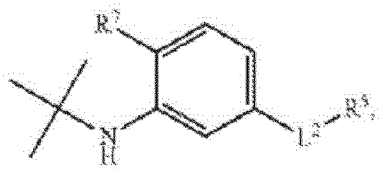
Should be replaced with the formula: 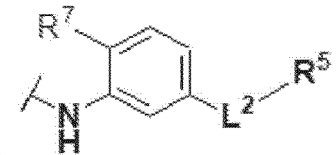 .
In Claim 1, at Column 265, Lines 28-34, the formula: 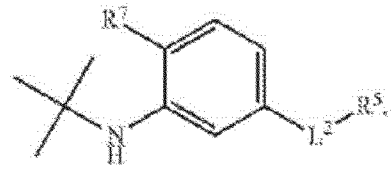
Should be replaced with the formula: 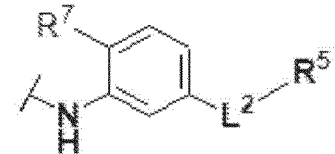 .
In Claim 2, at Column 266, Lines 41-47, the formula: 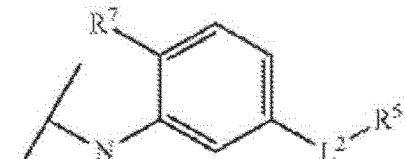

CERTIFICATE OF CORRECTION (continued)
U.S. Pat. No. 11,352,354 B2

Should be replaced with the formula: 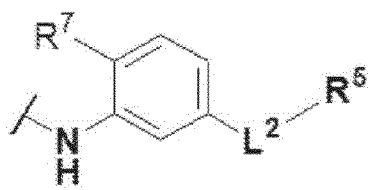 .

In Claim 2, at Column 267, Lines 41-47, the formula: 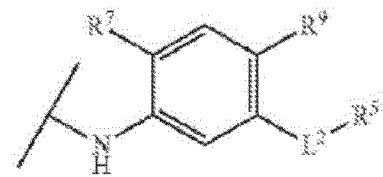

Should be replaced with the formula: 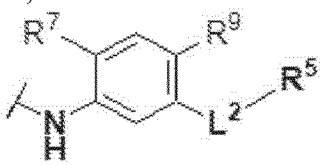 .

In Claim 3, at Column 268, Lines 58-64, the formula: 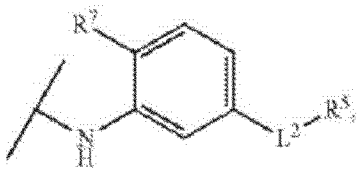

Should be replaced with the formula: 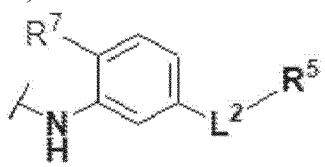 .

In Claim 10, at Column 290, Lines 16-26, the formula: 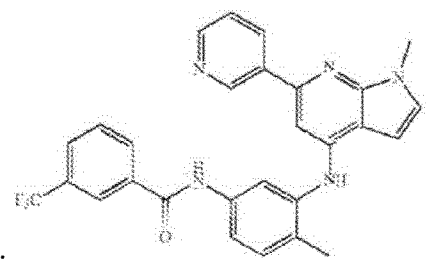

Should be replaced with the formula: 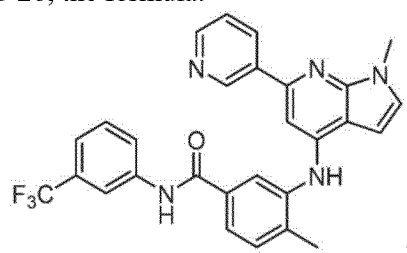 .

In Claim 10, at Column 290, Lines 28-38, the formula:
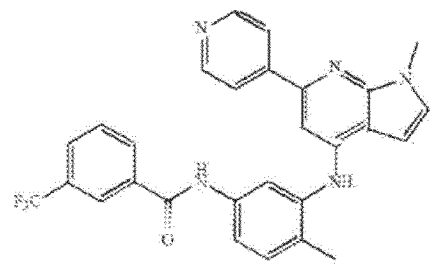
Should be replaced with the formula:
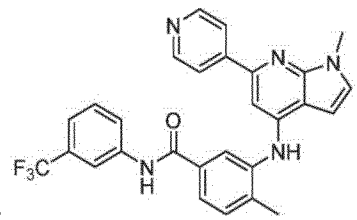
In Claim 10, at Column 290, Lines 40-52, the formula:
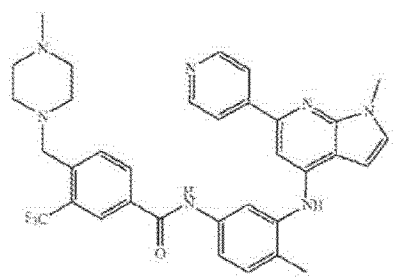
Should be replaced with the formula:
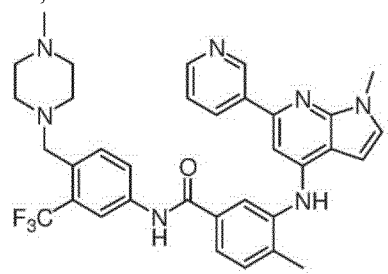
In Claim 10, at Column 294, Lines 44-56, the formula:
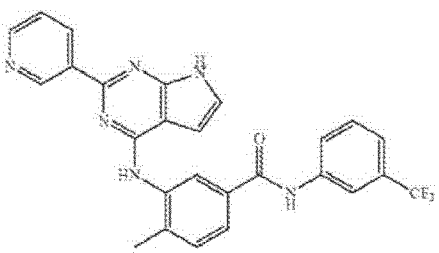
Should be replaced with the formula:
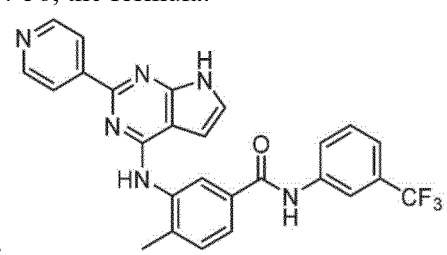

In Claim 10, at Column 295, Lines 27-40, the formula:
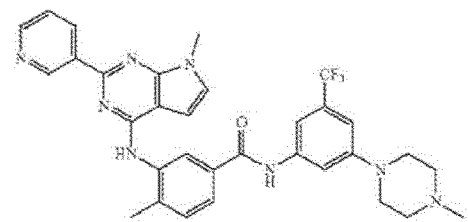
Should be replaced with the formula:
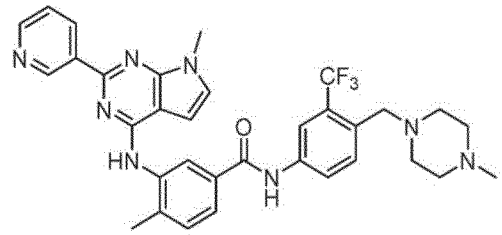
In Claim 10, at Column 295, Lines 57-67, the formula:
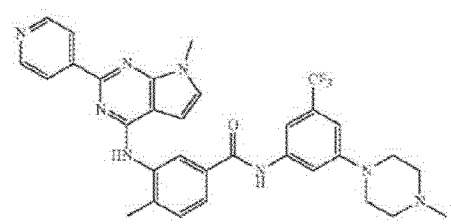
Should be replaced with the formula:
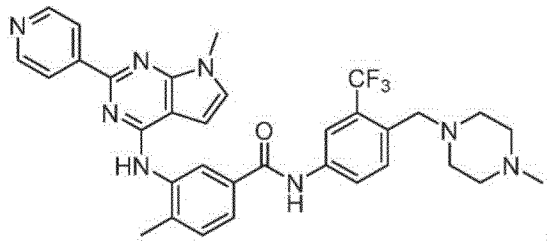
In Claim 10, at Column 297, Lines 3-13, the formula:
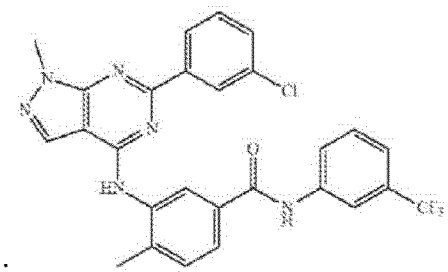
Should be replaced with the formula:
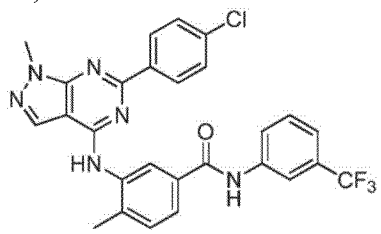

In Claim 10, at Column 299, Lines 2-16, the formula:
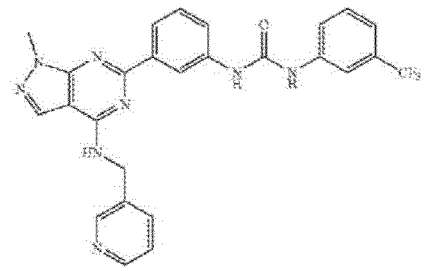
Should be replaced with the formula:
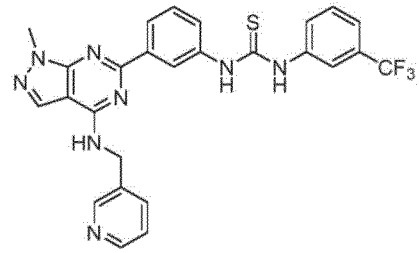
In Claim 10, at Column 299, Lines 18-32, the formula:
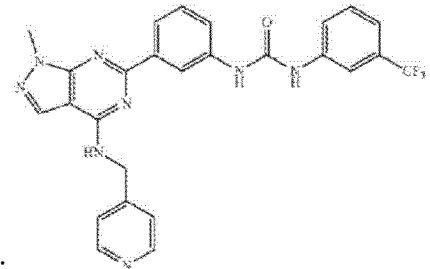
Should be replaced with the formula:
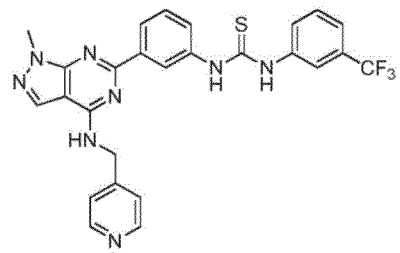
In Claim 10, at Column 299, Lines 52-67, the formula:
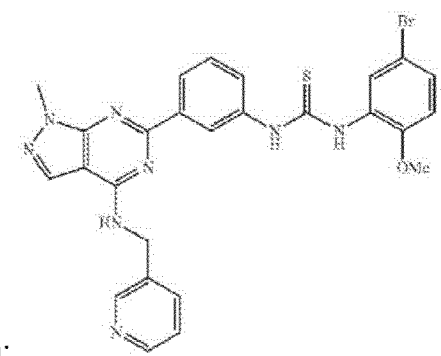

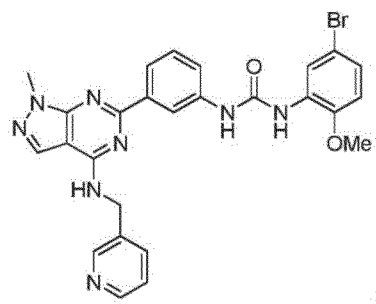
Should be replaced with the formula: 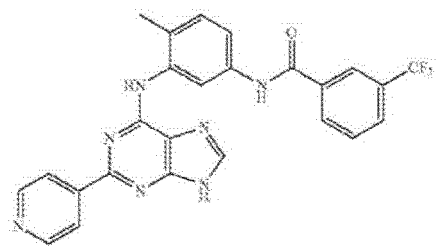
In Claim 10, at Column 300, Lines 28-39, the formula: 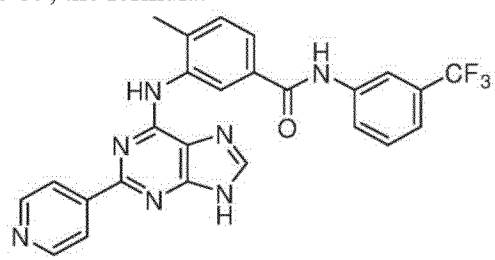
Should be replaced with the formula: 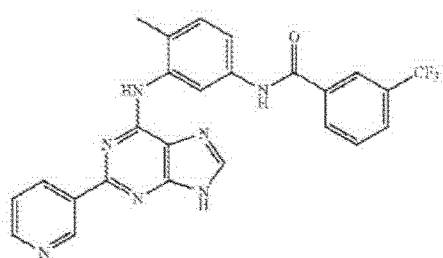
In Claim 10, at Column 300, Lines 41-52, the formula: 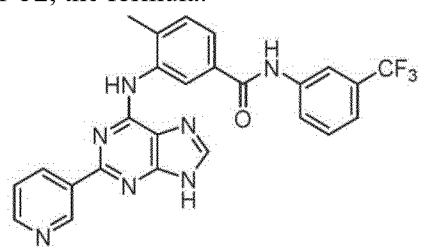
Should be replaced with the formula:

CERTIFICATE OF CORRECTION (continued)
U.S. Pat. No. 11,352,354 B2

In Claim 10, at Column 300, Lines 54-67, the formula:

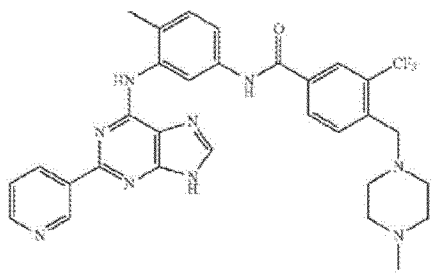

Should be replaced with the formula:

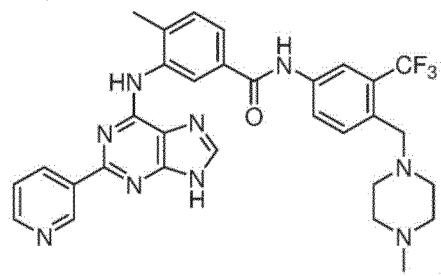

In Claim 10, at Column 301, Lines 3-16, the formula:

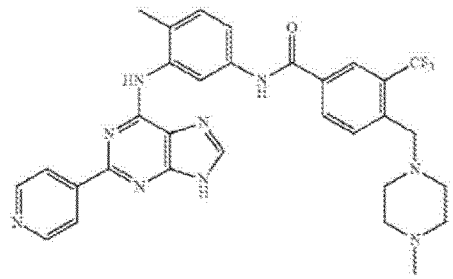

Should be replaced with the formula:

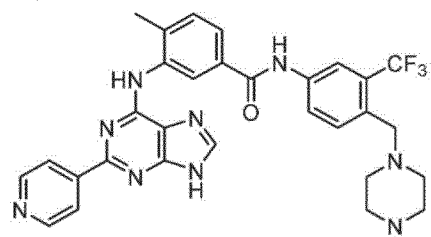

In Claim 10, at Column 301, Lines 18-28, the formula:

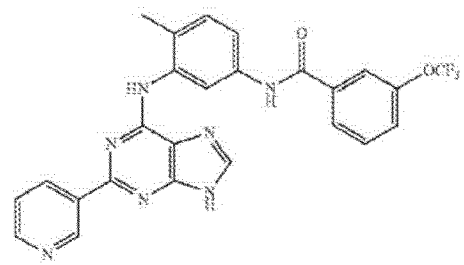

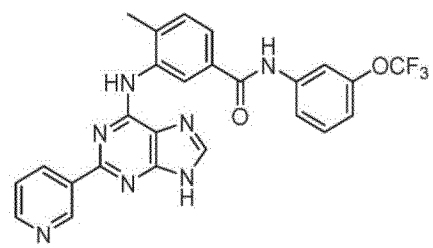
Should be replaced with the formula: 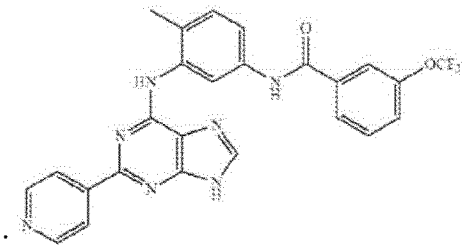 .
In Claim 10, at Column 301, Lines 30-41, the formula: 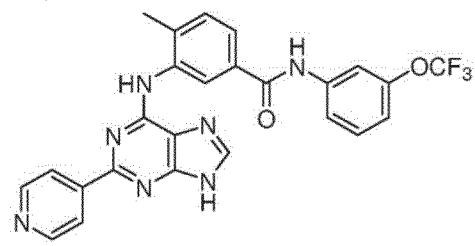
Should be replaced with the formula: 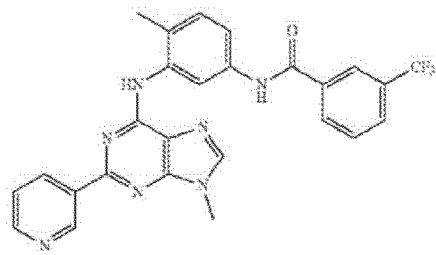 .
In Claim 10, at Column 301, Lines 55-67, the formula: 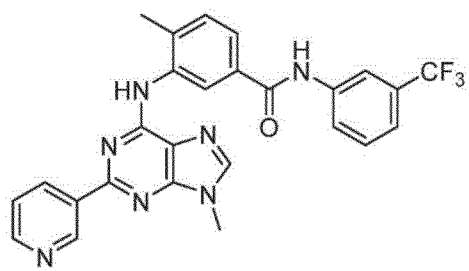
Should be replaced with the formula: 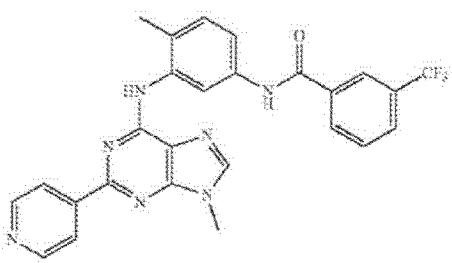 .
In Claim 10, at Column 302, Lines 3-14, the formula:

CERTIFICATE OF CORRECTION (continued)
U.S. Pat. No. 11,352,354 B2

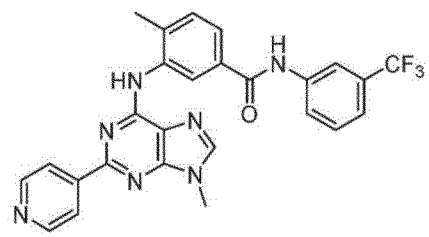

Should be replaced with the formula: 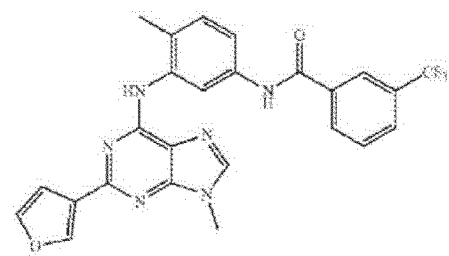

In Claim 10, at Column 302, Lines 17-27, the formula: 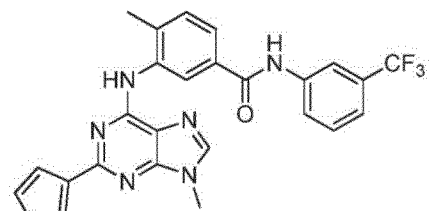

Should be replaced with the formula: 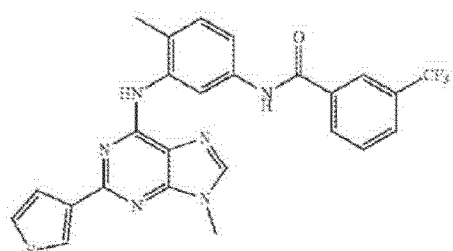

In Claim 10, at Column 302, Lines 29-39, the formula: 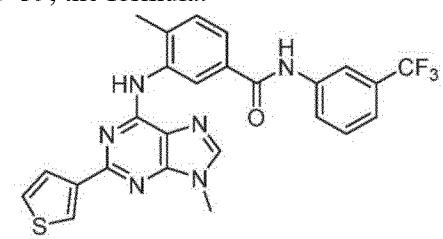

Should be replaced with the formula: 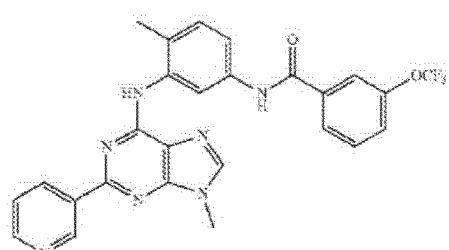

In Claim 10, at Column 303, Lines 43-53, the formula:

Should be replaced with the formula: 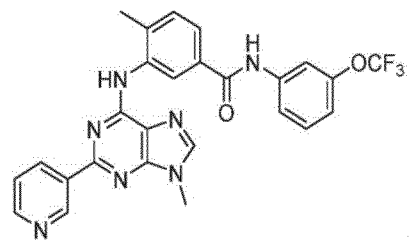 .
In Claim 10, at Column 303, Lines 66-67, the formula: 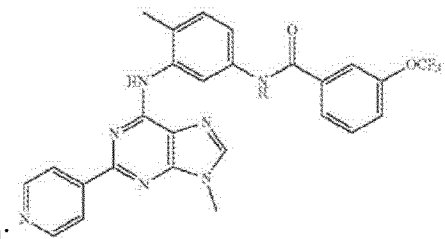
Should be replaced with the formula: 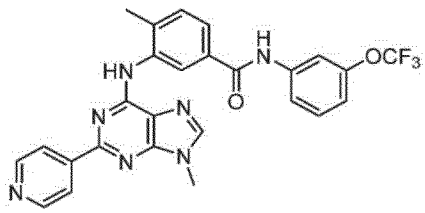 .
In Claim 10, at Column 304, Lines 3-14, the formula: 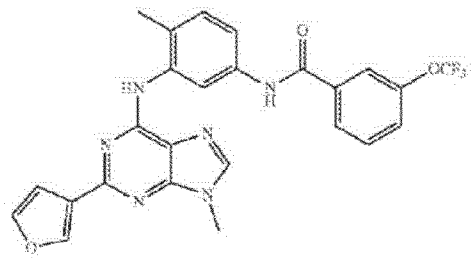
Should be replaced with the formula: 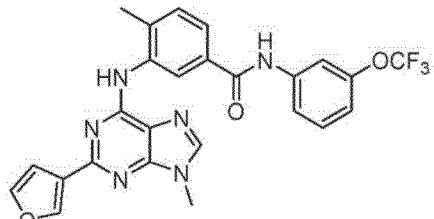 .
In Claim 10, at Column 305, Lines 57-67, the formula: 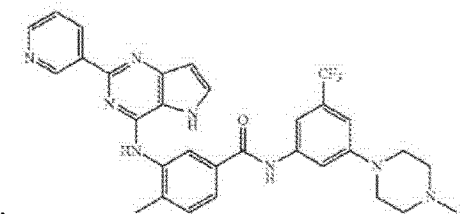

Should be replaced with the formula: 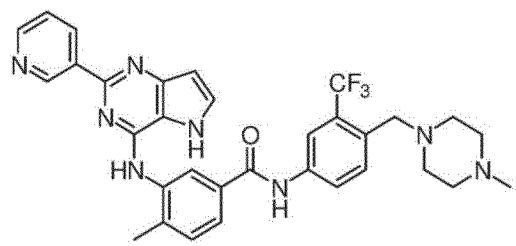 .
In Claim 10, at Column 308, Lines 28-38, the formula: 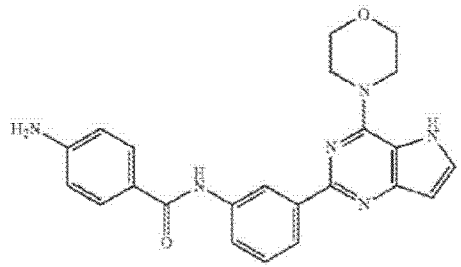
Should be replaced with the formula: 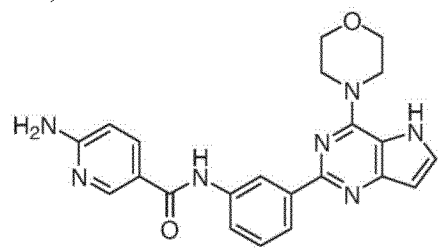 .
In Claim 10, at Column 313, Lines 54-67, the formula: 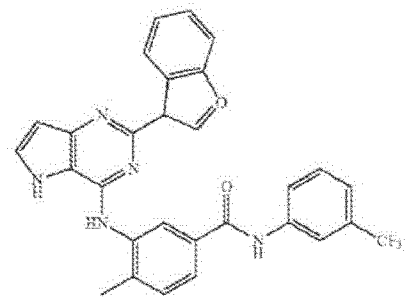
Should be replaced with the formula: 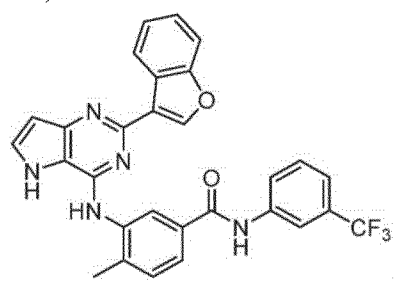 .

CERTIFICATE OF CORRECTION (continued)
U.S. Pat. No. 11,352,354 B2

In Claim 10, at Column 316, Lines 28-40, the formula:

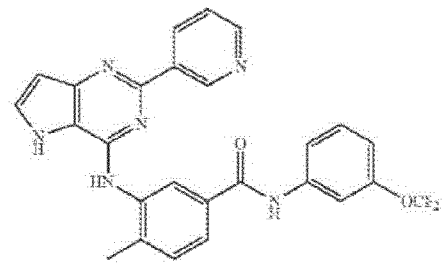

Should be replaced with the formula:

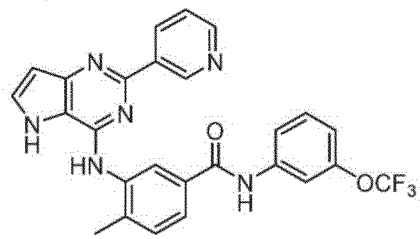

In Claim 10, at Column 325, Lines 55-67, the formula:

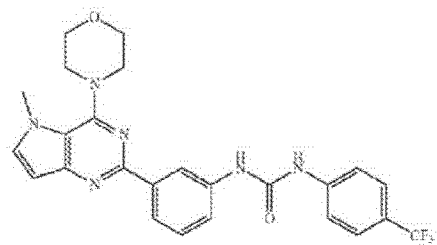

Should be replaced with the formula:

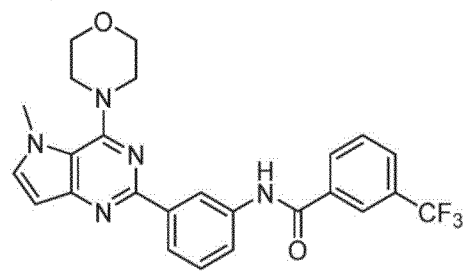

In Claim 10, at Column 326, Lines 17-28, the formula:

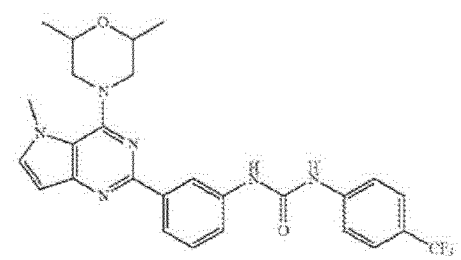

Should be replaced with the formula:

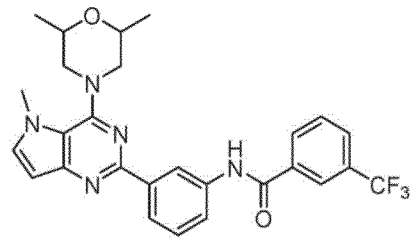

CERTIFICATE OF CORRECTION (continued)
U.S. Pat. No. 11,352,354 B2

In Claim 10, at Column 326, Lines 30-42, the formula:

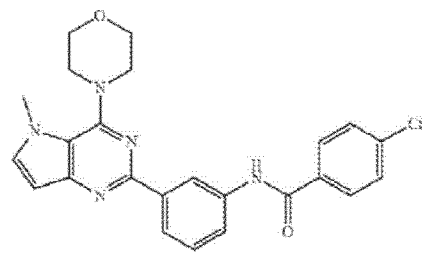

Should be replaced with the formula:

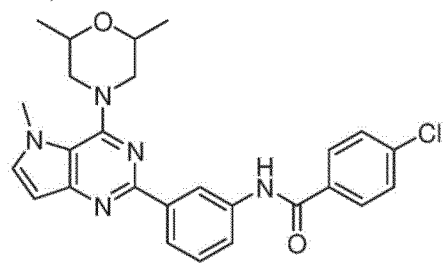

In Claim 10, at Column 335, Lines 3-16, the formula:

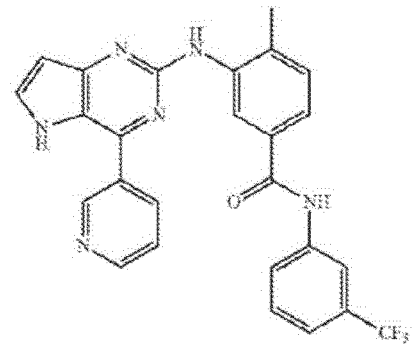

Should be replaced with the formula:

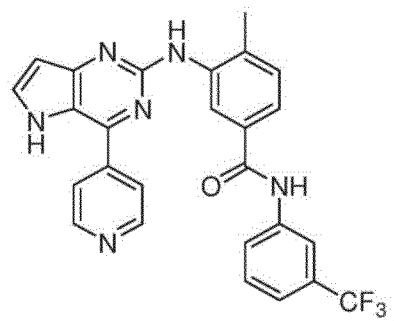

In Claim 10, at Column 346, Lines 3-18, the formula:

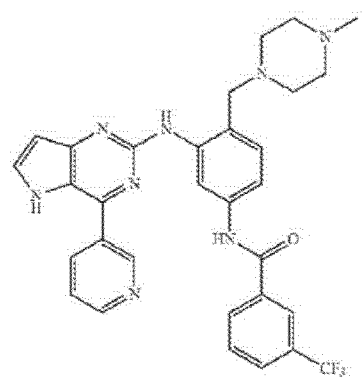

CERTIFICATE OF CORRECTION (continued)
U.S. Pat. No. 11,352,354 B2

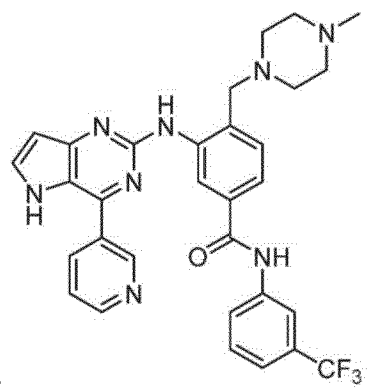

Should be replaced with the formula:

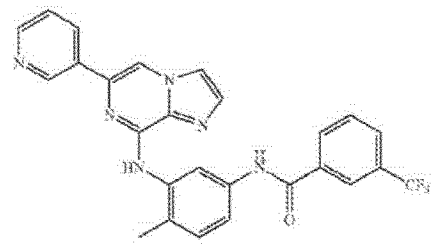

In Claim 10, at Column 347, Lines 33-43, the formula:

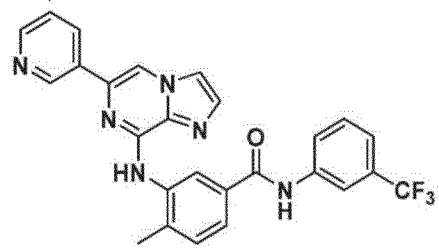

Should be replaced with the formula:

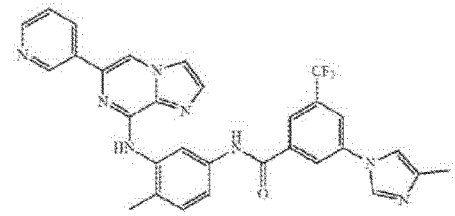

In Claim 10, at Column 347, Lines 46-55, the formula:

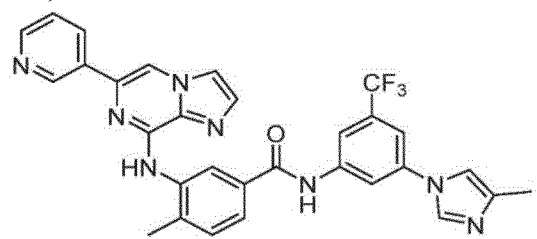

Should be replaced with the formula:

In Claim 10, at Column 347, Lines 56-66, the formula:
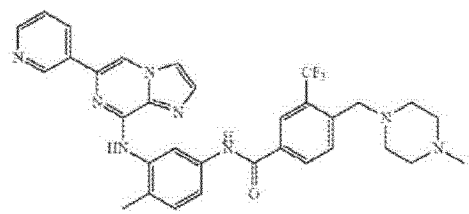
Should be replaced with the formula:
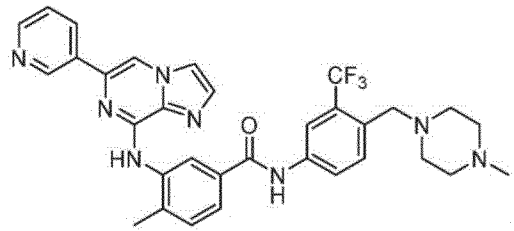
.
In Claim 10, at Column 348, Lines 3-14, the formula:
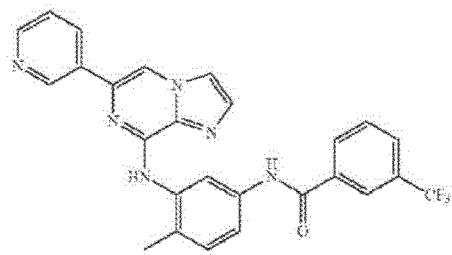
Should be replaced with the formula:
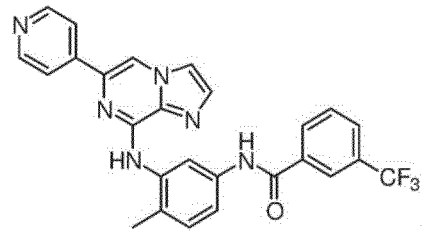
.
In Claim 10, at Column 348, Lines 31-41, the formula:
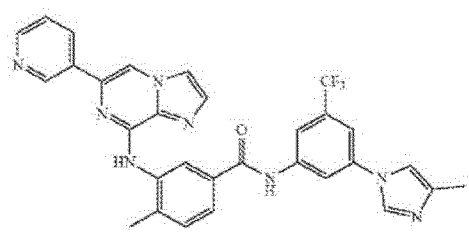
Should be replaced with the formula:
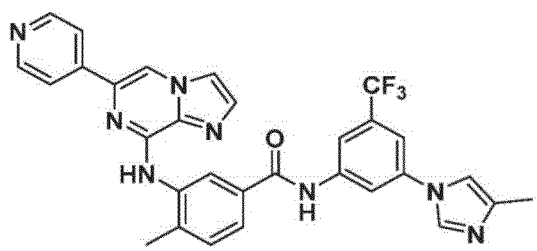
.

In Claim 10, at Column 348, Lines 43-53, the formula:
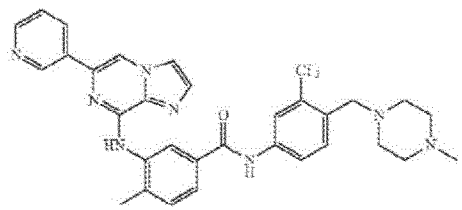
Should be replaced with the formula:
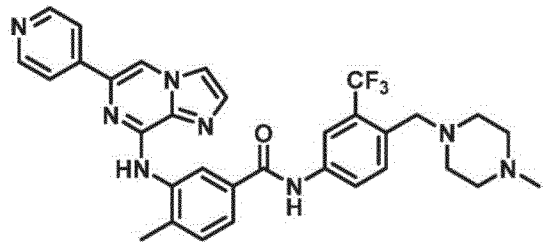
In Claim 10, at Column 349, Lines 3-12, the formula:
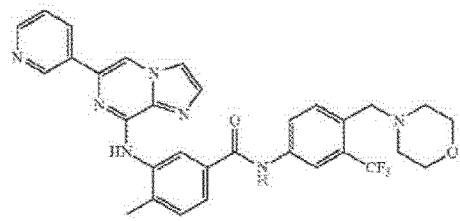
Should be replaced with the formula:
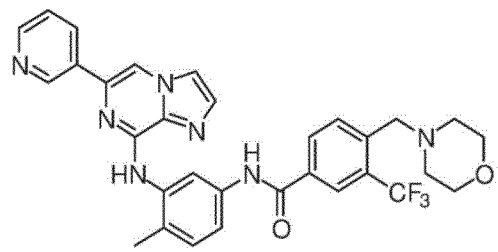
In Claim 10, at Column 349, Lines 16-27, the formula:
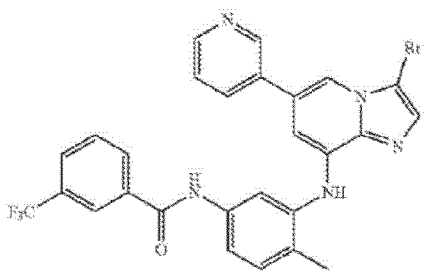
Should be replaced with the formula:
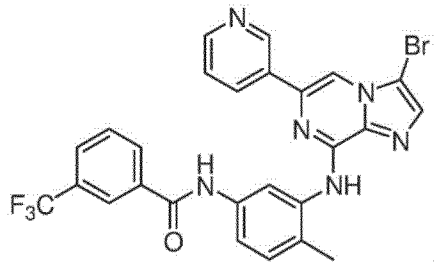

In Claim 10, at Column 349, Lines 29-40, the formula:
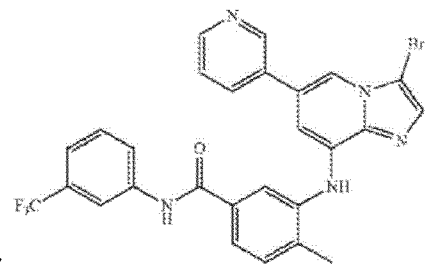
Should be replaced with the formula:
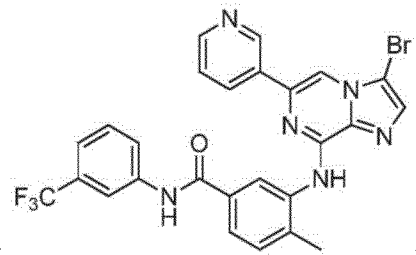
In Claim 10, at Column 349, Lines 43-53, the formula:
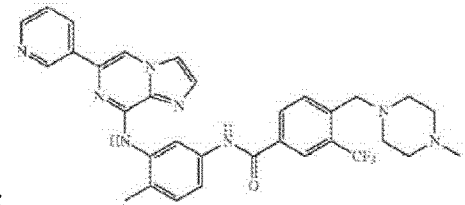
Should be replaced with the formula:
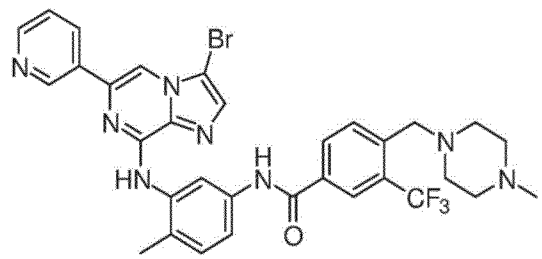
In Claim 10, at Column 350, Lines 28-40, the formula:
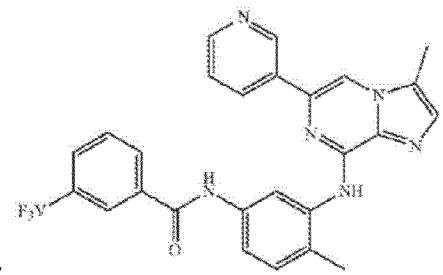
Should be replaced with the formula:
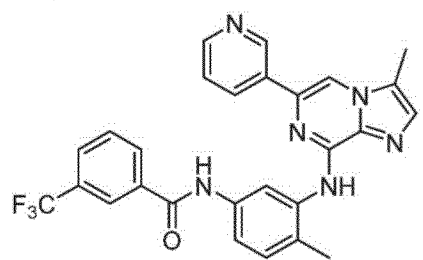

In Claim 10, at Column 350, Lines 43-53, the formula:
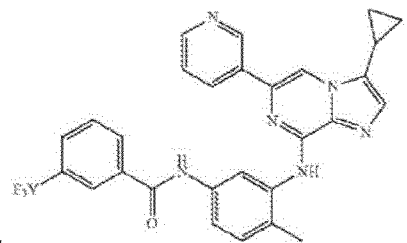
Should be replaced with the formula:
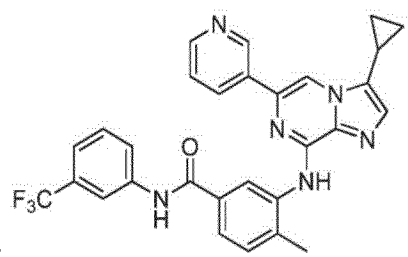
In Claim 10, at Column 351, Lines 14-23, the formula:
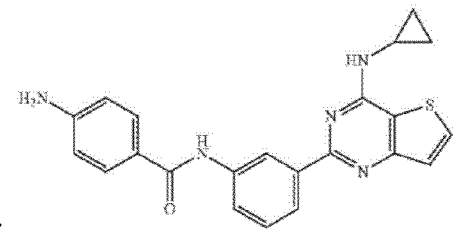
Should be replaced with the formula:
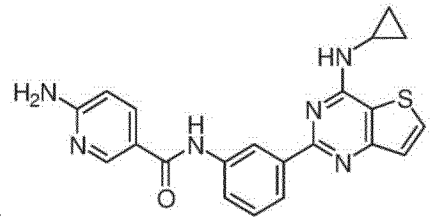
In Claim 10, at Column 351, Lines 25-38, the formula:
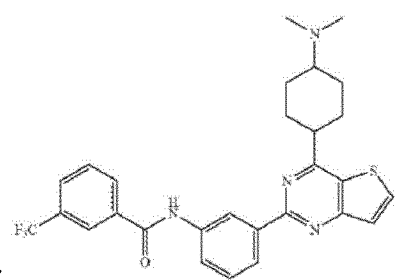
Should be replaced with the formula:
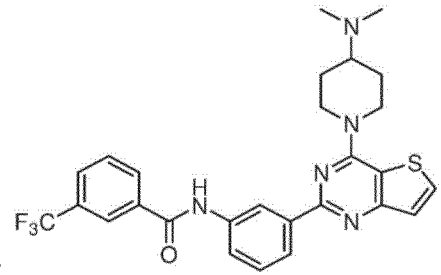

In Claim 10, at Column 351, Lines 40-58, the formula:
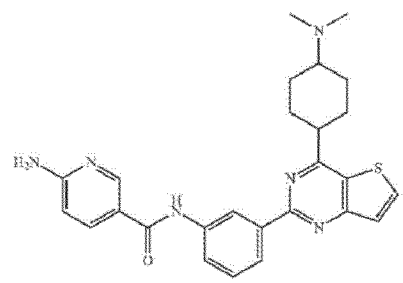
Should be replaced with the formula:
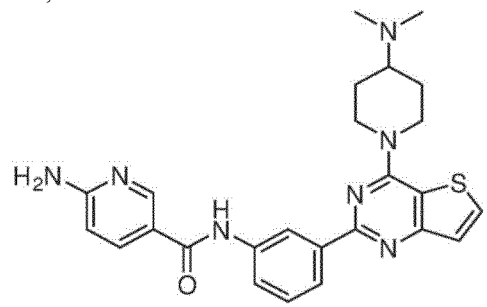
In Claim 10, at Column 351, Lines 55-67, the formula:
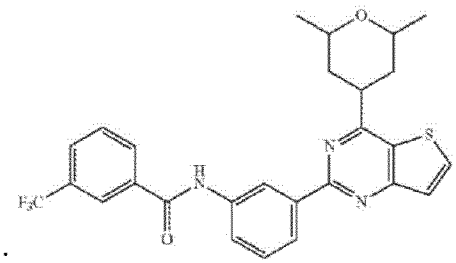
Should be replaced with the formula:
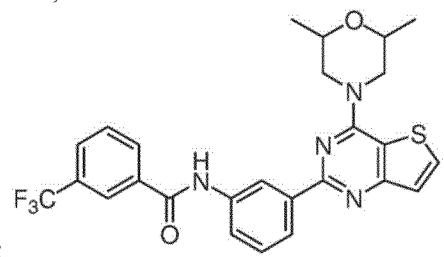
In Claim 10, at Column 352, Lines 2-15, the formula:
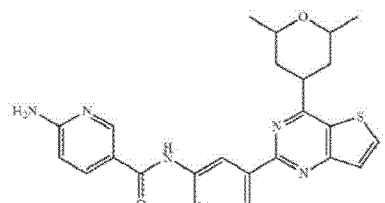
Should be replaced with the formula:
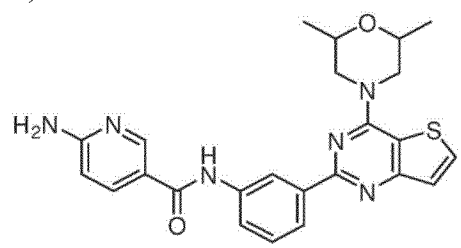

In Claim 10, at Column 352, Lines 17-28, the formula:
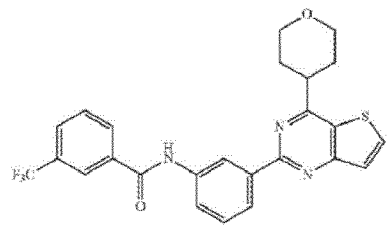
Should be replaced with the formula:
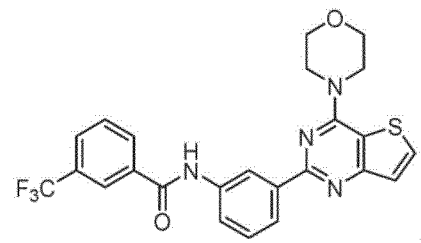
.
In Claim 10, at Column 355, Lines 43-53, the formula:
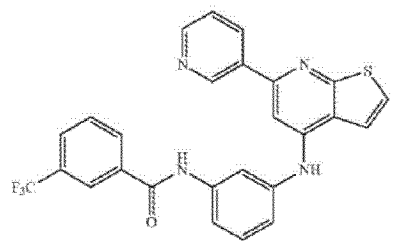
Should be replaced with the formula:
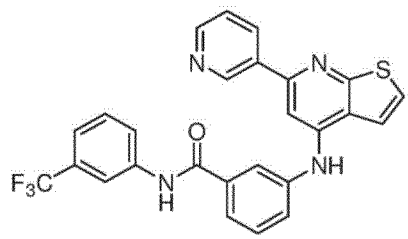
.
In Claim 10, at Column 355, Lines 56-67, the formula:
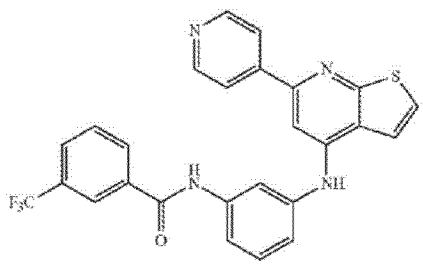
Should be replaced with the formula:
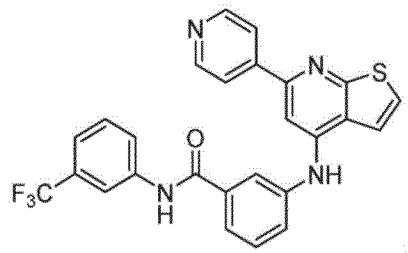
.

In Claim 10, at Column 356, Lines 3-13, the formula:
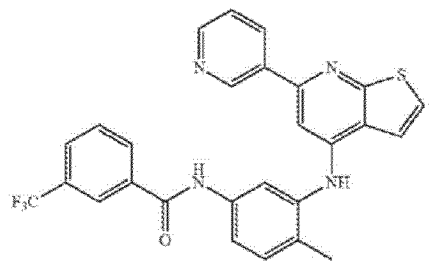
Should be replaced with the formula: 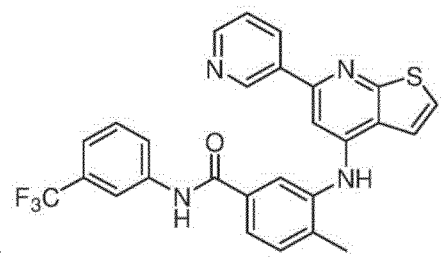 .
In Claim 10, at Column 356, Lines 16-26, the formula:
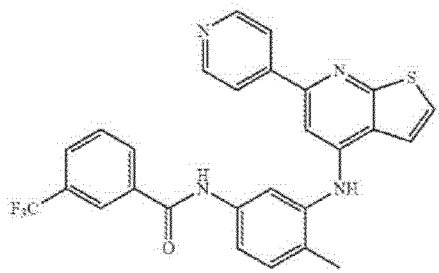
Should be replaced with the formula: 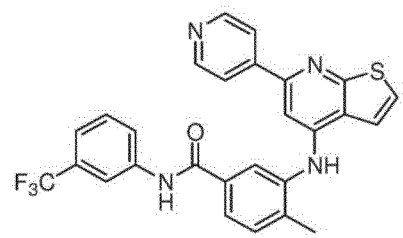 .